US008329683B2

(12) United States Patent
Chen et al.

(10) Patent No.: US 8,329,683 B2
(45) Date of Patent: *Dec. 11, 2012

(54) TREATMENT OF NEUROFIBROMATOSIS WITH RADICICOL AND ITS DERIVATIVES

(75) Inventors: Ruihong Chen, Foster City, CA (US); Allan E. Rubenstein, New York, NY (US); Jin-Chen Yu, Palo Alto, CA (US); Nicolas Winssinger, Strasbourg (FR); Sofia Barluenga, Strasbourg (FR)

(73) Assignees: Nexgenix Pharmaceuticals, LLC, New York, NY (US); Universite de Strasbourg, Strasbourg (FR)

( * ) Notice: Subject to any disclaimer, the term of this patent is extended or adjusted under 35 U.S.C. 154(b) by 41 days.

This patent is subject to a terminal disclaimer.

(21) Appl. No.: 12/631,667

(22) Filed: Dec. 4, 2009

(65) Prior Publication Data

US 2010/0292218 A1 Nov. 18, 2010

Related U.S. Application Data

(63) Continuation-in-part of application No. PCT/US2007/075739, filed on Aug. 10, 2007, which is a continuation-in-part of application No. PCT/US2007/070367, filed on Jun. 4, 2007, and a continuation-in-part of application No. PCT/US2009/031149, filed on Jan. 15, 2009.

(60) Provisional application No. 60/810,166, filed on Jun. 2, 2006, provisional application No. 61/011,163, filed on Jan. 15, 2008.

(51) Int. Cl.
*A61K 31/33* (2006.01)
(52) U.S. Cl. .................................................. 514/183
(58) Field of Classification Search ................... 514/183
See application file for complete search history.

(56) References Cited

U.S. PATENT DOCUMENTS

| 2005/0080002 A1 | 4/2005 | Jacks et al. |
| 2005/0203173 A1 | 9/2005 | Garlich et al. |
| 2005/0272755 A1 | 12/2005 | Denis et al. |
| 2006/0079493 A1 | 4/2006 | Fritz et al. |

FOREIGN PATENT DOCUMENTS

| WO | WO 01/03692 A1 | 1/2001 |
| WO | WO 02/16369 A2 | 2/2002 |
| WO | WO 2006/083979 A2 | 8/2006 |
| WO | WO 2007/143630 A2 | 12/2007 |

OTHER PUBLICATIONS

Chaudhury et al., "Hsp90 as a Target for Drug Development," Chem. Med. Chem. 1:1331-1340 (2006).
Economou, "International Search Report," 5 pages, PCT appl. No. PCT/US07/75739, European Patent Office (mailed Feb. 26, 2008).
Economou, "Written Opinion of the International Searching Authority," 7 pages, PCT appl. No. PCT/US07/75739, European Patent Office (mailed Jan. 10, 2008).
Harrisingh et al., "The Ras/Raf/ERK signalling pathway drives Schwann cell dedifferentiation," EMBO J. 23:3061-3071 (2004).
Hostein et al., "Inhibition of Signal Transduction by the HSP90 Inhibitor 17-Allylamino-17-demethoxygeldanamycin Results in Cytostasis and Apoptosis," Cancer Res. 61:4003-4009 (2001).
Hu et al., "Phosphoinositol lipids bind to phosphatidylinositol 3 (PI3)-kinase enhancer GTPase and mediate its stimulatory effect on PI3-kinase and Akt signalings," Proc. Natl. Acad. Sci. USA 102(46):16853-16858 (2005).
Ikuina et al., "Synthesis and Antitumor Activity of Novel O-Carbamoylmethyloxime Derivatives of Radicicol," J. Med. Chem. 46:2534-2541 (2003).
Sano et al., "Radicicol Potentiates Neurotrophin-Mediated Neurite Outgrowth and Survival of Cultured Sensory Neurons from Chick Embryo," J. Neurochem. 72:2256-2263 (1999).
Shiotsu et al., "Novel oxime derivatives of radicicol induce erythroid differentiation associated with preferential G1 phase accumulation against chronic myelogenous leukemia cells through destabilization of Bcr-Abl with Hsp90 complex," Blood 96(6):2284-2291 (2000).
Soga et al., "KF25706, a novel oxime derivative of radicicol, exhibits in vivo antitumor activity via selective depletion of Hsp90 binding signaling molecules," Dialog(R)File 159:Cancerlit, 2 pages (1999).
Soga et al., "Stereospecific antitumor activity of radicicol oxime derivatives," Cancer Chemother. Pharmacol. 48:435-445 (2001).
Young, "International Search Report," 2 pages, PCT appl. No. PCT/US07/70366, United States Patent and Trademark Office (mailed Oct. 31, 2007). Young, "International Search Report," 2 pages, PCT appl. No. PCT/US07/70367, United States Patent and Trademark Office (mailed Jan. 10, 2008).
Young, "Written Opinion of the International Searching Authority," 5 pages, PCT appl. No. PCT/US07/70366, United States Patent and Trademark Office (mailed Oct. 31, 2007).
Young, "Written Opinion of the International Searching Authority," 6 pages, PCT appl. No. PCT/US07/70367, United States Patent and Trademark Office (mailed Jan. 10, 2008).

*Primary Examiner* — Brandon Fetterolf
*Assistant Examiner* — Christopher R Stone
(74) *Attorney, Agent, or Firm* — Cooley LLP

(57) ABSTRACT

The present invention provides compounds of formulae Ia, Ia', IIa, IIa', IIIa, IIIa', IVa, or Va and the therapeutic use thereof. The present invention also includes methods of treating NF2-deficient or NF1-deficient cells or neurodegenerative diseases with radicicol or its derivatives, such as one or more compounds of formula I, II, III, IV, V, Ia, Ia', IIa, IIa', IIIa, IIIa', IVa, or Va. Furthermore, the present invention is directed to methods of inhibiting the growth of NF2-deficient or NF1-deficient tumors. The methods comprise contacting NF2-deficient or NF1-deficient tumor cells with radicicol or its derivatives, such as one or more compounds of formula I, II, III, IV, V, Ia, Ia', IIa, IIa', IIIa, IIIa', IVa, or Va. The present invention is also directed to the combinational use of radicicol or its derivatives, such as one or more compounds of formula I, II, III, IV, V, Ia, Ia', IIa, IIa', IIIa, IIIa', IVa, or Va with at least one additional active agent, such as one or more HSP90 inhibitors.

13 Claims, 3 Drawing Sheets

NXD30001 (24 hr treatment)

0   8   40   200   1000   nM

EGFR

Akt c-Raf

Cdk4

Actin

Figure 3

IC50 (μM) on cell proliferation

| | NXD30001 | NXD30002 | NXD30017 | 17AAG |
|---|---|---|---|---|
| I. NF2 cells | | | | |
| *Nf2-/-* MESC | 0.008 | 0.24 | | 0.008 |
| SF1335 | 0.04 | 0.85 | 0.045 | 0.11 |
| HEI193 | 0.015 | 0.31 | 0.007 | 0.003 |
| BAR | 0.03 | 0.61 | | 0.007 |
| RAV | 0.043 | | 0.026 | 0.029 |
| BLA | 0.08 | 0.78 | 0.039 | 0.03 |
| II. NF1 cells | | | | |
| ST88-14 MPNST | 0.021 | | | 0.043 |
| sNF96.2 MPNST | 0.18 | | | 0.088 |

TREATMENT OF NEUROFIBROMATOSIS WITH RADICICOL AND ITS DERIVATIVES

CROSS REFERENCE TO RELATED APPLICATIONS

This application is a continuation-in-part (CIP) of pending International Application No. PCT/US2007/075739, filed on Aug. 10, 2007, which is a continuation-in-part (CIP) of International Application No. PCT/US2007/070367, filed Jun. 4, 2007, which claims priority to U.S. Ser. No. 60/810,166, filed on Jun. 2, 2006, and this application also is a continuation-in-part (CIP) of pending International. Application No. PCT/US2009/031149 filed on Jan. 15, 2009, which claims priority to U.S. Provisional Patent Application No. 61/011,163, filed Jan. 15, 2008; all of which are herein incorporated by reference in their entirety.

FIELD OF THE INVENTION

The present invention relates to the use of radicicol and its derivatives for treatment of neurofibromatosis type 2 (NF2), neurofibromatosis type 1 (NF1), and neurodegenerative diseases. The present invention also provides derivatives, analogs and intermediates of the natural products radicicol and the pochonins, and to their syntheses. The present invention is further directed to use of these compounds as inhibitors of kinases and of the enzyme family known as heat shock protein 90 (HSP90).

BACKGROUND OF THE INVENTION

The invention claimed herein was made by or on behalf of Universite de Strasbourg, Le Center National De La Recherche Scientifique, AND NexGenix Pharmaceuticals, LLC, who are parties to a joint research agreement signed on Jul. 1, 2007 and related to macrocyclic compounds, such as radicicol and its derivatives, which are useful as kinase and HSP90 inhibitors.

Neurofibromatosis includes two diseases, neurofibromatosis type 1 (NF1) and neurofibromatosis type 2 (NF2). Both NF1 and NF2 are inherited disorders and both encompass mutations which predispose individuals to multiple tumors of the central or peripheral nervous system, and occasionally to other malignancies. Major tumor types associated with NF1 and NF2 involve glial cells (e.g. Schwann cells and astrocytes). Although there is the similarity of the involvement of Schwann cells in NF1 and NF2 tumors, NF1 and NF2 have a spectrum of tumors which involve different types of cells. In addition, NF1 and NF2 are caused by different gene mutations.

Neurofibromatosis Type 2

Neurofibromatosis type 2 (NF2) is a rare form of neurofibromatosis, which is a dominantly inherited tumor suppressor disorder, that affects approximately 1 in 25,000 individuals and is characterized by multiple tumors on the cranial and spinal nerves. NF2 is a different disease from NF1, neurofibromatosis type 1. Although both NF1 and NF2 are tumor predisposition syndromes in the nervous system, the tumor suppressor genes are different and signaling pathways are likely to be different.

Individuals with NF2 are at a high risk for developing brain tumors, in particular tumors on both the seventh and eighth cranial nerves. Bilateral vestibular schwannomas, a type of tumor which occurs on these nerves, occurs in about 95% of affected individuals. Consequently, hearing loss, ringing in the ears, and problems with balance are symptoms frequently associated with NF2.

Schwannomas are tumors consisting of nerve sheath cells or Schwann cells (SCs). Schwann cells support and protect nerve cells and provide nerves with the insulation they need to conduct information. Bilateral vestibular schwannomas, also known as acoustic neuromas, as well as spinal schwannomas and schwannomas of the peripheral nerves are common manifestations of NF2. The symptoms of a schwannoma will depend on its location.

In addition to schwannomas, individuals with NF2 may develop other types of tumors emanating from the nerves, meningeal envelopes, brain and spinal cord. The most common tumor of this type is meningioma; other less common tumors include ependymomas and astrocytomas. Moreover, NF2 patients may have an increased risk for developing mesotheliomas.

Molecular Role of Merlin

NF2 is an autosomal dominant genetic trait, meaning it affects both genders equally and each child of an affected parent has a fifty percent chance of inheriting the gene. NF2 results from a mutation or a deletion of the NF2 gene and is transmitted on chromosome 22 (Sainz et al., 1994, Hum. Mol. Genet. 3: 885-891; Ruttledge et al., 1994, Nat. Genet. 6: 180-184; Rubio et al., 1994, Cancer Res. 54: 45-47; Huynh et al., 1997, J. Neuropathol. Exp. Neurol. 56: 382-390).

The NF2 gene is a tumor suppressor gene that encodes a 595-amino acid protein, termed Merlin. Merlin belongs to the ezrin, radixin, and moesin (ERM) family of proteins (Trofatter et al., 1993, Cell. 75: 826).

Over-expression of Merlin can block both cell proliferation and oncogene-induced transformation (Lutchman and Rouleau, 1995, Cancer Res. 55(11): 2270-2274; Tikoo et al., 1994, J. Biol. Chem. 269(38): 23387-23390). Indeed, Merlin can negatively regulate cyclin D1 levels (Xiao et al., 2002, J. Biol. Chem. 277: 883-886) and loss of Merlin results in overexpression of cyclin D1 (Lallemand et al., 2003, Genes Dev. 17: 1090-1100). However, given its predominant localization to the membrane and cytoskeleton interface, Merlin is not likely to directly control the cell cycle machinery.

The mechanism by which loss of NF2 may contribute to tumor development is not clear. Many studies have focused on this issue using both genetic and biochemical approaches. Several lines of evidence suggest that Merlin can regulate receptor tyrosine kinase activity, trafficking, and degradation. Merlin has been shown to interact directly with the focal adhesion component paxillin in a complex that contains integrin-β1 and ErbB2 (Fernandez-Valle et al., 2002, Nat. Genet. 31(4): 354-362), HGF receptor substrate (HRS) (Scoles et al., 2002, Hum. Mol. Genet. 11(25): 3179-3189; Gutmann et al., 2001, Hum. Mol. Genet. 10(8): 825-834; Soles et al., 2000, Hum. Mol. Genet. 9(11): 1567-1574), and platelet derived growth factor receptor (PDGFR) indirectly through interaction with a PDZ-containing adaptor protein EBP50/NHE-RF (Maudsley et al., 2000, Mol. Cell. Biol. 20(22): 8352-8363; Murthy et al., 1998, J. Biol. Chem. 273(3): 1273-1276). Neuregulin growth factors (EGF family of growth factors), VEGF, and HGF are important mitogens for Schwann cells (SCs) (Krasnoselsky et al., 1994, J. Neurosci. 14:7284-7290; DeClue et al., 2000, J. Clin. Invest. 105(9):1233-1241; Caye-Thomasen et al., 2005, Otol. Neurotol. 26(1):98-101). Neuregulin/ErbB pathways are constitutively activated in human NF2 vestibular schwannomas and inhibitors of these pathways (e.g. antibody against neuregulin and Iressa) block proliferation of NF2-deficient schwannoma cells (Stonecypher et al., 2006, J. Neuropathol. Exp. Neurol. 65:162-175;

Hansen et al., 2006, Glia 53:593-600). Recent evidence from *Drosophila* indicates that Merlin can regulate abundance/turnover of many signaling and adhesion receptors such as Notch, the EGF receptor, Patched, Smoothened, E-cadherin, and Fat. Loss of merlin results in accumulation of these cell surface receptors and activation of the associated signaling pathways (e.g. the EGFR pathway and the Wingless pathway) (Maitra et al., 2006, *Curr. Biol.* 16(7):702-709).

In addition to cell surface receptors, Merlin has been shown to interact with downstream components of various signaling pathways, including Rac-PAK (p21-activated kinase) pathway. Rac is a member of the Rho family of small GTPases, which organize the actin cytoskeleton and control many cellular processes such as cell proliferation, transformation, and cell motility (Etienne-Manneville and Hall, 2002, Nature. 420(6916): 629-635; Sahai and Marshall, 2002, Nat. Rev. Cancer 2(2): 133-142). PAK can phosphorylate 5518 of Merlin (Xiao et al., 2002, J. Biol. Chem. 277: 883-886; Kissel et al., 2002, J. Biol. Chem. 277(12): 10394-10399) which leads to conformational change and loss of growth-suppressing activity (Shaw et al., 1998, J. Biol. Chem. 273(13): 7757-7764; Shaw et al., 2001, Dev. Cell. 1(1): 63-72). Merlin can also act as a negative regulator of Rac-PAK signaling (Shaw et al., 2001, Dev. Cell. 1:63-72; Kissil et al., 2003, Mol. Cell. 12:841-849; Lallemand et al., 2003, Genes Dev. 17: 1090-1100; Hirokawa et al., 2004, Cancer J. 10: 20-26). Loss of Merlin results in the inappropriate phosphorylation and activation of PAK. Over-expression of Merlin inhibits PAK activation and blocks Rac-induced transformation. (Shaw et al., 2001, Dev. Cell. 1(1): 63-72; Kissil et al., 2003, Mol. Cell. 12(4):841-849). Preliminary evidence indicates that loss of Merlin also leads to activation of the Ras/Raf/Mek/Erk pathway and PI3K-Akt pathway (Rangwala et al., 2005, *J. Biol. Chem.* 280(12):11790-11797; our preliminary data). A recent study from *Drosophila* has proposed that Merlin and a related protein expanded function upstream of the Hippo signaling pathway to regulate cell proliferation and apoptosis (Hamaratoglu et al., 2006, Nat. cell biol. 8:27-36; Willecke et al., 2006, *Curr Biol.* 16(21):2090-2100).

The link between Merlin and growth factor receptor signaling indicates that growth factor receptors may play direct roles in NF2-associated tumor formation and progression. However, possible involvement of Merlin with multiple signaling pathways presents a challenge in developing drugs for the treatment of NF2.

Neurofibromatosis Type 1

NF1 is one of the most common single gene disorder to affect the human nervous system, with an incidence of 1 in 3500 individuals (Sorensen S A, Mulvihill J J, Nielsen A. Ann N Y Acad Sci 1986; 486:30-7.). NF1 affects approximately 1.5 million people worldwide and there is no racial, ethnic, or geographic predilection for the disease. NF1 is an autosomal dominantly inherited genetic disorder with frequent germline deletion or loss-of-function mutations of the NF1 gene, and is caused by mutation in the NF1 gene, which encodes Neurofibromin, a tumor suppressor. Neurofibromin shares a region of similarity with the p120RasGAP protein, therefore functioning as a negative regulator of the Ras pathway. A high spontaneous mutation rate (50%) at the NF1 locus and the substantial variability of its expression ensure that the disorder is unlikely to decrease significantly in the population due to genetic screening.

The signs of NF1 include café-au-lait macules, skin freckling, skeletal defects, learning disability, Lisch nodules, dermal and plexiform neurofibromas (most common), benign tumors of the brain or other organs (e.g. optic pathway astrocytomas, optic neuromas, optic gliomas, cerebral astrocytomas, cerebral gliomas, ganglioneuromas, ependymomas, pheochromocytomas and ganglioneuromas), and malignant neoplasms (e.g. rhabdomyosarcomas, neurofibrosarcomas or malignant peripheral nerve sheath tumors ("MPNST") or malignant schwannomas) (Korf B R. J Child Neurol 2002; 17(8):573-7; discussion 602-4, 46-51.) Children affected by NF1 also have increased risk for developing a rare form of leukemia-juvenile myelomonocytic leukemia (JMML) (Stiller C A, Chessells J M, Fitchett M. Br J Cancer 1994; 70(5):969-72.). Dermal neurofibromas, subdermal neurofibromas, plexiform neurofibromas and MPNSTs are primarily derived from Schwann cells or their progenitors. Optic gliomas and astrocytomas are derived from astrocytes. Pheochromocytomas are derived from neural crest components (as are neurofibromas and MPNSTs).

The typical characteristic of NF1 is the neurofibroma, of which there are clinically and histologically distinct types. Ninety-five % of patients have discrete benign neurofibromas within the dermis which may develop at any time in life, but their numbers are usually small before puberty. The total number of neurofibromas seen in adults varies from just a few to hundreds or even thousands. These tumors may cause disfigurement, chronic pain and pruritus. Certain patients may develop some of the same disfiguring symptoms that are associated with Elephant Man's disease, a separate disorder originally thought to be NF1. Plexiform neurofibromas may be congenital and are present in 30% of patients with NF1. These tumors represent a major cause of morbidity in NF1. They affect long portions of nerves and infiltrate the nerve and surrounding tissue, resulting in disfiguration and neuralgic complications. In about 2-5% of patients, plexiform neurofibromas transform to malignant peripheral nerve-sheath tumors, which have a significant mortality rate. Although NF1 is usually not a lethal disorder, affected individuals often face a lifetime of morbidity and disfigurement.

The Nf1 gene was identified in 1990 (Wallace et al. 1990 *Science* 249:181-186; Cawthon et al. 1990 *Cell* 62:193-201) and its gene product, neurofibromin, is a 250 kD protein of 2818 amino acids that has a catalytic domain related to the GTPase-activating protein (GAP) domain of p120RasGAP (Marchuk et al., 1991 *Genomics* 11:931-940; Gutmann et al., 1991. *Proc. Natl. Acad. Sci. U.S.A.* 88: 9658-9662; DeClue et al., 1991. *Proc. Natl. Acad. Sci. U.S.A.* 88:9914-9918; Martin et al., 1990. *Cell* 63:843-849; Xu et al., 1990. *Cell* 63: 835-841; Xu et al., 1990. *Cell* 62: 599-608). Loss of Nf1 in human neurofibromas, MPNSTs, leukemias, and tumor-derived cell lines results in the elevation of Ras-GTP levels and activation of Ras-Raf-Mek-Erk2 and other MAP kinase pathways (Guha et al., 1996 *Oncogene* 12: 507-513; Bollag et al., 1996. *Nat. Genet.* 12:144-148; Basu et al. 1992. *Nature* 356: 713-715; DeClue et al., 1992 *Cell* 69:265-273). For example, Ras-GTP levels from a few NF1MPNST-derived cell lines ST88-14, 88-3 and 90-8 are much higher compared to other cell lines with normal neurofibromin. These cell lines also have activated downstream MAP kinase pathways. In addition, cell proliferation and soft agar growth of ST88-14 can be inhibited by injection of an antibody against Ras and expression of the GAP domain of neurofibromin, respectively. Therefore, controlling Ras pathway activity in these cells is important in blocking the transformation properties.

HSP90 and HSP90 Inhibitors/Modulators

In the mid-1950's, it was discovered that phosphorylation can reversibly alter the function of enzymes by means of protein kinases which catalyze phosphorylation, or by protein phosphatases which are involved in the dephosphorylation step. These reactions play an essential role in regulating many cellular processes, especially signaling transduction pathways. In the late 1970's, the Rous sarcoma virus (v-Src)'s transforming factor was discovered to be a protein kinase, and also tumor-promoting phorbol esters were found to be potent activators of protein kinase C, revealing the first known connection between disease and abnormal protein phosphorylation. Since then transduction mechanistic defects have been found to cause numerous oncogenic processes and to have a role in diabetes, inflammatory disorders, and cardiovascular diseases. (T. Hunter, *Cell,* 100:113-127 (2000); P. Cohen, *Nat. Rev. Drug Discov.,* 1:309 (2002)). Thus selective kinase and phosphatase inhibitors have emerged as important drug targets, and inhibition of kinase phosphorylation activity is one of the most promising strategies for chemotherapy.

Macrocyclic resorcylic acid lactones such as radicicol and the related pochonins, are a structurally related group of secondary metabolites isolated from cultures of the clavicipitaceous hyphomycete *Pochonia* genus, such as *Pochonia chlamydosporia* var. *catenulate* strain P0297. See, e.g., V. Hellwig et al., *J. Natural Prod.,* 66(6):829-837 (2003). These compounds and analogs or derivatives of the compounds have been evaluated as kinase inhibitors or inhibitors of HSP90. Halohydrin and oxime derivatives of radicicol were prepared and evaluated for their v-src tyrosine kinase inhibitory, antiproliferative, and antitumor in vitro activity (T. Agatsuma et al., *Bioorg. & Med. Chem.,* 10(11):3445-3454 (2002).

The heat shock protein 90 (HSP90) is an ATP-dependent molecular chaperone whose function is to ensure the proper folding and stability of a number of its client proteins such as kinases and transcription factors (Pearl and Prodromou, 2001 *Adv. Protein Chem.* 59: 157-186). HSP90 belongs to the ATPase superfamily and consists of three protein domains: the N-terminal ATPase domain, a middle domain responsible for client protein binding, and a C-terminal dimerization domain which also contains a weak ATP-binding domain (Pearl and Prodromou, 2001 *Adv Protein Chem.* 59: 157-186). Four genes of the HSP90 family are found in humans and their gene products have different cellular locations. The two major cytoplasmic isoforms are HSP90 alpha and HSP90 beta (Hickey et al., 1989, *Mol Cell Biol.* 9: 2615-2626). Other major isoforms are GRP94 in the endoplasmic reticulum (Argon and Simen, 1999, *Semin. Cell Dev. Biol.* 10: 495-505) and TRAP1/HSP75 in mitochondria (Felts et al., 2000, *J. Biol. Chem.* 275: 3305-12). HSP 90 is found to be part of a series of dynamic multiprotein complexes made of co-chaperones including HSP70, HSP40, and Hop. Hydrolysis of ATP causes HSP90 to alter its conformation and allows other co-chaperones such as p23, CDC37, or immunophilins to associate with HSP90 to form a mature complex, which catalyzes the folding and maturation of the client proteins (Pearl & Prodromou, 2000, Curr. Opin. Struct. Biol. 10: 46-51.). The adaptor co-chaperone protein CDC37 mediates interactions between HSP90 and kinases (Pearl, 2005, Curr. Opin. Genet. Dev. 15:55-61; Roe et al., 2004, Cell 116: 87-98.).

Like kinases, heat shock proteins (HSPs) interact with ATP and are important targets for controlling disease, however they have a different mechanistic effect. Immediately after exposure to a stress such as heat, hypoxia or acidosis, cells in most tissues rapidly escalate production rate of the HSPs. It is now believed that heat HSPs are molecular chaperones, i.e., they prevent improper associations and assist in the correct folding of other cellular proteins collectively termed clients and substrates. HSP's are also found in association with tumors and other pathophysiological conditions. In fact, chaperone proteins facilitate the survival of tumor cells in stressful environments by facilitating tolerance of alterations inside the cell. HSPs are ubiquitous, highly conserved among the species, and usually classified by molecular weight to the following major families: HSP100, HSP90, HSP70, HSP60 and small HSPs. These families have structural and functional differences, but work cooperatively at different stages of protein folding. HSP90 has attracted particular attention due to its association with many types of signaling molecules such as v-Src and Raf that play a critical role in malignant transformation and metastasis development. Thus, HSP90 inhibitors are desired for designing chemotherapies, and also for elucidating the interplay in complex signaling networks.

Heat Shock Protein 90's (Hsp90s) are ubiquitous chaperone proteins that maintain the proper conformation of many "client" proteins (see Kamal et. al. *Trends Mol. Med.* 2004, 10, 283-290; Dymock et. al. *Expert Opin. Ther. Patents* 2004, 14, 837-847; Isaacs et. al. *Cancer Cell,* 2003, 3, 213; Maloney et. al. *Expert Opin. Biol. Ther.* 2002, 2, 3-24 and Richter et. al. *J. Cell. Physiol.* 2001, 188, 281-290), and are involved in folding, activation and assembly of a wide range of proteins, including key proteins involved in signal transduction, cell cycle control and transcriptional regulation. Researchers have reported that HSP90 chaperone proteins are associated with important signaling proteins, such as steroid hormone receptors and protein kinases, including, e.g., Raf-1, EGFR, v-Src family kinases, Cdk4, and ErbB-2 (Buchner, TIBS, 1999, 24, 136-141; Stepanova et. al., *Genes Dev.* 1996, 10, 1491-502; Dai et. al., *J. Biol. Chem.* 1996, 271, 22030-4). Studies further indicate that certain co-chaperones, e.g., Hsp70, p60/Hop/Sti1, Hip, Bag1, HSP40/Hdj2/Hsj1, immunophilins, p23, and p50, may assist HSP90 in its function (see for example Caplan, *Trends in Cell Biol.,* 1999, 9, 262-268). Inhibition of Hsp90 causes these client proteins to adopt aberrant conformations, and these abnormally folded proteins are rapidly eliminated by the cell via ubiquitinylation and proteasome degradation. Interestingly, the list of Hsp90 client proteins includes a series of notorious oncogenes. Four of them are clinically validated cancer targets: HER-2/neu (Herceptin® (trastuzumab)), Bcr-Abl (Gleevec® (imatinib mesylate)), the estrogen receptor (tamoxifen), and the androgen receptor (Casodex® (bicalutamide)), while the others play a critical role in the development of cancer. Some of the most sensitive Hsp90 clients are involved in growth signaling (Raf-1, Akt, cdk4, Src, Bcr-Abl, etc). In contrast, few tumor suppressor genes, if any, seem to be clients of Hsp90 (for lists of client proteins see Pratt et. al. *Exp. Biol. Med.* 2003, 228, 111-133; Workman et. al. *Cancer Lett.* 2004, 206, 149-157 and Zhang et. al. *J. Mol. Med.* 2004, 82, 488-499.), and consequently, inhibition of Hsp90 has an overall anti-proliferative effect. In addition, some client proteins are involved in other fundamental processes of tumorigenesis, namely apoptosis evasion (e.g. Apaf-1, RIP, Akt), immortality (e.g. hTert), angiogenesis (e.g. VEGFR, Flt-3, FAK, HIF-1), and metastasis (c-Met).

The numerous client proteins of HSP90 play a crucial role in growth control, cell survival and development processes, and those clients are known to include receptor tyrosine kinases, serine/threonine kinases, steroid hormone receptors, transcription factors and telomerase. In addition to anti-cancer and antitumorgenic activity, HSP90 inhibitors have also been implicated in a wide variety of other utilities, including use as anti-inflammation agents, anti-infectious disease agents, agents for treating autoimmunity, agents for treating ischemia, and agents useful in treating neurodegenerative diseases and in promoting nerve regeneration (see M. Waza et al, *Nature Med.* 11:1088 (2005); Rosen et al., WO 02/09696; PCT/US01/23640; Degranco et al., WO 99/51223; PCT/US99/07242; Gold, U.S. Pat. No. 6,210,974 B1). There are reports in the literature that fibrogenetic disorders including but not limited to scleroderma, polymyositis, systemic lupus, rheumatoid arthritis, liver cirrhosis, keloid formation, interstitial nephritis, and pulmonary fibrosis may be treatable. (Strehlow, WO 02/02123; PCT/US01/20578).

There are over one hundred HSP90 client proteins reported in the literature (Solit and Rosen, 2006, *Curr. Top. Med. Chem.* 6:1205-14). Major HSP90 client proteins include steroid hormone receptors such as the androgen, estrogen and glucocorticoid receptors (AR, ER, and GR) (Whitesell and Cook, 1996, Mol. Endocrinol. 10: 705-712; Segnitz and Gehring, 1997, J Biol. Chem. 272(30):18694-701; Czar et al., 1997 *Biochemistry*. 1997, 36:7776-85), tyrosine and serine/threonine kinases such as HER2 (ErbB2) (Munster et al., 2002, Cancer Res. 62: 3132-3137.), the insulin-like growth factor-1 receptor (IGF-1R) (Sepp-Lorenzino et al., 1995, J. Biol. Chem. 270: 16580-16587.), Met (Webb et al., 2000, Cancer Res. 60: 342-349.), Flt-3 (Yao et al., 2003, Clin. Cancer Res. 9: 4483-4493.), ZAP70 (Castro et al., 2005, Blood 106: 2506-2512.), Src family kinases (Bijlmakers and Marsh, 2000, *Mol Biol Cell.* 11:1585-1595.) Raf-1 (Schulte et al., 1995, J. Biol. Chem. 270: 24585-24588.), cyclin-dependent kinases 4 and 6 (Cdk4/6) (Stepanova et al., 1996, Genes Dev. 10: 1491-1502.), MLK3 (Zhang et al., 2004, J. Biol. Chem. 279: 19457-19463.), and Akt (Basso et al., 2002, J. Biol. Chem. 277: 39858-39866.), mutant proteins including v-Src (Xu et al., 1993, Proc. Natl. Acad. Sci. USA 90: 7074-7078; Whitesell et al., 1994, Proc. Natl. Acad. Sci. USA 91:8324-8328), mutant EGFR (Shimamura et al., 2005, Cancer Res. 65: 6401-6408.), mutant B-Raf (da Rocha Dias et al., 2005, Cancer Res. 65: 10686-10691; Grbovic et al., 2006, Proc. Natl. Acad. Sci. USA 103: 57-62.), Bcr-Abl (Gone et al., 2002, Blood 100: 3041-3044; Nimmanapalli et al., 2001, Cancer Res. 61: 1799-1804.) and mutant p53 (Whitesell et al., 1998, Mol. Cell. Biol. 18: 1517-1524.), and other proteins such as HIF-1alpha (Isaacs et al., 2002, J. Biol. Chem. 277: 29936-29944; Mabjeesh et al., 2002, Cancer Res. 62: 2478-2482.), Mdm2 (Peng et al., J. Biol. Chem. 276: 40583-40590.), and HSF-1 (Zou et al., 1998, Cell 94: 471-480.). Many of these HSP90 client proteins are important in controlling cell growth and proliferation, differentiation, and cell survival. This is a putative rationale for the use of HSP90 inhibitors in the treatment of cancer. This subject has been extensively reviewed in the recent literature (Chiosis and Neckers, 2006, *ACS. Chem. Biol.* 1(5):279-284; Janin, 2005, *J. Med. Chem.* 48(24):7503-7512; Sharp and Workman, 2006, *Adv. Cancer Res.* 95:323-348; Solit and Rosen, 2006, *Curr. Top. Med. Chem.* 6(11):1205-1214). The identification of specific HSP90 clients that are important for the growth of specific cancer types is an active area of research.

Two structurally unrelated natural products, geldanamycin and radicicol, were isolated in 1970 from *Streptomyces hygrocopicus* and in 1953 from the fungus *Monosporium bonorden*, respectively. Geldanamycin is a benzoquinone-based ansamycin antibiotic, and radicicol is a macrocyclic lactone antibiotic. They were believed to be kinase inhibitors initially and later found to inhibit HSP90 function via the interaction with the N-terminal ATP binding domain of HSP90 (DeBoer et al., 1970, J. Antibiot. 23: 442-447, Roe et al., 1999, *J. Med. Chem.* 42:260-266; Schulte and Neckers, 1998, *Cancer Chemother. Pharmacol.* 42:273-279; Prodromou et al., 1997, Cell 90:65-75; Whitesell et al., 1994, *Proc. Natl. Acad. Sci. U.S.A.* 91:8324-8328). More compounds have been found to inhibit the function of HSP90 and are generally referred to as HSP90 inhibitors. Most HSP90 inhibitors inhibit the intrinsic ATPase activity by binding to the N-terminal nucleotide binding site of HSP90 and thus block the formation of the mature complex between HSP90, co-chaperones, and the client proteins since the formation of the mature complex is dependent on ATP hydrolysis. The client proteins are then degraded through the ubiquitin-proteasome degradation pathway (Connell et al., 2001, *Nat. Cell Biol.* 3: 93-96.). The coumarin antibiotic novobiocin binds to the C-terminal ATP-binding site of HSP90 but with a very weak activity to degrade HSP90 client proteins (Marcu et al., 2000, *J. Natl. Cancer Inst.* 92:242-248; Marcu et al., 2000, *J. Biol. Chem.* 275:37181-37186).

Both geldanamycin and radicicol demonstrate good cellular potency but are not suitable for clinical development. Geldanamycin has severe hepatotoxicity and radicicol is not stable in serum thereby having no in vivo anti-tumor activity (Agatsuma et al., 2002, Bioorg. Med. Chem. 10:3445-3454; Soga et al., 2003, Curr. Cancer Drug Targets, 3:359-369). Thus, analogs of radicicol, such as oxime derivatives of radicicol, and analogs of geldanamycin, such as 17-(Ally-lamino)-17-demethoxygeldanamycin (17-AAG), the more water soluble analogue 17-demethoxy, 17-(2-dimethy-lamino) ethylamino geldanamycin (17-DMAG), and hydroquinone analogue of 17-AAG, have been synthesized and tested. These analogs generally exhibit good efficacy at tolerated doses in in vitro studies and in vivo animal xenograft models (Ikuina et al., 2003, J. Med. Chem., 46:2534-2541; Ge et al., 2006, J. Med. Chem. 49:4606-4615; Maroney et al., 2006, Biochemistry, 45:5678-5685; Shiotsu et al., 2000, Blood, 96(6):2284-2291; Sydor et al., 2006, *Proc. Natl. Acad. Sci. U.S.A.* 103(46):17408-17413). Several geldanamycin analogs have entered clinical trials for the treatment of cancer. These agents have demonstrated promising results in several types of cancer (e.g. breast cancer, leukemia, melanoma, and etc.).

The clinical experience of 17-AAG has stimulated a search for new HSP90 inhibitors with better pharmacological properties and safety profiles. A number of HSP90 inhibitors in various compound classes have been developed as potential agents for cancer treatment. These include purine-based compounds (PCT publications WO/2006/084030; WO/2002/036075; U.S. Pat. No. 7,138,401; US20050049263; Biamonte et al., 2006, *J. Med. Chem.* 49:817-828; Chiosis, 2006, *Curr. Top. Med. Chem.* 6:1183-1191; He et al., 2006, J. Med. Chem. 49:381-390), pyrazole-based compounds (Rowlands et al., 2004, *Anal. Biochem.* 327:176-183; Dymock et al., 2005, *J. Med. Chem.* 48:4212-4215; PCT publication WO/2007/021966; WO/2006/039977; WO/2004/096212; WO/2004/056782; WO/2004/050087; WO/2003/055860; U.S. Pat. No. 7,148,228), peptidomimetic shepherdin (Plescia et al., 2005, Cancer Cell 7:457-468; US publication 20060035837), and HSP90 inhibitors in other compound classes (PCT publications WO/2006/123165; WO/2006/109085; WO/2005/028434; U.S. Pat. No. 7,160,885; U.S. Pat. No. 7,138,402; U.S. Pat. No. 7,129,244; US20050256183; US20060167070; US20060223797; WO2006091963). Furthermore, small molecules that modulate HSP functions have been reported. For instance, HDAC inhibitors such as Trichostatin A, SAHA, and FK228 are capable of inhibiting deacetylation of HSP90 and thus modulating the function of HSP90 (Kovacs et al., 2005, Molecular Cell, 18: 601-607). Other molecules modulating the level of HSPs, such as HSP70 and HSP27 may also affect the function of the HSP90 complex (Zaarur et al., 2006, Cancer Res. 66(3):1783-1791). None of these HSP90 inhibitors have previously been shown to inhibit the growth of NF1- or NF2-deficient tumor cells.

Some resorcylic acid lactones have been found to inhibit HSP90, thus natural products radicicol and geldanamycin (P. Delmotte and J. Delmotte-Plaquee, *Nature (London)*, 171:

344 (1953); and C. DeBoer et al., *J Antibiot (Tokyo)*, 23:442 (1970), respectively) were shown to suppress the transformed phenotype of cell expressing activated Src (H. J. Kwon et al., *Cancer Research*, 52:6926 (1992); Y. Uehara et al., *Virology*, 164:294 (1988)). Related compounds such as herbimycin have been reported to have similar effects (S. Omura et al., *J Antibiot (Tokyo)*, 32:255 (1979).

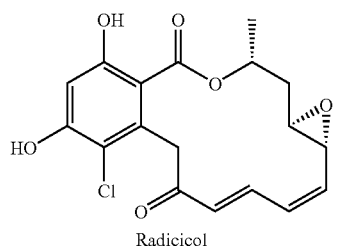
Radicicol

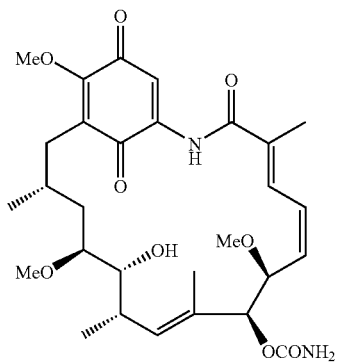
Geldanamycin

Other resorcylic acid lactones (RALs) studied in this respect include 17-allylamino-17-demethoxygeldanamycin (17AAG) (D. B. Solit et al., *Clin. Cancer Res.*, 8:986 (2002); L. R. Kelland et al., *J. Natl. Cancer Inst.*, 91:1940 (1999)); 17DMAG (J. L. Eiseman et al., *Cancer Chemother. Pharmacol.*, 55:21-32 (2005)); IPI-504 (J. Ge et al., *J. Med. Chem.*, 49:4606 (2006); oxime derivatives such as KF25706 (S. Soga, et al., *Cancer Res.*, 59:2931 (1999)) and KF55823 (S. Soga et al., *Cancer Chemotherapy and Pharmacology*, 48:435 (2001)); and Danishefsky et al.'s cycloproparadicicol (A. Rivkin et al., *Ibid.*, 44:2838 (2005)). Structurally related variants include chimeric inhibitors having radicicol's carboxyresorcinol and the geldanamycin's benzoquinone (R. C. Clevenger and B. S. Blagg, *Org. Lett.*, 6:4459 (2004); G. Shen and B. S. Blagg, *Ibid.* 7:2157 (2004); G. Shen et al., *J. Org. Chem.*, 71:7618 (2006)).

Radicicol-based HSP90 inhibitors

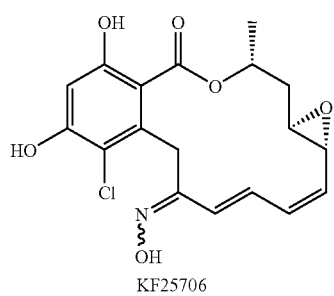
KF25706

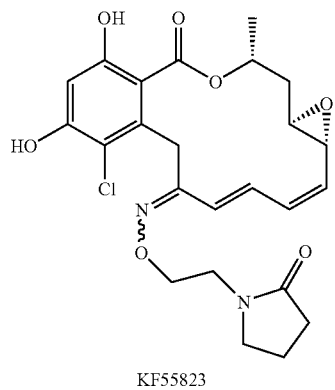
KF55823

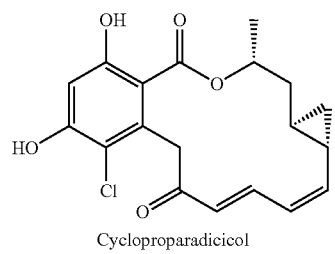
Cycloproparadicicol

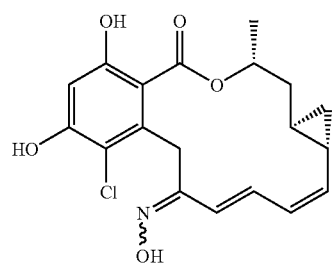

Considerable interest in radicicol's medicinal applications has followed the initial findings. (See U.S. Pat. No. 6,946,456; and U.S. Patent Application Publication Nos. 2003-0211469, 2004-0102458, 2005-0074457, 2005-0261263, 2005-0267087, 2006-0073151, 2006-0251574, 2006-0269618, 2007-0004674, and 2007-0010432).

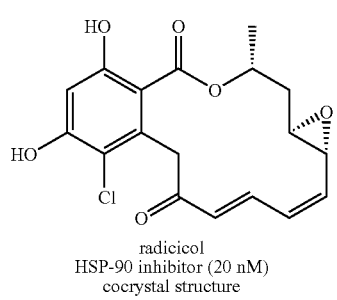
radicicol
HSP-90 inhibitor (20 nM)
cocrystal structure

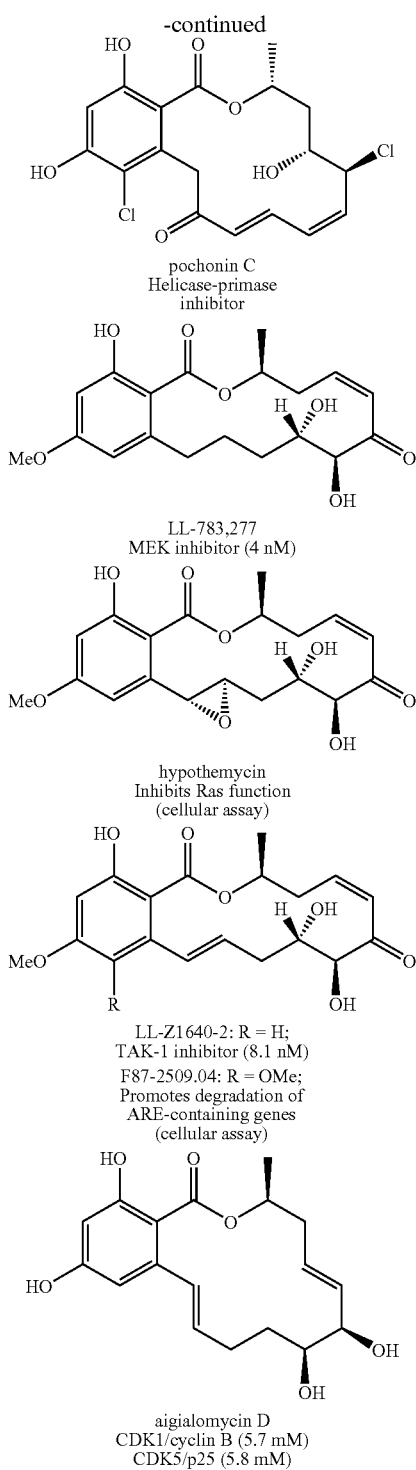

pochonin C
Helicase-primase inhibitor

LL-783,277
MEK inhibitor (4 nM)

hypothemycin
Inhibits Ras function
(cellular assay)

LL-Z1640-2: R = H;
TAK-1 inhibitor (8.1 nM)
F87-2509.04: R = OMe;
Promotes degradation of
ARE-containing genes
(cellular assay)

aigialomycin D
CDK1/cyclin B (5.7 mM)
CDK5/p25 (5.8 mM)

Strikingly, some resorcylic macrolides that are close analogs of radicicol are known to inhibit kinases but not HSP90. Indeed, LL-Z1640-2 was found to be a potent and selective inhibitor of TAK1 kinase for which radicicol and other resorcylides were not active. (J. Ninomiya-Tsuji et al., *J. Biol. Chem.*, 278:18485 (2003); P. Rawlins et al., *Int. J. Immunopharma.*, 21:799 (1999); K. Takehana et al., *Biochem. Biophys. Res. Comm.*, 257:19 (1999); A. Zhao et al., *J. Antibiotics*, 52:1086 (1999)). Closely related LL-783,227, where one of the olefins has been reduced, is a potent inhibitor of MEK kinase. (A. Zhao et al., *J. Antibiotics* 52:1086 (1999)). Compound F87-2509.04 was found to induce degradation of mRNA containing AU-rich elements (ARE) (T. Kastelic et al., *Cytokine*, 8:751 (1996)) and hypothemycin was found to inhibit the Ras-mediated cellular signaling. (H. Tanaka et al., *Jap. J. Cancer Res.*, 90:1139 (1999)). It has been shown that aigialomycin D is a CDK inhibitor. (S. Barluenga et al., *Angew. Chem., Int. Ed.*, 46(24):3951 (2006)).

Other close analogs of radicicol do inhibit HSP90. Pochonin D is a potent inhibitor of HSP90. (E. Moulin et al., *J. Am. Chem. Soc.*, 127(19):6999 (2005)). And pochonin A has been reported to be a 90 nM inhibitor of HSP90. Pochonin C was found to be an inhibitor of herpes' helicase-primase, which is an ATPase rather than a kinase. (V. Hellwig et al., *J. Nat. Prod.*, 66:829 (2003)). Although radicicol and pochonin C are structurally very similar, they have very different conformations in solution, and different biological activities. (S. Barluenga et al., *Chem. Eur. J.*, 11:4935 (2005). Thus it appears the "floppiness" of the macrocyclic may play an essential role in inhibitory differences among resorcylic acid macrolides, and in any case makes those effects difficult to predict by theoretical methods.

Some resorcylic acid macrolides had been known as kinase or phosphatase inhibitors (U.S. Pat. Nos. 5,674,892; 5,728,726; 5,731,343; and 5,795,910), or to inhibit other enzymes (U.S. Pat. No. 5,710,174 inhibiting FXIIIa catalysis of fibrin cross-linking). Resorcylic acid macrolides were also employed for other medical indications (U.S. Pat. Nos. 3,453,367; 3,965,275; 4,035,504; 4,670,249; 4,778,821; 4,902,711; and 6,635,671).

Radicicol and the pochonins are natural products; intermediates for synthesizing some of their analogues of them may be obtained by fermentation, however relying only upon those natural products or their fermentation derivatives severely limits the range of compounds. Thus a number of novel resorcylic acid macrolides have been synthesized. Many of these are zearalane and related compounds in which the macrocyclic ring contains no carbon-carbon double bond other than between carbons of the phenyl ring. (U.S. Pat. Nos. 3,373,038; 3,586,701; 3,621,036; 3,631,179; 3,687,982; 3,704,249; 3,751,431; 3,764,614; 3,810,918; 3,836,544; 3,852,307; 3,860,616; 3,901,921; 3,901,922; 3,903,115; 3,957,825; 4,042,602; 4,751,239; 4,849,447; and 2005-0256183). Syntheses have also been reported for resorcylic acid macrolides characterized by one double bond between ring carbons outside the phenyl ring. (U.S. Pat. Nos. 3,196,019; 3,551,454; 3,758,511; 3,887,583; 3,925,423; 3,954,805; and 4,088,658). Most of those are 14-member macrocycles, but syntheses have also been reported for the 12-member macrocycle analogs. (U.S. Pat. Nos. 5,710,174; 6,617,348; and 2004-0063778. and PCT publication no. WO 02/48135)

Syntheses have also been reported for radicicol-related compounds having two non-aromatic double bonds and either a halide or a 1,2-oxo group (i.e., an epoxide) on the macrocyclic ring. (U.S. Pat. Nos. 4,228,079; 5,597,846; 5,650,430; 5,977,165; 7,115,651; and Japanese patent document nos. JP 6-279279A, JP 6-298764A, JP 9-202781A, JP 10-265381A2; and JP 2000-236984). Syntheses of oximes of radicicol-related compounds are disclosed in U.S. Pat. Nos. 5,977,165; 6,239,168; 6,316,491; 6,635,662; 2001-0027208; 2004-0053990; Japanese patent document no. JP 2003-113183A2; and PCT publication no. WO 99/55689 Synthesis of cyclopropa-analogs of radicicol is disclosed in U.S. Pat. No. 7,115,651 and PCT Publication No. WO 05/061481. Syntheses of some other resorcylic acid macrolide analogs are disclosed in U.S. patent publication no. 2006-0247448 and in PCT publication no. WO 02/48135. Radicicol as well as Pochonins A and C have also been synthesized. (S. Barluenga et al., *Angew. Chemie*, 43(26):3467-3470 (2004); S. Barluenga et al., *Chemistry—A European Journal*, 11(17): 4935-4952 (Aug. 19, 2005); E. Moulin et al., et al., *Organic Letters*, 7(25):5637-5639 (Dec. 8, 2005).

U.S. Pat. No. 7,115,651 to Danishefsky et al., which is incorporated by reference herein in its entirety, describes derivatives of radicicol, including cyclopropyl analogs, and the use of these compounds as therapeutic agents.

International Publication No. WO 2008/021213 to Winssinger et al., which is incorporated by reference herein in its entirety, describes certain analogs and derivatives of radicicol and pochonins useful as inhibitors of HSP90, including pharmaceutical compositions comprising the compounds and methods for the treatment of various diseases mediated by HSP90.

International Publication No. WO 2008/150302 to Nexgenix Pharmaceuticals, which is incorporated by reference herein in its entirety, describes uses and methods for the treatment of neurofibromatosis with analogs and derivatives of radicicol and pochonins.

Despite the progress described above, chemical biologists continue to suffer from a limited ability to knock out specific kinase activity in order to deconvolute the role of specific kinases within complex signaling networks. Small molecules that can permeate cells have promise for solving this problem. And it has become increasingly apparent that the biological function of kinases is often regulated by their conformation, which is in turn dictated by their phosphorylation level and by intra- and inter-molecular associations. Small molecule inhibitors also have the potential to discriminate between different conformations of a given kinase, thus small molecules offer a means to dissect the respective functions of those conformation. Unfortunately the portfolio of known kinase inhibitors cannot yet support the full range of work to be done in parsing the roles of the various members of the kinome. This is not a merely academic pursuit, because the rationality of drug design will continue to suffer until kinase mechanisms and their selectivity is understood.

Current treatments for NF2- and NF1-associated tumors consist of surgical removal and focused-beam radiation. Neither treatment is considered optimal. Most patients with NF2 and NF1 require multiple surgical and/or focused beam radiation procedures during their lifetime. Since the tumors of NF2 most frequently lie on nerves near the brain and spinal cord, their surgical removal is not without risk. For instance, surgical removal of vestibular schwannomas typically results in complete hearing loss and frequent facial nerve damage. Focused-beam radiation also has a significant incidence of hearing loss and facial nerve damage. Accordingly, a strong need exists for safer treatment options for NF2 and associated tumors (e.g. schwannomas, meningiomas, and mesotheliomas) and NF1 and associated tumors (e.g. dermal neurofibromas, subdermal neurofibromas, plexiform neurofibromas, MPNSTs, gliomas, astrocytomas, and JMML). The present invention provides a novel method for treating NF2 and related NF2-deficient tumors and NF1 and related NF1-deficient tumors and their associated signs and symptoms by administering radicicol or its derivatives.

SUMMARY OF THE INVENTION

In one embodiment, the present invention provides a method of treating, preventing or ameliorating tumors or symptoms resulting from neurofibromatosis in a subject suffering neurofibromatosis type 2 (NF2) or a condition associated with the loss of NF2 function or neurofibromatosis type 1 (NF1) or a condition associated with the loss of NF1 function comprising administering to said subject a therapeutically effective amount of at least one compound of formula I, II, III, IV or V, or a pharmaceutically acceptable tautomer, salt, solvate, ester, and/or prodrug thereof.

In one embodiment, the present invention provides use of a compound of formula I, or a pharmaceutically acceptable tautomer, salt, solvate, ester, and/or prodrug thereof, for the manufacture of a medicament for the treatment, prevention, or amelioration of tumors or symptoms resulting from neurofibromatosis in a subject suffering neurofibromatosis type 2 (NF2) or a condition associated with the loss of NF2 function or neurofibromatosis type 1 (NF1) or a condition associated with the loss of NF1 function.

In one embodiment, the present invention provides a method of treating, preventing or ameliorating a neurodegenerative disease in a patient comprising administering to said patient a therapeutically effective amount of at least one compound of formula I, II, III, IV, or V, or a pharmaceutically acceptable tautomer, salt, solvate, ester, and/or prodrug thereof.

In one embodiment, the present invention provides use of a compound of formula I, II, III, IV, or V, or a pharmaceutically acceptable tautomer, salt, solvate, ester, and/or prodrug thereof, for the manufacture of a medicament for the treatment, prevention, or amelioration of a neurodegenerative disease, In another embodiment, the present invention provides a method of inhibiting or reducing the growth or number of NF2-deficient tumor cells or NF1-deficient tumor cells comprising contacting said NF2-deficient tumor cells or NF1-deficient tumor cells with at least one compound of formula I, II, III, IV or V, or a pharmaceutically acceptable tautomer, salt, solvate, ester, and/or prodrug thereof.

The compound of formula I has the following structure:

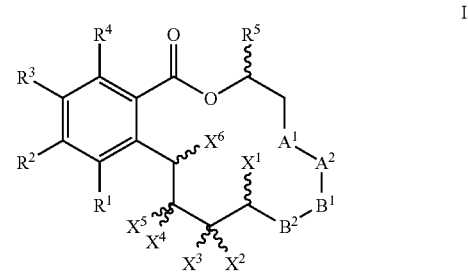

wherein:

$R^1$, $R^2$, $R^3$, $R^4$ and $R^5$ are independently hydrogen, halogen, nitro, cyano, alkyl, lower alkyl, alkenyl, alkynyl, alkylaryl, aralkyl, aryl, heteroalkyl, alkylheteroaryl, heterocyclyl, heteroaryl, OH, OR, $NH_2$, $NR_2$, SR, S(O)R, $S(O)_2R$, $—S(O)_2NR_2$, $—N(R)SO_2R$, —NC(O)R, $—NC(O)NR_2$, —NC(O)OR, —OC(O)R, —C(O)R, —C(O)OR, $—C(O)NR_2$, —OC(O)OR, or $—OC(O)NR_2$;

$A^1$ and $A^2$ together are $—CH_2—CH_2—$, —CH=CH—, —CH(OH)—CH(OH)—, —CH(OH)—CH(halogen)-, —CH(halogen)-CH(OH)—, 1,2-cyclopropadiyl, or 1,2-oxirane;

$B^1$ and $B^2$ together are $—CH_2—CH_2—$ or $B_1$ and $B_2$ together represent a covalent bond;

$X^1$ is hydrogen, halogen, OH, OR, $NH_2$, $NR_2$, NH—OR, SR, S(O)R, $S(O)_2R$, $—N—O—(CH_2)_n—CO_2—R$; or $X^1$ together with $X^2$ or $X^3$ represents a covalent bond;

$X^2$ and $X^3$ are both hydrogen, or one of $X^2$ and $X^3$ is hydrogen and the other together with $X^1$ represents a covalent bond;

$X^4$ and $X^5$ together are =O, =S, =N—OR, =N—O—$(CH_2)_n$C(O)OR, =N—O—$(CH_2)_n$CONR$_2$, =N—N—S(O)R or =N—N—S(O)$_2$R; or one of $X^4$ and $X^5$ is hydrogen and the other is OH, OR, OC(O)R, OC(O)OR or OC(O)NR$_2$; or one of $X^4$ and $X^5$ together with $X^6$ represents a covalent bond and the other of $X^4$ and $X^5$ is OH, OR, OC(O)R, OC(O)OR, or OC(O)NR$_2$;

$X^6$ is hydrogen or $X^6$ together with one of $X^4$ and $X^5$ represents a covalent bond;

each R is independently the same or different, and is hydrogen, alkyl, lower alkyl, acyl including acetyl and trifluoroacetyl, aryl, alkaryl, arylalkyl including benzyl, heteroalkyl, heteroaryl, heterocyclyl, or a protecting group; or two R on the same nitrogen are taken together with the nitrogen to form a 5-8 membered heterocyclic or heteroaryl ring; and n is 0, 1, 2 or 3.

The compound of formula II has the following structure:

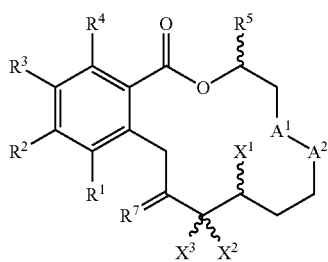

II wherein, $R^7$ is =O, =S, =N—O—$(CH_2)_n$—C(O)OR, =N—O—$(CH_2)_n$OC(O)NR$_2$, =N—NR$_2$, =N—N—S(O)R or =N—N—S(O)$_2$R.

The compound of formula III has the following structure:

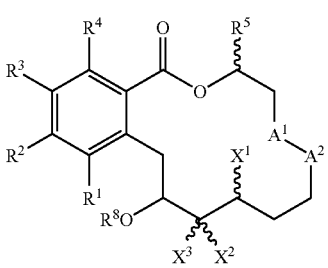

III wherein $R^8$ is hydrogen, alkyl, arylalkyl, acyl or a protecting group.

The compound of formula IV has the following structure:

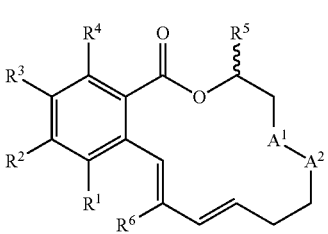

IV wherein $R^6$ is hydrogen, OR, or NR$_2$.

The compound of formula V has the following structure:

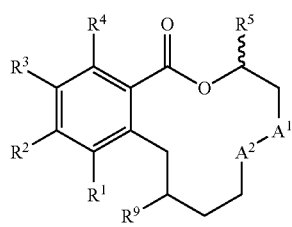

V wherein $R^9$ is $(CH_2)_n$C(O)OR, or —$(CH_2)$—C(O)NR$_2$; and n is 0, 1, 2 or 3.

Novel analogs of the pochonin macrolides of formulae I, I', II, II', III, III', IV and V, tautomers thereof, pharmaceutically acceptable salts, solvates, esters or prodrugs thereof, and pharmaceutical compositions comprising the compounds for the treatment of kinase-mediated or HSP90-mediated disorders are provided. Also presented are methods for the treatment of kinase-mediated or HSP90-mediated disorders using the compounds. In another embodiment, the invention provides the use of the compounds of formulae Ia, Ia', IIa, IIa', IIIa, IVa and Va, in the treatment of a kinase-mediated or HSP90-mediated disorder or in the manufacture of a medicament for the treatment of a kinase-mediated or HSP90-mediated disorder in a patient. The compounds of the invention are active as kinase inhibitors and inhibitors of HSP90. In addition, improved processes for the preparation of the compounds are provided.

In one embodiment, the invention provides a compound of formula Ia or Ia', or a tautomer thereof, or a pharmaceutically acceptable salt, solvate, ester or prodrug thereof:

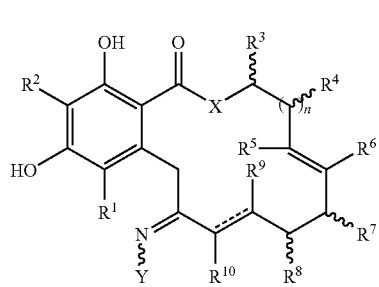

Ia, Ia' wherein:

X is O, S or NR;

Y is —OR, —O—$(CH_2)_m$COOR, —O—$(CH_2)_m$CON(R)$_2$, —N(R)$_2$, —N(R)SOR or —N(R)SO$_2$R, wherein the groups bound to the nitrogen atom may be in Z- or E-configuration;

$R^1$ and $R^2$ are independently hydrogen, halogen, OR, N(R)$_2$, SR, azido, nitro, cyano, aliphatic, aryl, alkylaryl, arylalkyl, heterocyclyl, heteroaryl, —S(O)R, —S(O)$_2$R, —SO$_2$N(R)$_2$, —N(R)SO$_2$R, —N(CO)R, —N(CO)N(R)$_2$, —N(CO)OR, —O(CO)R, —(CO)R, —(CO)OR, —(CO)N(R)$_2$, —O(CO)OR, or —O(CO)N(R)$_2$;

$R^3$, $R^4$, $R^5$, $R^6$, $R^7$, $R^8$, $R^9$ and $R^{10}$ are independently hydrogen, halogen, azido, nitro, cyano, aliphatic, alkylaryl, aralkyl, aryl, heteroalkyl, alkylheteroaryl, heterocyclyl, heteroaryl, OR, N(R)$_2$, SR, —O(CH$_2$)$_m$N(R)C(O)(CH$_2$)$_p$R, —O(CH$_2$)$_m$ OC(O)(CH$_2$)$_p$R, —O(CH$_2$)$_m$C(O)(CH$_2$)$_p$N(R)$_2$, —O(CH$_2$)$_m$C(O)(CH$_2$)$_p$OR, —O(CH$_2$)$_m$N(R)C(O)(CH$_2$)$_p$OR, —O(CH$_2$)$_m$N(R)C(O)(CH$_2$)$_p$N(R)$_2$, —O(CH$_2$)$_m$OC(O)(CH$_2$)$_p$OR, —O(CH$_2$)$_m$OC(O)(CH$_2$)$_p$N(R)$_2$, —NR(CH$_2$)$_m$N(R)C(O)(CH$_2$)$_p$R, —NR(CH$_2$)$_m$OC(O)(CH$_2$)$_p$R, —NR(CH$_2$)$_m$C(O)(CH$_2$)$_p$N(R)$_2$, —NR(CH$_2$)$_m$C(O)(CH$_2$)$_p$OR, —NR(CH$_2$)$_m$N(R)C(O)(CH$_2$)$_p$OR, —NR(CH$_2$)$_m$N(R)C(O)(CH$_2$)$_p$N(R)$_2$, —NR(CH$_2$)$_m$OC(O)(CH$_2$)$_p$OR, —NR(CH$_2$)$_m$OC(O)(CH$_2$)$_p$N(R)$_2$, —(CH$_2$)$_m$N(R)C(O)CH$_2$)$_p$R, —(CH$_2$)$_m$ OC(O)(CH$_2$)$_p$R, —(CH$_2$)$_m$C(O)(CH$_2$)$_p$N(R)$_2$, —(CH$_2$)$_m$C(O)(CH$_2$)$_p$OR, —(CH$_2$)$_m$N(R)C(O)(CH$_2$)$_p$OR, —(CH$_2$)$_m$N(R)C(O)(CH$_2$)$_p$N(R)$_2$, —(CH$_2$)$_m$OC(O)(CH$_2$)$_p$OR, —(CH$_2$)$_m$OC(O)(CH$_2$)$_p$N(R)$_2$, —(CH$_2$)$_m$N$_3$, —O(CH$_2$)$_m$ N$_3$ —(CH$_2$)$_m$N(R)$_2$, —(CH$_2$)$_m$OR, —(CH$_2$)$_m$S(O)(CH$_2$)$_p$ R, —(CH$_2$)$_m$S(O)$_2$(CH$_2$)$_p$R, —(CH$_2$)$_m$SO$_2$(CH$_2$)$_p$ N(R)$_2$, or —(CH$_2$)$_m$N(R)SO$_2$(CH$_2$)$_p$R; and each R is independently R$^{11}$, hydrogen, aliphatic, amino, azido, cyano, nitro, alkylamino, dialkylamino, OH, alkoxy, carbonylamino, aminocarbonyl, alkoxycarbonyl, carbonyloxy, carboxy, acyl, aryl, alkaryl, arylalkyl including benzyl, heteroalkyl, heteroaryl, heterocyclyl, or a protecting group; or two R on the same nitrogen are taken together with the nitrogen to form a 5-8 membered heterocyclic or heteroaryl ring; wherein where a group contains more than one R substituent; wherein R is optionally substituted, and each R can be the same or different;

R$^{11}$ is the group

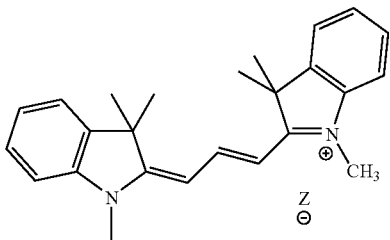

where Z is an inorganic or organic counterion;

n is 0, 1 or 2;

m and p are independently 0, 1, 2, 3, 4 or 5; and the dashed lines indicate either a single or a double bond, where the valence requirements are fulfilled by additional hydrogen atoms;

wherein in formula Ia', when n is 1, and X is O and a double bond is present between the carbon atoms bearing R$^9$ and R$^{10}$, then at least one of R$^5$, R$^6$, R$^7$, R$^8$, R$^9$ or R$^{10}$ is not hydrogen; and wherein in formula Ia', when n is 1 and X is O and the bond between the carbon atoms bearing R$^9$ and R$^{10}$ is a single bond, then at least one of R$^5$, R$^6$, R$^7$ or R$^8$ is not hydrogen.

In one embodiment of formulae Ia or Ia', R$^1$ and R$^2$ are independently hydrogen or halogen. In another embodiment of formulae Ia or Ia', X is O or NR. In still another embodiment of formulae Ia or Ia', X is O, S or NR; Y is —OR, —O—(CH$_2$)$_m$COOR, or —O—(CH$_2$)$_m$CON(R)$_2$.

In another embodiment, a compound of formula IIa or IIa', or a tautomer, pharmaceutically acceptable salt, solvate, ester or prodrug thereof, is provided:

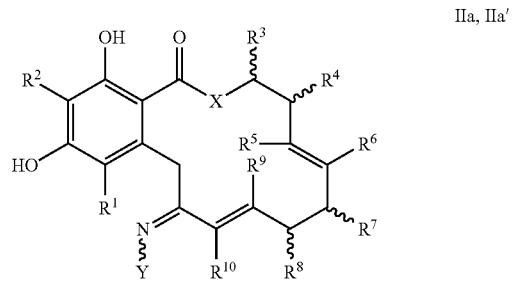

IIa, IIa' where the variables X, Y, R$^1$, R$^2$, R$^3$, R$^4$, R$^5$, R$^6$, R$^7$, R$^8$, R$^9$, R$^{10}$, R, m and p are as defined for formula Ia; and wherein in formula IIa', when X is O, then at least one of R$^5$, R$^6$, R$^7$, R$^8$, R$^9$ or R$^{10}$ is not hydrogen.

In one embodiment of formulae IIa or IIa', R$^1$ and R$^2$ are independently hydrogen or halogen. In another embodiment, R$^3$ and are R$^4$ are independently alkyl or hydrogen. In still another embodiment of formulae IIa or IIa', variables R$^9$ and R$^{10}$ are independently hydrogen or aliphatic.

In another embodiment of formulae IIa or IIa', X is O; Y is —O—(CH$_2$)$_m$COOR or —O—(CH$_2$)$_m$CON(R)$_2$, wherein the groups bound to the nitrogen atom may be in the Z- or E-configuration; R$^1$, R$^2$ are independently hydrogen or halogen; and R$^9$ and R$^{10}$ are independently hydrogen or aliphatic.

In another embodiment, the invention provides a compound of formulae Ma or or a tautomer, pharmaceutically acceptable salt, solvate, ester or prodrug thereof:

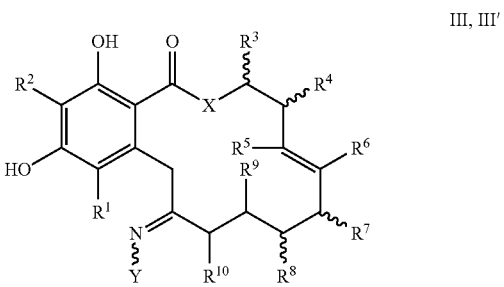

III, III' where the variables X, Y, R$^1$, R$^2$, R$^3$, R$^4$, R$^5$, R$^6$, R$^7$, R$^8$, R$^9$, R$^{10}$, R, m and p are as defined for formula Ia, and wherein in formula IIIa', when X is O, then at least one of R$^5$, R$^6$, R$^7$ or R$^8$ is not hydrogen.

In one embodiment of formulae IIIa or IIIa', X is O or NR. In another embodiment, Y is —O—(CH$_2$)$_m$COOR or —O—(CH$_2$)$_m$CON(R)$_2$, wherein the groups bound to the nitrogen atom may be in the Z- or E-configuration. In still another embodiment of formulae Ma or IIIa', X is O, Y is —O—(CH$_2$)$_m$ COOR or —O—(CH$_2$)$_m$CON(R)$_2$, wherein the groups bound to the nitrogen atom may be in the Z- or E-configuration; R$^1$ and R$^2$ are independently hydrogen or halogen; and R$^9$ and R$^{19}$ are hydrogen.

In another aspect, the invention provides a compound of formula IVa, or a tautomer thereof, or a pharmaceutically acceptable salt, solvate, ester or prodrug thereof:

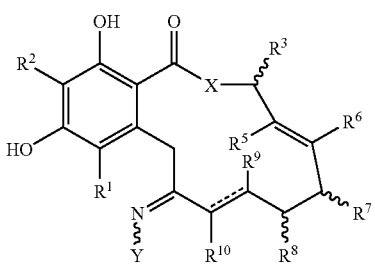

IV where the variables X, Y, $R^1$, $R^2$, $R^3$, $R^5$, $R^6$, $R^7$, $R^8$, $R^9$, $R^{10}$, R, m and p are as defined for formula I above, and the dashed lines represents a single or double bond.

In yet another aspect, the invention provides a compound of formula Va, or a tautomer thereof, or a pharmaceutically acceptable salt, solvate, ester or prodrug thereof:

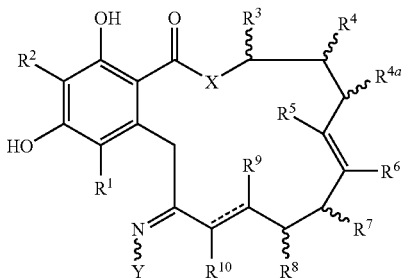

V where the variables X, Y, $R^1$, $R^2$, $R^3$, $R^4$, $R^5$, $R^6$, $R^7$, $R^8$, $R^9$, $R^{10}$, R, m and p are as defined for formula Ia; $R^{4a}$ has the same definition as $R^4$ in formula I above; and the dashed lines represents a single or double bond.

In various other embodiments, the invention provides the macrocyclic compounds shown in Table 1a below, or tautomers thereof; or pharmaceutically acceptable salts, solvates, esters or prodrugs thereof.

Pharmaceutical compositions comprising an effective HSP 90-inhibiting amount of a compound of formulae Ia, Ia', IIa, IIa', IIIa, IIIa', IVa or Va, in combination with a pharmaceutically acceptable carrier are provided for the treatment of a disorder mediated by HSP 90. Also provided are pharmaceutical composition comprising an effective kinase-inhibiting amount of a compound of the invention, in combination with a pharmaceutically acceptable carrier. In some embodiments, the pharmaceutical compositions comprise particles that are less than about 2 microns average particle size. In other embodiments, the invention provides pharmaceutical compositions wherein the carrier is suitable for oral, parenteral, intravenous, inhalation, topical, or intradermal administration. In addition, pharmaceutical compositions comprising the compounds of the invention in combination with other active agents and pharmaceutically acceptable carriers are provided.

In another aspect of the invention, a method of treating a patient with a disease comprising administering to the patient an effective amount of a compound of formulae Ia, Ia', IIa, IIa', IIIa, IVa or Va is provided, wherein the disease may be an autoimmune disease, an inflammatory disease, a neurological or neurodegenerative disease, cancer, a cardiovascular disease, an allergy, asthma, or a hormone-related disease. In one embodiment, the patient is a human patient. In another embodiment, use of the compounds in the manufacture of a medicament for the treatment of the diseases is provided.

In one embodiment, the disease to be treated by a compound of formulae Ia, Ia', IIa, IIa', IIIa, IIIa', IVa or Va is cancer. The cancers that may be treated with the compounds include, but are not limited to, a solid tumor, blood borne tumor, breast, ovary, cervix, prostate, testis, genitourinary tract, esophagus, larynx, glioblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity, pharynx, lip, tongue, mouth, pharynx, small intestine, colon-rectum, large intestine, rectum, brain and central nervous system, or leukemia.

In another embodiment, the method provided is for treating an inflammatory disease with a compound of formulae Ia, Ia', IIa, IIa', IVa or Va. In various embodiments, the inflammatory disease may be excessive or abnormal stimulation of endothelial cells, atherosclerosis, vascular malfunctions, abnormal wound healing, inflammatory and immune disorders, Bechet's disease, gout or gouty arthritis, abnormal angiogenesis accompanying rheumatoid arthritis, skin diseases, psoriasis, diabetic retinopathy, retinopathy of prematurity, retrolental fibroplasia, macular degeneration, corneal graft rejection, neovascular glaucoma or Osler Weber syndrome.

BRIEF DESCRIPTION OF THE DRAWINGS

FIG. 1A shows graphs of Western blots demonstrating NXD30001 down-regulates HSP90 client proteins and upregulates HSP70 in NF2-deficient mouse and human cells, while

FIG. 3 shows the IC50 of radicicol derivatives, namely NXD30001, NXD30002, and NXD30017, and the IC50 of 17AAG on cell proliferation of NF1 and NF2 cells.

DETAILED DESCRIPTION OF THE INVENTION

Figure 1A:
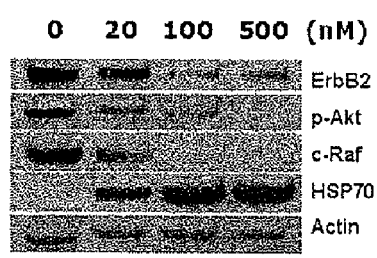
Figure 1A:
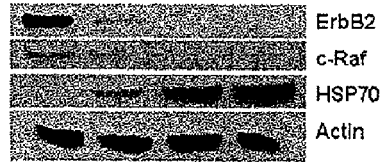
Figure 1A:

Tumors in NF2 and NF1 patients are unique in that they are slow growing tumors. Both NF2 and NF1 tumors have mutations or loss of heterozygosity in tumor suppressor genes although the tumor suppressor genes are different—NF2 or NF1 genes, respectively. The inventors of the present invention have discovered that inhibitors of HSP90 potently blocked the proliferation of NF2-deficient and NF1-deficient tumor cells and also delay the growth of NF2-deficient and NF1-deficient tumors in mice. Merlin regulates the abundance and turnover of multiple cell surface receptors and interacts with multiple pathways. Many of these proteins are client proteins of HSP90. For instance, ErbB2 and other receptor tyrosine kinases, AKT, and Raf are well-established client proteins of HSP90. In addition, aberrant activation of the PI3K/AKT pathway has been found in human schwannomas from NF2 patients (as compared to normal nerves), in human NF2-deficient tumor xenografts (e.g. meningiomas and mesotheliomas), and in mouse Nf2-deficient Schwann cell tumors (reference is made to a PCT/US2007/70366 entitled "Treatment of Neurofibromatosis with Inhibitors of a Signal Transduction Pathway," filed on Jun. 4, 2007, which is incorporated in its entirety by reference). Neurofibromin is a negative regulator of Ras. Raf, the direct downstream effector of Ras, is a well-known client protein of HSP90. Neurofibromin has also been shown to regulate AKT. Therefore, a compound that inhibits HSP90 will likely be able to reduce the amount of AKT and other HSP90 client proteins such as ErbB2, IGF-IR, and Raf in the NF2-deficient cells or NF1-deficient cells. Reduction of the amount or activity of these proteins may be useful to reduce or stabilize the proliferation of NF2-deficient cells or NF1-deficient cells or to cause apoptosis of NF2-deficient cells or NF1-deficient cells. A compound that inhibits the activity of HSP90 is a compound that directly binds to the HSP90 protein or modifies the HSP90 protein post-translationally or regulate the transcription of HSP proteins such as HSP70 and HSP27 (Zaarur et al., 2006, Cancer Res. 66(3):1783-1791). For instance, HSP90 can be acetylated and inactivated by histone deacetylase (HDAC) inhibitors (Kovacs et al., 2005, Mol. Cell. 18(5):601-607; Fuino et al., 2003, Mol. Cancer. Ther. 2:971-984; Aoyagi and Archer, 2005, *Trends Cell. Biol.* 15(11):565-567). For this reason, HSP90 inhibitory compounds are determined to be useful for the treatment of NF2-deficient tumors and NF1-deficient tumors which may not respond well to traditional chemotherapy and other cancer therapies which target fast growing and heterogeneous cancer cells.

NF2—Associated Tumors

Patients with neurofibromatosis type-2 (NF2) have NF2-deficient tumors. This genetic characteristic, i.e., inactivation of the NF2 gene, differentiates tumors found in NF2 patients from genetically heterogeneous tumors such as breast and colon cancer tumors. For instance, NF2 patients have NF2-deficient meningiomas whereas some non-NF2-deficient meningiomas may contain mutations in many different oncogenes or tumor suppressor genes.

As used herein, "NF2-deficient tumors" refer to tumors which contain a non-functioning NF2 gene. A non-functioning NF2 gene can be the result of a one or more insertion or deletion mutations within the NF2 gene, for instance, missense or nonsense mutations, mutations in the promoter or enhancer or introns that lead to no/low expression of the NF2 gene, or the deletion of the entire NF2 gene. NF2-deficient tumors are found in mesotheliomas and in patients with NF2, and include schwannomas, meningiomas, and other tumors associated with the nervous system. NF2-deficient tumors are also found in all patients with sporadic schwannomas and in 50%-70% of patients with meningiomas.

The presence of NF2-deficient bilateral vestibular schwannomas, i.e., Schwann cell tumors, is a hallmark of NF2. The methods of the present invention can be used to inhibit the growth and/or kill NF2-deficient schwannoma cells, including those associated with vestibular schwannomas, spinal cord and other peripheral nerve schwannomas and sporadic schwannomas.

Merlin and Signaling Proteins and Pathways

As used herein, "NF2-deficient tumors" refer to tumors which contain a non-functioning NF2 gene. Merlin interacts with or regulates, but is not limited to, proteins and pathways such as Paxillin/Integrin-β1/ErbB2, EGFR, Patched/Smoothened, HRS, CD44, E-Cadherin, Fat, EBP50/NHE-RF/PDGFR, Wingless, Notch, Rac-PAK, PI3K-AKT, Ras-Raf-Mek-Erk2, Hippo pathways, and downstream proteins thereof. FIG. 1 is a schematic of involvement of Merlin with multiple cell surface proteins and signaling pathways. Targeting multiple proteins or pathways may be necessary for treating NF2.

NF1—Associated Tumors

Patients with neurofibromatosis type-1 (NF1) have NF1-deficient tumors. This genetic characteristic, i.e., inactivation of the NF1 gene, differentiates tumors found in NF1 patients from genetically heterogeneous tumors such as breast and colon cancer tumors. For instance, tumors found in NF1 patients all have NF1 gene mutations whereas patients with other cancers have mutations in different genes or overexpression of different genes.

As used herein, "NF1-deficient tumors" refer to tumors which contain a non-functioning NF1 gene. A non-functioning NF1 gene can be the result of one or more insertion or deletion mutations within the NF1 gene, for instance, missense or nonsense mutations, mutations in the promoter or enhancer or introns that lead to no/low expression of the NF1 gene, or the deletion of the entire NF1 gene. NF1-deficient tumors are found in patients with NF1, and include dermal, subdermal, plexiform neurofibromas, and MPNST and other tumors associated with the nervous system. NF1-deficiency also predisposes individuals to a rare form of leukemia, JMML.

NF1 diagnosis is confirmed by fulfilling NIH clinical criteria or by finding an NF1 mutation with mutational analysis. The methods of the present invention can be used to inhibit the growth and/or kill NF1-deficient tumors, including dermal, subdermal, plexiform neurofibromas, MPNST, gliomas, astrocytomas, pheochromocytomas and JMML.

Radicicol and Derivatives Thereof

The present invention provides the use of radicicol or its derivatives based on the resorcylic acid lactones, preferably compounds of formula I, II, III, IV or V, as HSP90 inhibitors for the treatment, prevention, or amelioration of tumors or symptoms resulted from neurofibromatosis. Also provided are compositions comprising the compounds and processes for the preparation of the compounds.

In one embodiment of the present invention, the compound of formula I has the following structure:

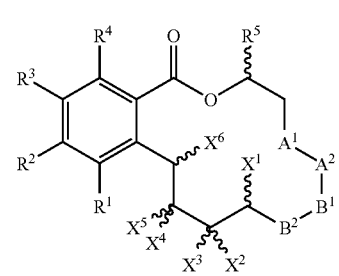

I wherein:

$R^1$, $R^2$, $R^3$, $R^4$ and $R^5$ are independently hydrogen, halogen, nitro, cyano, alkyl, lower alkyl, alkenyl, alkynyl, alkylaryl, aralkyl, aryl, heteroalkyl, alkylheteroaryl, heteroaryl, heterocyclyl, heteroaryl, OH, OR, $NH_2$, $NR_2$, SR, S(O)R, $S(O)_2R$, $—S(O)_2NR_2$, $—N(R)SO_2R$, $—NC(O)R$, $—NC(O)NR^2$, $—NC(O)OR$, $—OC(O)R$, $—C(O)R$, $—C(O)OR$, $—C(O)NR_2$, $—OC(O)OR$, or $—OC(O)NR_2$; or $R^1$, $R^2$, $R^3$, and $R^5$ are independently hydrogen, halogen, nitro, cyano, alkyl, lower alkyl, alkenyl, alkynyl, alkylaryl, aralkyl, aryl, heteroalkyl, alkylheteroaryl, heteroaryl, heterocyclyl, heteroaryl, OH, OR, $NH_2$, $NR_2$, SR, S(O)R, $S(O)_2R$, $—S(O)_2NR_2$, $—N(R)SO_2R$, $—NC(O)R$, —NC(O)NR$_2$, —NC(O)OR, —OC(O)R, —C(O)R, —C(O)OR, —C(O)NR$_2$, —OC(O)OR, or —OC(O)NR$_2$, and R$^4$ has the structure of formula Ia:

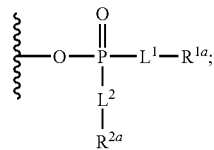

L$^1$ and L$^2$ are each independently a covalent bond, —O—, or —NR$^{3a}$—;

R$^{1a}$ and R$^{2a}$ are each independently H, alkyl, cyclylalkyl, heteroaryl, heterocyclyl, alkenyl, alkynyl, arylalkyl, heteroarylalkyl, heterocyclylalkyl, -alkylene-C(O)—O—R$^{4a}$, —(alkylene)-C(O)—O—R$^{4a}$, -alkylene-O—C(O)—O—R$^{4a}$, or -(alkylene)-O—C(O)—O—R$^{4a}$; and R$^{1a}$ and R$^{4a}$ are each independently H, alkyl, cyclylalkyl, heterocyclyl, heteroaryl, alkenyl, alkynyl, arylalkyl, or heterocyclylalkyl;

A$^1$ and A$^2$ together are —CH$_2$—CH$_2$—, —CH=CH—, —CH(OH)—CH(OH)—, —CH(OH)—CH(halogen)-, —CH(halogen)-CH(OH)—, 1,2-cyclopropadiyl, or 1,2-oxirane;

B$^1$ and B$^2$ together are —CH$_2$—CH$_2$— or B$_1$ and B$_2$ together represent a covalent bond;

X$^1$ is hydrogen, halogen, OH, OR, NH$_2$, NR$_2$, NH—OR, SR, S(O)R, S(O)$_2$R, —N—O—(CH$_2$)$_n$—CO$_2$—R; or X$^1$ together with X$^2$ or X$^3$ represents a covalent bond;

X$^2$ and X$^3$ are both hydrogen, or one of X$^2$ and X$^3$ is hydrogen and the other together with X$^1$ represents a covalent bond;

X$^4$ and X$^5$ together are =O, =S, =N—OR, =N—O—(CH$_2$)$_n$C(O)OR, =N—O—(CH$_2$)—CONR$_2$, =N—NR$_2$, =N—N—S(O)R or =N—N—S(O)$_2$R; or one of X$^4$ and X$^5$ is hydrogen and the other is OH, OR, OC(O)R, OC(O)OR or OC(O)NR$_2$; or one of X$^4$ and X$^5$ together with X$^6$ represents a covalent bond and the other of X$^4$ and X$^5$ is OH, OR, OC(O)R, OC(O)OR, or OC(O)NR$_2$;

X$^6$ is hydrogen or X$^6$ together with one of X$^4$ and X$^5$ represents a covalent bond;

each R is independently the same or different, and is hydrogen, alkyl, lower alkyl, acyl including acetyl and trifluoroacetyl, aryl, alkaryl, arylalkyl including benzyl, heteroalkyl, heteroaryl, heterocyclyl, or a protecting group; or two R on the same nitrogen are taken together with the nitrogen to form a 5-8 membered heterocyclic or heteroaryl ring; and n is 0, 1, 2 or 3.

In one preferred embodiment, R$^4$ has the structure of formula Ia, which may increase the water solubility and/or bioavailability of the compound of formula I.

In another embodiment of the present invention, the compound of formula I has the structure of formula II:

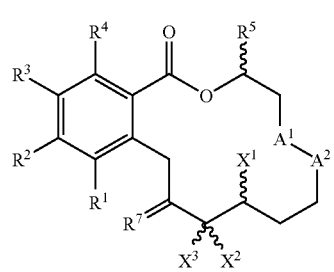

wherein, R$^7$ is =O, =S, =N—OR, =N—O—(CH$_2$)$_n$—C(O)OR, =N—O—(CH$_2$)$_n$—C(O)NR$_2$, =N—NR$_2$, =N—N—S(O)R or =N—N—S(O)$_2$R.

In one embodiment of the compound of formula II, R$^1$ is H, halogen or heterocyclyl.

In another embodiment of the compound of formula II, R$^5$ is hydrogen, alkyl, lower alkyl, aryl, heteroaryl or arylalkyl.

In another embodiment of the compound of formula II, A$^1$ and A$^2$ together are —CH=CH—.

In another embodiment of the compound of formula II, A$^1$ and A$^2$ together are —CH(OH)—CH(OH)—, —CH(OH)—CH(halogen)- or —CH(halogen)-CH(OH)—.

In another embodiment of the compound of formula II, A$^1$ and A$^2$ together are 1,2-oxirane.

In another embodiment of the compound of formula II, R$^1$ is H, Cl or heterocyclyl; R$^2$ and R$^4$ are independently OH or OR; R$^5$ is hydrogen, alkyl, aryl or aralkyl; A$^1$ and A$^2$ together are —CH=CH— or —C(OH)—C(OH)—; X$^1$ is hydrogen, halogen or NH—OR; and R$^7$ is =O, =S, =N—OR, =N—O—(CH$_2$)$_n$C(O)OR, =N—O—(CH$_2$)—C(O)NR$_2$, =N—NR$_2$, =N—N—S(O)R, =N—N—S(O)$_2$R. It is preferable that R$^7$ is =O. It is also preferable that R$_7$ is =N—OR, =N—O—(CH$_2$)$_n$C(O)OR, or =N—O—(CH$_2$)$_n$C(O)NR$_2$.

In another embodiment of the compound of formula II, R$^1$ is H, Cl or heterocyclyl; R$^2$ and R$^4$ are independently OH or OR; R$^5$ is hydrogen, alkyl, aryl or aralkyl; A$^1$ and A$^2$ together are 1,2-oxirane; X$^1$ is hydrogen, halogen or NH—OR; and R$^7$ is =O, =S, =N—OR, =N—O—(CH$_2$)$_n$C(O)OR, =N—O—(CH$_2$)$_n$C(O)NR$_2$, =N—NR$_2$, =N—N—S(O)R, =N—N—S(O)$_2$R.

In another embodiment of the compound of formula II, R$^1$ is H, Cl or heterocyclyl; R$^2$ and R$^4$ are independently OH or OR; R$^5$ is hydrogen, alkyl, aryl or aralkyl; A$^1$ and A$^2$ together are —CH=CH— or —C(OH)—C(OH)—; X$^1$ together with X$^2$ represent a bond; and R$^7$ is =O, =S, =N—OR, =N—O—(CH$_2$)$_n$C(O)OR, =N—O—(CH$_2$)$_n$C(O)NR$_2$, =N—NR$_2$, =N—N—S(O)R, =N—N—S(O)$_2$R. Preferably, R$^1$ is H or Cl; R$^5$ is hydrogen, methyl, propyl, isopropyl or phenyl; and R$^7$ is =N—OR, =N—O—(CH$_2$)$_n$C(O)OR, or =N—O—(CH$_2$)$_n$C(O)NR$_2$ with R$^1$ is Cl and R$^5$ is hydrogen; or R$^7$ is =N—OR, =N—O—(CH$_2$)—C(O)OR, or =N—O—(CH$_2$)$_n$C(O)NR$_2$, and n is 1; or R$^5$ is hydrogen and R$^7$ is =N—O—(CH$_2$)$_n$C(O)OR, or =N—O—(CH$_2$)$_n$C(O)NR$_2$; or R$^5$ is hydrogen and R$^7$ is =N—OR more preferable.

In another embodiment of the compound of formula II, R$^1$ is H, Cl or heterocyclyl; R$^2$ and R$^4$ are independently OH or OR; R$^5$ is hydrogen, alkyl, aryl or aralkyl; A$^1$ and A$^2$ together are 1,2-oxirane; X$^1$ together with X$^2$ represent a bond; and R$^7$ is =O, =S, =N—OR, =N—O—(CH$_2$)$_n$C(O)OR, =N—O—(CH$_2$)$_n$C(O)NR$_2$, =N—NR$_2$, =N—N—S(O)R, =N—N—S(O)$_2$R. It is preferred that R$_7$ is =O. It is also preferred that R$_7$ is =N—OR, =N—O—(CH$_2$)$_n$C(O)OR, or =N—O—(CH$_2$)$_n$C(O)NR$_2$.

In another embodiment of the present invention, the compound of formula I has the structure of formula III:

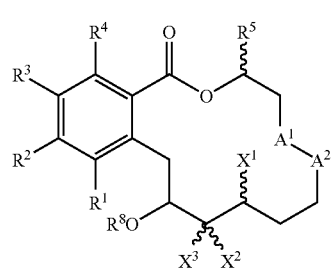

wherein R⁸ is hydrogen, alkyl, arylalkyl, acyl or a protecting group.

In one embodiment of the compound of formula III, R is hydrogen or acyl; and R₁ is H, halogen or heterocyclyl.

In another embodiment of the compound of formula III, R⁵ is hydrogen, alkyl, lower alkyl, aryl, heteroaryl or arylalkyl.

In another embodiment of the compound of formula III, X¹ together with X² represent a covalent bond.

In another embodiment of the compound of formula III, wherein X¹ is hydrogen, halogen, NH—OR NH—O—(CH₂)ₙC(O)OR, or NH—O—(CH₂)ₙC(O)NR₂.

In another embodiment of the compound of formula III, A¹ and A² together are —CH=CH—.

In another embodiment of the compound of formula III, A¹ and A² together are —CH(OH)—CH(OH)—, —CH(OH)—CH(halogen)- or —CH(halogen)-CH(OH)—.

In another embodiment of the compound of formula III, A₁ and A₂ together are 1,2-oxirane.

In another embodiment of the present invention, the compound of formula I has the structure of formula IV:

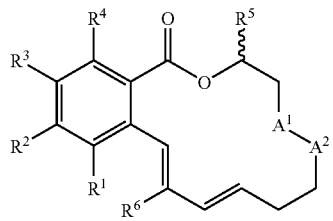

IV wherein R⁶ is hydrogen, OR, or NR₂.

In one embodiment of the compound of formula IV, R is hydrogen or acyl.

In another embodiment of the compound of formula IV, R¹ is H, halogen or heterocyclyl.

In another embodiment of the compound of formula IV, R⁵ is hydrogen, alkyl, lower alkyl, aryl, heteroaryl or arylalkyl.

In another embodiment of the compound of formula IV, A¹ and A² together are —CH=CH—.

In another embodiment of the compound of formula IV, A¹ and A² together are —CH(OH)—CH(OH)—, —CH(OH)—CH(halogen)- or —CH(halogen)-CH(OH)—.

In another embodiment of the compound of formula IV, A¹ and A² together are 1,2-oxirane.

In another embodiment of the present invention, the compound of formula I has the structure of formula V:

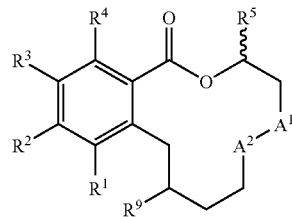

V wherein R⁹ is (CH₂)ₙC(O)OR, or —(CH₂)ₙC(O)NR₂; and n is 0, 1, 2 or 3.

In one embodiment of the compound of formula V, R⁶ is —CH₂C(O)N(Me)OMe.

In another embodiment of the compound of formula V, R¹ is H, halogen or heterocyclyl.

In another embodiment of the compound of formula V, R⁵ is hydrogen, alkyl, lower alkyl, aryl, heteroaryl or arylalkyl.

In another embodiment of the compound of formula V, A¹ and A² together are —CH=CH—.

In another embodiment of the compound of formula V, A¹ and A² together are —CH(OH)—CH(OH)—, —CH(OH)—CH(halogen)- or —CH(halogen)-CH(OH)—.

In another embodiment of the compound of formula V, A¹ and A² together are 1,2-oxirane.

It should be understood that each of the R group described above can be independently the same or different. For example, —NR₂ can be —N(Rˣ)₂, —N(Rʸ)₂, or —NRˣRʸ.

In specific embodiments of the present invention, the compounds presented in Table 1 or a pharmaceutically acceptable tautomer, salt, solvate, ester, and/or prodrug thereof are provided:

TABLE 1

| Compound Designation | Structure |
| --- | --- |
| (R)-2-85e (Ex. 134-I) | 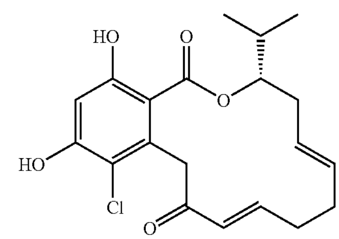 |
| (R)-2-85f | 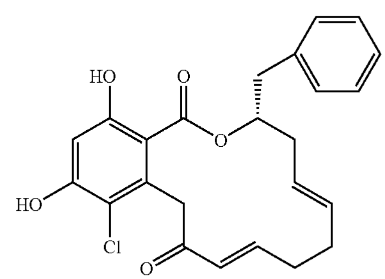 |
| (S)-2-85 (Ex. 134-F) | 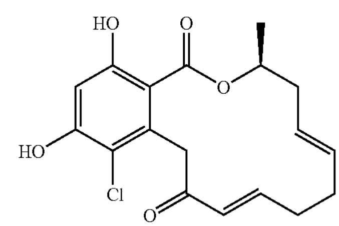 |
| (R)-2-85a (Ex. 134-G) | 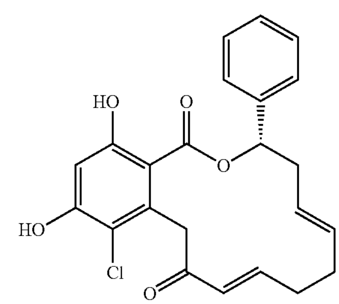 |

TABLE 1-continued

| Compound Designation | Structure |
|---|---|
| (S)-2-85a (Ex. 134-H) | 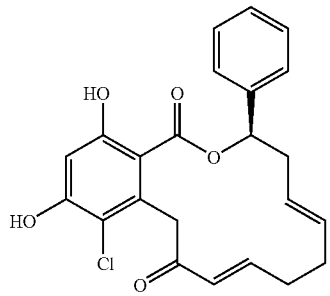 |
| (S)-145a | 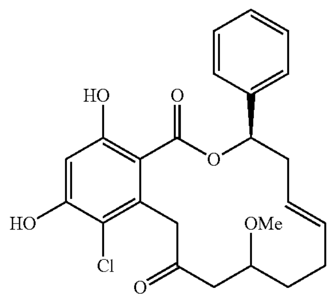 |
| (R)-2-103d (Ex. 134-N) | 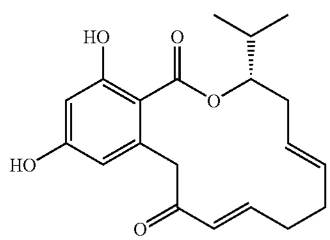 |
| (R)-2-103a (Ex. 134-L) | 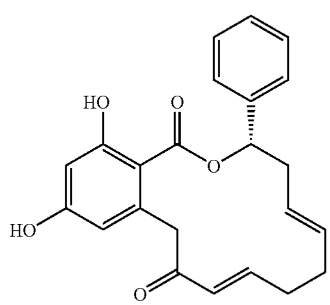 |
| (S)-2-103a (Ex. 134 M) | 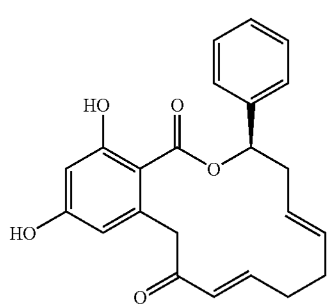 |
| (R)-2-103e (Ex. 134-O) | |
| (S)-2-103 | |
| (R)-2-103f | |
| 2-121g | |
| d-2-121g | |

TABLE 1-continued
| Compound Designation | Structure |
|---|---|
| (S)-d-2-121 (Ex. 134-A) | 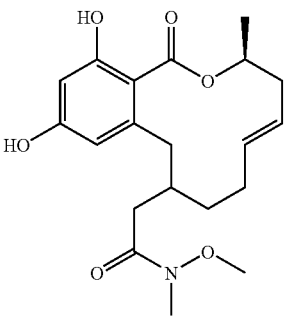 |
| (R)-d-2-121d (Ex. 134-D) | 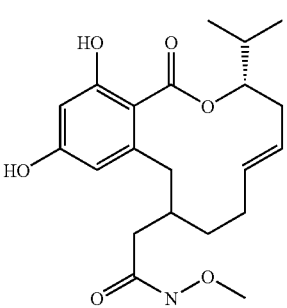 |
| (R)-d-2-121a (Ex. 134-B) | 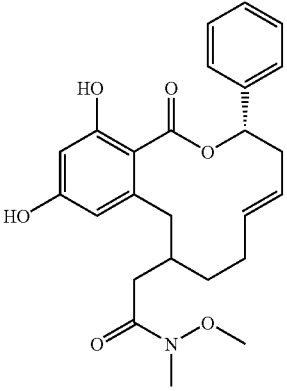 |
| (R)-2-152a | 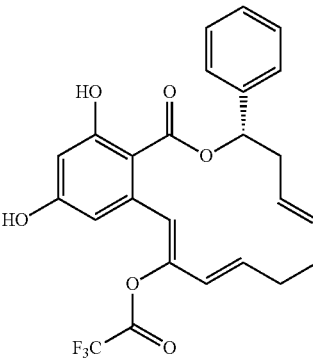 |
| (S)-2-152a | 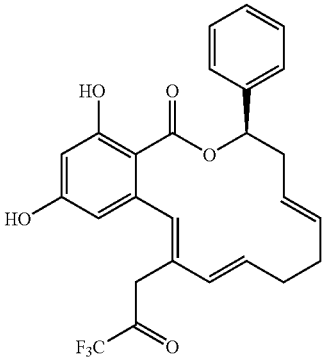 |
| (S)-2-152a-1 X = Cl | 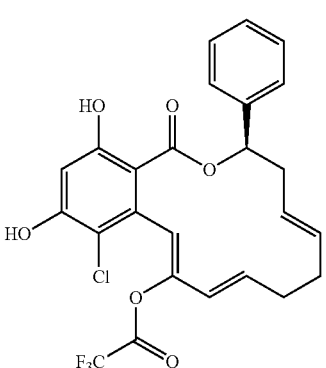 |
| (S)-d-2-121a (Ex. 134C) | 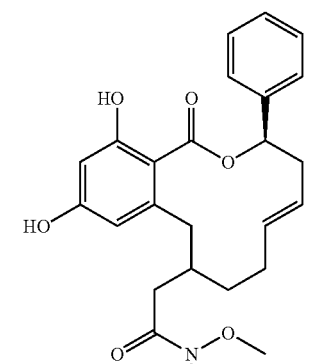 |
| (S)-2-145a X = Cl | 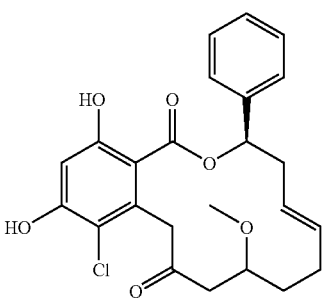 |

TABLE 1-continued

| Compound Designation | Structure |
|---|---|
| (R)-2-149-1 X = Cl | |
| (R)-2-151 | |
| (R)-2-151-1 X = Cl | |
| (R)-2-151a-1 X = Cl | |
| (R)-2-142-1 X = Cl (Ex. 136-A) | |
| (R)-2-144-1 X = Cl | |
| (R)-2-146-1 X = Cl | |
| (R)-2-147-1 X = Cl | |
| (R)-trans-2-150-1 (Ex. 125) | |
| (R)-2-150c-1 X = Cl | |
| (R)-2-150e | |
| Z-(R)-2-155-1 | |

TABLE 1-continued
| Compound Designation | Structure |
|---|---|
| E-(R)-2-155-1 | 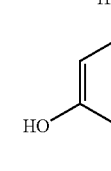 |
| (R)-2-147-4 X = Cl | 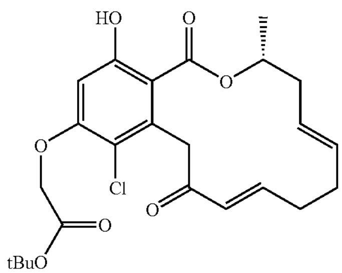 |
| (R)-2-153 | 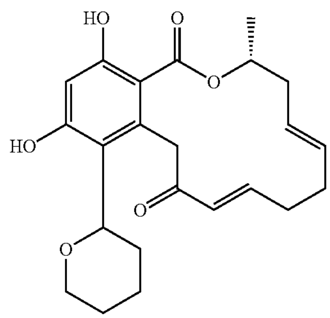 |
| (S)-2-150-1 X = Cl | 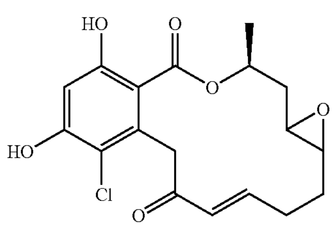 |
| (S)-cis-2-150 | 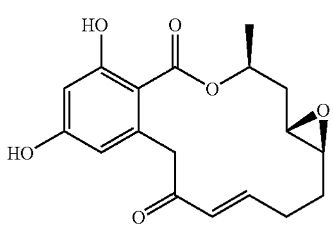 |
TABLE 1-continued
| Compound Designation | Structure |
|---|---|
| (R)-2-150f | 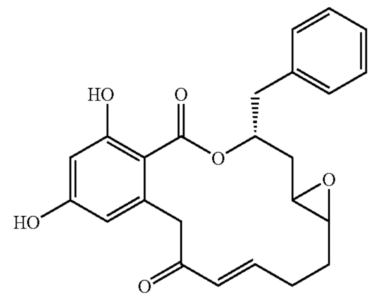 |
| (R)-cis-2-150e | 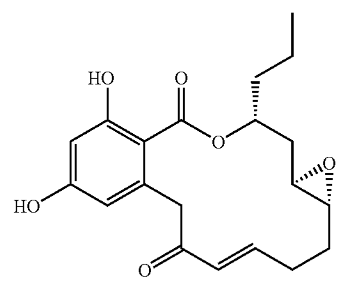 |
| (S)-trans-2-150 | 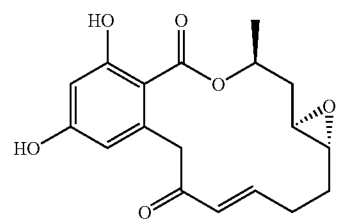 |
| (S)-2-150a-1 X = Cl | 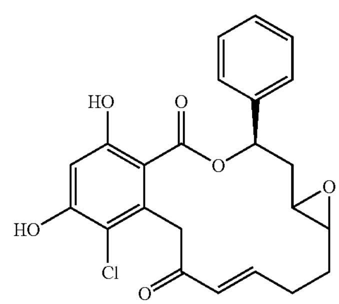 |
| (S)-2-150a | 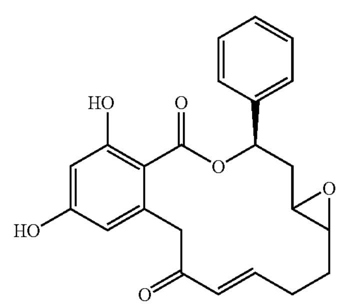 |

TABLE 1-continued

| Compound Designation | Structure |
|---|---|
| (R)-2-150a | 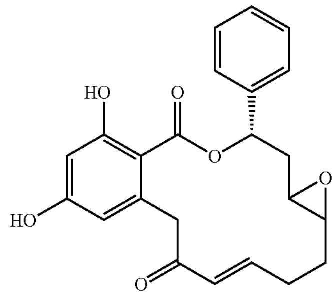 |
| (R)-trans-2-150e | 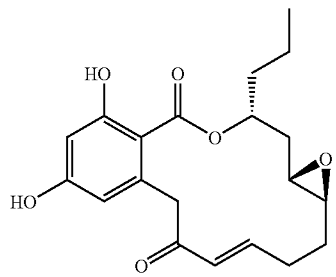 |
| E-(R)-2-155-1 | 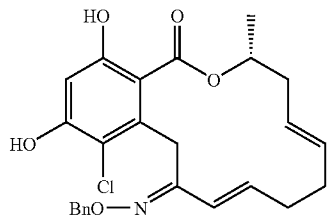 |
| 2-147-3 | 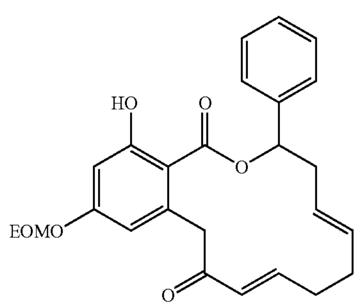 |
| (R)-2-147-3 X = Cl | 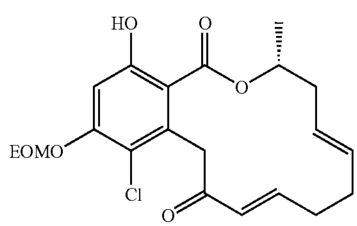 |
| (R)-2-147-2 | 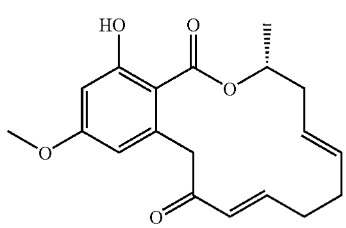 |
| 2-103h | |
| (R)-cis-2-150d | |
| (R)-trans-2-150d- | |
| Z-(R)-2-158-1 X = Cl | |
| (R)-2-112d (Ex. 133-D) | |
| (S)-2-112 | |

TABLE 1-continued

| Compound Designation | Structure |
|---|---|
| (R)-2-112a (Ex. 3) | 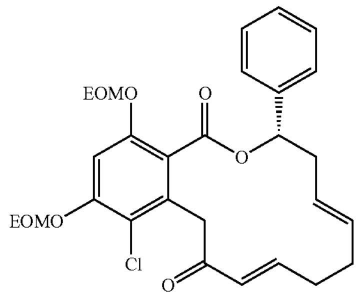 |
| (S)-2-112a (Ex. 133-C) | 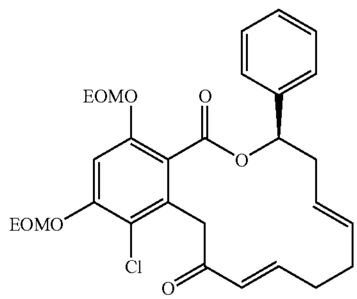 |
| (R)-2-120d (Ex. 133-I) | 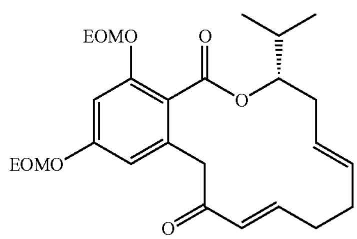 |
| (R)-2-120a (Ex. 133-G) | 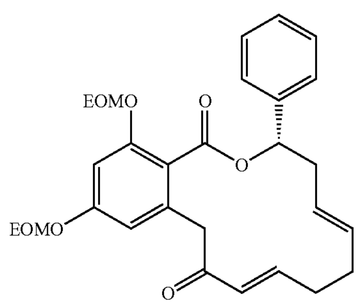 |
| 2-112 | 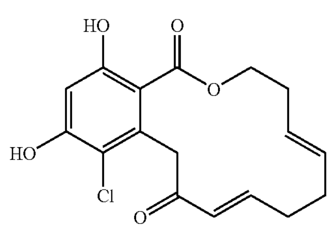 |
| 2-142g | 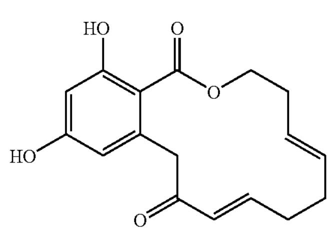 |
| (R)-2-112 (Ex. 105) | |
| (S)-2-120aa (Ex. 133-H) | |
| (R)-2-112e (Ex. 133-J) | |
| (R)-2-112f X = Cl | |
| (R)-2-128 | |
| Z-(R)-2-157-1 | |

TABLE 1-continued

| Compound Designation | Structure |
|---|---|
| E-(R)-2-157-1 | (structure) |
| (R)-2-154-1 | (structure) |
| (R)-2-112 | (structure) |
| (S)-2-120 (Ex. 133-F) | (structure) |
| (R)-2-141-2 X = Cl | (structure) |
| (R)-2-141 X = Cl | (structure) |
| 2-142 X = Cl | (structure) |
| (R)-2-143 X = Cl | (structure) |
| 2-154-2 bis R¹ = Cl | (structure) |
| 2-158-2 bis R¹ = Cl | (structure) |

TABLE 1-continued

| Compound Designation | Structure |
|---|---|
| 7-1<br>R¹ = H<br>R⁴X = O | (structure) |
| 2-156-2 | (structure) |
| 2-156-3 | (structure) |
| (R) 2-147-5 | (structure) |
| 2-154-4 | (structure) |
| 2-154-6 | (structure) |
| 2-154-5 | (structure) |
| 2-154-7 | (structure) |
| 2-154-8 | (structure) |

TABLE 1-continued

| Compound Designation | Structure |
|---|---|
| 2-154-3 | (structure) |
| 2-154-9 | (structure) |
| 2-170 | (structure) |
| 2-171 | (structure) |
| 2-172-1 X = H | (structure) |
| 2-172-4 | (structure) |
| 2-172-6 | (structure) |
| 2-172-7 | (structure) |
| 2-172-2, | (structure) |

TABLE 1-continued

| Compound Designation | Structure |
|---|---|
| 2-172-9 | (structure) |
| (R)-2-154d-1 | (structure) |
| (R)-2-154d-5 | (structure) |
| (R)-2-154d-3 | (structure) |
| (R)-2-154a-1 | (structure) |
| (R)-2-154a-5 | (structure) |
| (R)-2-154a-3 | (structure) |
| (S)-2-154a-1 | (structure) |

TABLE 1-continued

| Compound Designation | Structure |
|---|---|
| (R)-2-154a-5 | 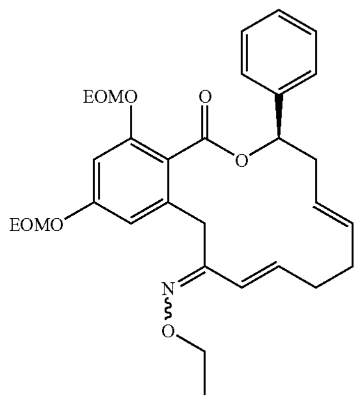 |
| (S)-2-154a-3 | 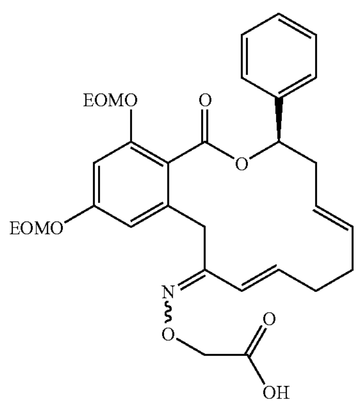 |
| (R)-2-154d-5 | 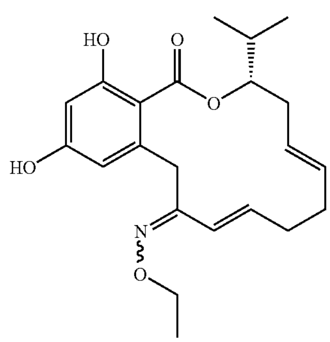 |
| (R)-2-154d-3 | 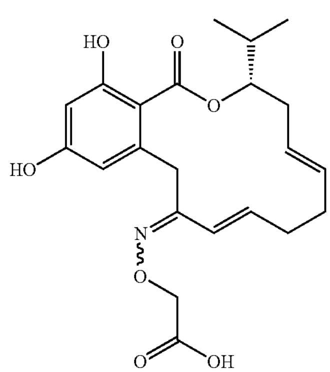 |
| (R)-2-172a-1 | |
| (R)-2-172d-1 | |
| (R)-2-172a-5 | |
| (R)-2-172a-2 | |

TABLE 1-continued

| Compound Designation | Structure |
| --- | --- |
| (S)-2-172a-1 | |
| (S)-2-173a-5 | |
| (S)-2-172a-2 | |
| 2-155-4 | |
| 2-155-7 | 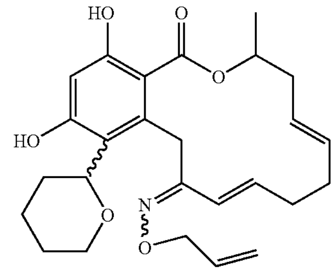 |
| 2-144 | 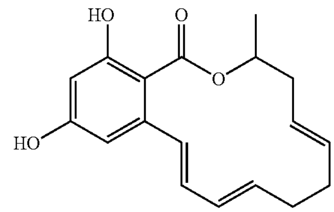 |
| (R)-2-144a | 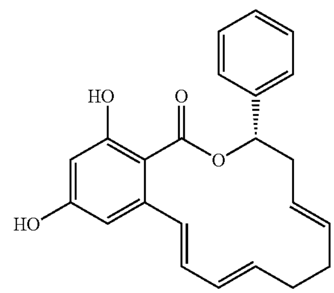 |
| 2-141d | 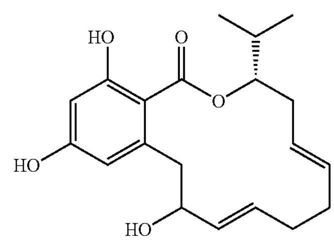 |
| 2-174d | 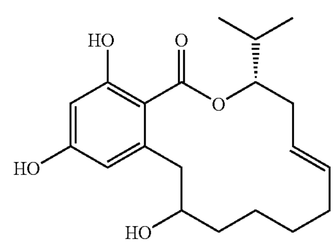 |
| 2-174 | 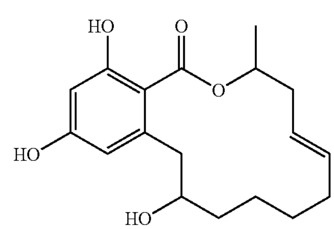 |

TABLE 1-continued

| Compound Designation | Structure |
|---|---|
| (S)-2-142-1 X = Cl | 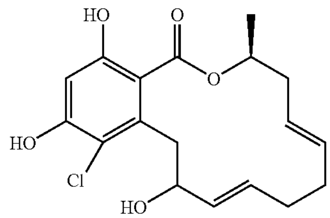 |
| (S)-2-142 | 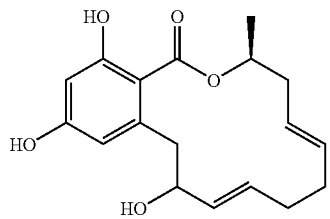 |
| 2-172-4 | 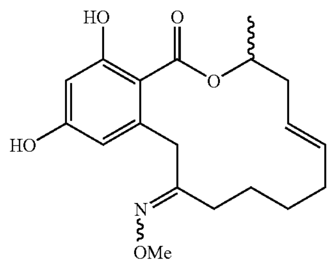 |
| 2-172-1 | 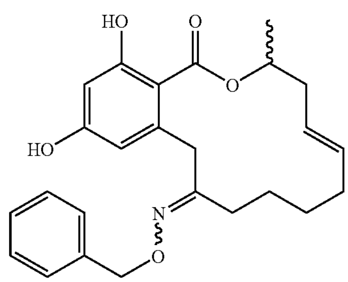 |
| (R)-2-120f | 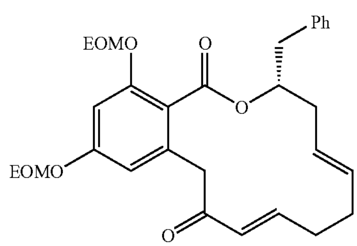 |
| 2-172-7 | 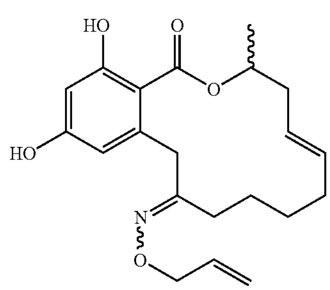 |
| 2-172-2 | |
| (R)-2-120 | |
| (S)-2-174 | |
| (R)-2-154d-3 | |
| (R)-172-2 | |
| 2-43b | |

TABLE 1-continued

| Compound Designation | Structure |
|---|---|
| Z-2-a1 | (structure) |
| E-2a1 | (structure) |
| Z-2-a1-1 | (structure) |
| E-2-a1 | (structure) |
| (R)-p-2-150 | (structure) |
| (R)-2-175 | (structure) |
| 2-163 | (structure) |
| 2-164 | (structure) |
| 2-165 | (structure) |

TABLE 1-continued

| Compound Designation | Structure |
|---|---|
| 2-166 | (structure) |
| 2-167 | (structure) |
| 2-168 | (structure) |
| 2-169 | (structure) |
| 2-a2 | (structure) |
| 2-a3 | (structure) |
| 2-a4 | (structure) |
| 2-a5 | (structure) |
| 2-a6 | (structure) |

TABLE 1-continued

| Compound Designation | Structure |
| --- | --- |
| 2-a7 | (structure) |
| 2-a8 | (structure) |
| 2-a9 | (structure) |
| 2-a10 | (structure) |
| 2-a11 | (structure) |
| 2-a12 | (structure) |
| 2-a12 | (structure) |
| 2-a13 | (structure) E isomer |
| 2-a14 | (structure) |

TABLE 1-continued

| Compound Designation | Structure |
|---|---|
| 2-a15 | 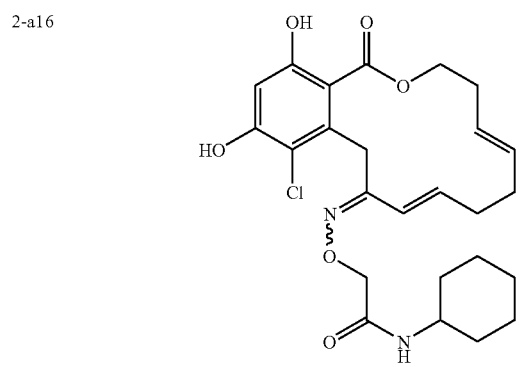 |
| 2-a16 | 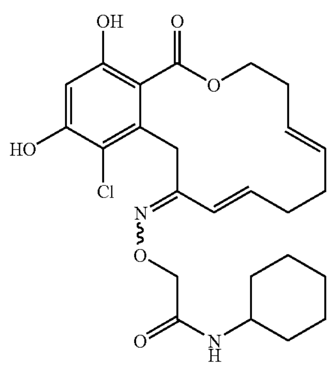 |
| 2-a17 | 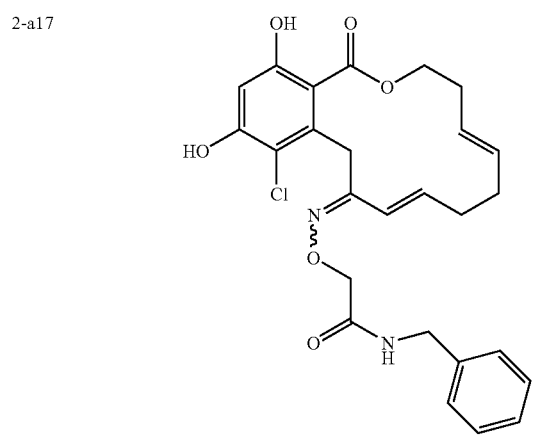 |
| 2-a18 | 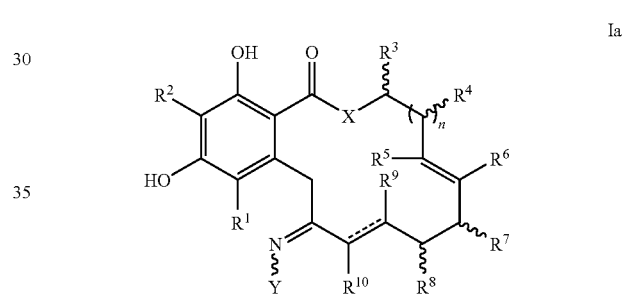 |

Additional Radicicol Derivatives of Formulae Ia, Ia, IIa, IIa', IIIa, IVa, and Va.

In an additional embodiment of the invention, a compound of formula Ia, a tautomer thereof, or a pharmaceutically acceptable salt, solvate, ester or prodrug thereof, is provided:

Ia wherein
X is O, S or NR;
Y is —OR, —O—$(CH_2)_m$COOR, —O—$(CH_2)_m$CON$(R)_2$, —N$(R)_2$, —N(R)SOR or —N(R)SO$_2$R, wherein the groups bound to the nitrogen atom may be in Z- or E-configuration;

$R^1$ and $R^2$ are independently hydrogen, halogen, OR, N$(R)_2$, SR, azido, nitro, cyano, aliphatic, aryl, alkylaryl, arylalkyl, heterocyclyl, heteroaryl, —S(O)R, —S(O)$_2$R, —SO$_2$N$(R)_2$, —N(R)SO$_2$R, —N(CO)R, —N(CO)N$(R)_2$, —N(CO)OR, —O(CO)R, —(CO)R, —(CO)OR, —(CO)N$(R)_2$, —O(CO)OR, or —O(CO)N$(R)_2$;

$R^3, R^4, R^5, R^6, R^7, R^8, R^9$ and $R^{10}$ are independently hydrogen, halogen, azido, nitro, cyano, aliphatic, alkylaryl, aralkyl, aryl, heteroalkyl, alkylheteroaryl, heterocyclyl, heteroaryl, OR, N$(R)_2$, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, —NR$(CH_2)_m$OC(O)$(CH_2)_p$N$(R)_2$, —$(CH_2)_m$N(R)C(O)$(CH_2)_p$R, —$(CH_2)_m$OC(O)$(CH_2)_p$R, —$(CH_2)_m$C(O)$(CH_2)_p$N$(R)_2$, —$(CH_2)_m$C(O)$(CH_2)_p$OR, —$(CH_2)_m$N(R)C(O)$(CH_2)_p$OR, —(CH$_2$)$_m$N(R)C(O)(CH$_2$)$_p$N(R)$_2$, —(CH$_2$)$_m$OC(O)(CH$_2$)$_p$ OR, —(CH$_2$)$_m$OC(O)(CH$_2$)$_p$N(R)$_2$, —(CH$_2$)$_m$N$_3$, —O(CH$_2$)$_m$ N$_3$—(CH$_2$)$_m$N(R)$_2$, —(CH$_2$)$_m$OR, —(CH$_2$)$_m$S (O)(CH$_2$)$_p$ R, —(CH$_2$)$_m$S(O)$_2$(CH$_2$)$_p$R, —(CH$_2$)$_m$SO$_2$ (CH$_2$)$_p$ N(R)$_2$, or —(CH$_2$)$_m$N(R)SO$_2$(CH$_2$)$_p$R; and each R is independently R$^{11}$, hydrogen, aliphatic, amino, azido, cyano, nitro, alkylamino, dialkylamino, OH, alkoxy, carbonylamino, aminocarbonyl, alkoxycarbonyl, carbonyloxy, carboxy, acyl, aryl, alkaryl, arylalkyl including benzyl, heteroalkyl, heteroaryl, heterocyclyl, or a protecting group; or two R on the same nitrogen are taken together with the nitrogen to form a 5-8 membered, optionally substituted heterocyclic or heteroaryl ring; wherein R is optionally substituted, and each R can be the same or different;

R$^{11}$ is the group:

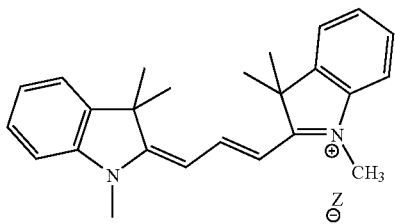

where Z is an inorganic or organic counterion;

n is 0, 1 or 2;

m and p are independently 0, 1, 2, 3, 4 or 5; and the dashed lines indicate either a single or a double bond, where the valence requirements are fulfilled by additional hydrogen atoms.

In a second additional embodiment, a compound of formula Ia', a tautomer thereof, or a pharmaceutically acceptable salt, solvate, ester or prodrug thereof, is provided,

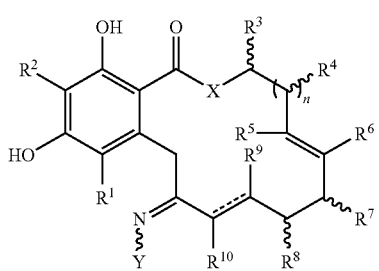

wherein X, Y, R$^1$, R$^2$, R$^3$, R$^4$, R$^5$, R$^6$, R$^7$, R$^8$, R$^9$, R$^{10}$, R, n, m and p are as defined for formula I above and the dashed lines represent a single or double bond, with the provisos that when n is 1, and X is O and a double bond is present between the carbon atoms bearing R$^9$ and R$^{10}$, then at least one of R$^5$, R$^6$, R$^7$, R$^8$, R$^9$ or R$^{10}$ is not hydrogen; and when n is 1 and X is O and the bond between the carbon atoms bearing R$^9$ and R$^{10}$ is a single bond, then at least one of R$^5$, R$^6$, R$^7$ or R$^8$ is not hydrogen.

In one embodiment of formula Ia or Ia', n is 0. In another embodiment of formula Ia or Ia', n is 1. In still another embodiment of formula Ia or Ia', n is 2.

In another embodiment of formula Ia or Ia', X is O or NR and n is 1. In another embodiment of formula Ia or Ia', X is O or NR, n is 1 and a double bond is present between the carbon atoms bearing R$^9$ and R$^{10}$.

In yet another embodiment of formula Ia or Ia', X is O or NR, n is 1 and the bond between the carbon atoms bearing R$^9$ and R$^{10}$ is a single bond.

In another embodiment of formula Ia or Ia', Y is —O—(CH$_2$)$_m$COOR or —O—(CH$_2$)$_m$CON(R)$_2$, wherein the groups bound to the nitrogen atom may be in the Z- or E-configuration.

In another embodiment of formula Ia or Ia', R$^1$ and R$^2$ are hydrogen.

In still another embodiment of formula Ia or Ia', R$^3$ and R$^4$ are independently alkyl or hydrogen.

In still another embodiment of formula Ia or Ia', X is O, and R$^9$ and R$^{10}$ are hydrogen.

In another embodiment of formula Ia or Ia', X is O, Y is —O—(CH$_2$)$_m$COOR or —O—(CH$_2$)$_m$CON(R)$_2$, wherein the groups bound to the nitrogen atom may be in the Z- or E-configuration; R$^1$ and R$^2$ are independently hydrogen or halogen; and R$^9$ and R$^{10}$ are hydrogen.

In another embodiment of formula Ia or Ia', R$^7$ or R$^8$ are not hydrogen or aliphatic.

In another embodiment of formula Ia or Ia', R$^3$ or R$^4$ are not hydrogen or aliphatic.

In one embodiment of formula Ia or Ia', the invention provides a compound wherein:

X is O or NR;

Y is —O—(CH$_2$)$_m$COOR or —O—(CH$_2$)$_m$CON(R)$_2$, wherein the groups bound to the nitrogen atom may be in the Z- or E-configuration;

R$^1$ and R$^2$ are independently hydrogen, halogen, OR, N(R)$_2$ or aliphatic;

R$^3$ and R$^4$ are independently hydrogen, aliphatic, OR, N(R)$_2$, —(CH$_2$)$_m$N(R)C(O)CH$_2$)$_p$R, —(CH$_2$)$_m$OC(O) (CH$_2$)$_p$ R, —(CH$_2$)$_m$C(O)(CH$_2$)$_p$N(R)$_2$, —(CH$_2$)$_m$C(O) (CH$_2$)$_p$OR, —(CH$_2$)$_m$N(R)C(O)(CH$_2$)$_p$OR, —(CH$_2$)$_m$N(R) C(O)(CH$_2$)$_p$ N(R)$_2$, —(CH$_2$)$_m$OC(O)(CH$_2$)$_p$OR, —(CH$_2$)$_m$ OC(O)(CH$_2$)$_p$ N(R)$_2$, —(CH$_2$)$_m$N$_3$, —O(CH$_2$)$_m$N$_3$—(CH$_2$)$_m$ N(R)$_2$, —(CH$_2$)$_m$OR, —(CH$_2$)$_m$S(O)(CH$_2$)$_p$R, —(CH$_2$)$_m$S (O)$_2$(CH$_2$)$_p$R, —(CH$_2$)$_m$SO$_2$(CH$_2$)$_p$N(R)$_2$, or —(CH$_2$)$_m$N (R)SO$_2$(CH$_2$)$_p$R;

R$^5$, R$^6$, R$^9$ and R$^{10}$ are independently hydrogen, aliphatic, alkylaryl, aralkyl, aryl, heteroalkyl, alkylheteroaryl, heterocyclyl, heteroaryl, OR, SR, —O(CH$_2$)$_m$N(R)C(O)(CH$_2$)$_p$R, —O(CH$_2$)$_m$OC(O)(CH$_2$)$_p$R, —O(CH$_2$)$_m$C(O)(CH$_2$)$_p$N(R)$_2$, —O(CH$_2$)$_m$C(O)(CH$_2$)$_p$OR, —O(CH$_2$)$_m$N(R)C(O)(CH$_2$)$_p$ OR, —O(CH$_2$)$_m$N(R)C(O)(CH$_2$)$_p$N(R)$_2$, —O(CH$_2$)$_m$OC(O) (CH$_2$)$_p$OR, —O(CH$_2$)$_m$OC(O)(CH$_2$)$_p$N(R)$_2$, —NR(CH$_2$)$_m$N (R)C(O)(CH$_2$)$_p$R, —NR(CH$_2$)$_m$OC(O)(CH$_2$)$_p$R, —NR (CH$_2$)$_m$C(O)(CH$_2$)$_p$N(R)$_2$, —NR(CH$_2$)$_m$C(O)(CH$_2$)$_p$ OR, —NR(CH$_2$)$_m$N(R)C(O)(CH$_2$)$_p$OR, —NR(CH$_2$)$_m$N(R)C(O) (CH$_2$)$_p$N(R)$_2$, —NR(CH$_2$)$_m$OC(O)(CH$_2$)$_p$OR, —NR(CH$_2$)$_m$ OC(O)(CH$_2$)$_p$N(R)$_2$, —(CH$_2$)$_m$N(R)C(O)CH$_2$)$_p$R, —(CH$_2$)$_m$ OC(O)(CH$_2$)$_p$R, —(CH$_2$)$_m$C(O)(CH$_2$)$_p$N(R)$_2$, —(CH$_2$)$_m$C(O)(CH$_2$)$_p$OR, —(CH$_2$)$_m$N(R)C(O)(CH$_2$)$_p$OR, —(CH$_2$)$_m$N(R)C(O)(CH$_2$)$_p$N(R)$_2$, —(CH$_2$)$_m$OC(O)(CH$_2$)$_p$ OR, —(CH$_2$)$_m$OC(O)(CH$_2$)$_p$N(R)$_2$, —(CH$_2$)$_m$N$_3$, —O(CH$_2$)$_m$ N(R)$_2$, —(CH$_2$)$_m$N(R)$_2$, —(CH$_2$)$_m$OR, —(CH$_2$)$_m$ S(O)(CH$_2$)$_p$R, —(CH$_2$)$_m$S(O)$_2$(CH$_2$)$_p$R, —(CH$_2$)$_m$ SO$_2$(CH$_2$)$_p$N(R)$_2$, or —(CH$_2$)$_m$N(R)SO$_2$(CH$_2$)$_p$R;

R$^7$ and R$^8$ are independently hydrogen, halogen, aliphatic, alkylaryl, aralkyl, aryl, heteroalkyl, alkylheteroaryl, heterocyclyl, heteroaryl, OR, N(R)$_2$, SR, —O(CH$_2$)$_m$N(R)C(O) (CH$_2$)$_p$R, —O(CH$_2$)$_m$OC(O)(CH$_2$)$_p$R, —O(CH$_2$)$_m$C(O) (CH$_2$)$_p$N(R)$_2$, —O(CH$_2$)$_m$C(O)(CH$_2$)$_p$OR, —O(CH$_2$)$_m$N(R) C(O)(CH$_2$)$_p$OR, —O(CH$_2$)$_m$N(R)C(O)(CH$_2$)$_p$N(R)$_2$, —O(CH$_2$)$_m$OC(O)(CH$_2$)$_p$OR, —O(CH$_2$)$_m$OC(O)(CH$_2$)$_p$N (R)$_2$, —NR(CH$_2$)$_m$N(R)C(O)(CH$_2$)$_p$R, —NR(CH$_2$)$_m$OC(O) (CH$_2$)$_p$R, —NR(CH$_2$)$_m$C(O)(CH$_2$)$_p$N(R)$_2$, —NR(CH$_2$)$_m$C (O)(CH$_2$)$_p$OR, —NR(CH$_2$)$_m$N(R)C(O)(CH$_2$)$_p$OR, —NR(CH$_2$)$_m$N(R)C(O)(CH$_2$)$_p$N(R)$_2$, —NR(CH$_2$)$_m$OC(O)(CH$_2$)$_p$OR, —NR(CH$_2$)$_m$OC(O)(CH$_2$)$_p$N(R)$_2$, —(CH$_2$)$_m$N(R)C(O)CH$_2$)$_p$R, —(CH$_2$)$_m$OC(O)(CH$_2$)$_p$R, —(CH$_2$)$_m$C(O)(CH$_2$)$_p$N(R)$_2$, —(CH$_2$)$_m$C(O)(CH$_2$)$_p$OR, —(CH$_2$)$_m$N(R)C(O)(CH$_2$)$_p$OR, —(CH$_2$)$_m$N(R)C(O)(CH$_2$)$_p$N(R)$_2$, —(CH$_2$)$_m$OC(O)(CH$_2$)$_p$OR, —(CH$_2$)$_m$OC(O)(CH$_2$)$_p$N(R)$_2$, —(CH$_2$)$_m$N$_3$, —O(CH$_2$)$_m$N$_3$—(CH$_2$)$_m$N(R)$_2$, —(CH$_2$)$_m$OR, —(CH$_2$)$_m$S(O)(CH$_2$)$_p$R, —(CH$_2$)$_m$S(O)$_2$(CH$_2$)$_p$R, —(CH$_2$)$_m$SO$_2$(CH$_2$)$_p$N(R)$_2$, or —(CH$_2$)$_m$N(R)SO$_2$(CH$_2$)$_p$R.

In yet another embodiment of formula Ia or Ia', X is O or NR;

Y is —O—(CH$_2$)$_m$COOR or —O—(CH$_2$)$_m$CON(R)$_2$, wherein the groups bound to the nitrogen atom may be in the Z- or E-configuration;

$R^1$ and $R^2$ are independently hydrogen, halogen;

$R^3$ and $R^4$ are independently hydrogen, aliphatic, —(CH$_2$)$_m$N(R)C(O)CH$_2$)$_p$R, —(CH$_2$)$_m$OC(O)(CH$_2$)$_p$R, —(CH$_2$)$_m$N(R)C(O)(CH$_2$)$_p$OR, —(CH$_2$)$_m$N(R)C(O)(CH$_2$)$_p$N(R)$_2$, —(CH$_2$)$_m$OC(O)(CH$_2$)$_p$OR, —(CH$_2$)$_m$OC(O)(CH$_2$)$_p$N(R)$_2$, —(CH$_2$)$_m$N$_3$, —(CH$_2$)$_m$N(R)$_2$, or —(CH$_2$)$_m$OR;

$R^5$, $R^6$, $R^9$ and $R^{10}$ are independently hydrogen, aliphatic, aralkyl, heteroalkyl, heterocyclyl, or heteroaryl; and $R^7$ and $R^8$ are independently hydrogen, aliphatic, alkylaryl, aralkyl, aryl, heteroalkyl, alkylheteroaryl, heterocyclyl, heteroaryl, OR, N(R)$_2$, SR, —O(CH$_2$)$_m$N(R)C(O)(CH$_2$)$_p$R, —O(CH$_2$)$_m$OC(O)(CH$_2$)$_p$R, —O(CH$_2$)$_m$C(O)(CH$_2$)$_p$N(R)$_2$, —O(CH$_2$)$_m$C(O)(CH$_2$)$_p$OR, —O(CH$_2$)$_m$N(R)C(O)(CH$_2$)$_p$OR, —O(CH$_2$)$_m$N(R)C(O)(CH$_2$)$_p$N(R)$_2$, —O(CH$_2$)$_m$OC(O)(CH$_2$)$_p$OR, —O(CH$_2$)$_m$OC(O)(CH$_2$)$_p$N(R)$_2$, —NR(CH$_2$)$_m$N(R)C(O)(CH$_2$)$_p$R, —NR(CH$_2$)$_m$OC(O)(CH$_2$)$_p$R, —NR(CH$_2$)$_m$C(O)(CH$_2$)$_p$N(R)$_2$, —NR(CH$_2$)$_m$C(O)(CH$_2$)$_p$OR, —NR(CH$_2$)$_m$N(R)C(O)(CH$_2$)$_p$OR, —NR(CH$_2$)$_m$N(R)C(O)(CH$_2$)$_p$N(R)$_2$, —NR(CH$_2$)$_m$OC(O)(CH$_2$)$_p$OR, or —NR(CH$_2$)$_m$OC(O)(CH$_2$)$_p$N(R)$_2$.

In still another embodiment of formula Ia or Ia', X is O or NR;

Y is —O—(CH$_2$)$_m$COOR or —O—(CH$_2$)$_m$CON(R)$_2$, wherein the groups bound to the nitrogen atom may be in the Z- or E-configuration;

$R^1$ and $R^2$ are independently hydrogen, halogen;

$R^3$ and $R^4$ are independently hydrogen, aliphatic, —(CH$_2$)$_m$N(R)C(O)CH$_2$)$_p$R, —(CH$_2$)$_m$OC(O)(CH$_2$)$_p$R, —(CH$_2$)$_m$N(R)C(O)(CH$_2$)$_p$OR, —(CH$_2$)$_m$N(R)C(O)(CH$_2$)$_p$N(R)$_2$, —(CH$_2$)$_m$OC(O)(CH$_2$)$_p$OR, —(CH$_2$)$_m$OC(O)(CH$_2$)$_p$N(R)$_2$, —(CH$_2$)$_m$N$_3$, —(CH$_2$)$_m$N(R)$_2$, or —(CH$_2$)$_m$OR;

$R^5$, $R^6$, $R^9$ and $R^{10}$ are independently hydrogen, aliphatic, aralkyl, heteroalkyl, heterocyclyl, or heteroaryl;

$R^7$ and $R^8$ are independently alkylaryl, aralkyl, aryl, heteroalkyl, alkylheteroaryl, heterocyclyl, heteroaryl, OR, N(R)$_2$, SR, —O(CH$_2$)$_m$N(R)C(O)(CH$_2$)$_p$R, —O(CH$_2$)$_m$OC(O)(CH$_2$)$_p$R, —O(CH$_2$)$_m$C(O)(CH$_2$)$_p$N(R)$_2$, —O(CH$_2$)$_m$C(O)(CH$_2$)$_p$OR, —O(CH$_2$)$_m$N(R)C(O)(CH$_2$)$_p$OR, —O(CH$_2$)$_m$N(R)C(O)(CH$_2$)$_p$N(R)$_2$, —O(CH$_2$)$_m$OC(O)(CH$_2$)$_p$OR, —O(CH$_2$)$_m$OC(O)(CH$_2$)$_p$N(R)$_2$, —NR(CH$_2$)$_m$N(R)C(O)(CH$_2$)$_p$R, —NR(CH$_2$)$_m$OC(O)(CH$_2$)$_p$R, —NR(CH$_2$)$_m$C(O)(CH$_2$)$_p$N(R)$_2$, —NR(CH$_2$)$_m$C(O)(CH$_2$)$_p$OR, —NR(CH$_2$)$_m$N(R)C(O)(CH$_2$)$_p$OR, —NR(CH$_2$)$_m$N(R)C(O)(CH$_2$)$_p$N(R)$_2$, —NR(CH$_2$)$_m$OC(O)(CH$_2$)$_p$OR, or —NR(CH$_2$)$_m$OC(O)(CH$_2$)$_p$N(R)$_2$.

In one embodiment of formula Ia or Ia', R is $R^{11}$, where the counterion Z is a halogen, acetate, formate, sulfonate, sulfate or phosphate counterion.

In another embodiment, a compound of formula IIa, a tautomer thereof, or a pharmaceutically acceptable salt, solvate, ester or prodrug thereof, is provided:

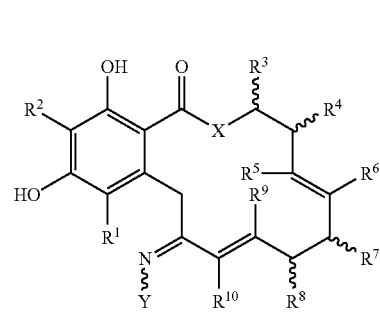

IIa wherein the variables X, Y, $R^1$, $R^2$, $R^3$, $R^4$, $R^5$, $R_6$, $R^7$, $R^8$, $R^9$, $R^{10}$, R, m and p are as defined for formula Ia above.

In another embodiment, a compound of formula IIa', a tautomer thereof, or a pharmaceutically acceptable salt, solvate, ester or prodrug thereof, is provided:

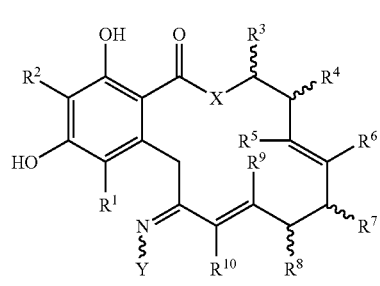

IIa' wherein the variables X, Y, $R^1$, $R^2$, $R^3$, $R^4$, $R^5$, $R^6$, $R^7$, $R^8$, $R^9$, $R^{10}$, R, m and p are as defined for formula Ia above; with the proviso that when X is O, then at least one of $R^5$, $R^6$, $R^7$, $R^8$, $R^9$ or $R^{10}$ is not hydrogen.

In one embodiment of formula IIa or IIa', X is O or NR.

In another embodiment of formula IIa or IIa', Y is —O—(CH$_2$)$_m$COOR or —O—(CH$_2$)$_m$CON(R)$_2$, wherein the groups bound to the nitrogen atom may be in the Z- or E-configuration.

In another embodiment of formula IIa or IIa', $R^1$ and $R^2$ are hydrogen.

In still another embodiment of formula IIa or IIa', $R^3$ and $R^4$ are independently alkyl or hydrogen.

In still another embodiment of formula IIa or IIa', X is O, and $R^9$ and $R^{10}$ are hydrogen.

In another embodiment of formula IIa or IIa', $R^7$ or $R^8$ are not hydrogen or aliphatic.

In another embodiment of formula IIa or IIa', $R^3$ or $R^4$ are not hydrogen or aliphatic.

In another embodiment of formula IIa or IIa', X is O, Y is —O—(CH$_2$)$_m$COOR or —O—(CH$_2$)$_m$CON(R)$_2$, wherein the groups bound to the nitrogen atom may be in the Z- or E-configuration; $R^1$ and $R^2$ are independently hydrogen or halogen; and $R^9$ and $R^{10}$ are hydrogen.

In one embodiment of formula IIa or IIa', the invention provides a compound wherein:

X is O or NR;

Y is —O—(CH$_2$)$_m$COOR or —O—(CH$_2$)$_m$CON(R)$_2$, wherein the groups bound to the nitrogen atom may be in the Z- or E-configuration;

$R^1$ and $R^2$ are independently hydrogen, halogen, OR, N(R)$_2$ or aliphatic;

$R^3$ and $R^4$ are independently hydrogen, aliphatic, OR, N(R)$_2$, —(CH$_2$)$_m$N(R)C(O)CH$_2$)$_p$R, —(CH$_2$)$_m$OC(O)(CH$_2$)$_p$ R, —(CH$_2$)$_m$C(O)(CH$_2$)$_p$N(R)$_2$, —(CH$_2$)$_m$C(O)

$(CH_2)_pOR$, $-(CH_2)_mN(R)C(O)(CH_2)_pOR$, $-(CH_2)_mN(R)C(O)(CH_2)_p N(R)_2$, $-(CH_2)_mOC(O)(CH_2)_pOR$, $-(CH_2)_m OC(O)(CH_2)_p N(R)_2$, $-(CH_2)_mN_3$, $-O(CH_2)_mN_3$ $-(CH_2)_m N(R)_2$, $-(CH_2)_mOR$, $-(CH_2)_mS(O)(CH_2)_pR$, $-(CH_2)_mS(O)_2(CH_2)_pR$, $-(CH_2)_mSO_2(CH_2)_pN(R)_2$, or $-(CH_2)_mN(R)SO_2(CH_2)_pR$;

$R^5$, $R^6$, $R^9$ and $R^{10}$ are independently hydrogen, aliphatic, alkylaryl, aralkyl, aryl, heteroalkyl, alkylheteroaryl, heterocyclyl, heteroaryl, $-(CH_2)_mN(R)C(O)CH_2)_pR$, $-(CH_2)_m OC(O)(CH_2)_pR$, $-(CH_2)_mC(O)(CH_2)_pN(R)_2$, $-(CH_2)_mC(O)(CH_2)_pOR$, $-(CH_2)_mN(R)C(O)(CH_2)_pOR$, $-(CH_2)_mN(R)C(O)(CH_2)_pN(R)_2$, $-(CH_2)_mOC(O)(CH_2)_pOR$, $-(CH_2)_m OC(O)(CH_2)_pN(R)_2$, $-O(CH_2)_mN_3-(CH_2)_mN(R)_2$, $-(CH_2)_mOR$, $-(CH_2)_mS(O)(CH_2)_pR$, $-(CH_2)_mS(O)_2 (CH_2)_pR$, $-(CH_2)_mSO_2(CH_2)_pN(R)_2$, or $-(CH_2)_mN(R)SO_2(CH_2)_pR$; and $R^7$ and $R^8$ are independently hydrogen, halogen, aliphatic, alkylaryl, aralkyl, aryl, heteroalkyl, alkylheteroaryl, heterocyclyl, heteroaryl, OR, $N(R)_2$, SR, $-O(CH_2)_mN(R)C(O)(CH_2)_pR$, $-O(CH_2)_mOC(O)(CH_2)_pOR$, $-O(CH_2)_mC(O)(CH_2)_pN(R)_2$, $-O(CH_2)_mC(O)(CH_2)_pOR$, $-O(CH_2)_mN(R)C(O)(CH_2)_pOR$, $-O(CH_2)_mN(R)C(O)(CH_2)_pN(R)_2$, $-O(CH_2)_mOC(O)(CH_2)_pOR$, $-O(CH_2)_mOC(O)(CH_2)_pN(R)_2$, $-NR(CH_2)_mN(R)C(O)(CH_2)_pR$, $-NR(CH_2)_mOC(O)(CH_2)_pR$, $-NR(CH_2)_mC(O)(CH_2)_pN(R)_2$, $-NR(CH_2)_mC(O)(CH_2)_pOR$, $-NR(CH_2)_mN(R)C(O)(CH_2)_pOR$, $-NR(CH_2)_mN(R)C(O)(CH_2)_pN(R)_2$, $-NR(CH_2)_mOC(O)(CH_2)_pOR$, $-NR(CH_2)_mOC(O)(CH_2)_pN(R)_2$, $-(CH_2)_mN(R)C(O)CH_2)_pR$, $-(CH_2)_mOC(O)(CH_2)_pR$, $-(CH_2)_mC(O)(CH_2)_pN(R)_2$, $-(CH_2)_mC(O)(CH_2)_pOR$, $-(CH_2)_mN(R)C(O)(CH_2)_pOR$, $-(CH_2)_mN(R)C(O)(CH_2)_pN(R)_2$, $-(CH_2)_m OC(O)(CH_2)_pOR$, $-(CH_2)_mOC(O)(CH_2)_pN(R)_2$, $-(CH_2)_m N_3$, $-O(CH_2)_mN_3-(CH_2)_mN(R)_2$, $-(CH_2)_mOR$, $-(CH_2)_m S(O)(CH_2)_pR$, $-(CH_2)_mS(O)_2(CH_2)_pR$, $-(CH_2)_mSO_2 (CH_2)_pN(R)_2$, or $-(CH_2)_mN(R)SO_2(CH_2)_pR$.

In yet another embodiment of formula IIa or IIa', X is O or NR;

Y is $-O-(CH_2)_mCOOR$ or $-O-(CH_2)_mCON(R)_2$, wherein the groups bound to the nitrogen atom may be in the Z- or E-configuration;

$R^1$ and $R^2$ are independently hydrogen or halogen;

$R^3$ and $R^4$ are independently hydrogen, aliphatic, $-(CH_2)_m N(R)C(O)CH_2)_pR$, $-(CH_2)_mOC(O)(CH_2)_pR$, $-(CH_2)_mN(R)C(O)(CH_2)_pOR$, $-(CH_2)_mN(R)C(O)(CH_2)_p N(R)_2$, $-(CH_2)_mOC(O)(CH_2)_pOR$, $-(CH_2)_mOC(O)(CH_2)_p N(R)_2$, $-(CH_2)_mN_3$, $-(CH_2)_mN(R)_2$, or $-(CH_2)_mOR$;

$R^5$, $R^6$, $R^9$ and $R^{10}$ are independently hydrogen, aliphatic, aralkyl, heteroalkyl, heterocyclyl, or heteroaryl; and $R^7$ and $R^8$ are independently hydrogen, aliphatic, alkylaryl, aralkyl, aryl, heteroalkyl, alkylheteroaryl, heterocyclyl, heteroaryl, OR, $N(R)_2$, SR, $-O(CH_2)_mN(R)C(O)(CH_2)_pR$, $-O(CH_2)_mOC(O)(CH_2)_pR$, $-O(CH_2)_mC(O)(CH_2)_pN(R)_2$, $-O(CH_2)_mC(O)(CH_2)_pOR$, $-O(CH_2)_mN(R)C(O)(CH_2)_pOR$, $-O(CH_2)_mN(R)C(O)(CH_2)_pN(R)_2$, $-O(CH_2)_mOC(O)(CH_2)_pOR$, $-O(CH_2)_mOC(O)(CH_2)_pN(R)_2$, $-NR(CH_2)_mN(R)C(O)(CH_2)_pR$, $-NR(CH_2)_mOC(O)(CH_2)_pR$, $-NR(CH_2)_mC(O)(CH_2)_pN(R)_2$, $-NR(CH_2)_mC(O)(CH_2)_pOR$, $-NR(CH_2)_mN(R)C(O)(CH_2)_pOR$, $-NR(CH_2)_mN(R)C(O)(CH_2)_pN(R)_2$, $-NR(CH_2)_mOC(O)(CH_2)_pOR$, or $-NR(CH_2)_mOC(O)(CH_2)_pN(R)_2$.

In still another embodiment of formula IIa or IIa', X is O or NR;

Y is $-O-(CH_2)_mCOOR$ or $-O-(CH_2)_mCON(R)_2$, wherein the groups bound to the nitrogen atom may be in the Z- or E-configuration;

$R^1$ and $R^2$ are independently hydrogen or halogen;

$R^3$ and $R^4$ are independently hydrogen, aliphatic, $-(CH_2)_m N(R)C(O)CH_2)_pR$, $-(CH_2)_mOC(O)(CH_2)_pR$, $-(CH_2)_mN(R)C(O)(CH_2)_pOR$, $-(CH_2)_mN(R)C(O)(CH_2)_p N(R)_2$, $-(CH_2)_mOC(O)(CH_2)_pOR$, $-(CH_2)_mOC(O)(CH_2)_p N(R)_2$, $-(CH_2)_mN_3$, $-(CH_2)_mN(R)_2$, or $-(CH_2)_mOR$;

$R^5$, $R^6$, $R^9$ and $R^{10}$ are independently hydrogen, aliphatic, aralkyl, heteroalkyl, heterocyclyl, or heteroaryl;

$R^7$ and $R^8$ are independently alkylaryl, aralkyl, aryl, heteroalkyl, alkylheteroaryl, heterocyclyl, heteroaryl, OR, $N(R)_2$, SR, $-O(CH_2)_mN(R)C(O)(CH_2)_pR$, $-O(CH_2)_mOC(O)(CH_2)_pR$, $-O(CH_2)_mC(O)(CH_2)_pN(R)_2$, $-O(CH_2)_mC(O)(CH_2)_pOR$, $-O(CH_2)_mN(R)C(O)(CH_2)_pOR$, $-O(CH_2)_m N(R)C(O)(CH_2)_pN(R)_2$, $-O(CH_2)_mOC(O)(CH_2)_pOR$, $-O(CH_2)_mOC(O)(CH_2)_pN(R)_2$, $-NR(CH_2)_mN(R)C(O)(CH_2)_pR$, $-NR(CH_2)_mOC(O)(CH_2)_pR$, $-NR(CH_2)_mC(O)(CH_2)_pN(R)_2$, $-NR(CH_2)_mC(O)(CH_2)_pOR$, $-NR(CH_2)_mN(R)C(O)(CH_2)_pOR$, $-NR(CH_2)_mN(R)C(O)(CH_2)_pN(R)_2$, $-NR(CH_2)_mOC(O)(CH_2)_pOR$, or $-NR(CH_2)_mOC(O)(CH_2)_pN(R)_2$.

In yet another embodiment of formula IIa or IIa', X is O or NR;

Y is $-O-(CH_2)_mCOOR$ or $-O-(CH_2)_mCON(R)_2$, wherein the groups bound to the nitrogen atom may be in the Z- or E-configuration; $R^1$ and $R^2$ are independently hydrogen or halogen;

$R^3$ and $R^4$ are independently hydrogen, aliphatic, $-(CH_2)_m N(R)C(O)CH_2)_pR$, $-(CH_2)_mOC(O)(CH_2)_pR$, $-(CH_2)_mN(R)C(O)(CH_2)_pOR$, $-(CH_2)_mN(R)C(O)(CH_2)_p N(R)_2$, $-(CH_2)_mOC(O)(CH_2)_pOR$, $-(CH_2)_mOC(O)(CH_2)_p N(R)_2$, $-(CH_2)_mN_3$, $-(CH_2)_mN(R)_2$, or $-(CH_2)_mOR$;

$R^5$, $R^6$, $R^9$ and $R^{10}$ are independently hydrogen, aliphatic, aralkyl, heteroalkyl, heterocyclyl, or heteroaryl; and $R^7$ and $R^8$ are independently $-OR$, $-N(R)_2$, $-SR$, $-O(CH_2)_mN(R)C(O)(CH_2)_pR$, $-O(CH_2)_mOC(O)(CH_2)_pR$, $-O(CH_2)_mC(O)(CH_2)_pN(R)_2$, $-O(CH_2)_mC(O)(CH_2)_pOR$, $-O(CH_2)_mN(R)C(O)(CH_2)_pOR$, $-O(CH_2)_mN(R)C(O)(CH_2)_pN(R)_2$, $-O(CH_2)_mOC(O)(CH_2)_pOR$, $-O(CH_2)_mOC(O)(CH_2)_pN(R)_2$, $-NR(CH_2)_mN(R)C(O)(CH_2)_pR$, $-NR(CH_2)_mOC(O)(CH_2)_pR$, $-NR(CH_2)_mC(O)(CH_2)_pN(R)_2$, $-NR(CH_2)_mC(O)(CH_2)_pOR$, $-NR(CH_2)_mN(R)C(O)(CH_2)_pOR$, $-NR(CH_2)_mN(R)C(O)(CH_2)_pN(R)_2$, $-NR(CH_2)_mOC(O)(CH_2)_pOR$, or $-NR(CH_2)_mOC(O)(CH_2)_pN(R)_2$.

In another additional embodiment, a compound of formula IIIa, a tautomer thereof, or a pharmaceutically acceptable salt, solvate, ester or prodrug thereof, is provided:

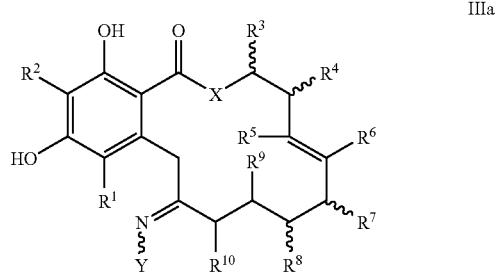

IIIa wherein the variables X, Y, $R^1$, $R^2$, $R^3$, $R^4$, $R^5$, $R^6$, $R^7$, $R^8$, $R^9$, $R^{10}$, R, m and p are as defined for formula Ia above.

In another additional embodiment of the invention, a compound of formula IIIa', a tautomer thereof, or a pharmaceutically acceptable salt, solvate, ester or prodrug thereof, is provided:

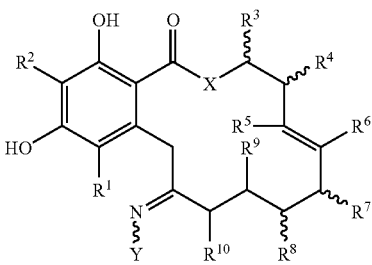

IIIa' wherein the variables X, Y, $R^1$, $R^2$, $R^3$, $R^4$, $R^5$, $R^6$, $R^7$, $R^8$, $R^9$, $R^{10}$, R, m and p are as defined for formula Ia above; with the proviso that at least one of $R^5$, $R^6$, $R^7$ or $R^8$ is not hydrogen.

In one embodiment of formula IIIa or IIIa', X is O or NR.

In another embodiment of formula IIIa or IIIa', Y is —O—$(CH_2)_m$COOR or —O—$(CH_2)_m$CON$(R)_2$, wherein the groups bound to the nitrogen atom may be in the Z- or E-configuration.

In another embodiment of formula IIIa or IIIa', $R^1$ and $R^2$ are hydrogen.

In still another embodiment of formula IIIa or IIIa', $R^3$ and $R^4$ are independently alkyl or hydrogen.

In still another embodiment of formula IIIa or IIIa', X is O, and $R^9$ and $R^{10}$ are hydrogen.

In another embodiment of formula IIIa or IIIa', $R^3$ or $R^4$ are not hydrogen or aliphatic.

In another embodiment of formula IIIa or IIIa', $R^7$ or $R^8$ are not hydrogen or aliphatic.

In still another embodiment of formula IIIa or IIIa', $R^9$ or $R^{10}$ are independently OR, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$N(R)C(O)$(CH_2)_p$N$(R)_2$, or —NR$(CH_2)_m$OC(O)$(CH_2)_p$OR, —NR$(CH_2)_m$OC(O)$(CH_2)_p$N$(R)_2$.

In another embodiment of formula IIIa or IIIa', X is O, Y is —O—$(CH_2)_m$COOR or —O—$(CH_2)_m$CON$(R)_2$, wherein the groups bound to the nitrogen atom may be in the Z- or E-configuration; $R^1$ and $R^2$ are independently hydrogen or halogen; and $R^9$ and $R^{10}$ are hydrogen.

In one embodiment of formula IIIa or IIIa', the invention provides a compound wherein:

X is O or NR;

Y is —O—$(CH_2)_m$COOR or —O—$(CH_2)_m$CON$(R)_2$, wherein the groups bound to the nitrogen atom may be in the Z- or E-configuration;

$R^1$ and $R^2$ are independently hydrogen, halogen, OR, N$(R)_2$ or aliphatic;

$R^3$ and $R^4$ are independently hydrogen, aliphatic, OR, N$(R)_2$, —$(CH_2)_m$N(R)C(O)CH$_2)_p$R, —$(CH_2)_m$OC(O)$(CH_2)_p$R, —$(CH_2)_m$C(O)$(CH_2)_p$N$(R)_2$, —$(CH_2)_m$C(O)$(CH_2)_p$OR, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —O$(CH_2)_m$N$_3$—$(CH_2)_m$N$(R)_2$, —$(CH_2)_m$OR, —$(CH_2)_m$S(O)$_2(CH_2)_p$R, —$(CH_2)_m$S(O)$_2(CH_2)_p$R, —$(CH_2)_m$SO$_2(CH_2)_p$N$(R)_2$, or —$(CH_2)_m$N(R)SO$_2(CH_2)_p$R;

$R^5$ and $R^6$ are independently hydrogen, aliphatic, alkylaryl, aralkyl, aryl, heteroalkyl, alkylheteroaryl, heterocyclyl, heteroaryl, OR, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, —NR$(CH_2)_m$OC(O)$(CH_2)_p$N$(R)_2$, —$(CH_2)_m$N(R)C(O)CH$_2)_p$R, —$(CH_2)_m$OC(O)$(CH_2)_p$R, —$(CH_2)_m$C(O)$(CH_2)_p$N$(R)_2$, —$(CH_2)_m$C(O)$(CH_2)_p$OR, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —O$(CH_2)_m$N$_3$—$(CH_2)_m$N$(R)_2$, —$(CH_2)_m$OR, —$(CH_2)_m$S(O)$(CH_2)_p$R, —$(CH_2)_m$S(O)$_2(CH_2)_p$R, —$(CH_2)_m$SO$_2(CH_2)_p$N$(R)_2$, or —$(CH_2)_m$N(R)SO$_2(CH_2)_p$R;

$R^7$, $R^8$, $R^9$ and $R^{10}$ are independently hydrogen, halogen, aliphatic, alkylaryl, aralkyl, aryl, heteroalkyl, alkylheteroaryl, heterocyclyl, heteroaryl, OR, N$(R)_2$, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, —NR$(CH_2)_m$OC(O)$(CH_2)_p$N$(R)_2$, —$(CH_2)_m$N(R)C(O)$(CH_2)_p$R, —$(CH_2)_m$OC(O)$(CH_2)_p$R, —$(CH_2)_m$C(O)$(CH_2)_p$N$(R)_2$, —$(CH_2)_m$C(O)$(CH_2)_p$OR, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —O$(CH_2)_m$N$_3$—$(CH_2)_m$N$(R)_2$, —$(CH_2)_m$OR, —$(CH_2)_m$S(O)$(CH_2)_p$R, —$(CH_2)_m$S(O)$_2(CH_2)_p$R, —$(CH_2)_m$SO$_2(CH_2)_p$N$(R)_2$, or —$(CH_2)_m$N(R)SO$_2(CH_2)_p$R; and R, m and p are as defined above for formula Ia.

In yet another embodiment of formula IIIa or IIIa', X is O or NR;

Y is —O—$(CH_2)_m$COOR or —O—$(CH_2)_m$CON$(R)_2$, wherein the groups bound to the nitrogen atom may be in the Z- or E-configuration;

$R^1$ and $R^2$ are independently hydrogen, halogen;

$R^3$ and $R^4$ are independently hydrogen, aliphatic, OR, N$(R)_2$, —$(CH_2)_m$N(R)C(O)CH$_2)_p$R, —$(CH_2)_m$OC(O)$(CH_2)_p$R, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —$(CH_2)_m$N$(R)_2$, or —$(CH_2)_m$OR;

$R^5$ and $R^6$ are independently hydrogen, aliphatic, aralkyl, heteroalkyl, heterocyclyl, or heteroaryl; and $R^7$, $R^8$, $R^9$ and $R^{10}$ are independently hydrogen, aliphatic, alkylaryl, aralkyl, aryl, heteroalkyl, alkylheteroaryl, heterocyclyl, heteroaryl, OR, N$(R)_2$, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, or —NR$(CH_2)_m$OC(O)$(CH_2)_p$N$(R)_2$.

In yet another embodiment of formula IIIa or IIIa', X is O or NR;

Y is —O—(CH$_2$)$_m$COOR or =O—(CH$_2$)$_m$CON(R)$_2$, wherein the groups bound to the nitrogen atom may be in the Z- or E-configuration; R$^1$ and R$^2$ are independently hydrogen, halogen;

R$^3$ and R$^4$ are independently hydrogen, aliphatic, —(CH$_2$)$_m$ N(R)C(O)CH$_2$)$_p$R, —(CH$_2$)$_m$OC(O)(CH$_2$)$_p$R,—(CH$_2$)$_m$N(R)C(O)(CH$_2$)$_p$OR, —(CH$_2$)$_m$N(R)C(O)(CH$_2$)$_p$N(R)$_2$, —(CH$_2$)$_m$OC(O)(CH$_2$)$_p$OR, —(CH$_2$)$_m$OC(O)(CH$_2$)$_p$N(R)$_2$, —(CH$_2$)$_m$N$_3$, —(CH$_2$)$_m$N(R)$_2$, or —(CH$_2$)$_m$OR;

R$^5$ and R$^6$ are independently hydrogen, aliphatic, aralkyl, heteroalkyl, heterocyclyl, or heteroaryl;

R$^7$, R$^8$ are independently alkylaryl, aralkyl, aryl, heteroalkyl, alkylheteroaryl, heterocyclyl, heteroaryl, OR, N(R)$_2$, SR, —O(CH$_2$)$_m$N(R)C(O)(CH$_2$)$_p$R, —O(CH$_2$)$_m$OC(O)(CH$_2$)$_p$R, —O(CH$_2$)$_m$C(O)(CH$_2$)$_p$N(R)$_2$, —O(CH$_2$)$_m$C(O)(CH$_2$)$_p$OR, —O(CH$_2$)$_m$N(R)C(O)(CH$_2$)$_p$OR, —O(CH$_2$)$_m$ N(R)C(O)(CH$_2$)$_p$N(R)$_2$, —O(CH$_2$)$_m$OC(O)(CH$_2$)$_p$OR, —O(CH$_2$)$_m$OC(O)(CH$_2$)$_p$N(R)$_2$, —NR(CH$_2$)$_m$N(R)C(O)(CH$_2$)$_p$R, —NR(CH$_2$)$_m$OC(O)(CH$_2$)$_p$R, —NR(CH$_2$)$_m$C(O)(CH$_2$)$_p$N(R)$_2$, —NR(CH$_2$)$_m$C(O)(CH$_2$)$_p$OR, —NR(CH$_2$)$_m$N(R)C(O)(CH$_2$)$_p$OR, —NR(CH$_2$)$_m$N(R)C(O)(CH$_2$)$_p$N(R)$_2$, —NR(CH$_2$)$_m$OC(O)(CH$_2$)$_p$OR, or —NR(CH$_2$)$_m$OC(O)(CH$_2$)$_p$N(R)$_2$; and R$^9$ and R$^{10}$ independently hydrogen, aliphatic, alkylaryl, aralkyl, aryl, heteroalkyl, alkylheteroaryl, heterocyclyl, heteroaryl, OR, N(R)$_2$, SR, —O(CH$_2$)$_m$N(R)C(O)(CH$_2$)$_p$R, —O(CH$_2$)$_m$OC(O)(CH$_2$)$_p$R, —O(CH$_2$)$_m$C(O)(CH$_2$)$_p$N(R)$_2$, —O(CH$_2$)$_m$C(O)(CH$_2$)$_p$OR, —O(CH$_2$)$_m$N(R)C(O)(CH$_2$)$_p$OR, —O(CH$_2$)$_m$N(R)C(O)(CH$_2$)$_p$N(R)$_2$, —O(CH$_2$)$_m$OC(O)(CH$_2$)$_p$OR, —O(CH$_2$)$_m$OC(O)(CH$_2$)$_p$N(R)$_2$, —NR(CH$_2$)$_m$N(R)C(O)(CH$_2$)$_p$R, —NR(CH$_2$)$_m$OC(O)(CH$_2$)$_p$R, —NR(CH$_2$)$_m$C(O)(CH$_2$)$_p$N(R)$_2$, —NR(CH$_2$)$_m$C(O)(CH$_2$)$_p$OR, —NR(CH$_2$)$_m$N(R)C(O)(CH$_2$)$_p$OR, —NR(CH$_2$)$_m$N(R)C(O)(CH$_2$)$_p$N(R)$_2$, —NR(CH$_2$)$_m$OC(O)(CH$_2$)$_p$OR, or —NR(CH$_2$)$_m$OC(O)(CH$_2$)$_p$N(R)$_2$.

In yet another embodiment of formula IIIa or IIIa', X is O or NR;

Y is —O—(CH$_2$)$_m$COOR or —O—(CH$_2$)$_m$CON(R)$_2$, wherein the groups bound to the nitrogen atom may be in the Z- or E-configuration;

R$^1$ and R$^2$ are independently hydrogen, halogen;

R$^3$ and R$^4$ are independently hydrogen, aliphatic, —(CH$_2$)$_m$ N(R)C(O)CH$_2$)$_p$R, —(CH$_2$)$_m$OC(O)(CH$_2$)$_p$R, —(CH$_2$)$_m$N(R)C(O)(CH$_2$)$_p$OR, —(CH$_2$)$_m$N(R)C(O)(CH$_2$)$_p$N(R)$_2$, —(CH$_2$)$_m$OC(O)(CH$_2$)$_p$OR, —(CH$_2$)$_m$OC(O)(CH$_2$)$_p$N(R)$_2$, —(CH$_2$)$_m$N$_3$, —(CH$_2$)$_m$N(R)$_2$, or —(CH$_2$)$_m$OR;

R$^5$ and R$^6$ are independently hydrogen, aliphatic, aralkyl, heteroalkyl, heterocyclyl, or heteroaryl;

R$^7$, R$^8$ are independently OR, N(R)$_2$, SR, —O(CH$_2$)$_m$N(R)C(O)(CH$_2$)$_p$R, —O(CH$_2$)$_m$OC(O)(CH$_2$)$_p$R, —O(CH$_2$)$_m$C(O)(CH$_2$)$_p$N(R)$_2$, —O(CH$_2$)$_m$C(O)(CH$_2$)$_p$OR, —O(CH$_2$)$_m$N(R)C(O)(CH$_2$)$_p$OR, —O(CH$_2$)$_m$N(R)C(O)(CH$_2$)$_p$N(R)$_2$, —O(CH$_2$)$_m$OC(O)(CH$_2$)$_p$OR, —O(CH$_2$)$_m$OC(O)(CH$_2$)$_p$N(R)$_2$, —NR(CH$_2$)$_m$N(R)C(O)(CH$_2$)$_p$R, —NR(CH$_2$)$_m$OC(O)(CH$_2$)$_p$R, —NR(CH$_2$)$_m$C(O)(CH$_2$)$_p$N(R)$_2$, —NR(CH$_2$)$_m$C(O)(CH$_2$)$_p$OR, —NR(CH$_2$)$_m$N(R)C(O)(CH$_2$)$_p$OR, NR(CH$_2$)$_m$ N(R)C(O)(CH$_2$)$_p$N(R)$_2$, —NR(CH$_2$)$_m$OC(O)(CH$_2$)$_p$OR, or —NR(CH$_2$)$_m$OC(O)(CH$_2$)$_p$N(R)$_2$; and R$^9$ and R$^{10}$ independently hydrogen, aliphatic, alkylaryl, aralkyl, aryl, heteroalkyl, alkylheteroaryl, heterocyclyl, heteroaryl, OR, N(R)$_2$, SR, —O(CH$_2$)$_m$N(R)C(O)(CH$_2$)$_p$R, —O(CH$_2$)$_m$OC(O)(CH$_2$)$_p$R, —O(CH$_2$)$_m$C(O)(CH$_2$)$_p$N(R)$_2$, —O(CH$_2$)$_m$C(O)(CH$_2$)$_p$OR, —O(CH$_2$)$_m$N(R)C(O)(CH$_2$)$_p$OR, —O(CH$_2$)$_m$N(R)C(O)(CH$_2$)$_p$N(R)$_2$, —O(CH$_2$)$_m$OC(O)(CH$_2$)$_p$OR, —O(CH$_2$)$_m$OC(O)(CH$_2$)$_p$N(R)$_2$, —NR(CH$_2$)$_m$N(R)C(O)(CH$_2$)$_p$R, —NR(CH$_2$)$_m$OC(O)(CH$_2$)$_p$R, —NR(CH$_2$)$_m$C(O)(CH$_2$)$_p$N(R)$_2$, —NR(CH$_2$)$_m$C(O)(CH$_2$)$_p$OR, —NR(CH$_2$)$_m$N(R)C(O)(CH$_2$)$_p$OR, —NR(CH$_2$)$_m$N(R)C(O)(CH$_2$)$_p$N(R)$_2$, —NR(CH$_2$)$_m$OC(O)(CH$_2$)$_p$OR, or NR(CH$_2$)$_m$OC(O)(CH$_2$)$_p$N(R)$_2$.

In another embodiment of the invention, a compound of formula IVa, a tautomer thereof, or a pharmaceutically acceptable salt, solvate, ester or prodrug thereof, is provided:

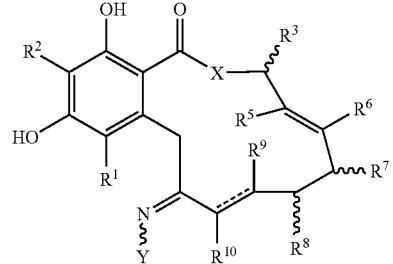

IV wherein the variables X, Y, R$^1$, R$^2$, R$^3$, R$^5$, R$^6$, R$^7$, R$^8$, R$^9$, R$^{10}$, R, m and p are as defined for formula Ia above; and the dashed lines represents a single or double bond.

In one embodiment of formula IV, X is O or NR.

In another embodiment of formula IV, Y is —O—(CH$_2$)$_m$COOR or —O—(CH$_2$)$_m$CON(R)$_2$, wherein the groups bound to the nitrogen atom may be in the Z- or E-configuration.

In another embodiment of formula IV, R$^1$ and R$^2$ are hydrogen.

In still another embodiment of formula IV, R$^3$ and R$^4$ are independently alkyl or hydrogen.

In still another embodiment, X is O, and R$^9$ and R$^{10}$ are hydrogen.

In another embodiment of formula IV, R$^7$ or R$^8$ are not hydrogen or aliphatic.

In another embodiment of formula IV, R$^3$ or R$^4$ are not hydrogen or aliphatic.

In another embodiment of formula IV, X is O, Y is —O—(CH$_2$)$_m$COOR or —O—(CH$_2$)$_m$CON(R)$_2$, wherein the groups bound to the nitrogen atom may be in the Z- or E-configuration; R$^1$ and R$^2$ are independently hydrogen or halogen; and R$^9$ and R$^{10}$ are hydrogen.

In another embodiment of formula IV, X is O or NR, and a double bond is present between the carbon atoms bearing R$^9$ and R$^{10}$.

In yet another embodiment of formula IV, X is O or NR, and the bond between the carbon atoms bearing R$^9$ and R$^{10}$ is a single bond.

In another embodiment of formula IV, Y is —O—(CH$_2$)$_m$COOR or —O—(CH$_2$)$_m$CON(R)$_2$, wherein the groups bound to the nitrogen atom may be in the Z- or E-configuration.

In one embodiment of formula IV, the invention provides a compound wherein:

X is O or NR;

Y is —O—(CH$_2$)$_m$COOR or —O—(CH$_2$)$_m$CON(R)$_2$, wherein the groups bound to the nitrogen atom may be in the Z- or E-configuration;

R$^1$ and R$^2$ are independently hydrogen, halogen, OR, N(R)$_2$ or aliphatic;

R$^3$ is hydrogen, aliphatic, OR, N(R)$_2$, —(CH$_2$)$_m$N(R)C(O)CH$_2$)$_p$R, —(CH$_2$)$_m$OC(O)(CH$_2$)$_p$R, —(CH$_2$)$_m$C(O)(CH$_2$)$_p$N(R)$_2$, —(CH$_2$)$_m$C(O)(CH$_2$)$_p$OR, —(CH$_2$)$_m$N(R)C(O)(CH$_2$)$_p$ OR, —(CH$_2$)$_m$N(R)C(O)(CH$_2$)$_p$N(R)$_2$, —(CH$_2$)$_m$OC(O)(CH$_2$)$_p$OR, —(CH$_2$)$_m$OC(O)(CH$_2$)$_p$N(R)$_2$, —(CH$_2$)$_m$N$_3$, —O(CH$_2$)$_m$N$_3$—(CH$_2$)$_m$N(R)$_2$, —(CH$_2$)$_m$OR, —(CH$_2$)$_m$S(O)(CH$_2$)$_p$R, —(CH$_2$)$_m$S(O)$_2$(CH$_2$)$_p$R, —(CH$_2$)$_m$SO$_2$(CH$_2$)$_p$N(R)$_2$, or —(CH$_2$)$_m$N(R)SO$_2$(CH$_2$)$_p$R;

R$^5$, R$^6$, R$^9$ and R$^{10}$ are independently hydrogen, aliphatic, alkylaryl, aralkyl, aryl, heteroalkyl, alkylheteroaryl, heterocyclyl, heteroaryl, OR, SR, —O(CH$_2$)$_m$N(R)C(O)(CH$_2$)$_p$R, —O(CH$_2$)$_m$OC(O)(CH$_2$)$_p$R, —O(CH$_2$)$_m$C(O)(CH$_2$)$_p$N(R)$_2$, —O(CH$_2$)$_m$C(O)(CH$_2$)$_p$OR, —O(CH$_2$)$_m$N(R)C(O)(CH$_2$)$_p$OR, —O(CH$_2$)$_m$N(R)C(O)(CH$_2$)$_p$N(R)$_2$, —O(CH$_2$)$_m$OC(O)(CH$_2$)$_p$OR, —O(CH$_2$)$_m$OC(O)(CH$_2$)$_p$N(R)$_2$, —NR(CH$_2$)$_m$N(R)C(O)(CH$_2$)$_p$R, —NR(CH$_2$)$_m$OC(O)(CH$_2$)$_p$R, —NR(CH$_2$)$_m$C(O)(CH$_2$)$_p$N(R)$_2$, —NR(CH$_2$)$_m$C(O)(CH$_2$)$_p$OR, —NR(CH$_2$)$_m$N(R)C(O)(CH$_2$)$_p$OR, —NR(CH$_2$)$_m$N(R)C(O)(CH$_2$)$_p$N(R)$_2$, —NR(CH$_2$)$_m$OC(O)(CH$_2$)$_p$OR, —NR(CH$_2$)$_m$OC(O)(CH$_2$)$_p$N(R)$_2$, —(CH$_2$)$_m$N(R)C(O)(CH$_2$)$_p$R, —(CH$_2$)$_m$OC(O)(CH$_2$)$_p$R, —(CH$_2$)$_m$C(O)(CH$_2$)$_p$N(R)$_2$, —(CH$_2$)$_m$C(O)(CH$_2$)$_p$OR, —(CH$_2$)$_m$N(R)C(O)(CH$_2$)$_p$OR, —(CH$_2$)$_m$N(R)C(O)(CH$_2$)$_p$N(R)$_2$, —(CH$_2$)$_m$OC(O)(CH$_2$)$_p$OR, —(CH$_2$)$_m$OC(O)(CH$_2$)$_p$N(R)$_2$, —(CH$_2$)$_m$N$_3$, —O(CH$_2$)$_m$N$_3$—(CH$_2$)$_m$N(R)$_2$, —(CH$_2$)$_m$OR, —(CH$_2$)$_m$S(O)(CH$_2$)$_p$R, —(CH$_2$)$_m$S(O)$_2$(CH$_2$)$_p$R, —(CH$_2$)$_m$SO$_2$(CH$_2$)$_p$N(R)$_2$, or —(CH$_2$)$_m$N(R)SO$_2$(CH$_2$)$_p$R; and R$^7$ and R$^8$ are independently hydrogen, halogen, aliphatic, alkylaryl, aralkyl, aryl, heteroalkyl, alkylheteroaryl, heterocyclyl, heteroaryl, OR, N(R)$_2$, SR, —O(CH$_2$)$_m$N(R)C(O)(CH$_2$)$_p$R, —O(CH$_2$)$_m$OC(O)(CH$_2$)$_p$R, —O(CH$_2$)$_m$C(O)(CH$_2$)$_p$N(R)$_2$, —O(CH$_2$)$_m$C(O)(CH$_2$)$_p$OR, —O(CH$_2$)$_m$N(R)C(O)(CH$_2$)$_p$OR, —O(CH$_2$)$_m$N(R)C(O)(CH$_2$)$_p$N(R)$_2$, —O(CH$_2$)$_m$OC(O)(CH$_2$)$_p$OR, —O(CH$_2$)$_m$OC(O)(CH$_2$)$_p$N(R)$_2$, —NR(CH$_2$)$_m$N(R)C(O)(CH$_2$)$_p$R, —NR(CH$_2$)$_m$OC(O)(CH$_2$)$_p$R, —NR(CH$_2$)$_m$C(O)(CH$_2$)$_p$N(R)$_2$, —NR(CH$_2$)$_m$C(O)(CH$_2$)$_p$OR, —NR(CH$_2$)$_m$N(R)C(O)(CH$_2$)$_p$OR, —NR(CH$_2$)$_m$N(R)C(O)(CH$_2$)$_p$N(R)$_2$, —NR(CH$_2$)$_m$OC(O)(CH$_2$)$_p$OR, —NR(CH$_2$)$_m$OC(O)(CH$_2$)$_p$N(R)$_2$, —(CH$_2$)$_m$N(R)C(O)(CH$_2$)$_p$R, —(CH$_2$)$_m$OC(O)(CH$_2$)$_p$R, —(CH$_2$)$_m$C(O)(CH$_2$)$_p$N(R)$_2$, —(CH$_2$)$_m$C(O)(CH$_2$)$_p$OR, —(CH$_2$)$_m$N(R)C(O)(CH$_2$)$_p$OR, —(CH$_2$)$_m$N(R)C(O)(CH$_2$)$_p$N(R)$_2$, —(CH$_2$)$_m$OC(O)(CH$_2$)$_p$OR, —(CH$_2$)$_m$OC(O)(CH$_2$)$_p$N(R)$_2$, —(CH$_2$)$_m$N$_3$, —O(CH$_2$)$_m$N$_3$—(CH$_2$)$_m$N(R)$_2$, —(CH$_2$)$_m$OR, —(CH$_2$)$_m$S(O)(CH$_2$)$_p$R, —(CH$_2$)$_m$S(O)$_2$(CH$_2$)$_p$R, —(CH$_2$)$_m$SO$_2$(CH$_2$)$_p$N(R)$_2$, or —(CH$_2$)$_m$N(R)SO$_2$(CH$_2$)$_p$R.

In yet another embodiment of formula IV, X is O or NR;

Y is —O—(CH$_2$)$_m$COOR or —O—(CH$_2$)$_m$CON(R)$_2$, wherein the groups bound to the nitrogen atom may be in the Z- or E-configuration;

R$^1$ and R$^2$ are independently hydrogen, halogen;

R$^3$ is hydrogen, aliphatic, OR, N(R)$_2$, —(CH$_2$)$_m$N(R)C(O)CH$_2$)$_p$R, —(CH$_2$)$_m$OC(O)(CH$_2$)$_p$R, —(CH$_2$)$_m$N(R)C(O)(CH$_2$)$_p$OR, —(CH$_2$)$_m$N(R)C(O)(CH$_2$)$_p$N(R)$_2$, —(CH$_2$)$_m$OC(O)(CH$_2$)$_p$OR, —(CH$_2$)$_m$OC(O)(CH$_2$)$_p$N(R)$_2$, —(CH$_2$)$_m$N$_3$, —(CH$_2$)$_m$N(R)$_2$, or —(CH$_2$)$_m$OR;

R$^5$, R$^6$, R$^9$ and R$^{10}$ are independently hydrogen, aliphatic, aralkyl, heteroalkyl, heterocyclyl, or heteroaryl;

R$^7$ and R$^8$ are independently OR, N(R)$_2$, SR, —O(CH$_2$)$_m$N(R)C(O)(CH$_2$)$_p$R, —O(CH$_2$)$_m$OC(O)(CH$_2$)$_p$R, —O(CH$_2$)$_m$C(O)(CH$_2$)$_p$N(R)$_2$, —O(CH$_2$)$_m$C(O)(CH$_2$)$_p$OR, —O(CH$_2$)$_m$N(R)C(O)(CH$_2$)$_p$OR, —O(CH$_2$)$_m$N(R)C(O)(CH$_2$)$_p$N(R)$_2$, —O(CH$_2$)$_m$OC(O)(CH$_2$)$_p$OR, —O(CH$_2$)$_m$OC(O)(CH$_2$)$_p$N(R)$_2$, —NR(CH$_2$)$_m$N(R)C(O)(CH$_2$)$_p$R, —NR(CH$_2$)$_m$OC(O)(CH$_2$)$_p$R, —NR(CH$_2$)$_m$C(O)(CH$_2$)$_p$N(R)$_2$, —NR(CH$_2$)$_m$C(O)(CH$_2$)$_p$OR, —NR(CH$_2$)$_m$N(R)C(O)(CH$_2$)$_p$OR, —NR(CH$_2$)$_m$N(R)C(O)(CH$_2$)$_p$N(R)$_2$, —NR(CH$_2$)$_m$OC(O)(CH$_2$)$_p$OR, or —NR(CH$_2$)$_m$OC(O)(CH$_2$)$_p$N(R)$_2$.

In another embodiment of the invention, a compound of formula Va, a tautomer thereof, or a pharmaceutically acceptable salt, solvate, ester or prodrug thereof, is provided,

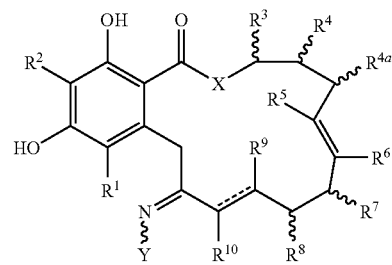

wherein the variables X, Y, R$^1$, R$^2$, R$^3$, R$^4$, R$^5$, R$^6$, R$^7$, R$^8$, R$^9$, R$^{10}$, R, m and p are as defined for formula Ia above; and R$^{4a}$ is as defined for R$^4$ in formula I above; and the dashed lines represents a single or double bond.

In one embodiment of formula Va, X is O or NR. In another embodiment of formula V, X is O or NR, and a double bond is present between the carbon atoms bearing R$^9$ and R$^{10}$.

In yet another embodiment of formula Va, X is O or NR, and the bond between the carbon atoms bearing R$^9$ and R$^{10}$ is a single bond.

In another embodiment of formula Va, Y is —O—(CH$_2$)$_m$COOR or —O—(CH$_2$)$_m$CON(R)$_2$, wherein the groups bound to the nitrogen atom may be in the Z- or E-configuration.

In another embodiment of formula Va, R$^1$ and R$^2$ are hydrogen.

In still another embodiment of formula Va, R$^3$ is alkyl or hydrogen.

In still another embodiment of formula Va, R$^4$ and R$^{4a}$ are independently alkyl or hydrogen.

In still another embodiment of formula Va, X is O, and R$^9$ and R$^{10}$ are hydrogen.

In another embodiment of formula Va, X is O, Y is —O—(CH$_2$)$_m$COOR or —O—(CH$_2$)$_m$CON(R)$_2$, wherein the groups bound to the nitrogen atom may be in the Z- or E-configuration; R$^1$ and R$^2$ are independently hydrogen or halogen; and R$^9$ and R$^{10}$ are hydrogen.

In one embodiment of formula Va, the invention provides a compound wherein:

X is O or NR;

Y is —O—$(CH_2)_m$COOR or —O—$(CH_2)_m$CON$(R)_2$, wherein the groups bound to the nitrogen atom may be in the Z- or E-configuration;

$R^1$ and $R^2$ are independently hydrogen, halogen, OR, N$(R)_2$ or aliphatic;

$R^3$, $R^4$ and $R^{4a}$ are independently hydrogen, aliphatic, OR, N$(R)_2$, —$(CH_2)_m$N(R)C(O)$(CH_2)_p$R, —$(CH_2)_m$OC(O)$(CH_2)_p$ R, —$(CH_2)_m$C(O)$(CH_2)_p$N$(R)_2$, —$(CH_2)_m$C(O)$(CH_2)_p$OR, —$(CH_2)_m$N(R)C(O)$(CH_2)_p$OR, —$(CH_2)_m$N(R)C(O)$(CH_2)_p$ N$(R)_2$, —$(CH_2)_m$OC(O)$(CH_2)_p$OR, —$(CH_2)_m$OC(O)$(CH_2)_p$ N$(R)_2$, —$(CH_2)_m$N$_3$, —O$(CH_2)_m$N$_3$—$(CH_2)_m$N$(R)_2$, —$(CH_2)_m$OR, —$(CH_2)_m$S(O)$(CH_2)_p$R, —$(CH_2)_m$S(O)$_2$$(CH_2)_p$R, —$(CH_2)_m$SO$_2$$(CH_2)_p$N$(R)_2$, or —$(CH_2)_m$N(R)SO$_2$$(CH_2)_p$R;

$R^5$, $R^6$, $R^9$ and $R^{10}$ are independently hydrogen, aliphatic, alkylaryl, aralkyl, aryl, heteroalkyl, alkylheteroaryl, heterocyclyl, heteroaryl, OR, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$ OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, —NR$(CH_2)_m$OC(O)$(CH_2)_p$N$(R)_2$, —$(CH_2)_m$N(R)C(O)$(CH_2)_p$R, —$(CH_2)_m$ OC(O)$(CH_2)_p$R, —$(CH_2)_m$C(O)$(CH_2)_p$N$(R)_2$, —$(CH_2)_m$C(O)$(CH_2)_p$OR, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$ OR, —$(CH_2)_m$OC(O)$(CH_2)_p$N$(R)_2$, —$(CH_2)_m$N$_3$, —O$(CH_2)_m$ N$_3$—$(CH_2)_m$N$(R)_2$, —$(CH_2)_m$OR, —$(CH_2)_m$S(O)$(CH_2)_p$ R, —$(CH_2)_m$S(O)$_2$$(CH_2)_p$R, —$(CH_2)_m$SO$_2$$(CH_2)_p$ N$(R)_2$, or —$(CH_2)_m$N(R)SO$_2$$(CH_2)_p$R;

$R^7$ and $R^8$ are independently hydrogen, halogen, aliphatic, alkylaryl, aralkyl, aryl, heteroalkyl, alkylheteroaryl, heterocyclyl, heteroaryl, OR, N$(R)_2$, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, —NR$(CH_2)_m$OC(O)$(CH_2)_p$N$(R)_2$, —$(CH_2)_m$N(R)C(O)$(CH_2)_p$R, —$(CH_2)_m$OC(O)$(CH_2)_p$R, —$(CH_2)_m$C(O)$(CH_2)_p$N$(R)_2$, —$(CH_2)_m$C(O)$(CH_2)_p$OR, —$(CH_2)_m$N(R)C(O)$(CH_2)_p$OR, —$(CH_2)_m$N(R)C(O)$(CH_2)_p$N$(R)_2$, —$(CH_2)_m$ OC(O)$(CH_2)_p$OR, —$(CH_2)_m$OC(O)$(CH_2)_p$N$(R)_2$, —$(CH_2)_m$ N$_3$, —O$(CH_2)_m$N$_3$—$(CH_2)_m$N$(R)_2$, —$(CH_2)_m$OR, —$(CH_2)_m$S(O)$(CH_2)_p$R, —$(CH_2)_m$S(O)$_2$$(CH_2)_p$R, —$(CH_2)_m$SO$_2$$(CH_2)_p$ N$(R)_2$, or —$(CH_2)_m$N(R)SO$_2$$(CH_2)_p$R.

In yet another embodiment of formula Va, X is O or NR;

Y is —O—$(CH_2)_m$COOR or —O—$(CH_2)_m$CON$(R)_2$, wherein the groups bound to the nitrogen atom may be in the Z- or E-configuration; $R^1$ and $R^2$ are independently hydrogen, halogen;

$R^3$, $R^4$ and $R^{4a}$ are independently hydrogen, aliphatic, OR, N$(R)_2$, —$(CH_2)_m$N(R)C(O)$(CH_2)_p$R, —$(CH_2)_m$OC(O)$(CH_2)_p$ R, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —$(CH_2)_m$N$(R)_2$, or —$(CH_2)_m$ OR;

$R^5$, $R^6$, $R^9$ and $R^{10}$ are independently hydrogen, aliphatic, aralkyl, heteroalkyl, heterocyclyl, or heteroaryl; and $R^7$ and $R^8$ are independently hydrogen, aliphatic, alkylaryl, aralkyl, aryl, heteroalkyl, alkylheteroaryl, heterocyclyl, heteroaryl, OR, N$(R)_2$, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$ OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$ OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, or —NR$(CH_2)_m$OC(O)$(CH_2)_p$N$(R)_2$.

In yet another embodiment of formula Va, X is O or NR;

Y is —O—$(CH_2)_m$COOR or —O—$(CH_2)_m$CON$(R)_2$, wherein the groups bound to the nitrogen atom may be in the Z- or E-configuration;

$R^1$ and $R^2$ are independently hydrogen, halogen;

$R^3$, $R^4$ and $R^{4a}$ are independently hydrogen, aliphatic, —$(CH_2)_m$N(R)C(O)$(CH_2)_p$R, —$(CH_2)_m$OC(O)$(CH_2)_p$R, —$(CH_2)_m$N(R)C(O)$(CH_2)_p$OR, —$(CH_2)_m$N(R)C(O)$(CH_2)_p$N$(R)_2$, —$(CH_2)_m$OC(O)$(CH_2)_p$OR, —$(CH_2)_m$OC(O)$(CH_2)_p$N$(R)_2$, —$(CH_2)_m$N$_3$, —$(CH_2)_m$N$(R)_2$, or —$(CH_2)_m$OR;

$R^5$, $R^6$, $R^9$ and $R^{10}$ are independently hydrogen, aliphatic, aralkyl, heteroalkyl, heterocyclyl, or heteroaryl;

$R^7$ and $R^8$ are independently OR, N$(R)_2$, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, or —NR$(CH_2)_m$OC(O)$(CH_2)_p$N$(R)_2$.

In specific embodiments of the present invention, the compounds presented in Table 1a, tautomers thereof, or pharmaceutically acceptable salts, solvates, esters or prodrugs thereof, are provided:

TABLE 1a
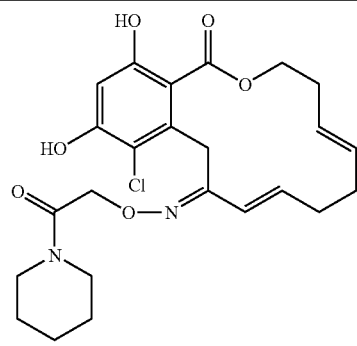
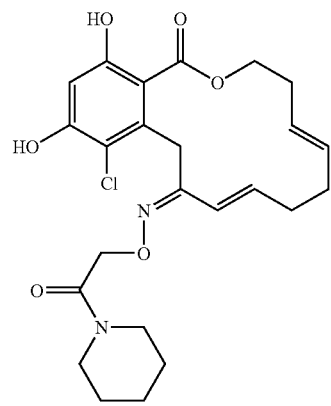
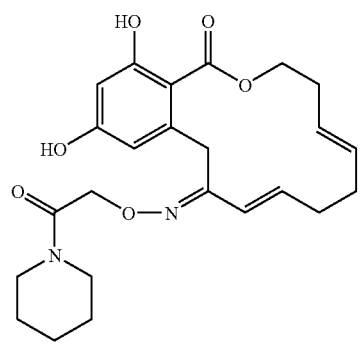
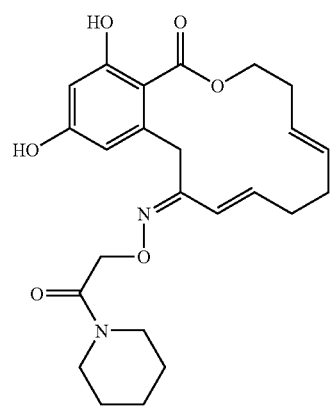

TABLE 1a-continued
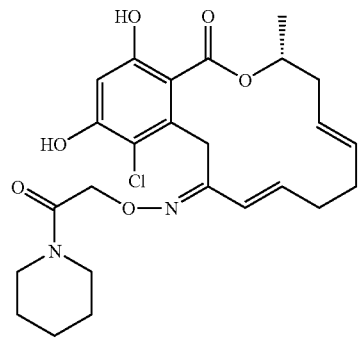
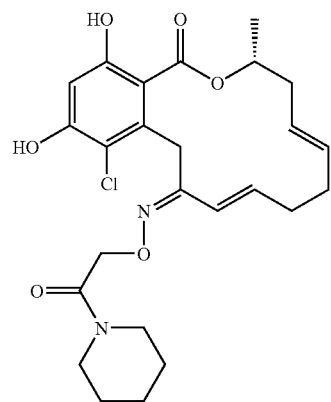
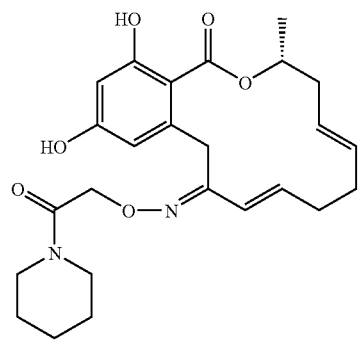
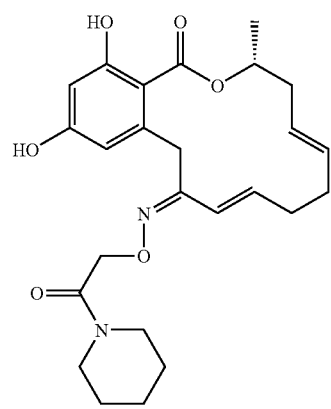

TABLE 1a-continued
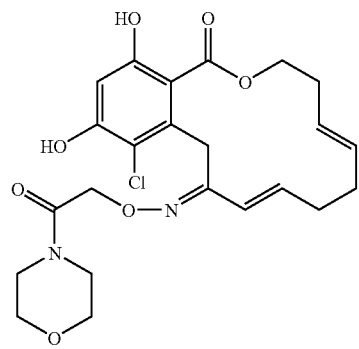
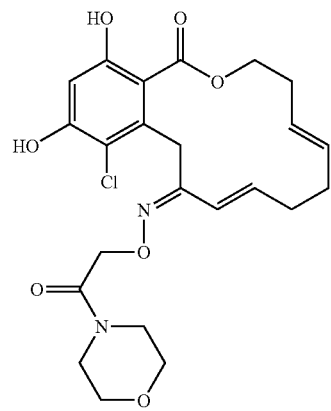
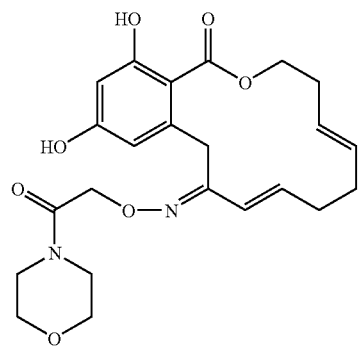
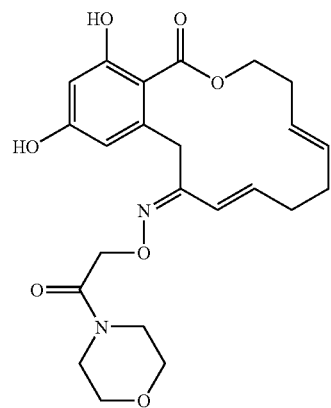

TABLE 1a-continued
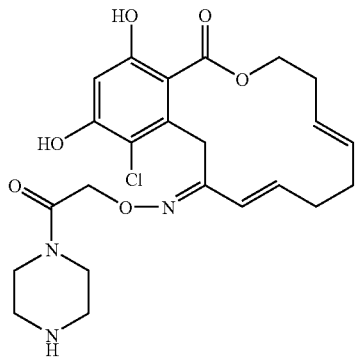
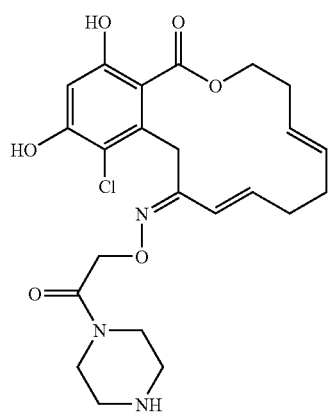
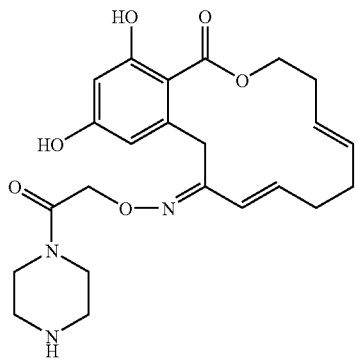
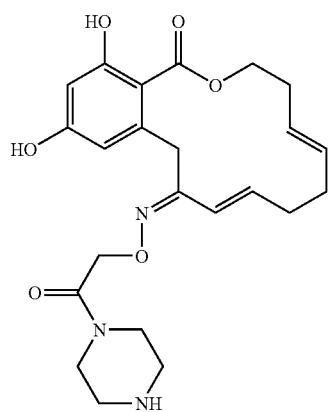

TABLE 1a-continued
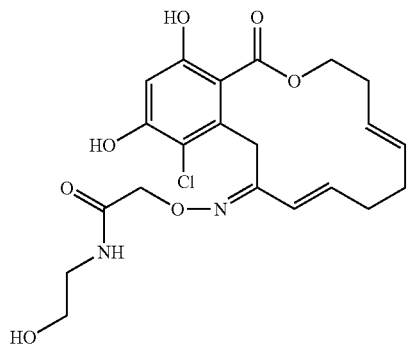
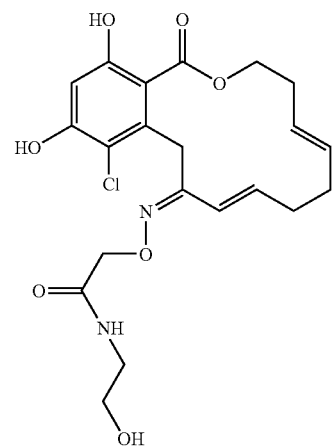
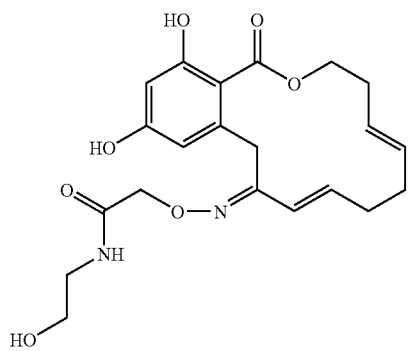
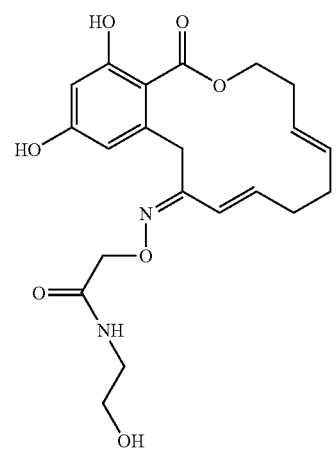

TABLE 1a-continued
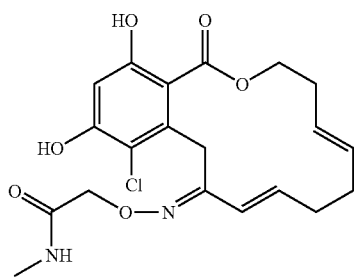
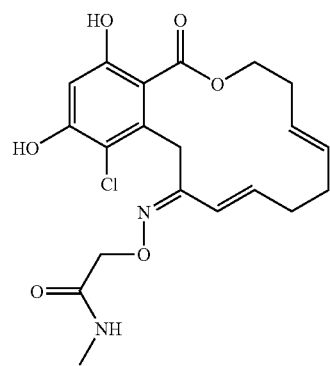
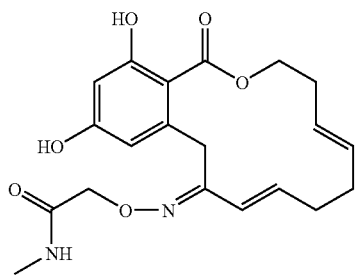
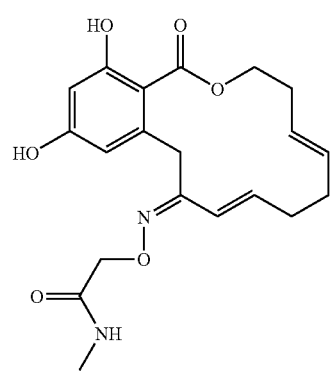
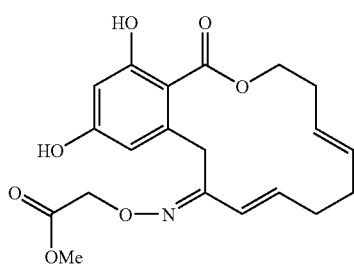

TABLE 1a-continued
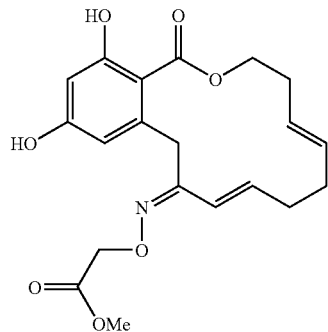
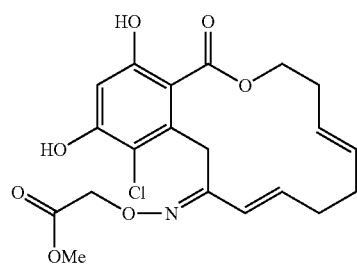
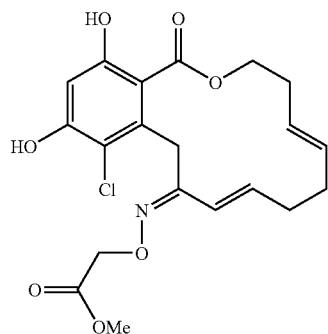
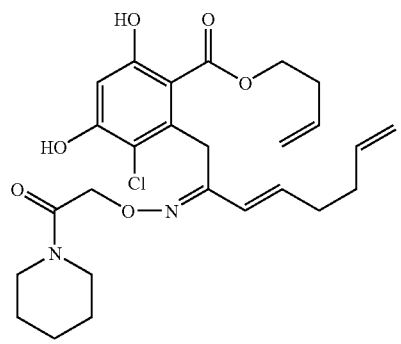

TABLE 1a-continued
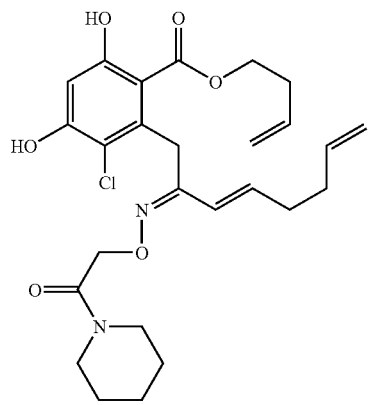
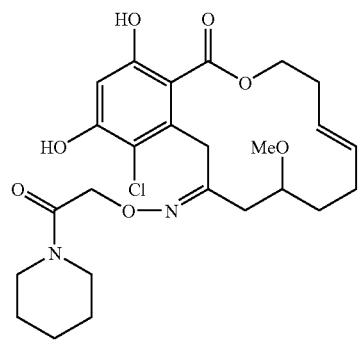
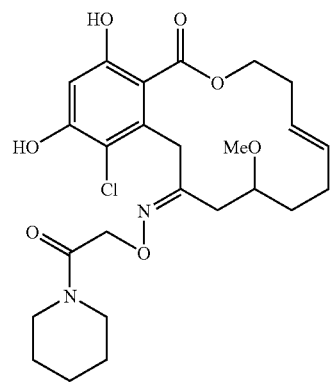
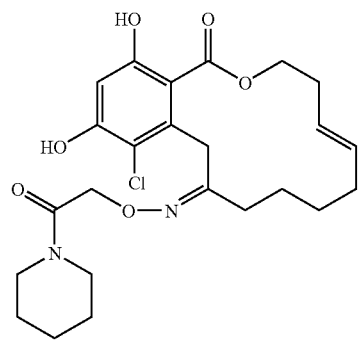

TABLE 1a-continued
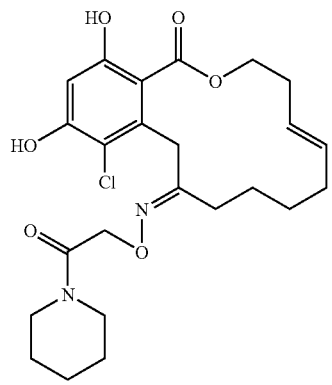
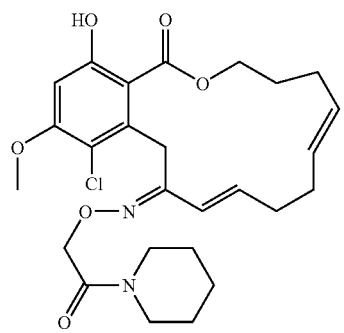
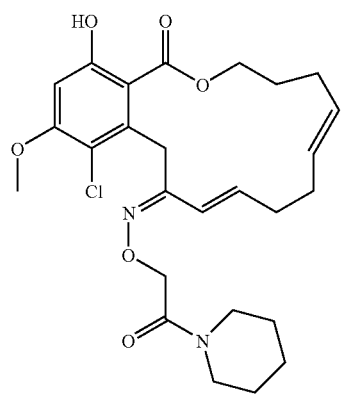
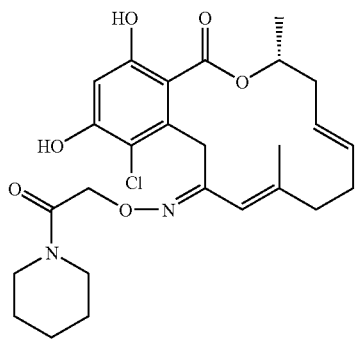

TABLE 1a-continued
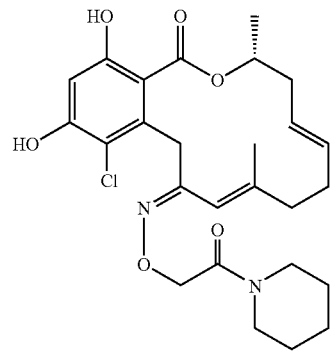
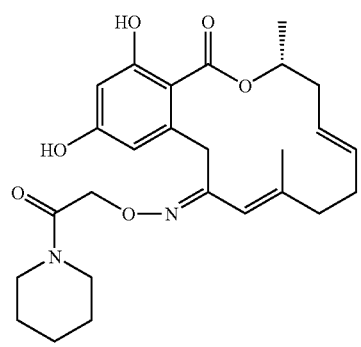
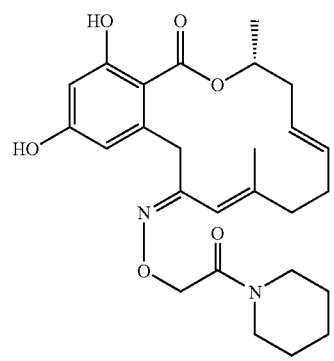
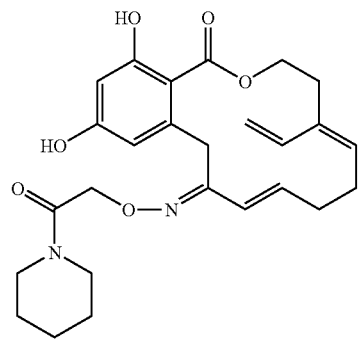

TABLE 1a-continued
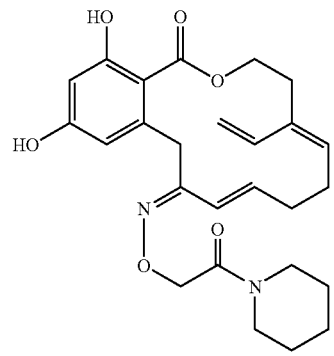
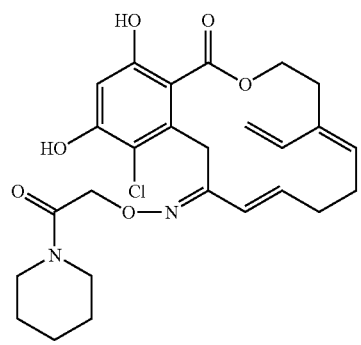
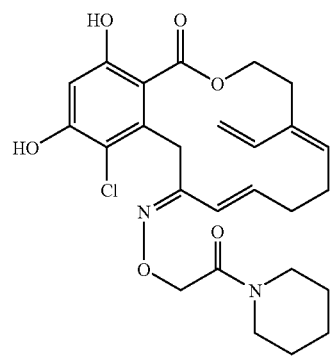
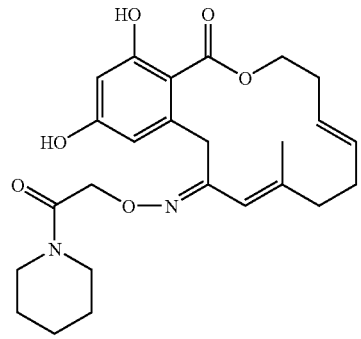

TABLE 1a-continued
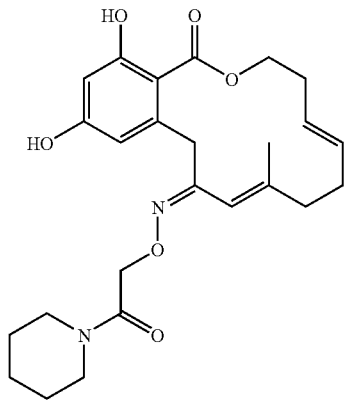
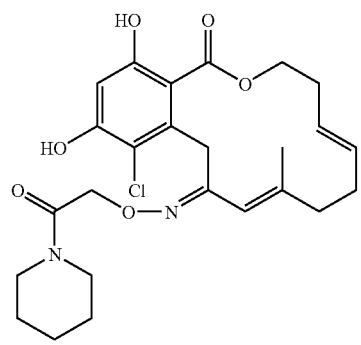
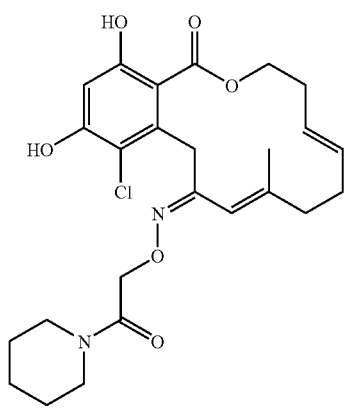
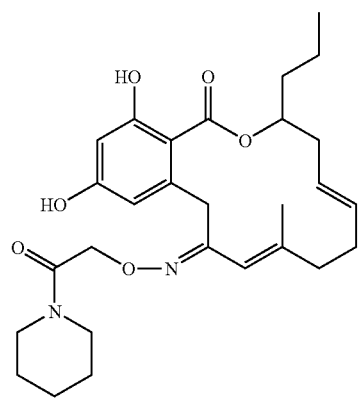

TABLE 1a-continued
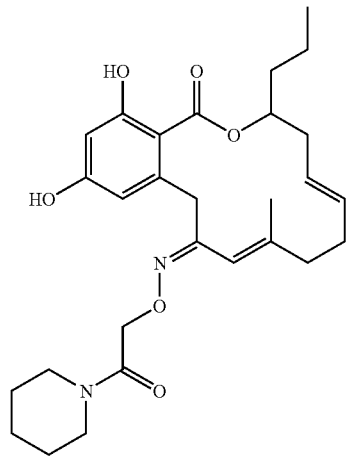
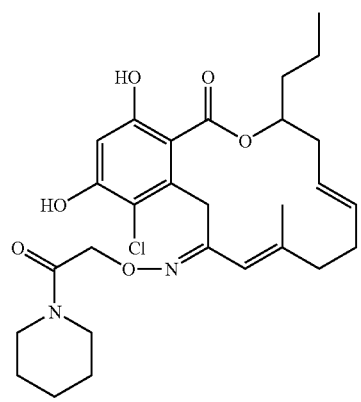
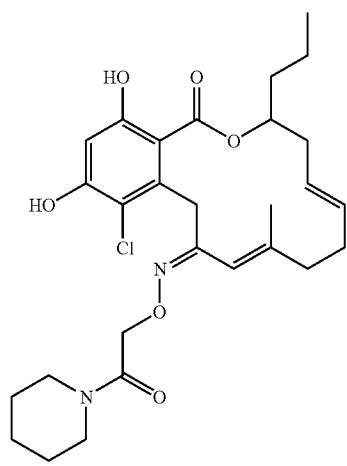

TABLE 1a-continued
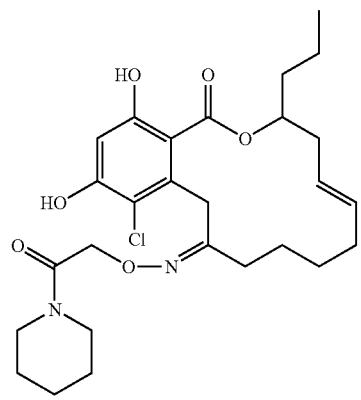
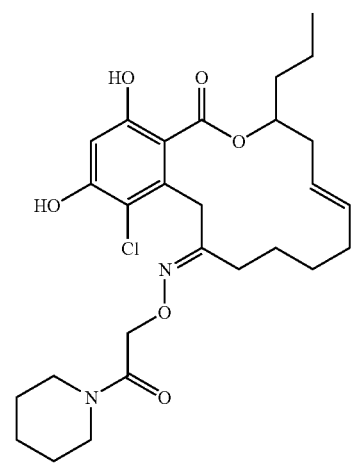
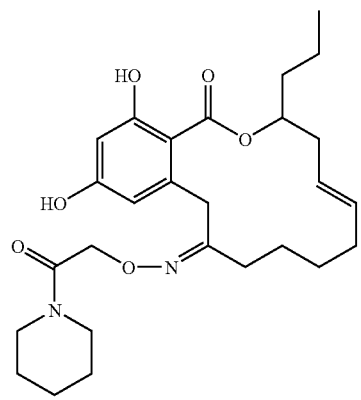

TABLE 1a-continued
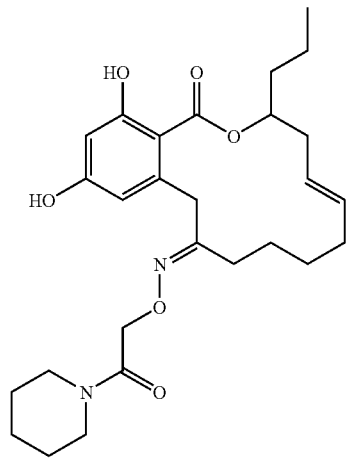
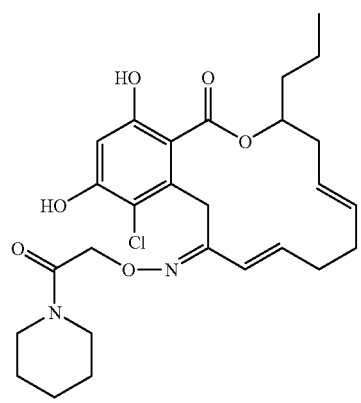
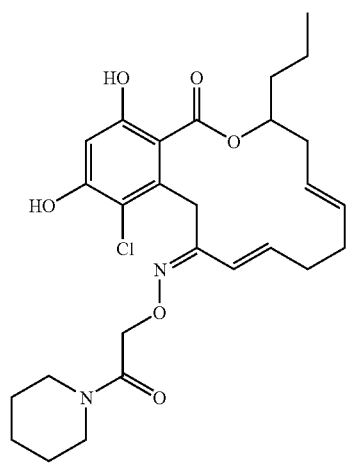

TABLE 1a-continued
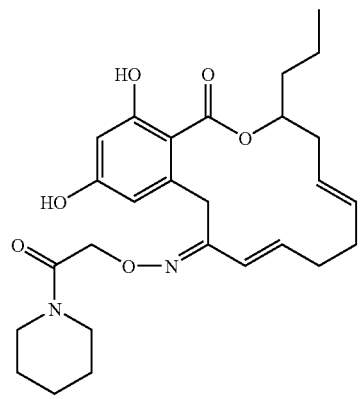
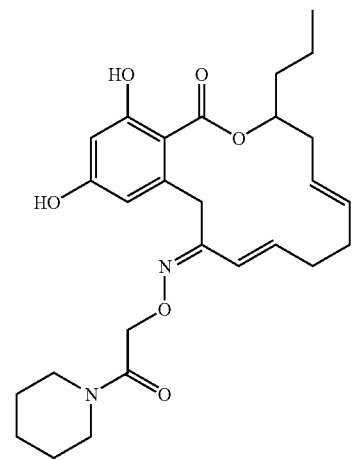
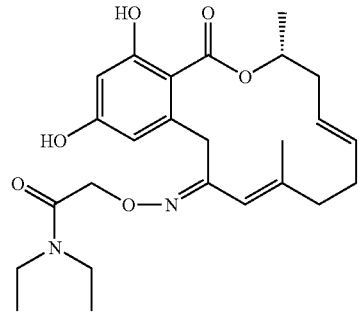
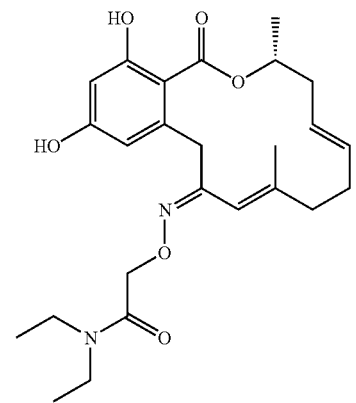

TABLE 1a-continued
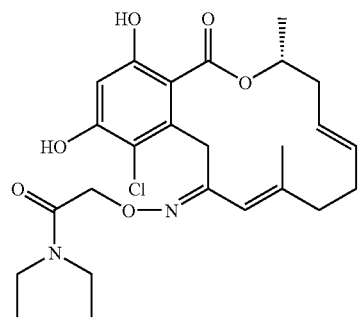
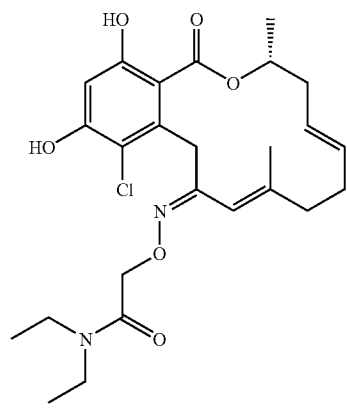
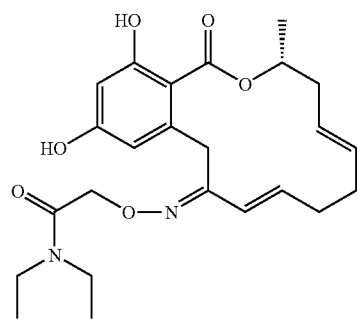
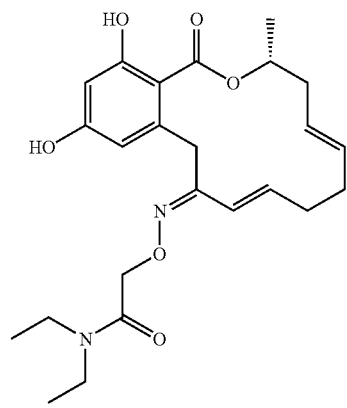

TABLE 1a-continued
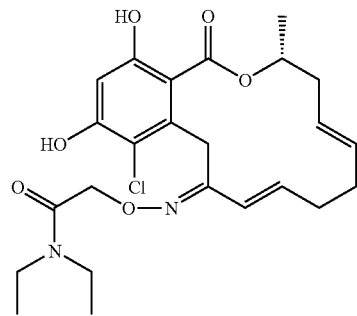
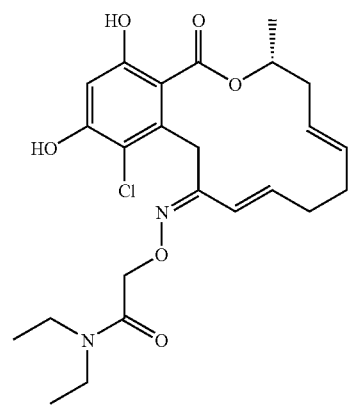
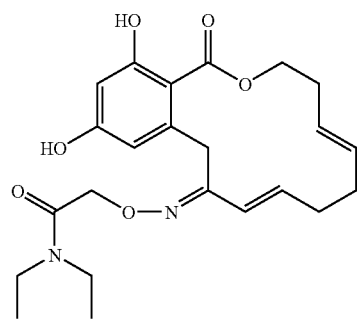
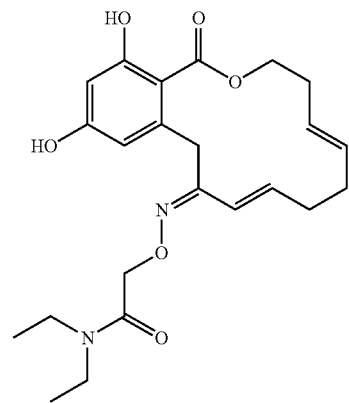

TABLE 1a-continued
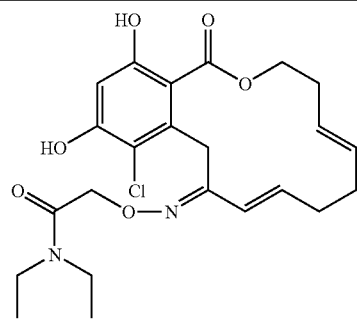
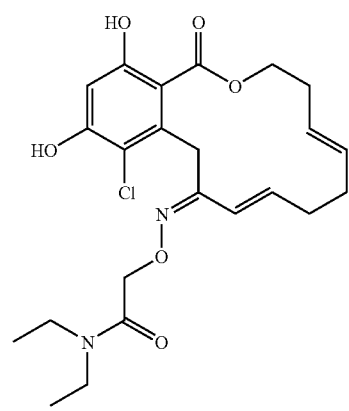
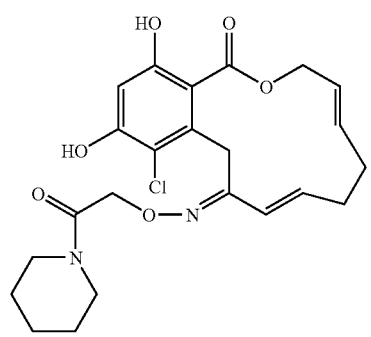
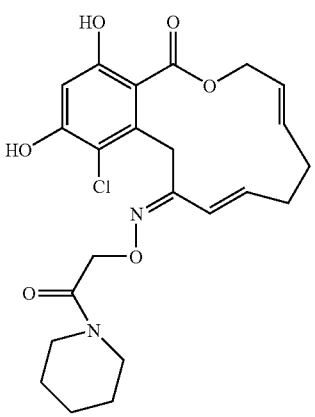

TABLE 1a-continued
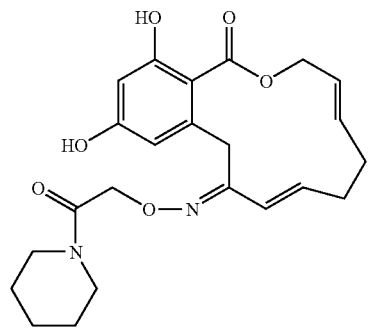
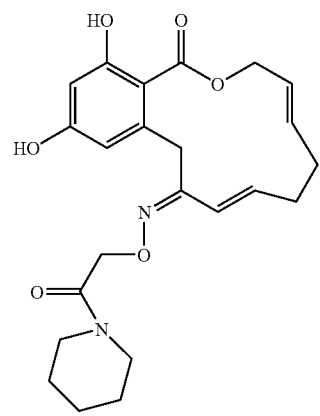
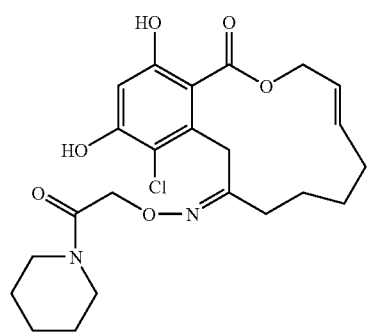
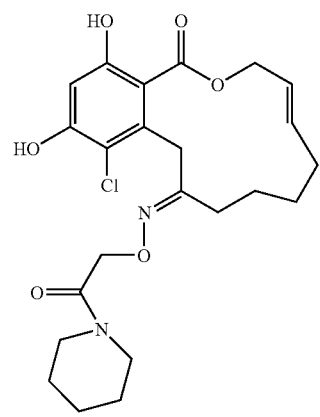

TABLE 1a-continued
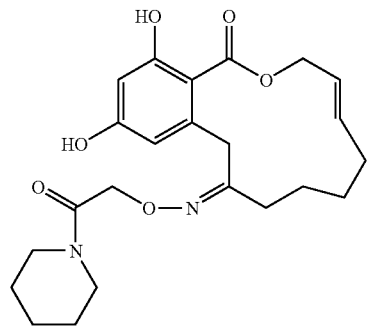
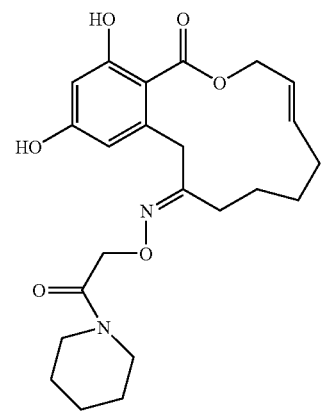
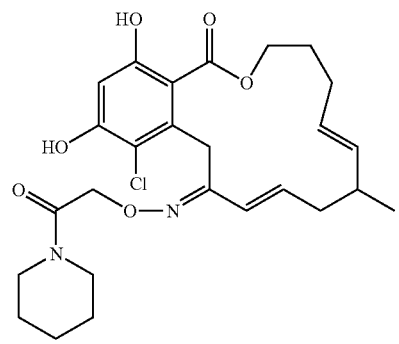
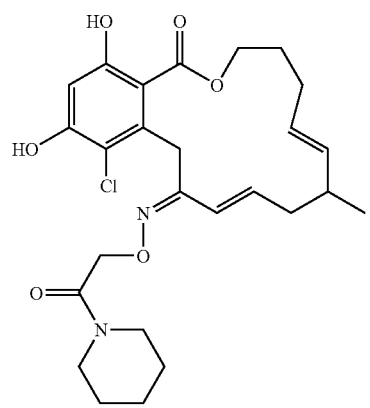

TABLE 1a-continued
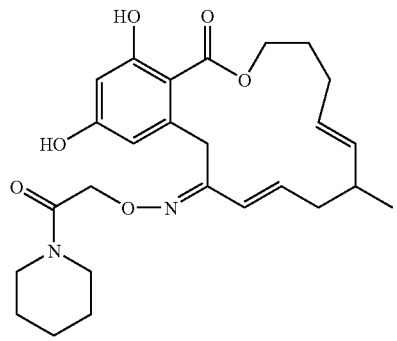
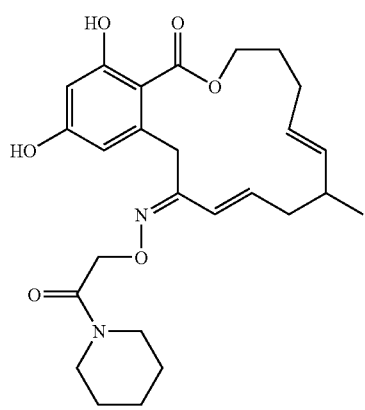
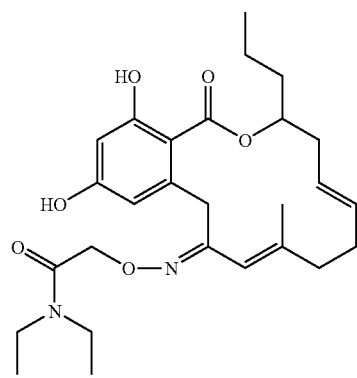
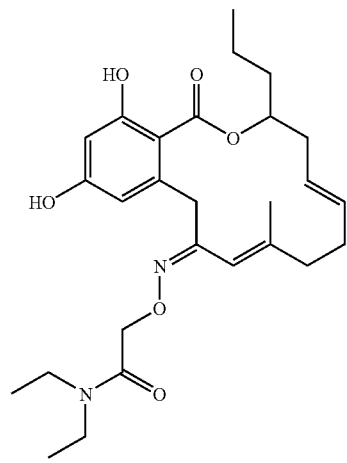

TABLE 1a-continued
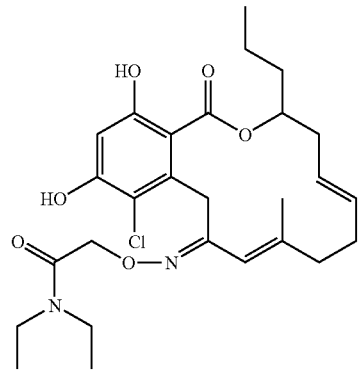
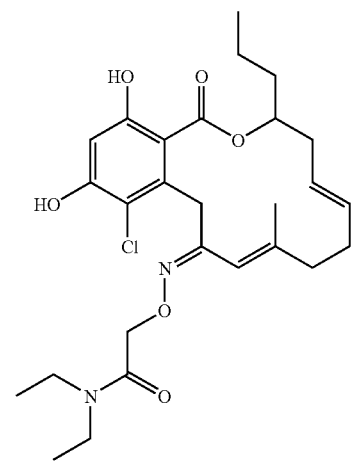
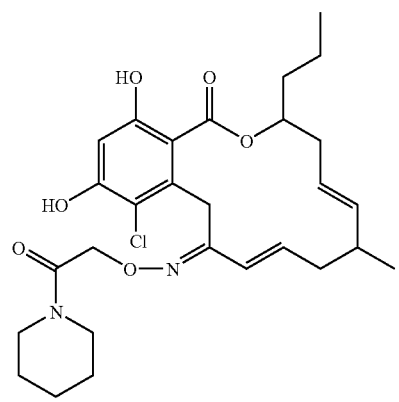

TABLE 1a-continued
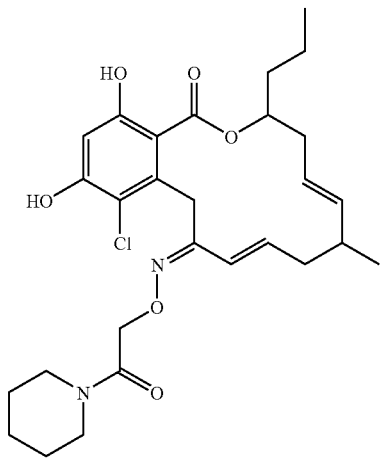
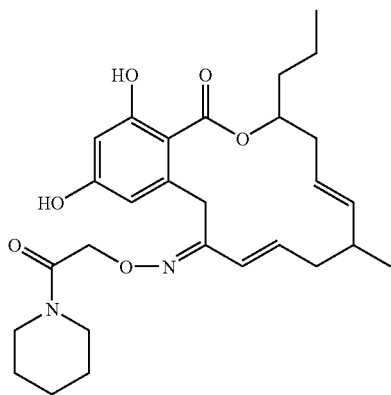
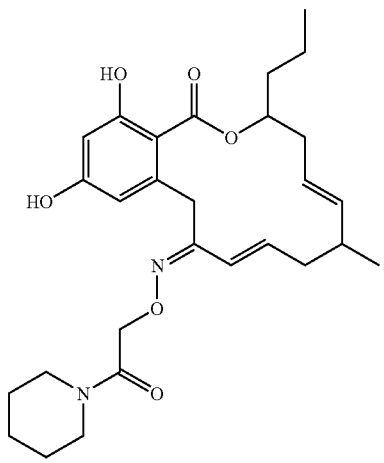
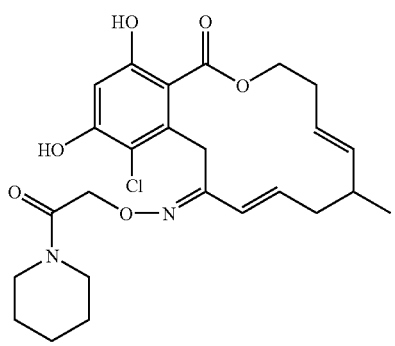

TABLE 1a-continued
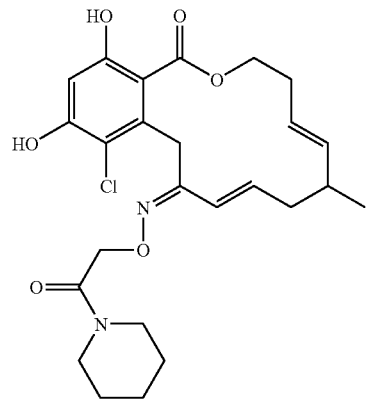
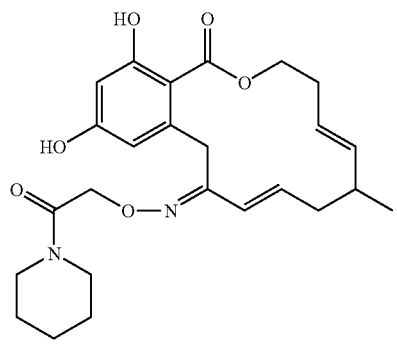
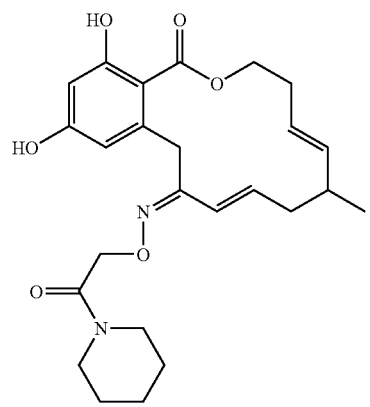
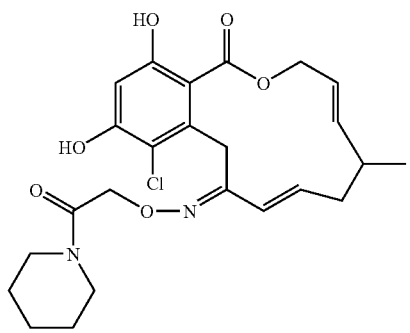

TABLE 1a-continued
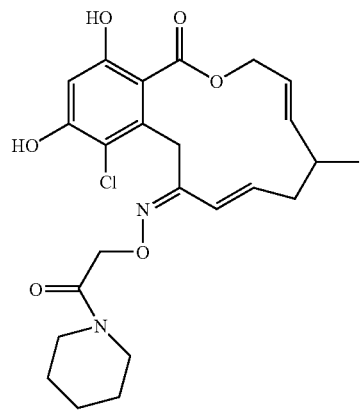
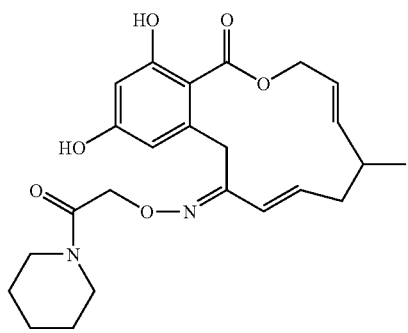
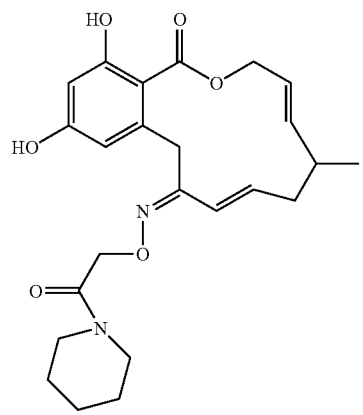
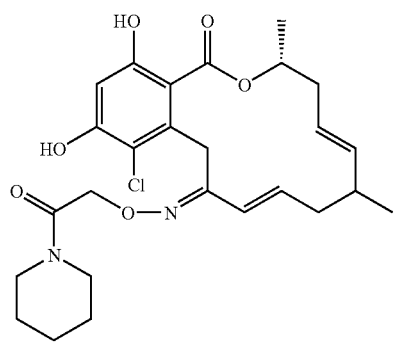

TABLE 1a-continued
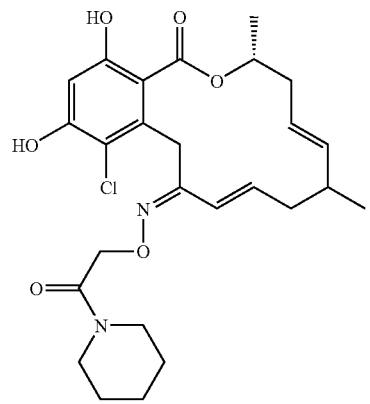
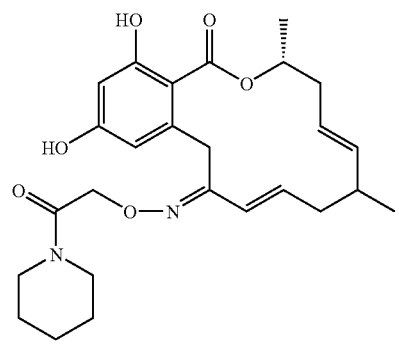
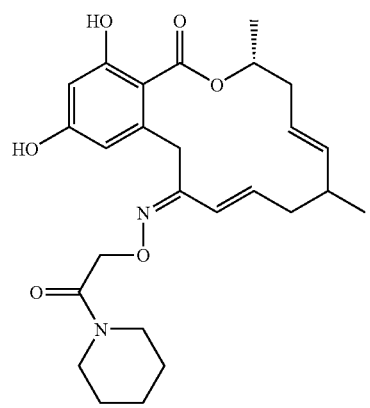
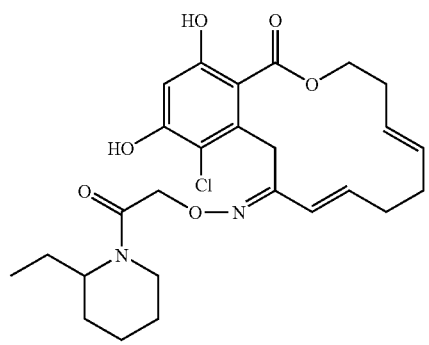

TABLE 1a-continued
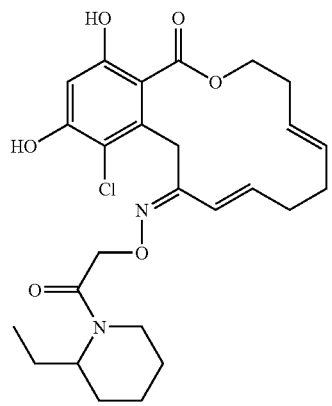
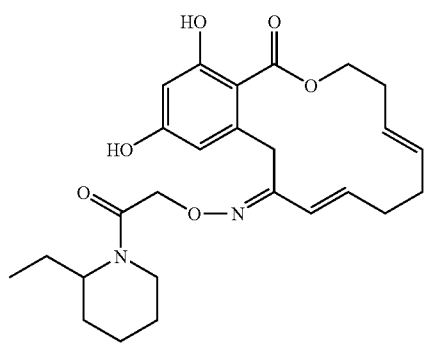
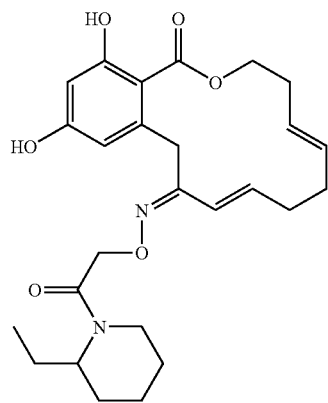
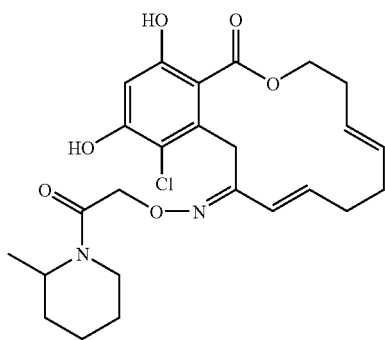

TABLE 1a-continued
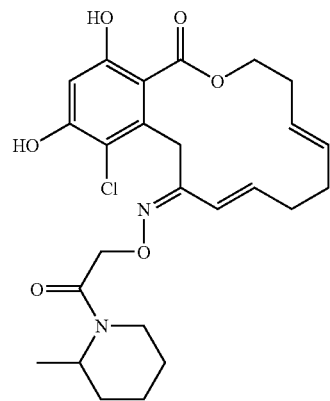
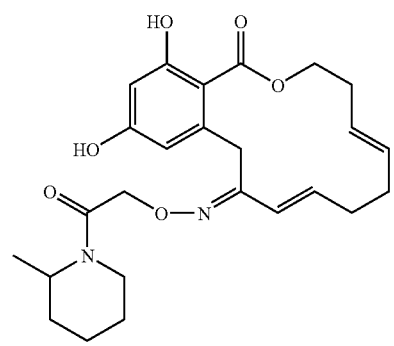
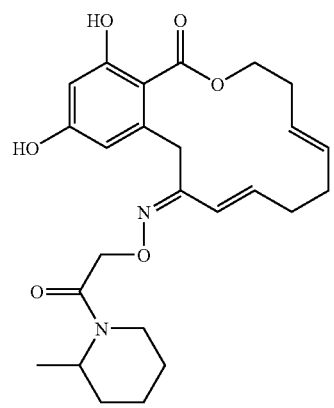
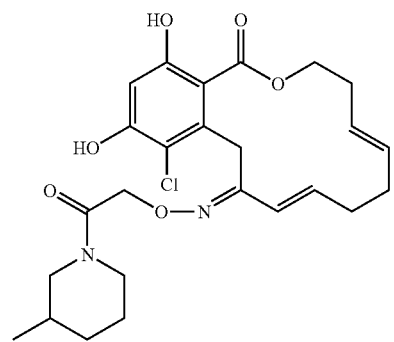

TABLE 1a-continued
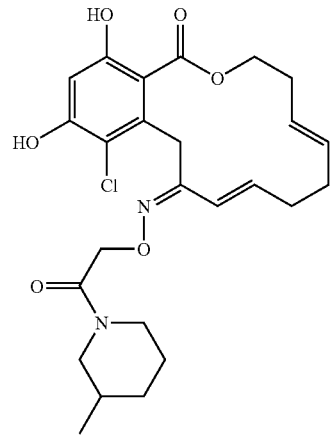
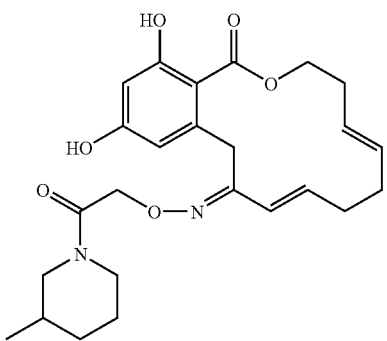
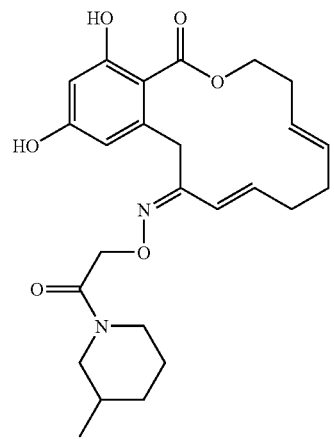
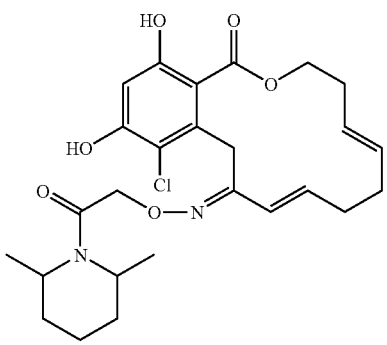

TABLE 1a-continued
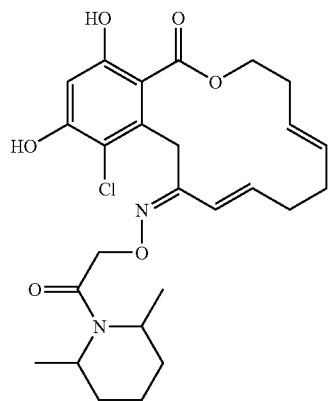
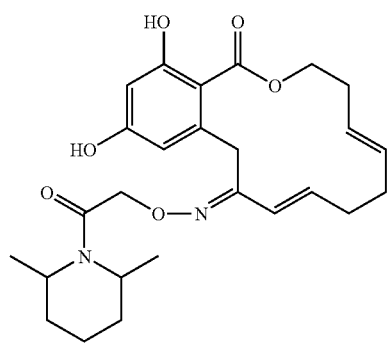
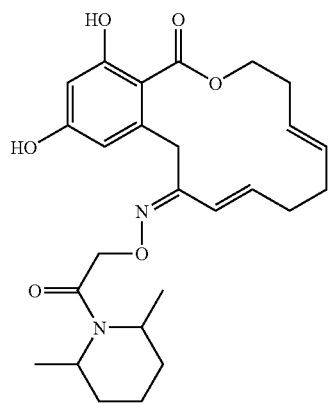
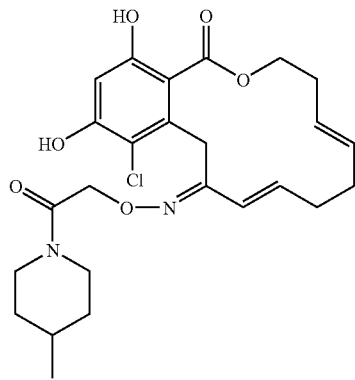

TABLE 1a-continued
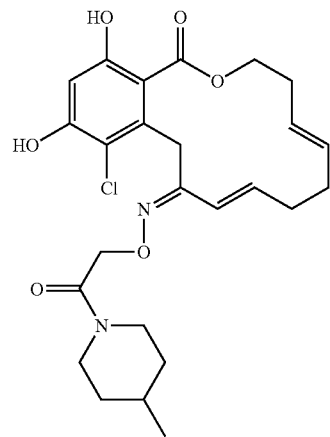
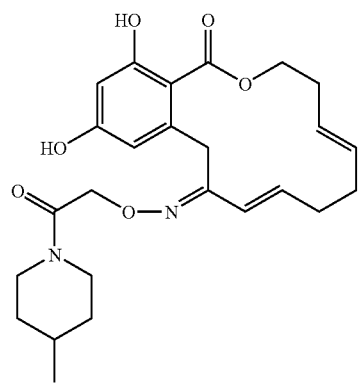
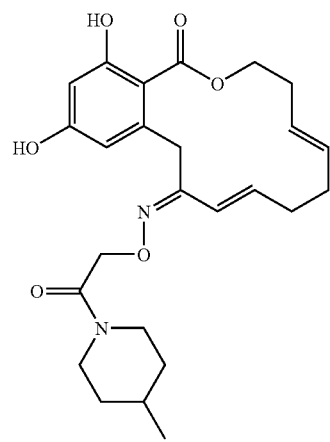

TABLE 1a-continued
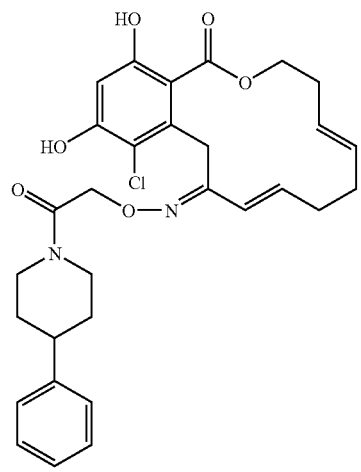
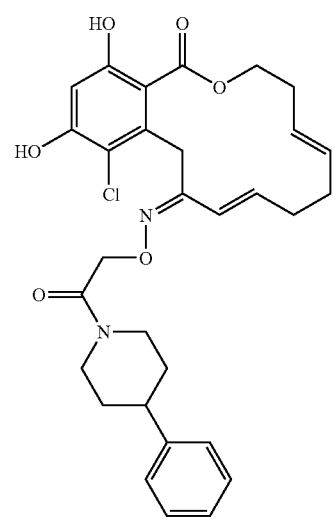
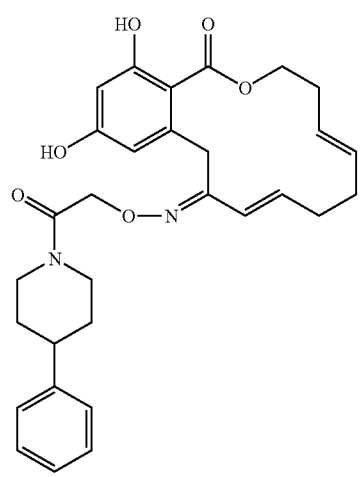

TABLE 1a-continued
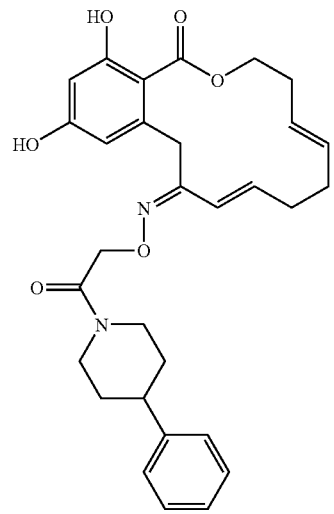
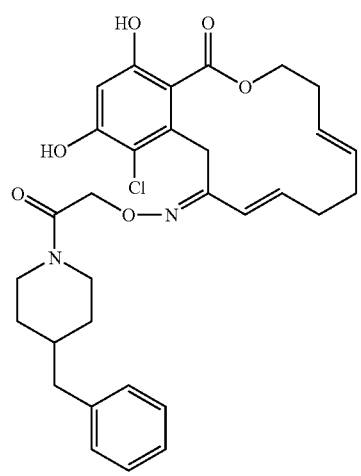
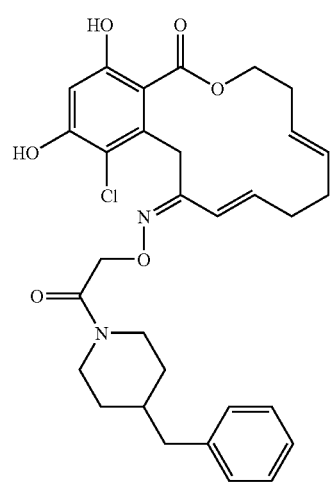

TABLE 1a-continued
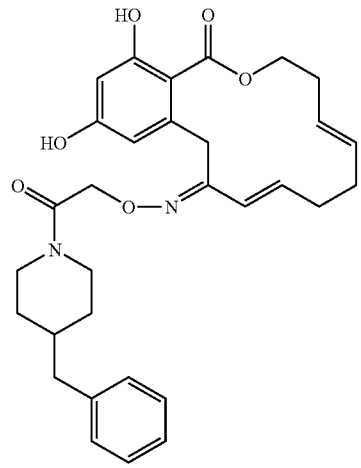
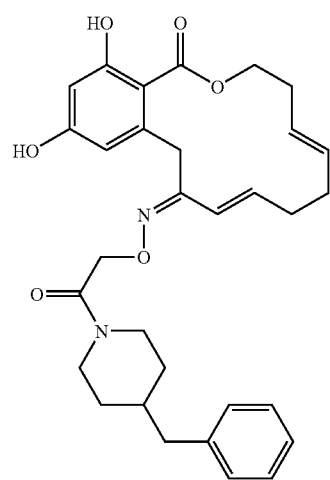
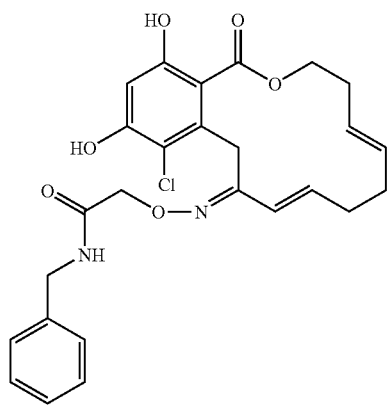

TABLE 1a-continued
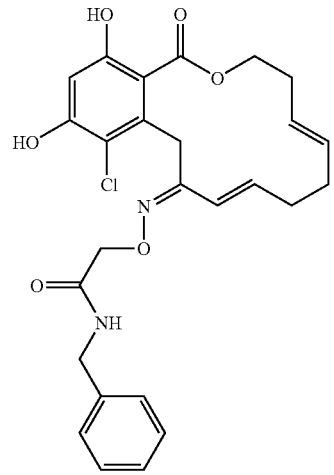
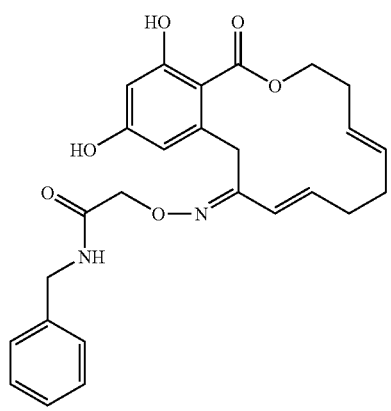
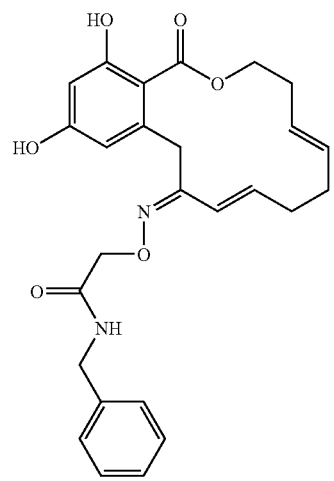

TABLE 1a-continued
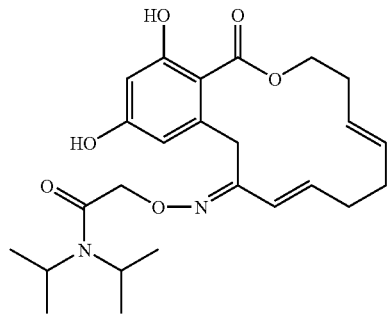
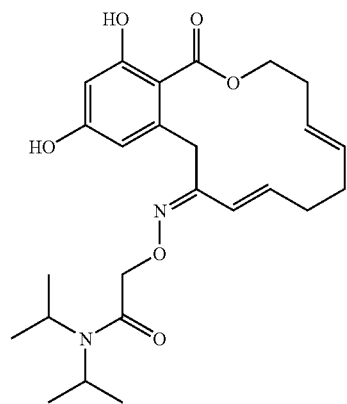
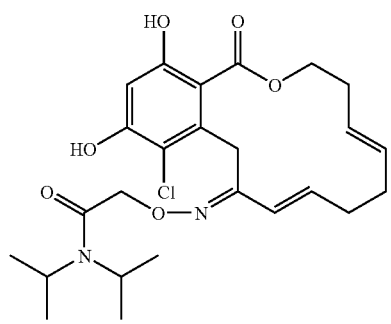
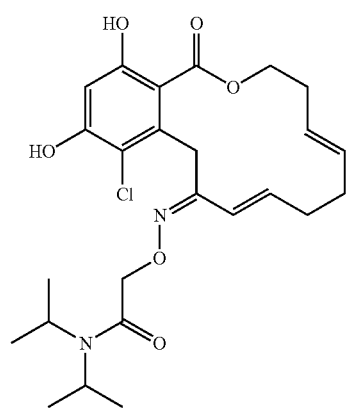

TABLE 1a-continued
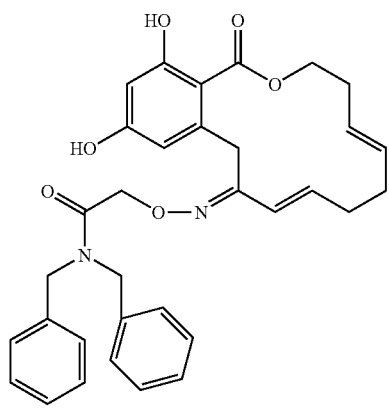
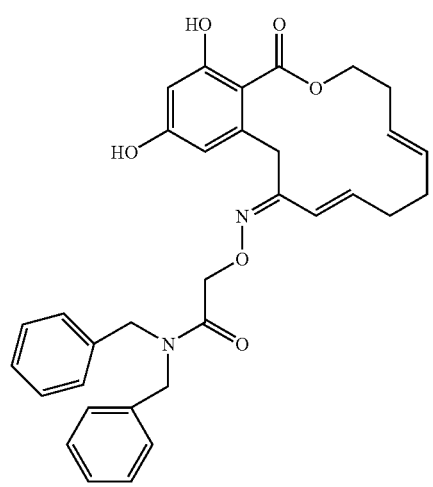
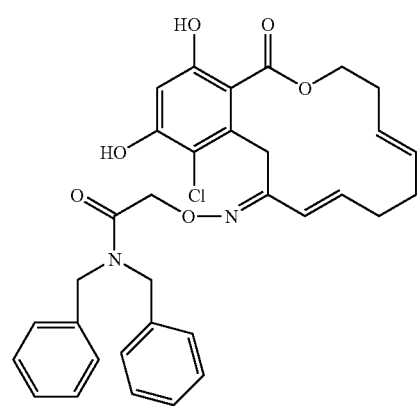

TABLE 1a-continued
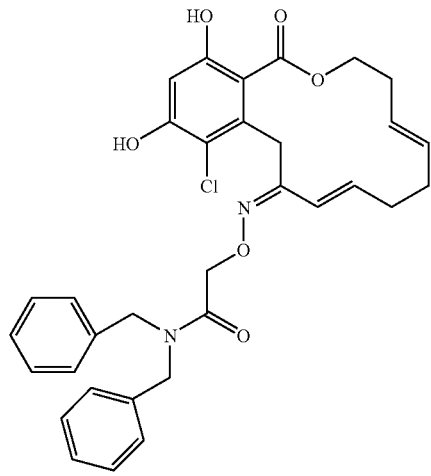
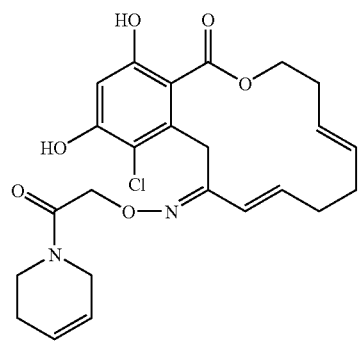
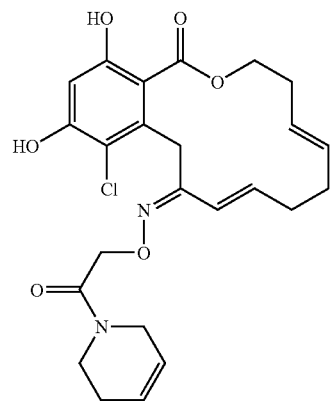
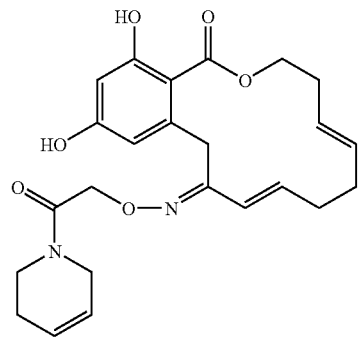

TABLE 1a-continued
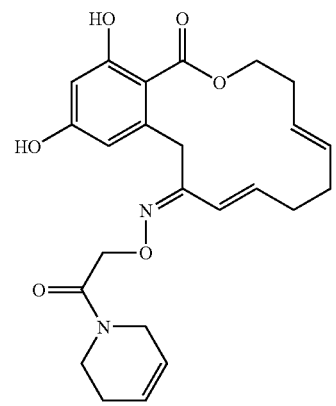
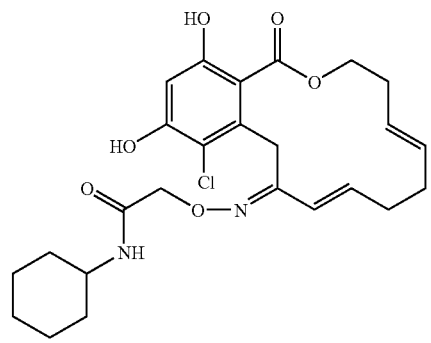
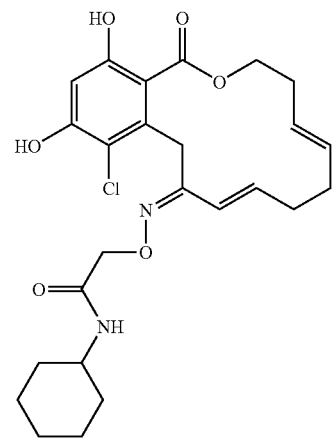
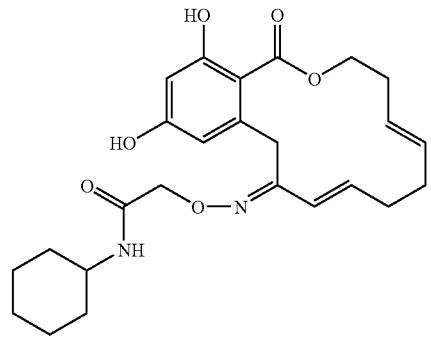

TABLE 1a-continued
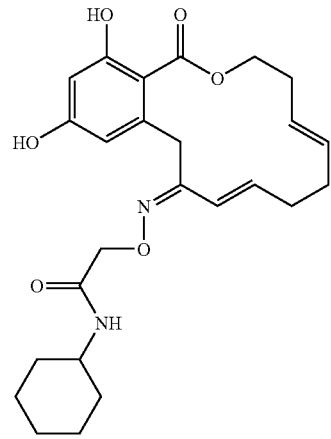
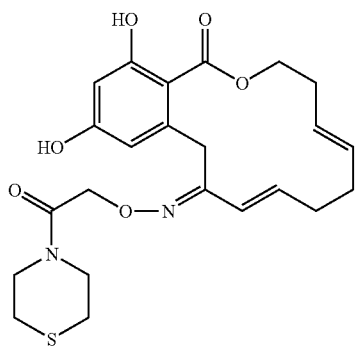
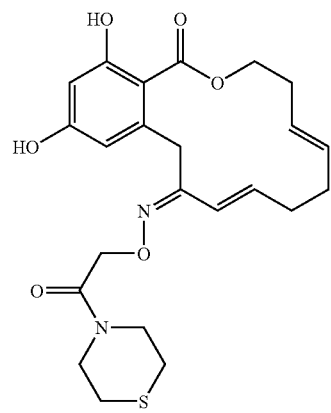
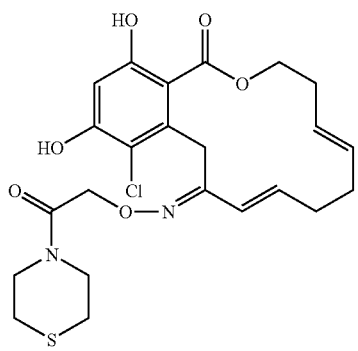

TABLE 1a-continued
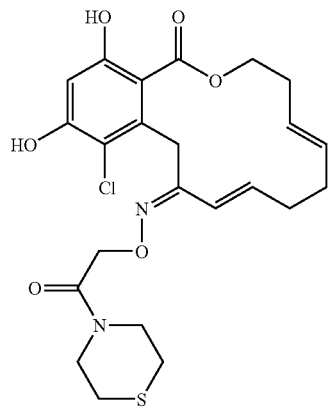
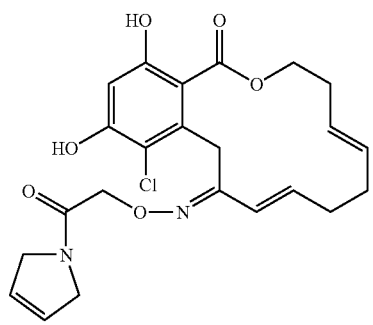
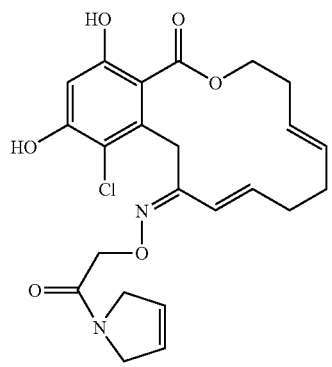
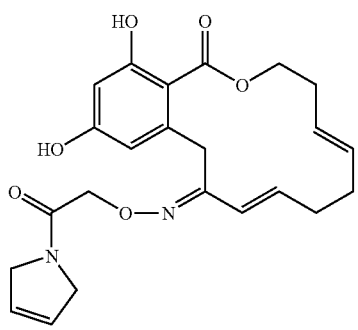

TABLE 1a-continued
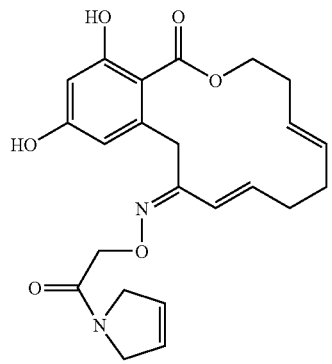
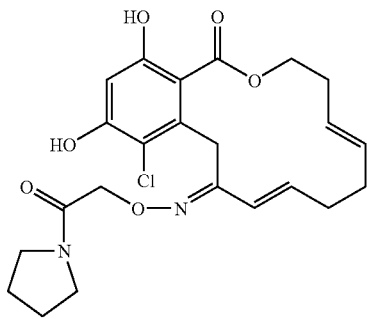
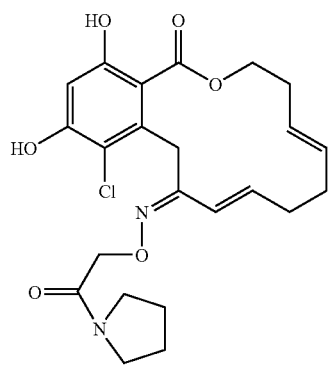
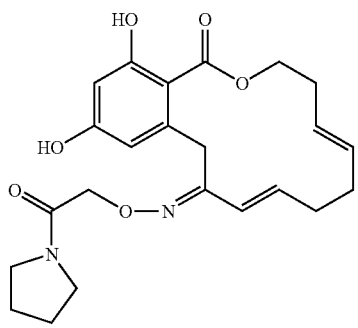

TABLE 1a-continued
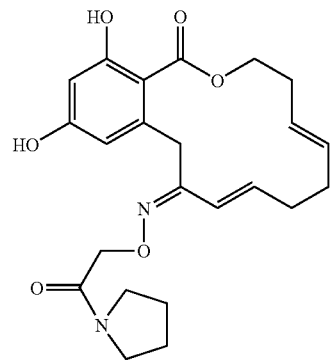
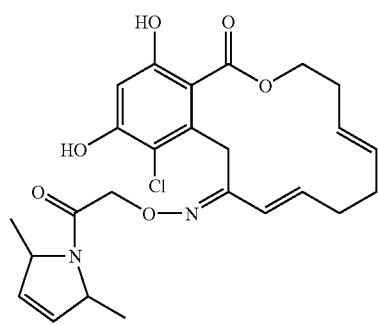
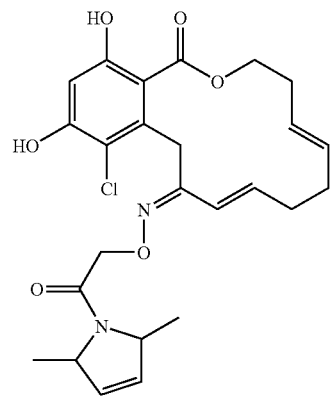
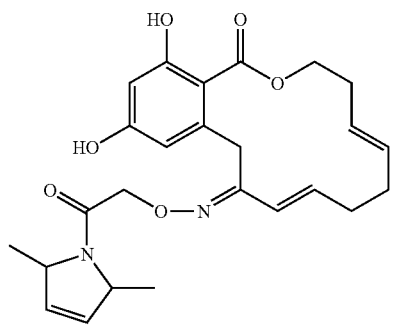

TABLE 1a-continued
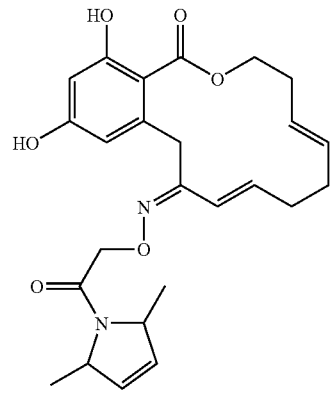
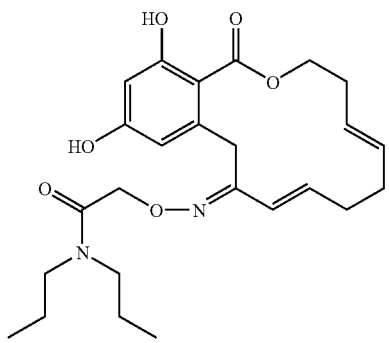
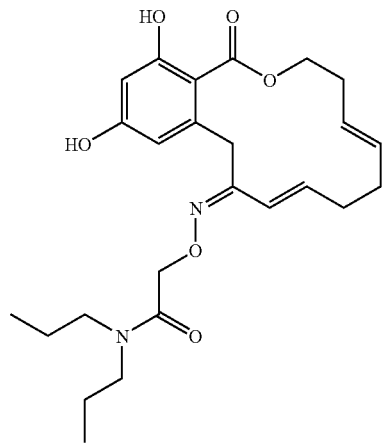
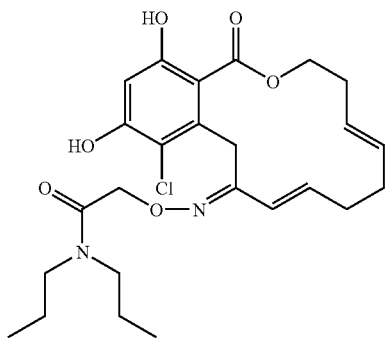

TABLE 1a-continued
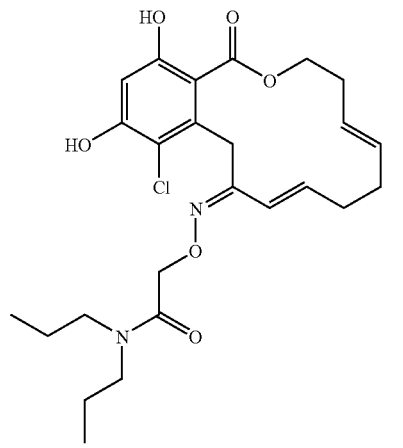
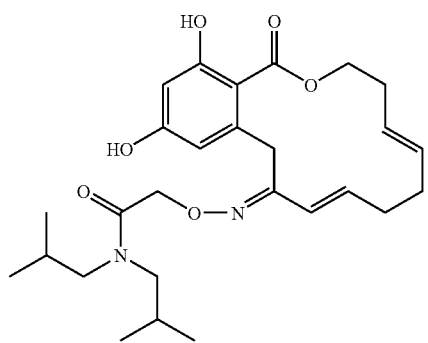
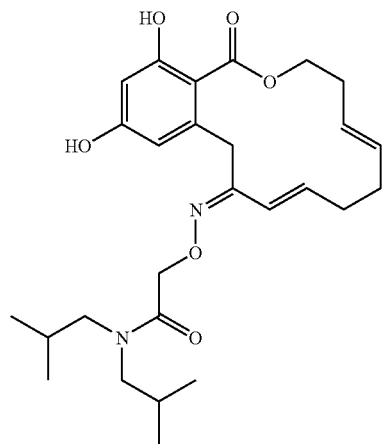
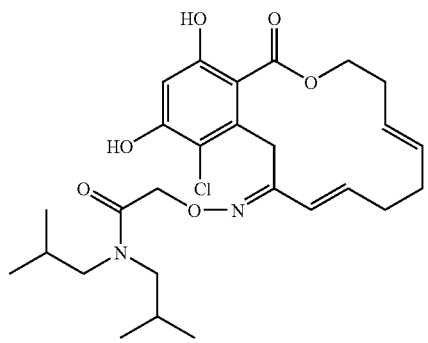

TABLE 1a-continued
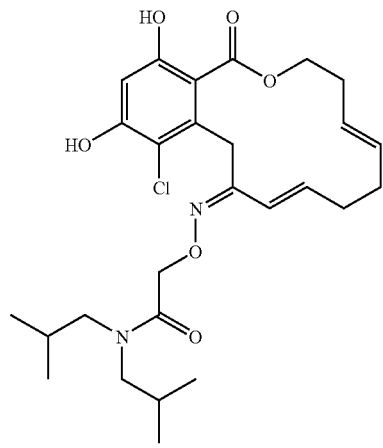
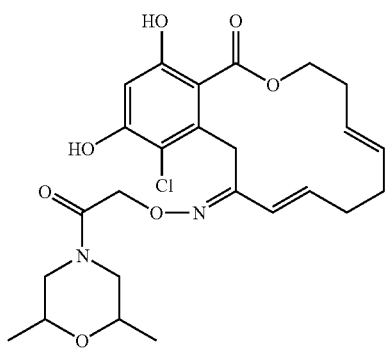
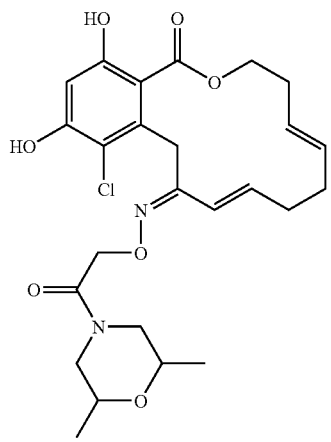
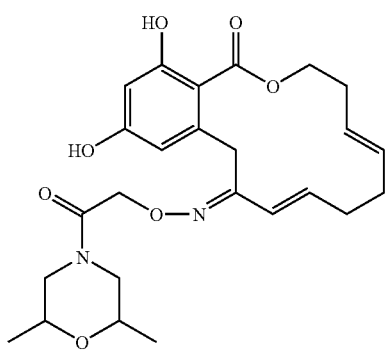

TABLE 1a-continued
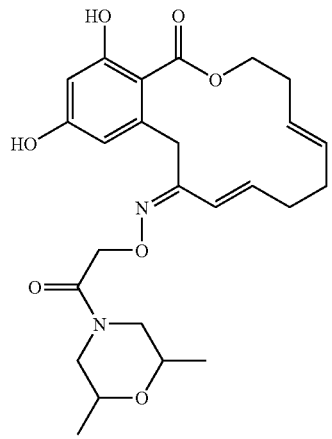
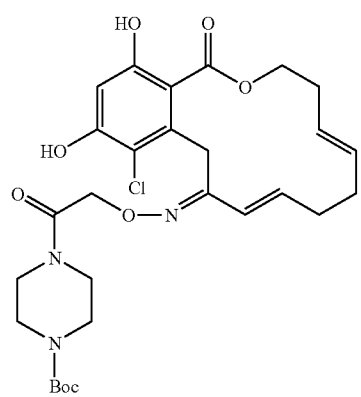
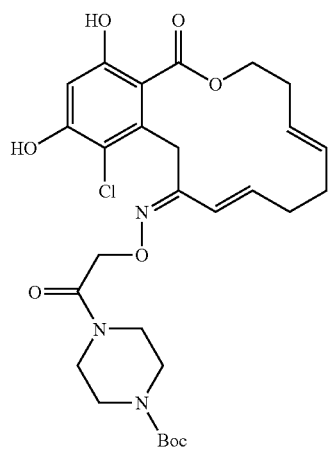

TABLE 1a-continued
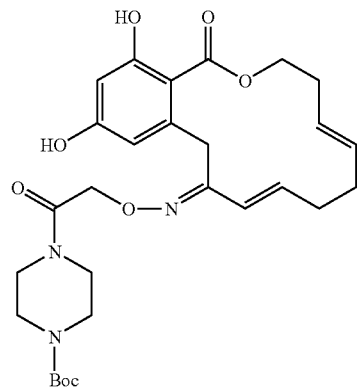
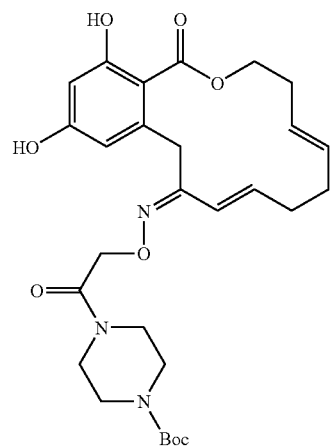
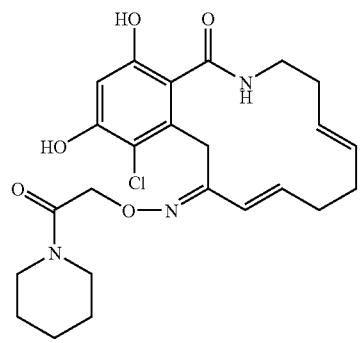
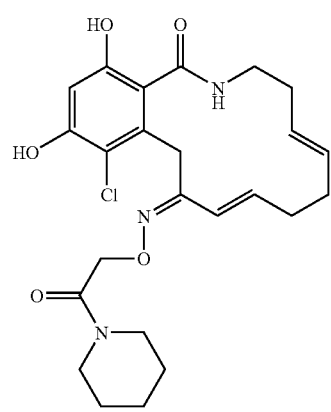

TABLE 1a-continued
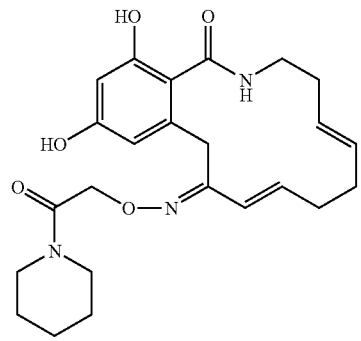
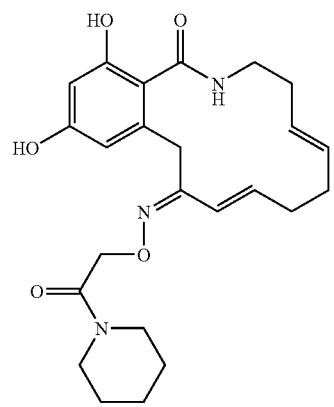
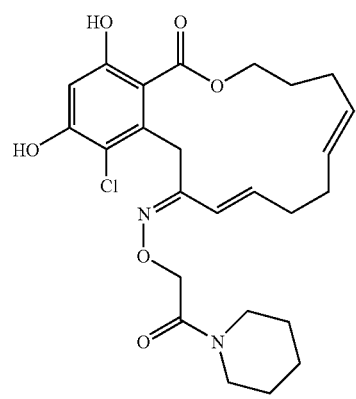
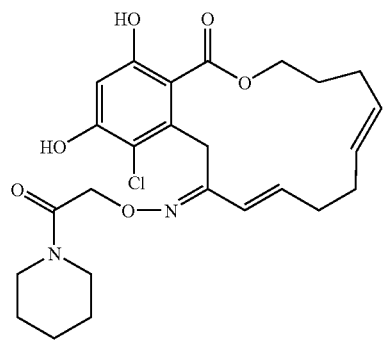

TABLE 1a-continued
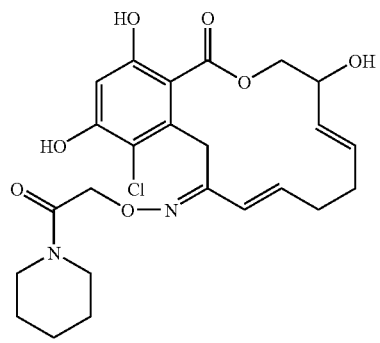
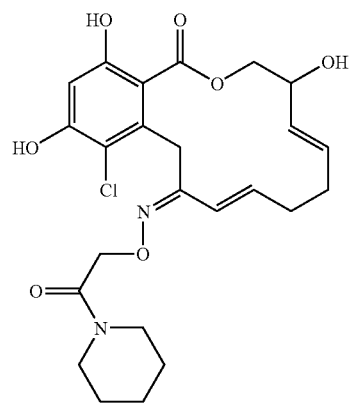
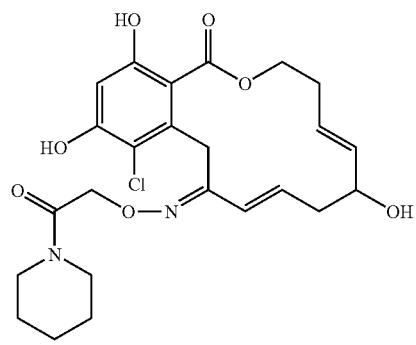
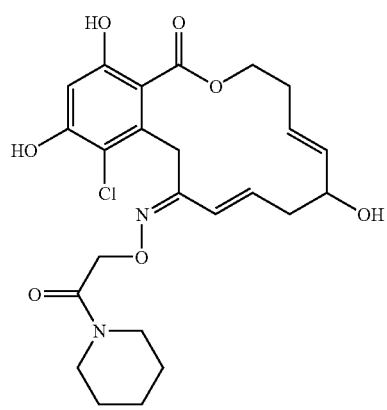

TABLE 1a-continued
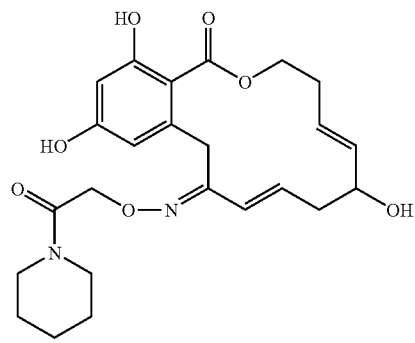
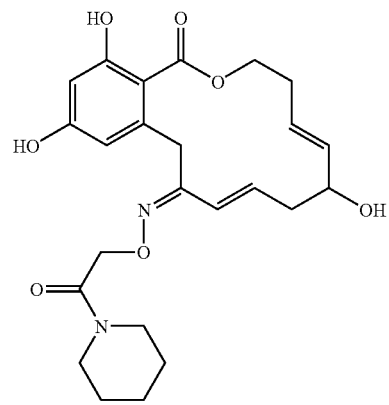
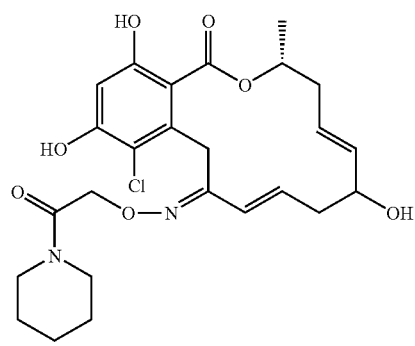
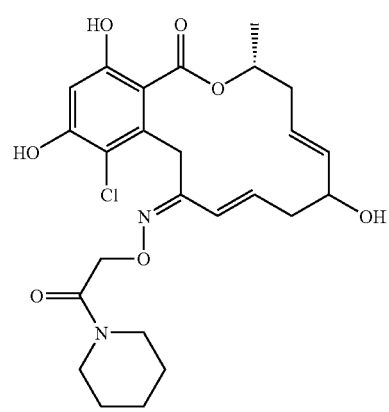

TABLE 1a-continued
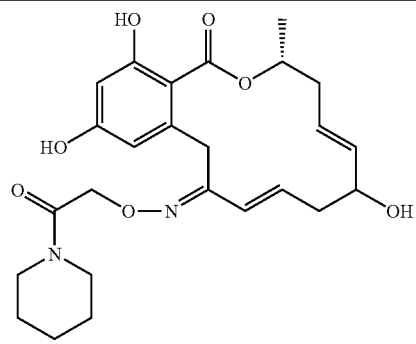
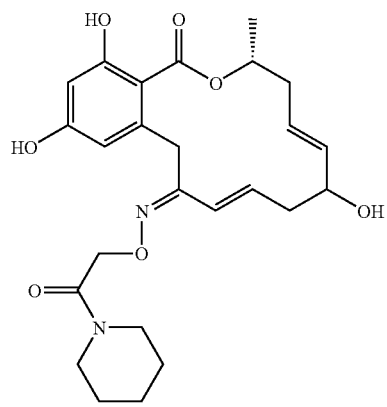
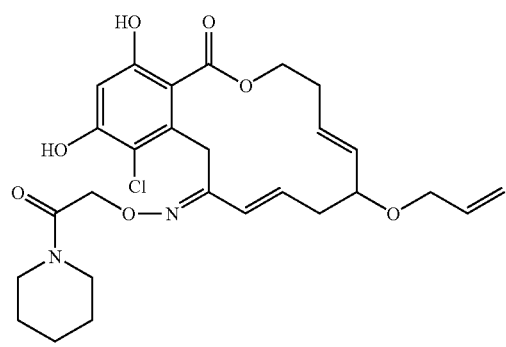
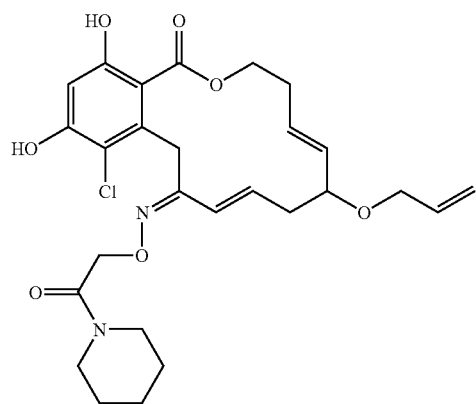

TABLE 1a-continued
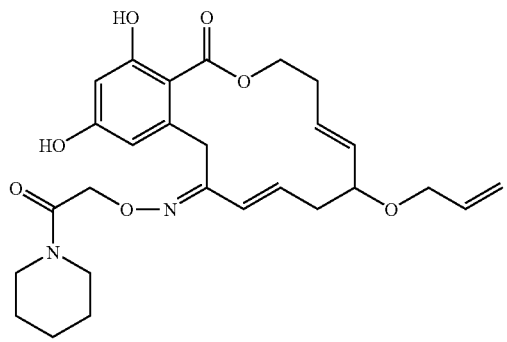
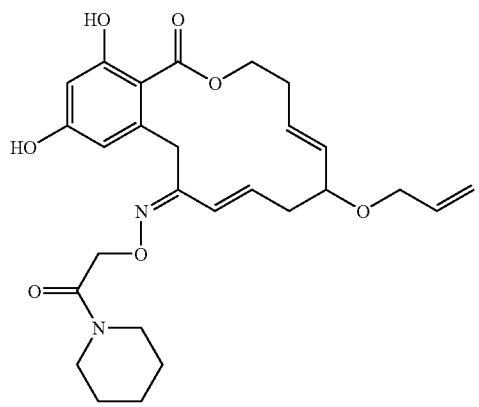
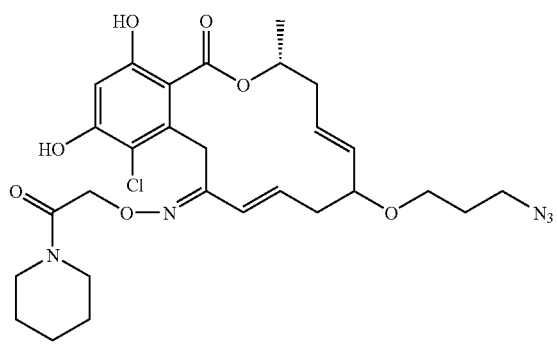
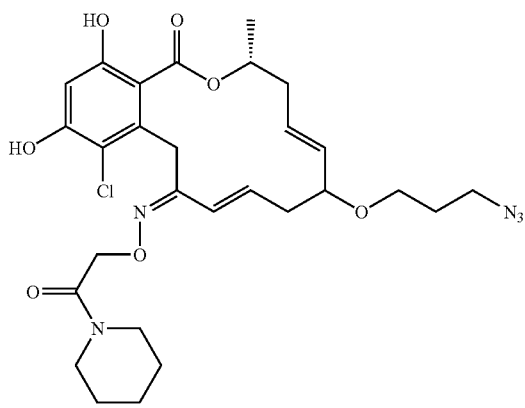

TABLE 1a-continued
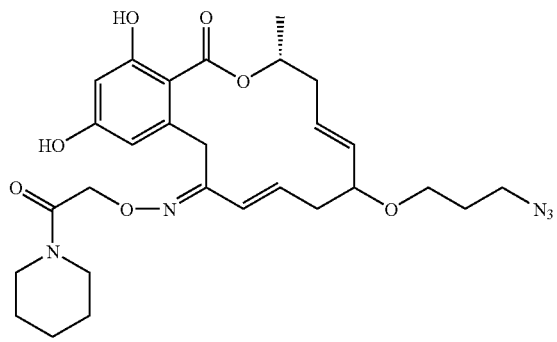
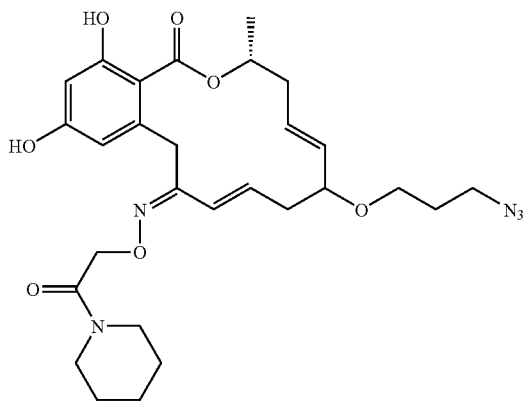
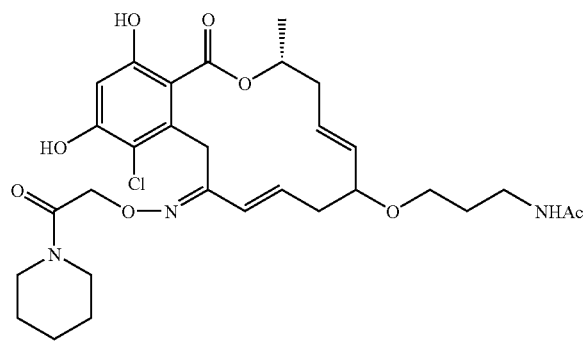
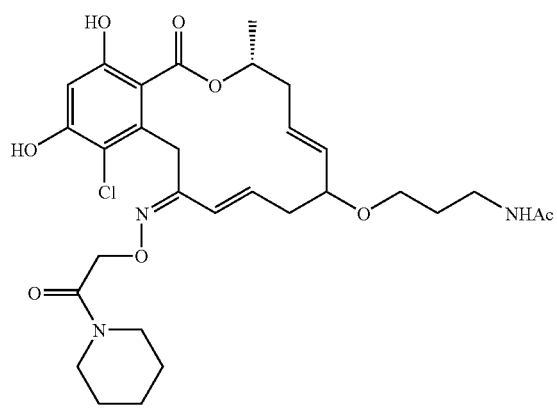

TABLE 1a-continued
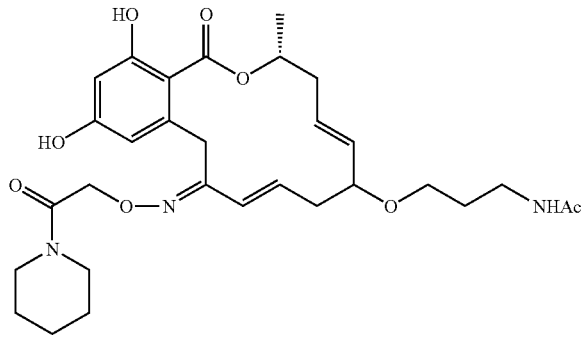
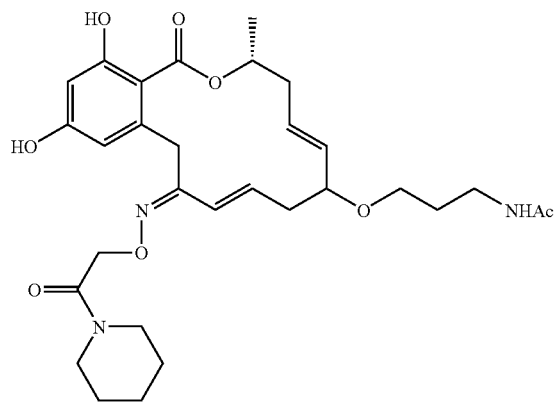
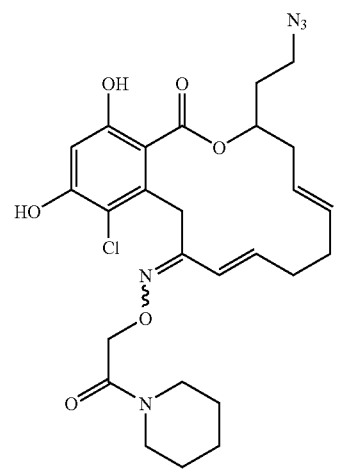

TABLE 1a-continued
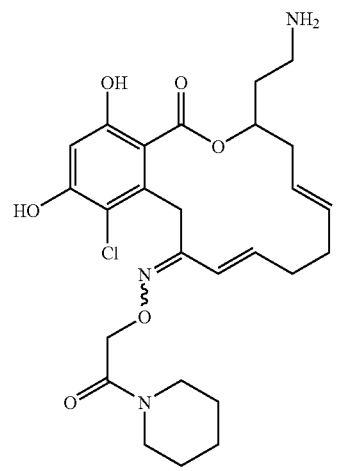
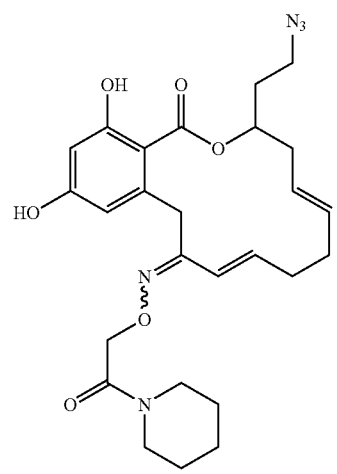
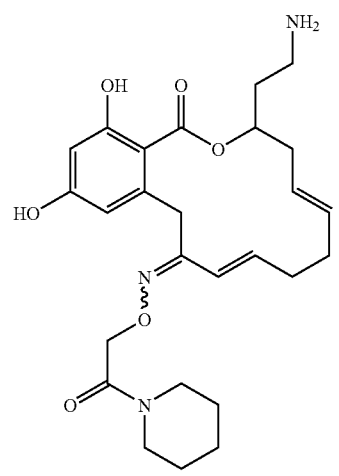

TABLE 1a-continued
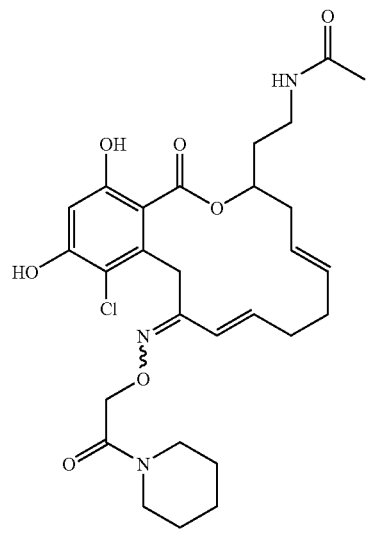
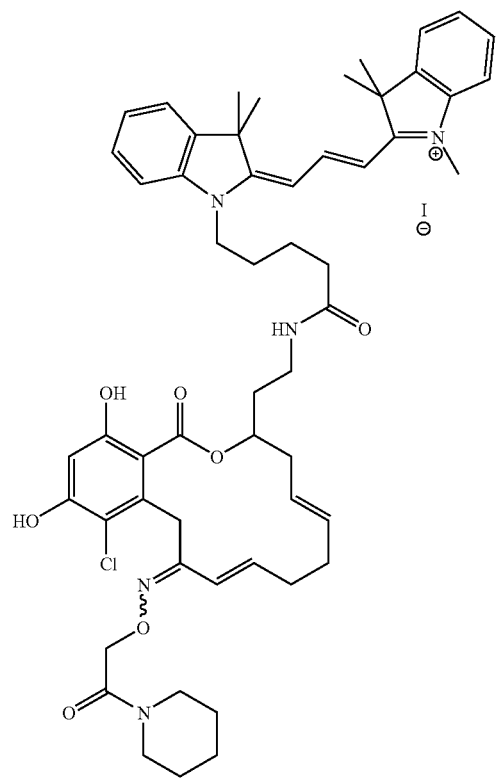

TABLE 1a-continued
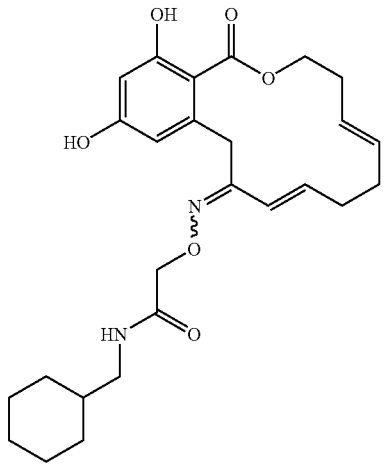
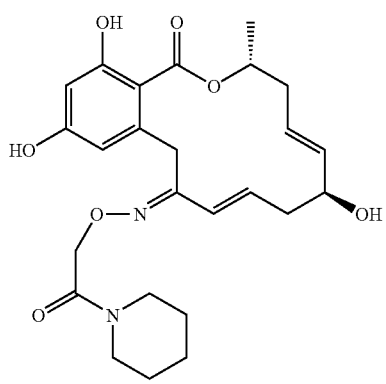
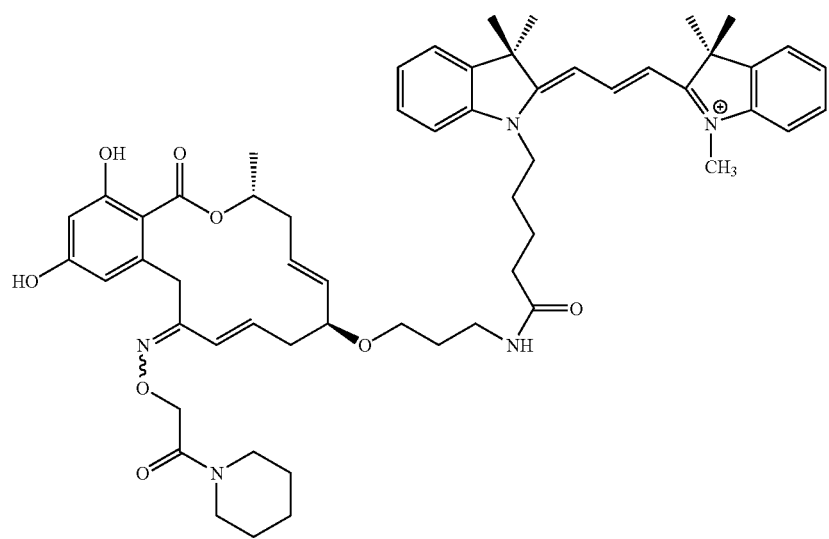

TABLE 1a-continued
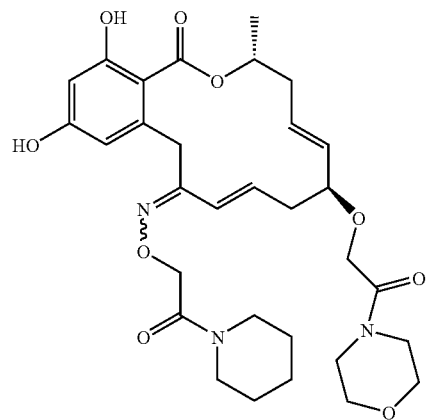
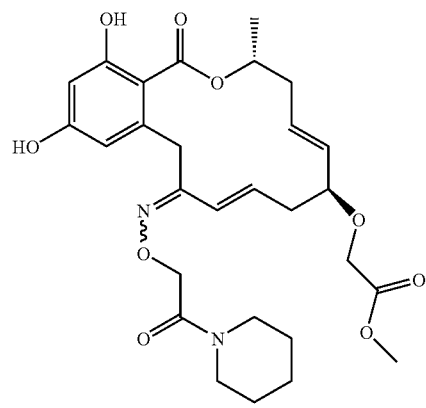
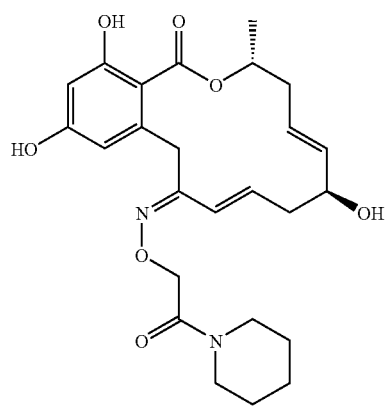
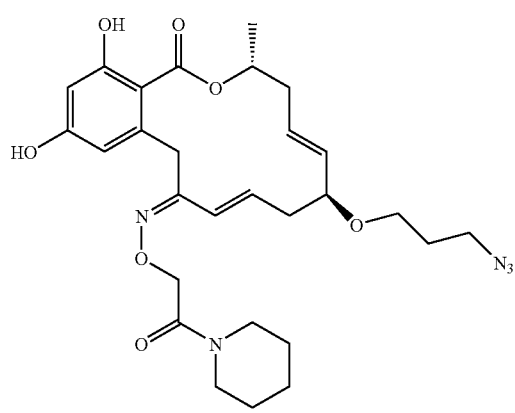

TABLE 1a-continued

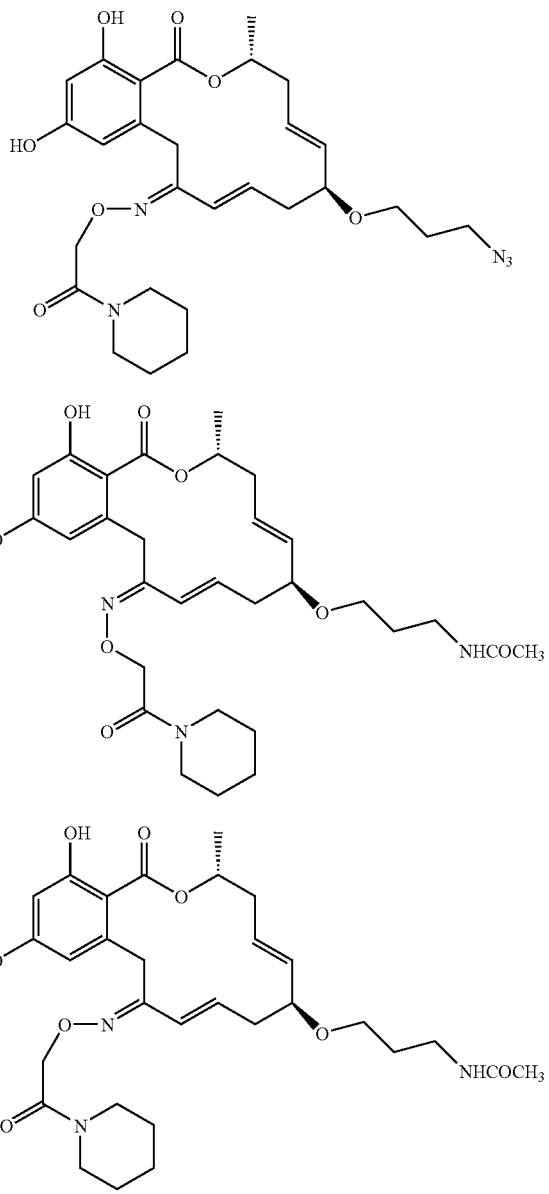

Pharmaceutically Acceptable Salts and Prodrugs

Nonlimiting examples of pharmaceutically acceptable salts are (a) acid addition salts formed with inorganic acids such as sulfate, nitrate, bicarbonate, and carbonate salts (for example, hydrochloric acid, hydrobromic acid, sulfuric acid, phosphoric acid, nitric acid, and the like), and salts formed with organic acids including tosylate, methanesulfonate, acetate, citrate, malonate, tartarate, succinate, benzoate, ascorbate, α-ketoglutarate, and α-glycerophosphate salts, such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid; (b) base addition salts formed with metal cations such as zinc, calcium, bismuth, barium, magnesium, aluminum, copper, cobalt, nickel, cadmium, sodium, potassium, lithium and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the formula —NR$^+$A$^-$, wherein R is as defined above and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

Pharmaceutically acceptable salts may be obtained using standard procedures well known in the art, for example by reacting a sufficiently basic compound such as an amine with a suitable acid affording a physiologically acceptable anion.

Pharmaceutically acceptable "prodrugs" refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

Stereoisomerism and Polymorphism

Compounds of the present invention having a chiral center may exist in and be isolated in optically active and racemic forms. The present invention encompasses any racemic, optically-active, diastereomeric, polymorphic, or stereoisomeric form, or mixtures thereof, of a compound of the invention, which possess the useful properties described herein.

In one embodiment, the compounds are prepared in optically active form by asymmetric synthesis using the processes described herein or synthetic transformations known to those skilled in the art.

Examples of methods to obtain optically active materials are known in the art, and include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chrial catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent; or xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

Definitions

Unless stated otherwise, the following terms and phrases as used herein are intended to have the following meanings:

When trade names are used herein, applicants intend to independently include the tradename product and the active pharmaceutical ingredient(s) of the tradename product.

As used herein, "the compound(s)", "the present compound(s)", "compound(s) of the invention", "compound(s) of the present invention", or "compounds of formula I, II, III, IV, V, Ia, Ia', IIa, IIa', IIIa, IVa, or Va" means one or more compounds of formula I, II, III, IV, V, Ia, Ia', IIa, IIa', IIIa, IVa, or Va, or a pharmaceutically acceptable tautomer, salt, solvate, prodrug, or physiologically functional derivative thereof. Similarly, with respect to isolatable intermediates, such as for example, the phrase "a compound of formula (number)" means a compound of that formula and pharmaceutically acceptable tautomers, salts, solvates and physiologically functional derivatives thereof.

"Ester thereof" means any ester of a nicotinic desensitizer in which any of the —COOH functions of the molecule is replaced by a —COOR function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. The term "ester thereof" includes but is not limited to pharmaceutically acceptable esters thereof.

"Salt thereof" means any acid and/or base addition salt of a compound of the present invention; preferably a pharmaceutically acceptable salt thereof "Pharmaceutically acceptable salt" means a salt of a compound of the present invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. Where applicable and compatible with the chemical properties of the nicotinic desensitizer, the term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1-19.

"Solvate thereof" means a nicotinic desensitizer formed by solvation (the combination of solvent molecules with molecules or ions of the solute), or an aggregate that consists of a solute ion or molecule (the nicotinic desensitizer) with one or more solvent molecules.

"Chiral" refers to molecules which have the property of non-superimposability of the mirror image partner, while the term "achiral" refers to molecules which are superimposable on their mirror image partner.

"Tautomers" refer to isomers of nicotinic desensitizers in which the isomers change into one another with great ease so that they ordinarily exist together in equilibrium.

"Stereoisomers" refer to nicotinic desensitizers which have identical chemical constitution, but differ with regard to the arrangement of the atoms or groups in space.

"Diastereomer" refer to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a nicotinic desensitizer which are non-superimposable mirror images of one another.

Stereochemical definitions and conventions used herein generally follow S. N. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether-nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene and Peter G. M. Wuts (John Wiley & Sons, Inc., New York, 1999, ISBN 0-471-16019-9) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti-infective activity of their own.

Whenever a term in the specification is identified as a range (i.e. $C_{1-4}$ alkyl), the range independently refers to each element of the range. As a non-limiting example, $C_{1-4}$ alkyl means, independently, $C_1$, $C_2$, $C_3$ or $C_4$ alkyl. Similarly, when one or more substituents are referred to as being "independently selected from" a group, this means that each substituent can be any element of that group, and any combination of these groups can be separated from the group. For example, if $R^1$ and $R^2$ can be independently selected from X, Y and Z, this separately includes the groups $R^1$ is X and $R^2$ is X; $R^1$ is X and $R^2$ is Y; $R^1$ is X and $R^2$ is Z; $R^1$ is Y and $R^2$ is X; $R^1$ is Y and $R^2$ is Y; $R^1$ is Y and $R^2$ is Z; $R^1$ is Z and $R^2$ is X; $R^1$ is Z and $R^2$ is Y; and $R^1$ is Z and $R^2$ is Z.

The term "alkyl" as used herein, unless otherwise specified, refers to a saturated straight, branched, or cyclic, primary, secondary, or tertiary hydrocarbon, including but not limited to groups with $C_1$ to $C_{10}$.

The term "lower alkyl" refers to a saturated straight, branched, or cyclic, primary, secondary, or tertiary hydrocarbon, including groups with $C_1$ to $C_4$, and if appropriate a cyclic alkyl group (for example cyclopropyl).

Illustrative examples of alkyl groups are methyl, ethyl, propyl, isopropyl, cyclopropyl, butyl, secbutyl, isobutyl, tertbutyl, cyclobutyl, 1-methylbutyl, 1,1-dimethylpropyl, pentyl, cyclopentyl, isopentyl, neopentyl, cyclopentyl, hexyl, isohexyl, and cyclohexyl. Unless otherwise specified, the alkyl group can be unsubstituted or substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, thiol, imine, sulfonic acid, sulfate, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, 3rd Edition, 1999.

The term "halo" or "halogen", as used herein, includes chloro, bromo, iodo, and fluoro.

The term "alkylthio" refers to a straight or branched chain alkylsulfide of the number of carbons specified, such as for example, $C_{1-4}$alkylthio, ethylthio, —S-alkyl, —S-alkenyl, —S-alkynyl, etc.

The terms "alkylamino" or "arylamino" refer to an amino group that has one or two alkyl or aryl substituents, respectively. Unless otherwise specifically stated in this application, when alkyl is a suitable moiety, then it is a lower alkyl, whether substituted or unsubstituted.

The term "alkylsulfonyl" means a straight or branched alkylsulfone of the number of carbon atoms specified, as for example, $C_{1-6}$ alkylsulfonyl or methylsulfonyl.

The term "alkoxycarbonyl" refers to a straight or branched chain ester of a carboxylic acid derivative of the number of carbon atoms specified, such as for example, a methoxycarbonyl, MeOC(O)—.

As used herein, the term "nitro" means —$NO_2$; the term "sulfhydryl" means —SH; and the term "sulfonyl" means —$S(O)_2$.

The terms "alkenyl" and "alkynyl" refer to alkyl moieties, including both substituted and unsubstituted forms wherein at least one saturated C—C bond is replaced by a double or triple bond. Thus, $C_{2-6}$ alkenyl may be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl. Similarly, $C_{2-6}$ alkynyl may be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl.

The term "alkylene" includes a saturated, straight chain, divalent alkyl radical of the formula —$(CH_2)_n$—, wherein "n" may be any whole integer from 1 to 10.

"Alkyl", "alkoxy", "alkenyl", "alkynyl", etc., includes both straight chain and branched groups. However, reference to an individual radical such as "propyl" embraces only that straight-chain radical, whereas a branched chain isomer such as "isopropyl" is specifically termed such.

The term "aryl" as used herein and unless otherwise specified refers to any stable monocyclic, bicyclic, or tricyclic carbon ring of up to 8 members in each ring, wherein at least one ring is aromatic as defined by the Huckel 4n+2 rule, and especially phenyl, biphenyl, or naphthyl. The term includes both substituted and unsubstituted moieties. The aryl group can be substituted with any described moiety, including but not limited to one or more moieties selected from the group consisting of halogen (fluoro, chloro, bromo or iodo), hydroxyl, amino, azido, alkylamino, arylamino, alkoxy, aryloxy, nitro, cyano, sulfonic acid, sulfate, phosphonic acid, phosphate, or phosphonate, either protected or unprotected as necessary, as known to those skilled in the art, for example, as taught in Greene et al., *Protective Groups in Organic Synthesis*, John Wiley & Sons, 3rd Ed., 1999.

The term "alkaryl" or "alkylaryl" refers to an alkyl group with an aryl substituent or an alkyl group linked to the molecule through an aryl group as defined herein. The term "aralkyl" or "arylalkyl" refers to an aryl group substituted with an alkyl substituent or linked to the molecule through an alkyl group as defined above.

The term "cycloalkyl" includes a ring of $C_{3-8}$, including but not limited to cyclopropyl, cyclobutyl, cyclopentyl, cyclohexyl, cycloheptyl and cyclooctyl.

The term "alkoxy" means a straight or branched chain alkyl group having an attached oxygen radical, the alkyl group having the number of carbons specified or any number within this range. For example, a "—O-alkyl", $C_{1-4}$ alkoxy, methoxy, etc.

The term "acyl" or "O-linked ester" includes a group of the formula C(O)R', wherein R' is an straight, branched, or cyclic alkyl (including lower alkyl), carboxylate residue of an amino acid, aryl including phenyl, heteroaryl, alkaryl, aralkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxy-trityl, substituted benzyl, alkaryl, aralkyl including benzyl, alkoxyalkyl including methoxymethyl, aryloxyalkyl such as phenoxymethyl. Aryl groups in the esters optimally comprise a phenyl group. In nonlimiting embodiments, acyl groups include acetyl, trifluoroacetyl, methylacetyl, cyclopropylacetyl, cyclopropyl-carboxy, propionyl, butyryl, isobutyryl, hexanoyl, heptanoyloctanoyl, neo-heptanoyl, phenylacetyl, 2-acetoxy-2-phenylacetyl, diphenylacetyl, α-methoxy-α-trifluoromethyl-phenylacetyl, bromoacetyl, 2-nitro-benzeneacetyl, 4-chlorobenzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, methoxyacetyl, 2-thiopheneacetyl, chlorosulfonylacetyl, 3-methoxyphenylacetyl, phenoxyacetyl, tert-butylacetyl, trichloroacetyl, monochloro-acetyl, dichloroacetyl, 7H-dodecafluoro-heptanoyl, perfluoro-heptanoyl, 7H-dodeca-fluoroheptanoyl, 7-chlorododecafluoro-heptanoyl, 7-chloro-dodecafluoro-heptanoyl, 7H-dodecafluoroheptanoyl, 7H-dodeca-fluoroheptanoyl, nona-fluoro-3,6-dioxa-heptanoyl, nonafluoro-3,6-dioxaheptanoyl, perfluoroheptanoyl, methoxybenzoyl, methyl 3-amino-5-phenylthiophene-2-carboxyl, 3,6-dichloro-2-methoxy-benzoyl, 4-(1,1,2,2-tetrafluoro-ethoxy)-benzoyl, 2-bromo-propionyl, omega-aminocapryl, decanoyl, n-pentadecanoyl, stearyl, 3-cyclopentyl-propionyl, 1-benzene-carboxyl, O-acetylmandelyl, pivaloyl acetyl, 1-adamantane-carboxyl, cyclohexane-carboxyl, 2,6-pyridinedicarboxyl, cyclopropane-carboxyl, cyclobutane-carboxyl, perfluorocyclohexyl carboxyl, 4-methylbenzoyl, chloromethyl isoxazolyl carbonyl, perfluorocyclohexyl carboxyl, crotonyl, 1-methyl-1H-indazole-3-carbonyl, 2-propenyl, isovaleryl, 1-pyrrolidinecarbonyl, 4-phenylbenzoyl.

The term "acylamino" includes a group having a structure of "—N(R')—C(O)—R", wherein each R is independently as defined above.

The term "carbonyl" includes a group of the structure "—C(O)—X—R" or "X—C(O)—R", where X is O, S, or a bond, and each R is independently as defined above.

The term "heteratom" includes an atom other than carbon or hydrogen in the structure of a heterocyclic compound, nonlimiting examples of which are nitrogen, oxygen, sulfur, phosphorus or boron.

The term "heterocycle", "heterocyclyl", or "heterocyclic" as used herein includes non-aromatic ring systems having four to fourteen members, preferably five to ten, in which one or more ring carbons, preferably one to four, are each replaced by a heteroatom.

Examples of heterocyclic rings include 3-1H-benzimidazol-2-one, (1-substituted)-2-oxo-benzimidazol-3-yl, 2-tetrahydro-furanyl, 3-tetrahydrofuranyl, 2-tetrahydropyranyl, 3-tetrahydropyranyl, 4-tetra-hydropyranyl, [1,3]-dioxalanyl, [1,3]-dithiolanyl, [1,3]-dioxanyl, 2-tetra-hydro-thiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, 3-furazanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 2-pyrazolyl, 3-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, and benzoisoxazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" also refers to rings that are optionally substituted. The term "heteroaryl" may be used interchangeably with the term "heteroaryl ring" or the term "heteroaromatic".

The term "amino" as used herein unless otherwise specified, includes a moiety represented by the structure "—$NR_2$", and includes primary, secondary and tertiary amines optionally substituted by alkyl, aryl, heterocyclyl, and/or sulfonyl groups. Thus $R_2$ may represent two hydrogen atoms, two alkyl moieties, or one hydrogen and one alkyl moiety.

The term "amido" as used herein includes an amino-substituted carbonyl, while the term "amidino" means a group having the structure "—C(NH)—$NH_2$".

The term "quaternary amine" as used herein includes quaternary ammonium salts that have a positively charged nitrogen. They are formed by the reaction between a basic nitrogen in the compound of interest and an appropriate quaternizing agent such as, for example, methyliodide or benzyliodide. Appropriate counterions accompanying a quaternary amine include acetate, trifluoroacetate, chloro, bromo and iodo ions.

The term "substituted" includes multiple degrees of substitution by one or more named substituents such as, for example, halo, hydroxyl, thio, alkyl, alkenyl, alkynyl, nitro, cyano, azido, amino, carboxamido, etc. Where multiple substituent possibilities exist, the compound can be substituted by one or more of the disclosed or claimed substituent groups, independently from one another, and taken singly or plurally.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

It should be understood that the various possible stereoisomers of the groups mentioned above and herein are within the meaning of the individual terms and examples, unless otherwise specified. As an illustrative example, "1-methyl-butyl" exists in both (R) and the (S) form, thus, both (R)-1-methyl-butyl and (S)-1-methyl-butyl is covered by the term "1-methyl-butyl", unless otherwise specified.

The term "biological sample", as used herein, includes, without limitation, cell cultures or extracts thereof; preparations of an enzyme suitable for in vitro assay; biopsied material obtained from a mammal or extracts thereof; and blood, saliva, urine, feces, semen, tears, or other body fluids or extracts thereof.

The term "pharmaceutically acceptable carrier" refers to a non-toxic carrier, adjuvant, or vehicle that may be administered to a patient, together with a compound of this invention, and which does not destroy the pharmacological activity thereof.

It should also be understood that when a carbon to carbon double bond group, such as C=C, or a carbon to nitrogen double bond group, such as C=N, has more than one substituents, the double bond geometry can be either E or Z. Both the E and Z forms of the double bond geometry fall within the scope of the present invention.

Method of Inhibiting the Growth of NF2 and NF1 Tumor Cells

The present invention includes methods of inhibiting the growth of NF2-deficient and/or NF1-deficient tumor cells by contacting, i.e., treating, the NF2-deficient or NF1-deficient tumor cells with radicicol and its derivatives, such as one or more compounds of formula I, II, III, IV, or V as described above. The present invention also includes methods of decreasing proliferation of NF2-deficient or NF1-deficient tumor cells by contacting the cells with radicicol and its derivatives, such as one or more compounds of formula I, II, III, IV, or V as described above.

In one embodiment, inhibition of the growth of NF2 or NF1 cells is determined by comparing a sample of NF2-deficient or NF1-deficient tumor cells treated with radicicol and its derivatives to a control, such as a sample of untreated NF2-deficient or NF1-deficient tumor cells or a sample of cells treated with a known inert compound. Prior to contacting cells with radicicol and its derivatives, both samples of NF2-deficient cells or NF1-deficient cells (treated and control) should consist of approximately the same number of cells and be of the same cell type, e.g., NF2-deficient schwannomas or NF1-deficient MPNST cells. NF2-deficient tumor cells or NF1-deficient tumor cells treated with radicicol and its derivatives may decrease in number by at least about 10%, at least about 20%, at least about 30%, at least about 40%, at least about 50%, at least about 60%, at least about 70%, at least about 80%, at least about 90%, or about 100% following compound treatment compared to the control.

Radicicol, a macrocyclic lactone antibiotic, has been shown to inhibit the function of HSP90. To further investigate the biological mechanism of radicicol and its analogs in regulating HSP90 and establish the fundamental structure-activity relationship, a number of radicicol analogs have been synthesized and studied. The term "radicicol analogs" or "radicicol derivatives" as used herein denotes macrocyclic lactone compounds that are structurally similar to radicicol. Specifically, the "radicicol analogs" or "radicicol derivatives" refer to compounds of fused bicyclic ring structure wherein a six-membered aromatic ring shares two carbon atoms with a 12- to 16-membered non-aromatic ring containing a lactone group and at least one olefin group in the core of the 12- to 16-membered ring. The radicicol analogs/derivatives may have one or more substituents on the six-membered aromatic ring or the 12- to 16-membered non-aromatic ring. It is noted that the terms "analog" and "derivative" are used interchangeably in the present application.

A number of radicicol analogs have been disclosed in patent publications including WO 96/33989, WO 98/18780, WO 99/55689, U.S. Pat. No. 7,115,651, U.S. Pat. No. 5,731,343, and U.S. Pat. No. 5,077,165, all of which are herein incorporated by reference in their entirety. Radicicol and its representative analogs are shown in Scheme 1A.

SCHEME 1A

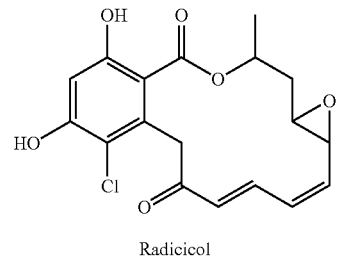

Radicicol

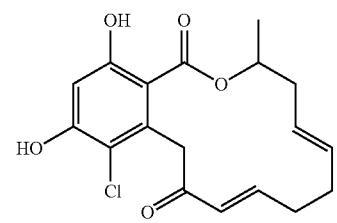

Pochonin D

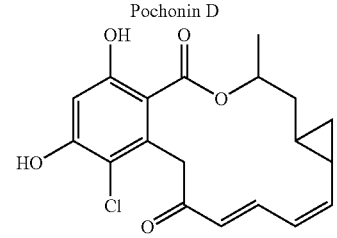

Cyclopropane Radicicol

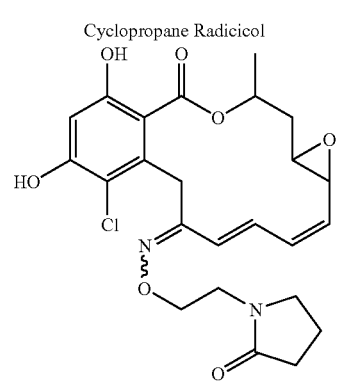

KF58333

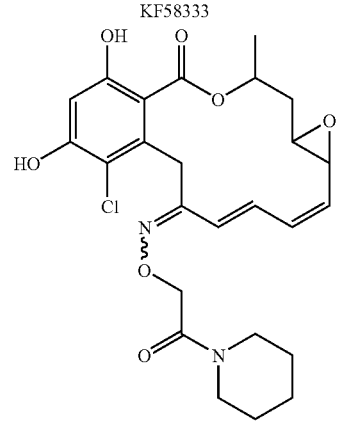

O-Carbamoylmethyl derivative of Radicicol
(compound 9b, Ikuina, 2003, *J. Med. Chem.*, 46, 2534)

In one embodiment of the present invention, radicicol and derivatives thereof have a structure of formula I, II, III, IV, or V as described above.

In another embodiment of the present invention, radicicol and derivatives thereof are used in combination with at least one additional active agent to inhibit the growth of NF2-deficient and/or NF1-deficient tumor cells. Preferably, the at least one additional active agent is one or more HSP90 inhibitors. That is, the methods of inhibiting the growth of NF2-deficient and/or NF1-deficient tumor cells further comprises contacting, i.e., treating, the NF2-deficient or NF1-deficient tumor cells with at least one additional active agent, such as one or more HSP90 inhibitors. In one embodiment, the compound of the present invention contacts the NF2-deficient or NF1-deficient tumor cells with another active agent. The term "active agent" as used herein refers to a chemical or biological entity that can be used, for example, as a therapeutic. Active agents can also be used to mitigate toxicity. For instance, a PAK inhibitor can be used in conjunction with a compound of the present invention to inhibit cell growth or cause cell death.

HSP90 functions as a chaperone for its client proteins as part of dynamic multiprotein complexes, here define as "HSP90 complexes" or "HSP90 chaperone machineries, which consist of co-chaperones such as HSP90, HSP70, HSP27, HSP40, HOP, p23, and CDC37 and individual client protein. These multimeric chaperone/co-chaperone complexes are quite dynamic and involve a series of cycles of association and dissociation of several co-chaperones with HSP90 and/or client proteins.

As used herein, "a HSP90 inhibitor," "a HSP90 inhibitor compound," "a HSP inhibitory compound," "an inhibitor compound", or "an inhibitor" refers to a substance that inhibits or reduces the growth of or number of NF2-deficient tumor cells or NF1-deficient tumor cells by inhibiting HSP90 function in these cells. Any compound that modulates the activity of HSP90, i.e., a HSP90 modulator, may also be used to inhibit the growth of NF2-deficient tumor cells. For example, a HSP90 modulator may modulate HSP90 by inhibiting or down-regulating, i.e., reducing, the activity of one or more proteins of the HSP90 complex.

In one embodiment of the present invention, biological agents or molecules that inhibit or reduce the activity of the HSP90 complex may also be used to inhibit the growth of NF2-deficient or NF1-deficient tumor cells. Examples of the biological agents or molecules of the present invention, include, but are not limited to antibodies, peptides, siRNAs, antisense nucleic acids, and any combinations thereof.

Inhibition by a HSP90 inhibitor can occur through a reduction in the capability of the HSP90 protein or complex to assist its client proteins to function in or to activate a signaling pathway. The HSP90 inhibitor may reduce the amount of total or phosphorylated forms of specific client proteins of HSP90 which in turn inhibits the activity of the downstream pathways of these client proteins. The HSP90 inhibitor/modulator can upregulate the amount of the HSP70 protein and other HSP proteins in the HSP90 complex. HSP90 function can be inhibited or modulated, for example, such as by binding of a compound as disclosed herein to HSP90 or by modifying the HSP90 protein postranslationally. Also, such as by inhibition of a kinase activity of a protein, by inhibition of dimerization of a protein, inhibition of DNA binding of a protein, or inhibition of transactivation of a protein. HSP90 inhibitors can inhibit one or more proteins in the HSP90 complex by an antibody specific for it or by employing antisense, siRNA, or ribozyme technologies to reduce the level of mRNA coding for the protein.

The HSP90 inhibitors or modulators useful for the present invention include, but are not limited to benzoquinone-based ansamycin antibiotics, purine scaffold-based HSP90 inhibitors, pyrazole or imidazole scaffold-based HSP90 inhibitors, tetrahydroindolone- or tetrahydroindazolone-based HSP90 inhibitors, novobiocin and its analogs, and any combinations thereof.

One well-known class of HSP90 inhibitors are benzoquinone-based ansamycin antibiotics, the structure of which typically contain a 1,4-benzoquinone ring fused with a 18- to 20-membered non-aromatic ring containing a lactam group and at least one olefin group in the core of the 18- to 20-membered ring. (See, for example, WO 98/51702, which is herein incorporated by reference in its entirety) Some representative benzoquinone-based ansamycin antibiotics are shown in Scheme 2A.

SCHEME 2A

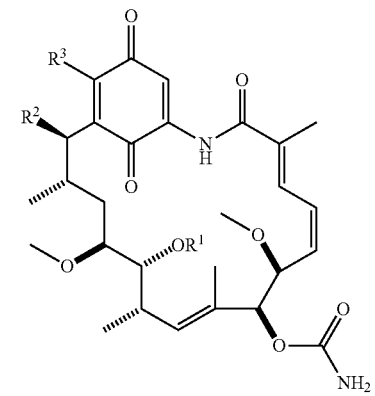

Geldanamycin: $R_1 = H$, $R^2 = H$, $R^3 = OCH_3$
Herbimycin: $R^1 = CH_3$, $R^2 = OCH_3$, $R^3 = H$
17-AAG: $R^1 = H$, $R^2 = H$, $R^3 = $ —NHCH$_2$CH=CH$_2$
17-DMAG: $R^1 = H$, $R^2 = H$, $R^3 = $ —NHCH$_2$CH$_2$N(CH$_3$)$_2$

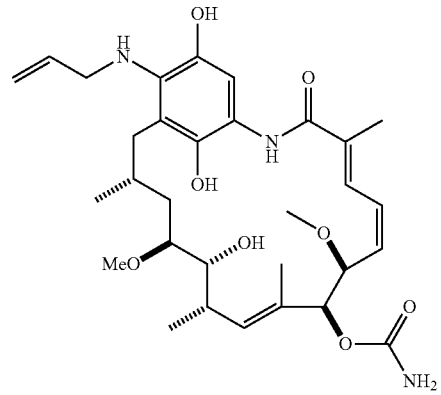

Dihydroquinone derivative of 17-AAG

It has been reported that certain purine scaffold-based compounds are HSP90 inhibitors. (See, for example, WO 02/36705, WO 03/037860, and WO 2006/084030, all of which are herein incorporated by reference in their entirety) These purine scaffold-based HSP90 inhibitors typically have a structure wherein an adenine ring and a six-membered aryl or heteroaryl ring are linked through a linker which can be methylene, fluorinated methylene, sulfur, oxygen, nitrogen, carbonyl, imine, sulfinyl, or sulfonyl. Scheme 3A shows two compounds exemplifying the purine scaffold-based HSP90 inhibitors.

SCHEME 3A

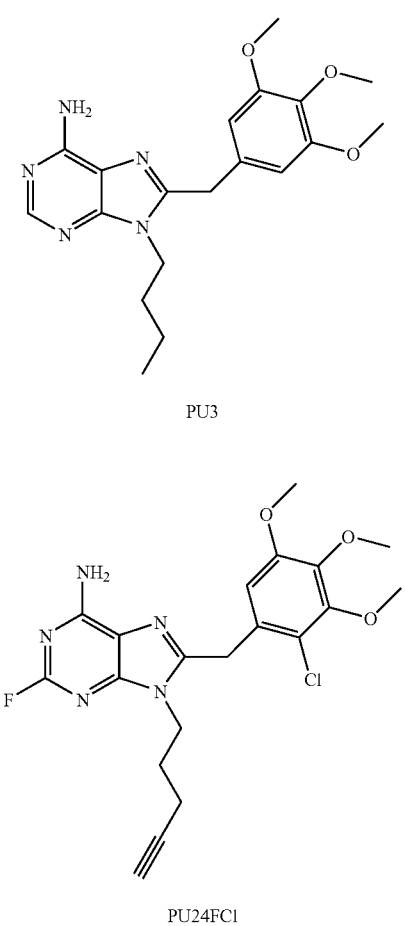

PU3

PU24FCl

-continued

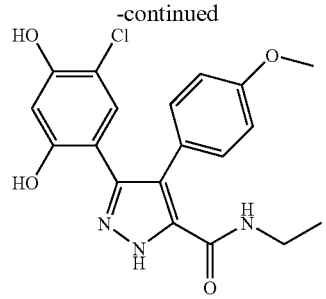

CCT0129397
VER49009

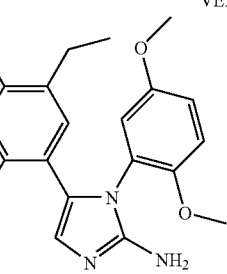

Compound 1 in Table 5
WO 2007/021877

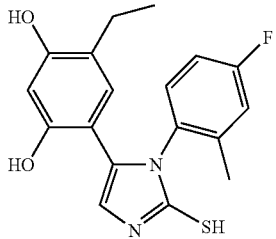

Compound 2 in Table 5
WO 2007/021877

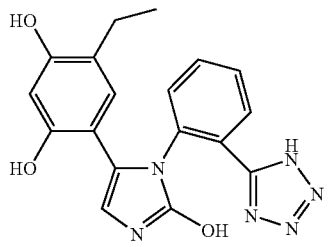

Compound 3 in Table 5
WO 2007/021877

Some pyrazole or imidazole scaffold-based compounds are known to inhibit HSP90. These pyrazole or imidazole scaffold-based HSP90 inhibitors are typically non-fused tricyclic compounds wherein two aryl or heteroaryl rings are attached to two adjacent positions (carbon or nitrogen atom) of a pyrazole or imidazole ring, respectively. (See, for example, WO 2007/021877, which is herein incorporated by reference in its entirety, or Vernalis Ltd, Bioorg Med Chem Lett, 2006, 16, 2543-2548, or Sharp et al., Molecular Cancer Therapeutics, 2007, 6, 1198-1211). Examples of pyrazole or imidazole scaffold-based HSP90 inhibitors are shown in Scheme 4A.

SCHEME 4A

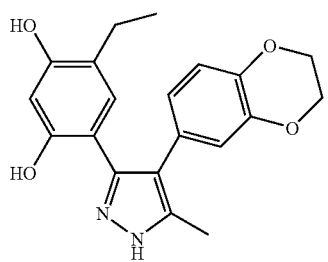

CCT018159

Another class of HSP90 inhibitors are tetrahydroindolone and tetrahydroindazolone derivatives reported in WO 2006/091963, the disclosure of which is herein incorporated by reference in its entirety. These tetrahydroindolone or tetrahydroindazolone based HSP90 inhibitors generally have a structure wherein a substituted aryl group is directly attached to the nitrogen atom of a tetrahydroindolone or tetrahydroindazolone. Scheme 5A shows certain examples in WO 2006/091963.

SCHEME 5A

Example 3

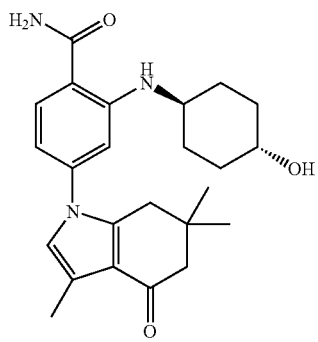

WO 2006/091963

-continued

Example 11

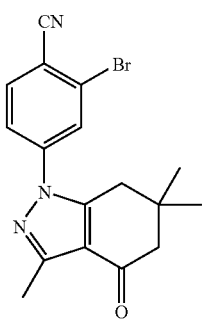

WO 2006/091963

The aminoglycoside antibiotic, Novobiocin, has also been reported to inhibit HSP90. (See, for example, Yu et al., J. Am. Chem. Soc., 2005, 127, 12778-12779) The structure of Novobiocin is shown in Scheme 6A.

SCHEME 6A

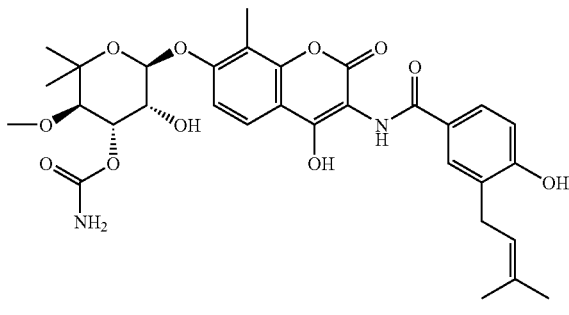

Novobiocin

Many client proteins of HSP90 are kinases which are involved in phosphorylation cascades. For this reason, presence and/or activity of a client protein of HSP90 can be assessed by measuring the phosphorylation of the protein and/or a downstream protein. Inhibition of phosphorylation or hypophosphorylation is an indication of a decrease or inhibition of activity of a protein. In one embodiment, the proliferation of NF2-deficient tumor cells or NF1-deficient cells can be reduced or stabilized by the administration of a HSP90 inhibitory compound that inhibits or reduces the phosphorylation of one or more proteins of the PI3K/Akt pathway or Ras-Raf pathway including, but not limited to, Akt, mTOR, FKHR, GSK3, S6, S6K, Bad, Raf, Mek, and Erk1/2 proteins.

In another embodiment of the invention, the proliferation of NF2-deficient or NF1-deficient tumor cells can be reduced or stabilized by the administration of a compound of the present invention and/or a HSP90 inhibitory compound that reduces or degrades ErbB2 or phospho-ErbB2.

In another embodiment of the invention, the proliferation of NF2-deficient or NF1-deficient tumor cells can be reduced or stabilized by the administration of a compound of the present invention and/or a HSP90 inhibitory compound that reduces or degrades other receptor tyrosine kinases.

A cytotoxic agent and a compound of the present invention can also be contacted together with NF2-deficient or NF1-deficient tumor cells, either simultaneously or sequentially. In this embodiment, the cytotoxic agent, i.e., chemotherapeutic drug, can act synergistically with the HSP90 inhibitor compound to inhibit growth and kill NF2-deficient or NF1-deficient tumor cells. Cytotoxic agents that can be co-administered with the compound of the present invention are chemotherapy drugs known in the art.

Growth of NF2-deficient or NF1-deficient tumor cells can be inhibited in vitro or ex vivo. NF2-deficient or NF1-deficient tumor cells can be primary cell culture cells or a tissue culture cell line cells. Cells can be mammalian cells, including, but not limited to, human, canine, rat and murine Nf2-deficient or Nf1-deficient tumor cells. For instance, methods of the invention include the use of Nf2-deficient mouse cells (e.g., Schwann cells) or NF2-deficient human tumor cells (e.g., Schwann cells) or Nf1-deficient mouse cells (e.g. Schwann cells and MPNST cells) or NF1-deficient human tumor cells (e.g. MPNST cells, astrocytoma cell, JMML cells). Cells can be confluent or subconfluent when contacted with radicico or its derivatives.

In another embodiment, NF2-deficient or NF1-deficient tumor cells are contacted with radicicol or its derivatives in vivo. In this embodiment, radicicol or its derivatives is administered to a subject with a NF2-deficient or NF1-deficient tumor. The subject can be any mammal, including, but not limited to, a human, canine, rat, mouse, and farm animals. Radicicol or its derivatives can be administered at the site of a NF2-deficient or NF1-deficient tumor or elsewhere in the body.

NF2-deficient or NF1-deficient tumor cells can be contacted in vitro or ex vivo with very small amounts of compound of the present invention to trigger inhibition of cell growth and/or resulting in cell death. For instance, NF2-deficient or NF1-deficient cells can be contacted with at least about 0.001 µM of compound of the present invention, at least about 0.01 µM of compound of the present invention, at least about 0.05 µM of compound of the present invention, at least about 0.08 µM of compound of the present invention, at least about 0.09 µM of compound of the present invention, at least about 0.1 µM of compound of the present invention, at least about 0.2 µM of compound of the present invention, at least about 0.3 µM of compound of the present invention, at least about 0.4 µM of compound of the present invention, at least about 0.5 µM of compound of the present invention, at least about 0.6 µM of compound of the present invention, at least about 0.7 µM of compound of the present invention, at least about 0.8 µM of compound of the present invention, at least about 0.9 µM of compound of the present invention, at least about 1 µM of compound of the present invention, at least about 1.5 µM of compound of the present invention, at least about 2 µM of compound of the present invention or about 2 µM to 10 µM of compound of the present invention to inhibit cell growth and/or trigger cell apoptosis. Appropriate amounts of the compound to contact with the cells can be determined by persons skilled in the art to obtain the desired level of inhibition of cell growth or the corresponding amount of cell death.

Inhibition of cell growth or cell death can be measured by methods known in the art. For instance, in vitro and ex vivo inhibition of cell growth and cell death can be measured by a cell proliferation assay and a cell apoptosis assay. Cell death or inhibition of proliferation can be measured in terms of the IC50 of the compound of the present invention. In one embodiment, the IC50 of NF2-deficient tumor cells treated in vitro or ex vivo is at least about 0.001 µM, at least about 0.01 µM, at least about 0.05 µM, at least about 0.08 µM, at least about 0.09 µM, at least about 0.1 µM, at least about 0.2 at least about 0.3 µM, at least about 0.4 µM, at least about 0.5 µM, at least about 0.6 µM, at least about 0.7 µM, at least about 0.8

μM, at least about 0.9 μM, at least about 1 μM, at least about 1.5 μM, at least about 2 μM, or about 2 μM to 10 μM compound of the present invention.

In another embodiment, NF2-deficient or NF1-deficient tumor cells are contacted with a compound of the present invention in vivo. In this embodiment, a compound of the present invention is administered to a subject with a NF2-deficient or NF1-deficient tumor. The subject can be any mammal, including, but not limited to, a human, canine, rat, mouse, and farm animals. The compound can be administered at the site of the tumor or elsewhere in the body.

When a compound of the present invention is administered in vivo, it can be administered such that the serum levels mimic those levels found to cause inhibition of cell growth and/or cell death in vitro. In one embodiment, the compound of the present invention contacts the NF2-deficient or NF1-deficient tumor cells with another agent.

Methods of Treatment by Using Compounds of the Present Invention, including compounds of Formulae I, II, III, IV, V, Ia, Ia', IIa, IIa', IIIa, IVa, and Va:

The present invention provides methods of treating a subject diagnosed with neurofibromatosis type-2 or a condition associated with the loss of NF2 function (i.e., the loss of the protein, Merlin), including, but not limited to sporadic schwannomas, and other NF2 related tumors, such as sporadic meningiomas and sporadic mesotheliomas. The method comprises administering to a patient a therapeutically effective amount of one or more compounds of the present invention, including compounds of formulae I, II, III, IV, V, Ia, Ia', IIIa, IIa', IIIa, IVa, and Va. "Subject" and "patient" are used interchangeably herein, and refer to a mammalian subject to be treated, including, but not limited to, human patients. A subject can be diagnosed with NF2 by methods known in the art, including, but not limited to, a direct gene test and the bilateral occurrence of vestibular schwannomas. The methods of treatment are similar for a subject diagnosed with NF1 or a condition associated with the loss of NF1 function (i.e., the loss of the protein, neurofibromin).

The present invention also provides methods of treating a subject diagnosed with a neurodegenerative disease. A neurodegenerative disease is a central nervous system disorder characterized by gradual and progressive loss of neural tissue. Neurodegenerative diseases result from deterioration of neurons which over time will lead to neurodegeneration and disabilities resulting from this. Examples of neurodegenerative diseases include, but are not limited to Alzheimer's disease, amyotrophic lateral sclerosis (ALS), Creutzfeldt-Jakob disease, Huntington disease, multiple sclerosis, Parkinson disease, and spinal muscular atrophy but other neurodegenerative diseases are known to persons skilled in the field.

As used herein, "therapeutically effective amount" refers to an amount sufficient to inhibit the growth of one or more NF-2 deficient tumors or NF1-deficient tumors, or to slow, stop, or reverse the gradual and progressive loss of neural tissue. "Inhibition", as used herein, means that the size of a tumor stabilizes and does not increase. In one embodiment, the tumor may be reduced in size following administration of a compound of the present invention. For instance, the tumor may be reduced in size at least about 10%, at least about 20%, at least about 30%, at least about 40%, at least about 50%, at least about 60%, at least about 70%, at least about 80%, at least about 90%, or about 100% compared to the size of the tumor prior to treatment, i.e., a baseline measurement. The inhibition of tumor growth can be assessed by methods known in the art, including, but not limited to, magnetic resonance imaging or a CAT scan.

As can be appreciated by a skilled artisan, a "therapeutically effective amount" will vary depending on the tumor load of the patient and the age, weight, and other conditions of the patient to be treated. Further, a therapeutically effective amount may vary based on the specific compound of the present invention administered and pharmaceutical composition as well as the route of administration.

The methods of the present invention can be used to treat a variety of NF2-deficient tumors or NF1-deficient tumors. For instance, the compound of the present invention can be administered to treat a vestibular schwannoma, for instance, a unilateral schwannoma or a bilateral schwannoma. Inhibition of the growth of these tumors and/or death of tumor cells can mitigate the symptoms associated with schwannomas, including but not limited to vestibular schwannomas. For instance, treatment with a compound of the present invention may result in an improvement in hearing, tinnitus and/or balance.

The methods of the invention can be used to treat other types of NF2-deficient schwannomas as well or type of NF1-deficient tumors. For instance, administration of a compound of the present invention can be used to treat a patient suffering from one or more spinal cord schwannomas/neurofibromas and other peripheral nerve schwannomas/neurofibromas and sporadic schwannomas/neurofibromas. Treatment of peripheral nerve tumors, including spinal cord tumors, can decrease a patient's pain. Further, neurological deficits associated with NF1 may be reversible with the treatment of the present invention.

In one embodiment of the invention, administration of a compound of the present invention, including compounds of formulae I, II, III, IV, V, Ia, Ia', IIa, IIa', IIIa, IVa, and Va, results in a decrease in a patient's tumor load. For instance, administration of a compound of the present invention can result in at least about a 5%, at least about a 10%, at least about a 15%, at least about a 20%, at least about a 25%, at least about a 30%, at least about a 40%, at least about a 50%, at least about a 60%, at least about a 70%, at least about an 80%, at least about a 90%, or about a 100% decrease in tumor load.

Pharmaceutical Compositions

The compound of the present invention, including compounds of formulae I, II, III, IV, V, Ia, Ia', IIa, IIa', IIIa, IVa, and Va, may be formulated for administration in a pharmaceutically acceptable carrier or excipient in accordance with known techniques in the art. See, e.g., Remington, The Science And Practice of Pharmacy ($9^{th}$ Ed. 1995). In the manufacture of a pharmaceutical composition according to the invention, the compound (including the physiologically acceptable salts thereof) is typically admixed with, inter alfa, an acceptable carrier. The carrier must, of course, be acceptable in the sense of being compatible with any other ingredients in the composition and must not be deleterious to the patient. The carrier may be a solid or a liquid, or both, and is preferably formulated with the compound as a unit-dose formulation, for instance, a tablet, which may contain from 0.01 or 0.5% to 95% or 99% by weight of compound. In one embodiment of the invention, the pharmaceutical composition administered to the patient contains more than one type of HSP90 inhibitor.

Pharmaceutical compositions include those suitable for oral, rectal, topical, buccal (e.g., sub-lingual), vaginal, parenteral (e.g., subcutaneous, intramuscular, intradermal, intraperitoneal, intravenous, etc.), topical (e.g., both skin and mucosal surfaces, including airway surfaces) and transdermal administration.

In one embodiment of the invention, the pharmaceutical composition is applied directly to the site of a NF2-deficient tumor or NF1-deficient tumor. For instance, the HSP90 inhibitor can be applied by local treatment which encompasses both topical treatment and intralesional or intradermal treatment at the site of the tumor. Therefore, the inhibitor can be injected into, topically applied onto or near a NF2-deficient tumor or NF1-deficient tumor. In one embodiment of the invention, the inhibitor is applied intralesionally to NF2-deficient tumors or NF1-deficient tumors by methods known in the art.

Alternatively, the pharmaceutical composition can take the form of an implant. Such a composition can be surgically implanted at or near the site of a tumor for slow release of the compound of the present invention.

In another embodiment of the invention, a pharmaceutical composition is administered by transcatheter arterial embolization by methods known in the art.

Pharmaceutical compositions suitable for oral administration may be presented in discrete units, such as capsules, cachets, lozenges, or tablets, each containing a predetermined amount of a compound of the present invention; as a powder or granules; as a solution or a suspension in an aqueous or non-aqueous liquid; or as an oil-in-water or water-in-oil emulsion.

Pharmaceutical compositions suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Pharmaceutical compositions of the present invention suitable for parenteral administration comprise sterile aqueous and non-aqueous injection solutions of the active compound, which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents.

In one embodiment of the invention, a pharmaceutical composition of the compound of the present invention is applied topically. For instance, a pharmaceutical composition can be applied to the skin near a NF2-deficient tumor or a NF1-deficient tumor. Compositions suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Pharmaceutical compositions suitable for transdermal administration may be presented as discrete patches adapted to remain in intimate contact with the epidermis of the recipient for a prolonged period of time. Such compositions may be applied near or at the site of a NF2-deficient tumor or a NF1-deficient tumor. Formulations suitable for transdermal administration may also be delivered by iontophoresis (see, for example, Pharmaceutical Research 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

The present invention also includes methods of treating a subject with NF2 or NF1 by administering a liposomal formulation of a compound of the present invention. The technology for forming liposomal suspensions is well known in the art. When the inhibitor is water-insoluble, the salt may be substantially entrained within the hydrophobic lipid bilayer which forms the structure of the liposome. The liposomes which are produced may be reduced in size, as through the use of standard sonication and homogenization techniques. The liposomal formulations containing the compound of the present invention disclosed herein or salts thereof, may also be lyophilized to produce a lyophilizate which may be reconstituted with a pharmaceutically acceptable carrier, such as water, to regenerate a liposomal suspension.

Other pharmaceutical compositions, such as aqueous base emulsions, may be prepared from compounds of the present invention. In such an instance, the composition will contain a sufficient amount of pharmaceutically acceptable emulsifying agent to emulsify the desired amount of compounds of the present invention. Particularly useful emulsifying agents include phosphatidyl cholines and lecithin.

The therapeutically effective dosage of any specific compound of the present invention for treatment of a NF2-deficient tumor or a NF1-deficient tumor will vary from patient to patient, and will depend upon factors such as the age, weight, gender and condition of the patient and the route of delivery. As a general proposition, a dosage from about 0.01 or 0.1 to about 50, 100 or 500 mg/kg will have therapeutic efficacy, with all weights being calculated based upon the weight of the compound, including the cases where a salt is employed.

Mammals, and specifically humans, suffering from a respiratory disorder can be treated by the inhalation, systemic, oral, topical, or transdermal administration of a composition comprising an effective amount of the compounds described herein or a pharmaceutically acceptable salt, ester or prodrug thereof, optionally in a pharmaceutically acceptable carrier or diluent.

In a separate embodiment, the compounds of the invention are in the form of an inhaled dosage. In this embodiment, the compounds may be in the form of an aerosol suspension, a dry powder or liquid particle form. The compounds may be prepared for delivery as a nasal spray or in an inhaler, such as a metered dose inhaler. Pressurized metered-dose inhalers ("MDI") generally deliver aerosolized particles suspended in chlorofluorocarbon propellants such as CFC-11, CFC-12, or the non-chlorofluorocarbons or alternate propellants such as the fluorocarbons, HFC-134A or HFC-227 with or without surfactants and suitable bridging agents. Dry-powder inhalers can also be used, either breath activated or delivered by air or gas pressure such as the dry-powder inhaler disclosed in the Schering Corporation International Patent Application No. PCT/US92/05225, published 7 Jan. 1993 as well as the Turbuhaler™ (available from Astra Pharmaceutical Products, Inc.) or the Rotahaler™ (available from Allen & Hanburys) which may be used to deliver the aerosolized particles as a finely milled powder in large aggregates either alone or in combination with some pharmaceutically acceptable carrier e.g. lactose; and nebulizers.

The compounds of the invention may be also administered in specific, measured amounts in the form of an aqueous suspension by use of a pump spray bottle. The aqueous suspension compositions of the present invention may be prepared by admixing the compounds with water and other pharmaceutically acceptable excipients. The aqueous suspension compositions according to the present invention may contain, inter alia, water, auxiliaries and/or one or more of the excipients, such as: suspending agents, e.g., microcrystalline cellulose, sodium carboxymethylcellulose, hydroxpropyl-methyl cellulose; humectants, e.g. glycerin and propylene glycol; acids, bases or buffer substances for adjusting the pH, e.g., citric acid, sodium citrate, phosphoric acid, sodium phosphate as well as mixtures of citrate and phosphate buffers; surfactants, e.g. Polysorbate 80; and antimicrobial preservatives, e.g., benzalkonium chloride, phenylethyl alcohol and potassium sorbate.

Typical systemic dosages for all of the herein described conditions are those ranging from 0.01 mg/kg to 1500 mg/kg of body weight per day as a single daily dose or divided daily doses. Preferred dosages for the described conditions range from 0.5-1500 mg per day. A more particularly preferred dosage for the desired conditions ranges from 5-750 mg per day. Typical dosages can also range from 0.01 to 1500, 0.02 to 1000, 0.2 to 500, 0.02 to 200, 0.05 to 100, 0.05 to 50, 0.075 to 50, 0.1 to 50, 0.5 to 50, 1 to 50, 2 to 50, 5 to 50, 10 to 50, 25 to 50, 25 to 75, 25 to 100, 100 to 150, or 150 or more mg/kg/day, as a single daily dose or divided daily doses. In one embodiment, the compounds are given in doses of between about 1 to about 5, about 5 to about 10, about 10 to about 25 or about 25 to about 50 mg/kg. Typical dosages for topical application are those ranging from 0.001 to 100% by weight of the active compound.

The compounds are conveniently administered in units of any suitable dosage form, including but not limited to one containing from about 7 to 3000 mg, from about 70 to 1400 mg, or from about 25 to 1000 mg of active ingredient per unit dosage form. For example, an oral dosage of from about 50 to 1000 mg is usually convenient, including in one or multiple dosage forms of 50, 100, 200, 250, 300, 400, 500, 600, 700, 800, 900 or 1000 mgs. Lower dosages may be preferable, for example, from about 10-100 or 1-50 mgs. Also contemplated are doses of 0.1-50 mg, 0.1-20 mgs., or 0.1-10 mgs. Furthermore, lower doses may be utilized in the case of administration by a non-oral route, as for example, by injection or inhalation.

The compound is administered for a sufficient time period to alleviate the undesired symptoms and the clinical signs associated with the condition being treated.

The active compound is included in the pharmaceutically acceptable carrier or diluent in an amount sufficient to deliver to a patient a therapeutic amount of compound in vivo in the absence of serious toxic effects. Pharmaceutically acceptable carriers that may be used in these pharmaceutical compositions are generally known in the art. They include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, solvents, salts or electrolytes, such as protamine sulfate, disodium hydrogen phosphate, potassium hydrogen phosphate, sodium chloride, zinc salts, silicates, colloidal silica, magnesium trisilicate, polyvinyl pyrrolidone, cellulose-based substances, polyethylene glycol, sodium carboxymethylcellulose, polyacrylates, waxes, oils, polyethylene-polyoxypropylene-block polymers, polyethylene glycol and wool fat. Pharmaceutically accepted vehicles can contain mixtures of more than one excipient in which the components and the ratios can be selected to optimize desired characteristics of the formulation including but not limited to shelf-life, stability, drug load, site of delivery, dissolution rate, self-emulsification, control of release rate and site of release, and metabolism.

Formulations can be prepared by a variety of techniques known in the art. Examples of formulation techniques can be found in literature publications and in texts such as "Water-insoluble drug formulation", edited by Rong Liu, 2000, Interpharm Press.

If administered intravenously, carriers can be physiological saline, bacteriostatic water, Cremophor EL™ (BASF, Parsippany, N.J.) or phosphate buffered saline (PBS). Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other surface-active emulsifying agents or bioavailability enhancers which are commonly used in the manufacture of pharmaceutically acceptable solid, liquid, or other dosage forms may also be used for the purposes of formulation.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

One mode of administration of the active compound for systemic delivery is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound or its salts can be administered as a component of an elixir, suspension, syrup, wafer, chewing gum or the like. A syrup may contain, in addition to the active compounds, sucrose as a sweetening agent and certain preservatives, dyes and colorings and flavors.

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the compound is then introduced into the container. The container is then swirled by hand to free lipid material from the sides of the container and to disperse lipid aggregates, thereby forming the liposomal suspension.

Suitable vehicles or carriers for topical application can be prepared by conventional techniques, such as lotions, suspensions, ointments, creams, gels, tinctures, sprays, powders, pastes, slow-release transdermal patches, suppositories for application to rectal, vaginal, nasal or oral mucosa. In addition to the other materials listed above for systemic administration, thickening agents, emollients, and stabilizers can be used to prepare topical compositions. Examples of thickening agents include petrolatum, beeswax, xanthan gum, or polyethylene, humectants such as sorbitol, emollients such as mineral oil, lanolin and its derivatives, or squalene.

Combination Therapy

The compound of present invention can also be mixed with other active agents which do not impair the desired action, or with materials that supplement the desired action. The one or more active agents can be administered in conjunction, i.e. combination or alternation, with other medications used in the treatment of disorders or conditions associated with NF1 or NF2. The term "active agent" has the same meaning as described above. In other words, methods of the invention include co-administering a compound of the present invention with another therapeutic agent, either concurrently or sequentially. Preferably, the compounds of the present invention can be administered in combination or alternation with one or more HSP90 inhibitors as described above.

In one embodiment, a compound of the present invention can be administered with a cytotoxic agent known in the art to inhibit tumor growth or kill the tumor(s). Co-administration of a HSP90 pathway inhibitor with a cytotoxic agent may reduce the toxic side-effects otherwise associated with the cytotoxic agent. Toxicity would be reduced because less cytotoxic agent would need to be administered to the patient to inhibit tumor growth or kill one or more tumors than if the cytotoxic agent were administered alone.

In addition to co-administration of the compound of the present invention with a cytotoxic agent such a chemotherapy drug, the compound of the present invention can also be administered with radiation therapy in combination. As with chemotherapy, administration of the compound of the present invention with radiation therapy allows less radiation therapy to be used for treatment, and thus, reduces the risk of toxic side effects.

The compound of the present invention can also be administered before or after surgical removal of a tumor to kill or inhibit the growth of any remaining NF2-deficient or NF1-deficient tumor cells. This embodiment is especially useful for tumors of the brain and spine where removing all NF2-deficient or NF1-deficient tumor cells could put the patient at risk for permanent nerve damage or even death.

In another embodiment, the compound of the present invention is administered to a patient with a PAK inhibitor.

It is also possible to combine any compound of the invention with one or more other active agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active agents generally refers to simultaneous or sequential administration of a compound of the invention and one or more other active agents, such that therapeutically effective amounts of the compound of the invention and one or more other active agents are both present in the body of the patient.

Co-administration includes administration of unit dosages of the compounds of the invention before or after administration of unit dosages of one or more other active agents, for example, administration of the compounds of the invention within seconds, minutes, or hours of the administration of one or more other active agents. For example, a unit dose of a compound of the invention can be administered first, followed within seconds or minutes by administration of a unit dose of one or more other active agents. Alternatively, a unit dose of one or more other active agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active agents. In other cases, it may be desirable to administer a unit dose of one or more other active agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

Methods of Screening for NF2 and NF1 HSP90 Inhibitor Therapeutics

The present invention also includes methods of screening HSP90 inhibiting compounds for efficacious treatment of NF2 or NF1. For instance, the methods of the invention can be used to determine the efficacy of a compound in pre-clinical experiments. This is useful because it can allow researchers to reduce the number of drugs to be tested for efficacious treatment of NF2 or NF1. The methods of the invention can also be used to repurpose existing drugs that were developed and/or are used for other indications. This is useful because such drugs presumably have established safety data and can thus be brought to market quicker and with less expense than uncharacterized compounds.

As used herein, "efficacious treatment" means that a test compound results in the inhibition or reduction of cell growth. In one embodiment, efficacious treatment results in cell death or inhibition of proliferation. An efficacious treatment can be correlated with a reduction in the amount or activity of one or more client proteins of HSP90 or an increase in other HSP proteins such as HSP70. For instance, a reduction in the amount of ErbB2 protein leads to the reduction in the amount of phospho-ErbB2 and the activity of ErbB2 which can be correlated with the inhibition or reduction of growth of NF2-deficient cells. In addition, a reduction in the amount of AKT or phospho-AKT may lead to the reduction in the phosphorylation of mTOR, GSK3, FKHR, S6 and S6K which can also be correlated with the inhibition or reduction of growth of NF2-deficient cells or apoptosis of NF2-deficient cells. Moreover, a reduction in the amount of Raf may lead to the reduction in the activity of downstream MAP kinase signaling pathway which can be correlated with the inhibition or reduction of growth of NF1-deficient cells.

Methods known in the art can be used to assess whether a test drug reduces the activity of one or more client proteins of the HSP90 complex. Such assays can be conducted in vitro, ex vitro using cells or tumor specimens from human patients or animal models, or, in the case of animal models, in vivo (Roe et al., 2004, Cell 116: 87-98; Smith et al., 2005, Cancer Chemother. Pharmacol. 56:126-137; Banerji et al., 2005, Clin. Cancer Res. 11:7023-7032; Eiseman et al., 2005, Cancer Chemother. Pharmacol. 55: 21-32; Goetz et al., 2005, *J. Clin. Oncol.* 23(6):1078-1087; Solit et al., 2002, *Clin. Cancer. Res.* 8(5):986-993)

In one embodiment of the invention, the ability of a drug to reduce the activity of a client protein (e.g. a kinase) of HSP90 or the downstream pathway of the client protein is assessed by contacting the proteins of the cells with an anti-phospho antibody specific for the particular protein. For instance, Western blots can be used by methods known in the art and can be probed with anti-phospho antibodies to phosphorylated AKT, phosphorylated ErbB2, phosphorylated GSK3, phosphorylated S6, phosphorylated S6K, phosphorylated mTOR, phosphorylated Mek, and phosphorylated downstream proteins thereof.

Embodiments of the Invention are Summarized as Follows:

The present invention is directed to a method of treating, preventing or ameliorating tumors or symptoms resulting from neurofibromatosis in a subject comprising administering to said subject with neurofibromatosis type 2 (NF2) or a condition associated with the loss of NF2 function or with neurofibromatosis type 1 (NF1) or a condition associated with the loss of NF1 function a therapeutically effective amount of at least one composition comprising at least one heat shock protein 90 (HSP90) inhibitor which inhibits or slows growth of one or more NF2-deficient tumors or NF1-deficient tumors, reduces the number of said tumors or inhibits and/or reduces associated symptoms as compared to no treatment with the composition as a control level to determine treatment utility. The method is particularly directed to the administration of the at least one composition comprising HSP90 resulting in a decrease in size and/or number of one or more NF2-deficient tumors or of one or more NF1-deficient tumors.

The method of the present invention comprises administering a HSP90 inhibitor comprising a compound which inhibits or reduces the function of HSP90 complex. More specifically, the HSP90 inhibitor comprises a compound that binds and inhibits the HSP90 protein, modifies HSP90 protein posttranslationally, and/or increases HSP70 or other HSP proteins from their normal levels in the NF2-deficient or NF1-deficient tumors. The administration of the HSP90 inhibitor results in the upregulation or increase in HSP70 in said subject. Further, the method comprises administering a HSP90 inhibitor comprising a compound that degrades or reduces one or more client proteins of HSP90 and the phosphorylated forms of the client proteins. Additionally, the method comprises administering a HSP90 inhibitor comprises a compound that inhibits or reduces activity or phosphorylation of signaling pathway proteins associated with one or more client proteins of HSP90. The one or more client proteins are selected from the group consisting of ErbB2, AKT, and Raf. The HSP90 inhibitor inhibits or reduces activity or phosphorylation of the signaling pathways proteins, such as PI3K, mTOR, GSK3, 4E-BP1, Bad, FKHR, HSP90, S6K, S6, Mek, and Erk1/2.

In a further embodiment, the method comprises administering a HSP90 inhibitor comprising a biological agent or molecule that is a peptide, antibody, siRNA and antisense nucleic acid molecule.

In still a further embodiment, the method comprises administering at least one composition comprising at least one heat shock protein 90 (HSP90) inhibitor comprising radicicol or a derivative thereof, 17-AAG or a derivative thereof, a purine scaffold-based HSP90 inhibitor or a derivative thereof, a pyrazole scaffold-based HSP90 inhibitor or a derivative thereof, an imidazole scaffold-based HSP90 inhibitor or a derivative thereof, a tetrahydroindolone- or tetrahydroindazolone-based HSP90 inhibitor or a derivative thereof, Novobiocin or a derivative thereof, or any combination thereof. Further, in a further embodiment, the HSP90 inhibitor comprises a HSP90 modulator compound such as a HDAC inhibitor and specifically HDAC6 inhibitor. This HSP90 modulator compound may further comprise Trichostatin A, SAHA, LAQ824, FK228, or derivatives thereof. Further, the method comprises administering a HSP90 inhibitor comprising an inhibitor or compound that modulates or increases the level of HSPs such as HSP70 and HSP27. The HSP90 inhibitor further comprises NZ28 (NCS-134754) or a derivative thereof.

The method comprises administering the HSP90 inhibitor orally, intravenously or locally, such as intralesionally or topically. The method also encompasses administering the HSP90 inhibitor before, during or after surgical removal of a tumor, Another mode of administration allows the HSP90 inhibitor to be co-administered before, during or after radiation therapy or with a PAK inhibitor or a cytotoxic compound.

The method of the present invention treats, prevents or ameliorates tumors or symptoms resulting from neurofibromatosis type 2 (NF2) or condition(s) associated with the loss of NF2 function. More specifically the one or more NF2-deficient tumors comprise vestibular schwannomas, and more specifically comprise a unilateral vestibular schwannoma or a bilateral vestibular schwannoma. Additionally, the one or more NF2-deficient tumors that are treated comprise spinal cord schwannomas, sporadic schwannomas, peripheral nerve schwannomas, schwannoma, meningioma, mesothelioma, ependymoma, glioma and astrocytoma.

The method comprises the administration of the HSP90 inhibitor to obtain results in an improvement in at least one of the subject's hearing, balance and vision; increase in muscle mass, reduction in tumor burden in the subject, which the latter is identified using a MM or a CAT scan.

The method of the present invention treats, prevents or ameliorates tumors or symptoms resulting from neurofibromatosis type 1 (NF1) or condition(s) associated with the loss of NF1 function. More specifically the one or more NF1-deficient tumors comprise a dermal and plexiform neurofibromas, optic pathway astrocytomas, optic neuromas, optic gliomas, cerebral astrocytomas, cerebral gliomas, ependymomas, pheochromocytomas and ganglioneuromas, rhabdomyosarcomas, neurofibrosarcomas, malignant peripheral nerve sheath tumors ("MPNST"), malignant schwannomas, and JMML.

The present invention also includes a method of inhibiting or reducing the growth or number of NF2-deficient tumor cells or NF1-deficient tumor cells comprising contacting said NF2-deficient tumor cells or NF1-deficient tumor cells with at least one composition comprising at least one heat shock protein 90 (HSP90) inhibitor which inhibits or slows growth and/or reduces the number of one or more NF2-deficient tumors or NF1-deficient tumors. This method comprises contacting said NF2-deficient tumor cells or NF1-deficient tumor cells with said compound occurs in vitro or ex vivo. The NF2-deficient tumor cells are Nf2-deficient mouse Schwann cells and said NF1-deficient tumor cells are Nf1-deficient mouse Schwann cells. Or the NF2-deficient tumor cells are NF2-deficient human schwannoma cells and said NF1-deficient tumor cells are NF1-deficient human Schwann cells. The NF2-deficient tumor cells are selected from the group consisting of NF2-deficient schwannoma cell line cells, NF2-deficient meningioma cell line cells and NF2-deficient mesothelioma cell line cells. The NF2-deficient tumor cells are selected from the group consisting of HEI193 cells, SF1335 cells, BAR cells and RAV cells. The NF1-deficient tumor cells are selected from the group consisting of human MPNST cells, primary neurofibroma cells derived from NF1 patients, mouse NAp53-deficient MPNST cell lines established from cisNf1;p53 mice, and Nf1−/− mouse cells, such as Schwann cells, mouse embryonic cells, and leukemia cells. More specifically, the NF1-deficient tumor cells are selected from the group consisting of ST88-14, 88-3, 90-8, and sNF96.2. The NF2-deficient tumor cells or NF1-deficient tumor cells that are contacted with said HSP90 inhibitor can occur in vivo. The NF2-deficient tumor cells or said NF1-deficient tumor cells are from a human, canine, rat or mouse.

The method of the present invention comprises contacting the NF2-deficient tumor cells or the NF1-deficient tumor cells with a HSP90 inhibitor that results in an inhibition of HSP90 function. The method further comprises contacting the NF2-deficient tumor cells or said NF1-deficient tumor cells with said HSP90 inhibitor that results in an upregulation of HSP70. Further the contact of the NF2-deficient tumor cells or the NF1-deficient tumor cells with the HSP90 inhibitor results in degradation of ErbB2 and/or phosphorylated ErbB2, in degradation of Akt and/or phosphorylated Akt or in degradation of Raf and/or phosphorylated Raf. More specifically, the contact of the NF2-deficient tumor cells or said NF1-deficient tumor cells with the HSP90 inhibitor results in a reduction in phosphorylation of proteins downstream of the ErbB2, Akt or Raf signaling pathway. The degradation or upregulation of the proteins or reduction in phosphorylated proteins is detected using an antibody.

The method also contacts a HSP90 inhibitor with the NF1-deficient and NF2-deficient cells where the HSP90 inhibitor comprises a biological agent or molecule, wherein the biological agent or molecule is selected from the group consisting of peptide, antibody, siRNA and antisense nucleic acid.

In still a further embodiment, the method comprises contacting the NF2-deficient tumor and NF1-deficient tumors with at least one composition comprising at least one heat shock protein 90 (HSP90) inhibitor comprising radicicol or a derivative thereof, 17-AAG or a derivative thereof, a purine scaffold-based HSP90 inhibitor or a derivative thereof, a pyrazole scaffold-based HSP90 inhibitor or a derivative thereof, an imidazole scaffold-based HSP90 inhibitor or a derivative thereof, a tetrahydroindolone- or tetrahydroindazolone-based HSP90 inhibitor or a derivative thereof, Novobiocin or a derivative thereof, or any combination thereof. Further, in a further embodiment, the HSP90 inhibitor comprises a HSP90 modulator compound such as a HDAC inhibitor and specifically HDAC6 inhibitor. This HSP90 modulator compound may further comprise Trichostatin A, SAHA, LAQ824, FK228, or derivatives thereof. Further, the method comprises administering a HSP90 inhibitor comprising an inhibitor or compound that modulates or increases the level of HSPs such as HSP70 and HSP27. The HSP90 inhibitor further comprises NZ28 (NCS-134754) or a derivative thereof. The HSP90 inhibitor also comprises an inhibitor or compound that modulates (e.g. increases) the level of HSPs such as HSP70 and HSP27. The HSP90 inhibitor may also comprise NZ28 (NCS-134754) or a derivative thereof. The method also comprises contacting the NF-2-deficient cells or NF-1-deficient cells are contacted with said compound and a compound that inhibits or reduces PAK activity.

In another embodiment, the present invention includes a method for screening a test compound for treatment of NF-2 or NF-1 comprising treating or contacting NF-2-deficient cells or NF-1-deficient cells with said test compound, wherein a degradation of one or more client proteins of HSP90 or a decrease in activity of signaling pathways associated with one or more client proteins of HSP90 or an increase in HSP70 is indicative of an efficacious treatment of NF-2 or NF-1. The method further comprises assessing inhibition of HSP90 function. The inhibition of HSP90 function results in an upregulation of HSP70. The one or more client proteins of HSP90 are selected from the group consisting of ErbB2, AKT, and Raf. Additionally, the signaling pathways are associated with one or more client proteins of HSP90 are ErbB2 pathway, AKT pathway or Raf pathway which contain at least one protein selected from group consisting of ErbB2, AKT, Raf, mTOR, GSK3, 4E-BP1, Bad, FKHR, S6K, S6, Mek, and Erk1/2. Specifically, the one or more client proteins is AKT, the AKT is degraded by said test compound, resulting in reduced phosphorylation of AKT. The treatment results in reduced phosphorylation of S6, GSK3, FKHR, Mek, or Erk1/2. The reduced phosphorylation is detected using an antibody.

The method of the present invention further comprises measuring NF-2-deficient cells or NF-1-deficient cells following treatment with the test compound, wherein a decrease in the number of NF2-deficient cells or NF-1-deficient cells following treatment with the test compound or a decrease in proliferation of NF2-deficient cells or NF-1-deficient cells following treatment with the test compound is indicative of an efficacious treatment. Additionally, the method further comprises comparing the NF2-deficient cells or NF-1-deficient cells following treatment to untreated NF2 deficient cells or NF-1-deficient cells, wherein a decrease in one or more client proteins of the HSP90 following treatment with the test compound compared to untreated NF2-deficient cells or NF-1-deficient cells is indicative of an efficacious treatment. Additionally, the method further comprising comparing the NF2- deficient cells or NF-1-deficient cells following treatment to untreated NF2 deficient cells or NF-1-deficient cells, wherein a decrease in number of NF2 deficient cells or NF-1-deficient cells following treatment with the test compound or a decrease in proliferation of NF2-deficient cells or NF-1-deficient cells following treatment with the test compound compared to untreated NF2-deficient cells or NF-1-deficient cells is indicative of an efficacious treatment. The treatment of the NF2-deficient cells or NF1-deficient cells with said test compound occurs in vitro or ex vivo. The NF2-deficient tumor cells are Nf2-deficient mouse Schwann cells and the NF1-deficient tumor cells are Nf1-deficient mouse Schwann cells. Also the NF2-deficient tumor cells are NF2-deficient human schwannoma cells and said NF1-deficient tumor cells are NF1-deficient human Schwann cells.

The NF2-deficient tumor cells are selected from the group consisting of NF2-deficient schwannoma cell line cells, NF2-deficient meningioma cell line cells and NF2-deficient mesothelioma cell line cells. The NF2-deficient tumor cells are selected from the group consisting of HEI193 cells, SF1335 cells, BAR cells and RAV cells. The NF1-deficient tumor cells are selected from the group consisting of human MPNST cells, primary neurofibroma cells derived from NF1 patients, mouse Nf1;p53-deficient MPNST cell lines established from cisNf1;p53 mice, and Nf1−/− mouse cells, such as Schwann cells, mouse embryonic cells, and leukemia cells. More specifically, the NF1-deficient tumor cells are selected from the group consisting of ST88-14, 88-3, 90-8, and sNF96.2. The NF2-deficient tumor cells or NF1-deficient tumor cells that are contacted with said HSP90 inhibitor can occur in vivo. The NF2-deficient tumor cells or said NF1-deficient tumor cells are from a human, canine, rat or mouse.

Processes for the Preparation of the Compounds of Formulae I, II, III, IV, or V:

Modular synthetic processes directed to the synthesis of pochonin D and pochonin A were adapted to the synthesis of a library of resorcylic acid lactones that extend beyond the natural resorcylides. The syntheses developed utilize resin-assisted or solid phase synthesis to minimize and facilitate the isolation of intermediate and final products. First, a description of the synthetic protocols directed to the natural resorsylic acid lactones is presented followed by the synthesis of the library of compounds.

The following abbreviations are used herein.
Ac Acetyl (CH3C=O)
ADP Adenosine diphosphate
AIBN Azobis(isobutyronitrile)
All Allyl
ATP Adenosine triphosphate
BER Borohydride exchange resin
BBN Borabicyclononane
Bn Benzyl
Bz Benzoyl
CAN Ceric ammonium nitrate
CSA Camphorsulfonic acid
δ Chemical shift (NMR)
dba Dibenzylideneacetone
DBU 1,8-Diazabicyclo[5.4.0]undec-7-ene
DDQ 2,3-Dichloro-5,6-dicyano-1,4-benzoquinone
DEAD Diethyl azodicarboxylate
DIAD Diisopropyl azodicarboxylate
d.e. Diastereoisomeric excess
DET Diethyl tartrate
DHP Dihydropyran
DIBAL or Dibal-H Diisobutylaluminum hydride
DIC N,N'-diisopropylcarbodiimide
DMAP 4-Dimethylaminopyridine
DMDO Dimethyldioxirane
DMF Dimethylformamide
DMPI Dess-Martin periodinane
DMSO Dimethylsulfoxide
DNA Desoxyribo nucleic acid
dppe 1,2-Bis(diphenylphosphino)ethane
$EC_{50}$ Plasma concentration required for obtaining 50% of maximum effect in vivo
EDC 1-Ethyl-3-[3-dimethylaminopropyl]carbodiimide hydrochloride
EDTA Ethylenediaminetetraacetic acid
e.e. Enantiomeric excess
EOM Ethoxymethyl ($CHC_3H_2OCH_2$—)
FDA Food and Drug Administration
Fmoc 9-Fluorenylmethoxycarbonyl
$GI_{50}$ Concentration required for 50% inhibition of cell growth
Grubbs' II Grubbs' second generation catalyst: (ruthenium [1,3-bis(2,4,6-trimethylphenyl)-2-imidazolinylidene) dichloro(phenylmethylene) (tricyclohexylphosphane)

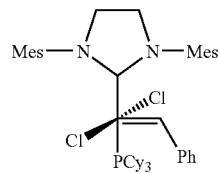

Grubbs' II

HFIP Hexafluoroisopropanol
HMDS Hexamethyldisilazide
HMPA Hexamethylphosphorictriamide
HOBT N-Hydroxybenzotriazole
HPLC High performance chromatography
HRMS High resolution mass spectrometry
HSP90 Heat shock protein 90
Hunig's Base Diisopropylethylamine
$IC_{50}$ Concentration of a drug that is required for 50% inhibition in vitro
imid. Imidazole
$Ipc_2BH$ Bis-isopinocamphorylborane
J Coupling constant
KHMDS Potassium hexamethyldisilylamide
L.C. Liquid chromatography
LDA Lithium diisopropylamide
LiHMDS Lithium hexamethyldisilazide ($LiN(SiMe_3)_2$)
μM Micromolar concentration (μmol·l$^{-1}$)
MAP Mitogen-activated protein
mCPBA meta-Chloroperoxybenzoic acid
MOM Methoxymethyl ($CH_3OCH_2$—)
mRNA Messenger ribonucleic acid
M.S. Mass spectrum
NaHMDS Sodium hexamethyldisilazide
NMR Nuclear magnetic resonance
NMM N-Methylmorpholine
NMO N-Methylmorpholine-N-oxide
NOE(SY) Nuclear overhauser effect
PCC Pyridinium chlorochromate
PDC Pyridinium dichromate
PG Protecting Group PMB para-Methoxybenzyl
PNA Peptide nucleic acid
Piv Pivaloyl
PS—Polymer supported
PS-TBD (1,5,7)-Triaza-bicyclo[4.4.0]dodeca-5-ene-7-methyl polystyrene
Pyr or Py Pyridine
rac Racemic
RAL Resorcylic acid lactone
RCM Ring-closing metathesis
RedAl Sodium bis(methoxyethoxy) aluminum hydride
Rf Retention factor
RNA Ribonucleic acid
RT Room temperature
SAE Sharpless asymmetric epoxidation
SAR Structure-activity relationship
SEM 2-Trimethylsilylethoxymethoxy
TBAF Tetra-n-butylammonium fluoride
TBAI Tetra-n-butylammonium iodide
TBDPS t-Butyldiphenylsilyl
TBHP t-Butylhydroperoxide
TBS t-Butyldimethylsilyl
Teoc 2-(Trimethylsilyl)ethoxycarbonyl
Tf Triflate (CF$_3$SO$_3$)
TFA Trifluoroacetic acid
TFAA Trifluoroacetic acetic anhydride
THF Tetrahydrofuran
THP Tetrahydropyran
TLC Thin layer chromatography
TMS Trimethylsilyl
Ts Tosyl (p-CH$_3$C$_6$H$_4$SO$_2$)
p-TSOH para-Toluenesulfonic acid I. Synthesis of Pochonin D Preliminary Studies Retrosynthetic disconnections for pochonin D (2-85) depicting the synthetic strategy are shown below. A Mitsunobu esterification, an acylation and a ring-closing metathesis are shown as the main disconnections using three building blocks: acid 2-87, alcohol (S)-2-27 and Weinreb amide 2-88.

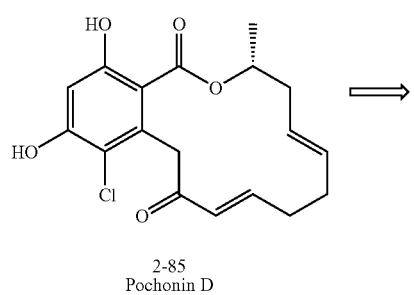

2-85
Pochonin D

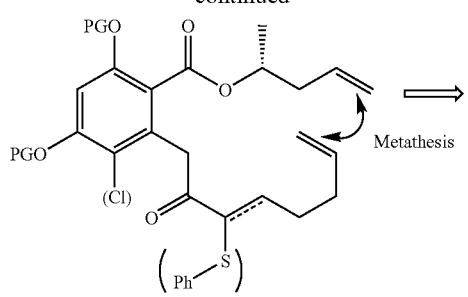

2-86

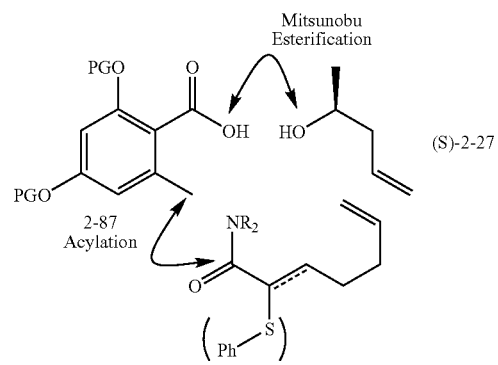

2-88

Retrosynthetic analysis for pochonin D based on radicicol and pochonin C syntheses The Weinreb amide moiety 2-88 was synthesized as shown in Scheme 1. Thus, alkylation of intermediate 2-7 with 5-iodo-1-pentene yielded Weinreb amide 2-88 in two steps from thiophenol.

Scheme 1: First generation of Weinreb amide synthesis

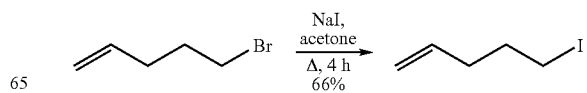

a)

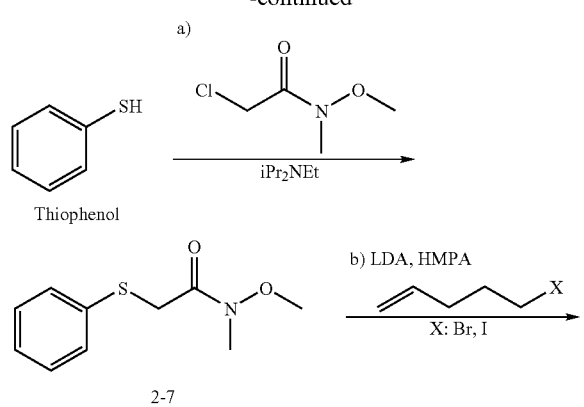

Thiophenol 2-7

Best conditions: X = I, LDA 30 min at -78° C., HMPA 30 min at -78° C., o.n. R.T.

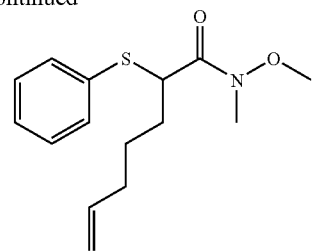

2-88 a) thiophenol (1.0 equiv.), $K_2CO_3$ (1.0 equiv.), DMF, 23° C.; 2-chloro-N-methoxy-N-methylacetamide (1.0 equiv.), 23° C., 4 h, 95%; b) LDA (2.0 equiv.), HMPA (2.0 equiv.), 5-iodo-1-pentene (2.0 equiv.), -78 → 23° C., 13 h, 30%.

In parallel, an alternative synthetic pathway was developed, starting with commercially available cis-6-nonen-1-ol (Scheme 2).

Scheme 2: Second generation of Weinreb amide synthesis

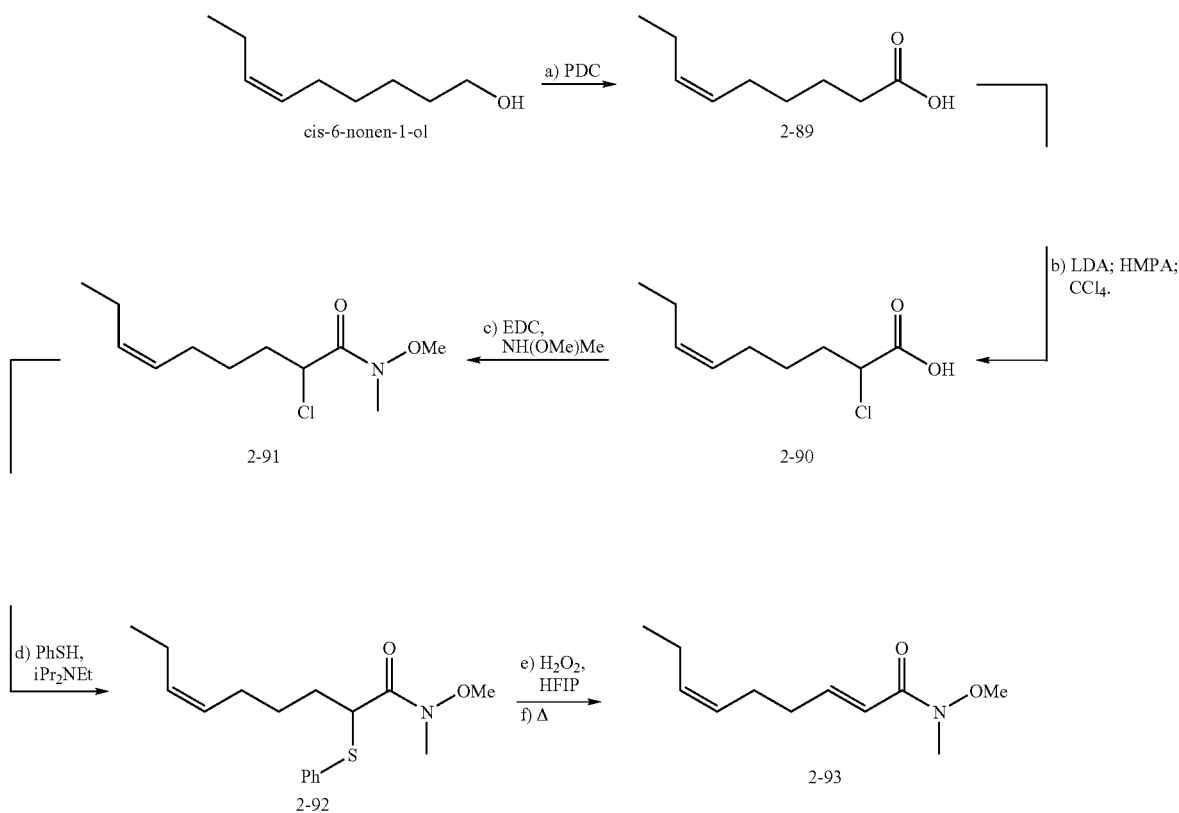

a) PDC (2.0 equiv.), DMF, 23° C., 12 h, quant.; b) iPr$_2$NH (2.6 equiv.), nBuLi (2.2 equiv.), HMPA, CCl$_4$ (5.0 equiv.), THF, -78 → 0° C., 3 h, c) N,O-dimethylhydroxylamine hydrochloride (2.0 equiv.), DMAP (cat.), EDC (2.0 equiv.), CH$_2$Cl$_2$, 23° C., 4 h, 88% (2 steps); d) iPr$_2$NEt (0.9 equiv.), thiophenol (0.9 equiv.), DMF, 80° C., 12 h, 84%; e) H$_2$O$_2$ (2.0 equiv.), HFIP, 23° C., 3 h; f) toluene, 80° C., 8 h, 75% over 2 steps.

Following a classical oxidation procedure (PDC in DMF), acid 2-89 was then α-chlorinated by formation of the enolate using LDA and subsequent chlorine addition using carbon tetrachloride (Snider, B. B. & Kulkami, Y. S., *J Org Chem* 1987, 52, 307-310). After work-up, compound 2-90 was obtained as a black oil although as a pure compound by $^1$H NMR. Efforts to purify this acid proved disappointed and it was used directly in the following step. Further amide formation using N,O-dimethylhydroxylamine and EDC and displacement of the chlorine atom with thiophenol afforded compound 2-92 in 74% overall yield from cis-6-nonen-1-ol. Via the oxidation/elimination reaction, the thioether Weinreb amide 2-92 could be converted in its closely related derivative 2-93.

Due to the high cost of commercially available 2,4-dihydroxy-6-methylbenzoic acid, a protocol was developed that allows the synthesis of 2,4-dihydroxy-6-methylbenzaldehyde which can further be derivatized in the corresponding acid using various protecting groups (Scheme 3). Starting from orcinol and following a Vilsmeier-Haack procedure, aldehyde 2-94a was obtained in 45% yield (72% based on recovered S.M.). As described in the experimental section, this aldehyde precipitates at pH=7 and is recovered with good purity (>95% as judged by $^1$H NMR).

Scheme 3: Resorcylic acid synthesis from orcinol

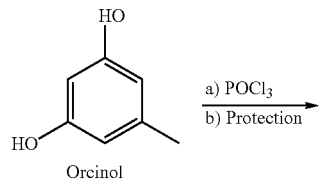

Orcinol

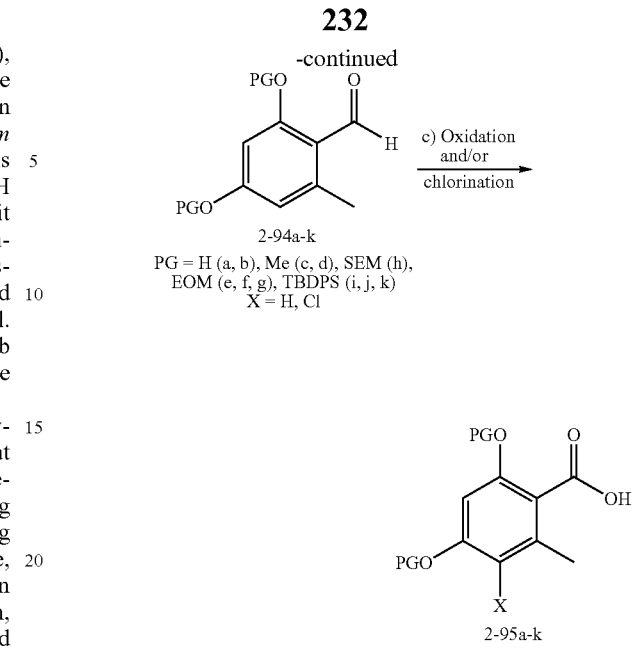

2-94a-k
PG = H (a, b), Me (c, d), SEM (h),
EOM (e, f, g), TBDPS (i, j, k)
X = H, Cl 2-95a-k
a) POCl$_3$ (4.0 equiv.), DMF, 0 → 23 → 80° C., 3 h, 45%; b) General procedure: PGCl, iPr$_2$NEt, CH$_2$Cl$_2$, 23° C., 1 h, see experimental sections for each PG; c) See the following table.

Compound 2-94a was then protected with different groups to generate aldehydes 2-94c-k which were subsequently oxidized to afford the corresponding acids 2-95a-k in good yields (Scheme 3, Table 2). By varying the oxidation conditions, it was found possible to chlorinate the ring in a one pot sequence (oxidation/chlorination) in the required position for the synthesis of pochonin D.

TABLE 2

Oxidation conditions to yield various protected resorcylic acid

| 2-95 | PG$_1$ | PG$_2$ | X | Acid | NaClO$_2$ | Solvent sytem[a] | Time[b] | Yield [%] |
|---|---|---|---|---|---|---|---|---|
| a | H | H | H | NH$_2$SO$_3$H | 3.25 equiv. | A | 1 h | 86 |
| b | H | H | Cl | NH$_2$SO$_3$H[c] | 2.0 equiv. | B | 12 h | 90 |
| c | Me | Me | H | NH$_2$SO$_3$H | 3.25 equiv. | A | 1 h | 82 |
| d | Me | Me | Cl | NH$_2$SO$_3$H | 3.25 equiv. | B | 12 h | 89 |
| e | EOM | EOM | H | NaH$_2$PO$_4$ | 5.0 equiv. | C | 12 h | 68 |
| f | EOM | EOM | Cl | NaH$_2$PO$_4$ | 5.0 equiv. | B | 12 h | 89 |
| g[d] | EOM | H | H | NaH$_2$PO$_4$ | 5.0 equiv. | C | 12 h | 87 |
| h | SEM | H | Cl | NH$_2$SO$_3$H | 3.25 equiv. | B | 12 h | 70 |
| i | TBDPS | H | Cl | NH$_2$SO$_3$H | 3.25 equiv. | B | 30 min | 93 |
| j | TBDPS | TBDPS | H | NH$_2$SO$_3$H | 3.25 equiv. | A | 30 min | 92 |
| k | TBDPS | TBDPS | Cl | NH$_2$SO$_3$H | 3.25 equiv. | B | 30 min | 95 |

[a] A: H$_2$O/THF/DMSO (20:10:1) or B: H$_2$O/THF (2:1) or C: DMSO,
[b] When run for more than 1 h, the reaction was heated up slowly to room temperature,
[c] In this case, only 2 equiv. of acid were used to avoid over-chlorination,
[d] This compound was previously assigned as compound 2-66.

Depending on the protecting group, two different acidic buffers (NH$_2$SO$_3$H or NaH$_2$PO$_4$) and various solvent systems were used (Table 2). To avoid any chlorination reaction, a small percentage of DMSO as a mixture in THF/H$_2$O along with sulfamic acid ((a) Lindgren, B. O. & Nilsson, *Acta Chem. Scand.* 27, 888-890 (1973), (b) Colombo, L et al., *J. Chem. Soc., Perkin Trans.* 1, 136440 (1980)). proved to be essential and very effective to quench HOCl (entries a, c, j).[165b] The one pot oxidation/chlorination sequence was done in absence of DMSO and required longer time to reach completion (entries b, d, f, h). Due to the acidic liability of the EOM protecting groups, NaH$_2$PO$_4$ was used as instead of sulfamic acid and the oxidation was carried out in pure DMSO. Importantly, trials to oxidize TBDPS protected aldehydes 2-94i-k in the presence of NaH$_2$PO$_4$ failed and oxidation of the mono-EOM protected aldehyde 2-94g led to uncompleted reaction. This forced us to work with the bis-protected compound which could be selectively deprotected to afford the chlorinated analog of compound 2-95g in 77% yield over the two steps (vide infra). In the first sequence used for the synthesis of this pochonin, we started with mono-MOM protected acid 2-96. Mitsunobu esterification under standard conditions (DIAD, PPh₃) between this acid 2-96 and racemic alcohol 2-27 afforded the desired ester 2-97 which was further converted to the bis-protected ester 2-98 (Scheme 4).

Scheme 4: Synthesis of MOM protected Monocillin II (2-102)

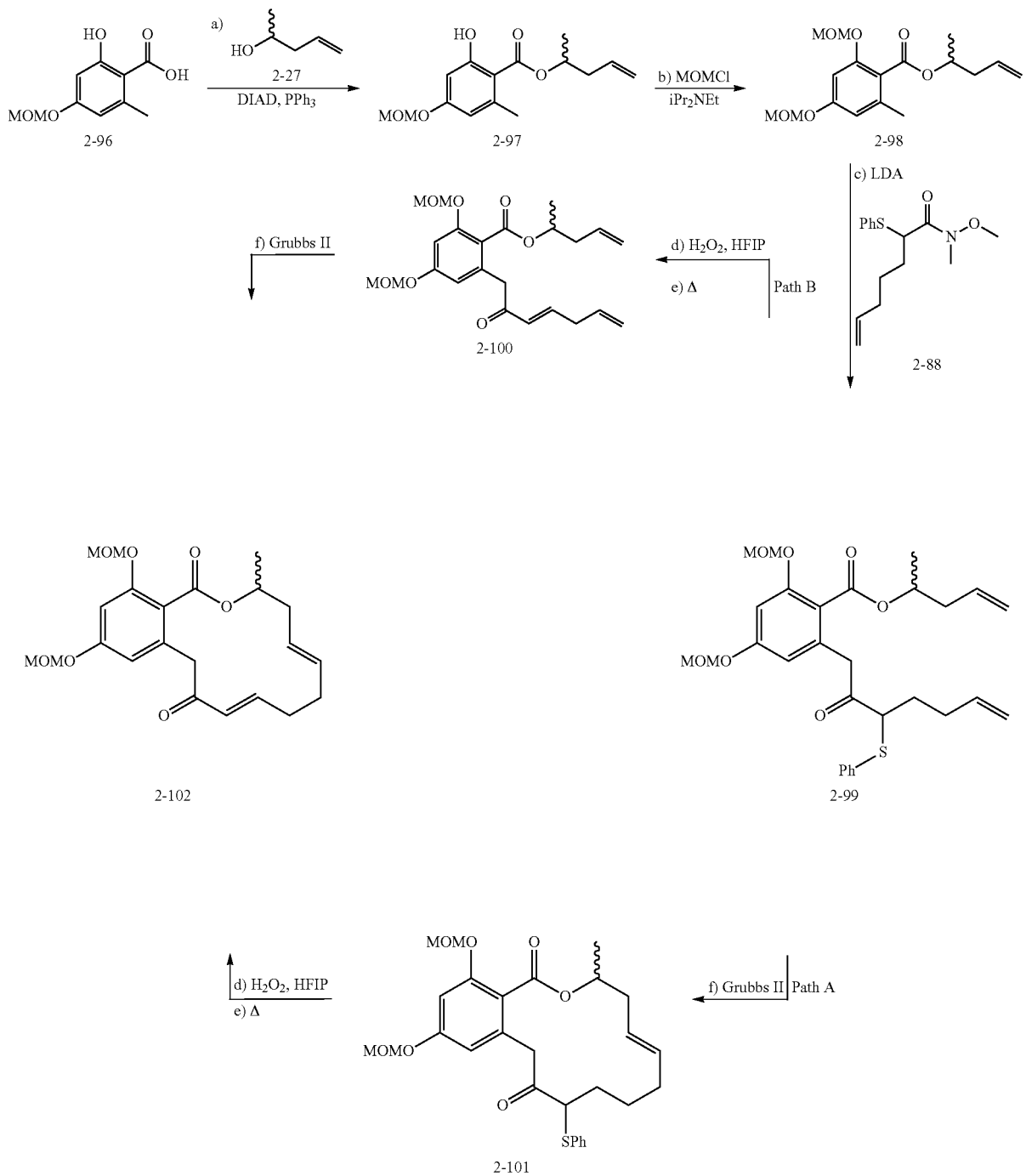

a) 2-27 (1.0 equiv.), P(mClPh)₃ (2.0 equiv.), DIAD (2.0 equiv.), toluene, 23° C., 3 h, 59%; b) MOMCl (4.0 equiv.), Et/Pr₂N (4.0 equiv.), TBAI (cat.), DMF, 80° C., 3 h, 78%; c) LDA (2.0 equiv.), THF, -78° C.; 2-88 (1.0 equiv.), 10 min, 50%; d) H₂O₂ (2.0 equiv.), HFIP, 23° C., 3 h; e) toluene, 80° C., 4 h, 68% two steps (Path A), 48% two steps (Path B); f) Grubbs' II (5% mol), toluene (2 mM), reflux, 15 min, 63% (path A, trans/cis 4:1), quant. (path B, trans/cis 7:1).

Acylation using previously optimised conditions (2 equiv. of LDA at −78° C.) allowed the formation of the acyclic precursor 2-99 along with some unreacted starting material. We envisioned two different sequences (oxidation/elimination followed by ring-closing metathesis (path A) or vice-versa (path B)) to yield compound 2-102. Both pathways proved similar (same overall yield) albeit with a higher selectivity in the metathesis reaction when following path B (cis/trans ratio 7:1 vs. 4:1 for path A). Having compound 2-102, MOM deprotection and chlorination of the aromatic ring should have allowed the formation of pochonin D (2-85, Scheme 5).

Scheme 5: Synthesis of racemic Monocillin II (2-103)

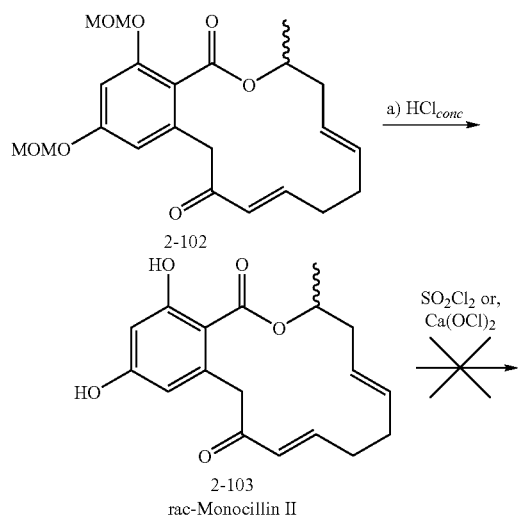

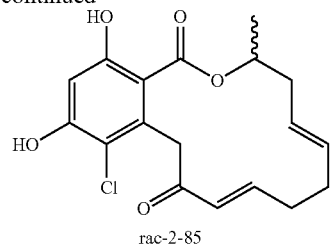

rac-2-85 a) HCl$_{conc}$ (2.5% in dioxane), 0 → 23° C., 1 h, 79%; b) SO$_2$Cl$_2$, Et$_2$O or CH$_2$Cl$_2$, 0° C., or Ca(OCl)$_2$, Acetone, H$_2$O/AcOH, 0° C.

Deprotection of the MOM groups following a well-known procedure allowed easily the generation of racemic monocillin II (2-103) but the chlorination proved much more challenging than expected. All attempts to chlorinate compound 2-103 with either SO$_2$Cl$_2$ or Ca(OCl)$_2$ failed, leading to several by-products and only traces of desired compound 2-85 as determined by L.C./M.S. Trials of chlorination on macrocycle 2-102 led to disappointment and on compound 2-101 led mostly to the exclusive oxidation of the thioether moiety. Attempts on compounds 2-98 and 2-97 led to the isolation of some chlorinated compound albeit in low yield and along with chlorination of the terminal olefin.

As an alternative, starting with the chlorinated analog of acid 2-96 and following the two steps sequence developed for MOM-protected Monocillin II (Scheme 4), compound 2-104 was obtained in good quantities (Scheme 6). Although acylation reaction using Weinreb amide 2-7 led to the isolation of compound 2-103 in 37% yield, no reaction was observed when using Weinreb amide 2-88. We thought that the failure of this last reaction might be due to the thioether linkage present on the Weinreb amide moiety and decided to use directly its α,β-conjugated analog 2-93.

Scheme 6: Acylation trials with various Weinreb amide

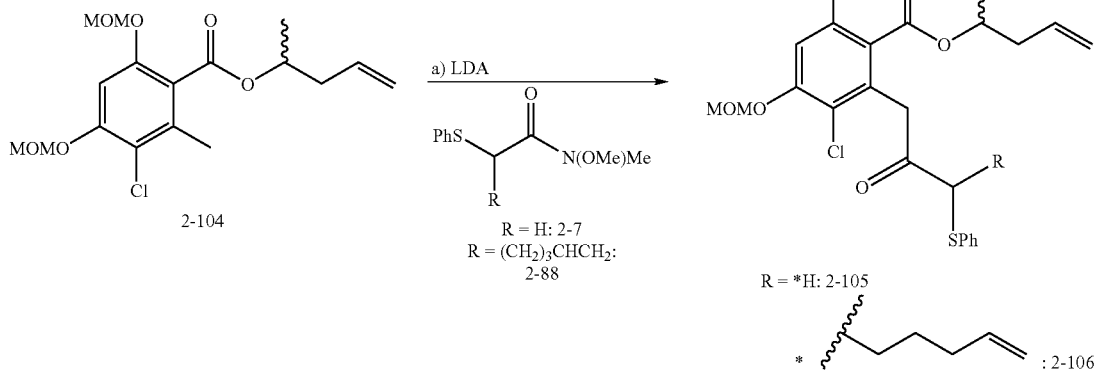

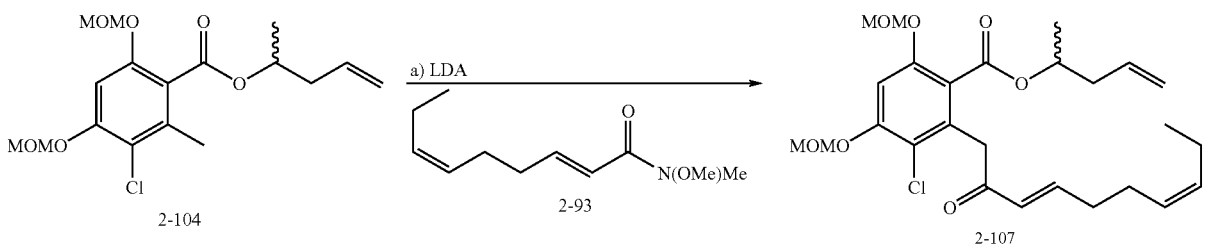

a) LDA (2.0 equiv.), THF, -78° C.; 2-7 or 2-88 or 2-93 (1.0 equiv.), 10 min, 37% (2-105), 40% (2-107).

Indeed, acylation reaction between the toluic anion of ester 2-104 and Weinreb amide 2-93 led to the isolation of acyclic compound 2-107 in 40% yield along with some unreacted starting material. Attempts to improve this yield were disappointed probably because of steric effects of the chlorine atom. However, the possibility of achieving the acylation reaction on the chlorinated toluic ester opened the door for the completion of pochonin D synthesis.

Total Synthesis of Pochonin D

EOM protecting groups were chosen for phenolic protection. Using the chemistry described above to synthesize toluic acids, mono-EOM chlorinated acid 2-108 was synthesized in three steps from formylated orcinol 2-94a (Scheme 7). The selective deprotection of the ortho-phenol was achieved using a specific concentration of TFA in a THF/MeOH mixture (THF/TFA/MeOH 7:1.5:1 (vol.)) without any bis-deprotection. Further Mitsunobu esterification using standard protocol (DIAD, PPh$_3$, toluene) and reprotection of the ortho-phenol allowed the formation of compound 2-110 in 51% yield from acid 2-108.

Scheme 7: First total synthesis of pochonin D

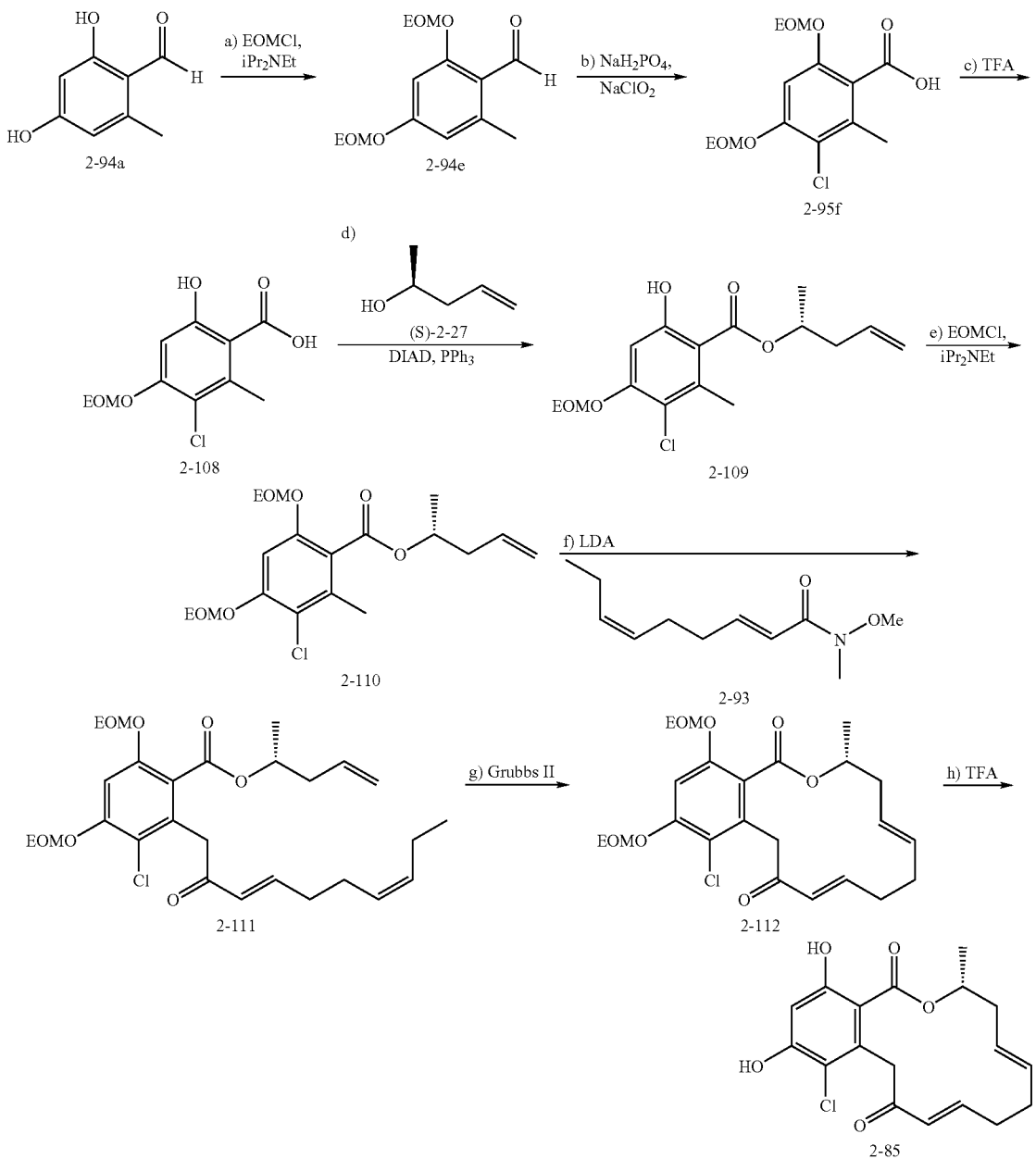

a) EOMCl (4.0 equiv.), iPr$_2$NEt (4.0 equiv.), CH$_2$Cl$_2$, 23° C., 1 h, 81%; b) NaH$_2$PO$_4$ (5.0 equiv.), NaClO$_2$ (5.0 equiv.), H$_2$O/THF 2:1, 0 → 23° C., 12 h, 89%; c) THF/TFA/MeOH 7:1.5:1, 23° C., 45 min, 80%; d) (S)-2-27 (1.0 equiv.), PPh$_3$ (2.0 equiv.), DIAD (2.0 equiv.), toluene, 23° C., 3 h, 72%; e) EOMCl (2.0 equiv.), EtiPr$_2$N (2.0 equiv.), TBAI (cat.), DMF, 80° C., 3 h, 70%; f) LDA (2.0 equiv.), THF, -78° C.; 2-93 (1.0 equiv.), 10 min, 52%; g) Grubbs' II (10% mol), toluene (2 mM), 80° C., 12 h, 94%; h) TFA (20%), CH$_2$Cl$_2$, 23° C., 2 h, 72%.

Deprotonation of the toluic ester 2-110 followed by addition of Weinreb amide 2-93 afforded the desired metathesis precursor 2-111 in 52% yield along with some unreacted starting material. Treatment of triene 2-111 with the Grubbs' second generation catalyst[173] at 120° C. for 15 min afforded the desired cyclization product 2-112 in an excellent yield albeit as an unseparable mixture of cis/trans olefins 1:4. Metathesis reaction under thermodynamic control at 80° C. overnight[174] shifted the equilibrium to the trans intermediate 2-112 with >95% selectivity (as judged by $^1$H NMR) and 94% yield. It should be noted that this reaction could be performed at millimolar concentration without any detectable amount of dimerization or oligomerization. Importantly, the 10-membered ring macrocycle was not observed. Further EOM deprotection using TFA in dichloromethane allowed the first total synthesis of pochonin D which was found to have an identical NMR spectrum to the natural product.

For the purpose of diversity-oriented synthesis and as the presence of a thioether linkage was not possible having the chlorine atom on the aromatic ring, a more concise synthesis of pochonin D with polymer-supported reagents was developed ((a) Ley, S. V. & Baxendale, I. R., Nat Rev Drug Discov 1, 573-86 (2002), (b) Ley, S. V. et al., J. Chem. Soc., Perkin Trans. 1 23, 3815-4195 (2000)). The Mitsunobu reaction using directly 2,4-dihydroxy-6-methylbenzoic acid was envisaged leading to an even more concise pathway to pochonin D. As (S)-4-penten-2-ol ((S)-2-27) is commercially available, improvements to the sequence leading to the aliphatic Weinreb amide 2-93 were undertaken. Indeed, although gram quantities could be obtained from the second generation synthesis (Scheme 2), several purifications were necessary. To circumvent this problem, a protocol using solid-support was developed. Commercially available 2-chloro-N-methoxy-N-methylacetamide (Scheme 8) was selectively S-alkylated with 3-mercaptophenol using one equivalent of base, and then loaded onto Merrifield resin in the same pot reaction by the successive addition of a second equivalent of $K_2CO_3$, the resin, and raising the temperature to 50° C., as previously described in Chapter II (Part II).

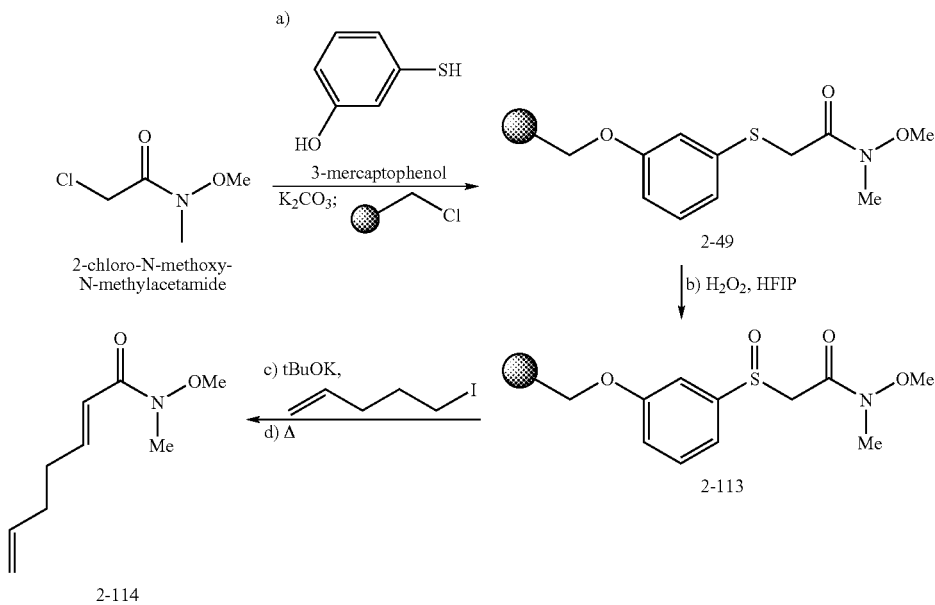

Scheme 8: Solid-phase synthesis of Weinreb amide 2-114 a) 3-mercaptophenol (1.0 equiv.), $K_2CO_3$ (1.0 equiv.), DMF, 23° C., after 8 hours, $K_2CO_3$ (1.7 equiv.), Merrifield resin, TBAI (cat.), 12 h, 50° C., 98%; b) $H_2O_2$ (2.0 equiv.), HFIP/$CH_2Cl_2$ 1:1, 12 h; c) tBuOK (1.0 equiv.), 5-iodo-1-pentene (1.0 equiv.), DMSO, 23° C., 3 h; d) toluene, 80° C., 8 h, 77%.

While preparations of thiol resins have been reported by direct lithiation of the resin followed by a quench with elemental sulfur, (Farrall, M. J. & Frechet, J. M. J., J Org Chem 41, 3877-82 (1976)). this method was found more practical as it affords the polymer-bound Weinreb amide 2-49 in one step. Oxidation of the thioether 2-49 to the corresponding sulfoxide 2-113 was carried out using the aforementioned procedure involving $H_2O_2$ in HFIP/$CH_2Cl_2$.[163] This oxidation procedure was found practical and reliable with no overoxidation to the sulfone and easy recycling of the fluorinated solvent as the reaction was carried out on solid phase. The amidosulfoxide 99 was then deprotonated with tBuOK, and the resulting enolate was quenched with 5-iodo-1-pentene. The use of DMSO was found crucial for the success of this reaction, DMF, tBuOH, and 1,4-dioxane giving only poor results. However, the polar nature of DMSO was unfavorable for the sulfoxide elimination, and the reaction could be heated up to 60° C. without any elimination. The use of solid-support was again valuable in cleaning the compound from DMSO. Resuspension of the resin in toluene and heating up to 80° C. released, after elimination, the desired fragment 2-114 with 77% yield and 95% purity (judged by $^1$H NMR). This methodology on solid support was found very practical in terms of yield and purity of the building block 2-114 as no column chromatography was needed.

Based on the chemistry developed in solution (Scheme 7), a selective Mitsunobu esterification of 2,4-dihydroxy-6-methylbenzoic acid (2-95a) with (S)-4-penten-2-ol ((S)-2-27) using polymer-bound DEAD afforded ester 2-116 (Scheme 9). The use of (mClPh)$_3$P was found essential to suppress any competing ether formation with the para-phenol.[182] Protection of both phenols with EOM groups afforded non-chlorinated ester 2-117, which could be used in the subsequent alkylation without further purification.

Scheme 9: Synthesis of intermediates 2-110 and 2-117 using polymer-bound reagents

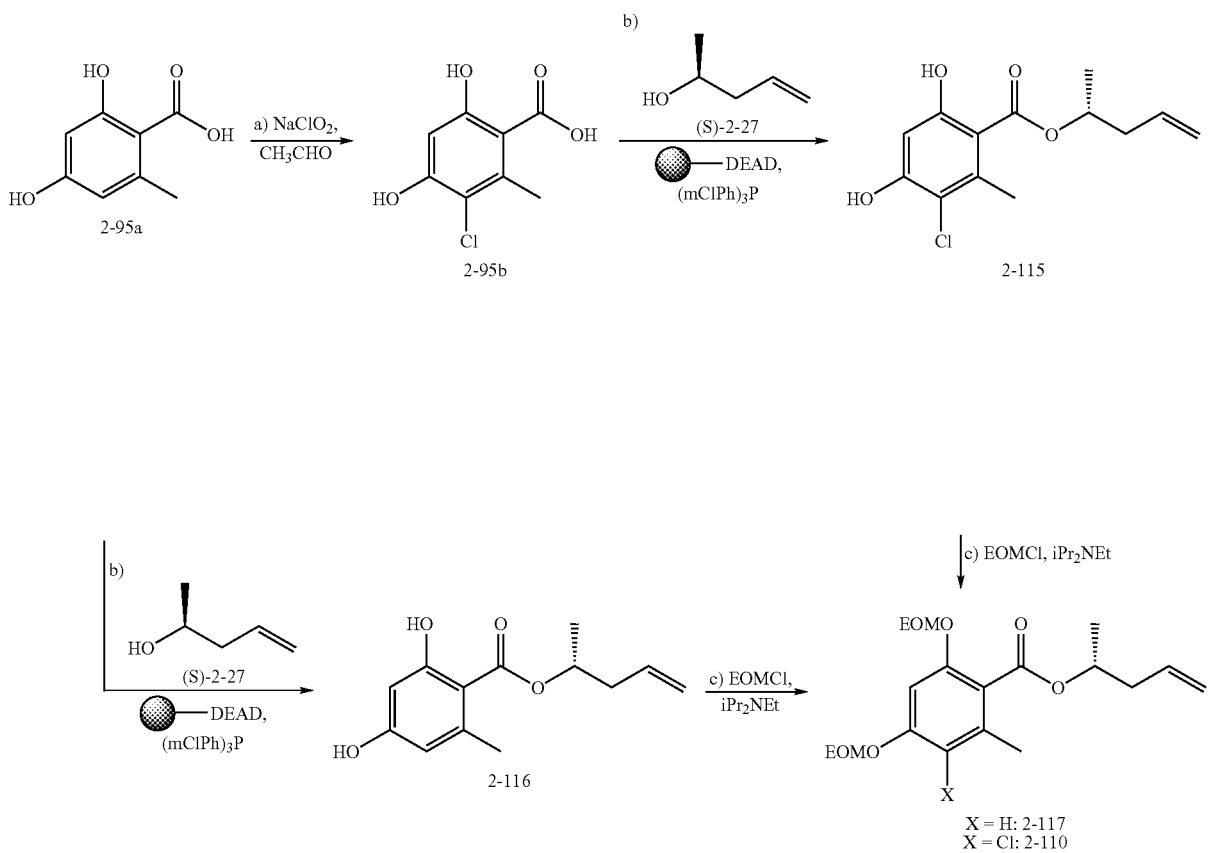

a) NaClO$_2$ (5.0 equiv.), NH$_2$SO$_3$H (5.0 equiv.), CH$_3$CHO (1.0 equiv.), THF/H$_2$O 5:1, 0° C., 0.5 h, 92%; b) PS-DEAD (2.5 equiv.), 1.3 mmol.g$^{-1}$), (S)-4-penten-2-ol (1.0 equiv.), P(mClPh)$_3$ (2.0 equiv.), CH$_2$Cl$_2$, 23° C., 0.5 h, 68% for 2-117 and 65% for 2-110: c) iPr$_2$EtN (4.0 equiv.), EOMCl (4.0 equiv.), TBAI (cat.), DMF, 80° C., 5 h, 95%.

In parallel and as the chlorine atom could not be introduced at a later stage (vide supra), the halogen was thus introduced prior to esterification using HClO generated in situ by the oxidation of acetaldehyde with NaClO$_2$/sulfamic acid. Acid 2-95b was obtained from its non-chlorinated parent 2-95a in 92% yield without seeing any over-chlorination. Esterification of this product under the same conditions as for 2-95a afforded compound 2-115. Further bis-protection with EOM groups led to ester 2-110 which could also be used in subsequent reactions without any purification. Deprotonation of the toluic esters 2-110 and 2-117 followed by addition of Weinreb amide 2-114 afforded the desired metathesis precursors 2-118 and 2-119 which could be used directly in the following step (Scheme 10). When the acylation reaction was performed on the non-chlorinated ester 2-117, 20% of product stemming from a 1,4-conjugated addition on the Weinreb amide was obtained.

Scheme 10: Synthesis of pochonin D (2-85) and monocillin II (2-103) using supported reagents

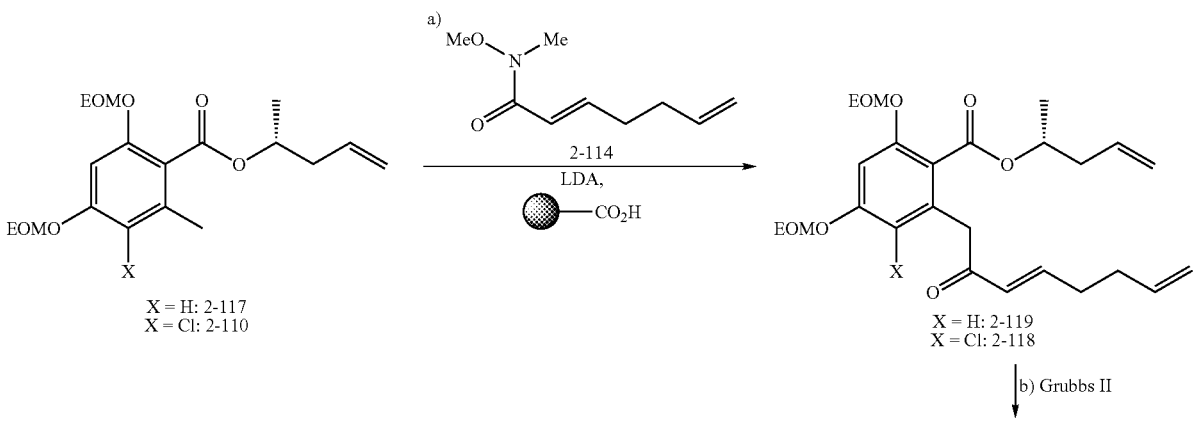

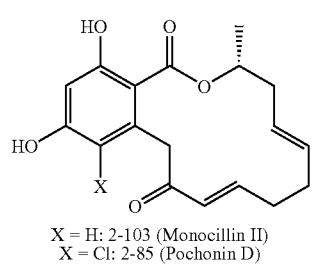

X = H: 2-103 (Monocillin II)
X = Cl: 2-85 (Pochonin D)

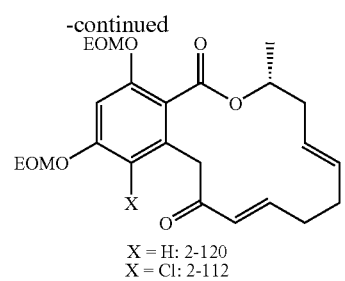

X = H: 2-120
X = Cl: 2-112

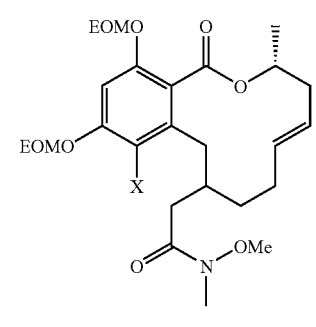

2-121 a) LDA (2.0 equiv.), THF, -78° C.; 2-114 (1.0 equiv.), 10 min, Amberlite IRC-50 (20.0 eq, 10.0 mmol.g$^{-1}$); b) Grubbs' II (10% mol), toluene (2 mM), 80° C., 12 h, 40% for 2-120 and 44% for 2-112 after two steps; c) PS-TsOH (10 equiv., 3.2 mmol.g$^{-1}$), MeOH, 40° C., 4 h, 90% for 2-85 and 92% for 2-103.

Treatment of crude trienes 2-118 and 2-119 with the Grubbs' second generation catalyst under thermodynamic control at 80° C. overnight led exclusively (more than 95% selectivity) to the trans macrocycles 2-112 and 2-120. A simple filtration through a path of silica was then used to remove all of the catalyst and its by-products, affording compound 2-112 in 44% yield over two steps. While the metathesis reaction carried out on purified triene 2-118 was nearly quantitative, it was found more practical to carry out the whole synthetic sequence from compound 2-95a without any purification, thus affording the protected pochonin D 2-112 in 25% yield over five steps. For compound 2-120, a column chromatography was necessary to separate the 12-membered macrocycle 2-121 coming from the side reaction (1,4-addition) occurring during the acylation reaction. Removal of EOM groups from both macrocycles 2-112 and 2-120 using sulfonic acid resin in MeOH allowed the synthesis of both pochonin D (2-85) and monocillin II (2-103) in 90% and 92% yield, respectively. As shown for the acylation reaction, the presence or absence of the chlorine atom on the aromatic ring seems to influence the reactivity of the conjugated olefin. Indeed, deprotection of compound 2-120 with HCl (2.5% in dioxane) led to the conjugated addition of the chlorine ion, whereas compound 2-112 could be deprotected with HCl to obtain pochonin D (2-85). This synthesis using polymer-supported reagents allowed the achievement of pochonin D and monocillin II in six (23% yield) and five (24% yield) steps respectively. Starting from commercially available building blocks, only one chromatographic purification of the final compound is required for all the synthetic pathway and this methodology could be used for the synthesis of libraries. Evaluation for HSP90 affinity in a competition assay with geldanamycin revealed that pochonin D is a good ligand for HSP90 with an IC$_{50}$ of 80 nM as compared to 20 nM for radicicol (vide infra).

II Synthesis of Pochonin A

Having access to pochonin D (2-85), pochonin A (2-122) was then prepared not only to confirm its structure but also to compare its biological activity to pochonin D and radicicol.

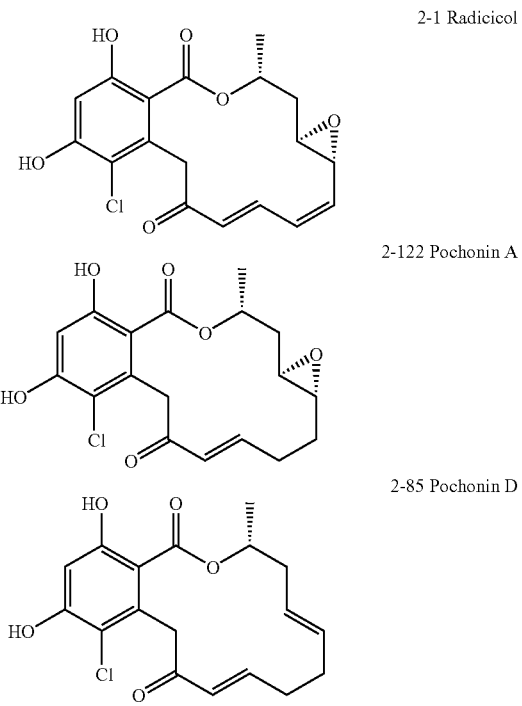

2-1 Radicicol 2-122 Pochonin A 2-85 Pochonin D

Epoxidation of pochonin D using DMDO allowed the formation of pochonin A as a 1:1 mixture of diastereoisomers that could be separated by column chromatography. Attempts to improve the selectivity of this reaction using epoxone ((a) Tu, Y. et al., *J Am Chem Soc* 118, 9806-9807 (1996), (b) Wang, Z.-X. et al., *J Org Chem* 62, 2328-2329 (1997)) as a chiral auxiliary failed completely with no conversion at 0° C. or at room temperature. The lack of solubility of pochonin D at low temperature did not allow for improvement of this selectivity and other routes were pursued. As depicted in Scheme 11, the epoxidation of the bis-EOM protected pochonin D (2-112) did not improve the selectivity and deprotection of the EOM in the presence of the epoxide did not give satisfactory results under a variety of conditions.

Scheme 11: Direct conversion of bis-EOM pochonin D (2-112)

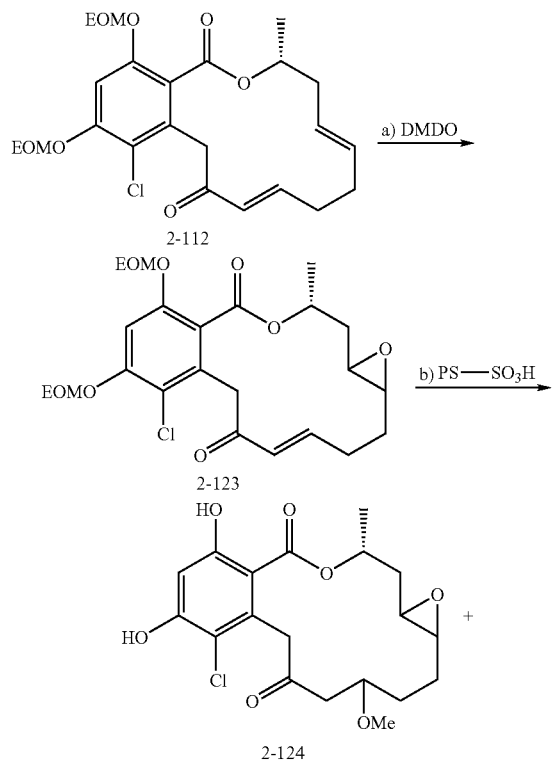

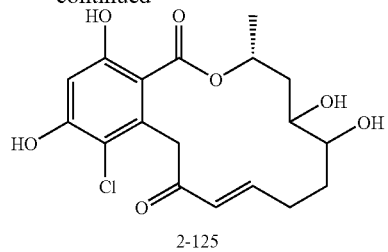

2-125 a) DMDO (1.0 equiv.), CH$_3$CN, 0° C. → 23° C., 1.5 h, 79%; b) PS-TsOH (10.0 equiv., 3.2 mmol.g$^{-1}$), MeOH, 40° C., 1 h.

The suitability of silyl based protecting groups to access this type of molecules was investigated. This was also motivated by the fact that it was known that a silylated carboxylic acid could be converted to an acid chloride under acid-free conditions which are compatible with silyl protected phenols (Wisnner, A. & Grudzinskas, C. V., *J Org Chem* 43, 3972-3974 (1978)). Thus, persilylation of benzoic acid 81b (Scheme 12), followed by "acid-free" conversion of the silyl ester to the corresponding acyl chloride yielded key intermediate 112 upon esterification with alcohol (R)-27. The low yield reported for this three steps sequence was attributed to the lability of the ortho-TBS group. Attempts to improve the efficiency of this protocol either by purifying the persilylated intermediate (column on neutralized silica, filtration on neutral alumina, distillation or azeotrope to evaporate the excess of TBSCl) or by isolating the acid chloride only led to disappointing results.

Scheme 12: Pochonin A synthesis using TBS-protecting groups

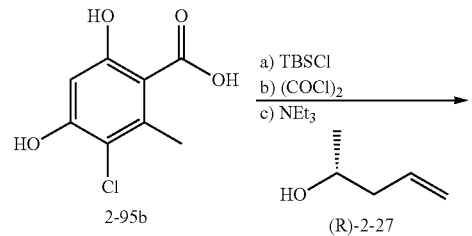

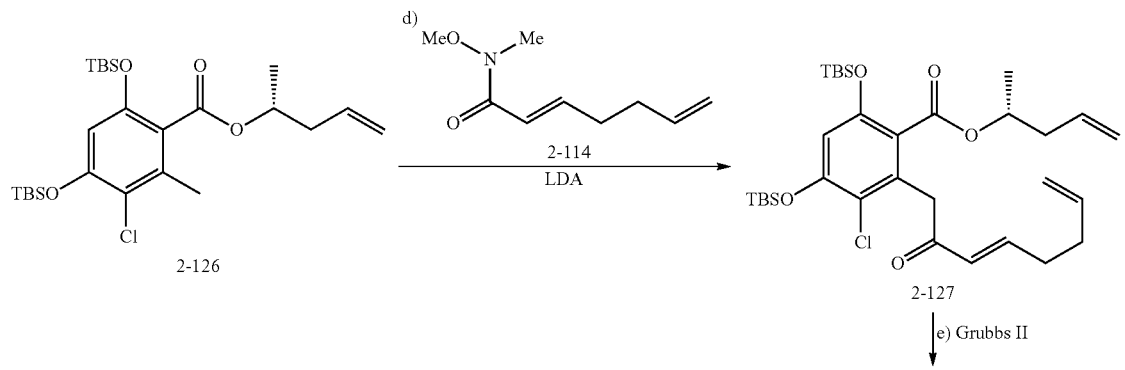

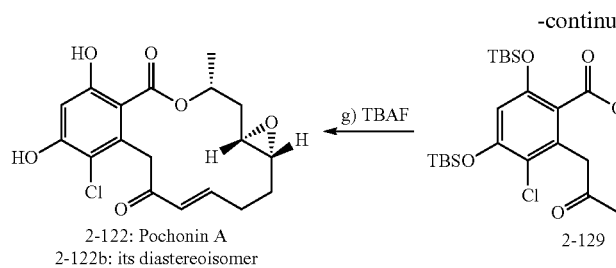

2-122: Pochonin A
2-122b: its diastereoisomer 2-129

2-128 a) iPr₂EtN (6.0 equiv.), TBSCl (3.0 equiv.), CH₂Cl₂, 23° C., 3 h; b) Oxalyl chloride (1.0 equiv.), DMF (cat.), CH₂Cl₂, 0 → 23° C., 1 h; c) Et₃N (2.26 equiv.), R-(-)-penten-2-ol (3.0 equiv.), DMAP, 0 → 23° C., 12 h, 29% over 3 steps; d) LDA (2.0 equiv.), THF, -78° C., Weinreib amide 100 (1.0 equiv.), 10 min, 35%; e) Grubbs' II (10% mol), toluene (2 mM), 80° C., 12 h, 79%; f) CF₃COCH₃, NaHCO₃ (7.0 equiv.), Oxone (4.7 equiv.), Na₂·EDTA (4 × 10⁻⁴ M), CH₃CN/Dimethoxymethane, 0° C., 2 h, 83%; g) TBAF (2.2 equiv.), THF, 23° C., 20 min, 80%, 3:1 mixture of diastereoisomers.

Deprotonation of the toluic ester 2-126 followed by reaction with Weinreb amide 2-114 afforded metathesis precursor 2-127 in modest yield. Ring-closing metathesis using Grubbs' second generation catalyst[173] under aforementioned thermodynamic conditions[174] (80° C., overnight) afforded macrocycle 2-128 in good yield and excellent cis/trans ratio (<5% cis). Epoxidation of the non-conjugated olefin was optimal when carried out at 0° C. with methyl(trifluoromethyl)-dioxirane generated in situ (Yang, D., et al. J. Org. Chem., 60, 3887-3889 (1995) affording TBS-protected pochonin A (2-129) in excellent yield as an inseparable 3:1 diastereoisomeric mixture. Attempts to further improve the stereoselectivity of the epoxidation by reducing the temperature (-10° C.) or using epoxone were not productive. Deprotection of compound 2-129 using classical silyl deprotection conditions (TBAF in THF) afforded a separable diastereomeric mixture and confirmed that the major product was indeed the desired pochonin A (2-122).[1]

Alternative protecting groups were evaluated to improve the yield of the esterification and acylation reactions. Based on their stability toward basic conditions but also on their liability towards TBAF, SEM protecting groups were considered. Following the procedure described for the polymer-assisted synthesis of pochonin D, selective Mitsunobu reaction between benzoic acid 2-95b and chiral alcohol (S)-2-27 using polymer-bound DEAD and subsequent protection with SEM-Cl afforded ester 2-130 in 72% yield (Scheme 13).

Scheme 13: Pochonin A synthesis using SEM-protecting groups

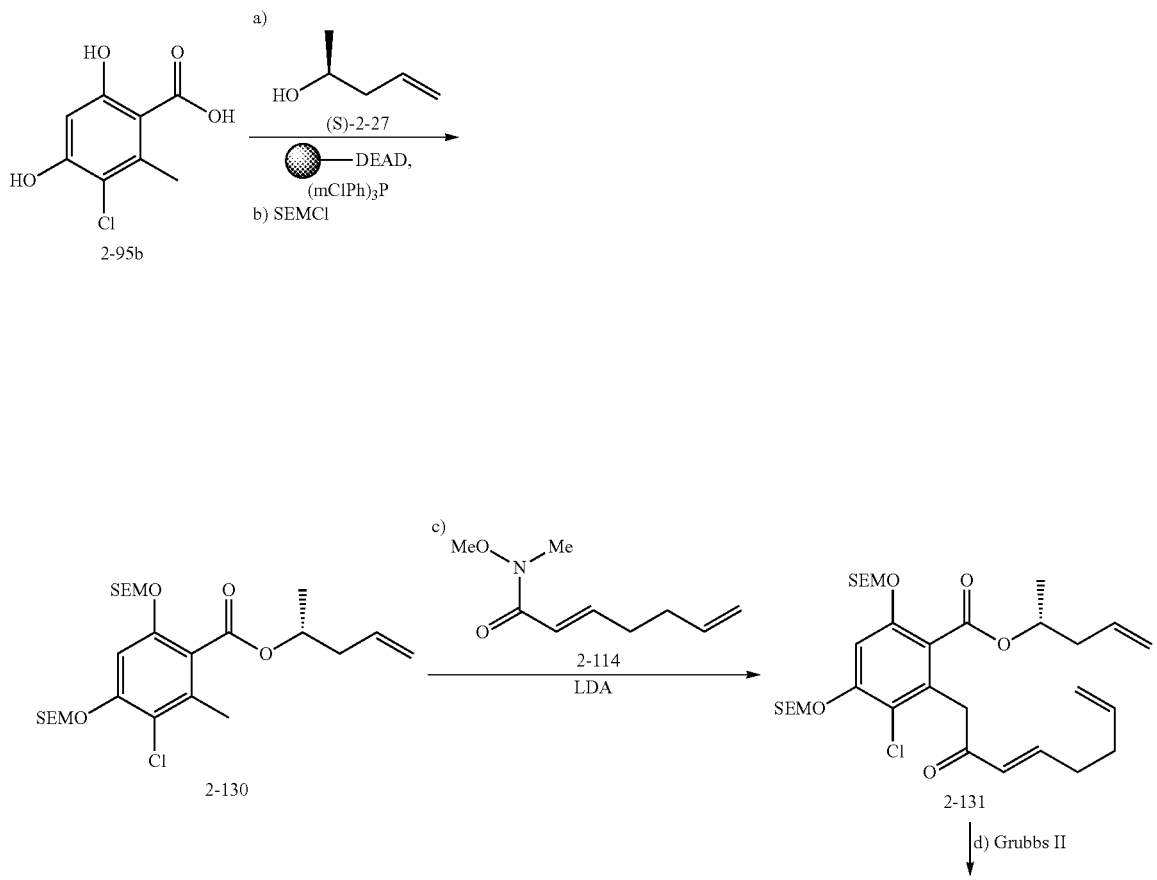

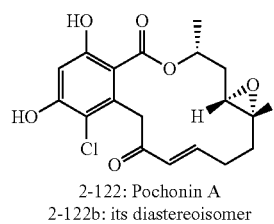

2-122: Pochonin A
2-122b: its diastereoisomer

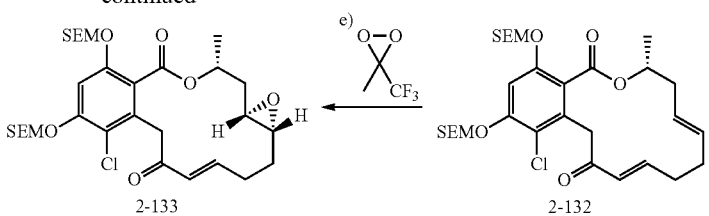

2-133                     2-132 a) PS-DEAD (2.5 equiv., 1.3 mmol.g⁻¹), S-(-)-4-penten-2-ol (2.0 equiv.), P(mClPh)₃ (2.0 equiv.), toluene, 23° C., 10 min; b) NaH 60% (4.0 equiv.), SEMCl (4.0 equiv.), THF, 0° C., 2 h, 72% over 2 steps; c) LDA (2.0 equiv.), THF, -78° C., Weinreb amide 2-114 (1.0 equiv.), 10 min, 60%; d) Grubbs' II (10% mol), toluene (2 mM), 80° C., 12 h, 87%; e) DMDO (1.0 equiv.), CH₃CN, 0 → 23° C., 1.5 h, 83%, 1:1 mixture of diastereoisomers; f) MgBr₂•Et₂O (8.0 equiv.), CH₂Cl₂, 23° C., 1 h, 70%.

Acylation of toluate ester 2-130 using Weinreb amide 2-114 led to the isolation of the acyclic precursor 2-131 in 60% yield. Treatment of the triene 2-131 with the Grubbs' second generation catalyst under thermodynamic conditions (80° C., overnight) afforded the corresponding macrocycle 2-132 in 87% yield (<5% cis olefin), which was epoxidized under the same conditions as for the TBS-protected compound 2-128[methyl(trifluoromethyl)-dioxirane], yielding compound 2-133 in 83% yield albeit in a 1:1 diastereomeric ratio (inseparable). All attempts to deprotect the SEM groups using TBAF were unsuccessful (even when performed on macrocycle 2-132), leading mostly to the formation of isocoumarin. Other methodologies were then examined such as sulfonic acid resin in MeOH at 40° C., Montmorillonite K10 in toluene at 50° C. and MgBr₂.Et₂O in dichloromethane at room temperature. The use of either sulfonic acid resin or Montmorillonite K10 led to the opening of the epoxide. However, 8.0 equiv. of MgBr₂.Et₂O afforded the desired pochonin A (2-122) along with its diastereoisomer (2-122b) as a separable mixture. The yield was limited by reaction conversion, since longer times led to the formation of the corresponding bromohydrine. In the case of EOM-protected product 2-123, treatment with MgBr₂ was found to open the epoxide faster than to deprotect the EOM. Pochonin A was found to be a good ligand of HSP90 with an IC₅₀ of 90 nM (vide infra).

III. Diversity Oriented Synthesis of Pochonin Analogues

With the objective to extend the diversity of the RAL, we turned our attention to the synthesis of a library. This library was envisioned to stem from five points of diversity around the resorcylic macrolide scaffold: modifications of the para-phenol (R¹, a number of natural resorcylides bearing a methyl group at this position), the group on C17 (R², both stereochemistry are present in natural resorcylides; however, only with a methyl substituent),

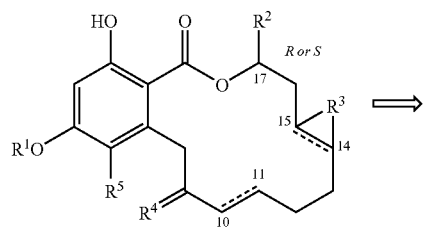

the C14-C15 olefin (R³), the C9 carbonyl (R⁴), the olefin C10-C11, and the meta position on the aryl ring (R⁵, a number of natural resorcylides bear a chlorine at this position). To minimize traditional chromatography, a prerequisite in designing the chemistry used to elaborate the molecular diversity of this scaffold was its ability to be carried out by using polymer-bound reagents. Therefore, the assembly of the macrocycle was thought to rely on the chemistry developed for the synthesis of pochonin D using polymer-bound reagents (Schemes 9 and 10).

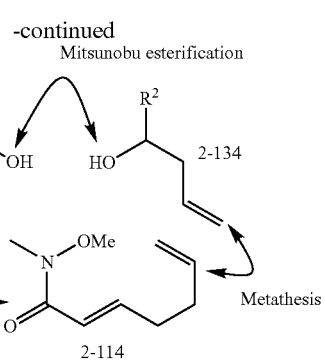

General structure and retrosynthetic analysis of the library

A variety of homoallylic alcohols 2-134 bearing various substituent at R² was envisioned. Homoallylic alcohols 2-134 that are not commercially available may be obtained in by any suitable method. In one embodiment, the homoallylic alcohols 2-134 were obtained in their highest enantiomeric form either by enzymatic resolution[2] of the racemic alcohol or by means of Brown allylation[168] of the corresponding aldehyde (H. E. Master et al., *Tet. Lett.*, 37:9253 (1996); S. Singh et al., *Tet. Asymm.*, 13:2679 (2002) or via Brown allylation of the corresponding aldehyde. (H. C. Brown and P. K. Jadhav *J. Am. Chem. Soc.*, 105:2092 (1983). The phenyl (2-134a), the pyridinyl (2-134b) and the furyl (2-134c) alcohols were prepared by enzymatic resolution (Scheme 14). Racemic alcohols 2-134a-c were obtained after Grignard addition of commercially available allylmagnesium bromide on their corresponding aldehyde 2-134a-c.

Scheme 14: Synthesis of chiral alcohols 2-134a-c using enzymatic resolution

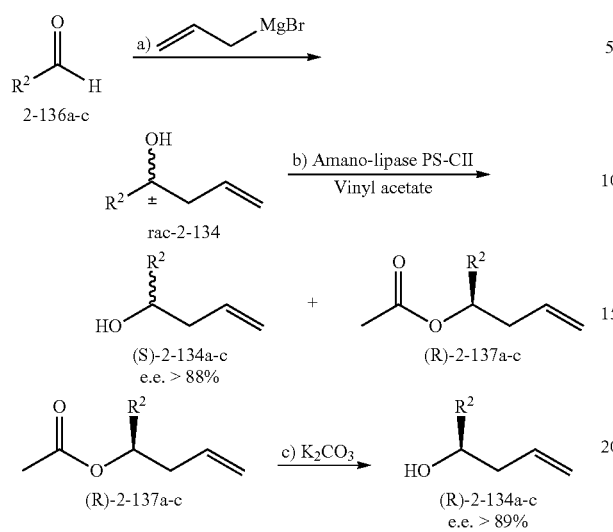

a: Ph
b: Pyr
c: Fur a) AllylMgBr (1.5 equiv.), THF, 0.5 h, 0° C., 71% (2-134a), 41% (2-134b), 74% (2-134c); b) $R^2$═Ph: vinyl acetate (32.5 equiv.), Amano Lipase PS-C II (50 mg/mmol of 2-134), 23° C., 30 h (monitored by $^1$H NMR), $R^2$=Pyr, Fur: vinyl acetate (10.0 equiv.), Amano Lipase PS-C II (50 mg/mmol of 2-134), THF, 23° C., 5-30 h (monitored by $^1$H NMR); c) $K_2CO_3$ (0.8 equiv.), MeOH, 23° C., 98% ((R)-2-134a), 92% ((R)-2-134b), 84% ((R)-2-134c).

Kinetic enzymatic resolution of racemic alcohols 2-134a-c was realized using the highly efficient Amano lipase (an immobilized version of *Pseudomonas cepacia*). This enzyme catalyzed a selective transesterification of alcohols (R)-2-134a-c with vinyl acetate as an acyl donor, the (S) alcohols 2-134a-c being isolated in excellent yields and good enantiomeric excesses (Table 3).

Scheme 15: Synthesis of chiral alcohols 120d-f using Brown allylation

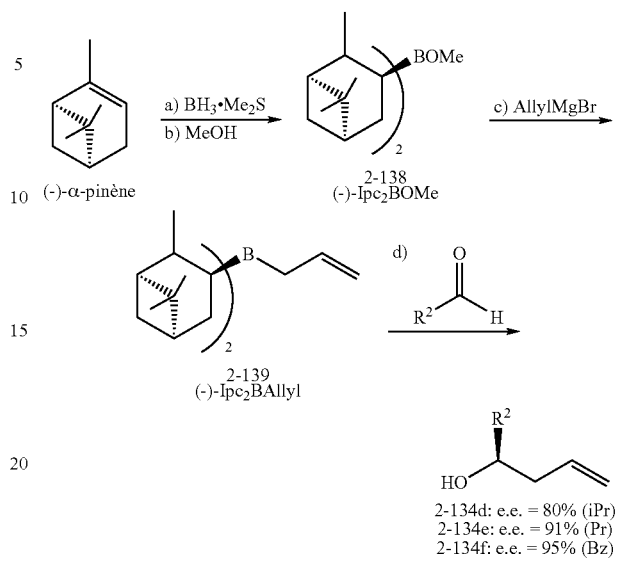

a) (-)-α-pinene (2.4 equiv.), $BH_3$•$Me_2S$ (1.0 equiv.), THF, 23° C. for 1 h and then 4° C. for 12 h, 76%; b) MeOH (1.2 equiv.), $Et_2O$, 0° C., 2 h, 94%; c) AllylMgBr (0.95 equiv.), $Et_2O$, 0 → 23° C., 1 h, 92%; d) 122d-f (1.05 equiv.), $Et_2O$, -100° C., 0.5 h; 3N NaOH, $H_2O_2$ 35%, reflux, 3 h, 77-93%. Enantiomeric excesses of alcohols were determined by chiral HPLC analysis after acylation with 3,5-dinitrobenzoyl chloride.

(−)-B-Allyldiisopinocampheylborane (2-139, (−)-Ipc$_2$BAllyl) was synthesized in a three steps sequence from (−)-a-pinene involving an hydroboration, the formation of the corresponding MeO-borinic ester 2-138 and its treatment with a Grignard reagent. Further condensation on aldehydes 2-134d-f followed by oxidation of the resulting borinates with alkaline hydrogen peroxide allowed the formation of the chiral homoallylic alcohols 2-134d-f in good enantiomeric excess.

The macrocycle assembly was modeled after the synthesis of pochonin D. (E. Moulin, V. Zoete, S. Barluenga, M. Karplus, N. Winssinger, *J. Am. Chem. Soc.*, 127:6999 (2005)).

TABLE 3

Enantioselective acylation of alcohols rac-2-134a-c by transesterification with lipase

| Entry | Substrate | Time (h) | Conv. Ratio (%) (OH/OAc) | Yield (%) (S)-2-134 | e.e. (%) (S)-2-134 | Yield (%) (R)-2-134 | e.e. (%) (R)-2-134 |
|---|---|---|---|---|---|---|---|
| 1 | rac-2-134a | 30 | 50:50 | 45 | 98 | 49 | 93 |
| 2 | rac-2-134b | 30 | 52:48 | 50 | 89 | 39 | 94 |
| 3 | rac-2-134c | 5 | 49:51 | 44 | 88 | 49 | 89 |

Enantiomeric excess obtained with this methodology are all above 88% and crucially depends on the conversion of the reaction. Acetylated alcohols (R)-2-137 were then hydrolysed to the corresponding alcohols (R)-2-134a-c in excellent yields. In addition, a second process based on Brown allylation was developed for the synthesis of the isopropyl (2-134d), the propyl (2-134e) and the benzyl (2-1341) alcohols (Scheme 15).

Thus as shown in Scheme 16, commercially available benzoic acid 2-95a and its chlorinated analog 2-95b (the chlorine atom was introduced on acid 2-95a prior to esterification using HClO generated in situ by the oxidation of acetaldehyde with $NaClO_2$/sulfamic acid were esterified with fifteen different homoallylic alcohols using polymer-supported DEAD to yield esters 2-115a-g and 2-116a-g in excellent purity. (E. Moulin et al., *J. Am. Chem. Soc.*, 127:6999 (2005)).

The products 2-115a-g and 2-116a-g were then protected with ethoxymethylene chloride (EOM-Cl) in the presence of Hunig's base to obtain the corresponding protected toluic esters 2-110a-g and 2-117a-g which could be used in the subsequent carbon-acylation reaction without further purification.

Scheme 16: Synthesis of macrocylic precursors 2-112a-g, 2-120a-g and 2-121a-g

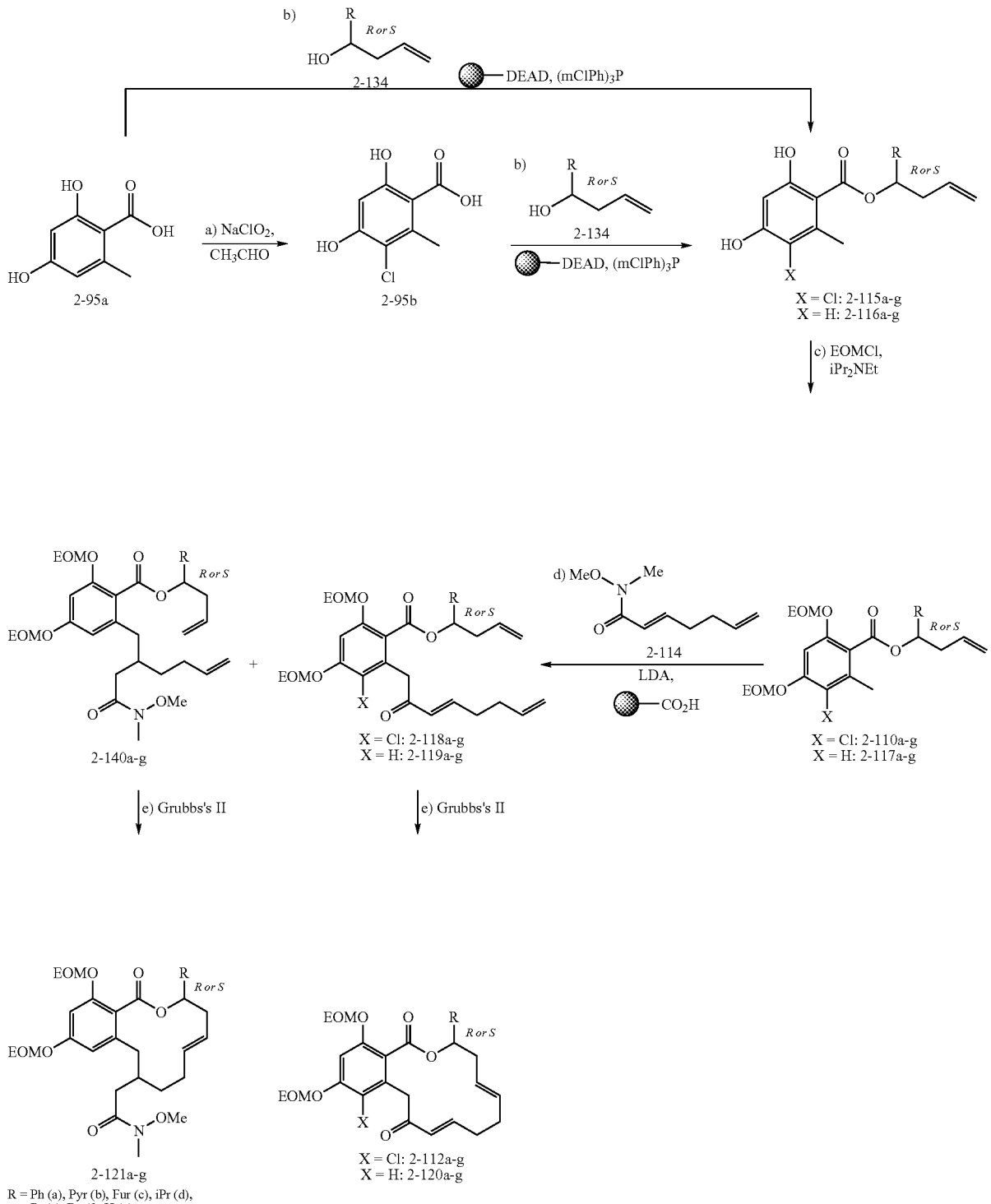

R = Ph (a), Pyr (b), Fur (c), iPr (d), Pr (e), Bz (f), H (g)

a) NaClO$_2$ (5.0 equiv.), NH$_2$SO$_3$H (5.0 equiv.), CH$_3$CHO (1.0 equiv.), THF/H$_2$O 5:1, 0° C., 0.5 h, 92%;
b) PS-DEAD (2.5 equiv., 1.3 mmol•g$^{-1}$), (R)- 2-134a-g or (S)- 2-134a-g (1.0 equiv.), P(mClPh)$_3$ (2.0 equiv.), CH$_2$Cl$_2$, 23° C., 0.5 h, 60-80%; c) iPr$_2$EtN (4.0 equiv.), EOMCl (4.0 equiv.), TBAI (cat.), DMF, 80° C., 5 h, 80-90%; d) LDA (2.0 equiv.), THF, -78° C., 2-114 (1.0 equiv.), 10 min, Amberlite IRC-50 (20.0 eq, 10.0 mmol•g$^{-1}$); e) Grubbs's II (10% mol), toluene (2 mM), 80° C., 12 h, 38-70% after two steps.

Deprotonation of the toluic esters 2-110a-g and 2-117a-g using two equivalents of LDA, followed by addition of the α,β-unsaturated Weinreb amide prepared via solid phase chemistry (E. Moulin et al., *J. Am. Chem. Soc.*, 127:6999 (2005)) afforded acylation products 2-118a-g and 2-119a-g. The reaction was quenched with a polymer bound acid which also sequestered all the diisopropyl amine. This reaction can lead to some level of 1,4-conjugate addition product. (S. Barluenga et al., *Chem. Eur. J.*, 11:4935 (2005)). While the bulky chlorine present in pochonin D suppresses this reaction, compounds lacking the aryl chloride afforded 20% of the conjugate addition products 2-140a-g. Nevertheless, the crude mixtures of these reactions were used in the subsequent cyclization step. The trienes were then subjected to ring closing metathesis using Grubbs' second generation catalyst (A. K. Chatteijee et al., *J. Am. Chem. Soc.*, 122:3783 (2000); M. Scholl et al., *Org. Lett.*, 1:953 (1999)) under thermodynamic conditions (C. W. Lee, and R. H. Grubbs, *Org. Lett.*, 2:2145 (2000)), affording the desired 14-membered macrocycles. In the cases where metathesis reactions were carried out with a mixture of 2-118a-g, 2-119a-g and 2-140a-g, the corresponding 12-membered ring product 2-121a-g was obtained in addition to 2-112a-g and 2-120a-g as a separable mixture. All successful reaction sequences were purified by standard chromatography at this stage yielding the macrocycle 2-112a-g and 2-120a-g and 2-121a-g in 30-60% and 8-10% overall yield respectively from 2-95.

Macrocycles 2-112a-g and 2-120a-g were then used as the starting point for further diversifications. Deprotection of the EOM groups of 2-112a-g and 2-120a-g using sulfonic acid resin afforded compounds 2-103a-g and 2-85a-g in pure form and excellent yields after simple filtration of the resin and evaporation of the solvents (Scheme 17). The 12-membered ring products 2-121a-g were deprotected just as smoothly (not shown). As expected, EOM deprotection under acid catalysis were slower for the chlorinated analogues and had to be monitored as prolonging the reaction times could lead to conjugate additions. Treatment of 2-112a-g and 2-120a-g with reducing agents led to either carbonyl reduction using Dibal or mixtures of carbonyl and 1,4-reduction with NaBH$_4$. It is known that using non-C(O)ORdinating counter ion for borohydride can favor the carbonyl reduction (H. W. Gibson and F. C. Baily, *J. Chem. Soc. Chem. Commun.*, 1977:815; A. Kirschning, *J. Prakt. Chem.*, 2000:342). This was most conveniently achieved using a polymer supported quaternary ammonium borohydride known as borohydride exchange resin (BER). Thus, ketones 2-112a-g and 2-120a-g could be reduced using BER-resin to obtain both diastereoisomers of 2-141a-g in ~60% yield. Deprotection of the EOMs with sulfonic acid resin under regular conditions afforded compounds 2-142a-g. Acetylation of the reduced intermediates 2-141a-g using PS-NMM/Ac$_2$O yielded compounds 2-143a-g which led to elimination upon deprotection to afford trienes 2-144 as a mixture of olefin geometries.

Scheme 17: Deprotection and Synthesis of the Reduced Ketone Analogues.

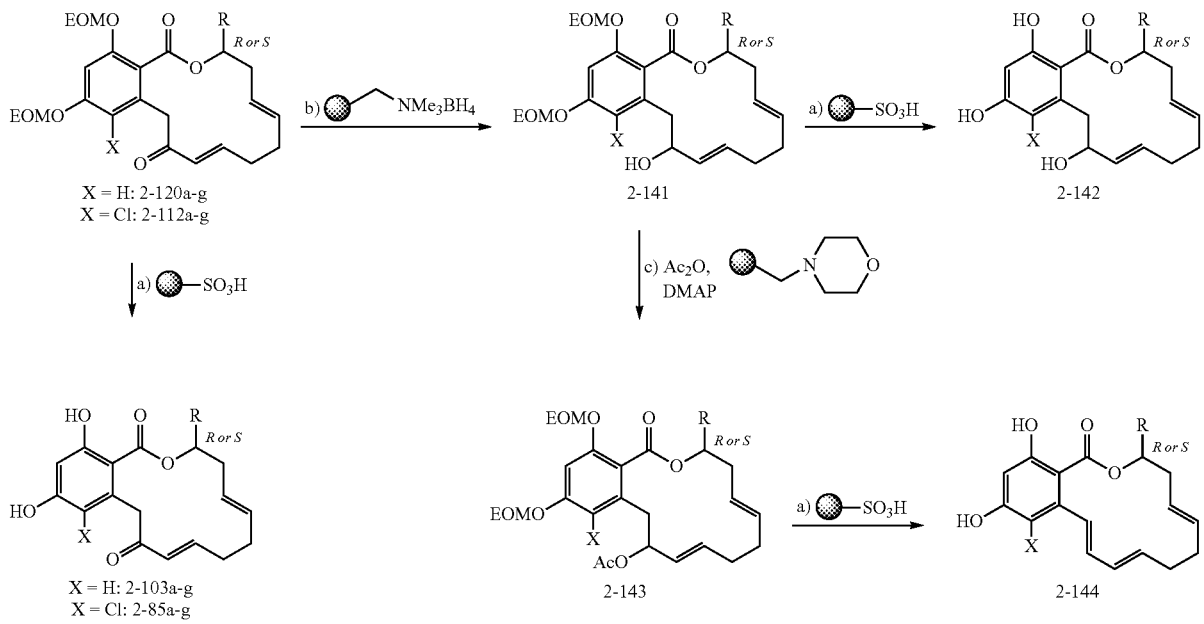

a) PS-TsOH (10.0 equiv., 3.2 mmol•g$^{-1}$), MeOH, 40° C., 4 h, >90%; b) BER resin (1.0 equiv., 2.5 mmol•g$^{-1}$), MeOH, 0° C., 12 h, ~60%; c) Ac$_2$O (1.2 equiv.), PS-NMM (1.2 equiv., 3.20 mmol.g$^{-1}$), DMAP (0.05 equiv.), DMF, 23° C., 0.5 h, ~80%. BER resin = borohydride exchange resin, PS-TsOH = sulfonic acid resin MP, DIBAL = diisobutylaluminum hydride, DMAP = dimethylaminopyridine, DMF = dimethylformamide, PS-NMM = morpholinomethyl polystyrene.

Prolonged exposure of resorcylides 2-112a-g and 2-120a-g to methanol in the presence of sulfonic acid resin was found to lead to conjugate addition; this observation was exploited to drive the reaction to completion cleanly. Thus phenol 2-85a-g was quantitatively converted to product 2-145a-g in 15 h (Scheme 18). This product could obviously be obtained directly from 2-120a-g under the same conditions.

Scheme 18: Synthesis of Analogues 2-145 by Conjugate Addition.

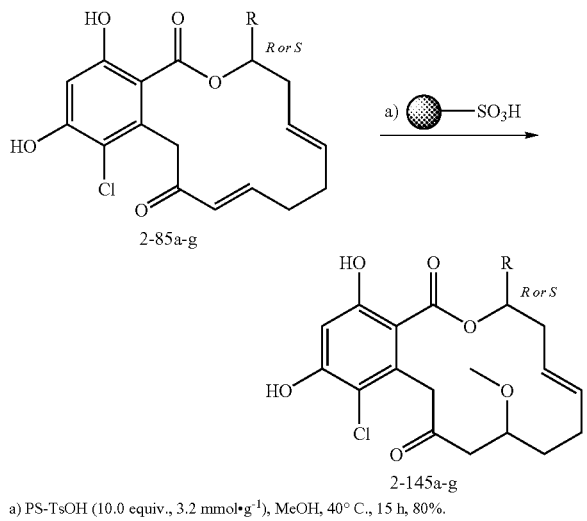

a) PS-TsOH (10.0 equiv., 3.2 mmol•g⁻¹), MeOH, 40° C., 15 h, 80%.

Compounds 2-103a-g and 2-85a-g were also used as the starting points for further diversifications (Scheme 19). Thus, treatment of 2-103a-g and 2-85a-g with polymer-bound cyanoborohydride afforded the 1,4-reduction products 2-146 in moderate yields. The more acidic para-hydroxyl groups of 2-103a-g and 2-85a-g were substituted via either Mitsunobu reaction using polymer bound DEAD or alkylation using a polymer-bound base to afford compounds with general structure 2-147 and 2-148 respectively. Oxidation with $OsO_4$ afforded the dihydroxylation products 2-149 as a mixture of isomers as well as the products corresponding to the dihydroxylation of the conjugate olefin (product not shown). Treatment of 2-103a-g and 2-85a-g with freshly prepared dimethyldioxirane led to the selective epoxidation of the non-conjugated olefin as a mixture of distereoisomers of pochonin A analogues 2-150. Although higher diastereoselectivity may be obtained for pochonin A if the phenols are protected with TBS (E. Moulin et al., *Org. Lett.*, 7:5637 (2005)), protection was not needed here.

Scheme 19: Derivatization of Compounds 2-85a-g and 2-103a-g.

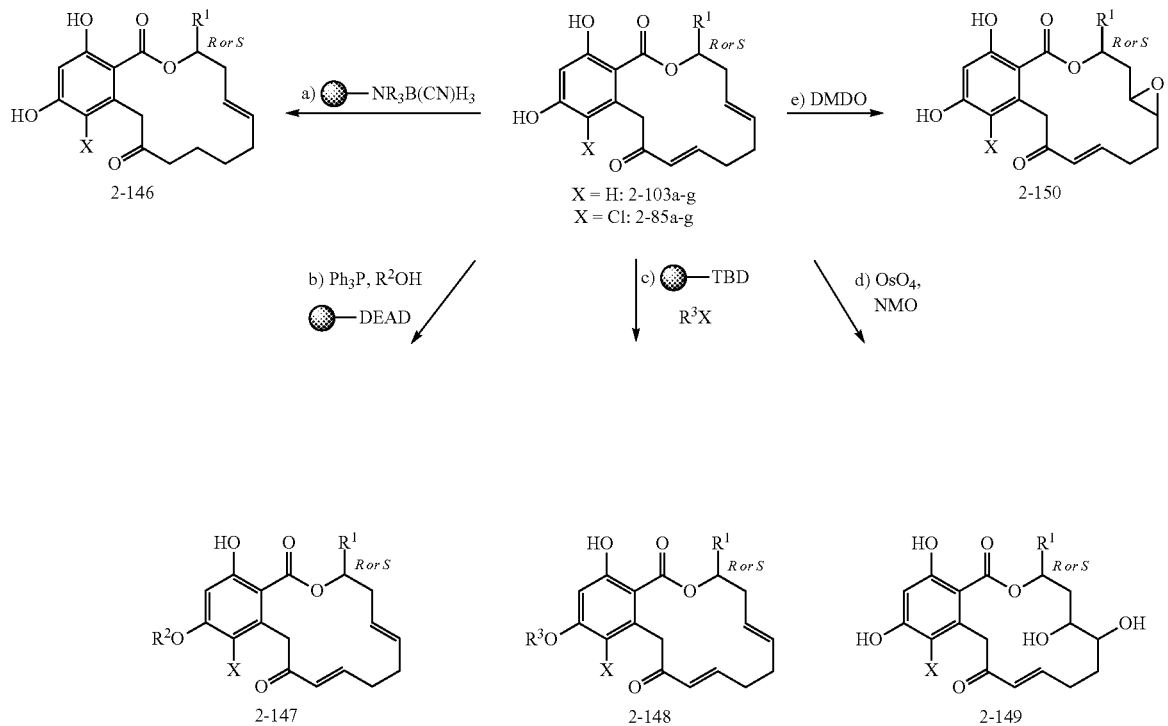

$R^2$ = Allyl, Me
$R^3X$ = EOMCl, BrCH₂COOtBu a) PS-TMABH₃CN (2.0 equiv., 3.5 mmol•g⁻¹), CH₂Cl₂/AcOH 10:1, 23° C., 4 h, ~50%; b) PPh₃ (2.0 equiv.), R²OH (2.0 equiv.), PS-DEAD (2.0 equiv., 1.3 mmol•g⁻¹), CH₂Cl₂, 23° C., 8 h, ~60%; c) R³X (0.9 equiv.), PS-TBD (2.0 equiv., 2.9 mmol•g⁻¹), CH₂Cl₂, 23° C., 3 h, ~90%; d) OsO₄ (0.1 equiv.), NMO (1.0 equiv.), Acetone/H₂O 10:1, 23° C., 1 h, > 70%; e) DMDO (1.2 equiv., 0.04 M in acetone), CH₃CN, 0° C., 30 min, > 90%. AllOH = Allylalcohol, DMDO = dimethyldioxirane, NMO = 4-methylmorpholine N-oxide, PS-DEAD = ethoxycarbonylazocarboxymethyl polystyrene, PS-TBD = TBD-methyl polystyrene, PS-TMABH₃CN = (polystirylmethyl)trimethylammonium cyanoborohydride.

It is interesting to note that the conjugated olefin proved to have different reactivity depending on the presence or absence of the chlorine atom on the aryl ring. Whereas EOM deprotection of compound 2-120 where X=Cl and R=Me could be carried out with HCl in dioxane, treatment of the corresponding compound 2-112 where X=H and R=Me by the same conditions led to the conjugate addition of the chlorine ion during the deprotection, affording compound 2-151 (Scheme 20). The difference in reactivity may be attributed to the different conformation of this compound. It is conceivable that the differences in conformation affect the level of conjugation between the olefin and the adjacent carbonyl group. Nevertheless, the n-chlorine could be cleanly eliminated in the presence of polymer-bound base to recover the conjugate compound 2-103a-g.

fonic acid resin in methanol followed by treatment with sulfonic acid resin in DCM in the presence of dihydropyran afforded oximes 2-155 bearing a pyran substitution on the aromatic ring as a mixture of diastereoisomers. In the case where the side chain contains an acid ($R^2X$=$OCH_2COOH$), the deprotection of the EOM with the sulfonic acid resin in methanol was accompanied by esterification of the carboxylate. Treatment of compounds 2-120a and 2-112a with trifluoroacetic led to the formation of trifluoroacetate 2-152. Finally, all attempts at oxime formation in the chlorinated analogues with or without EOM protecting groups generated mostly the corresponding 1,4-addition of the hydroxylamines (Scheme 21). Surprisingly, when pochonin D was protected with TBS groups, (2-128a-g, Scheme 21) the formation of the desired oxime 2-157a-g was the only product observed under

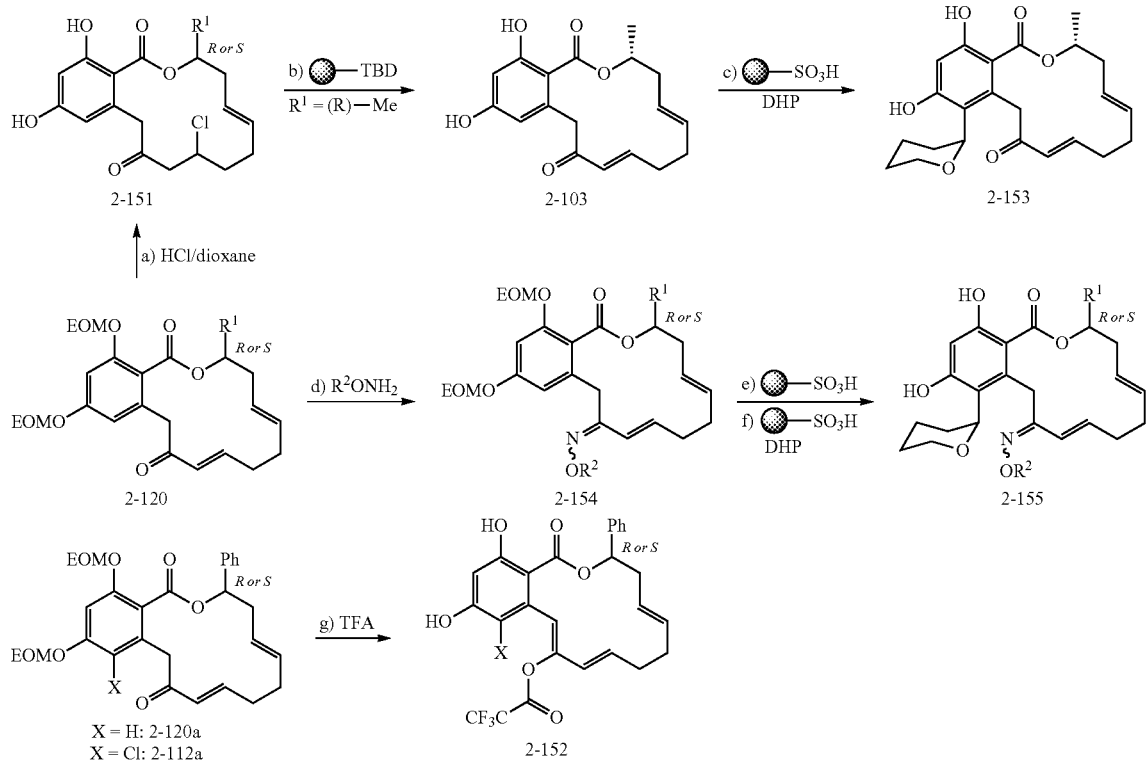

Scheme 20: Derivatization of Macrocycles 2-120 and 2-120a-g.

$R^2O$ = OBn, $OCH_2COOMe$, $OCH_2COOH$, OMe, OEt, OH, OAllyl, OTHP, $OCH_2C_6H_4p(NO_2)$ a) HCl (2.5% in dioxane), 23° C., 3 h, >75%; b) PS-TBD (0.5 equiv., 2.6 mmol•$g^{-1}$), $CH_2Cl_2$, 23° C., 8 h, ~90%; c) PS-TsOH (1.0 equiv., 3.2 mmol•$g^{-1}$), DHP (1.0 equiv.), $CH_2Cl_2$, 23° C., 5 h, ~80%; d) $R^2ONH_2$•HCl (5.0 equiv.), Pyr/AcOH 5:1, 40° C., 12 h, ~90%; e) PS-TsOH (10.0 equiv., 3.2 mmol•$g^{-1}$), MeOH, 40° C., 4 h, ~80% f) PS-TsOH (cat., 3.2 mmol•$g^{-1}$), DHP (1.0 equiv.), $CH_2Cl_2$, 23° C., 5 h, ~70%; g) TFA (20%), $CH_2Cl_2$, 23° C., 2 h. DHP = dihydropyran, PS-TBD = TBD-methyl polystyrene, PS-TsOH = sulfonic acid resin.

While evaluating protecting groups for the phenols, it was noticed that dihydropyran, in the presence of a strong acid such as sulfonic acid, led to electrophilic aromatic substitution rather than phenol protection. (see also T. Kometani et al., *Synthesis*, 1988:1005). Applying these conditions to compounds 2-103 (Scheme 20) afforded 2-153 as a separable mixture of diastereoisomers.

The formation of oxime proved to be sluggish for compounds with unprotected phenols. However, compounds 2-120 (X=H, Scheme 20) protected with EOM groups underwent smooth oxime formation with nine different hydroxylamines to obtain compounds 2-154 as E/Z mixtures with variable ratios. EOM deprotection of 2-154 with sulthe same reaction conditions. Deprotection of the TBS groups was than achieved using TBAF to obtain oximes 2-158a-g. Treatment of pochonin D with amines $RONH_2$ led to the formation of the 1,4-addition product 2-156. This difference in reactivity is presumably due to the level of conjugation between the olefin and the carbonyl, which in turn is a product of the conformation of the macrocycle. It is suspected that the bulky protecting group on the ortho phenol has a steric effect on the macrocycle conformation, as compared to the phenol which forms a hydrogen bond to the carbonyl. Such effect are known to affect the efficiency of ring closing metathesis reactions (E. A. Couladouros et al., *Org. Lett.*, 6:977 (2004)) and epoxidation diastereoselectivity. (E. Moulin et al., *Org. Lett.*, 7:5637 (2005)).

Scheme 21: Oxime Formation with Compounds 2-85.

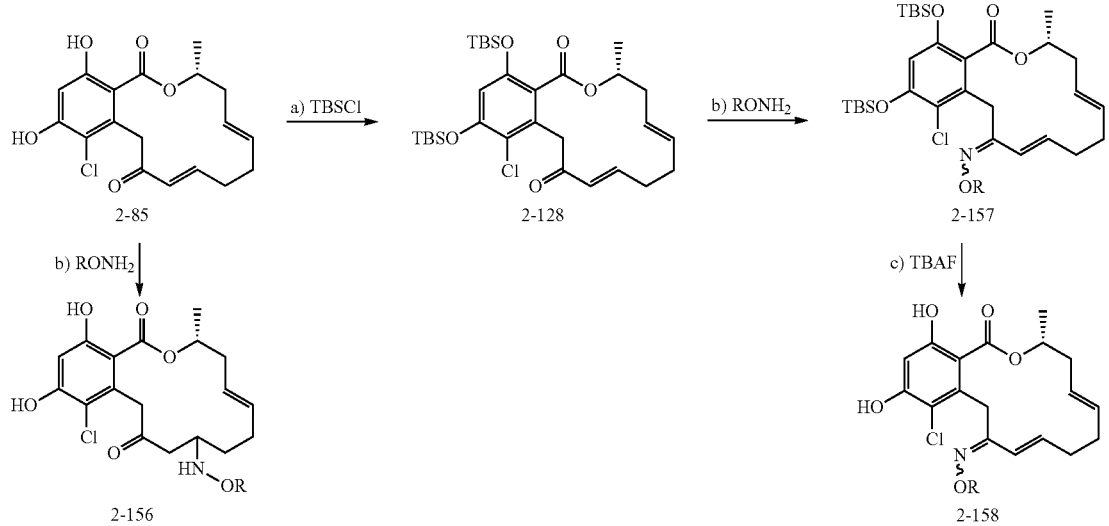

R = OBn, OCH₂COOMe, OCH₂COOH, OMe, OEt, OH, OAllyl, OTHP, OCH₂C₆H₄p(NO₂)

a) TBSCl (5.0 equiv.), imid. (5.0 equiv.), DMF, 23° C., 3 h, ~90%; b) RONH₂•HCl (5.0 equiv.), Pyr/AcOH 5:1, 40° C., 12 h, ~90%; c) TBAF (2.5 equiv.), THF, 23° C., 2 h, ~80%. DMF = dimethylformamide, Imid. = imidazole, TBAF = tetrabutylammonium fluoride, TBS-Cl = tert-butyldimethylsilyl chloride.

In another embodiment, the bis-methylated compounds 2-164 were prepared (Scheme 22). Acid 2-108 was used in a standard Mitsunobu esterification with alcohol 2-159. Compound 2-160 was protected as the ortho-phenol followed by acylation reaction with Weinreb amide 2-114 to yield the acyclic precursor 2-162. Ring-closing metathesis followed by removal of the EOM protecting groups on compound 2-163 using sulfonic acid resin furnished the bis-methylated analog 2-164.

Scheme 22: Synthesis of bis-methyl substituted analog (2-164) of pochonin D

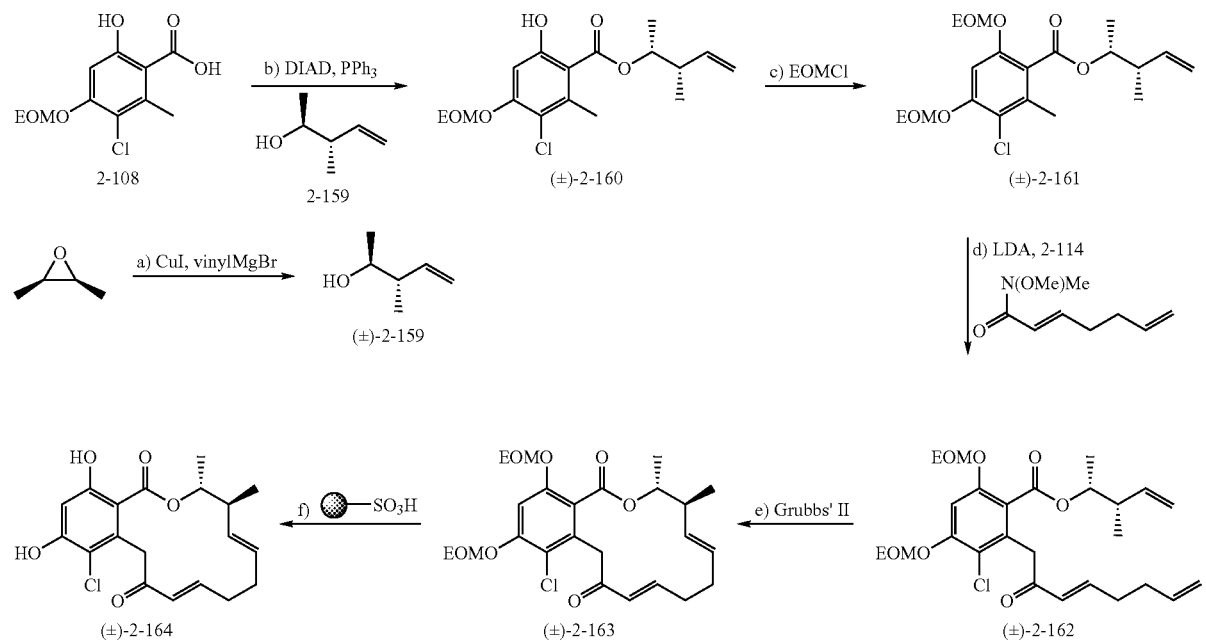

a) VinylMgBr (2.0 equiv.), CuI (0.3 equiv.), Et₂O, -30 → 23° C., 12 h, 65%; b) 2-159 (1.0 equiv.), PPh₃ (2.0 equiv.), DIAD (2.0 equiv.), toluene, 23° C., 3 h, 23%; c) EOMCl (2.0 equiv.), NaH 60% (2.0 equiv.), THF, 0° C., 2 h, 66%; d) LDA (2.0 equiv.), THF, -78° C.; 2-114 (1.0 equiv.), 10 min, 57%; e) Grubbs' II (10% mol), toluene (2 mM), 80° C., 12 h, 57%; f) PS-TsOH (10 equiv., 3.2 mmol.g⁻¹), MeOH, 40° C., 2.5 h 40%.

Additionally, oxime derivatives 2-165 and 2-167 were synthesized from macrocycle 2-163 as a separable mixture with the 1,4-addition product (Scheme 23). The carboxylic acid moiety of oxime 2-167 was then esterified to form the corresponding piperidine amide oxime 2-168.[94] Removal of the EOM groups using sulfonic acid resin allowed the isolation of both oximes 2-166 and 2-167 from 2-165 and 2-168 respectively. These two compounds along with their parent compound 2-164 and the 113 compounds from the library (FIG. 39) were then tested in biological assays for treating NF1 and NF2.

Scheme 23: Synthesis of oxime derivatives of compounds 2-164

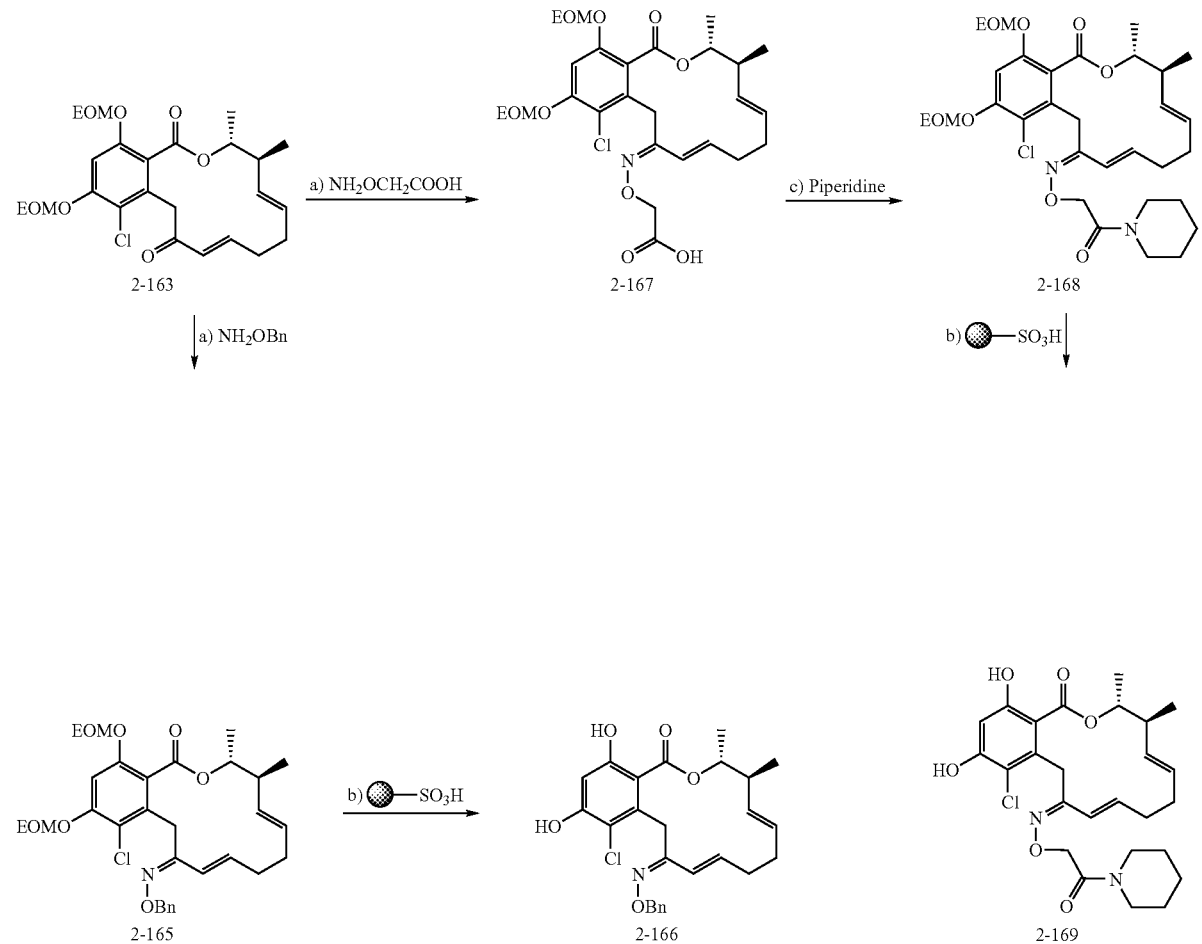

a) BnONH$_2$•HCl or NH$_2$OCH$_2$CO$_2$H (5.0 equiv.), Pyr/AcOH 5:1, 40° C., 24 h, 20-35%; b) PS-TsOH (10.0 equiv., 3.2 mmol•g$^{-1}$), MeOH, 40° C., 2.5 h, 77-80%; c) Piperidine (1.1 equiv.), EDC (1.1 equiv.), HOBt (1.1 equiv.), DMF, 23° C., 2 h, 75-80%.

In another embodiment, the pochonin oximes were prepared from cyclization of the pre-formed oximes as shown in Scheme 24. For example protected pre-formed oxime 1 was bound to Wang resin using N,N'-diisopropylcarbodiimide and dimethylaminopyridine. The allyl protecting group was removed and the phenol was functionalized under Mitsonubo conditions. This was followed by deprotection of the carboxylic acid and esterification with $R^3OH$. Ring-closing was effected with the use of Grubbs II catalyst as described before to provide resin-bound oxime 5. Deprotection and removal from the resin was achieved with trifluoroacetic acid to provide oxime 6. The carboxylic acid can be reacted with a variety of groups $R^4XH$ to provide the oximes 7, wherein X is oxygen, sulfur, amino or substituted amino. The oximes 7 were generally obtained as a 1:1 mixture of E:Z isomers which could be separated by reverse-phase chromatograpy (C18).

shows a non-limiting example for the formation of the macrocyle 2-al via a Mitsunobu esterification. Orcinol (compound 8) is oxidized with phosphoryl chloride in DMF to provide aldehyde 9, which is protected as the di-ethoxymethyl ether and subjected to oxidative chlorination with $NaClO_2$ to produce carboxylic acid 10. The carboxylic acid is protected as a trimethylsilylethyl ester and treated with LDA and Weinreb amide 12 (Scheme 26) to provide the α,β-unsaturated ketone 13. Ketone 13 is reacted with carboxymethoxylamine hemihydrochloride in pyridine at 40° C. to produce the corresponding oximes as a mixture of E and Z isomers. The oximes were converted to the desired amides 14 as a mixture of E and Z isomers by treatment with EDC and piperidine. Macrocyclization of precursor 14 to protected compound 15 was performed under Mitsunobu conditions by slow addition of DIAD to a solution of compound 14 and $PhP_3$ in toluene. The phenol groups were deprotected by

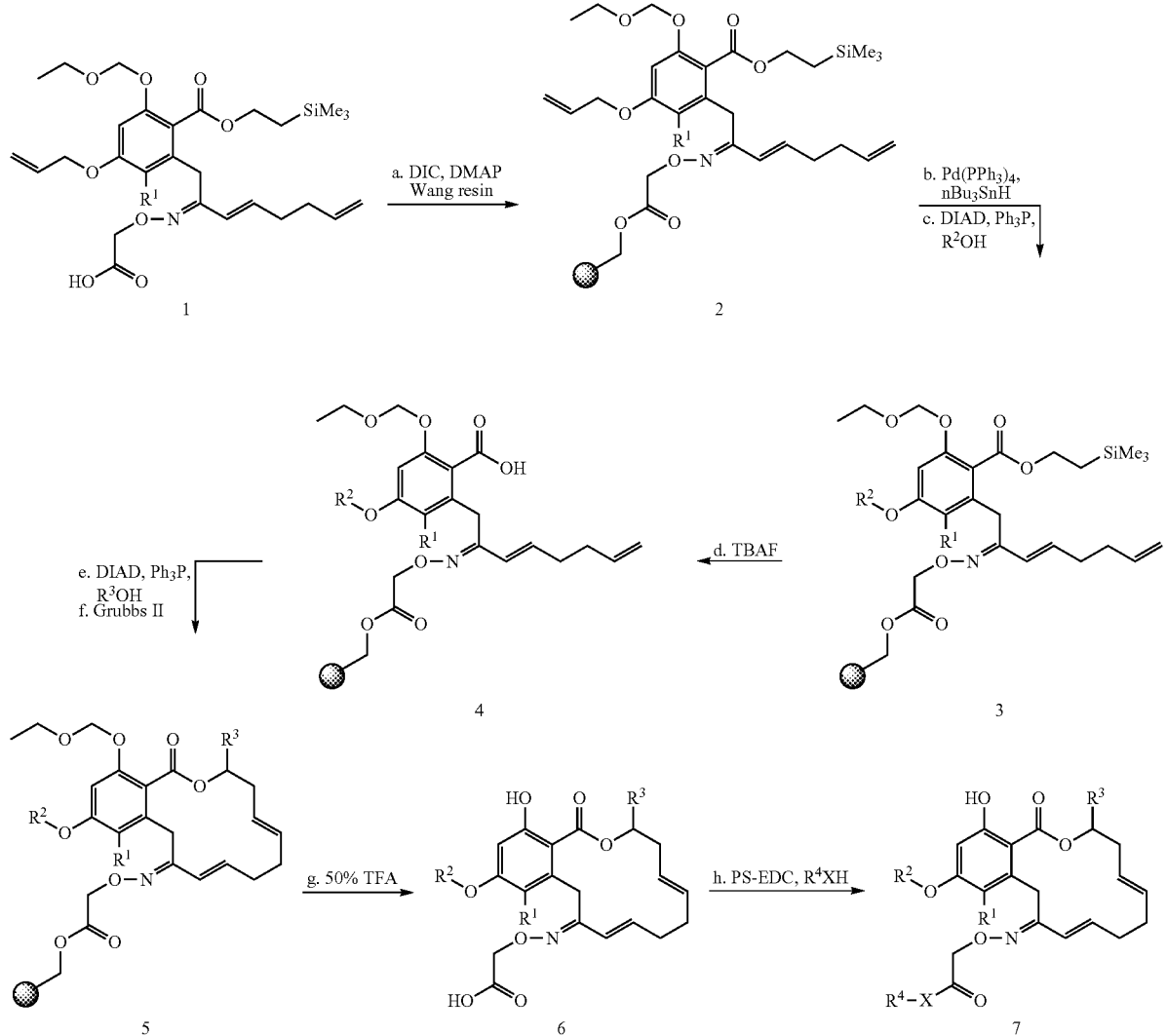

Scheme 24

In another embodiment, the pochonin oximes were prepared by an alternate process which utilized a Mitsunobu cyclization to construct the macrocylic ring. Scheme 25 treatment with sulfonic acid resin at 40° C. to produce 2a-1 as a mixture of E and Z isomers. The mixture of E- and Z-isomers was separated to obtain the pure E and Z isomers 2a-1.

Scheme 25: Cyclization under Mitsunobu Conditions
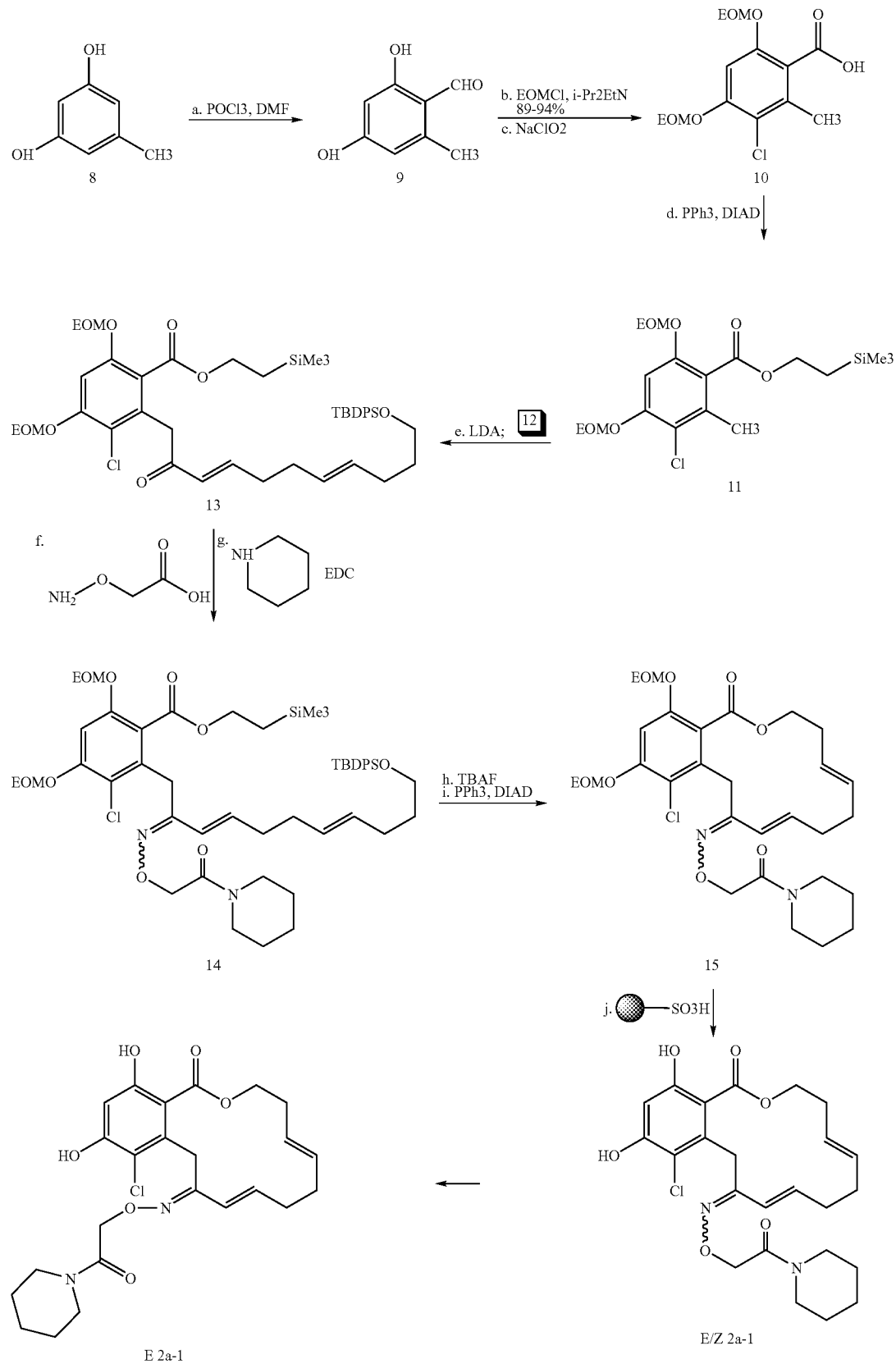

The diene Weireb amide 12 was prepared according to the process shown in Scheme 26. Trans-3-hexenedioic acid dimethyl ester 16 was reduced to the corresponding diol with lithium aluminum hydride. The diol was mono-protected as the tert-butyldiphenylsilyl ether 17, and the free alcohol was converted to aldehyde 20 in three steps via the nitrile 19. Aldehyde 20 was then treated with Weireb amide ylide 21 to produce the diene Weireb amide 12, which was used to prepare compound 13 (Scheme 24).

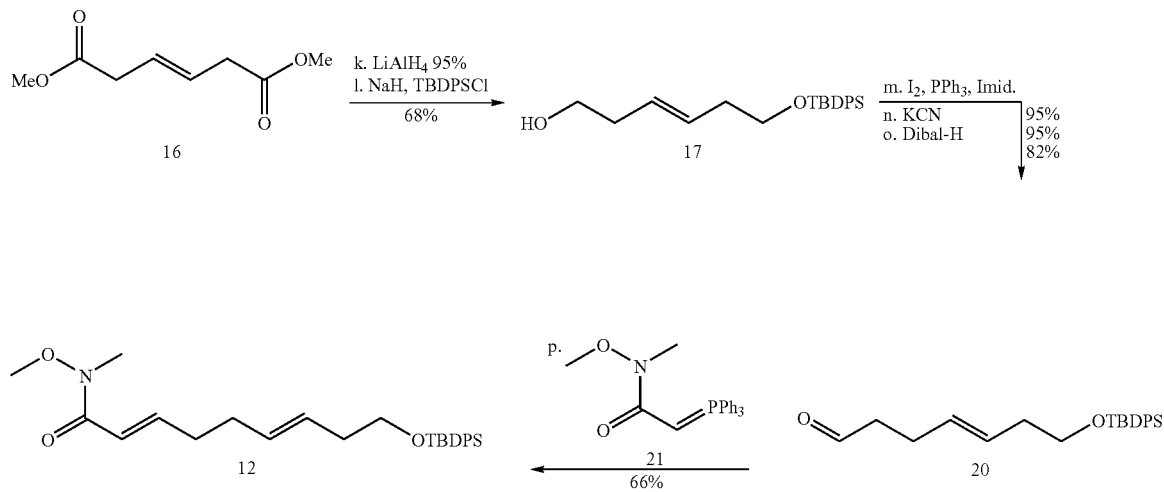

Scheme 26

Figure 1B:
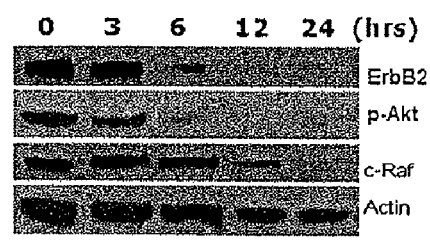
FIG. 1B shows graphs of Western blots demonstrating that the downregulation of HSP90 client proteins by NXD30001 is time-dependent.
Figure 2:
FIG. 2 shows graphs of actin immunoblots demonstrating the downregulation of HSP90 client proteins in ST88-14 NF1-deficient MPNST cell line resulted by NXD30001.
Figure 2:
Figure 2:
Figure 2:
Figure 2:

Crystal structures of the E-izomer 2a-1 and the related E-oxime 2a-13, which lacks the chloro substituent on the aromatic ring, were obtained. The crystal structures are shown in FIGS. 1 and 2.

The solubility of compounds 2a-1 and 2a-13 was determined. Both compounds were determined to be highly soluble in DMSO and DMA (>5 g/mL). The good solubility of the compounds in DMSO and DMA enable formulations for intravenous or intraperitoneal administration. In one non-limiting example, a formulation of the oximes in DMSO/ Tween 20/0.9% NaCl (Oct. 5, 1985) was prepared.

Biological Activity

Pochonin Analogs Selected for IC50 Determination (R)-2-112a

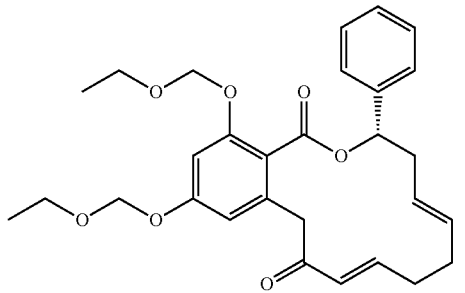

A-1

(R)-2-151a-1

(S)-2-145a

-continued

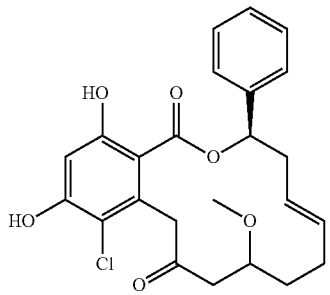

A-2

A-3

(R)-2-150d-1

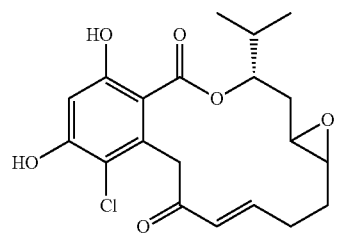

(S)-2-150a

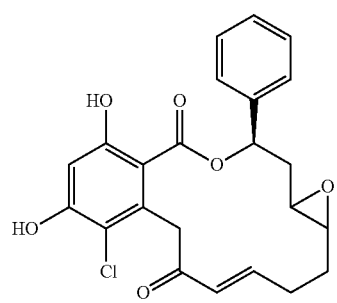

(R)-2-150f

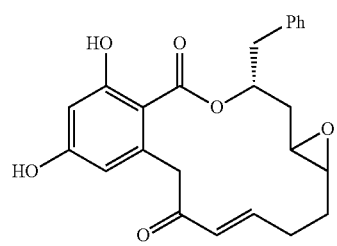

(S)-2-150

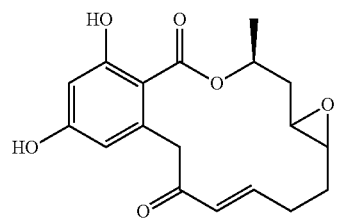

(R)-2-147-3

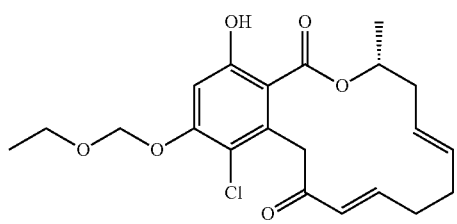

A-4

A-5

A-6

A-7

A-8

EXAMPLES

General Techniques. All reactions were carried out under a nitrogen atmosphere with dry (anhydrous) solvents under anhydrous conditions, unless otherwise noted. Anhydrous solvents were obtained by passing them through commercially available alumina column (Innovative Technology, Inc.,® VA). All substituted polystyrene resins (100-200 mesh, 1% DVB) were purchased from Novabiochem® or Aldrich®. The Grubbs' II catalyst was purchased from Materia Inc.® Solid phase reactions were carried on a Quest® 210 or round bottom flasks and filtered in fritted funnels. Reactions were monitored by thin layer chromatography (TLC) carried out on 0.25 mm E. Merck® silica gel plates (60E-254) using UV light as visualizing agent and 10% ethanolic phosphomolybdic acid or vanillin solution and heat as developing agents. E. Merck® silica gel (60, particle size 0.040-0.063 mm) was used for flash column chromatography. PTLC (preparative thin layer chromatography) were carried out on 0.25 mm E. Merck® silica gel plates. NMR spectra were recorded on a Bruker Advance-400® instrument and calibrated by using residual undeuterated solvent as an internal reference. The following abbreviations were used to explain the multiplicities: s=singlet, d=doublet, t=triplet, q=quartet, m=multiplet, b=broad. IR spectra were recorded on a Perkin-Elmer 1600 series FT-IR spectrometer. LC-MS were recorded using an Agilent 1100® HPLC with a Bruker® micro-TOF instrument (ESI). Unless otherwise stated, a Supelco® C8 (5 cm×4.6 mm, 5 μm particles) column was used with a linear elution gradient from 100% $H_2O$ (0.5% $HCO_2H$) to 100% MeCN in 13 min at a flow rate of 0.5 ml/min. Unless otherwise stated, LDA was prepared at a concentration of 0.566 M by treating a solution of diisopropylamine (1.0 equiv.) in THF at −78° C. with n-butyllithium (1.0 equiv.) and stirred for 30 min at this temperature before use.

Example 1

General Procedure for the Synthesis of Compounds 4

As depicted in Scheme 1, a solution of acid 2-95A or 2-95b (1.0 equiv), homoallylic alcohol (1.0 equiv) and tris-(3-chlorophenyl)phosphine (2.0 equiv) in anhydrous toluene (0.05 M) was treated at room temperature with PS-DEAD (2.5 equiv, 1.3 mmol g$^{-1}$). After stirring for 10 min, the reaction mixture was filtered on silica and washed with hexane/EtOAc (10/1, 100 ml) and hexane/EtOAc (3/1, 100 ml). The 3/1 mixture was concentrated under reduced pressure to yield compound 3 (60-80%). Without further purification, compound 3 (1.0 equiv) and tetrabutylammonium iodide (catalytic amount) were dissolved in DMF (0.15 M) and treated with diisopropylethylamine (4.0 equiv) and (chloromethyl) ethyl ether (4.0 equiv). After stirring overnight at 80° C., the reaction mixture was diluted with EtOAc and washed several times with a saturated NH$_4$Cl solution. The organic phase was dried over MgSO$_4$ and concentrated under reduce pressure to yield compounds 4 (80-90%). Using this method, a variety of compounds 4 were prepared.

(R)-2-217d

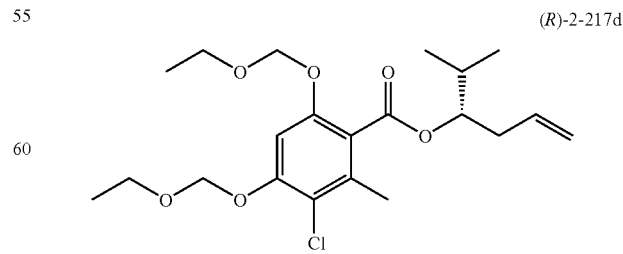

$^1$H NMR (CDCl$_3$, 400 MHz, 25° C.) δ 7.04 (s, 1H), 5.89 (ddt, J=17.0, 10.5, 7.0 Hz, 1H), 5.31 (s, 2H), 5.21 (s, 2H), 5.22-5.06 (m, 3H), 3.79 (q, J=7.0 Hz, 2H), 3.72 (q, J=7.0 Hz, 2H), 2.48-2.44 (m, 2H), 2.36 (s, 3H), 2.01 (qd, J=12.4, 7.0 Hz, 1H), 1.25 (t, J=7.0 Hz, 3H), 1.23 (t, J=7.0 Hz, 3H), 1.02 (d, J=6.4 Hz, 3H), 1.01 (d, J=7.0 Hz, 3H); $^{13}$C NMR (CDCl$_3$, 100 MHz, 25° C.) δ 167.3, 154.0, 152.9, 134.8, 134.1, 120.4, 117.5, 117.1, 101.5, 93.9, 93.4, 79.0, 64.6, 64.3, 35.6, 30.8, 18.4, 17.6, 17.5, 15.0 (×2); HRMS (ESI-TOF) m/z 437.1574 ([M+Na$^+$], C$_{21}$H$_{31}$O$_6$ClNa requires 437.1701).
The following non-limiting examples of compounds 4 were prepared.
(S)-2-117a
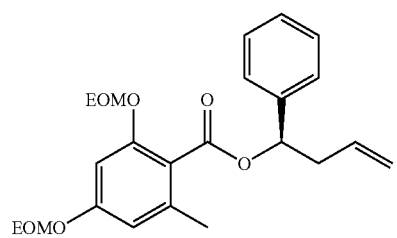
(S)-2-117b
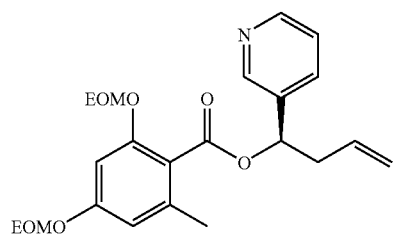
(R)-2-117c
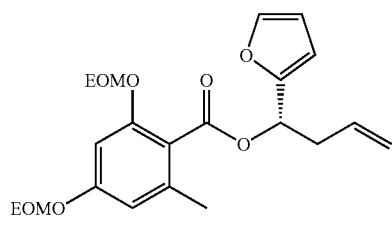
(R)-2-117d
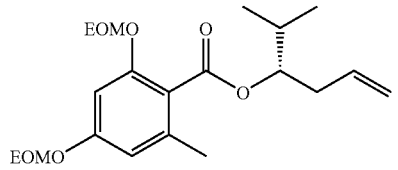
(R)-2-117e
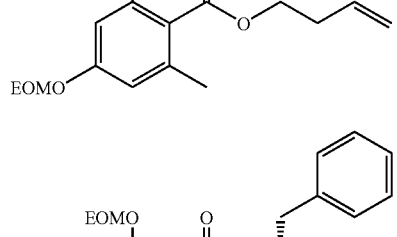
(R)-2-117f
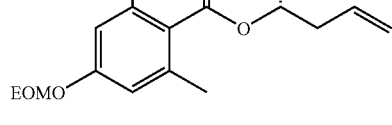
-continued
2-117g
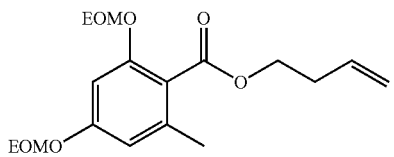
(S)-2-117
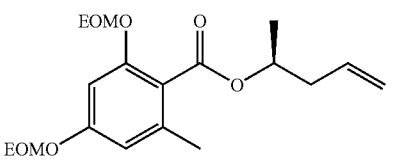
(S)-2-110
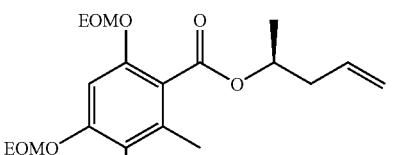
2-110
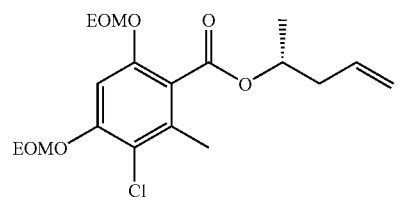
(R)-2-110a
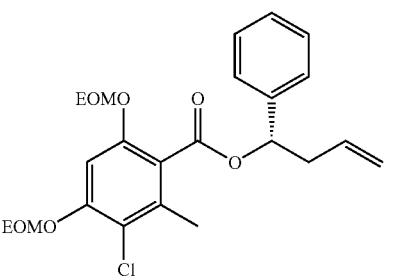
(S)-2-110a
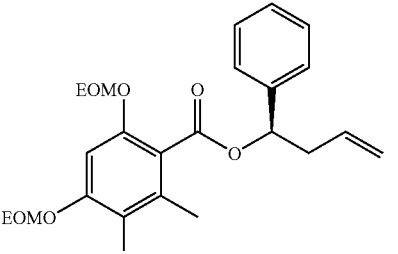
(S)-2-110b
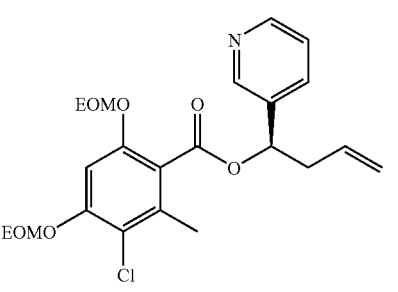

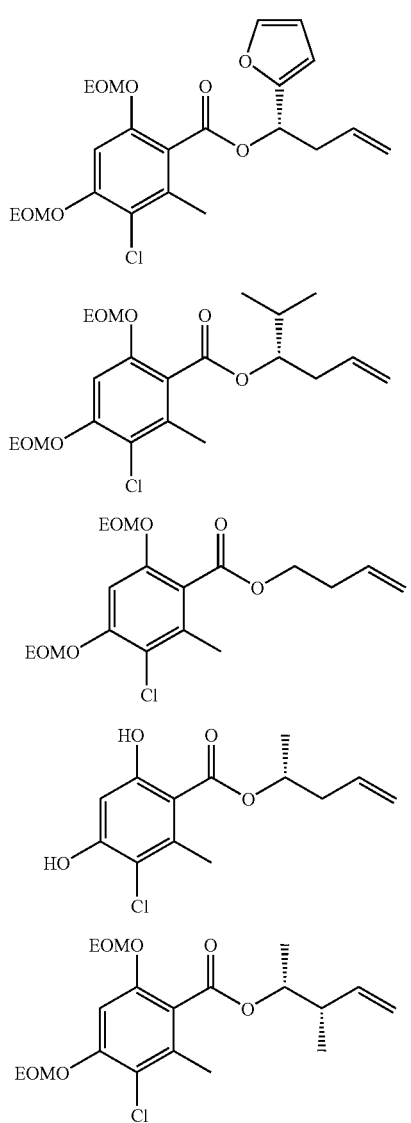

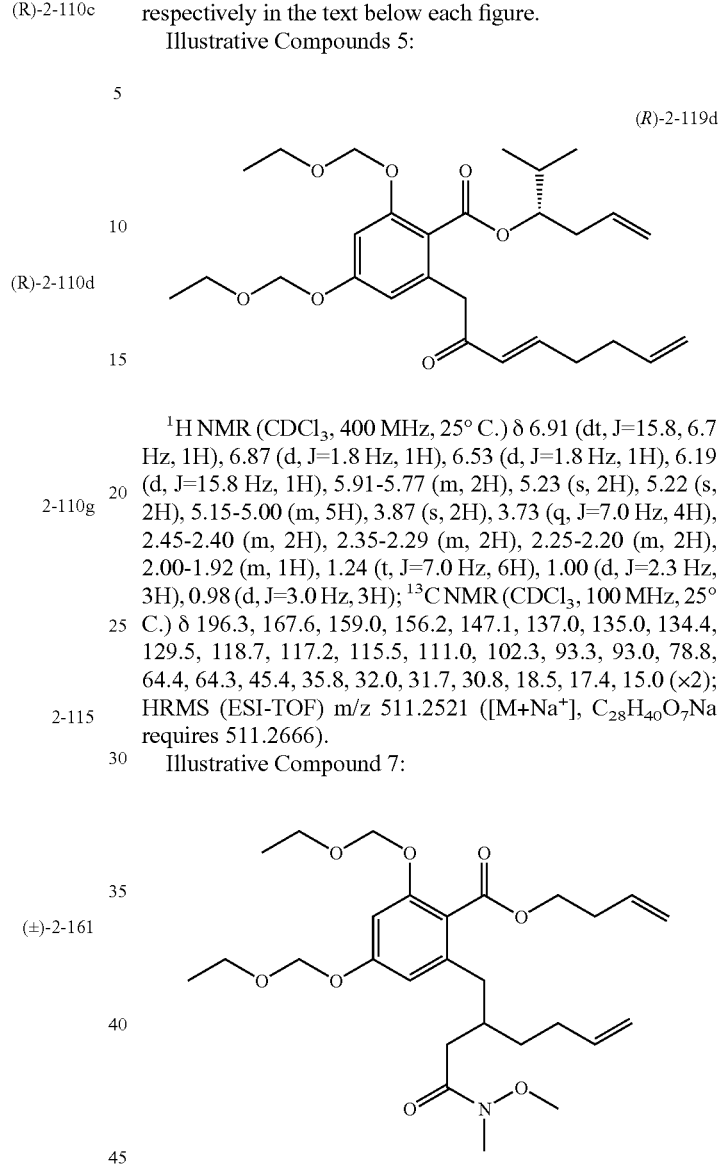

of compounds 5 and 7 follow; their characterization follows respectively in the text below each figure.

Illustrative Compounds 5:

$^1$H NMR (CDCl$_3$, 400 MHz, 25° C.) δ 6.91 (dt, J=15.8, 6.7 Hz, 1H), 6.87 (d, J=1.8 Hz, 1H), 6.53 (d, J=1.8 Hz, 1H), 6.19 (d, J=15.8 Hz, 1H), 5.91-5.77 (m, 2H), 5.23 (s, 2H), 5.22 (s, 2H), 5.15-5.00 (m, 5H), 3.87 (s, 2H), 3.73 (q, J=7.0 Hz, 4H), 2.45-2.40 (m, 2H), 2.35-2.29 (m, 2H), 2.25-2.20 (m, 2H), 2.00-1.92 (m, 1H), 1.24 (t, J=7.0 Hz, 6H), 1.00 (d, J=2.3 Hz, 3H), 0.98 (d, J=3.0 Hz, 3H); $^{13}$C NMR (CDCl$_3$, 100 MHz, 25° C.) δ 196.3, 167.6, 159.0, 156.2, 147.1, 137.0, 135.0, 134.4, 129.5, 118.7, 117.2, 115.5, 111.0, 102.3, 93.3, 93.0, 78.8, 64.4, 64.3, 45.4, 35.8, 32.0, 31.7, 30.8, 18.5, 17.4, 15.0 (×2); HRMS (ESI-TOF) m/z 511.2521 ([M+Na$^+$], C$_{28}$H$_{40}$O$_7$Na requires 511.2666).

Illustrative Compound 7:

$^1$H NMR (CDCl$_3$, 400 MHz, 25° C.) δ 6.72 (s, 1H), 6.57 (s, 1H), 5.89-5.71 (m, 2H), 5.20-5.16 (m, 4H), 5.12-4.90 (m, 4H), 4.33 (t, J=6.8 Hz, 2H), 3.69 (2×q, J=7.0 Hz, 4H), 3.57 (s, 3H), 3.13 (s, 3H), 2.69-2.64 (m, 1H), 2.53-2.45 (m, 4H), 2.32 (m, 2H), 2.08-2.03 (m, 2H), 1.19 (t, J=6.8 Hz, 6H), 1.01 (t, J=6.5 Hz, 2H); HRMS (ESI-TOF) m/z 508.2873 ([M+H$^+$], C$_{27}$H$_{42}$O$_8$N requires 508.2905).

Using the procedure above, the following non-limiting examples of compounds 5 shown below were prepared.

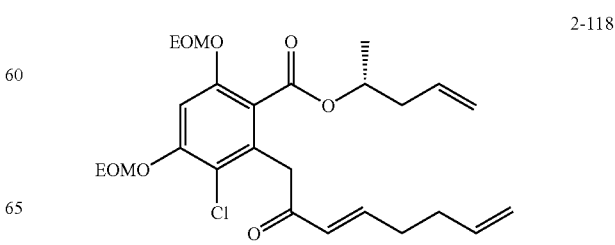

Example 2

General Procedure for the Synthesis of Compounds 2-118, 2-119 and 2-140

As depicted in Scheme 1, a solution of compound 2-110 or 2-117 (1.0 equiv) in anhydrous THF (0.2 M) was treated at −78° C. with freshly made LDA (2.0 equiv). Immediately after, the α,β-unsaturated Weinreb amide (S. V. Ley and I. R. Baxendale, *Nat. Rev. Drug Discov.*, 1:573 (2002)) was added to the cooled solution (1.0 equiv). The resulting mixture was then stirred for 10 min at −78° C. and quenched by addition of Amberlite® resin (20 equiv). Upon warming up to room temperature, the reaction was filtered on a pad of silica and washed with EtOAc. Concentration under reduced pressure afforded the desired compound 5. This compound was used directly in the metathesis reaction without any further purification. When X═H, 20% of the corresponding 1,4-addition compound was observed and a fraction of the mixture was purified for characterization of compounds 5 and 7 (SiO$_2$, 0-20% EtOAc/cyclohexane gradient). Illustrative examples 2-119
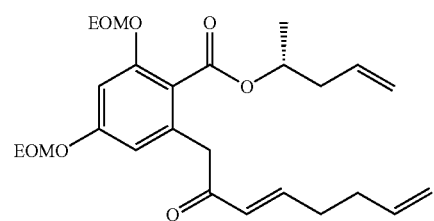
(S)-2-119
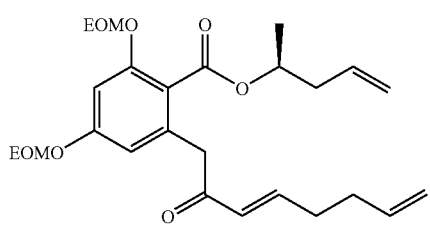
(R)-2-119a
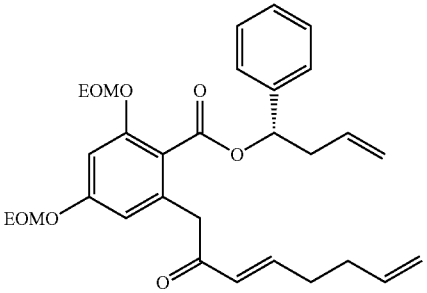
(S)-2-119a
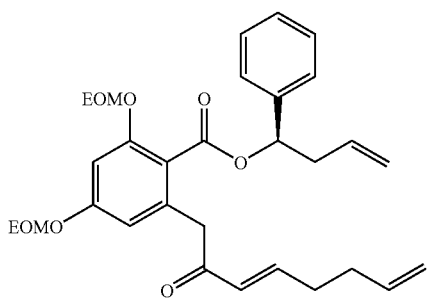
(R)-2-119d
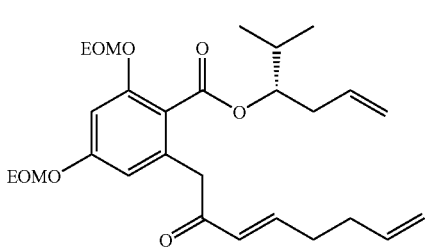
(R)-2-119e
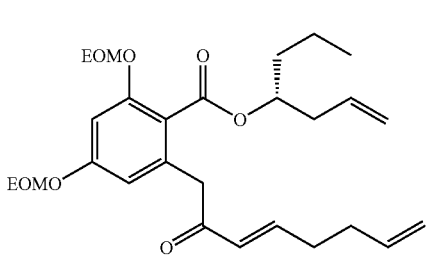
(R)-2-119f
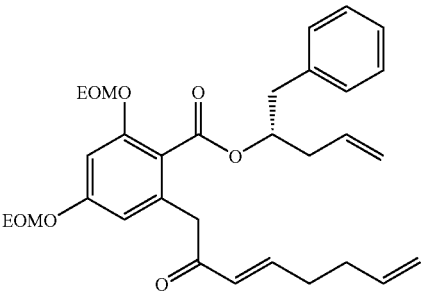
2-119g
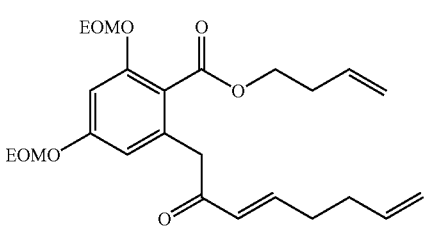
The following non-limiting examples of compounds 2-140 were prepare according to the procedure described here.
(S)-2-140
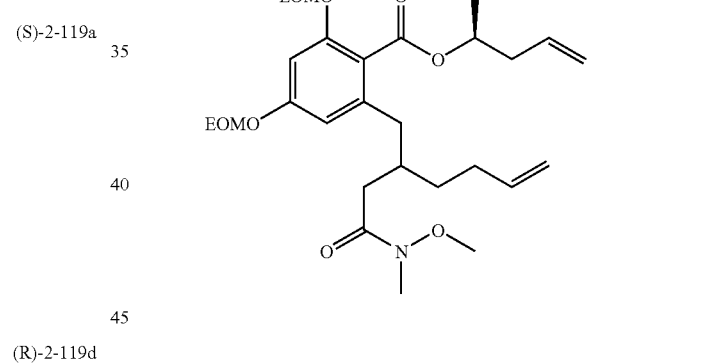
(R)-2-140a
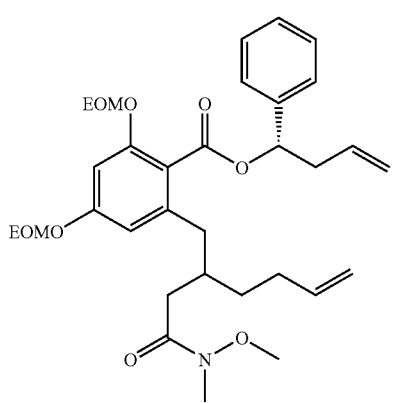

279

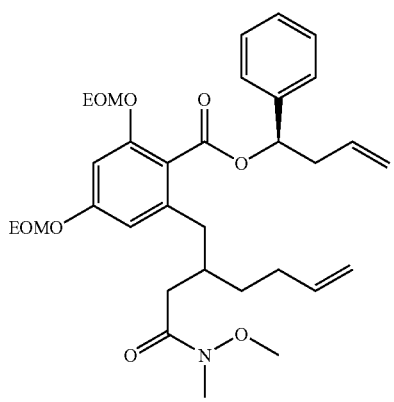

(S)-2-140a

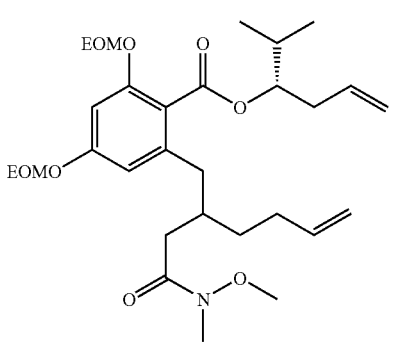

(R)-2-140d

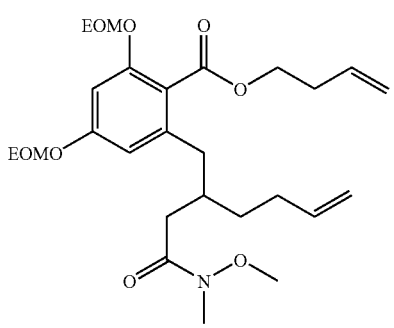

2-140g

Example 3

General Procedure for the Metathesis Reaction

As depicted in Scheme 1, a solution of crude 2-118 or 2-119 (or mixture 2-118/2-119 and 2-140 when X=Cl), in anhydrous toluene (2 mM) was treated with Grubbs' second generation catalyst (0.10 equiv) and heated at 80° C. for 12 h. The reaction was cooled down to room temperature and the mixture was filtered through a pad of SiO₂, washed with CH₂Cl₂ followed by a mixture EtOAc/cyclohexane 1/1 and concentrated under reduced pressure. Purification by flash chromatography (SiO₂, 0-25% EtOAc/cyclohexane gradient) afforded compounds 2-112 or 2-120 or 2-140 (60-85% over two steps). Illustrative examples of compounds 2-112 or 2-120 and 2-140 follow; their characterization follows respectively in the text below each figure.

280

Illustrative Compounds 2-112/2-120:

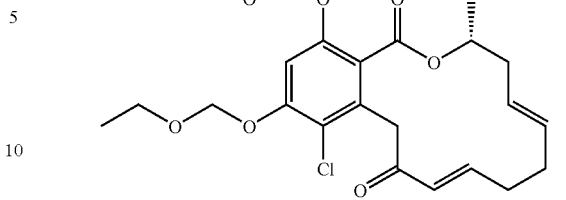

$^1$H NMR (CDCl$_3$, 400 MHz, 25° C.) δ 7.14 (s, 1H), 6.72-6.66 (m, 1H), 5.88 (d, J=15.2 Hz, 1H), 5.33-5.17 (m, 6H), 4.92-4.88 (m, 1H), 4.21 (d, J=17.0 Hz, 1H), 3.92 (d, J=17.0 Hz, 1H), 3.79-3.67 (m, 4H), 2.33-2.17 (m, 5H), 2.07-1.96 (m, 2H), 1.23 (t, J=7.0 Hz, 3H), 1.21 (t, J=7.0 Hz, 3H), 1.00 (d, J=5.8 Hz, 6H); $^{13}$C NMR (CDCl$_3$, 100 MHz, 25° C.) δ 195.7, 167.1, 154.7, 154.4, 147.4, 133.7, 131.2, 128.8, 128.4, 119.7, 118.0, 102.7, 93.9, 93.5, 80.0, 64.8, 64.5, 44.1, 32.3, 31.2, 30.7, 30.6, 18.3, 17.2, 15.0, 14.9; HRMS (ESI) m/z 517.1844 ([M+Na$^+$], C$_{26}$H$_{35}$O$_7$ClNa requires 517.1964); [α]$^{25}_D$+21.3 (c 1.00, CHCl$_3$).

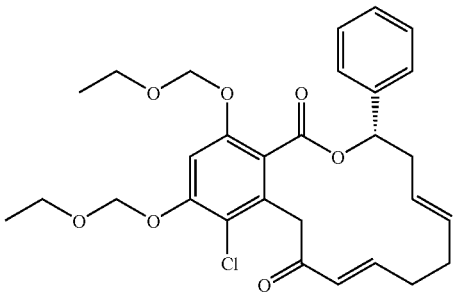

$^1$H NMR (CDCl$_3$, 400 MHz, 25° C.) δ 7.49-7.47 (m, 2H), 7.40-7.29 (m, 3H), 7.10 (s, 1H), 6.84-6.77 (m, 1H), 5.98 (d, J=15.2 Hz, 1H), 5.78 (d, J=8.8 Hz, 1H), 5.44-5.30 (m, 4H), 5.15 (d, J=7.0 Hz, 1H), 5.05 (d, J=6.8 Hz, 1H), 4.07 (d, J=17.0 Hz, 1H), 3.90 (d, J=17.0 Hz, 1H), 3.80 (d, J=7.0 Hz, 2H), 3.60-3.51 (m, 2H), 2.68-2.62 (m, 1H), 2.50-2.47 (m, 1H), 2.38-2.29 (m, 2H), 2.14-2.02 (m, 2H), 1.25 (t, J=7.0 Hz, 3H), 1.17 (t, J=7.0 Hz, 3H); $^{13}$C NMR (CDCl$_3$, 100 MHz, 25° C.) δ 195.7, 166.7, 154.8, 154.2, 147.3, 140.7, 133.3, 132.1, 128.5, 128.3 (×2), 128.2, 127.9, 127.7, 126.7 (×2), 120.1, 118.1, 102.9, 93.9, 93.4, 77.4, 64.8, 64.4, 44.5, 40.5, 30.7, 15.0, 14.9; HRMS (ESI) m/z 551.1807 ([M+Na$^+$], C$_{29}$H$_{33}$O$_7$ClNa requires 551.1680); [α]$^{25}_D$-40.4 (c 0.79, CHCl$_3$).

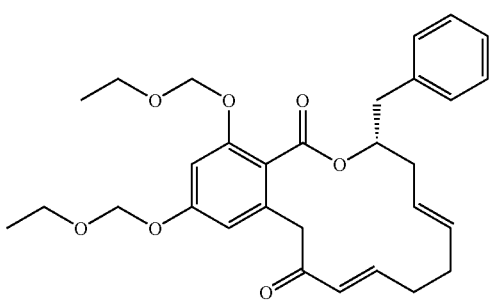

¹H NMR (CDCl₃, 400 MHz, 25° C.) δ 7.39-7.33 (m, 4H), 7.31-7.27 (m, 1H), 6.82 (s, 1H), 6.82-6.75 (m, 1H), 6.63 (s, 1H), 6.02 (d, J=16.4 Hz, 1H), 5.35-5.29 (m, 2H), 5.27-5.20 (m, 5H), 4.16 (d, J=14.6 Hz, 1H), 3.79-3.70 (m, 4H), 3.52 (d, J=14.6 Hz, 1H), 3.37 (dd, J=13.4, 4.1 Hz, 1H), 2.78 (dd, J=13.5, 9.4 Hz, 1H), 2.37-2.12 (m, 5H), 2.06-2.02 (m, 1H), 1.26 (t, J=7.0 Hz, 3H), 1.24 (t, J=7.0 Hz, 3H); ¹³C NMR (CDCl₃, 100 MHz, 25° C.) δ 197.6, 167.8, 159.2, 156.5, 149.0, 137.3, 135.5, 131.8, 129.9, 129.5 (×2), 128.6 (×2), 128.4, 126.7, 118.1, 109.9, 102.3, 93.5, 93.1, 75.8, 64.6, 64.4, 44.4, 41.0, 36.2, 31.0, 30.6, 15.0 (×2); HRMS (ESI) m/z 531.2350 ([M+Na⁺], C₃₀H₃₆O₇Na requires 531.2359); [α]²⁵_D −24.1 (c 0.33, CHCl₃).

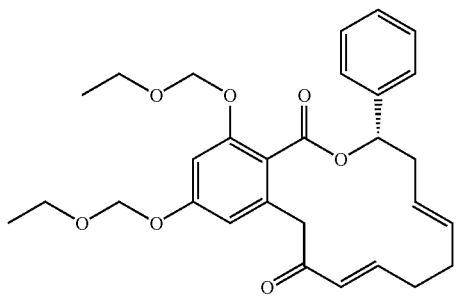

¹H NMR (CDCl₃, 400 MHz, 25° C.) δ 7.56-7.54 (m, 2H), 7.41-7.29 (m, 3H), 6.89-6.82 (m, 1H), 6.78 (d, J=2.3 Hz, 1H), 6.61 (d, J=1.8 Hz, 1H), 6.06 (d, J=16.4 Hz, 1H), 5.98 (dd, J=11.7, 2.4 Hz, 1H), 5.53-5.51 (m, 2H), 5.20 (d, J=7.0 Hz, 1H), 5.17 (d, J=6.4 Hz, 1H), 5.07 (d, J=7.0 Hz, 1H), 4.96 (d, J=7.0 Hz, 1H), 4.20 (d, J=14.6 Hz, 1H), 3.73-3.68 (m, 2H), 3.54-3.45 (m, 3H), 2.71-2.66 (m, 1H), 2.55-2.51 (m, 1H), 2.38-2.32 (m, 2H), 2.23-2.06 (m, 2H), 1.22 (t, J=7.0 Hz, 3H), 1.14 (t, J=7.0 Hz, 3H); ¹³C NMR (CDCl₃, 100 MHz, 25° C.) δ 197.6, 167.4, 159.3, 156.6, 149.0, 140.8, 135.6, 132.2, 129.9, 128.5, 128.2 (×2), 127.9, 126.9 (×2), 117.9, 109.9, 102.3, 93.2, 93.0, 76.6, 64.4, 64.3, 44.4, 40.5, 31.0, 30.6, 15.0, 14.9; HRMS (ESI) m/z 517.2062 ([M+Na], C₂₉H₃₄O₇Na requires 517.2197). [α]²⁵_D −108.3 (c 1.00, CHCl₃).

Illustrative Compounds 2-140:

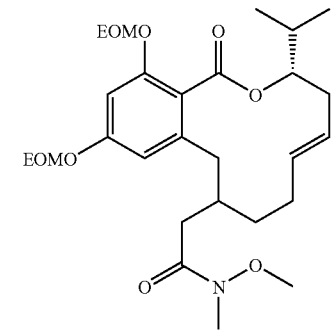

Mixture of 4 diastereoisomers: ¹H NMR (CDCl₃, 400 MHz, 25° C.) δ 6.77 (s, 1H), 6.52 (s, 0.5H), 6.46 (s, 0.5H), 5.59-5.37 (m, 2H), 5.21-5.18 (m, 4H), 5.09-4.92 (m, 1H), 3.75-3.70 (m, 4H), 3.53-3.48 (m, 3H), 3.38-3.34 (m, 1H), 3.19-3.10 (m, 3H), 2.65-2.47 (m, 3H), 2.29-2.04 (m, 6H), 1.89-1.72 (m, 2H), 1.31-1.20 (m, 6H), 1.06-0.96 (m, 6H); HRMS (ESI-TOF) m/z 544.2907 ([M+Na⁺], C₂₈H₄₃O₈NNa requires 544.2881).

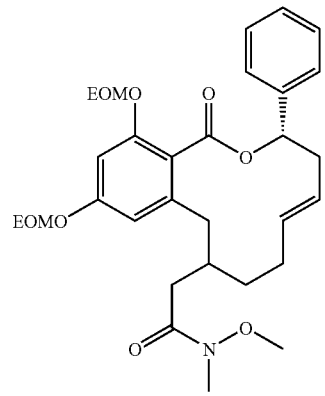

Mixture of 4 diastereoisomers: ¹H NMR (CDCl₃, 400 MHz, 25° C.) δ 7.51-7.42 (m, 2H), 7.38-7.31 (m, 3H), 6.73-6.70 (m, 1H), 6.60-6.49 (m, 1H), 6.45-6.31 (m, 1H), 5.73-5.39 (m, 2H), 5.23-5.00 (m, 4H), 3.75-3.69 (m, 2H), 3.56-3.34 (m, 6H), 3.19-3.09 (m, 3H), 2.66-2.08 (m, 8H), 1.31-1.19 (m, 5H), 1.10-1.04 (m, 3H); HRMS (ESI-TOF) m/z 578.2715 ([M+Na⁺], C₃₁H₄₁O₈NNa requires 578.2724).

Example 4

General Procedure for the EOM Deprotection to Generate Compounds Deprotected-2-121 and 2-85

As depicted in Scheme 17 for compounds 2-103/2-85, to a solution of the corresponding compound 2-120/2-112 or 2-140 (1.0 equiv) in MeOH (0.03 M) was added PS-TsOH (10.0 equiv, 3.2 mmol/g) and the suspension was shaken at 40° C. for 1 to 4 h. The reaction mixture was filtered and the methanolic solution concentrated under reduced pressure. Purification by flash chromatography (SiO₂, 0-20% EtOAc/cyclohexane gradient) afforded the corresponding compound deprotected-2-140 or compound 2-103/2-85. (>90%). Illustrative examples of compounds deprotected-2-140 and of 2-103/2-85 follow; their characterization follows respectively in the text below each figure.

Illustrative Compound Deprotected-2-140:

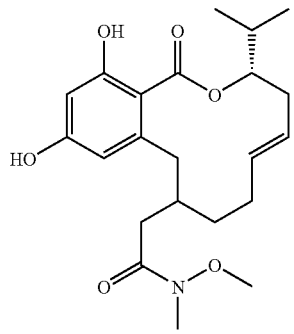

Mixture of 4 diastereoisomers: ¹H NMR (CDCl₃, 400 MHz, 25° C.) δ 11.54 (s, 1H), 6.33 (d, J=2.3 Hz, 1H), 6.25 (s, 1H), 5.53-5.51 (m, 1H), 5.44-5.41 (m, 1H), 5.11-5.08 (m, 1H), 4.01 (d, J=11.7 Hz, 2H), 3.45 (s, 3H), 3.11 (s, 3H), 2.83-2.73 (m, 1H), 2.68-2.59 (m, 1H), 2.27-2.20 (m, 1H), 2.10-1.87 (m, 6H), 1.82-1.72 (m, 1H), 1.01-0.94 (m, 6H); HRMS (ESI-TOF) m/z 428.2109 ([M+Na⁺], C₂₂H₃₁O₆NNa requires 428.2044).

Illustrative Compounds 2-103/2-85:

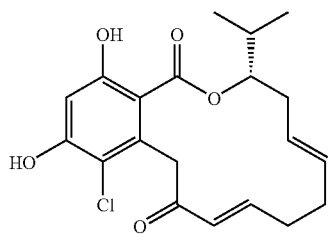

¹H NMR (C₆D₆, 400 MHz, 25° C.) δ 12.31 (s, 1H), 6.83 (s, 1H), 6.74-6.67 (m, 1H), 5.84 (bs, 1H), 5.82 (d, J=15.8 Hz, 1H), 5.03-4.95 (m, 1H), 4.88-4.86 (m, 1H), 4.76-4.70 (m, 1H), 4.40 (d, J=17.6 Hz, 1H), 4.15 (d, J=17.5 Hz, 1H), 2.40-2.34 (m, 1H), 2.22-2.18 (m, 1H), 1.87-1.65 (m, 4H), 1.53-1.48 (m, 1H), 0.92 (d, J=6.4 Hz, 3H), 0.66 (d, J=7.0 Hz, 3H); ¹³C NMR (C₆D₆, 100 MHz, 25° C.) δ 193.7, 164.2, 156.8, 145.8, 137.2, 131.8, 129.3, 126.3, 115.3, 107.9, 103.6, 82.1, 46.4, 33.3, 30.9, 30.7, 28.8, 20.1, 18.5, 18.3; HRMS (ESI-TOF) m/z 401.1170 ([M+Na⁺], C₂₀H₂₃ClO₅Na requires 401.1126); [α]²⁵_D -35.6 (c 0.52, CHCl₃).

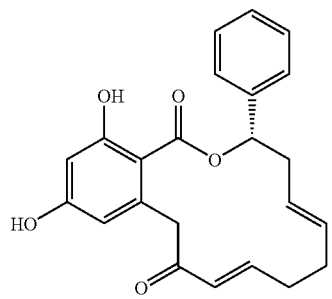

¹H NMR (C₆D₆, 400 MHz, 25° C.) δ 12.0 (bs, 1H), 7.32-7.29 (m, 3H), 7.19-7.15 (m, 2H), 6.86-6.79 (m, 1H), 6.51 (d, J=2.4 Hz, 1H), 6.27-6.25 (m, 1H), 6.11 (d, J=2.4 Hz, 1H), 6.02 (d, J=15.8 Hz, 1H), 5.49 (s, 1H), 5.17-5.10 (m, 1H), 4.97-4.90 (m, 1H), 4.40 (d, J=16.4 Hz, 1H), 3.97 (d, J=17.2 Hz, 1H), 2.83-2.76 (m, 1H), 2.45-2.38 (m, 1H), 1.89-1.78 (m, 2H), 1.67-1.58 (m, 2H); ¹³C NMR (C₆D₆, 100 MHz, 25° C.) δ 196.5, 169.6, 166.1, 161.3, 146.0, 140.5, 138.8, 132.1, 130.0, 128.6 (×2), 127.3, 126.6 (×2), 126.3, 112.2, 105.9, 103.0, 77.1, 48.6, 38.4, 30.9, 30.3; HRMS (ESI) m/z 401.1271 ([M+Na⁺], C₂₃H₂₂O₅Na requires 401.1359); [α]²⁵_D -10.3 (c 0.25, CHCl₃).

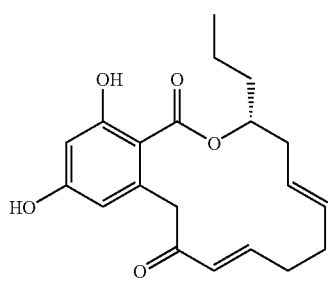

¹H NMR (CDCl₃, 400 MHz, 25° C.) δ 12.43 (s, 1H), 6.74 (d, J=1.7 Hz, 1H), 6.73-6.65 (m, 1H), 6.48 (d, J=1.7 Hz, 1H), 5.92 (d, J=15.8 Hz, 1H), 5.12-5.00 (m, 2H), 4.91-4.80 (m, 1H), 4.19 (d, J=17.0 Hz, 1H), 3.84 (d, J=16.4 Hz, 1H), 2.77 (m, 1H), 2.64-2.57 (m, 1H), 2.01-1.97 (m, 1H), 1.89-1.70 (m, 3H), 1.61-1.56 (m, 2H), 1.30-1.21 (m, 2H), 0.90 (t, J=6.7 Hz, 3H); ¹³C NMR (CDCl₃, 100 MHz, 25° C.) δ 197.5, 169.9, 165.6, 160.6, 147.5, 140.2, 131.9, 129.5, 127.0, 112.8, 106.1, 102.9, 76.2, 48.7, 35.7, 34.3, 31.1, 29.7, 19.4, 13.8; HRMS (ESI-TOF) m/z 367.1330 ([M+Na⁺], C₂₀H₂₄O₅Na requires 367.1521); [α]²⁵_D +21.6 (c 0.36, CHCl₃).

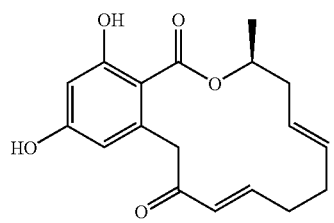

¹H NMR (CD₃OD, 400 MHz, 25° C.) δ 6.78-6.71 (m, 1H), 6.29 (d, J=2.4 Hz, 1H), 6.22 (d, J=2.0 Hz, 1H), 5.87 (d, J=15.5 Hz, 1H), 5.37-5.23 (m, 3H), 4.01 (d, J=17.2 Hz, 1H), 3.92 (d, J=17.0 Hz, 1H), 2.67-2.61 (m, 1H), 2.29-2.15 (m, 5H), 1.31 (d, J=6.4 Hz, 3H); ¹³C NMR (CD₃OD, 100 MHz, 25° C.) δ 198.5, 169.8, 164.2, 162.3, 148.4, 139.1, 131.6, 129.6, 127.3, 111.7, 101.7, 72.0, 47.7, 36.8, 30.8, 30.7, 17.4, (1 quartenary carbon is not visible); HRMS (ESI) m/z 339.1141 ([M+Na], C₁₈H₂₀O₅Na requires 339.1203). [α]²⁵_D -45.1 (c 0.27, CHCl₃).

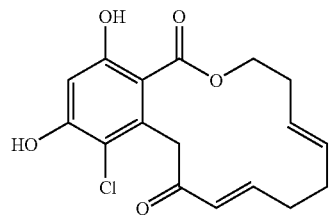

¹H NMR (CD₃OD, 400 MHz, 25° C.) δ 6.74-6.68 (m, 1H), 6.48 (s, 1H), 5.86 (d, J=15.2 Hz, 1H), 5.31-5.25 (m, 2H), 4.39 (t, J=5.3 Hz, 2H), 4.27 (s, 2H), 2.43-2.40 (m, 2H), 2.25 (m, 4H); ¹³C NMR (CD₃OD, 100 MHz, 25° C.) δ 196.9, 170.1, 161.9, 158.1, 147.8, 135.9, 130.9, 130.2, 129.9, 115.2, 107.3, 102.4, 65.9, 46.2, 31.3, 30.9, 30.5; HRMS (ESI) m/z 337.0797 ([M+H⁺], C₁₇H₁₈O₅Cl requires 337.0837).

Example 5

General Procedure for the Synthesis of Compounds 2-141

As depicted in Scheme 17, to a solution of corresponding compound 2-120/2-112 (1.0 equiv) in MeOH (0.03 M) at 0° C. was added BER-resin (Borohydride on Amberlite®, 1.0 equiv, 2.5 mmol g¹) and the reaction was stirred over 12 h. The reaction was then filtered and concentrated under reduced pressure. Purification by flash chromatography (SiO₂, 0-20% EtOAc/cyclohexane gradient) afforded 2-141 (~60%) as a mixture of two diastereoisomers (1:1). An illustrative example of compound 2-141 follows; its characterization data are in the text below the figure.

Illustrative Compound 2-141:

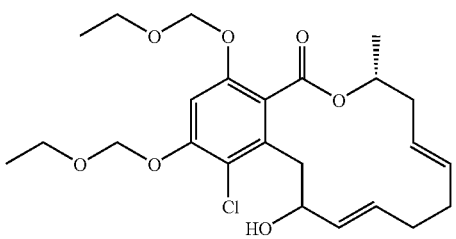

¹H NMR (CD₃Cl, 400 MHz) δ 7.05 (s, 1H), 6.99 (s, 1H), 5.64-5.57 (m, 2H), 5.54-5.53 (m, 2H), 5.49-5.35 (m, 6H), 5.31-5.28 (m, 4H), 5.24-5.16 (m, 4H), 5.13-5.08 (m, 1H, 35'), 4.68 (m, 1H, 35'), 4.56 (m, 1H, 35), 3.81-3.69 (m, 8H), 3.25 (dd, J=13.9, 8.0 Hz, 1H, 35), 3.19 (dd, J=13.7, 4.8 Hz, 1H, 35'), 3.11 (dd, J=13.5, 10.1 Hz, 1H, 35'), 2.90 (dd, J=13.9, 5.12 Hz, 1H, 35), 2.35 (m, 9H), 2.09-1.95 (m, 1H), 1.80-1.70 (m, 2H), 1.39 (d, J=2.9 Hz, 3H, 35), 1.37 (d, J=3.2 Hz, 3H, 35'), 1.24 (2×q, J=6.9 and 5.0 Hz, 12H, 35+35'); HRMS (ESI) m/z 491.1729 ([M+Na⁺], $C_{24}H_{33}ClO_7Na$ requires 491.1807).

Example 6

General Procedure for the Synthesis of Compounds 2-142

As depicted in Scheme 17, to a solution of the corresponding compound 2-141 (1.0 equiv) in MeOH (0.02 M) was added PS-TsOH (10.0 equiv, 3.2 mmol g⁻¹) and the suspension was shaken at 40° C. for 4 h. The reaction mixture was then filtered and the methanolic solution concentrated under reduced pressure. Purification by preparative TLC (SiO₂, 25% EtOAc/cyclohexane) afforded 2-142 (~90%) as a mixture of two diastereoisomers (1:1). An illustrative example of compound 2-142 follows; its characterization data are in the text below the figure.

Illustrative Compound 2-142:

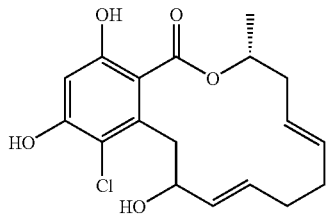

¹H NMR ((CD₃)₂CO, 400 MHz) δ 12.30 (s, 2H), 11.43 (s, 2H), 6.75 (s, 2H), 6.00 (bdd, J=6.4, 6.2 Hz, 1H), 5.97 (bdd, J=6.4, 6.2 Hz, 1H), 5.97 (bd, J=6.7 Hz, 1H), 5.77 (bd, J=6.7 Hz, 1H), 5.57-5.48 (m, 4H), 5.18-5.14 (m, 2H), 3.38-3.28 (m, 3H), 3.02 (dd, J=16.1, 10.5 Hz, 1H), 2.41-2.09 (m, 12H), 1.11 (d, J=6.2 Hz, 6H); HRMS (ESI) m/z 375.1029 ([M+Na⁺], $C_{18}H_{21}ClO_5Na$ requires 375.0970).

Example 7

General Procedure for the Synthesis of Compounds 2-143

As depicted in Scheme 17, to a solution of the corresponding compound 2-141 (1.0 equiv) in DMF (0.02 M) were added Ac₂O (1.2 equiv), morpholinomethyl polystyrene (1.2 equiv, 3.2 mmol g⁻¹) and DMAP (0.05 equiv) at 23° C. and the mixture was stirred for 30 min, followed by TLC until consumption of the starting material. Then, the resin was filtered and the organic phase was concentrated under reduced pressure. Purification by PTLC (SiO₂, 20% EtOAc/cyclohexane) afforded corresponding 2-143 (~80%) as a mixture of two diastereoisomers 1:1: An illustrative example of compound 2-143 follows; its characterization data are in the text below the figure.

Illustrative Compound 2-143:

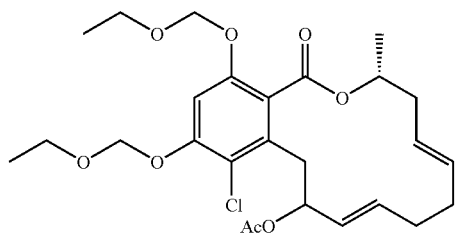

¹H NMR (CD₃Cl, 400 MHz) δ 7.04 (s, 1H), 7.01 (s, 1H), 5.86 (dd, J=15.0, 6.9 Hz, 1H), 5.67 (dd, J=12.4, 6.2 Hz, 1H), 5.60-5.54 (m, 4H), 5.48 (dd, J=7.2, 7.2 Hz, 1H), 5.41-5.34 (m, 3H), 5.32-5.30 (m, 4H), 5.28-5.23 (m, 2H), 5.21 (dd, J=11.0, 6.7 Hz, 2H), 5.17 (dd, J=11.8, 6.9 Hz, 2H), 3.81-3.69 (m, 8H), 3.43 (dd, J=14.2, 7.5 Hz, 1H), 3.23-3.15 (m, 2H), 2.85 (dd, J=13.9, 5.4 Hz, 1H), 2.30-2.17 (m, 8H), 2.12 (s, 3H), 2.06 (s, 3H), 1.95-2.00 (m, 4H), 1.39 (2×d, J=5.6 Hz, 6H), 1.24 (m, 12H); HRMS (ESI) m/z 533.1864 ([M+Na⁺], $C_{26}H_{35}ClO_8Na$ requires 533.1913).

Example 8

General Procedure for the Synthesis of Compounds 2-144

As depicted in Scheme 17, to a solution of corresponding compound 2-143 (1.0 equiv) in MeOH (0.02 M) was added PS-TsOH (10.0 equiv, 3.2 mmol/g) and the suspension was shaken at 40° C. for 4 h. The reaction mixture was filtered and the methanolic solution concentrated under reduced pressure. Purification by PTLC (SiO₂, 20% EtOAc/cyclohexane) afforded compounds 2-144 (~60% yield). An illustrative example of compound 2-144 follows; its characterization data are in the text below the figure.

Illustrative Compound 2-144:

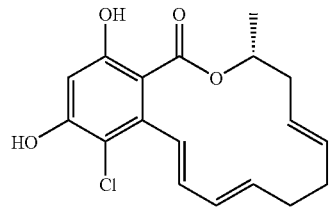

Mixture of diastereoisomers 2:1: ¹H NMR (CD₃Cl, 400 MHz) δ 12.6 (s, 1H), 12.12 (s, 0.5H), 6.93 (d, J=8.7 Hz, 0.5H), 6.66 (s, 1H), 6.64 (s, 0.5H), 6.62-6.60 (m, 1H), 6.10-6.05 (m, 3H), 5.47-5.33 (m, 4.5H), 2.60-2.53 (m, 1.5H), 2.26-2.02 (m, 7.5H), 1.44 (d, J=6.2 Hz, 1.5H), 1.43 (d, J=6.4 Hz, 3H); HRMS (ESI) m/z 357.0898 ([M+Na⁺], $C_{18}H_{19}ClO_4Na$ requires 357.0864).

Example 9

General Procedure for the Synthesis of Compounds 2-145

As depicted in Scheme 18, to a solution of corresponding compound 2-85 (1.0 equiv) in methanol (0.03 M) was added sulfamic acid resin (10.0 equiv) and the suspension was stirred for 15 h at 40° C. with. The reaction was then filtered, the resin washed several times with $CH_2Cl_2$. Concentration under reduced pressure followed by purification on PTLC (Hexane/EtOAc: 1/1) afforded desired compounds 2-145 as a mixture diastereoisomers (2:1). An illustrative example of compound 2-145 follows; its characterization data are in the text below the figure.

Illustrative Compound 2-145:

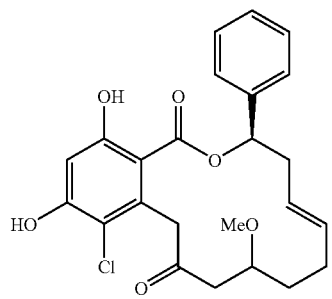

$^1$H NMR ($C_6D_6$, 400 MHz, 25° C.) δ 12.28 (s, 0.4H), 11.91 (s, 0.6H), 7.21-7.11 (m, 5H), 6.62 (s, 1H), 6.03-6.01 (m, 1H), 5.58 (bs, 1H), 5.38-5.33 (m, 1H), 5.27-5.20 (m, 1H), 4.76 (d, J=17.5 Hz, 0.6H), 4.02 (d, J=17.0 Hz, 0.4H), 4.18 (d, J=18.1 Hz, 0.6H), 4.09 (d, J=17.0 Hz, 0.4H), 3.87 (bs, 0.4H), 3.81 (bs, 0.6H), 3.15 (s, 1.8H), 3.12 (s, 1.2H), 2.83-2.78 (m, 1H), 2.45-2.30 (m, 2H), 2.18-2.16 (m, 1H), 2.02-1.97 (m, 2H), 1.79-1.72 (m, 2H); HRMS (ESI-TOF) m/z 467.1366 ([M+Na$^+$], $C_{24}H_{25}O_6$ClNa requires 467.1232).

Example 10

General Procedure for the Synthesis of Compounds 2-146

As depicted in Scheme 19, to a solution of corresponding compound 2-103/2-85 (1.0 equiv) in $CH_2Cl_2$/AcOH 10/1 (0.08 M) (polystyrylmethyl)trimethylammonium cyanoborohydride (2.0 equiv, 3.5 mmol g$^{-1}$) was added at 23° C. and the reaction was monitored by TLC until the starting material had been consumed (4 h). Then, the resin was filtered and the organic phase was concentrated under reduced pressure. Purification by PTLC (SiO$_2$, 30% EtOAc/cyclohexane) afforded compounds 2-146 (50-60%). An illustrative example of compound 2-146 follows; its characterization data are in the text below the figure.

Illustrative Compound 15:

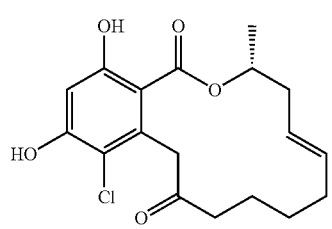

$^1$H NMR (CD$_3$Cl, 400 MHz) δ 11.75 (s, 1H), 6.65 (s, 1H), 5.48 (m, 2H), 5.49 (ddt, J=6.1, 3.5, 2.9 Hz, 1H), 4.53 (d, J=17.5 Hz, 1H), 4.04 (d, J=17.7 Hz, 1H), 2.61-2.54 (m, 2H), 2.48-2.28 (m, 3H), 2.19-2.14 (m, 1H), 2.08-1.99 (m, 1H), 1.72-1.61 (m, 3H), 1.41 (d, J=6.4 Hz, 3H); HRMS (ESI) m/z 375.1050 ([M+Na$^+$], $C_{18}H_{21}ClO_5$Na requires 375.0970).

Example 11

General Procedure for the Synthesis of Compounds 2-147

As depicted in Scheme 19, to a solution of corresponding compound 2-103/2-85 (1.0 equiv), in THF (0.05 M) were added in a sequential manner the corresponding alcohol (2.0 equiv), triphenylphosphine (2.0 equiv) and ethoxycarbonylazocarboxymethyl polystyrene (2.0 equiv, 1.3 mmol g$^{-1}$). The reaction mixture was shaken at room temperature for 8 hours, and then, the resin was filtered and the filtrates were directly purified by PTLC (SiO$_2$, 10% EtOAc/cyclohexane) to afford a mixture of compound 2-147 along with the bis-allylated product(78%). An illustrative example of compound 2-147 follows; its characterization data are in the text below the figure.

Illustrative Compound 2-147:

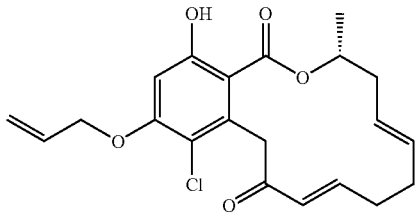

Mixture with the corresponding bis-allylated compound (1:1): $^1$H NMR (CD$_3$Cl, 400 MHz) δ 11.83 (s, 1H), 6.82 (ddd, J=15.7, 8.2, 4.6 Hz, 1H), 6.72-6.65 (m, 1H), 6.46 (s, 1H), 6.41 (s, 1H), 6.09-5.98 (m, 3H), 5.82 (d, J=15.7 Hz, 1H), 5.46-5.16 (m, 8H), 4.57-4.54 (m, 3H), 4.51-4.49 (m, 3H), 4.19 (d, J=17.5 Hz, 1H), 4.11 (d, J=14.6 Hz, 1H), 3.78 (d, J=17.0 Hz, 1H), 3.51 (d, J=14.2 Hz, 1H), 2.76-2.69 (m, 1H), 2.38-2.05 (m, 11H), 1.42 (d, J=6.2 Hz, 3H), 1.35 (d, J=6.3 Hz, 3H); mono-allylated compound HRMS (ESI) m/z 413.1103 ([M+Na$^+$], $C_{21}H_{23}ClO_5$Na requires 413.1132); bis-allylated compound HRMS (ESI) m/z 453.1422 ([M+Na$^+$], $C_{24}H_{27}ClO_5$Na requires 453.1449).

Example 12

General Procedure for the Synthesis of Compounds 2-148

As depicted in Scheme 19, to a solution of the corresponding compound 2-103/2-85 (1.0 equiv) in CH$_2$Cl$_2$ (0.05 M) was added TBD-methyl polystyrene (2.0 equiv, 2.9 mmol g$^{-1}$) and the corresponding alkyl bromide or chloride (BrCH$_2$COO$^t$Bu, EOMCl) (0.9 equiv) at 23° C. and the mixture was shaken for 3 h. The resin was then filtered and the filtrates were concentrated under reduced pressure. Purification by PTLC (SiO$_2$, 30% EtOAc/cyclohexane) afforded corresponding compound 2-148 (>90%). Illustrative examples of compound 2-148 follows; their characterization data are presented respectively in the text below each figure.

Illustrative Compounds 2-148:

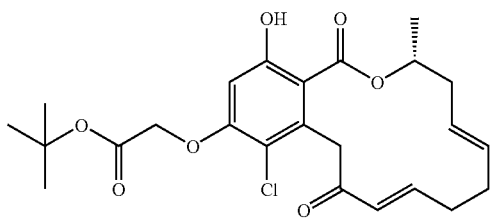

¹H NMR (CD₃Cl, 400 MHz) δ 11.84 (s, 1H), 6.69 (m, 1H), 6.41 (s, 1H), 5.76 (d, J=15.0 Hz, 1H), 5.43 (m, 1H), 5,26 (ddd, J=15.0, 9.1, 4.8 Hz, 1H), 5.18-5.11 (m, 1H), 4.65 (s, 2H), 4.33 (d, J=17.7 Hz, 1H), 4.16 (d, J=17.5 Hz, 1H), 2.65-2.58 (m, 1H), 2.37-2.34 (m, 2H), 2.25-2.21 (m, 1H), 2.12-2.01 (m, 2H), 1.53 (s, 9H), 1.34 (d, J=6.5 Hz, 3H); HRMS (ESI) m/z 487.1498 ([M+Na⁺], $C_{24}H_{79}ClO_7Na$ requires 487.1494).

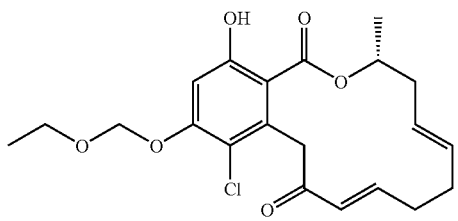

¹H NMR (C₆D₆, 400 MHz, 25° C.) δ 11.76 (s, 1H), 6.86 (s, 1H), 6.70 (dt, J=14.9, 7.3 Hz, 1H), 5.77 (d, J=15.8 Hz, 1H), 5.46-5.42 (m, 1H), 5.37 (s, 2H), 5.30-5.19 (m, 2H), 4.34 (d, J=17.6 Hz, 1H), 4.16 (d, J=18.1 Hz, 1H), 3.80 (q, J=7.0 Hz, 2H), 2.66-2.59 (m, 1H), 2.37-2.34 (m, 2H), 2.26-2.21 (m, 1H), 2.13-2.06 (m, 2H), 1.34 (d, J=6.4 Hz, 3H), 1.27 (t, J=7.0 Hz, 3H); HRMS (ESI) m/z ([M+Na], $C_{21}H_{25}O_6ClNa$ requires 431.1237).

Example 13

General Procedure for the Synthesis of Compounds 2-149

As depicted in Scheme 19, to a solution of compound 2-103/2-85 (1.0 equiv) in acetone/H₂O 10/1 (0.05 M) was added OsO₄ (0.1 equiv) followed by NMO (1.0 equiv) at 23° C. and the mixture was stirred for 1 h. The crude mixture was filtered through a plug of silica, concentrated and purified by PTLC (SiO₂, 30% EtOAc/cyclohexane) to afford 2-149 (>70%) as a mixture of two diastereoisomers. An illustrative example of compound 2-149 follows; its characterization data are in the text below the figure.

Illustrative Compound 2-149:

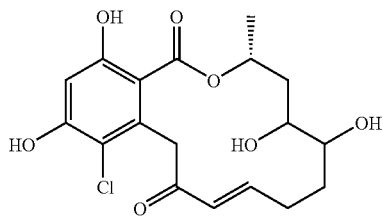

¹H NMR (CD₃OD, 400 MHz) δ 7.19 (m, 1H), 6.89-6.81 (m, 1H), 6.52 (s, 1H), 6.47 (s, 1H), 6.20 (d, J=16.1 Hz, 1H), 6.04 (d, J=15.6 Hz, 1H), 5.54-5.49 (m, 1H), 5.43-5.36 (m, 1H), 4.50 (d, J=17.7 Hz, 1H), 4.46 (d, J=17.7 Hz, 1H), 4.39 (d, J=17.2 Hz, 1H), 4.07 (d, J=17.2 Hz, 1H), 3.80-3.64 (m, 2H), 3.51-3.46 (m, 2H), 2.62-2.58 (m, 2H), 2.39-2.30 (m, 2H), 2.27-2.18 (m, 2H), 2.08-2.98 (m, 2H), 2.00-1.85 (m, 4H), 1.44 (d, J=6.4 Hz, 6H); HRMS (ESI) m/z 407.1031 ([M+Na⁺], $C_{18}H_{21}ClO_7Na$ requires 407.0868).

Example 14

General Procedure for the Synthesis of Compounds 2-150

As depicted in Scheme 19, to a solution of compound 2-103/2-85 (1.0 equiv) in CH₃CN (0.03 M) at 0° C. was added freshly made DMDO (1.2 equiv, 0.04 M in acetone) and the mixture was stirred for 30 min. After evaporation of the solvents under reduced pressure, purification by PTLC (SiO₂, 30% EtOAc/cyclohexane) afforded epoxides 2-150 (>90%) as a mixture of two diastereoisomers. Illustrative examples of compound 2-150 follow; their characterization data are presented respectively in the text below each figure.

Illustrative Compounds 2-150:

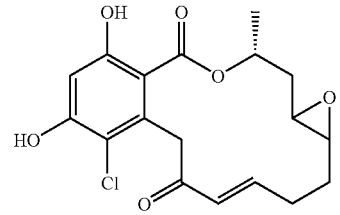

¹H NMR (CDCl₃, 400 MHz) δ 11.84 (s, 2H), 6.94-6.82 (m, 2H), 6.69 (s, 1H), 6.66 (s, 1H), 6.23 (d, J=17.1 Hz, 1H), 6.11 (dd, J=13.2, 1.6 Hz, 1H), 5.39 (tdd, J=7.5, 3.2, 2.7 Hz, 1H), 5.32 (m, 1H), 4.53 (d, J=17.7 Hz, 2H), 4.27 (d, J=17.7 Hz, 2H), 2.79-2.76 (m, 1H), 2.74-2.69 (m, 1H), 2.58 (m, 1H), 2.56 (m, 1H), 2.47-2.24 (m, 8H), 2.13-2.08 (m, 1H), 2.05-2.03 (m, 1H), 1.91 (dd, J=4.3, 4.3 Hz, 1H), 1.87 (dd, J=4.3, 4.3 Hz, 1H), 1.51 (d, J=6.4 Hz, 3H), 1.35 (d, J=6.4 Hz, 3H); HRMS (ESI) m/z 389.0724 ([M+Na⁺], $C_{18}H_{19}ClO_6Na$ requires 389.0762).

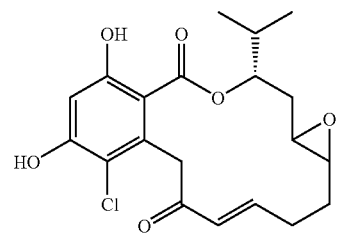

¹H NMR (C₆D₆, 400 MHz, 25° C.) δ 11.56 (2×s, 2H), 6.92-6.82 (m, 2H), 6.71 (s, 1H), 6.67 (s, 1H), 6.20 (m, 3H), 6.06 (d, J=15.8 Hz, 1H), 5.11 (bs, 1H), 5.94 (m, 1H), 4.46 (2×d, J=18.1 Hz, 2H), 4.20 (2×d, J=18.1 Hz, 2H), 2.72-2.70 (m, 2H), 2.53-2.48 (m, 4H), 2.38-2.35 (m, 3H), 2.25-2.13 (m, 5H), 1.84-1.77 (m, 2H), 1.05-1.01 (m, 6H), 0.91-0.88 (m,

3H), 0.86-0.84 (m, 3H); FIRMS (ESI) m/z 417.1128 ([M+Na⁺], $C_{20}H_{23}O_6ClNa$ requires 417.1075).

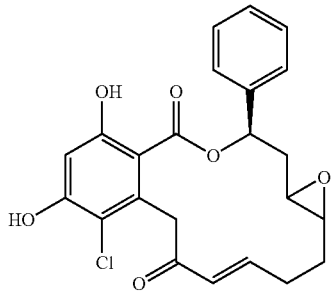

¹H NMR ($C_6D_6$, 400 MHz, 25° C.) δ 11.80 (2×s, 2H), 7.43-7.18 (m, 10H), 7.03-6.95 (m, 2H), 6.69 (s, 1H), 6.61 (s, 1H), 6.30 (d, J=16.4 Hz, 1H), 6.21 (d, J=15.8 Hz, 1H), 6.15-6.10 (m, 1H), 6.03 (d, J=11.1 Hz, 1H), 4.84 (2×d, J=18.1 Hz, 2H), 4.41 (2×d, J=17.6 Hz, 2H), 2.68-2.60 (m, 4H), 2.41-2.27 (m, 8H), 1.83-1.76 (m, 4H); HRMS (ESI) m/z 451.1028 ([M+Na], $C_{23}H_2O_6Cl$ Na requires 451.0919).

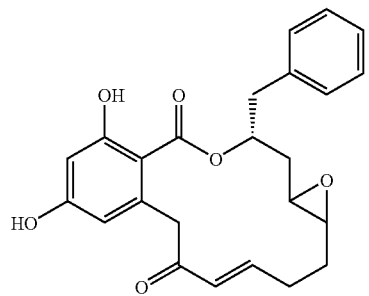

Major isomer: ¹H NMR ($C_6D_6$, 400 MHz, 25° C.) δ 11.94 (s, 1H), 7.36-7.28 (m, 5H), 6.95-6.88 (m, 1H), 6.42 (s, 1H), 6.22 (s, 1H), 6.11 (d, J=15.8 Hz, 1H), 5.47 (m, 1H), 5.41 (bs, 1H), 4.43 (d, J=17.5 Hz, 1H), 3.56 (d, J=17.6 Hz, 1H), 3.19 (dd, J=13.7, 6.0 Hz, 1H), 3.03 (dd, J=13.7, 7.9 Hz, 1H), 2.87 (bs, 1H), 2.70-2.28 (m, 4H), 2.03-1.93 (m, 2H); HRMS (ESI) m/z 431.1578 ([M+Na], $C_{24}H_{24}O_6Na$ requires 431.1465).

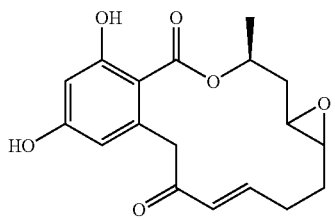

¹H NMR ($C_6D_6$, 400 MHz, 25° C.) δ 11.98 (s, 1H), 6.91-6.83 (m, 1H), 6.43 (d, J=2.3 Hz, 1H), 6.24 (d, J=2.4 Hz, 1H), 6.11 (d, J=15.8 Hz, 1H), 5.35 (bs, 1H), 5.29 (m, 1H), 4.52 (d, J=17.5 Hz, 1H), 3.63 (d, J=17.5 Hz, 1H), 2.77 (m, 2H), 2.57-2.52 (m, 2H), 2.46-2.27 (m, 2H), 2.14-2.10 (m, 1H), 1.93-1.88 (m, 1H), 1.48 (d, J=6.4 Hz, 3H); other isomer: ¹H NMR ($C_6D_6$, 400 MHz, 25° C.) δ 11.67 (s, 1H), 6.89-6.83 (m, 1H), 6.40 (d, J=2.4 Hz, 1H), 6.24 (d, J=2.9 Hz, 1H), 6.21 (d, J=16.4 Hz, 1H), 5.37 (bs, 1H), 5.22 (m, 1H), 4.20 (d, J=17.0 Hz, 1H), 4.06 (d, J=17.0 Hz, 1H), 2.74 (m, 2H), 2.57-2.20 (m, 4H), 1.80-1.76 (m, 1H), 1.68-1.60 (m, 1H), 1.37 (d, J=6.4 Hz, 3H); HRMS (ESI) m/z 355.1249 ([M+Na], $C_{18}H_{20}O_6Na$ requires 355.1152).

Example 15

General Procedure for the Synthesis of Compounds 2-151

As depicted in Scheme 20, to a solution of compound 2-120 (1.0 equiv) in dioxane (0.05 M) at 23° C. was added $HCl_{conc.}$ (20 equiv), and the mixture was stirred for 3 h. After that time the reaction was filtered through a plug of silica gel, the solvents were evaporated under reduced pressure, and purified by PTLC ($SiO_2$, 30% EtOAc/cyclohexane) to afford compound 2-151 (>75%) as a mixture of two diastereoisomers. Illustrative examples of compound 2-151 follow; their characterization data are presented respectively in the text below each figure.

Illustrative Compounds 2-151:

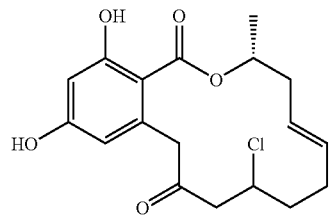

¹H NMR ($CDCl_3$, 400 MHz) δ 12.11 (s, 1H), 11.78 (s, 1H), 6.51 (s, 1H), 6.43 (s, 1H), 6.41 (d, J=2.4 Hz, 1H), 6.37 (d, J=2.7 Hz, 1H), 6.21 (d, J=2.4 Hz, 1H), 6.11 (d, J=2.4 Hz, 1H), 5.59-5.51 (m, 3H), 5.40-5.32 (m, 3H), 4.54 (d, J=17.2 Hz, 1H), 4.42 (d, J=17.2 Hz, 1H), 3.60 (d, J=17.2 Hz, 1H), 3.45 (d, J=17.0 Hz, 1H), 3.28 (dd, J=18.5, 9.4 Hz, 1H), 3.11 (dd, J=13.7, 6.2 Hz, 1H), 3.07 (dd, J=13.4, 4.6 Hz, 1H), 2.76 (dd, J=19.0, 6.2 Hz, 1H), 2.62 (ddd, J=15.5, 8.8, 4.0 Hz, 1H), 2.54 (ddd, J=15.3, 6.2, 3.2 Hz, 1H), 2.40-2.26 (m, 4H), 2.25-2.13 (m, 4H), 2.03-1.91 (m, 2H), 1.42 (d, J=6.4 Hz, 3H), 1.40 (d, J=6.4 Hz, 3H); HRMS (ESI) m/z 375.0928 ([M+Na⁺], $C_{18}H_{21}ClO_5Na$ requires 375.0970).

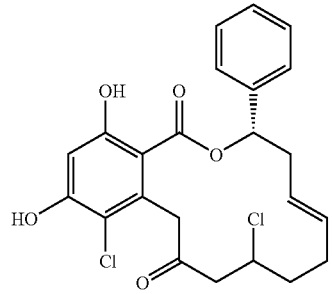

¹H NMR ($C_6D_6$, 400 MHz, 25° C.) δ 11.76 (s, 0.5H), 11.36 (s, 0.5H), 7.40-7.29 (m, 5H), 6.65 (s, 0.5H), 6.62 (s, 0.5H), 6.18 (t, J=5.8 Hz, 1H), 6.14 (s, 0.5H), 6.12 (s, 0.5H), 5.67-5.62 (m, 1H), 5.55-5.49 (m, 1H), 4.93 (d, J=18.1 Hz, 0.5H), 4.80 (d, J=17.1 Hz, 0.5H), 4.58-4.56 (m, 1H), 4.38 (d, J=18.1 Hz, 0.5H), 4.18 (d, J=17.1 Hz, 0.5H), 3.33-3.27 (m, 1H), 3.10 (dd, J=18.4, 3.8 Hz, 0.5H), 2.84-2.68 (m, 2.5H), 2.42-2.32 (m, 2H), 2.23-2.17 (m, 1H), 2.13-2.04 (m, 1H); HRMS (ESI-TOF) m/z 471.0754 ([M+Na⁺], $C_{23}H_{22}O_5Cl_2Na$ requires 471.0737).

Example 16

General Procedure for the Elimination of β-Cl from Compounds 2-151

As depicted in Scheme 20, to a solution of compound 2-151 (95 mg, 270 μmol) in CH$_2$Cl$_2$ (5 ml) at 23° C. PS-TBD (51 mg, 2.6 mmol/g) was added, and the mixture was stirred for 8 hours. After that time the reaction was filtered, the solvents were evaporated under reduced pressure, and purification by flash chromatography (SiO$_2$, 0-30% EtOAc/cyclohexane gradient) afforded 2-103 (X=Cl, R=Me) (84 mg, 98%).

Example 17

General Procedure for the Synthesis of Compounds 2-153

As depicted in Scheme 20, to a solution of compound 2-103 (X=Cl, R=Me) (12.9 mg, 40.8 μmol) in CH$_2$Cl$_2$ (1 ml) at 23° C. DHP (3.7 μL, 40.8 μmol) and PS-TsOH (12.7 mg, 40.8 3.2 mmol/g) were added, and the mixture was stirred for 5 hours. After that time the reaction was filtered and the solvents were evaporated under reduced pressure. Purification by PTLC (SiO$_2$, 30% EtOAc/cyclohexane) afforded 2-153 (13.8 mg, 85%) as a mixture of two diastereoisomers. An illustrative example of compounds 2-153 follows; its characterization data are in the text below the figure.

Illustrative Compound 2-153:

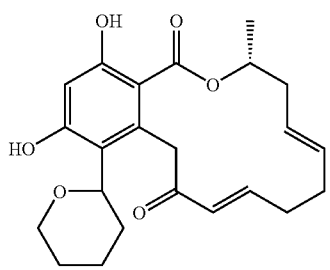

$^1$H NMR (CDCl$_3$, 400 MHz) δ 12.33 (s, 1H), 12.11 (s, 1H), 9.45 (s, 1H), 9.40 (s, 1H), 6.67, (m, 2H), 6.28 (2×s, 2H), 5.83 (d, J=13.2 Hz, 1H), 5.79 (d, J=12.9 Hz, 1H), 5.35-5.30 (m, 3H), 5.27-5.22 (m, 3H), 5.06 (bd, J=8.2 Hz, 2H), 4.10 (d, J=17.5 Hz, 2H), 3.90-3.85 (m, 1H), 3.80-3.76 (m, 1H), 3.65 (d, J=17.7 Hz, 2H), 3.57-3.52 (m, 2H), 3.46-3.41 (m, 2H), 2.77-2.71 (m, 3H), 2.53-2.49 (m, 3H), 2.36-2.29 (m, 4H), 2.24-1.56 (m, 12H), 1.31 (d, J=6.4 Hz, 3H), 1.28 (d, J=6.4 Hz, 3H); HRMS (ESI) m/z 423.1778 ([M+Na$^+$], C$_{23}$H$_{28}$O$_6$Na requires 423.1778.

Example 18

General Procedure for the Synthesis of Compounds 2-154

As depicted in Scheme 20, to a solution of corresponding compound 2-120 (1.0 equiv) in pyridine/AcOH (5/1, 0.03 M) was added the corresponding hydroxylamine (5.0 equiv) and the mixture was heated up to 40° C. After stirring overnight the solvents were evaporated under reduced pressure with SiO$_2$. Elution of the compound over a short path of SiO$_2$ with a mixture of 30% EtOAc/cyclohexane afforded after evaporation 2-154 (~99%) as a mixture of two diastereoisomers cis/trans). An illustrative example of compound 2-154 follows; its characterization data are in the text below the figure.

Illustrative Compound 2-154:

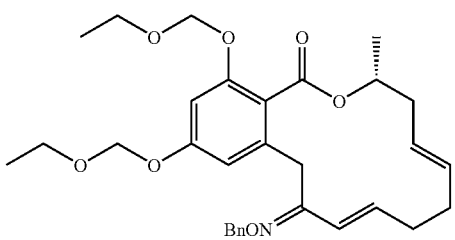

$^1$H NMR (CDCl$_3$, 400 MHz) δ 7.50-7.25 (m, 10H), 6.82 (s, 1H), 6.75 (s, 1H), 6.66 (s, 1H), 6.48 (s, 1H), 6.24-6.11 (m, 2H), 6.11-6.05 (m, 2H), 5.45-5.38 (m, 4H), 5.34-5.31 (m, 1H), 4.50 (d, J=17.2 Hz, 1H), 3.38-3.65 (m, 8H), 3.60 (d, J=17.1 Hz, 1H), 3.54 (d, J=17.1 Hz, 1H), 3.24 (d, J=17.2 Hz, 1H), 2.48-2.36 (m, 4H), 2.17-2.21 (m, 2H), 2.04-2.11 (m, 2H), 1.95-1.83 (m, 2H), 1.62-1.51 (m, 2H), 1.49 (d, J=6.4 Hz, 6H), 1.20-1.32 (m, 12H); $^{13}$C NMR (CDCl$_3$, 100 MHz) δ 168.02, 167.85, 159.08, 158.83, 157.23, 155.55, 155.36, 154.19, 140.75, 138.23, 138.19, 137.75, 136.93, 136.74, 132.32, 132.28, 128.34 (×2), 128.31 (×2), 128.18, 128.09 (×2), 127.99 (×2), 127.71, 127.63, 125.50, 118.82, 118.56, 118.34, 108.84, 108.50, 101.72, 101.68, 93.49, 93.44, 93.12 (×2), 77.21, 76.02, 75.88, 71.18, 70.99, 64.47, 64.45, 64.33, 64.31, 39.99, 39.96, 34.87, 32.42, 32.31, 31.63, 31.09, 28.86, 20.25, 20.19, 15.04 (×2), 14.98 (×2); HRMS (ESI) m/z 560.2627 ([M+Na$^+$], C$_{31}$H$_{39}$NO$_7$Na requires 560.2619.

Example 19

General Procedure for the Synthesis of Compounds 2-155

As depicted in Scheme 20, to a solution of compound 2-154 (1.0 equiv) in MeOH (0.02 M) was added PS-TsOH (10.0 equiv, 3.2 mmol/g) and the suspension was shaken at 40° C. for 4 h. The reaction mixture was filtered and the methanolic solution concentrated under reduced pressure. The crude product obtained was submitted without further purification to the next step. Thus to a solution in CH$_2$Cl$_2$ (0.02 M) of this crude at 23° C. were added DHP (1.0 equiv) and PS-TsOH (cat, 3.2 mmol/g) and the mixture was stirred for 5 hours. After that time the mixture was filtered, the solvents were evaporated under reduced pressure, and purification by PTLC (SiO$_2$, 30% EtOAc/cyclohexane) afforded two different diastereoisomers 1:1 of 2-155 (~65%). An illustrative example of compound 2-155 follows; its characterization data are in the text below the figure.

Illustrative Compound 2-155:

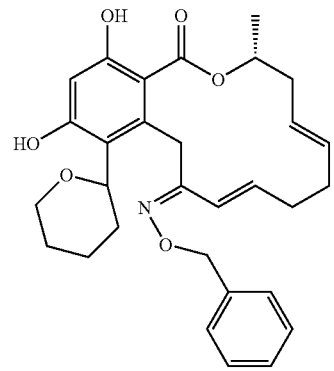

Less polar diastereoisomers: $^1$H NMR (CDCl$_3$, 400 MHz, 25° C.) δ 9.25 (s, 1H), 9.24 (s, 1H), 7.46-7.33 (m, 10H), 6.29 (s, 1H), 6.26 (s, 1H), 6.07-6.02 (m, 2H), 5.75 (d, J=15.8 Hz, 1H), 5.69 (d, J=15.8 Hz, 1H), 5.44-5.38 (m, 6H), 5.23 (s, 4H), 5.03 (d, J=8.8 Hz, 2H), 4.34-4.13 (m, 6H), 3.69-3.63 (m, 2H), 2.70-2.67 (m, 2H), 2.30-2.16 (m, 6H), 2.08-1.94 (m, 8H), 1.73-1.65 (m, 8H), 1.42 (t, J=6.4 Hz, 3H), 1.39 (t, J=7.0 Hz, 3H); HRMS (ESI) m/z 528.2562 ([M+Na$^+$], C$_{30}$H$_{35}$NO$_6$Na requires 528.2357. More polar diastereoisomers: $^1$H NMR (CDCl$_3$, 400 MHz, 25° C.) δ 11.61 (s, 1H), 9.27 (s, 1H), 7.41-7.33 (m, 5H), 6.62 (d, J=16.4 Hz, 1H), 6.47 (s, 1H), 6.15-6.07 (m, 1H), 5.50-5.38 (m, 3H), 5.16 (s, 2H), 5.04 (d, J=10.5 Hz, 1H), 4.30 (d, J=15.2 Hz, 1H), 4.24 (d, J=10.5 Hz, 1H), 3.84 (d, J=15.2 Hz, 1H), 3.66 (t, J=11.4 Hz, 1H), 2.71-2.65 (m, 1H), 2.28-2.08 (m, 6H), 1.73-1.64 (m, 5H), 1.38 (t, J=7.0 Hz, 3H); HRMS (ESI) m/z 528.2494 ([M+Na$^+$], C$_{30}$H$_{35}$NO$_6$Na requires 528.2357.

Example 20

General Procedure for the Synthesis of Compounds 2-128

As depicted in Scheme 21, to a solution of pochonin D (2-85, X=Cl and R=Me) (25 mg, 71.2 μmol) in DMF (5 ml) TBSCl (53.6 mg, 356 μmol) and imidazole (23.6 mg, 356 μmol) were added and the mixture was stirred for 3 hours at room temperature. Purification by column chromatography (SiO$_2$ 0-30% EtOAc/cyclohexane gradient) afforded after evaporation 2-128 (40 mg, 98%). An illustrative example of compound 2-128 follows; its characterization data are in the text below the figure.

Illustrative Compound 2-128:

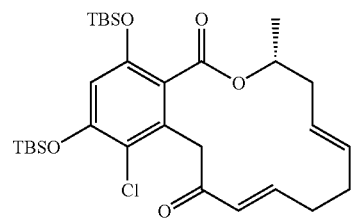

$^1$H NMR (CDCl$_3$, 400 MHz, 25° C.) δ 6.71 (dt, J=15.3, 7.3 Hz, 1H), 6.45 (s, 1H), 5.81 (d, J=15.3 Hz, 1H), 5.25 (s, 2H), 5.04-5.03 (m, 1H), 3.89 (d, J=17.4 Hz, 1H), 3.57 (d, J=17.4 Hz, 1H), 2.31-2.04 (m, 6H), 1.35 (d, J=6.4 Hz, 3H), 1.03 (s, 9H), 0.99 (s, 9H), 0.28-0.24 (m, 12H); $^{13}$C NMR (CDCl$_3$, 100 MHz, 25° C.) δ 195.8, 166.8, 152.9, 151.7, 146.5, 132.7, 131.9, 128.6, 126.8, 122.8, 119.7, 110.7, 71.9, 45.6, 38.5, 30.9, 25.7 (×4), 25.6 (×4), 18.7, 18.3, −4.1 (×2), −4.4 (×2); HRMS (ESI) m/z 601.2568 ([M+Na], C$_{30}$H$_{47}$ClO$_5$Si$_2$Na requires 601.2543).

Example 21

General Procedure for the Synthesis of Compounds 2-157

As depicted in Scheme 21, to a solution of compound 2-128 (1.0 equiv) in pyridine/AcOH (5/1, 250 μL) was added the corresponding hydroxylamine (5.0 equiv) and the mixture was heated up to 40° C. After stirring overnight the solvents were evaporated under reduced pressure, and filtration on SiO$_2$ with a mixture of 30% EtOAc/cyclohexane afforded after evaporation two isomers of 2-157~90%. An illustrative example of compound 2-157 follows; its characterization data are in the text below the figure.

Illustrative Compound 2-157:

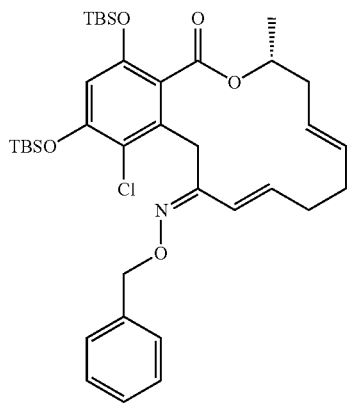

cis oxime NMR (CDCl$_3$, 400 MHz) δ 7.42 (bd, J=6.4 Hz, 2H), 7.36 (bdd, J=7.5, 6.9 Hz, 2H), 7.34-7.32 (m, 1H), 6.52 (d, J=16.1 Hz, 1H), 6.38 (s, 1H), 6.18-6.10 (m, 1H), 5.36-5.32 (m, 2H), 5.16 (bs, 2H), 4.99-4.95 (m, 1H), 3.79-3.76 (m, 2H), 2.40-1.99 (m, 6H), 1.45 (d, J=6.2 Hz, 3H), 1.03 (s, 9H), 0.99 (s, 9H), 0.28 (s, 3H), 0.26 (s, 3H), 0.20 (s, 6H); trans oxime $^1$H NMR (CDCl$_3$, 400 MHz) δ 7.44 (bd, J=6.5 Hz, 2H), 7.37 (bdd, J=7.6, 6.9 Hz, 2H), 7.33-7.31 (m, 1H), 6.41 (s, 1H), 6.04-5.97 (m, 1H), 5.48 (bd, J=15.0 Hz, 1H), 5.29-5.27 (m, 1H), 5.22 (bs, 2H), 5.00-4.95 (m, 1H), 3.98-3.89 (m, 2H), 2.39-2.02 (m, 6H), 1.37 (d, J=5.9 Hz, 3H), 1.04 (s, 9H), 0.99 (s, 9H), 0.28 (s, 3H), 0.27 (s, 3H), 0.23 (s, 3H), 0.22 (s, 3H).

Example 22

General Procedure for the Synthesis of Compounds 2-158

As depicted in Scheme 21, to a solution of corresponding compound 2-157 (1.0 equiv) in THF was added TBAF (2.5 equiv, 1M solution in THF) and the mixture was stirred at room temperature for 2 hours. The solvents were then evaporated under reduced pressure, and filtration on SiO$_2$ with a mixture of 30% EtOAc/cyclohexane afforded after evaporation, compounds 2-158 in >85% yield. An illustrative example of compound 2-158 follows; its characterization data are in the text below the figure.

Illustrative Compound 2-158:

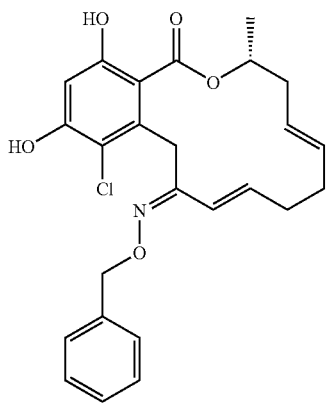

Cis: $^1$H NMR (CDCl$_3$, 400 MHz, 25° C.) δ 11.52 (s, 1H), 7.45-7.34 (m, 5H), 6.64 (s, 1H), 6.09-6.02 (m, 2H), 5.34-5.25 (m, 4H), 5.18-5.08 (m, 2H), 4.33 (d, J=17.0 Hz, 1H), 4.15 (d, J=17.6 Hz, 1H), 2.65-2.59 (m, 1H), 2.27-2.14 (m, 3H), 2.04-2.00 (m, 1H), 1.88-1.83 (m, 1H), 1.30 (t, J=6.4 Hz, 3H); HRMS (ESI) m/z 478.1372 ([M+Na$^+$], C$_{25}$H$_{26}$ClNO$_5$Na requires 478.1392).

Trans: $^1$H NMR (CDCl$_3$, 400 MHz, 25° C.) δ 11.73 (s, 1H), 7.32-7.26 (m, 5H), 6.64 (s, 1H), 6.50 (d, J=16.4 Hz, 1H), 6.06-5.98 (m, 2H), 5.43-5.24 (m, 3H), 4.91 (s, 2H), 4.22 (s, 2H), 2.61-2.55 (m, 1H), 2.46-2.33 (m, 2H), 2.20-2.02 (m, 3H), 0.98 (t, J=6.4 Hz, 3H); HRMS (ESI) m/z 478.1522 ([M+Na$^+$], C$_{25}$H$_{26}$ClNO$_5$Na requires 478.1392).

Example 23

General Procedure for the Synthesis of Compounds 2a-1 Via Mitsunobu Cyclization

As depicted in Scheme 24, the preparation of compound 2a-1 begins with commercially available orcinol, 8. The description below is not intended to be limiting and alternate analogs may be prepared with the same process.

Formylation of orcinol, synthesis of aldehyde 9. POCl$_3$ (54.9 mL, 600 mmol, 2.0 equiv) was added slowly to a flask containing DMF (100 mL) at 0° C. To this mixture was then added a solution of orcinol (42.65 g, 300 mmol, 1.0 equiv) as a solution in DMF (100 mL) and the reaction was allowed to warm up to 23° C. and stirred overnight. Then, the reaction was cooled to 0° C. and 200 mL of ice-water were added. The pH of the mixture was adjusted between 6 and 7 by addition of 10% of NaOH. The mixture was allowed to stand for 30 minutes and then the precipitates were filtered to afford the desired aldehyde 9 (29.2 g, 64%) as a white solid which was used in the subsequent step without further purification: Rf=0.31 (Hexane/EtOAc 3/1); $^1$H NMR ((CD$_3$)$_2$CO, 400 MHz, 25° C.) δ 12.48 (s, 1H), 10.10 (s, 1H), 9.53 (s, 1H), 6.30 (d, J=2.4 Hz, 1H), 6.17 (d, J=2.0 Hz, 1H), 2.54 (s, 3H); $^{13}$C NMR ((CD$_3$)$_2$CO, 100 MHz, 25° C.) δ 194.3, 167.3, 166.2, 146.1, 113.8, 111.5, 101.4, 18.2; HRMS MALDI-TOF) m/z 175.0373 ([M+Na$^+$], C$_8$H$_8$O$_3$Na requires 175.0371).

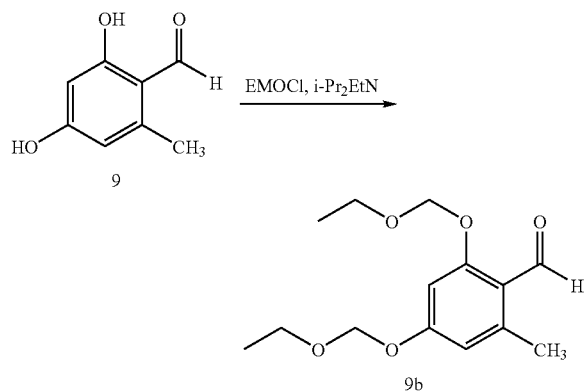

Bis-EOM-protection, synthesis of aldehyde 9b. To a solution of bis-phenol 9 (29.2 g, 191.9 mmol) in DMF (400 mL) at 0° C. were sequentially added iPr$_2$NEt (95.2 mL, 575.7 mmol, 3.0 equiv) and EOMCl (52.3 mL, 575.7 mmol, 3.0 equiv). The reaction was allowed to warm up to 23° C. and stirred overnight. Then, the reaction was quenched with sat. NH$_4$Cl$_{aq}$ (100 mL) and further diluted with CH$_2$Cl$_2$ (400 mL). The organic layer was separated and washed with sat. NH$_4$Cl$_{aq}$ (100 mL×2), brine (100 mL×2), and dried over anhydrous Na$_2$SO$_4$ (5.0 g). Filtration and evaporation of the solvents under reduced pressure followed by flash chromatography (SiO$_2$, Hexane/EtOAc 8/1) afforded protected aldehyde 9b as a colorless oil (46.5 g, 90%): Rf=0.51 (Hexane/EtOAc 3/1); $^1$H NMR (CDCl$_3$, 400 MHz, 25° C.) δ 10.48 (s, 1H), 6.71 (d, J=2 Hz, 1H), 6.49 (d, J=2 Hz, 1H), 5.27 (s, 2H), 5.22 (s, 2H), 3.72 (q, J=6.9 Hz, 2H), 3.69 (q, J=6.9 Hz, 2H), 2.54 (s, 3H), 1.20 (t, J=7.0 Hz, 3H), 1.19 (t, J=7.0 Hz, 3H); $^{13}$C NMR (CDCl$_3$, 100 MHz, 25° C.) δ 190.6, 163.0, 162.1, 144.2, 118.6, 112.3, 100.6, 93.6, 92.8, 64.8, 64.7, 22.2, 15.1 (×2); HRMS (MALDI-TOF) m/z 291.1224 ([M+Na$^+$], C$_{14}$H$_{20}$O$_5$Na requires 291.1209).

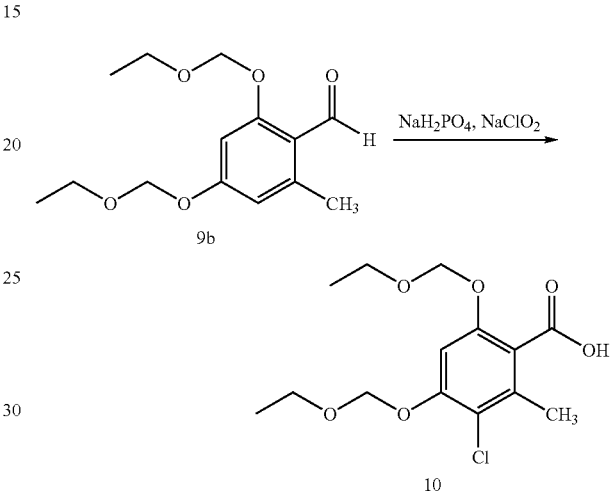

Oxidation-chlorination, synthesis of acid 10. To a solution of aldehyde 9b (46.5 g, 173 mmol) in THF (200 mL) was added a solution of NaH$_2$PO$_4$ (67.5 g, 433 mmol, 2.5 equiv) in H$_2$O (200 mL) and the mixture was cooled down to 0° C. Then a solution of NaClO$_2$ (48.9 g, 85%, 433 mmol, 2.5 equiv) in H$_2$O (200 mL) was added slowly to the reaction. After stirring overnight the mixture was diluted with EtOAc (500 mL), washed with brine (200 mL×3) and dried over Na$_2$SO$_4$ (5.0 g). Filtration and evaporation of the solvents under reduced pressure afforded acid 10 (49.6 g, 90%) as a white solid which was used in the next step without further purification: Rf=0.66 (CH$_2$Cl$_2$/MeOH 9/1); $^1$H NMR ((CD$_3$)$_2$CO, 400 MHz, 25° C.) δ 7.08 (s, 1H), 5.34 (s, 2H), 5.25 (s, 2H), 3.75 (q, J=7.1 Hz, 2H), 3.71 (q, J=7.1 Hz, 2H), 2.34 (s, 3H), 1.19 (t, J=7.1 Hz, 3H), 1.17 (t, J=7.1 Hz, 3H); $^{13}$C NMR ((CD$_3$)$_2$CO, 100 MHz, 25° C.) δ 168.1, 154.9, 153.9, 135.1, 121.8, 117.3, 102.8, 94.7, 94.6, 65.2, 65.0, 17.6, 15.4, 15.4; HRMS (MALDI-TOF) m/z 341.0713 ([M+Na$^+$], C$_{14}$H$_{19}$ClO$_6$Na requires 341.0768).

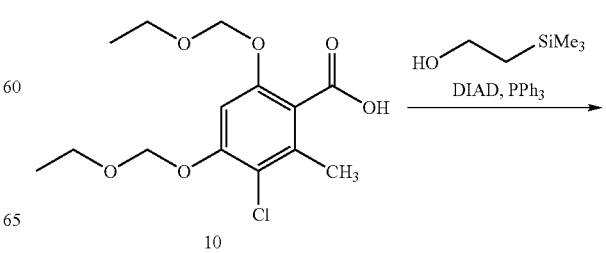

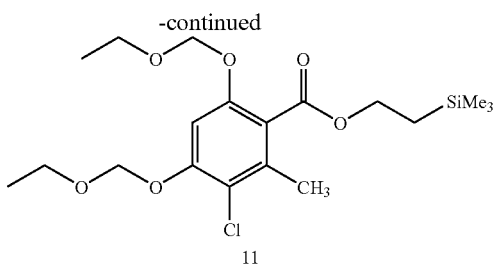

Mitsunobu esterification, synthesis of ester 11. To a solution of acid 10 (23.5 g, 73.7 mmol) in toluene (300 mL) at 0° C., were added sequentially trimethylsilylethanol (12.7 mL, 88.5 mmol, 1.2 equiv), PPh$_3$ (28.9 g, 110.5 mmol, 1.25 equiv) and DIAD (21.7 mL, 110.5 mmol, 1.25 equiv). The reaction was allowed to warm up to 23° C. and stirred for 3 hours. Evaporation of the solvents under reduced pressure followed by flash chromatography (SiO$_2$, Hexane/EtOAc 20/1 and 10/1) afforded ester 11 (24.7 g, 80%) as a white solid: Rf=0.60 (Hexane/EtOAc 3/1); $^1$H NMR (CDCl$_3$, 400 MHz, 25° C.) δ 6.98 (s, 1H), 5.28 (s, 2H), 5.18 (s, 2H), 4.41-4.36 (m, 2H), 3.75 (q, J=6.9 Hz, 2H), 3.70 (q, J=6.9 Hz, 2H), 2.32 (s, 3H), 1,21 (t, J=7.1 Hz, 3H), 1,20 (t, J=7.1 Hz, 3H), 1.12-1.07 (m, 2H), 0.06 (s, 3H); $^{13}$C NMR (CDCl$_3$, 100 MHz, 25° C.) δ 167.7, 154.2, 153.1, 135.0, 120.5, 117.3, 102.0, 94.0, 93.9, 64.7, 64.5, 63.8, 17.6, 15.1 (×2), −1.41 (×3); HRMS (MALDI-TOF) m/z 441.1487 ([M+Na$^+$], C$_{19}$H$_{31}$ClO$_6$SiNa requires 441.1476).

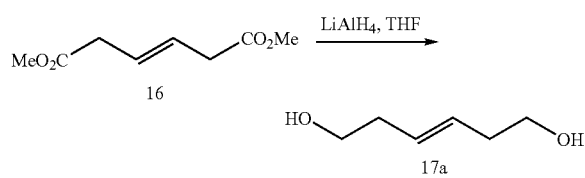

Reduction of diester 16, synthesis of diol 17a. To the suspension of LiAlH$_4$ (15.2 g, 400 mmol, 4 equiv) in THF (300 mL) at 0° C. was added drop wise a solution of trans-3-hexenedioic acid dimethyl ester (17.2 g, 100 mmol) in THF (100 mL). The reaction was stirred for 2 hours. After which, the reaction was quenched by addition of H$_2$O (15.2 mL), 15% of NaOH (15.2 mL), and H$_2$O again (45.6 mL). Then the mixture was poured into Et$_2$O (150 mL), stirred for 30 minutes, and filtered over Na$_2$SO$_4$ (5 g). Evaporation of the solvents under reduced pressure afforded diol 17a which was used without further purification (11.0 g, 95%): Rf=0.53 (CH$_2$Cl$_2$/MeOH 9/1); $^1$H NMR (CDCl$_3$, 400 MHz, 25° C.) δ 5.55-5.52 (m, 2H), 3.66 (dt, J=5.6, 5.2 Hz, 2H), 2.33-2.28 (m, 4H), the OH is not visible; $^{13}$C NMR (CDCl$_3$, 100 MHz, 25° C.) δ 129.8 (×2), 62.0 (×2), 36.16 (×2); HRMS (MALDI-TOF) m/z 139.0734 ([M+Na$^+$], C$_6$H$_{12}$O$_2$Na requires 139.0735).

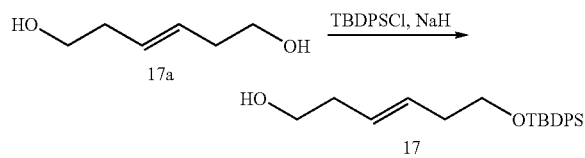

TBDPS-monoprotection of 17a, synthesis of alcohol 17. To a suspension of NaH (1.90 g, 47.4 mmol, 1.0 equiv) in THF (100 mL) at 0° C. a solution of diol 17a (5.5 g, 47.4 mmol, 1.0 equiv) in THF (20 mL) was added. After stirring for 45 minutes, TBDPSCl (12.4 ml, 47.4 mmol, 1.0 equiv) was added. The reaction mixture was allowed to warm up to 23° C. and stirred for 1 hour. Then, it was quenched with sat. NH$_4$Cl$_{aq}$ (200 mL) and extracted with EtOAc (150 mL×3), the combined organic layers were washed with brine (200 mL×2) and dried over Na$_2$SO$_4$ (10 g). Filtration and evaporation of the solvents under reduced pressure followed by flash chromatography (SiO$_2$, Hexane/EtOAc 20/1, 10/1 and 5/1) afforded desired alcohol 17 (11.5 g, 68%) as a colorless oil: Rf=0.46 (Hexane/EtOAc 3/1); $^1$H NMR (CDCl$_3$, 400 MHz, 25° C.) δ 7.68-7.65 (m, 4H), 7.43-7.36 (m, 6H), 5.56 (dt, J=15.2, 6.4 Hz, 1H), 5.44 (dt, J=15.2, 6.8 Hz, 1H), 3.69 (t, J=6.4 Hz, 2H), 3.62 (t, J=6.3 Hz, 2H), 2.31-2.24 (m, 4H), 1.05 (s, 9H), the OH is not visible; HRMS (MALDI-TOF) m/z 377.1927 ([M+Na$^+$], C$_{22}$H$_{30}$O$_2$SiNa requires 377.1913).

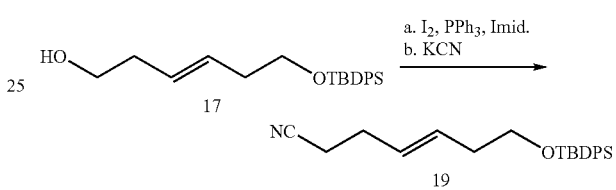

Synthesis of nitrile 19. To a solution of alcohol 17 (11.5 g, 32.4 mmol) in CH$_2$Cl$_2$ (150 mL) at 0° C. were added imidazole (4.30 g, 47.0 mmol, 1.45 equiv), triphenylphosphine (9.35 g, 35.7 mmol, 1.1 equi) and iodine (9.06 g, 35.7 mmol, 1.1 equiv) and the resulting solution was stirred at 0° C. for 6 hours. Then, the mixture was diluted with Et$_2$O/Hexane 1/1 (300 mL), washed with sat. NaHCO$_{3aq}$ (150 mL×2), sat. Na$_2$S$_2$O$_{5aq}$ (150 mL), brine (150 mL) and dried over Na$_2$SO$_4$ (5.0 g). The solvents were evaporated and resulting oily solids were triturated with hexanes (200 mL×2). Filtration and evaporation of the hexanes afforded the corresponding alkyl iodide 18 as a colorless oil which was directly used in the next step without further purification. Rf=0.46 (Hexane/EtOAc 3/1); $^1$H NMR (CDCl$_3$, 400 MHz, 25° C.) δ 7.70-7.67 (m, 4H), 7.45-7.36 (m, 6H), 5.58 (dt, J=15.2, 6.8 Hz, 1H), 5.44-5.37 (dt, J=15.2, 6.4 Hz, 1H), 3.69 (t, J=6.4 Hz, 2H), 3.11 (t, J=7.2 Hz, 2H), 2.54 (dt, J=7.2, 6.8 Hz, 2H), 2.26 (dt, J=6.4, 6.4 Hz, 2H), 1.05 (s, 9H); HRMS (MALDI-TOF) m/z 487.0923 ([M+H$^+$], C$_{22}$H$_{29}$IOSiH requires 487.0930).

To a solution of crude alkyl iodine 18 in DMSO (200 mL) was added KCN (21.0 g, 324 mmol, 1.0 equiv). The resulting mixture was stirred for 2 hours at 60° C. and then the reaction mixture was cooled down to 23° C., diluted with EtOAc (200 mL), washed with water (200 mL), brine (100 mL), and dried over Na$_2$SO$_4$ (5.0 g). Filtration and evaporation of the solvents under reduced pressure followed by flash chromatography (SiO$_2$, Hexane/EtOAc 20/1 and 10/1) afforded desired nitrile 19 (10.6 g, 90%) as a colorless oil: Rf=0.46 (Hexane/EtOAc 3/1); $^1$H NMR (CDCl$_3$, 400 MHz, 25° C.) δ 7.71-7.69 (m, 4H), 7.45-7.39 (m, 6H), 5.60 (dt, J=15.2, 6.4 Hz, 1H), 5.52-545 (m, 1H), 3.73 (t, J=6.4 Hz, 2H), 2.36-2.28 (m, 6H), 1.08 (s, 9H); $^{13}$C NMR (CDCl$_3$, 100 MHz, 25° C.) 135.7 (×4), 134.0 (×2), 130.5, 129.7 (×2), 127.8, 127.7 (×4), 119.4, 63.6, 35.9, 28.6, 27.0 (×3), 19.3, 17.6; HRMS (MALDI-TOF) m/z 386.1962 ([M+Na$^+$], C$_{23}$H$_{29}$OSiNNa requires 386.1916).

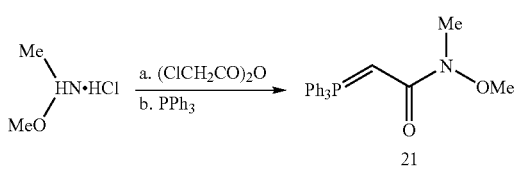

Synthesis of ylide 21. To a solution of N-methoxy-N-methylhydroxylamine hydrochloride (48.52 g, 500 mmol, 1.0 equiv) in $CH_2Cl_2$ (1.0 L) at 0° C. were added pyridine (80.63 mL, 1.0 mol) and chloroacetic anhydride (85.14 g, 500 mmol, 1.0 equiv). The resulting mixture was stirred for 15 min at 0° C., then warm up to 23° C. and stirred overnight. The reaction mixture was then poured carefully into sat. $NaHCO_{3aq}$ solution (1.0 L) and stirred 1 hour, after which the layers were separated, the aqueous phase was extracted with $CH_2Cl_2$ (400 mL) and the combined organic layers were washed with 1N HCl (200 mL×2), brine (200 mL×2), dried over $Na_2SO_4$ (10 g) and filtered. Evaporation of the solvents under reduced pressure afforded the corresponding acetamide (N-methoxy-N-methyl acetamide-2-chloride) as a green oil which was used in the next step without further purification. To a solution of this acetamide in $CH_3CN$ (800 mL) was added $Ph_3P$ (107.98 g, 411.7 mmol, 0.82 equiv) and the resulting mixture was refluxed for 18 hours. Then the solvents were removed under vacuum and the resulting viscous oil was dissolved in $CH_2Cl_2$ (1.0 L), washed with 2N KOH (400 mL×2), brine (400 mL) and dried over $Na_2SO_4$ (10.0 g). Filtration and evaporation of the solvents under reduced pressure afforded ylide 21 as a thick oil which solidified by standing (146.5 g, 80% over two steps). This compound was used in the next step without further purification. Rf=0.85 (Hexane/EtOAc 3/1); $^1H$ NMR ($CDCl_3$, 400 MHz, 25° C.) δ 7.71-7.65 (m, 6H), 7.55-7.50 (m, 3H), 7.48-7.42 (m, 6H), 3.74 (s, 3H), 3.08 (s, 3H), 1.86 (s, 1H); $^{13}C$ NMR ($CDCl_3$, 100 MHz, 25° C.) 133.3 (×3), 133,2 (×3), 131.9 (×3), 128.9 (×3), 128.8 (×3), 127.9, 61.3, 35.9.

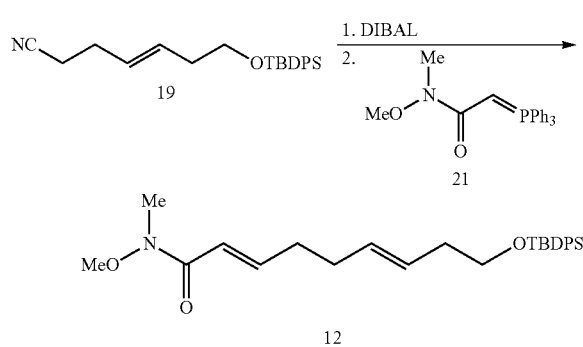

Synthesis of Weinreb amide 12. To a solution of nitrile 19 (22.94 g, 63.0 mmol, 1.0 equiv) in $CH_2Cl_2$ (250 mL) at −78° C., DIBAL (66.3 mL, 1M in toluene, 1.05 equiv) was added and the reaction was stirred for 30 min. To quench the reaction, a solution of sat. K/Na(tartrate)$_{aq}$ (300 mL) was added and the biphasic mixture was stirred until it became a clear biphasic system (over 2 h). The two phases were separated and the aqueous phase was further extracted with $CH_2Cl_2$ (200 mL×3). The combined organic layers were then washed with brine (200 mL) and dried over $Na_2SO_4$ (10 g). Filtration followed by evaporation of the solvents under reduced pressure afforded the corresponding aldehyde 20 which was used in the next step without further purification. Thus, the crude aldehyde 20 was dissolved in $CH_2Cl_2$ (200 mL) at 23° C. and ylide 21 was added (30 g, 81.9 mmol, 1.3 equiv). The reaction was then stirred overnight. Evaporation of the solvents under reduced pressure followed by flash chromatography ($SiO_2$, Hexane/EtOAc 20/1, 10/1 and 3/1) afforded desired Weinreb amide 12 (14.5 g, 61% over two steps) as a colorless oil: Rf=0.30 (Hexane/EtOAc 3/1); $^1H$ NMR ($CDCl_3$, 400 MHz, 25° C.) δ 7.69-7.67 (m, 4H), 7.43-7.36 (m, 6H), 6.98 (dt, J=15.3, 7.1 Hz, 1H), 6.40 (d, J=15.3 Hz, 1H), 5.48-5.46 (m, 2H), 3.68 (t, J=6.6 Hz, 2H), 3.67 (s, 3H), 3.24 (s, 3H), 2.32-2.24 (m, 4H), 2.19-2.14 (m, 2H), 1.06 (s, 9H); $^{13}C$ NMR ($CDCl_3$, 100 MHz, 25° C.) 167.1, 147.2, 135.7 (×4), 134.1, 131.0 (×2), 129.6 (×2), 127.8 (×4), 127.7, 119.0, 64.0, 61.7, 36.1, 32.6, 32.5, 31.5, 27.0 (×3), 19.3; HRMS (MALDI-TOF) m/z 474.2432 ([M+Na]$^+$, $C_{27}H_{37}NO_3SiNa$ requires 474.2440).

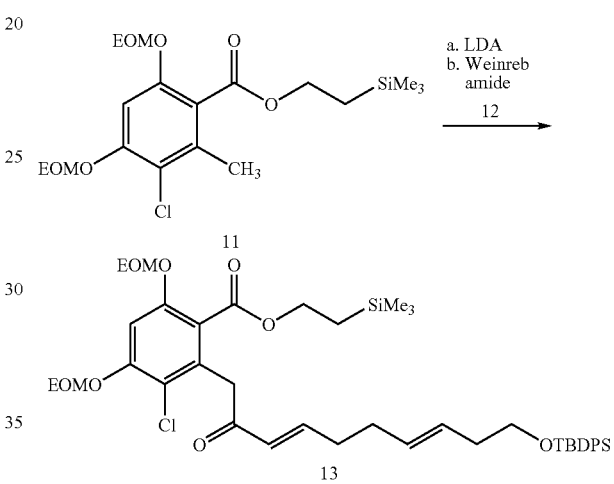

Coupling of toluate 11 and Weinreb amide 12, synthesis of ketone 13. A solution of compound 11 (8.38 g, 20.0 mmol, 1.0 equiv) in anhydrous THF (120 mL) at −78° C. was treated with freshly prepared LDA (71.4 mL, 0.56 M, 40.0 mmol, 2.0 equiv) added via cannula. Immediately after, a solution of Weinreb amide 12 (8.13 g, 18 mmol, 0.9 equiv) in THF (15 mL) at −78° C. was added via cannula. The resulting mixture was then stirred for 15 minutes and the reaction was quenched by addition of sat. $NH_4Cl_{aq}$ (20 mL). Upon warming to 23° C., the reaction mixture was extracted with EtOAc (200 mL×2), and the combined organic layers were then washed with brine (100 mL) and dried over $Na_2SO_4$ (5.0 g). Filtration and evaporation of the solvents under reduced pressure followed by flash chromatography ($SiO_2$, Hexane/EtOAc 20/1, 10/1 and 5/1) afforded desired ketone 13 (20.7 g, 65%): Rf=0.48 (Hexane/EtOAc 3/1); $^1H$ NMR ($CDCl_3$, 400 MHz, 25° C.) δ 7.70-7.68 (m, 4H), 7.42-7.38 (m, 6H), 7.10 (s, 1H), 6.94 (dt, J=15.8, 6.7 Hz, 1H), 6.19 (d, J=15.8 Hz, 1H), 5.49-5.46 (m, 2H), 5.30 (s, 2H), 5.22 (s, 2H), 4.36-4.32 (m, 2H), 4.06 (s, 2H), 3.79-3.68 (m, 6H), 2.30-2.25 (m, 4H), 2.18-2.13 (m, 2H), 1.23 (t×2, J=7.1 Hz, 6H), 1.07 (s, 9H), 1.08-1.03 (m, 2H), 0.06 (s, 9H); $^{13}C$ NMR ($CDCl_3$, 100 MHz, 25° C.) δ 194.5, 167.0, 154.6, 153.9, 147.1, 135.5 (×4), 133.9 (×2), 132.8, 130.5, 129.5 (×2), 129.1, 127.9, 127.6 (×4), 120.3, 117.7, 103.1, 93.9, 93.8, 64.6, 64.4, 63.8, 63.6, 60.3, 59.9, 43.0, 35.9, 32.4, 31.1, 26.8 (×3), 22.6, 22.0, 19.2, 17.4, 15.0, 14.2, 14.1, −1.40 (×3); HRMS (MALDI-TOF) m/z 831.3380 ([M+Na]$^+$, $C_{44}H_{61}ClO_8Si_2Na$ requires 831.3491).

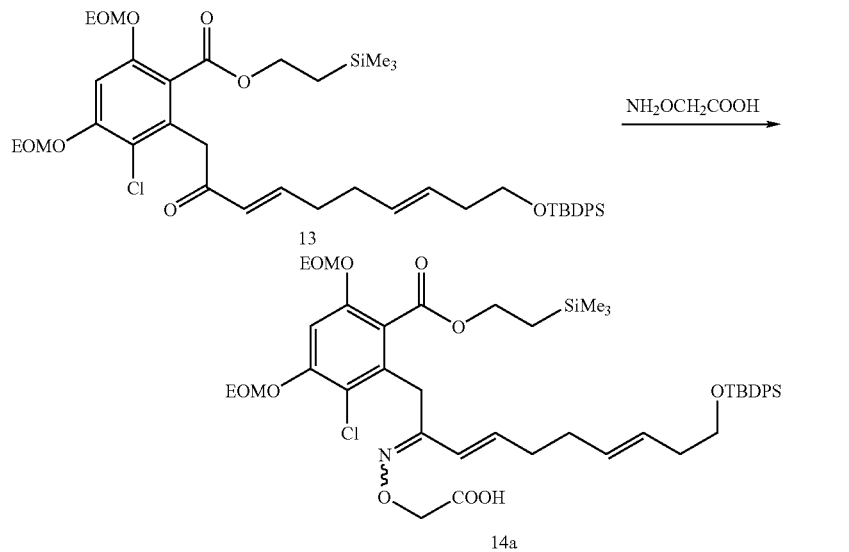

Synthesis of oximes 14a. To a solution of ketone 13 (18.6 g, 25.5 mmol) in pyridine (50 mL) at 40° C., carboxymethoxylamine hemihydrochloride (13.98 g, 127.5 mmol) was added and the reaction was stirred at such temperature for 24 hours. After evaporation of the pyridine, the residues were dissolved in $CH_2Cl_2$ (200 mL) and washed with sat. $NH_4Cl_{aq}$ (50 mL×2), brine (50 mL×2) and dried over anhydrous $Na_2SO_4$ (2.0 g). Filtration and evaporation of the solvents under reduced pressure followed by flash chromatography ($SiO_2$, Hexane/EtOAc 5/1 and 1/1) afforded desired oximes 14a (10.1 g, 50%) as a mixture of E/Z isomers in a 1/1 ratio: Rf=0.51 ($CH_2Cl_2$/MeOH 19/1); $^1$H NMR ($CDCl_3$, 400 MHz, 25° C.) δ 7.69-7.65 (m, 8H), 7.42-7.35 (m, 12H), 7.07 (s, 7.05 (s, 1H), 6.74 (d, J=15.8 Hz, 1H), 6.36 (dt, J=15.8, 6.8 Hz, 1H), 6.07 (dt, J=15.8, 6.8 Hz, 1H), 5.79 (d, J=15.8 Hz, 1H), 5.48-5.43 (m, 2H), 5.39-5.34 (m, 2H), 5.30 (s, 2H), 5.28 (s, 2H), 5.21 (s, 2H), 5.19 (s, 2H), 4.63 (s, 2H), 4.46 (s, 2H), 4.35-4.29 (m, 4H), 4.03 (s, 2H), 3.88 (s, 2H), 3.80-3.60 (m, 12H), 2.31-2.25 (m, 6H), 2.17-2.15 (m, 2H), 2.10-2.06 (m, 2H), 2.00-1.97 (m, 2H), 1.27-1.21 (m, 12H), 1.08 (s, 9H), 1.07 (s, 9H), 1.07-1.05 (m, 4H), 0.09 (s, 9H), 0.08 (s, 9H), the OH from the acids are not visible; $^{13}$C NMR ($CDCl_3$, 100 MHz, 25° C.) δ 172.0, 171.9, 167.9, 167.3, 157.0, 155.6, 154.6, 154.5, 153.7, 153.7, 141.4, 137.8, 135.7 (×8), 134.6, 134.1 (×4), 133.7, 131.2, 130.8, 129.7 (×4), 127.9, 127.7 (×8), 127.5, 124.2 (×2), 120.4, 119.1, 117.5, 117.4, 103.2, 102.8, 94.1, 94.0, 93.9, 93.8, 71.1, 70.5, 64.9, 64.9, 64.7, 64.6, 64.5, 64.0, 64.0, 63.9, 36.1 (×2), 33.5, 33.1, 32.9, 31.9, 31.9, 29.4, 27.0 (×6), 19.3 (×2), 17.5, 17.3, 15.1 (×4), −1.4 (×6).

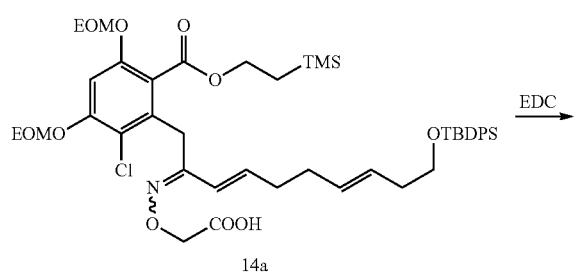

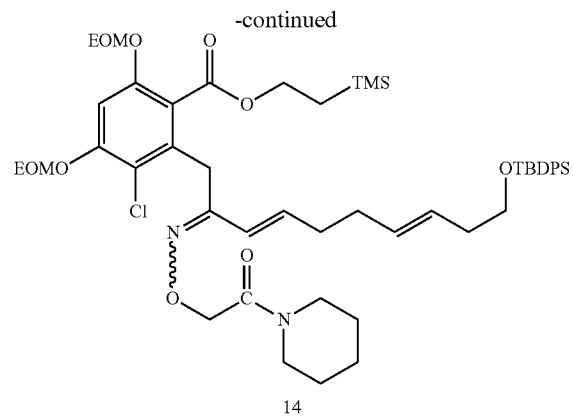

Synthesis of amides 14. To the solution of acid 14a (10.0 g, 11.33 mmol, 1.0 equiv) in $CH_2Cl_2$ (60 mL) at 0° C., was added EDC HCl (2.6 g, 13.6 mmol, 1.2 equiv) followed by a solution of piperidine (1.34 mL, 13.6 mmol, 1.2 equiv) in $CH_2Cl_2$ (10 mL). The reaction was allowed to warm up to 23° C., and stirred for 3 hours. The reaction mixture was then diluted with $CH_2Cl_2$ (200 mL), washed with sat. $NH_4Cl_{aq}$ (100 mL), brine (100 mL), and dried over anhydrous $Na_2SO_4$ (5 g). Filtration and evaporation of the solvents under reduced pressure followed by flash chromatography ($SiO_2$, Hexane/EtOAc 2/1 and 1/1) afforded desired amides 14 (6.60 g, 63%) as a mixture of two isomers in a 1/1 ratio: Rf=0.31 (Hexane/EtOAc 3/1); $^1$H NMR ($CDCl_3$, 400 MHz, 25° C.) δ 7.68-7.64 (m, 8H), 7.41-7.33 (m, 12H), 7.04 (s×2, 2H), 6.71 (d, J=16.0 Hz, 1H), 6.21 (dt, J=16.0, 6.7 Hz, 1H), 6.07 (dt, J=16.0, 6.7 Hz, 1H), 5.73 (d, J=16.0 Hz, 1H), 5.45-5.39 (m, 2H), 5.37-5.32 (m, 2H), 5.28 (s, 2H), 5.25 (s, 2H), 5.19 (s, 4H), 4.73 (s, 2H), 4.60 (s, 2H), 4.37-4.27 (m, 4H), 3.95 (s, 2H), 3.87 (s, 2H), 3.80-3.60 (m, 12H), 3.55-3.52 (m, 2H), 3.51-3.48 (m, 2H), 3.38-3.35 (m, 2H), 3.32-3.29 (m, 2H), 2.26-2.16 (m, 6H), 2.09-2.06 (m, 2H), 2.01-1.98 (m, 2H), 1.95-1.91 (m, 2H), 1.61-1.46 (m, 12H), 1.28-1.17 (m, 12H), 1.05-1.01 (m, 4H), 1.04 (s, 9H), 1.03 (s, 9H), 0.05 (s, 9H), 0.04 (s, 9H); $^{13}$C NMR ($CDCl_3$, 100 MHz, 25° C.) δ 167.1, 167.0 (×2), 166.8, 155.6, 154.3, 154.2, 153.5, 153.4, 153.1, 139.2, 136.5, 135.6

(×8), 134.7, 134.6, 134.1 (×4), 131.4, 131.1, 129.6 (×4), 127.6 (×8), 127.6, 127.1, 124.1, 121.0, 120.9, 119.5, 117.9, 117.7, 103.1, 102.9, 94.1, 94.0, 93.9, 73.1, 73.0, 64.8, 64.7, 64.6, 64.5, 64.0, 63.9, 63.9, 63.6, 60.4, 53.5, 46.4, 46.2, 43.0, 42.9, 36.1, 33.4, 33.0, 32.9, 32.0, 31.9, 30.0, 26.9 (×6), 26.6, 26.5, 25.6, 24.6, 19.3 (×2), 17.4, 17.3, 15.1 (×6), −1.42 (×6).

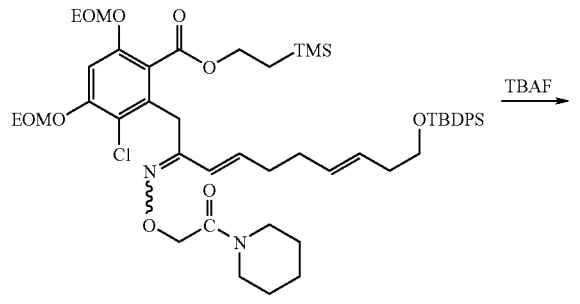

14

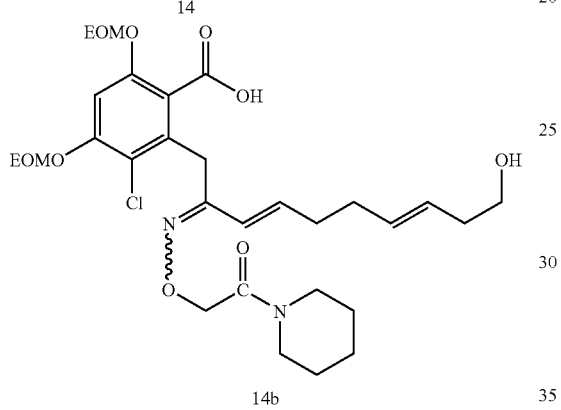

14b

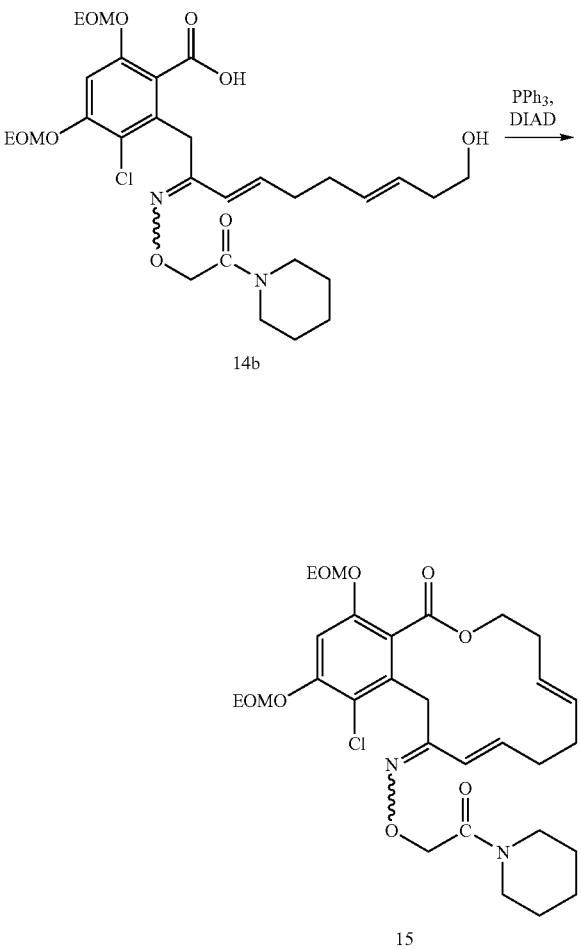

14b

15

Silyl deprotection, synthesis of macrocyclization precursor 14b. To a solution of ester 14 (6.60 g, 6.9 mmol, 1.0 equiv) in THF (70 mL) at 23° C. TBAF (17.3 mL, 1M in THF, 2.5 equiv) was added dropwise and the resulting mixture was stirred for 3 hours. Then, EtOAc (100 mL) was added to the reaction, and the resulting mixture was washed with 1M HCl (60 mL×3), brine (60 mL), and dried over $Na_2SO_4$ (1.0 g). Filtration and evaporation of the solvents under reduced pressure followed by flash chromatography ($SiO_2$, EtOAc and EtOAc/MeOH 4/1) afforded desired acids 14b (3.78 g, 89%) as a mixture of two isomers in a 1/1 proportion: Rf=0.35 ($CH_2Cl_2$/MeOH 9/1); $^1$H NMR ($CDCl_3$, 400 MHz, 25° C.) δ 7.03 (s, 1H), 6.99 (s, 1H), 6.62 (d, J=16.1 Hz, 1H), 6.23 (dt, J=16.1, 6.9 Hz, 1H), 6.11 (dt, J=16.1, 6.9 Hz, 1H), 5.95 (d, J=16.1 Hz, 1H), 5.55-5.30 (m, 4H), 5.26 (s×2, 4H), 5.21 (s, 2H), 5.20 (s, 2H), 4.72 (s, 2H), 4.63 (s, 2H), 4.05 (s, 2H), 4.00 (s, 2H), 3.81-3.66 (m, 8H), 3.65-3.57 (m, 4H), 3.54 (t, J=5.4 Hz, 2H), 3.44 (t, J=5.4 Hz, 2H), 3.31 (t, J=5.4 Hz, 2H), 3.24 (t, J=5.4 Hz, 2H), 2.23 (dt, J=6.5, 6.5 Hz, 4H), 2.18-2.04 (m, 8H), 1.67-1.49 (m, 10H), 1.42-1.40 (m, 2H), 1.25-1.16 (m, 12H), OH from the alcohols and the acids are not visible; $^{13}$C NMR ($CDCl_3$, 100 MHz, 25° C.) δ 168.73, 168.03, 156.47, 154.19, 152.99, 152.94, 140.23, 136.77, 134.37, 134.18, 132.45, 132.11, 127.53, 127.23, 125.91, 122.46, 119.28, 116.76, 102.91, 102.80, 94.16, 94.02, 93.96, 71.51, 71.25, 64.92, 64.82, 64.54, 64.46, 62.11, 46.24, 45.60, 43.39, 43.27, 36.06, 35.98, 33.08, 32.80, 32.09, 31.86, 31.61, 29.20, 26.26, 26.18, 25.38, 25.30, 24.41, 24.30, 15.28, 15.16; HRMS (MALDI-TOF) m/z 633.2562 ([M+Na$^+$]$C_{30}H_{43}ClN_2O_9Na$ requires 633.2555).

Macrocyclization of 14b, synthesis of compounds 15. To a solution of acid 14b (3.78 g, 6.18 mmol) in toluene (200 mL) at 0° C., was added PPh$_3$ (2.43 g, 9.27 mmol) followed by a slow addition of DIAD (1.83 mL, 9.3 mmol). The reaction was allowed to warm to 23° C. and stirred for 5 hours. Evaporation of the solvents under reduced pressure followed by flash chromatography ($SiO_2$, Hexane/EtOAc 4/1 and 1/1) afforded desired macrocycles 15 (2.09 g, 60%) as a mixture of two isomers in a 1/1 proportion: Rf=0.50 (Hexane/EtOAc 1/1); $^1$H NMR ($CDCl_3$, 400 MHz, 25° C.) δ 7.05 (s, 1H), 7.03 (s, 1H), 6.51 (d, J=16.0 Hz, 1H), 6.16 (dt, J=15.8, 6.5 Hz, 1H), 6.00 (dt, J=15.8, 7.7 Hz, 1H), 5.44 (d, J=16.0 Hz, 1H), 5.32 (m, 4H), 5.28 (s, 2H), 5.26 (s, 2H), 5.21 (s, 2H), 5.20 (s, 2H), 4.80 (s, 2H), 4.71 (s, 2H), 4.23 (t, J=5.1 Hz, 2H), 4.18 (t, J=5.1 Hz, 2H), 3.91 (bs, 2H), 3.80-3.66 (m, 10H), 3.60-3.51 (m, 4H), 3.48-3.46 (m, 2H), 3.41-3.38 (m, 2H), 2.40-2.32 (m, 4H), 2.19-2.16 (m, 1H), 2.11-2.00 (m, 7H), 1.67-1.51 (m, 12H), 1.23-1.19 (12H); $^{13}$C NMR ($CDCl_3$, 100 MHz, 25° C.) δ 167.5, 166.9, 154.8, 154.6, 154.4, 153.2, 141.0, 136.6, 134.1, 132.6, 128.5, 127.6; 124.6, 121.6, 119.5, 117.5, 102.94 (×2), 94.1 (×2), 93.8 (×2), 73.4, 73.2, 72.8, 72.7, 64.9, 64.8, 64.7 (×2), 64.3 (×2), 46.5, 46.3, 43.1 (×2), 35.7, 35.6, 32.5, 32.4, 32.2, 32.1, 31.9, 31.7, 30.2 (×2), 26.7 (×2), 26.6 (×2), 25.7 (×2), 24.7 (×4), 15.2 (×2), 15.1 (×2); HRMS (MALDI-TOF) m/z 615.2438 ([M+Na$^+$], $C_{30}H_{41}ClN_2O_8Na$ requires 615.2450).

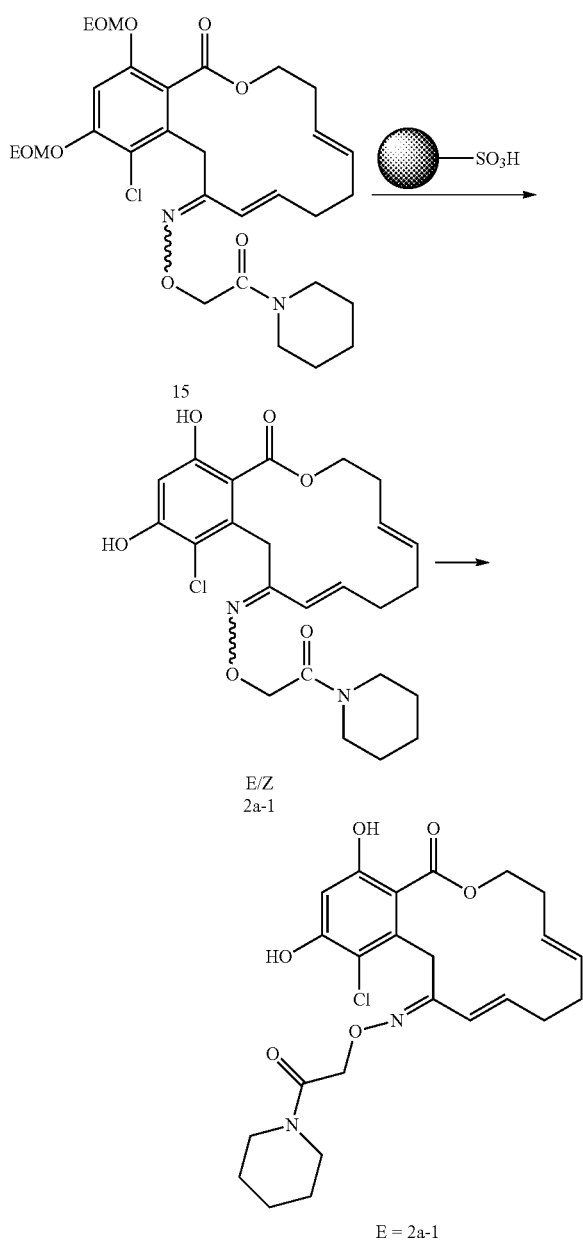

Deprotection, synthesis of 2a-1 as an E/Z mixture, isolation of the E isomer and isomerization of the Z isomer. To a solution of macrocycles 15 (2.8 g, 4.72 mmol) in MeOH (60 mL) at 40° C. sulfonic acid resin (7.87 g, 3.0 mmol/g, 23.6 mmol) was added, and the suspension was stirred for 2 hours. The mixture was diluted with $CH_2Cl_2$ (60 mL), filtered, and the resin was once rinsed with $CH_2Cl_2$ (20 mL×2). After removal of the solvent, the residue was re-dissolved in MeOH (50 mL) and sonicated. A precipitate began to form and the solution was allowed to stand for 12 h. The solution was filtered and rinsed with MeOH (30 mL). Evaporation of the combined solutions afforded 2a-1 (1.13 g, 9:1 E:Z as judged by LCMS). The remaining solid (pure Z-isomer, 900 mg) was dissolved in $CH_2Cl_2$ (180 mL) and treated with TFA (1.4 mL, 18.8 mmol) at 23° C. The mixture was stirred for 12 hours, after which toluene (50 mL) was added and the solvents were evaporated (LCMS of this crude indicated a 1:1 mixture of E/Z isomers). The residue obtained was re-dissolved in $CH_2Cl_2$ (30 mL). The insoluble precipitated was filtered and rinsed with MeOH (20 mL). Evaporation of the combined solutions afforded more of compound 2a-1 (450 mg) again as a 9:1 mixture in favor of the desired E isomer. The remaining solid (Z-isomer, 450 mg) was submitted to same isomerization conditions two more times. The combined batches of 8 were then purified by flash chromatography (70 g of C18, $CH_3CN/H_2O$ 35/65 and 0.01% TFA, 50 mL/min) to afford the pure E isomer as a white powder (1.10 g, 51% overall yield); Rf=0.44 (Hexane/EtOAc 1/2); $^1$HNMR ($CDCl_3$, 400 MHz, 25° C.) δ 11.64 (s, 1H), 6.64 (s, 1H), 6.01 (td, J=15.5 7.5 Hz, 1H), 5.11 (d, J=15.5 Hz, 1H), 5.10-5.03 (m, 2H), 4.85 (s, 2H), 4.37 (t, J=4.8 Hz, 2H), 4.17 (s, 2H), 3.60 (t, J=5.0 Hz, 2H), 3.46 (t, J=5.0 Hz, 2H), 2.34 (q, J=5.4 Hz, 2H), 2.10-2.02 (m, 2H), 1.99-1.92 (m, 2H), 1.70-1.54 (m, 6H); $^{13}$C NMR ($CDCl_3$, 100 MHz, 25° C.) δ 170.27, 167.42, 163.21, 157.38, 155.18, 138.21, 135.62, 131.82, 129.13, 124.76, 115.55, 107.60, 103.47, 72.63, 65.03, 46.38, 43.31, 33.21, 32.76, 31.94, 31.84, 26.65, 25.64, 24.57; HRMS (MALDI-TOF) m/z 499.1638 ([M+H$^+$], $C_{24}H_{29}ClN_2O_6H$ requires 499.1612).

Biological Assays

The present invention includes assaying compounds of the present invention, i.e., test compounds, for use as therapeutics for NF2 or NF1. Specifically, three compounds, namely NXD30001, NXD30002, and NXD30003, are described below as representative compounds of the present invention. It is noted that NXD30001 is also referred to as E-2a1 in Table 1 of this application, NXD30002 is also referred to as Z-2-al in Table 1 of this application, and NXD30017 is also referred to as 2-a13 in Table 1 of this application. NF2-deficient or NF1-deficient cells lines as well as NF2-deficient cells or NF1-deficient cells obtained from a patient with NF2 or NF1, respectively, are treated with varying amounts of test compounds, and the effects of the test compound on degradation of one or more client proteins of HSP90, on HSP70 upregulation, and on activity or phosphorylation status of proteins in pathways associated with one or more client proteins of HSP90 are measured. Compounds that cause a decrease in the amount and/or activity, e.g. decrease or increase in phosphorylation, of one or more client proteins of HSP90, an upregulation of HSP70, or a decrease in activity, e.g. decrease or increase in phosphorylation, of proteins in pathways associated with one or more client proteins of HSP90 can be identified as a putative therapeutic for NF2 or NF1.

The client proteins of HSP90 (e.g. ErbB2, Akt, c-Raf, Cdk4, and etc) are involved in many signaling pathways that control diverse cellular functions such as cell growth and proliferation, differentiation, and apoptosis. In order to determine proteins degraded and downstream pathways blocked by a HSP90 inhibitor in Nf1-/- Schwann cells or Nf1-/- Schwann cells, one or more client proteins and downstream proteins such as ErbB2, Akt, c-Raf, Cdk4, mTOR, S6K, S6, GSK3, Mek, Erk1/2, Cyclin D can be monitored. For example, the effect of a HSP90 inhibitor on ErbB2 is assessed by comparing the amounts of ErbB2, phospho-ErbB2, and several phosphorylated downstream proteins (e.g. phospho-Akt, phospho-S6K, phospho-S6, and phospho-GSK3) in cells treated with the compound and those treated with vehicle (control).

Cells that are useful for treatment include, but are not limited to, NF2-deficient Schwann cells (e.g. HEI-193), NF2-deficient malignant mesothelioma cells (e.g. BAR and RAV), NF2-deficient meningioma cells (e.g. SF1335), Nf2-deficient mouse cells (e.g. Schwann cells and mouse embryonic fibroblasts), and NF2-deficient schwannoma cells derived from schwannomas in a patient. For instance, HSP90 inhibitors can be evaluated in a panel of NF2 mutant human and mouse cells and cell lines. Antibodies to one or more client proteins of HSP90 (e.g. ErbB2, Akt, c-Raf, Cdk4, etc.) and activation-specific phospho-antibodies against these proteins or downstream proteins are ideal tools for this purpose (Cell Signaling Technology).

Cells that are useful for treatment include, but are not limited to, NF1-deficient human MPNST cells (e.g. ST88-14, 88-3, 90-8, and sNF96.2) (Basu et al., 1992, *Nature* 356: 713-715; DeClue et al., 1992, *Cell* 69: 265-273; Wallace et al., 2000, *Genes Chromosomes Cancer* 27(2):117-123; Muir et al., 2001, *Am. J. Pathol.* 158: 501-513), primary neurofibroma cells derived from NF1 patients, mouse Nf1;p53-deficient MPNST cell lines established from cisNf1;p53 mice (Vogel et al., 1999, *Science* 286: 2176-2179), and Nf1−/− mouse cells (e.g. Schwann cells, mouse embryonic cells, and leukemia cells).

1. NXD30001 Downregulates Akt, ErbB2, and c-Raf in NF2-Deficient Mouse and Human Tumor Cells It has been shown that inhibition of HSP90 function in breast cancer cells causes down-regulation of Akt (Basso et al., 2002, J. Biol. Chem. 277(42): 39858-39866). The inventors of the present invention have determined that phospho-Akt levels are elevated in Nf1−/− mouse Schwann cells, NF2 defient human schwannomas, NF2-deficient meningioma xenografts, NF2-deficient mesothelioma xenografts as compared to wild-type mouse Schwann cells and/or normal human peripheral nerves (reference is made to PCT/US2007/70366 application entitled "Treatment of Neurofibromatosis with Inhibitors of a Signal Transduction Pathway," filed on Jun. 4, 2007, which is herein incorporated by reference in its entirety). To assess the effect of HSP90 inhibitors on phospho-Akt in NF2 deficient cells, Western blots were prepared from Nf2−/− mouse Schwann cells as an example. The cells were treated with 0.02 µM, 0.5 µM NXD30001 for 24 hours. As control the same cells were treated with vehicle DMSO for 24 hours. The results show that treatment of NF2-deficient cells with NXD30001 caused a decline of phospho-Akt levels (FIGS. 1A and 1B). The loss of phospho-Akt was both dose- and time-dependent.

To assess the effect of the compounds of the present invention on ErbB2 and c-Raf in NF2-deficient cells, Western blots were prepared from various NF2-deficient cells, including Nf2−/− mouse Schwann cells, NF2-deficient meningioma cells, and NF2-deficient mesothelioma cells. The cells were treated similarly as described above. The inventors of the present invention have determined that treatment of NF2-deficient cells with NXD30001 caused a decline of both ErbB2 and c-Raf levels (FIG. 1A). The loss of ErbB2 and Raf proteins were both dose- and time-dependent, as shown in the result of Nf2−/− mouse Schwann cells treated with 0.1 µM NXD30001 for 3, 6, 12, 24 hours (FIG. 1B). The rapid decline of Akt phosphorylation might partially be caused by the degradation of ErbB2 upon NXD30001 treatment (FIG. 1A). ErbB2, one of the well-documented client proteins of HSP90, lies upstream of the Akt pathway in Schwann cells. Taken together, these data suggest that pharmacological inhibition of HSP90 function blocks the deregulated Akt pathway in NF2 mutant cells.

2. NXD30001 Causes Upregulation of HSP70 in NF2-Deficient Mouse and Human Tumor Cells To assess the effect of the compounds of the present invention on HSP70 in NF2-deficient cells, Western blots were prepared from various NF2-deficient cells, including Nf1−/− mouse Schwann cells, NF2-deficient schwannoma cells, NF2-deficient meningioma cells, and NF2-deficient mesothelioma cells. The blot was prepared as described above and probed with anti-HSP70 antibody. The inventors of the present invention have found that treatment of NF2-deficient cells with NXD30001 caused an upregulation of HSP70 (FIG. 1A). The increase of HSP70 protein level was dose-dependent.

3. NXD30001 Downregulates EGFR, Akt, c-Raf, and Cdk4 in NF1-Deficient Human MPNST Cells Ras-Raf-Mek-Erk1/2 pathway is activated due to the loss of NF1 in these cells. In addition, EGFR is overexpressed in a number of NF1-deficient human and mouse cells. Human malignant peripheral nerve sheath tumor (MPNST) cell ST88-14 was treated with increasing concentration (8-1000 nM) of NXD30001 for 24 hr. Cells were lysed and clarified lysates were subjected SDS-PAGE, followed by immunoblot analysis using indicated antibodies. FIG. 2 demonstrates NXD30001 induced degradation of HSP90 client proteins EGFR, Akt, and c-Raf, as well as a cell-cycle regulating kinase Cdk4 with an IC50 of approximate 100 nM after 24 hr treatment. Equal lysate protein loading is shown by actin immunoblot.

4. NXD30001, NXD30002, and NXD30017 Inhibit Proliferation of NF1- and NF2-Deficient Human and Mouse Cells Inhibitors of HSP90 function is assayed for the ability to decrease the number of NF2 deficient tumor cells in a tumor, i.e., shrink a tumor, or reduce the proliferation of NF2 deficient tumor cells. The ability of inhibitors to decrease the number of NF2 deficient tumor cells in a sample or reduce proliferation of NF2 deficient tumor cells is assessed using a variety of methods known in the art. A small library of compounds of the present invention (total 14 oxime compounds) were assayed for inhibition of proliferation of NF1- and NF2-deficient cells. Cells used are Nf2−/− mouse embryonic stem cell (MESC), NF2-deficient human SF1335 meningioma cells, NF2-deficient HEI193 schwanoma cells, NF2-deficient BAR and RAV mesothelioma cells, NF2-plus BLA mesothelioma cells, and NF1-deficient human malignant peripheral nerve sheath tumor (MPNST) cells. Appropriate number of cells that can reach ~70% confluence in 3 days (2000-6000 cells/well) were plated in 96-well plates. Various concentrations of each compound were added to the growing media and the cells were then cultured for 3 days. A positive control compound (17-AAG) and a vehicle (DMSO) control were included with each assay. Upon completion of the incubation, media were gently removed and 100 µl of ATPlite solution (Perkin Elmer) was added in each well. Viable cells were measured by detecting luminescence generated from reaction of ATPlite solution and the ATP in the cells. IC50, the concentration needed for 50% inhibition of cell proliferation, were determined and analyzed for each compound using XLfit 4.1 software. Efficacious compounds preferably have about an IC50<10 µM. IC50s of these compounds inhibiting proliferation of various NF1 and NF2 cells are shown in FIG. 3.

5. Pharmacodynamic Assays Measuring In Vivo Target Inhibition

Various pharmacodynamic (PD) assays are useful to measure in vivo target inhibition.

The present invention also includes screening for degradation of one or more client proteins of HSP90 or upregulation of HSP70 using peripheral blood mononuclear cells ("PMBC PD assay"). In this assay, whole blood from groups of about 5 similarly treated normal and/or mice harboring NF2-deficient or NF1-deficient tumors at efficacious doses is collected and pooled in a single heparinized Vacutainer tube (BD biosciences, NJ), and peripheral blood mononuclear cells (PBMCs) are isolated as reported (Graff et al., 2005, Cancer Res. 65(16): 7462-7469; Peralba et al., 2003, Clin. Cancer Res.

9(8): 2887-2892). PBMCs are collected at 0, 2, 4, 8, and 24 hours post dosing. PBMCs are lysed directly for Western blots or for immunoprecipitation first and then Western blots to detect target proteins. For example, HSP70 upregulation by a HSP90 inhibitor is detected in PBMCs (Ramanathan et al., 2007, *Clin. Cancer Res.* 13(6):1769-1774).

In yet another assay ("tumor tissue PD assay"), either target protein degradation (e.g. ErbB2, c-Raf, Akt, Cdk4), phosphorylation, and HSP70 upregulation in tumor lysates by Western blots or in tumor sections (i.e. paraffin-embedded sections) by immunohistochemistry are used to assay the effects of the test compound on target proteins. Tumor tissues are harvested at the same time points as described above for PBMCs. Each tumor sample is divided in two pieces with one flash frozen in liquid nitrogen immediately and the other fixed in 10% buffered formalin and then paraffin-embedded. ErbB2, phospho-Akt, and phospho-S6 levels in Nf2−/− Schwann cell xenografts have been shown to be very high and can be readily detected by immunohistochemistry (reference is made to a PCT application entitled "Treatment of Neurofibromatosis with Inhibitors of a Signal Transduction Pathway", filed on Jun. 4, 2007). Phospho-S6 level in Nf1−/− tumor cells is also elevated and is readily detected by immunohistochemistry (Johannessen et al., *Proc. Natl. Acad. Sci. U.S.A.* 2005, 102(24):8573-8578; Dasgupta et al., *Cancer Res.* 2005, 65(7):2755-2760).

6. Xenografts, Animal Models, and Treatment

The ability of a test compound to act as a therapeutic in NF2 or NF1 by modulating the HSP90 complex can also be assessed using animal xenograft experiments. Xenograft experiments are performed with subcutaneous tumor formation in nude mice or SCID mice using a human NF2-deficient⁻ malignant mesothelioma cell line RAV, a meningioma cell line or Nf1−/− SCs. A dermal neurofibroma (DNF) xenograft model has been established to evaluate compounds useful for treating NF1 neurofibromas (PCT publication WO 06/083979). In particular, these experiments have allowed the inventors of the present invention to define the treatment starting point for each xenograft model.

In order to assess the action of a test compound on the growth of the xenografts, tumor-bearing mice are randomized among control and treated groups with 8-12 mice in each experimental group. For oral dosing, compounds are suspended in 0.5% (w/v) methyl cellulose or other suitable dosing vehicles known in the art. Dosing starts from a predefined starting point for each cell system (i.e. 100-200 mm$^3$ at 3-5 days for Nf1−/− Schwann cells). Mice are dosed once or twice a day with high, medium, low doses and vehicle control for 4 weeks or less determined by preset tumor volume criteria. The actual dose should be calculated based on data of in vitro analyses, pharmacokinetic studies, and maximal tolerated dose (MTD) determined using normal mice or tumor-bearing mice. In some cases, it may be optimal to dose via intravenous, intraperitoneal or intralesional routes. For intraperitoneal dosing, mice are dosed twice daily, once daily, three times a week, two times a week, once a week. In case of significant variations in body weight during the treatment period, doses can be adjusted accordingly.

Mice are monitored daily and tumor growth, assessed based on tumor volume (V=[length×width$^2$]π/6), and measured twice a week with calipers. Tumor formation is monitored for the duration of the treatment or longer, for instance, 3-6 weeks. Animals are sacrificed earlier when they meet predetermined criteria established for minimizing pain and suffering. Treatment efficacy endpoints are assessed in terms of the compound's effects on tumor growth of treated mice relative to that of control vehicle-treated mice. Two evaluation criteria are used in parallel: (i) Growth Inhibition, calculated as the ratio of the mean tumor volume of drug-treated versus control groups: T/C percent=(mean tumor volume of compound-treated group on day X/mean tumor volume of control group on day X)×100, the optimal value, being the minimal T/C ratio which reflects the maximal tumor growth inhibition achieved and (ii) Specific Tumor Growth Delay (SGD), calculated as [Td (compound-treated group)-Td (vehicle-treated group)]/Td (vehicle-treated group), with Td being the tumor doubling time of compound-treated and control groups, defined as the time in days required for the tumor volume to double.

Various HSP90 inhibitors are tested in cisNf1;p53 mouse models developed previously (Vogel et al., 1999, *Science* 286: 2176-2179; Cichowski et al., 1999 *Science.* 286: 2172-2176). MPNSTs can harbor mutations in at least 2 tumor suppressor genes in addition to the NF1 loss of heterozygosity. In particular, several studies have reported mutations in the p53 gene. The Nf1;p53 mice develop tumors with a 100% incidence between 5 and 6 months of age. In all cases the tumors exhibit characteristics of NF1 associated malignancies of the peripheral nervous system, including MPNSTs, triton tumors and rhabdomyosarcomas, according to histopathological criteria. The full penetrance and reproducibility of tumor timing of appearance make the cisNf1;p53 mouse ideal for testing therapeutic compounds since reduction in tumor burden or delay in tumor appearance can be readily monitored.

Mice are randomized among control and treated groups with 15-20 mice in each experimental group. Mice are dosed every week day with high, medium, and low doses and vehicle control for 8 weeks or less beginning at 18-20 weeks of age, when 30-50% of mice begin to develop tumors. The high dose is defined as the MTD dose of the test compound with similar schedule. If toxicity is an issue for the proposed duration, lower starting dose, less frequent dosing schedule such as every other day, twice a week, or increase the sample size per group are implemented so that a sufficient number of live mice are evaluated at the end of the study. Test agents are administered via intraperitoneal (i.p.), intravenous (i.v.), or oral route. In case of significant variations in body weight during the treatment period, doses are adjusted accordingly or experiments can be repeated with the adjusted doses.

Typically, cisNf1;p53 mice that develop tumors become less active and assume classic rounded positions and ruffled coat. An untreated cohort of mice is expected to begin to develop signs of ill health within the fifth month of age. Pairs of control and test mice are sacrificed on a weekly basis once the signs of illness become apparent in control mice. All mice are carefully necropsied and the number, location and size of all tumors are noted. All tumor samples are evaluated for histologic and immunohistochemical analysis to determine pathology as well as evidence for apoptosis, necrosis, and proliferation.

For compound efficacy analysis, the mean tumor volume of each dosing group is compared to that of the vehicle control group. Student's t-test is used for statistical analysis of tumor volume. Differences with a p-value <0.05 is considered as statistically significant.

It is understood that the present invention is not limited to the particular methods and components, etc, described herein, as these may vary. It is also to be understood that the terminology used herein is used for the purpose of describing particular embodiments only, and is not intended to limit the scope of the present invention. It must be noted that as used herein, the singular forms "a," "an," and "the" include the plural reference unless the context clearly dictates otherwise.

Experimental procedures and characterization data for exemplary compounds follows. The compounds and data described below are understood to be non-limiting.

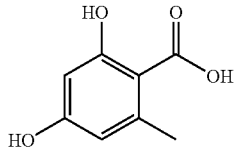

2-95a

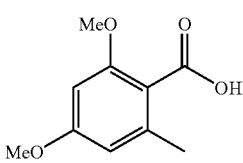

2-95c

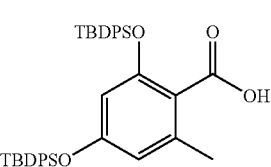

2-95j

General procedure for oxidation using solvent system A: A solution of aldehyde 2-94 (1.0 equiv.) in H$_2$O/THF/DMSO (20:10:1, 0.03 M) was sequentially treated at 0° C. with sulfamic acid (3.5 equiv.) and a solution of sodium chlorite (3.25 equiv.) in H$_2$O. After 0.5-1 h stirring at this temperature, the reaction mixture was diluted with Et$_2$O, washed with saturated NH$_4$Cl$_{aq}$. and dried over MgSO$_4$. Concentration under reduced pressure afforded the corresponding acid 2-95 which was used without any further purification in the next step.

2-95c: $^1$H NMR (400 MHz, (CD$_3$)$_2$CO, 25° C.): δ=6.48 (d, J=2.2 Hz, 1H), 6.45 (d, J=2.2 Hz, 1H), 3.84 (s, 3H), 3.83 (s, 3H), 2.33 (s, 3H).

2-94j: $^1$H NMR (400 MHz, (CD$_3$)$_2$CO, 25° C.): δ=7.58 (d, J=7.0 Hz, 4H), 7.47-7.35 (m, 10H), 7.31-7.21 (m, 6H), 6.31 (s, 1H), 5.89 (s, 1H), 2.35 (s, 3H), 1.05 (s, 9H), 0.93 (s, 9H).

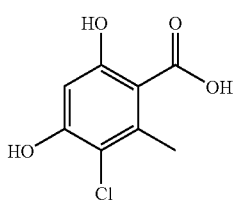

2-95b

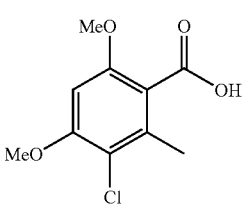

2-95d

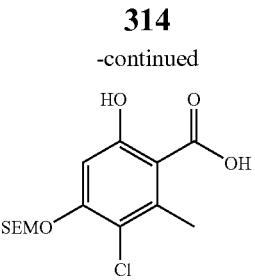

2-95h

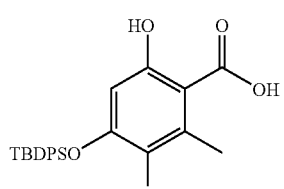

2-95i

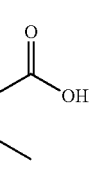

2-95k

General procedure for oxidation using solvent system B: A solution of aldehyde 2-94 (1.0 equiv.) in H$_2$O/THF (20:10, 0.03 M) was sequentially treated at 0° C. with sulfamic acid (3.5 equiv.) and a solution of sodium chlorite (3.25 equiv.) in H$_2$O. After 12 h stirring at room temperature, the reaction mixture was diluted with Et$_2$O, washed with saturated NH$_4$Cl$_{aq}$. and dried over MgSO$_4$. Concentration under reduced pressure afforded the corresponding acid 2-95 which was used without any further purification in the next step. For 2-95b, 2.0 equiv. of sulfamic acid were necessary to avoid over-chlorination. For 2-95i and 2-95k, the reaction was complete after 30 min at 0° C.

2-95b: $^1$H NMR (400 MHz, (CD$_3$)$_2$CO, 25° C.): δ=6.48 (s, 1H), 2.70 (s, 3H).

2-95d: $^1$H NMR (400 MHz, (CD$_3$)$_2$CO$_3$ 25° C.): δ=6.77 (s, 1H), 3.97 (s, 3H), 3.89 (s, 3H), 2.35 (s, 3H).

2-95h: $^1$H NMR (400 MHz, (CD$_3$)$_2$CO, 25° C.): δ=6.71 (s, 1H), 5.43 (s, 2H), 3.85 (t, J=8.2 Hz, 2H), 2.71 (s, 3H), 1.00 (t, J=8.2 Hz, 2H), 0.04 (s, 9H).

2-95i: $^1$H NMR (400 MHz, (CD$_3$)$_2$CO, 25° C.): δ=7.82-7.80 (m, 4H), 7.55-7.48 (m, 6H), 6.02 (s, 1H), 2.74 (s, 3H), 1.17 (s, 9H).

2-95k: $^1$H NMR (400 MHz, (CD$_3$)$_2$CO, 25° C.): δ=7.48-7.34 (m, 12H), 7.23-7.16 (m, 8H), 5.93 (s, 1H), 2.54 (s, 3H), 1.05 (s, 9H), 1.02 (s, 9H).

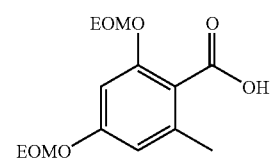

2-95e

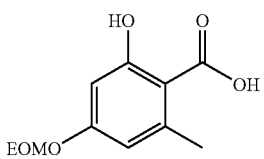

2-95g

General procedure for oxidation using solvent system C: To a solution of aldehyde 2-94 (1.0 equiv.) in DMSO (0.4 M) at 0° C., were added slowly in a sequential fashion, $NaH_2PO_4 \cdot H_2O$ (5.0 equiv.) dissolved in $H_2O$ (3 M) and $NaClO_2$ (5.0 equiv.) dissolved in $H_2O$ (3 M). After stirring for 12 h, the reaction was diluted with $Et_2O$, washed with saturated $NH_4Cl_{aq}$, and dried over $MgSO_4$. Concentration under reduced pressure resulted into the corresponding acid 2-95 used without further purification in the next step.

2-95e: $^1$H NMR (400 MHz, $(CD_3)_2CO$, 25° C.): δ=6.76 (d, J=1.9 Hz, 1H), 6.60 (d, J=1.6 Hz, 1H), 5.25 (s, 4H), 3.75-3.69 (m, 4H), 2.31 (s, 3H), 1.18 (t, J=7.0 Hz, 6H).

2-95g: $^1$H NMR (400 MHz, $(CD_3)_2CO$, 25° C.): δ=12.13 (bs, 1H), 6.46 (s, 2H), 5.30 (s, 2H), 3.73 (q, J=7.0 Hz, 4H), 2.58 (s, 3H), 1.19 (t, J=7.0 Hz, 3H).

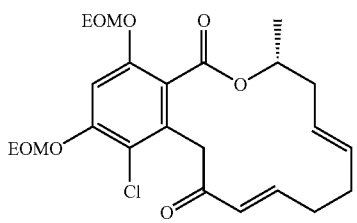

2-112

1-Chloro-2,4-bis-ethoxymethoxy-7-methyl-7,8,11,12-tetrahydro-16H-6-oxa-benzocyclotetradecene-5,15-dione (2-112): A 2 mM solution of compound 2-111 (200 mg, 0.38 mmol) in anhydrous toluene (190 mL) was treated with 10% mol of catalyst Grubbs' II (30 mg, 0.038 mmol) and heated at 80° C. overnight. The reaction mixture was then passed through a pad of silica, which was washed with $CH_2Cl_2$. The combined filtrates were concentrated under reduced pressure. Purification by flash chromatography (silica gel, 0-25% EtOAc/hexane gradient) afforded pure macrocycle 2-112 (167 mg, 94%). $^1$H NMR (400 MHz, $C_6D_6$, 25° C.): δ=7.27 (s, 1H), 6.85 (dt, J=15.2, 7.6 Hz, 1H), 6.15 (d, J=15.8 Hz, 1H), 5.16-4.94 (m, 7H), 4.41 (d, J=17.0 Hz, 1H), 4.13 (d, J=17.0 Hz, 1H), 3.61-3.45 (m, 4H), 2.18-2.07 (m, 2H), 1.86-1.62 (m, 4H), 1.38 (d, J=5.8 Hz, 3H), 1.11 (t, J=7.0 Hz, 3H), 1.04 (t, J=7.0 Hz, 3H); $^{13}$C NMR (100 MHz, $C_6D_6$, 25° C.): δ=193.5, 166.4, 155.0, 154.1, 146.0, 133.7, 131.5, 128.8, 127.7, 121.2, 118.1, 102.9, 93.7, 93.6, 71.6, 64.4, 64.4, 45.0, 39.2, 30.7, 30.4, 19.3, 14.9, 14.8; I.R. (film): $v_{max}$=2917, 1720, 1690, 1622, 1591, 1320, 1255, 1120, 1037 cm$^{-1}$; HRMS (ESI-TOF): m/z: calculated for $C_{24}H_{31}O_7ClNa$: 489.1651, found 489.1737 [M+Na$^+$]. (−)-(2R): $[\alpha]^{25}_D$=24.0 (c 0.59, CHCl$_3$).

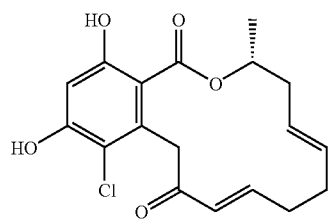

2-85

Pochonin D

Pochonin D (2-85): Compound 2-112 (50 mg, 0.1 mmol) was stirred for 2 h in a 5:1 mixture of $CH_2Cl_2$/TFA (3 mL). Concentration under reduced pressure, followed by flash chromatography (silica gel, 0-33% EtOAc/hexane gradient) afforded synthetic pochonin D 2-85 (25 mg, 72%). Synthetic pochonin D was found to have identical $^1$H NMR as natural pochonin D. $^1$H NMR (400 MHz, $C_6D_6$, 25° C.): δ=12.42 (s, 1H), 6.89 (s, 1H), 6.67-6.62 (m, 1H), 5.82 (d, J=15.6 Hz, 1H), 5.17-5.12 (m, 1H), 5.00-4.92 (m, 1H), 4.76-4.69 (m, 1H), 4.28 (d, J=17.2 Hz, 1H), 4.18 (d, J=17.7 Hz, 1H), 2.54-2.47 (m, 1H), 1.93-1.77 (m, 5H), 0.98 (d, J=6.4 Hz, 3H); $^1$H NMR (400 MHz, CDCl$_3$, 25° C.): δ=11.73 (s, 1H), 6.76-6.69 (m+s, 2H), 6.19 (s, 1H), 5.82 (d, J=15.2 Hz, 1H), 5.46-5.40 (m, 1H), 5.31-5.15 (m, 2H), 4.37 (d, J=17.6 Hz, 1H), 4.09 (d, J=17.0 Hz, 1H), 2.68-2.61 (m, 1H), 2.39-2.03 (m, 5H), 1.34 (d, J=7.0 Hz, 3H); $^1$H NMR (400 MHz, CD$_3$OD, 25° C.): δ=6.74 (dt, J=15.5, 7.6 Hz, 1H), 6.51 (s, 1H), 5.83 (d, J=15.5 Hz, 1H), 5.36-5.22 (m, 3H), 4.25 (d, J=17.7 Hz, 1H), 4.13 (d, J=17.7 Hz, 1H), 2.54-2.47 (ddd, J=14.5, 8.0, 4.0 Hz, 1H), 2.31-2.15 (m, 5H), 1.31 (d, J=6.6 Hz, 3H); $^{13}$C NMR (100 MHz, $C_6D_6$, 25° C.): δ=194.2, 169.9, 164.3, 157.3, 146.1, 137.1, 131.9, 128.1, 126.2, 115.5, 107.5, 103.6, 72.4, 45.0, 36.4, 31.0, 30.8, 17.2; I.R. (KBr): $v_{max}$=2936, 1654, 1603, 1347, 1313, 1239 cm$^{-1}$; HRMS (ESI-TOF): m/z: calculated for $C_{18}H_{19}O_5ClNa$: 373.0813, found 373.0903 [M+Na$^+$]. (+)-(2R): $[\alpha]^{25}_D$=+11.1 (c 0.72, CHCl$_3$).

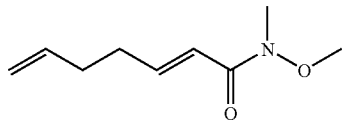

2-114

Hepta-2,6-dienoic acid methoxy-methyl-amide (2-114): To a solution of 2-chloro-N-methoxy-N-methylacetamide (6.0 g, 48.8 mmol) in dry DMF (20 mL) at 23° C. was added 3-mercaptophenol (4.44 mL, 48.8 mmol) and $K_2CO_3$ (6.7 g, 48.8 mmol). The resulting suspension was stirred at 23° C. overnight. After this period of time, Merrifield resin (24 g, <2 mmol·g$^{-1}$, <48.8 mmol) was added to the mixture followed by $K_2CO_3$ (11.4 g, 83.0 mmol) as well as TBAI (catalytic amount), and the suspension was heated up to 50° C. After 12 hours at this temperature, the resin was filtered and washed several times: HCl$_{aq}$. (50 mL), MeOH (50 mL), $CH_2Cl_2$ (50 mL) and Et$_2$O (50 mL). The resin was dried under reduced pressure to constant mass of 29.2 g. The final mass gain (5.2 g, 27.3 mmol) indicated an estimate loading of 0.81 mmol·g$^{-1}$. Resin 2-49 (10 g, 0.81 mmol·g$^{-1}$) was suspended in a 1:1 mixture of HFIP/CH$_2$Cl$_2$ (50 mL). To this suspension, $H_2O_2$ (3 mL, 16.0 mmol) was added at 23° C. and the resulting mixture was shaken for 12 h. Resin 2-113 was then filtered, washed using MeOH (50 mL), CH$_2$Cl$_2$ (50 mL) and Et₂O (50 mL) and dried under reduced pressure to constant mass before subsequent use. Resin 2-113 (4.0 g, <0.81 mmol·g⁻¹) was suspended in DMSO (40 mL) followed by the addition of tBuOK (336 mg, 3.0 mmol). After shaking the reaction for 1 h at room temperature, 5-iodo-1-pentene (588 mg, 3.0 mmol) was added to the suspension and the mixture was shaken for 3 h. The resin was filtered, washed and dried as before. Then, it was suspended in toluene and heated at 80° C. After 8 h at this temperature, the resin was filtered and washed several times with more toluene. The combined toluene solutions were evaporated giving pure compound 2-114 as a colourless oil (321 mg, 77%) of 95% purity judged by NMR. ¹H NMR (400 MHz, CDCl₃, 25° C.): δ=6.94 (dt, J=15.7, 6.7 Hz, 1H), 6.39 (d, J=15.2 Hz, 1H), 5.84-5.74 (m, 1H), 5.02 (dd, J=17.4, 1.7 Hz, 1H), 4.97 (d, J=10.1 Hz, 1H), 3.67 (s, 3H), 3.21 (s, 3H), 2.34-2.29 (m, 2H), 2.23-2.18 (m, 2H); ¹³C NMR (100 MHz, CDCl₃, 25° C.): δ=166.8, 146.7, 137.3, 119.1, 115.3, 61.6, 32.3, 31.7, (one carbon is not detected); I.R. (film): ν$_{max}$=2934, 1681, 1638, 1378, 1179 cm⁻¹.

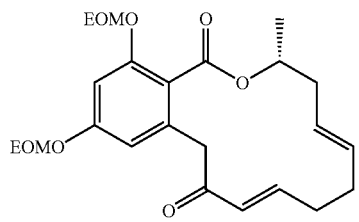

2-120

2,4-Bis-ethoxymethoxy-7-methyl-7,8,11,12-tetrahydro-16H-6-oxa-benzocyclotetradecene-5,15-dione (2-120). A 2 mM solution of crude 2-119 (1.5 mmol) in anhydrous toluene (750 mL) was treated with 10% mol of catalyst Grubbs' II (139 mg, 0.15 mmol), and heated at 80° C. overnight. The crude reaction mixture was then passed through a pad of silica, which was washed with CH₂Cl₂. The combined filtrates were concentrated under reduced pressure. Purification by flash chromatography (silica gel, 0-25% EtOAc/cyclohexane gradient) afforded pure 2-120 (260 mg, 40% over two steps). ¹H NMR (400 MHz, C₆D₆, 25° C.): δ=7.08 (d, J=2.2 Hz, 1H), 7.01 (d, J=2.2 Hz, 1H), 6.93-6.86 (m, 1H), 6.17 (d, J=16.1 Hz, 1H), 5.34-4.90 (m, 7H), 4.41 (d, J=14.5 Hz, 1H), 3.75 (d, J=14.5 Hz, 1H), 3.59-3.45 (m, 4H), 2.27-2.12 (m, 2H), 1.95-1.61 (m, 4H), 1.45 (d, J=6.2 Hz, 3H), 1.07 (t, J=7.0 Hz, 3H), 1.07 (t, J=7.0 Hz, 3H); ¹³C NMR (100 MHz, C₆D₆, 25° C.): δ=196.0, 167.2, 159.5, 156.6, 147.6, 135.8, 131.5, 130.2, 128.5, 119.1, 109.7, 102.3, 93.3, 92.9, 71.0, 64.2, 64.0, 44.5, 39.6, 30.9, 30.2, 20.1, 14.8, 14.8; I.R. (film): ν$_{max}$=2976, 1717, 1602, 1438, 1284, 1155, 1110, 1036, 1018 cm⁻¹; HRMS (ESI-TOF): m/z: calculated for C₂₄H₃₂O₇Na: 455.2040, found 455.2135 [M+Na⁺]. (−)-(2R): [α]$^{25}_D$=0.3 (c 1.00, CHCl₃).

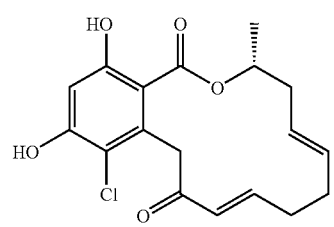

2-85

Pochonin D

Pochonin D (2-85) using polymer-bound reagents: PS-TsOH (300 mg, 3.2 mmol·g⁻¹) was added to a solution of compound 2-112 (50 mg, 0.1 mmol) in MeOH (3 mL) of and the suspension was shaken at 40° C. for 4 h. The reaction mixture was then filtered and the methanolic solution concentrated under reduced pressure. Purification by flash chromatography (silica gel, 0-20% EtOAc/cyclohexane gradient) afforded synthetic pochonin D 2-85 (32 mg, 90%).

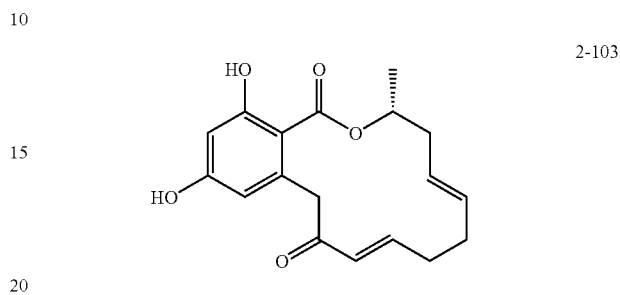

Monocillin II

Monocillin II (2-103) using polymer-bound reagents: PS-TsOH (145 mg, 3.2 mmol·g⁻¹) was added to a solution of compound 2-120 (20 mg, 0.05 mmol) in MeOH (1.5 mL) and the suspension was shaken at 40° C. for 4 h. The reaction mixture was then filtered and the methanolic solution concentrated under reduced pressure. Purification by flash chromatography (silica gel, 0-20% EtOAc/cyclohexane gradient) afforded synthetic monocillin II 2-103 (14 mg, 92%). ¹H NMR (400 MHz, C₆D₆, 25° C.): δ=12.49 (s, 1H), 6.70-6.62 (m, 1H), 6.49 (d, J=2.9 Hz, 1H), 6.09 (d, J=2.4 Hz, 1H), 5.86 (d, J=15.2 Hz, 1H), 5.08-4.95 (m, 2H), 4.82-4.75 (m, 1H), 4.14 (d, J=16.8 Hz, 1H), 3.71 (d, J=17.0 Hz, 1H), 2.64-2.57 (m, 1H), 1.83-1.76 (m, 3H), 1.74-1.66 (m, 2H), 0.97 (d, J=6.4 Hz, 3H); ¹³C NMR (100 MHz, C₆D₆, 25° C.): δ=195.7, 170.3, 166.5, 161.3, 146.1, 140.5, 131.7, 129.9, 126.5, 112.4, 102.8, 72.2, 49.1, 36.6, 31.0, 30.6, 17.5, (one carbon is not detected); I.R. (KBr): ν$_{max}$=2936, 1654, 1603, 1347, 1313, 1239 cm⁻¹; HRMS (ESI-TOF): m/z: calculated for C₁₈H₂₁O₅ requires 317.3980, found 317.3978 [M+H⁺]. (+)-(2R): [α]$^{25}_D$=+40.6 (c 0.18, CHCl₃).

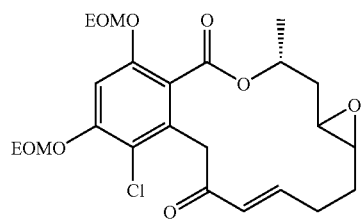

2-123

Macrocycle 2-122: To a solution of compound 2-112 (50 mg, 0.11 mmol) in CH₃CN (5 mL) at 0° C. was added freshly made DMDO (275 μL, 0.11 mmol, 0.04 M in acetone) and the mixture was stirred for 1.5 h. After evaporation of the solvents under reduced pressure, purification by flash chromatography (silica gel, 0-70% Et₂O/hexane gradient) afforded compound 2-122 (41 mg, 79%) as a 1:1 mixture of two diastereoisomers. ¹H NMR (400 MHz, CDCl₃, 25° C.): δ=7.12 (s, 1H), 7.11 (s, 1H), 6.90-6.76 (m, 2H), 6.11 (d, J=15.6 Hz, 1H), 6.05 (d, J=15.8 Hz, 1H), 5.37-5.27 (m, 6H), 5.26-5.21 (m, 4H), 4.14 (d, J=16.9 Hz, 1H), 4.12 (d, J=17.4 Hz, 1H), 4.04 (d, J=17.2 Hz, 1H), 3.82-3.70 (m, 9H), 2.81-2.78 (m, 1H), 2.74-2.72 (m, 1H), 2.67-2.62 (m, 2H), 2.38-2.11 (m, 8H), 2.05-2.03 (m, 1H), 2.03-2.00 (m, 1H), 1.74-1.60 (m, 2H), 1.41 (d, J=7.2 Hz, 3H), 1.39 (d, J=6.2 Hz, 3H), 1.27-1.22 (m, 12H); $^{13}$C NMR (100 MHz, CDCl$_3$, 25° C.): δ=195.1 (×2), 166.7, 166.3, 154.9, 154.8, 154.0, 153.5, 147.8, 147.4, 132.9, 132.4, 129.1, 129.0, 119.7 (×2), 118.0, 117.9, 102.9, 102.8, 93.9 (×2), 93.6 (×2), 71.1, 70.4, 64.8 (×2), 64.6 (×2), 58.4, 57.6, 56.9, 55.1, 43.4 (×2), 39.0, 37.9, 29.9, 29.7, 27.9 (×2), 18.4, 18.0, 15.0 (×4); HRMS (ESI-TOF): m/z: calculated for C$_{24}$H$_{32}$ClO$_8$: 483.1780, found 483.1814 [M+H$^+$].

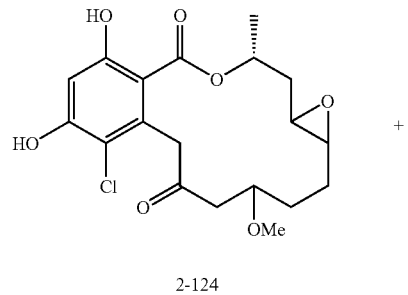

2-124

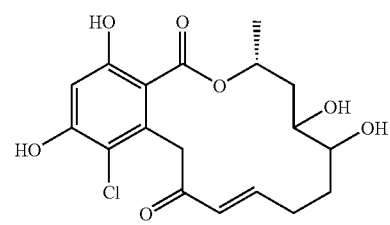

2-125

Macrocycles 2-124 and 2-125: PS-TsOH (264 mg, 3.2 mmol·g$^{-1}$) was added to a solution of compound 2-123 (41 mg, 85 mmol) in MeOH (3 mL) and the suspension was shaken at 40° C. until consumption of all starting material (~1 h). The reaction mixture was filtered and the methanolic solution concentrated under reduced pressure. L.C./M.S. analysis of the crude mixture showed clearly 2 peaks corresponding to methanol addition on the conjugated olefin (2-124) and opening of the epoxide as a diol (2-125).

2-125: $^1$H NMR (400 MHz, CD$_3$OD, 25° C.): δ=7.19 (m, 1H), 6.89-6.81 (m, 1H), 6.52 (s, 1H), 6.47 (s, 1H), 6.20 (d, J=16.1 Hz, 1H), 6.04 (d, J=15.6 Hz, 1H), 5.54-5.49 (m, 1H), 5.43-5.36 (m, 1H), 4.50 (d, J=17.7 Hz, 1H), 4.46 (d, J=17.7 Hz, 1H), 4.39 (d, J=17.2 Hz, 1H), 4.07 (d, J=17.2 Hz, 1H), 3.80-3.64 (m, 2H), 3.51-3.46 (m, 2H), 2.62-2.58 (m, 1H), 2.39-2.30 (m, 2H), 2.27-2.18 (m, 1H), 2.08-2.00 (m, 2H), 2.00-1.85 (m, 4H), 1.44 (d, J=6.4 Hz, 6H); HRMS (ESI-TOF): m/z: calculated for C$_{18}$H$_{22}$ClO$_7$: 385.1054, found 385.0944 [M+H$^+$].

2-124: compound 2-124 which was characterized as the MeOH-addition on the α,β-conjugated system based on the loose of olefinic protons in the NMR (a detailed assignment is not possible as product 2-124 represents a mixture of 4 compounds); HRMS (ESI-TOF): m/z: calculated for C$_{19}$H$_{24}$ClO$_7$: 399.1211, found 399.1030 [M+H$^+$].

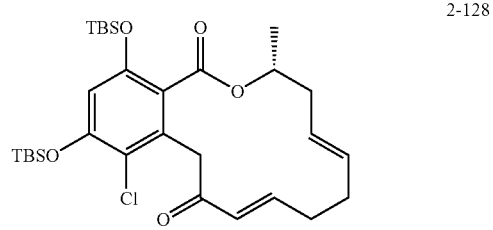

2-128

Macrocycle 2-128: A 2 mM solution of compound 2-127 (140 mg, 0.23 mmol) in anhydrous toluene (115 mL) was treated with 10% mol of catalyst Grubbs' II (18.4 mg, 0.023 mmol) and heated up to 80° C. for 12 h. The reaction mixture was then filtered through a pad of silica, which was washed with CH$_2$Cl$_2$. The combined filtrates were concentrated under reduced pressure. Purification by flash chromatography (silica gel, 0-25% EtOAc/hexane gradient) afforded macrocycle 2-128 (116 mg, 87%). $^1$H NMR (400 MHz, CDCl$_3$, 25° C.): δ=6.71 (dt, J=15.3, 7.3 Hz, 1H), 6.45 (s, 1H), 5.81 (d, J=15.3 Hz, 1H), 5.25 (s, 2H), 5.04-5.03 (m, 1H), 3.89 (d, J=17.4 Hz, 1H), 3.57 (d, J=17.4 Hz, 1H), 2.31-2.04 (m, 6H), 1.35 (d, J=6.4 Hz, 3H), 1.03 (s, 9H), 0.99 (s, 9H), 0.28-0.24 (m, 12H); $^{13}$C NMR (100 MHz, CDCl$_3$, 25° C.): δ=195.8, 166.8, 152.9, 151.7, 146.5, 132.7, 131.9, 128.6, 126.8, 122.8, 119.7, 110.7, 71.9, 45.6, 38.5, 30.9, 25.7 (×4), 25.6 (×4), 18.7, 18.3, −4.1 (×2), −4.4 (×2); HRMS (ESI-TOF): m/z: calculated for C$_{30}$H$_{47}$ClO$_5$Si$_2$Na: 601.2543, found 601.2568 [M+Na$^+$].

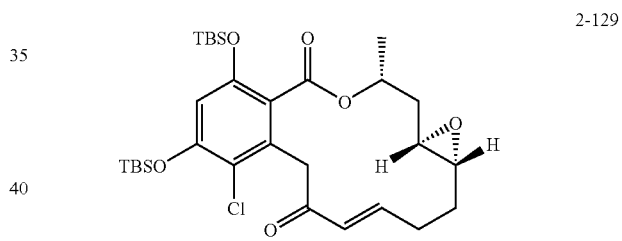

2-129

Macrocycle 2-129: An aqueous Na$_2$.EDTA solution (700 µL, 4×10$^{-4}$M) was added to a solution of compound 2-128 (80 mg, 0.14 mmol) in a 2:1 mixture of dimethoxymethane/acetonitrile (2.1 mL). The resulting mixture was cooled to 0° C. and treated with trifluoroacetone (150 µL) added via a precooled syringe. A mixture of sodium bicarbonate (88 mg, 1.05 mmol) and Oxone (430 mg, 0.70 mmol) was added in portions over a period of ~1 h to this homogeneous solution. The reaction was followed by TLC and found to be complete in 2 h. The reaction mixture was then poured into water (10 mL), extracted with CH$_2$Cl$_2$ (20 mL) and dried over Na$_2$SO$_4$. Removal of the solvent under reduced pressure afforded pure compound 2-129 (66 mg, 93%) as a mixture of 2 diastereoisomers in a 3:1 ratio. $^1$H NMR (400 MHz, CDCl$_3$, 25° C.): δ=6.90-6.77 (m, 1.33H), 6.45 (s, 1.33H), 6.06 (d, J=15.8 Hz, 1.33H), 5.31-5.29 (m, 1H), 5.29-5.21 (m, 0.33H), 4.03 (d, J=18.1 Hz, 1.33H), 3.63 (d, J=17.6 Hz, 1H), 2.82-2.80 (m, 1.33H), 2.74-2.71 (m, 1.33H), 2.62-2.60 (m, 1.33H), 2.41-2.11 (m, 4.6H), 2.02-1.95 (m, 0.33H), 1.80-1.78 (m; 1H), 1.78-1.68 (m, 0.7H), 1.41 (d, J=6.4 Hz, 3.9H), 1.05 (s, 12H), 0.97 (s, 12H), 0.26 (s, 16H); $^{13}$C NMR (100 MHz, CDCl$_3$, 25° C.): δ=195.4, 195.1, 167.0, 166.2, 153.1 (×2), 152.1, 151.5, 147.8, 146.9, 132.9, 132.2, 129.0, 128.3, 122.2, 121.4, 120.0, 119.7, 110.6, 110.3, 71.3, 70.1, 58.2, 57.9, 56.6, 55.2, 44.7, 43.9, 38.7, 37.6, 30.1, 29.4, 28.3, 27.5, 25.7 (×4), 25.6 (×4), 25.5 (×4), 25.4 (×4), 20.8, 17.8, −3.9, −4.0, −4.3 (×3), −4.4 (×3); HRMS (ESI-TOF): m/z: calculated for $C_{30}H_{48}O_6ClSi_2$: 595.2672, found 595. 2698 [M+H$^+$].

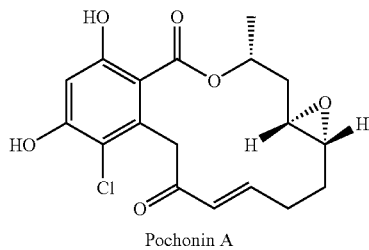

Pochonin A 2-122

Pochonin A (2-122): TBAF (244 μL, 1M solution in hexane, 0.24 mmol) was added to a solution of compound 2-129 (66 mg, 0.11 mmol) in THF (2 mL) and the mixture was stirred at room temperature for 20 min. The reaction was then quenched with saturated NH$_4$Cl$_{aq}$. (8 mL), extracted several times with EtOAc (10 mL) and dried over Na$_2$SO$_4$. Concentration under reduced pressure followed by purification by flash chromatography (silica gel, 0-70% Et$_2$O/hexane) afforded two different diastereoisomers pochonin A (2-122) and its diastereoisomer 2-122b as a 3:1 mixture (80% yield) The isomers were separated by preparative TLC with a 3:1 mixture of Et$_2$O/hexane. $^1$H NMR (400 MHz, [D$_6$]DMSO, 25° C.): δ=10.81 (s, 1H), 10.74 (s, 1H), 6.97-6.89 (m, 1H), 6.53 (s, 1H), 6.08 (d, J=15.8 Hz, 1H), 5.15-5.13 (m, 1H), 4.19 (d, J=17.5 Hz, 1H), 4.09 (d, J=17.5 Hz, 1H), 2.81 (s, 1H), 2.60 (m, 1H), 2.44-2.40 (m, 2H), 2.30-2.22 (m, 2H), 1.80-1.78 (m, 2H), 1.32 (d, J=6.4 Hz, 3H); $^1$H NMR (400 MHz, CDCl$_3$, 25° C.): δ=11.85 (s, 1H), 6.94-6.87 (m, 1H), 6.70 (s, 1H), 6.14 (s, 1H), 6.12 (d, J=16.4 Hz, 1H), 5.32-5.31 (m, 1H), 4.53 (d, J=18.1 Hz, 1H), 4.27 (d, J=18.1 Hz, 1H), 2.77 (s, 1H), 2.58-2.56 (m, 2H), 2.47-2.43 (m, 1H), 2.35-2.28 (m, 1H), 2.11-2.07 (m, 1H), 1.93-1.86 (m, 1H), 1.51 (d, J=6.4 Hz, 3H), 0.94-0.90 (m, 1H); $^{13}$C NMR (100 MHz, CDCl$_3$, 25° C.): δ=195.0, 170.0, 164.1, 156.4, 147.5, 135.7, 129.9, 115.0, 107.3, 103.8, 72.2, 57.0, 55.5, 45.1, 36.3, 30.9, 29.1, 17.9; HRMS (ESI-TOF): m/z: calculated for $C_{18}H_{19}ClO_6Na$: 389.0762, found 389.0724 [M+Na$^+$]. (−)-(2R,4R,5R): $[α]^{25}_D$=−7.0 (c 0.11, CHCl$_3$).

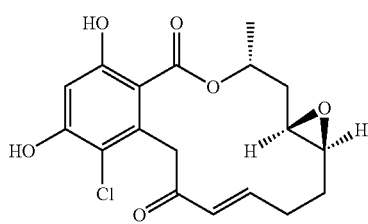

2-122b

Compound 2-122b: $^1$H NMR (400 MHz, [D$_6$]DMSO, 25° C.): δ=10.74 (s, 1H), 10.39 (s, 1H), 6.94-6.89 (m, 1H), 6.52 (s, 1H), 6.02 (d, J=16.4 Hz, 1H), 5.18 (m, 1H), 4.32 (d, J=17.5 Hz, 1H), 3.96 (d, J=17.5 Hz, 1H), 2.82 (s, 1H), 2.68 (s, 1H), 2.34-2.26 (m, 3H), 1.86-1.83 (m, 1H), 1.70-1.63 (m, 1H), 1.22 (d, J=5.8 Hz, 3H), 1H masked by the solvent peak; $^1$H NMR (400 MHz, CDCl$_3$, 25° C.): δ=11.37 (s, 1H), 6.90-6.83 (m, 1H), 6.67 (s, 1H), 6.24 (d, J=16.4 Hz, 1H), 6.08 (s, 1H), 5.39-5.37 (m, 1H), 4.52-4.36 (m, 2H), 2.72-2.62 (m, 2H), 2.56-2.52 (m, 1H), 2.45-2.40 (m, 1H), 2.40-2.37 (m, 1H), 2.08-2.04 (m, 1H), 1.91-1.86 (m, 1H), 1.35 (d, J=6.4 Hz, 3H), 1H masked by the solvent peak; HRMS (ESI-TOF): m/z: calculated for $C_{18}H_{19}ClO_6Na$: 389.0762; found 389.0796 [M+Na$^+$], (+)-(2R,4S,5S): $[α]^{25}_D$=+13.8 (c 0.13, CHCl$_3$).

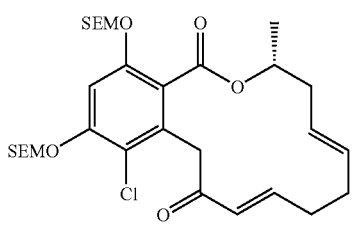

2-132

Macrocycle 2-132: A 2 mM solution of compound 2-131 (166 mg, 0.26 mmol) in anhydrous toluene (130 mL) was treated with 10% mol of Grubbs' II (20.8 mg, 0.026 mmol) and heated up to 80° C. for 12 h. The reaction mixture was then filtered through a pad of silica, which was washed with CH$_2$Cl$_2$. The combined filtrates were concentrated under reduced pressure. Purification by flash chromatography (silica gel, 0-25% EtOAc/hexane gradient) afforded macrocycle 2-132 (136 mg, 87%). $^1$H NMR (400 MHz, CDCl$_3$, 25° C.): δ=7.08 (s, 1H), 6.77-6.71 (m, 1H), 5.89 (d, J=15.2 Hz, 1H), 5.35-5.24 (m, 6H), 5.09-5.05 (m, 1H), 4.02 (d, J=17.0 Hz, 1H), 3.85-3.78 (m, 5H), 2.37-2.08 (m, 6H), 1.39 (d, J=5.8 Hz, 3H), 1.02-0.97 (m, 4H), 0.04 (s, 18H); $^{13}$C NMR (100 MHz, CDCl$_3$, 25° C.): δ=195.7, 166.8, 154.6, 153.9, 147.0, 132.8, 131.7, 128.6, 127.5, 120.6, 117.8, 102.7, 93.7, 93.3, 71.9, 66.9, 66.6, 44.7, 39.2, 30.8 (×2), 19.5, 18.0, 17.9, −1.4 (×6); HRMS (ESI-TOF): m/z: calculated for $C_{30}H_{47}O_7ClSi_2H_2O$: 628.2649, found 628.2870 [M+H$_2$O]. (−)-(2R): $[α]^{25}_D$=−16.3 (c 0.85, CHCl$_3$).

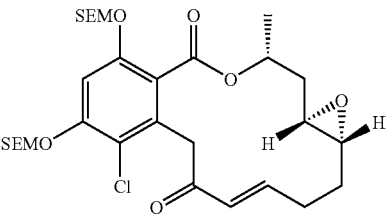

2-133

Macrocycle 2-133: An aqueous Na$_2$.EDTA solution (350 μL, 4×10$^{-4}$M) was added to a solution of compound 2-132 (40 mg, 65 mop in a 2:1 mixture of dimethoxymethane/acetonitrile (1.1 mL). The resulting solution was cooled to 0° C. and trifluoroacetone (75 μL) was added via a precooled syringe. A mixture of sodium bicarbonate (44 mg, 0.5 mmol) and Oxone (215 mg, 0.35 mmol) was then added in portions over a period of ~1 h to this homogeneous solution. The reaction was followed by TLC and found to be complete in 2 h. The reaction mixture was then poured into water (5 mL), extracted with CH$_2$Cl$_2$ (10 mL) and dried over Na$_2$SO$_4$. Removal of the solvent under reduced pressure afforded pure compound 2-133 (34 mg, 82%) as a 1:1 mixture of two diastereoisomers. $^1$H NMR (400 MHz, CDCl$_3$, 25° C.): δ=7.11 (s, 1H), 7.09 (s, 1H), 6.91-6.76 (m, 2H), 6.12 (d, J=15.8 Hz, 1H), 6.06 (d, J=15.8 Hz, 1H), 5.36-5.31 (m, 6H), 5.23-5.22 (m, 4H), 4.15 (d, J=16.9 Hz, 1H), 4.13 (d, J=16.0 Hz, 1H), 4.05 (d, J=17.5 Hz, 1H), 3.85-3.75 (m, 9H), 2.81-

2.79 (m, 1H), 2.75-2.73 (m, 1H), 2.68-2.62 (m, 2H), 2.42-2.29 (m, 10H), 1.72-1.60 (m, 2H), 1.41 (d, J=7.6 Hz, 3H), 1.39 (d, J=6.4 Hz, 3H), 1.02-0.96 (m, 8H), 0.03 (s, 36H); $^{13}$C NMR (100 MHz, CDCl$_3$, 25° C.): δ=195.1 (×2), 166.8, 166.3, 154.9 (×2), 154.2, 153.7, 147.8, 147.4, 132.9, 132.4, 129.1, 129.0, 119.8, 119.6, 117.9, 117.8, 102.8, 102.7, 93.7 (×2), 93.4 (×2), 71.1, 70.3, 66.9, 66.8, 66.6, 66.5, 58.4, 57.6, 56.9, 55.1, 43.5 (×2), 38.9, 37.9, 29.9, 29.7, 27.9 (×2), 20.7 (×2), 18.4, 18.0, 17.9 (×2), −1.40 (×12); HRMS (ESI-TOF): m/z: calculated for C$_{30}$H$_{48}$O$_8$ClSi$_2$: 627.2571, found 627.2551 [M+H$^+$].

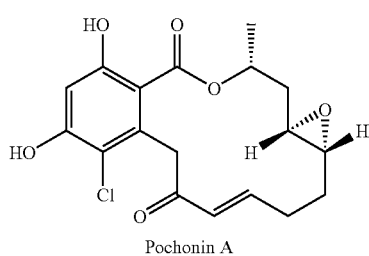

Pochonin A

Pochonin A (2-122) from macrocycle 2-133: A solution of compound 2-133 (21 mg, 33 µmol) in CH$_2$Cl$_2$ (2.5 mL) was treated at room temperature with MgBr$_2$·Et$_2$O (69 mg, 0.27 mmol). The reaction was followed by L.C./M.S. until bromohydrine started appearing (~1 h). The reaction was then diluted with EtOAc (5 mL), washed with saturated NH$_4$Cl$_{aq}$. (5 mL) and dried over MgSO$_4$. After concentration under reduced pressure, purification by flash chromatography (silica gel, 0-70% Et$_2$O/hexane gradient) afforded pochonin A (2-122) (8.6 mg, 70%) as a 1:1 mixture of diastereoisomers.

General procedure for the synthesis of compounds 2-110a-g and 2-117a-g: A solution of acid 2-95a or 2-95b (1.0 equiv.), homoallylic alcohol (R)-120a-g or (S)-120a-g (1.0 equiv.) and tris-(3-chlorophenyl)phosphine (2.0 equiv.) in anhydrous toluene (0.05 M) was treated at room temperature with PS-DEAD (2.5 equiv., 1.3 mmol·g$^{-1}$). After stirring for 30 min, the reaction mixture was filtered on silica and washed with hexane/EtOAc (10:1, 100 mL) and hexane/EtOAc (3:1, 100 mL). The 3:1 mixture was concentrated under reduced pressure to yield compound 2-115a-g or 2-116a-g (60-80%). Without further purification, compound 2-115a-g or 2-116a-g (1.0 equiv.) and TBAI (catalytic amount) were dissolved in DMF (0.15 M) and treated with diisopropylethylamine (4.0 equiv.) and chloromethylethyl ether (4.0 equiv.). After stirring overnight at 80° C., the reaction mixture was diluted with EtOAc and washed several times with a saturated NH$_4$Cl$_{aq}$. solution. The organic phase was dried over MgSO$_4$ and concentrated under reduced pressure to yield compounds 2-110a-g and 2-117a-g (80-90%).

General procedure for the synthesis of compounds 2-119a-g and 2-140a-g: A solution of compound 2-110a-g or 2-117a-g (1.0 equiv.) in anhydrous THF (0.2 M) cooled at −78° C. was treated with freshly prepared LDA (2.0 equiv.). Immediately after, the α,β-unsaturated Weinreb amide 2-114 was added to the cooled solution (1.0 equiv.). The resulting mixture was then stirred for 10 min at −78° C. and quenched by addition of Amberlite resin (20 equiv.). Upon warming up to room temperature, the reaction was filtered on a pad of silica and washed with EtOAc. Concentration under reduced pressure afforded the desired compound 2-118a-g or 2-119a-g. This compound was used directly in the metathesis reaction without any further purification. When X=H, 20% of the corresponding 1,4-addition compound was observed and a fraction of the mixture was purified for characterization of compounds 2-119a-g and 2-140a-g (silica gel, 0-20% EtOAc/hexane gradient).

General procedure for the metathesis reaction: A solution of crude 2-118a-g or 2-119a-g (or mixture 2-119a-g or 2-140a-g when X=H) in anhydrous toluene (2 mM) was treated with Grubbs' II (0.10 equiv.) and heated at 80° C. for 12 h. The reaction was cooled down to room temperature and the mixture was filtered through a pad of silica gel, washed with CH$_2$Cl$_2$ followed by a mixture EtOAc/cyclohexane 1:1, and concentrated under reduced pressure. Purification by flash chromatography (silica gel, 0-25% EtOAc/cyclohexane gradient) afforded compound 2-112a-g or 2-120a-g (and 2-121a-g) (38-70% over two steps).

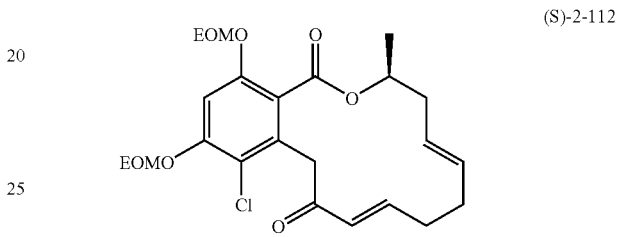

Compound (S)-2-112: $^1$H NMR (400 MHz, CDCl$_3$, 25° C.): δ=7.10 (s, 1H), 6.75-6.71 (m, 1H), 5.88 (d, J=15.8 Hz, 1H), 5.32 (s, 2H), 5.27-5.20 (m, 2H), 5.25 (s, 2H), 5.08-5.04 (m, 1H), 4.01 (d, J=17.0 Hz, 1H), 3.82-3.73 (m, 5H), 2.36-2.32 (m, 2H), 2.26-2.20 (m, 3H), 2.12-2.05 (m, 2H), 1.38 (d, J=5.8 Hz, 3H), 1.25 (t, J=7.0 Hz, 3H), 1.24 (t, J=7.0 Hz, 3H); $^{13}$C NMR (100 MHz, CDCl$_3$, 25° C.): δ=195.5, 166.7, 154.6, 153.8, 147.1, 132.8, 131.6, 128.6, 127.5, 120.7, 117.8, 103.0, 94.0, 93.7, 72.0, 64.8, 64.6, 44.7, 39.1, 30.8, 19.4, 15.0, 2C missing; HRMS (ESI-TOF): m/z: calculated for C$_{24}$H$_{31}$O$_7$ClNa: 489.1551, found 489.1651 [M+Na$^+$]. (+)-(2S): [α]$^{25}_D$=+25.0 (c 1.00, CHCl$_3$).

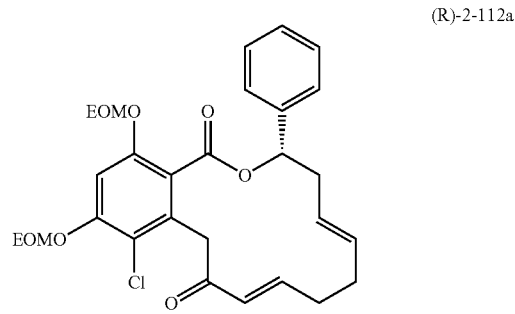

Compound (R)-2-112a: $^1$H NMR (400 MHz, CDCl$_3$, 25° C.): δ=7.49-7.47 (m, 2H), 7.40-7.29 (m, 3H), 7.10 (s, 1H), 6.84-6.77 (m, 1H), 5.98 (d, J=15.2 Hz, 1H), 5.78 (d, J=8.8 Hz, 1H), 5.44-5.30 (m, 4H), 5.15 (d, J=7.0 Hz, 1H), 5.05 (d, J=6.8 Hz, 1H), 4.07 (d, J=17.0 Hz, 1H), 3.90 (d, J=17.0 Hz, 1H), 3.80 (d, J=7.0 Hz, 2H), 3.60-3.51 (m, 2H), 2.68-2.62 (m, 1H), 2.50-2.47 (m, 1H), 2.38-2.29 (m, 2H), 2.14-2.02 (m, 2H), 1.25 (t, J=7.0 Hz, 3H), 1.17 (t, J=7.0 Hz, 3H); $^{13}$C NMR (100 MHz, CDCl$_3$, 25° C.): δ=195.7, 166.7, 154.8, 154.2, 147.3, 140.7, 133.3, 132.1, 128.5, 128.3 (×2), 128.2, 127.9, 127.7, 126.7 (×2), 120.1, 118.1, 102.9, 93.9, 93.4, 77.4, 64.8, 64.4, 44.5, 40.5, 30.7, 15.0, 14.9; HRMS (ESI-TOF): m/z: calcu-

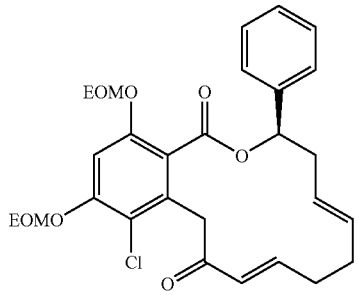

(S)-2-112a

Compound (S)-2-112a: $^1$H NMR (400 MHz, CDCl$_3$, 25° C.): δ=7.53-7.51 (m, 2H), 7.44-7.33 (m, 3H), 7.14 (s, 1H), 6.88-6.81 (m, 1H), 6.02 (d, J=15.2 Hz, 1H), 5.78 (dd, J=10.5, 1.8 Hz, 1H), 5.46-5.33 (m, 4H), 5.19 (d, J=7.0 Hz, 1H), 5.09 (d, J=7.6 Hz, 1H), 4.10 (d, J=17.0 Hz, 1H), 3.94 (d, J=17.5 Hz, 1H), 3.83 (d, J=7.0 Hz, 2H), 3.64-3.55 (m, 2H), 2.70-2.64 (m, 1H), 2.54-2.50 (m, 1H), 2.37-2.33 (m, 2H), 2.15-2.08 (m, 2H), 1.29 (t, J=7.3 Hz, 3H), 1.21 (t, J=7.0 Hz, 3H); $^{13}$C NMR (100 MHz, CDCl$_3$, 25° C.): δ=195.7, 166.7, 154.8, 154.2, 147.3, 140.7, 133.2, 132.1, 128.5, 128.2, 127.9, 127.7, 126.7, 120.1, 118.0, 102.8, 93.9, 93.5, 77.4, 64.8, 64.4, 44.5, 40.5, 30.7, 15.0, 14.9, (one carbon is not detected); HRMS (ESI-TOF): m/z: calculated for C$_{29}$H$_{33}$O$_7$ClNa: 551.1680, found 551.1704 [M+Na$^+$]. [α]$^{25}_D$=+48.8 (c 1.00, CHCl$_3$).

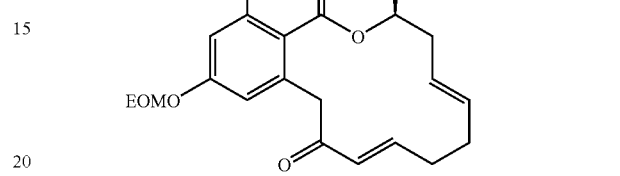

(R)-2-112d

Compound (R)-2-112d: $^1$H NMR (400 MHz, CDCl$_3$, 25° C.): δ=7.14 (s, 1H), 6.72-6.66 (m, 1H), 5.88 (d, J=15.2 Hz, 1H), 5.33-5.17 (m, 6H), 4.92-4.88 (m, 1H), 4.21 (d, J=17.0 Hz, 1H), 3.92 (d, J=17.0 Hz, 1H), 3.79-3.67 (m, 4H), 2.33-2.17 (m, 5H), 2.07-1.96 (m, 2H), 1.23 (t, J=7.0 Hz, 3H), 1.21 (t, J=7.0 Hz, 3H), 1.00 (d, J=5.8 Hz, 6H); $^{13}$C NMR (100 MHz, CDCl$_3$, 25° C.): δ=195.7, 167.1, 154.7, 154.4, 147.4, 133.7, 131.2, 128.8, 128.4, 119.7, 118.0, 102.7, 93.9, 93.5, 80.0, 64.8, 64.5, 44.1, 32.3, 31.2, 30.7, 30.6, 18.3, 17.2, 15.0, 14.9; HRMS (ESI-TOF): m/z: calculated for C$_{26}$H$_{35}$O$_7$ClNa: 517.1964, found 517.1844 [M+Na$^+$]. [α]$^{25}_D$=+21.3 (c 1.00, CHCl$_3$).

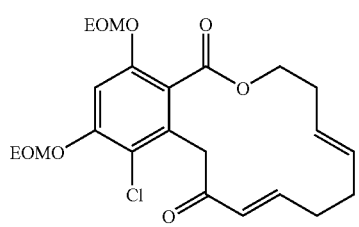

2-112g

Compound 2-112g: $^1$H NMR (400 MHz, CDCl$_3$, 25° C.): δ=7.12 (s, 1H), 6.76-6.70 (m, 1H), 5.87 (d, J=15.0 Hz, 1H), 5.33 (s, 2H), 5.26 (s, 2H), 5.24-5.16 (m, 2H), 4.25 (t, J=5.1 Hz, 2H), 3.82-3.73 (m, 6H), 2.40-2.36 (m, 2H), 2.16-2.13 (m, 4H), 1.27-1.23 (m, 6H); $^{13}$C NMR (100 MHz, CDCl$_3$, 25° C.): δ=195.2, 167.2, 154.6, 153.4, 146.8, 132.3, 131.3, 128.9, 128.5, 121.0, 117.8, 103.0, 94.0, 93.7, 64.8, 64.7, 64.6, 45.4, 31.9, 31.0, 30.7, 15.0, 15.0; HRMS (ESI-TOF): m/z: calculated for C$_{23}$H$_{30}$O$_7$Cl: 453.1675, found 453.1672 [M+H$^+$].

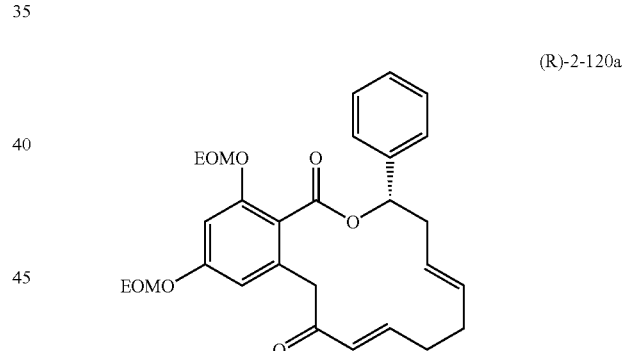

(S)-2-120

Compound (S)-2-120: $^1$H NMR (400 MHz, CDCl$_3$, 25° C.): δ=6.81-6.72 (m, 1H), 6.74 (d, J=1.8 Hz, 1H), 6.56 (d, J=1.8 Hz, 1H), 5.98 (d, J=15.8 Hz, 1H), 5.38-5.33 (m, 2H), 5.22-5.13 (m, 5H), 4.06 (d, J=14.6 Hz, 1H), 3.75-3.65 (m, 4H), 3.46 (d, J=14.6 Hz, 1H), 2.37-2.22 (m, 4H), 2.18-2.02 (m, 2H), 1.39 (d, J=5.8 Hz, 3H), 1.22 (t, J=7.0 Hz, 3H), 1.18 (t, J=7.0 Hz, 3H); $^{13}$C NMR (100 MHz, CDCl$_3$, 25° C.): δ=197.4, 167.7, 159.0, 156.1, 148.9, 135.0, 131.7, 129.8, 128.5, 118.5, 109.7, 102.2, 93.4, 93.0, 71.5, 64.5, 64.4, 44.3, 39.5, 30.9, 30.6, 20.2, 15.0 (×2); HRMS (ESI-TOF): m/z: calculated for C$_{24}$H$_{32}$O$_7$Na: 455.2040, found 455.1901 [M+Na$^+$]. (+)-(2S): [α]$^{25}_D$=+59.5 (c 1.00, CHCl$_3$).

(R)-2-120a

Compound (R)-2-120a: $^1$H NMR (400 MHz, CDCl$_3$, 25° C.): δ=7.56-7.54 (m, 2H), 7.41-7.29 (m, 3H), 6.89-6.82 (m, 1H), 6.78 (d, J=2.3 Hz, 1H), 6.61 (d, J=1.8 Hz, 1H), 6.06 (d, J=16.4 Hz, 1H), 5.98 (dd, J=11.7, 2.4 Hz, 1H), 5.53-5.51 (m, 2H), 5.20 (d, J=7.0 Hz, 1H), 5.17 (d, J=6.4 Hz, 1H), 5.07 (d, J=7.0 Hz, 1H), 4.96 (d, J=7.0 Hz, 1H), 4.20 (d, J=14.6 Hz, 1H), 3.73-3.68 (m, 2H), 3.54-3.45 (m, 3H), 2.71-2.66 (m, 1H), 2.55-2.51 (m, 1H), 2.38-2.32 (m, 2H), 2.23-2.06 (m, 2H), 1.22 (t, J=7.0 Hz, 3H), 1.14 (t, J=7.0 Hz, 3H); $^{13}$C NMR (100 MHz, CDCl$_3$, 25° C.): δ=197.6, 167.4, 159.3, 156.6, 149.0, 140.8, 135.6, 132.2, 129.9, 128.5, 128.2 (×2), 127.9, 126.9 (×2), 117.9, 109.9, 102.3, 93.2, 93.0, 76.6, 64.4, 64.3, 44.4, 40.5, 31.0, 30.6, 15.0, 14.9; HRMS (ESI-TOF): m/z: calculated for C$_{29}$H$_{34}$O$_7$Na: 517.2197, found 517.2062 [M+Na$^+$]. [α]$^{25}_D$=−108.3 (c 1.00, CHCl$_3$).

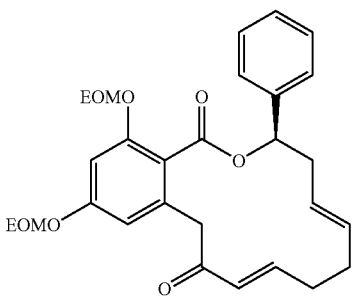

(S)-2-120a

Compound (S)-2-120a: $^{1}$H NMR (400 MHz, CDCl$_{3}$, 25° C.): δ=7.56-7.54 (m, 2H), 7.41-7.29 (m, 3H), 6.90-6.82 (m, 1H), 6.78 (d, J=2.4 Hz, 1H), 6.61 (d, J=1.8 Hz, 1H), 6.07 (d, J=16.4 Hz, 1H), 5.98 (dd, J=11.4, 2.0 Hz, 1H), 5.53-5.51 (m, 2H), 5.20 (d, J=7.0 Hz, 1H), 5.18 (d, J=7.0 Hz, 1H), 5.07 (d, J=7.0 Hz, 1H), 4.97 (d, J=7.0 Hz, 1H), 4.20 (d, J=14.6 Hz, 1H), 3.74-3.69 (m, 2H), 3.55-3.46 (m, 3H), 2.71-2.66 (m, 1H), 2.55-2.52 (m, 1H), 2.38-2.33 (m, 2H), 2.23-2.09 (m, 2H), 1.22 (t, J=7.0 Hz, 3H), 1.15 (t, J=7.0 Hz, 3H); $^{13}$C NMR (100 MHz, CDCl$_{3}$, 25° C.): δ=197.6, 167.5, 159.3, 156.6, 149.0, 140.8, 135.6, 132.2, 129.9, 128.5, 128.2 (×2), 127.9, 126.9 (×2), 117.9, 110.0, 102.3, 93.2, 93.0, 76.6, 64.4, 64.3, 44.4, 40.5, 31.0, 30.6, 15.0, 14.9; HRMS (ESI-TOF): m/z: calculated for C$_{29}$H$_{34}$O$_{7}$Na: 517.2197, found 517.2049 [M+Na$^{+}$]. [α]$^{25}$$_{D}$=+81.6 (c 1.00, CHCl$_{3}$).

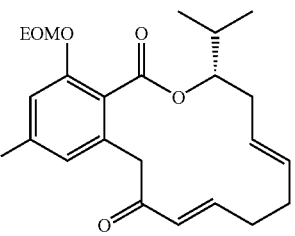

(R)-2-120d

Compound (R)-2-120d: $^{1}$H NMR (400 MHz, CDCl$_{3}$, 25° C.): δ=6.83 (d, J=1.7 Hz, 1H), 6.79-6.72 (m, 1H), 6.61 (d, J=1.2 Hz, 1H), 6.00 (d, J=16.4 Hz, 1H), 5.38-5.36 (m, 2H), 5.26-5.09 (m, 5H), 4.30 (d, J=14.6 Hz, 1H), 3.74-3.67 (m, 4H), 3.46 (d, J=14.6 Hz, 1H), 2.33-2.26 (m, 4H), 2.18-2.14 (m, 2H), 2.06-2.01 (m, 1H), 1.23 (t, J=7.0 Hz, 3H), 1.21 (t, J=7.0 Hz, 3H), 1.06 (d, J=6.6 Hz, 3H), 1.05 (d, J=7.0 Hz, 3H); $^{13}$C NMR (100 MHz, CDCl$_{3}$, 25° C.): δ=197.9, 167.6, 159.2, 156.9, 149.2, 136.4, 131.5, 129.9, 129.2, 117.4, 109.8, 102.0, 93.3, 93.0, 78.9, 64.4 (×2), 44.2, 33.0, 32.0, 31.0, 30.4, 18.3, 17.2, 15.0 (×2); HRMS (ESI-TOF): m/z: calculated for C$_{26}$H$_{36}$O$_{7}$Na: 483.2353, found 483.2215 [M+Na$^{+}$]. [α]$^{25}$$_{D}$=52.8 (c 1.00, CHCl$_{3}$).

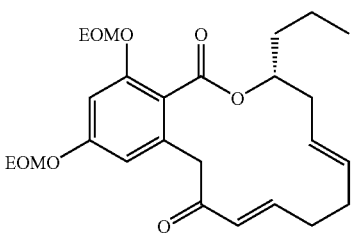

(R)-2-120e

Compound (R)-2-120e: $^{1}$H NMR (400 MHz, CDCl$_{3}$, 25° C.): δ=6.77 (d, J=1.8 Hz, 1H), 6.77-6.70 (m, 1H), 6.57 (d, J=1.7 Hz, 1H), 5.97 (d, J=16.4 Hz, 1H), 5.37-5.32 (m, 2H), 5.21-5.14 (m, 5H), 4.17 (d, J=14.6 Hz, 1H), 3.73-3.65 (m, 4H), 3.45 (d, J=14.6 Hz, 1H), 2.39-2.20 (m, 4H), 2.17-2.00 (m, 2H), 1.78-1.72 (m, 1H), 1.69-1.60 (m, 1H), 1.54-1.44 (m, 2H), 1.22 (t, J=7.0 Hz, 3H), 1.18 (t, J=7.0 Hz, 3H), 0.97 (d, J=7.3 Hz, 3H); $^{13}$C NMR (100 MHz, CDCl$_{3}$, 25° C.): δ=197.7, 167.6, 159.1, 156.6, 149.0, 135.8, 131.5, 129.9, 128.7, 117.9, 109.8, 102.1, 93.3, 93.0, 74.5, 64.4, 64.3, 44.2, 37.3, 37.0, 31.0, 30.5, 18.2, 15.0, 14.9, 14.2. [α]$^{25}$$_{D}$=−1.3 (c 1.00, CHCl$_{3}$).

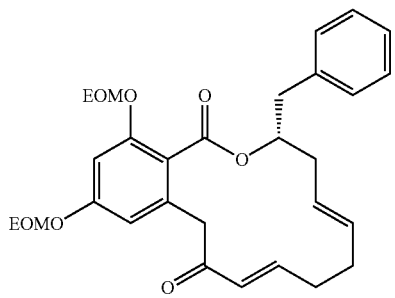

(R)-2-120f

Compound (R)-2-120f: $^{1}$H NMR (400 MHz, CDCl$_{3}$, 25° C.): δ=7.39-7.33 (m, 4H), 7.31-7.27 (m, 1H), 6.82 (s, 1H), 6.82-6.75 (m, 1H), 6.63 (s, 1H), 6.02 (d, J=16.4 Hz, 1H), 5.35-5.29 (m, 2H), 5.27-5.20 (m, 5H), 4.16 (d, J=14.6 Hz, 1H), 3.79-3.70 (m, 4H), 3.52 (d, J=14.6 Hz, 1H), 3.37 (dd, J=13.4, 4.1 Hz, 1H), 2.78 (dd, J=13.5, 9.4 Hz, 1H), 2.37-2.12 (m, 5H), 2.06-2.02 (m, 1H), 1.26 (t, J=7.0 Hz, 3H), 1.24 (t, J=7.0 Hz, 3H); $^{13}$C NMR (100 MHz, CDCl$_{3}$, 25° C.): δ=197.6, 167.8, 159.2, 156.5, 149.0, 137.3, 135.5, 131.8, 129.9, 129.5 (×2), 128.6 (×2), 128.4, 126.7, 118.1, 109.9, 102.3, 93.5, 93.1, 75.8, 64.6, 64.4, 44.4, 41.0, 36.2, 31.0, 30.6, 15.0 (×2); HRMS (ESI-TOF): m/z: calculated for C$_{30}$H$_{36}$O$_{7}$Na: 531.2359, found 531.2350 [M+Na$^{+}$]. [α]$^{25}$$_{D}$=−24.1 (c 0.33, CHCl$_{3}$).

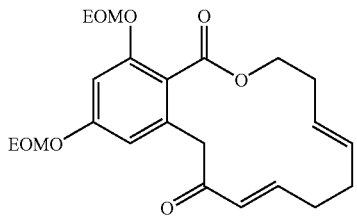

2-120g

Compound 2-120g: $^{1}$H NMR (400 MHz, CDCl$_{3}$, 25° C.): δ=6.85-6.78 (m+s, 2H), 6.56 (d, J=2.1 Hz, 1H), 6.00 (d, J=16.1 Hz, 1H), 5.38-5.34 (m, 2H), 5.23 (s, 2H), 5.19 (s, 2H), 4.33 (t, J=5.4 Hz, 2H), 3.75-3.70 (m, 6H), 2.45-2.41 (m, 2H), 2.19 (bs, 4H), 1.27-1.20 (m, 6H); $^{13}$C NMR (100 MHz, CDCl$_{3}$, 25° C.): δ=197.2, 168.1, 159.1, 155.8, 148.6, 134.5, 131.7, 129.8, 129.1, 118.9, 109.9, 102.4, 93.6, 93.1, 64.5, 64.5, 64.4, 45.4, 31.9, 31.1, 30.8, 15.0, 15.0; HRMS (ESI-TOF): m/z: calculated for C$_{23}$H$_{30}$O$_{7}$Na: 441.1884, found 441.1888 [M+Na$^{+}$].

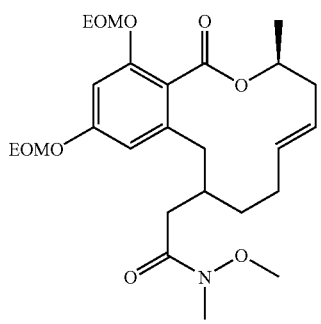

(S)-2-121

Compound (S)-2-121: Mixture of four diastereoisomers; ¹H NMR (400 MHz, CDCl₃, 25° C.): δ=6.77-6.72 (m, 1H), 6.57-6.47 (m, 1H), 5.62-5.35 (m, 3H), 5.24-5.16 (m, 4H), 3.77-3.70 (m, 4H), 3.62-3.60 (m, 1.5H), 3.53-3.49 (m, 1.5H), 3.17-3.11 (m, 3H), 3.04-2.97 (m, 1H), 2.57-2.44 (m, 2H), 2.36-1.99 (m, 6H), 1.37-1.33 (m, 3H), 1.28-1.21 (m, 8H); HRMS (ESI-TOF): m/z: calculated for $C_{26}H_{39}O_8NNa$: 516.2568, found 516.2596 [M+Na⁺].

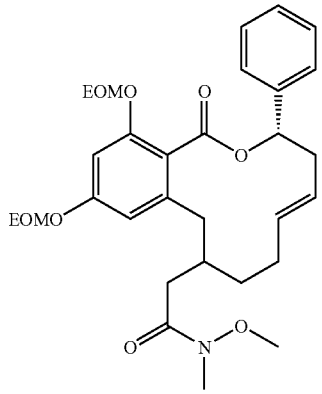

(R)-2-121a

Compound (R)-2-121a: Mixture of four diastereoisomers; ¹H NMR (400 MHz, CDCl₃, 25° C.): δ=7.51-7.42 (m, 2H), 7.38-7.31 (m, 3H), 6.73-6.70 (m, 1H), 6.60-6.49 (m, 1H), 6.45-6.31 (m, 1H), 5.73-5.39 (m, 2H), 5.23-5.00 (m, 4H), 3.75-3.69 (m, 2H), 3.56-3.34 (m, 6H), 3.19-3.09 (m, 3H), 2.66-2.08 (m, 8H), 1.31-1.19 (m, 5H), 1.10-1.04 (m, 3H); HRMS (ESI-TOF): m/z: calculated for $C_{31}H_{41}O_8NNa$: 578.2724, found 578.2715 [M+Na⁺].

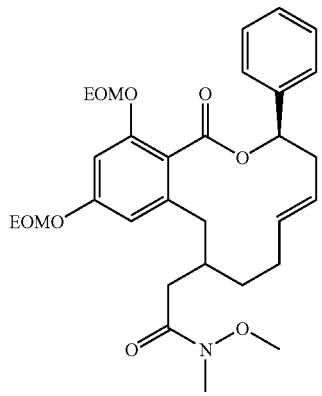

(S)-2-121a

Compound (S)-2-121a: Mixture of four diastereoisomers; ¹H NMR (400 MHz, CDCl₃, 25° C.): δ=7.51-7.42 (m, 2H), 7.38-7.29 (m, 3H), 6.73-6.70 (m, 1H), 6.60-6.49 (m, 1H), 6.45-6.31 (m, 1H), 5.73-5.42 (m, 2H), 5.25-5.01 (m, 4H), 3.76-3.69 (m, 2H), 3.62-3.34 (m, 6H), 3.20-3.09 (m, 3H), 2.66-2.50 (m, 2H), 2.22-2.12 (m, 4H), 1.72-1.66 (m, 2H), 1.31-1.19 (m, 5H), 1.10-1.04 (m, 3H); HRMS (ESI-TOF): m/z: calculated for $C_{31}H_{41}O_8NNa$: 578.2724, found 578.2720 [M+Na⁺].

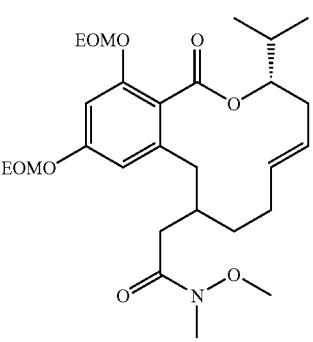

(R)-2-121d

Compound (R)-2-121d: Mixture of four diastereoisomers; ¹H NMR (400 MHz, CDCl₃, 25° C.): δ=6.77 (s, 1H), 6.52 (s, 0.5H), 6.46 (s, 0.5H), 5.59-5.37 (m, 2H), 5.21-5.18 (m, 4H), 5.09-4.92 (m, 1H), 3.75-3.70 (m, 4H), 3.53-3.48 (m, 3H), 3.38-3.34 (m, 1H), 3.19-3.10 (m, 3H), 2.65-2.47 (m, 3H), 2.29-2.04 (m, 6H), 1.89-1.72 (m, 2H), 1.31-1.20 (m, 6H), 1.06-0.96 (m, 6H); HRMS (ESI-TOF): m/z: calculated for $C_{28}H_{43}O_8NNa$: 544.2881, found 544.2907 [M+Na⁺].

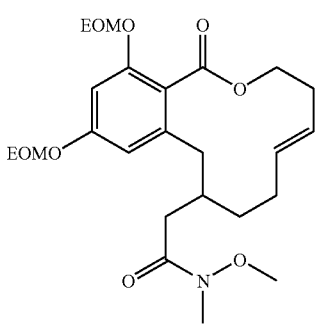

2-121g

Compound 2-121g: Mixture of two diastereoisomers; ¹H NMR (400 MHz, CDCl₃, 25° C.): δ=6.74-6.72 (m, 1H), 6.54 (d, J=1.8 Hz, 0.6H), 6.50 (d, J=1.7 Hz, 0.4H), 5.52-5.41 (m, 2H), 5.21 (s, 2H), 5.19 (s, 2H), 4.69-4.65 (m, 1H), 4.58-4.47 (m, 1H), 3.74-3.68 (m, 4H), 3.55 (s, 3H), 3.13 (s, 3H), 2.97-2.94 (m, 1H), 2.52-2.40 (m, 2H), 2.26-1.98 (m, 6H), 1.72-1.58 (m, 2H), 1.24-1.20 (m, 6H); HRMS (ESI-TOF): m/z: calculated for $C_{25}H_{38}O_8N$, 480.2567, found 480.2592 [M+H⁺].

General procedure for the EOM deprotection to generate compounds deprotected-2-121a-g, 2-85a-g and 2-103a-g: PS-TsOH (10.0 equiv., 3.2 mmol·g⁻¹) was added to a solution of the corresponding compound 2-121a-g or 2-112a-g or 2-120a-g (1.0 equiv.) in MeOH (0.03 M) and the resulting suspension was shaken at 40° C. for 1 to 4 h. After this time, the reaction mixture was filtered and the methanolic solution concentrated under reduced pressure. Purification by flash chromatography (silica gel, 0-33% EtOAc/cyclohexane gradient) afforded the corresponding compound deprotected-2-121a-g or 2-85a-g or 2-103a-g (>90%).

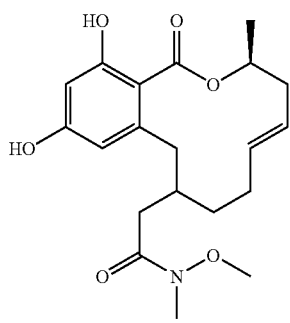

Deprotected (S)-2-121

Deprotected compound (S)-2-121: Mixture of four diastereoisomers; $^1$H NMR (400 MHz, CDCl$_3$, 25° C.): δ=12.90 (s, 0.5H), 12.83 (s, 0.5H), 12.12 (s, 0.5H), 12.02 (s, 0.5H), 6.92 (s, 0.5H), 6.84 (s, 0.5H), 6.83 (s, 1H), 6.79 (s, 0.5H), 6.60 (s, 1H), 6.54 (s, 0.5H), 5.60-5.29 (m, 4H), 5.17-4.99 (m, 2H), 4.14-3.99 (m, 2H), 2.98-2.72 (m, 12H), 2.60-1.92 (m, 16H), 1.31 (d, J=6.4 Hz, 1.5H), 1.22 (d, J=8.7 Hz, 1.5H), 1.13-1.02 (m, 7H); HRMS (ESI-TOF): m/z: calculated for C$_{20}$H$_{27}$O$_6$NNa: 400.1851, found 400.1731 [M+Na$^+$].

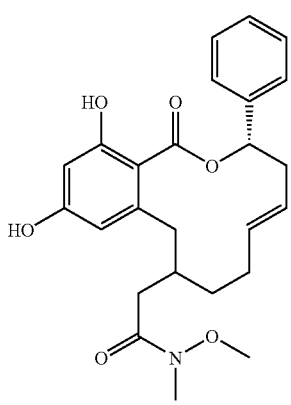

Deprotected (R)-2-121a

Deprotected compound (R)-2-121a: Mixture of four diastereoisomers; $^1$H NMR (400 MHz, CDCl$_3$, 25° C.): δ=11.90 (s, 0.25H), 11.08 (s, 0.5H), 10.98 (s, 0.25H), 7.38-7.29 (m, 5H), 6.39 (s, 0.25H), 6.33 (s, 0.25H), 6.29 (s, 1.25H), 6.26 (s, 0.25H), 6.05-5.95 (m, 1H), 5.70-5.52 (m, 2H), 4.18-4.03 (m, 1H), 3.51-3.49 (m, 3H), 3.16-3.14 (m, 3H), 2.75-2.62 (m, 2H), 2.36-2.29 (m, 2H), 2.12-1.96 (m, 4H), 1.81-1.73 (m, 2H), para-phenol not detected; HRMS (ESI-TOF): m/z: calculated for C$_{25}$H$_{30}$O$_6$N, 440.2068, found 440.2103 [M+H$^+$].

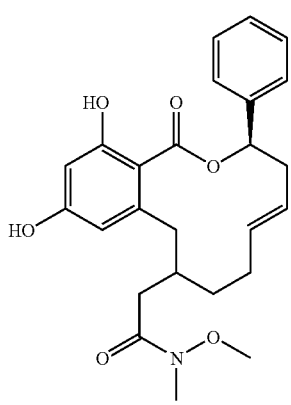

Deprotected (S)-2-121a

Deprotected compound (S)-2-121a: Mixture of four diastereoisomers; $^1$H NMR (400 MHz, CDCl$_3$, 25° C.): 3=11.90 (s, 0.25H), 11.08 (s, 0.5H), 10.98 (s, 0.25H), 7.38-7.31 (m, 5H), 6.38 (s, 0.25H), 6.33 (s, 0.25H), 6.29 (s, 1.25H), 6.26 (s, 0.25H), 6.05-5.95 (m, 1H), 5.71-5.54 (m, 2H), 4.13-4.04 (m, 1H), 3.53-3.50 (m, 3H), 3.19-3.14 (m, 3H), 2.78-2.63 (m, 2H), 2.33-2.29 (m, 2H), 2.16-2.04 (m, 4H), 1.81-1.68 (m, 2H), para-phenol not detected; HRMS (ESI-TOF): m/z: calculated for C$_{25}$H$_{29}$O$_6$NNa: 462.1887, found 462.2080 [M+Na$^+$].

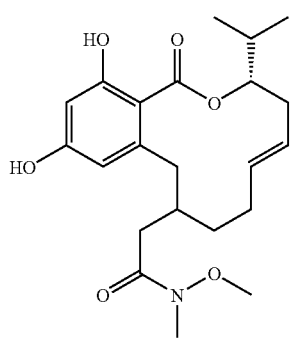

Deprotected (R)-2-121d

Deprotected compound (R)-2-121d: Mixture of four diastereoisomers; $^1$H NMR (400 MHz, CDCl$_3$, 25° C.): δ=11.54 (s, 1H), 6.33 (d, J=2.3 Hz, 1H), 6.25 (s, 1H), 5.53-5.51 (m, 1H), 5.44-5.41 (m, 1H), 5.11-5.08 (m, 1H), 4.01 (d, J=11.7 Hz, 2H), 3.45 (s, 3H), 3.11 (s, 3H), 2.83-2.73 (m, 1H), 2.68-2.59 (m, 1H), 2.27-2.20 (m, 1H), 2.10-1.87 (m, 6H), 1.82-1.72 (m, 1H), 1.01-0.94 (m, 6H), para-phenol not detected; HRMS (ESI-TOF): m/z: calculated for C$_{22}$H$_{31}$O$_6$NNa: 428.2044, found 428.2109 [M+Na$^+$].

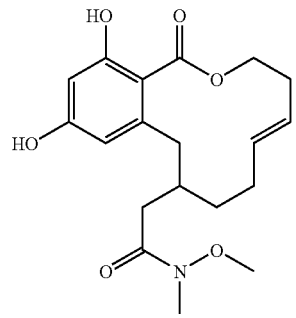

Deprotected 2-121g

Deprotected compound 2-121g: Mixture of two diastereoisomers; $^1$H NMR (400 MHz, CDCl$_3$, 25° C.): δ=12.33 (s, 0.5H), 11.85 (s, 0.5H), 6.34-6.32 (m, 1H), 6.25-6.22 (m, 1H), 5.62-5.45 (m, 2H), 4.54-4.37 (m, 1H), 4.29-4.21 (m, 1H), 3.53-3.49 (m, 3H), 3.15-3.12 (m, 3.5H), 2.95-2.86 (m, 0.5H), 2.67-2.52 (m, 2H), 2.39-1.96 (m, 8H), para-phenol not detected; HRMS (ESI-TOF): m/z: calculated for C$_{19}$H$_{26}$O$_6$N, 364.1755, found 364.1715 [M+H$^+$].

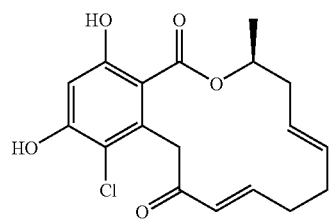

(S)-2-85

Compound (S)-2-85: $^1$H NMR (400 MHz, C$_6$D$_6$, 25° C.): δ=12.40 (s, 1H), 6.83 (s, 1H), 6.66-6.61 (m, 1H), 5.96 (bs, 1H), 5.80 (d, J=15.2 Hz, 1H), 5.16-5.12 (m, 1H), 4.99-4.91 (m, 1H), 4.75-4.68 (m, 1H), 4.26 (d, J=17.5 Hz, 1H), 4.13 (d, J=17.5 Hz, 1H), 2.52-2.45 (m, 1H), 1.86-1.79 (m, 3H), 1.75-1.67 (m, 1H), 1.54-1.49 (m, 1H), 0.97 (d, J=7.0 Hz, 3H); $^{13}$C NMR (100 MHz, C$_6$D$_6$, 25° C.): δ=193.8, 169.8, 164.3, 156.8, 146.0, 137.1, 131.9, 128.1, 126.2, 115.2, 107.6, 103.6, 72.4, 46.2, 36.3, 31.0, 30.8, 17.2. (−)-(2S): [α]$^{25}_D$=21.9 (c 0.62, CHCl$_3$).

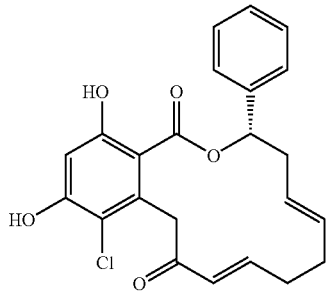

(R)-2-85a

Compound (R)-2-85a: $^1$H NMR (400 MHz, C$_6$D$_6$, 25° C.): δ=12.25 (bs, 1H), 7.32-7.29 (m, 2H), 7.19-7.15 (m, 3H), 6.80 (s, 1H), 6.81-6.75 (m, 1H), 6.29-6.26 (m, 1H), 5.92 (d, J=15.8 Hz, 1H), 5.80 (s, 1H), 5.05-4.99 (m, 1H), 4.81-4.75 (m, 1H), 4.56 (d, J=17.6 Hz, 1H), 4.12 (d, J=17.5 Hz, 1H), 2.73-2.66 (m, 1H), 2.39-2.35 (m, 1H), 1.86-1.76 (m, 2H), 1.64-1.49 (m, 2H); $^{13}$C NMR (100 MHz, C$_6$D$_6$, 25° C.): δ=194.2, 169.8, 164.4, 156.8, 145.5, 138.3, 137.0, 132.9, 129.9 (×2), 128.6, 127.3, 126.6 (×2), 125.8, 115.2, 107.5, 103.6, 77.6, 46.6, 38.3, 31.0, 30.6; HRMS (ESI-TOF): m/z: calculated for C$_{23}$H$_{21}$O$_5$ClNa: 435.0970, found 435.0914 [M+Na$^+$]. [α]$^{25}_D$=−12.0 (c 0.55, CHCl$_3$).

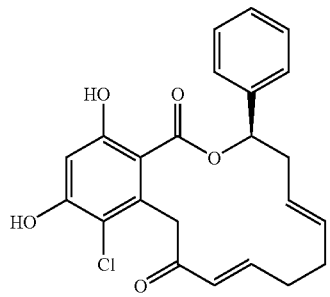

(S)-2-85a

Compound (S)-2-85a: $^1$H NMR (400 MHz, C$_6$D$_6$, 25° C.): δ=12.20 (bs, 1H), 7.15-7.09 (m, 3H), 6.75 (s, 1H), 6.77-6.71 (m, 1H), 6.25-6.22 (m, 1H), 5.88 (d, J=15.2 Hz, 1H), 5.72 (s, 1H), 5.00-4.95 (m, 1H), 4.77-4.73 (m, 1H), 4.52 (d, J=17.6 Hz, 1H), 4.08 (d, J=17.5 Hz, 1H), 2.68-2.62 (m, 1H), 2.35-2.31 (m, 1H), 1.81-1.78 (m, 2H), 1.56-1.49 (m, 2H), 2H masked by the solvent peak; $^{13}$C NMR (100 MHz, C$_6$D$_6$, 25° C.): δ=194.2, 169.8, 164.4, 156.8, 145.5, 138.3, 137.0, 132.2, 129.9 (×2), 128.5, 127.3, 126.5 (×2), 125.8, 115.2, 107.5, 103.6, 77.5, 46.6, 38.2, 31.0, 30.6; HRMS (ESI-TOF): m/z: calculated for C$_{23}$H$_{21}$O$_5$ClNa: 435.0970, found 435.0885 [M+Na$^+$]. [α]$^{25}_D$=+11.6 (c 0.51, CHCl$_3$).

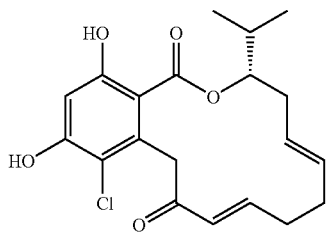

(R)-2-85d

Compound (R)-2-85d: $^1$H NMR (400 MHz, C$_6$D$_6$, 25° C.): δ=12.31 (s, 1H), 6.83 (s, 1H), 6.74-6.67 (m, 1H), 5.84 (bs, 1H), 5.82 (d, J=15.8 Hz, 1H), 5.03-4.95 (m, 1H), 4.88-4.86 (m, 1H), 4.76-4.70 (m, 1H), 4.40 (d, J=17.6 Hz, 1H), 4.15 (d, J=17.5 Hz, 1H), 2.40-2.34 (m, 1H), 2.22-2.18 (m, 1H), 1.87-1.65 (m, 4H), 1.53-1.48 (m, 1H), 0.92 (d, J=6.4 Hz, 3H), 0.66 (d, J=7.0 Hz, 3H); $^{13}$C NMR (100 MHz, C$_6$D$_6$, 25° C.): δ=193.7, 164.2, 156.8, 145.8, 137.2, 131.8, 129.3, 126.3, 115.3, 107.9, 103.6, 82.1, 46.4, 33.3, 30.9, 30.7, 28.8, 20.1, 18.5, 18.3; HRMS (ESI-TOF): m/z: calculated for C$_{20}$H$_{23}$ClO$_5$Na: 401.1126, found 401.1170 [M+Na$^+$]. [α]$^{25}_D$=−35.6 (c 0.52, CHCl$_3$).

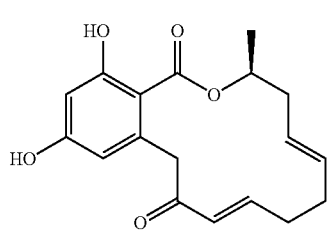

2-85g

Compound 2-85g: $^1$H NMR (400 MHz, CD$_3$OD, 25° C.): δ=6.74-6.68 (m, 1H), 6.48 (s, 1H), 5.86 (d, J=15.2 Hz, 1H), 5.31-5.25 (m, 2H), 4.39 (t, J=5.3 Hz, 2H), 4.27 (s, 2H), 2.43-2.40 (m, 2H), 2.25 (m, 4H), phenols not detected; $^{13}$C NMR (100 MHz, CD$_3$OD, 25° C.): S=196.9, 170.1, 161.9, 158.1, 147.8, 135.9, 130.9, 130.2, 129.9, 115.2, 107.3, 102.4, 65.9, 46.2, 31.3, 30.9, 30.5; HRMS (ESI-TOF): m/z: calculated for C$_{17}$H$_{18}$O$_5$Cl: 337.0837, found 337.0797 [M+H$^+$].

(S)-2-103

Compound (S)-2-103: $^1$H NMR (400 MHz, CD$_3$OD, 25° C.): δ=6.78-6.71 (m, 1H), 6.29 (d, J=2.4 Hz, 1H), 6.22 (d, J=2.0 Hz, 1H), 5.87 (d, J=15.5 Hz, 1H), 5.37-5.23 (m, 3H), 4.01 (d, J=17.2 Hz, 1H), 3.92 (d, J=17.0 Hz, 1H), 2.67-2.61 (m, 1H), 2.29-2.15 (m, 5H), 1.31 (d, J=6.4 Hz, 3H), phenols not detected; $^{13}$C NMR (100 MHz, CD$_3$OD, 25° C.): δ=198.5, 169.8, 164.2, 162.3, 148.4, 139.1, 131.6, 129.6, 127.3, 111.7, 101.7, 72.0, 47.7, 36.8, 30.8, 30.7, 17.4, (one quartenary carbon is not detected); HRMS (ESI-TOF): m/z: calculated for $C_{18}H_{20}O_5Na$: 339.1203, found 339.1141 [M+Na$^+$]. (−)-(2S): [α]$^{25}_D$=−45.1 (c 0.27, CHCl$_3$).

(R)-2-103a

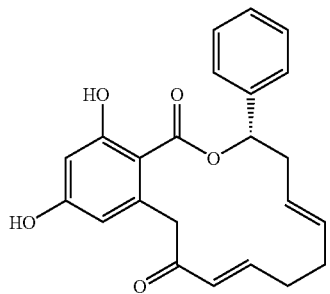

Compound (R)-2-103a: $^1$H NMR (400 MHz, C$_6$D$_6$, 25° C.): b=12.0 (bs, 1H), 7.32-7.29 (m, 3H), 7.19-7.15 (m, 2H), 6.86-6.79 (m, 1H), 6.51 (d, J=2.4 Hz, 1H), 6.27-6.25 (m, 1H), 6.11 (d, J=2.4 Hz, 1H), 6.02 (d, J=15.8 Hz, 1H), 5.49 (s, 1H), 5.17-5.10 (m, 1H), 4.97-4.90 (m, 1H), 4.40 (d, J=16.4 Hz, 1H), 3.97 (d, J=17.2 Hz, 1H), 2.83-2.76 (m, 1H), 2.45-2.38 (m, 1H), 1.89-1.78 (m, 2H), 1.67-1.58 (m, 2H); $^{13}$C NMR (100 MHz, C$_6$D$_6$, 25° C.): δ=196.5, 169.6, 166.1, 161.3, 146.0, 140.5, 138.8, 132.1, 130.0, 128.6 (×2), 127.3, 126.6 (×2), 126.3, 112.2, 105.9, 103.0, 77.1, 48.6, 38.4, 30.9, 30.3; HRMS (ESI-TOF): m/z: calculated for $C_{23}H_{22}O_5Na$: 401.1359, found 401.1271 [M+Na$^+$]. [α]$^{25}_D$=−10.3 (c 0.25, CHCl$_3$).

(S)-2-103a

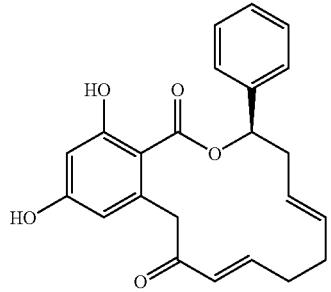

Compound (S)-2-103a: $^1$H NMR (400 MHz, C$_6$D$_6$, 25° C.): δ=12.0 (bs, 1H), 7.27-7.21 (m, 3H), 7.17-7.13 (m, 2H), 6.87-6.79 (m, 1H), 6.55 (d, J=2.3 Hz, 1H), 6.29-6.26 (m, 1H), 6.16 (d, J=2.3 Hz, 1H), 6.03 (d, J=15.8 Hz, 1H), 5.74 (s, 1H), 5.18-5.12 (m, 1H), 4.98-4.91 (m, 1H), 4.41 (d, J=15.8 Hz, 1H), 3.99 (d, J=16.9 Hz, 1H), 2.84-2.77 (m, 1H), 2.46-2.43 (m, 1H), 1.85-1.79 (m, 2H), 1.70-1.58 (m, 2H); $^{13}$C NMR (100 MHz, C$_6$D$_6$, 25° C.): δ=196.9, 169.6, 166.2, 161.5, 146.3, 140.5, 138.9, 132.1, 130.0, 128.6 (×2), 127.3, 126.6 (×2), 126.3, 112.2, 105.8, 103.0, 77.1, 48.6, 38.4, 30.9, 30.4; HRMS (ESI-TOF): m/z: calculated for $C_{23}H_{22}O_5Na$: 401.1359, found 401.1264 [M+Na$^+$][α]$^{25}_D$=+11.9 (c 0.51, CHCl$_3$).

(R)-2-103d

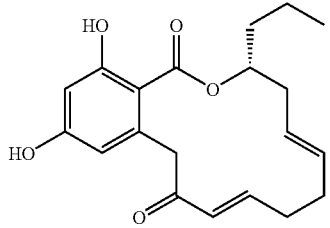

Compound (R)-2-103d: $^1$H NMR (400 MHz, C$_6$D$_6$, 25° C.): δ=12.10 (s, 1H), 6.79 (dt, J=15.2, 7.6 Hz, 1H), 6.59 (d, J=2.4 Hz, 1H), 6.22 (d, J=2.3 Hz, 1H), 5.96 (d, J=15.8 Hz, 1H), 5.88 (bs, 1H), 5.13-5.05 (m, 1H), 4.92-4.85 (m, 2H), 4.27 (d, J=15.8 Hz, 1H), 4.03 (d, J=15.8 Hz, 1H), 2.50-2.44 (m, 1H), 2.24-2.20 (m, 1H), 1.96-1.71 (m, 4H), 1.63-1.56 (m, 1H), 0.91 (d, J=6.3 Hz, 3H), 0.71 (d, J=6.4 Hz, 3H); $^{13}$C NMR (100 MHz, C$_6$D$_6$, 25° C.): δ=196.5, 169.7, 166.0, 161.4, 146.8, 140.8, 131.7, 129.5, 126.9, 112.3, 106.0, 103.0, 81.3, 48.5, 33.7, 30.9, 30.4, 29.6, 19.7, 18.4; HRMS (ESI-TOF): m/z: calculated for $C_{20}H_{24}O_5Na$: 367.1516, found 367.1424 [M+Na$^+$]. [α]$^{25}_D$=−31.9 (c 0.50, CHCl$_3$).

(R)-2-103e

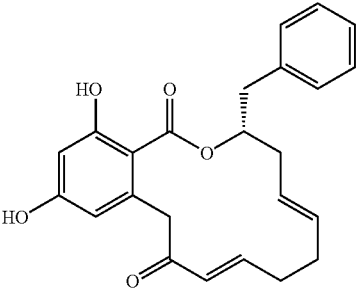

Compound (R)-2-103e: $^1$H NMR (400 MHz, CDCl$_3$, 25° C.): δ=12.43 (s, 1H), 6.74 (d, J=1.7 Hz, 1H), 6.73-6.65 (m, 1H), 6.48 (d, J=1.7 Hz, 1H), 5.92 (d, J=15.8 Hz, 1H), 5.12-5.00 (m, 2H), 4.91-4.80 (m, 1H), 4.19 (d, J=17.0 Hz, 1H), 3.84 (d, J=16.4 Hz, 1H), 2.77 (m, 1H), 2.64-2.57 (m, 1H), 2.01-1.97 (m, 1H), 1.89-1.70 (m, 3H), 1.61-1.56 (m, 2H), 1.30-1.21 (m, 2H), 0.90 (t, J=6.7 Hz, 3H), para-phenol not detected; $^{13}$C NMR (100 MHz, CDCl$_3$, 25° C.): δ=197.5, 169.9, 165.6, 160.6, 147.5, 140.2, 131.9, 129.5, 127.0, 112.8, 106.1, 102.9, 76.2, 48.7, 35.7, 34.3, 31.1, 29.7, 19.4, 13.8; HRMS (ESI-TOF): m/z: calculated for $C_{20}H_{25}O_5$: 345.1697, found 345.1739 [M+H$^+$]. [α]$^{25}_D$=+21.6 (c 0.36, CHCl$_3$).

(R)-2-103f

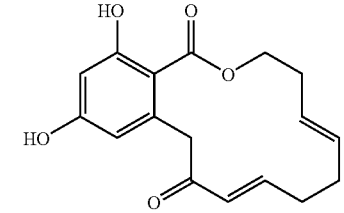

Compound (R)-2-103f: $^1$H NMR (400 MHz, CDCl$_3$, 25° C.): δ=12.31 (s, 1H), 7.19-7.13 (m, 5H), 6.80-6.72 (m, 1H), 6.53 (d, J=1.8 Hz, 1H), 6.05 (s, 1H), 5.89 (d, J=15.8 Hz, 1H), 5.47-5.44 (m, 1H), 5.11-5.05 (m, 1H), 4.85-4.81 (m, 1H), 4.10 (d, J=17.0 Hz, 1H), 3.62 (d, J=17.0 Hz, 1H), 2.89-2.84 (m, 1H), 2.67-2.60 (m, 2H), 2.08-2.04 (m, 1H), 1.90-1.69 (m, 3H), 1.52-1.44 (m, 1H), para-phenol not detected; $^{13}$C NMR (100 MHz, CDCl$_3$, 25° C.): δ=197.7, 169.9, 165.7, 160.7, 147.4, 140.2, 137.2, 132.2, 129.5, 128.8 (×2), 128.7 (×3), 126.8, 112.4, 105.9, 102.9, 48.9, 38.5, 35.3, 31.1 (×2), 29.7; HRMS (ESI-TOF): m/z: calculated for $C_{24}H_{25}O_5$: 393.1697, found 393.1765 [M+H$^+$]. [α]$^{25}_D$=+25.4 (c 0.41, CHCl$_3$).

2-103g

Compound 2-103g: ¹H NMR (400 MHz, CD₃OD, 25° C.): δ=6.75-6.69 (m, 1H), 6.29 (s, 1H), 6.29 (d, J=2.3 Hz, 1H), 5.90 (d, J=15.8 Hz, 1H), 5.30-5.28 (m, 2H), 4.39 (t, J=5.2 Hz, 2H), 4.02 (s, 2H), 2.45-2.41 (m, 2H), 2.28-2.24 (m, 4H), phenols not detected; ¹³C NMR (100 MHz, CD₃OD, 25° C.): δ=198.4, 170.6, 164.9, 162.5, 148.1, 139.2, 130.7, 130.6, 130.2, 112.2, 105.0, 101.6, 65.7, 47.7, 31.4, 30.9, 30.5; HRMS (ESI-TOF): m/z: calculated for C₁₇H₁₉O₅: 303.1227, found 303.1179 [M+H⁺].

General procedure for the synthesis of compounds 2-141: BER-resin (Borohydride on Amberlite, 1.0 equiv., 2.5 mmol·g⁻¹) was added to a solution of corresponding compound 2-112a-g or 2-120a-g (1.0 equiv.) in MeOH (0.03 M) at 0° C. and the reaction was stirred for 12 h. The reaction mixture was then filtered and concentrated under reduced pressure. Purification by flash chromatography (silica gel, 0-20% EtOAc/cyclohexane gradient) afforded 2-141 (~60% yield) as a mixture of two diastereoisomers 1:1.

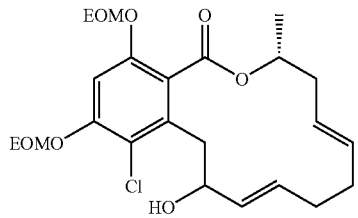

Selected example of compounds 2-141: ¹H NMR (400 MHz, CDCl₃, 25° C.): 7.05 (s, 1H), 6.99 (s, 1H), 5.64-5.57 (m, 2H), 5.54-5.53 (m, 2H), 5.49-5.35 (m, 7H), 5.31-5.28 (m, 4H), 5.24-5.16 (m, 4H), 5.13-5.08 (m, 1H), 4.68 (m, 1H), 4.56 (m, 1H), 3.81-3.69 (m, 8H), 3.25 (dd, J=13.9, 8.0 Hz, 1H), 3.19 (dd, J=13.7, 4.8 Hz, 1H), 3.11 (dd, J=13.5, 10.1 Hz, 1H), 2.90 (dd, J=13.9, 5.1 Hz, 1H), 2.35 (m, 9H), 2.09-1.95 (m, 1H), 1.80-1.70 (m, 2H), 1.39 (d, J=2.9 Hz, 3H), 1.37 (d, J=3.2 Hz, 3H,), 1.24 (2×q, J=6.9, 5.0 Hz, 12H); HRMS (ESI-TOF): m/z: calculated for C₂₄H₃₃ClO₇Na: 491.1807, found 491.1729 [M+Na⁺]. General procedure for the synthesis of compounds 2-142: PS-TsOH (10.0 equiv., 3.2 mmol·g⁻¹) was added to a solution of the corresponding compound 2-141 (1.0 equiv.) in MeOH (0.02 M) and the suspension was shaken at 40° C. for 4 h. The reaction mixture was then filtered and the methanolic solution concentrated under reduced pressure. Purification by preparative TLC (silica gel, 25% EtOAc/cyclohexane) afforded 2-142 (~90% yield) as a mixture of two diastereoisomers 1:1.

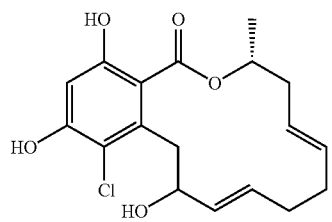

Selected example of compounds 2-142: ¹H NMR (400 MHz, (CD₃)₂CO, 25° C.): δ=12.30 (s, 2H), 11.43 (s, 2H), 6.75 (s, 2H), 6.00 (bdd, J=6.4, 6.2 Hz, 1H), 5.97 (bdd, J=6.4, 6.2 Hz, 1H), 5.97 (bd, J=6.7 Hz, 1H), 5.77 (bd, J=6.7 Hz, 1H), 5.57-5.48 (m, 4H), 5.18-5.14 (m, 2H), 3.38-3.28 (m, 3H), 3.02 (dd, J=16.1, 10.5 Hz, 1H), 2.41-2.09 (m, 12H), 1.11 (d, J=6.2 Hz, 6H), alcohols not detected; HRMS (ESI-TOF): m/z: calculated for C₁₈H₂₁ClO₅Na: 375.0970, found 375.1029 [M+Na⁺].

General procedure for the synthesis of compounds 2-143: Ac₂O (1.2 equiv.), morpholinomethyl polystyrene (1.2 equiv., 3.2 mmol·g⁻¹) and DMAP (0.05 equiv.) were added to a solution of the corresponding compound 2-141 (1.0 equiv.) in DMF (0.02 M) at 23° C. and the mixture was stirred for 30 min, followed by TLC until consumption of the starting material. The resin was then filtered and the organic phase was concentrated under reduced pressure. Purification by preparative TLC (silica gel, 20% EtOAc/cyclohexane) afforded corresponding compound 2-143 (~80% yield) as a mixture of two diastereoisomers 1:1.

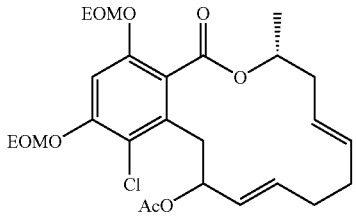

Selected example of compounds 2-143: ¹H NMR (400 MHz, CDCl₃, 25° C.): δ=7.04 (s, 1H), 7.01 (s, 1H), 5.86 (dd, J=15.0, 6.9 Hz, 1H), 5.67 (dd, J=12.4, 6.2 Hz, 1H), 5.60-5.54 (m, 4H), 5.48 (dd, J=7.2, 7.2 Hz, 1H), 5.41-5.34 (m, 3H), 5.32-5.30 (m, 4H), 5.28-5.23 (m, 2H), 5.21 (dd, J=11.0, 6.7 Hz, 2H), 5.17 (dd, J=11.8, 6.9 Hz, 2H), 3.81-3.69 (m, 8H), 3.43 (dd, J=14.2, 7.5 Hz, 1H), 3.23-3.15 (m, 2H), 2.85 (dd, J=13.9, 5.4 Hz, 1H), 2.30-2.17 (m, 8H), 2.12 (s, 3H), 2.06 (s, 3H), 2.00-1.95 (m, 4H), 1.39 (2×d, J=5.6 Hz, 6H), 1.24 (m, 12H); HRMS (ESI-TOF): m/z: calculated for C₂₆H₃₅ClO₈Na: 533.1913, found 533.1864 [M+Na⁺].

General procedure for the synthesis of compounds 2-144: PS-TsOH (10.0 equiv., 3.2 mmol·g⁻¹) was added to a solution of corresponding compound 2-143 (1.0 equiv.) in MeOH (0.02 M) and the suspension was shaken at 40° C. for 4 h. After this time, the reaction mixture was filtered and the methanolic solution concentrated under reduced pressure. Purification by preparative TLC (silica gel, 20% EtOAc/cyclohexane) afforded compound 2-144 (~60% yield).

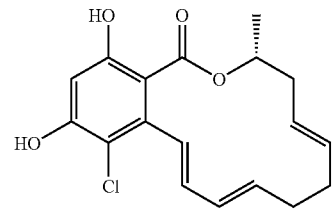

Selected example of compounds 2-144: Mixture of diastereoisomers 2:1; ¹H NMR (400 MHz, CDCl₃, 25° C.): δ=12.60 (s, 1H), 12.12 (s, 0.5H), 6.93 (d, J=8.7 Hz, 0.5H), 6.66 (s, 1H), 6.64 (s, 0.5H), 6.62-6.60 (m, 1H), 6.10-6.05 (m, 3H), 5.47-5.33 (m, 6H), 2.60-2.53 (m, 1.5H), 2.26-2.02 (m, 7.5H), 1.44 (d, J=6.2 Hz, 1.5H), 1.43 (d, J=6.4 Hz, 3H), para-phenol not detected; HRMS (ESI-TOF): m/z: calculated for C₁₈H₁₉ClO₄Na: 357.0864, found 357.0898 [M+Na⁺].

General procedure for the preparation of compounds 2-145: PS-TsOH (10.0 equiv.) was added to a solution of corresponding compound 2-85a-g (1.0 equiv.) in methanol (0.03 M) and the suspension was stirred for 15 h at 40° C. The reaction was then filtered and the resin washed several times with CH$_2$Cl$_2$. Concentration under reduced pressure followed by purification on preparative TLC (silica gel, 50% hexane/EtOAc) afforded desired compound 2-145 as a mixture of diastereoisomers 2:1.

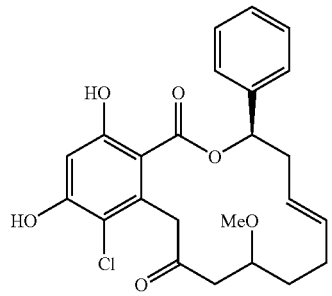

Selected example of compounds 2-145: $^1$H NMR (400 MHz, C$_6$D$_6$, 25° C.): S=12.28 (s, 0.4H), 11.91 (s, 0.6H), 7.21-7.11 (m, 5H), 6.62 (s, 1H), 6.03-6.01 (m, 1H), 5.58 (bs, 1H), 5.38-5.33 (m, 1H), 5.27-5.20 (m, 1H), 4.76 (d, J=17.5 Hz, 0.6H), 4.02 (d, J=17.0 Hz, 0.4H), 4.18 (d, J=18.1 Hz, 0.6H), 4.09 (d, J=17.0 Hz, 0.4H), 3.87 (bs, 0.4H), 3.81 (bs, 0.6H), 3.15 (s, 1.8H), 3.12 (s, 1.2H), 2.83-2.78 (m, 1H), 2.45-2.30 (m, 2H), 2.18-2.16 (m, 1H), 2.02-1.97 (m, 2H), 1.79-1.72 (m, 2H); HRMS (ESI-TOF): m/z: calculated for C$_{24}$H$_{25}$O$_6$ClNa: 467.1232, found 467.1366 [M+Na$^+$].

General procedure for the synthesis of compounds 2-146: (Polystyrylmethyl)trimethyl-ammonium cyanoborohydride (2.0 equiv., 3.5 mmol·g$^{-1}$) was added to a solution of corresponding compound 2-85a-g or 2-103a-g (1.0 equiv.) in CH$_2$Cl$_2$/AcOH 10:1 (0.08 M) at 23° C. and the reaction was monitored by TLC until consumption of the starting material (4 h). The resin was then filtered and the organic phase was concentrated under reduced pressure. Purification by preparative TLC (silica gel, 30% EtOAc/cyclohexane) afforded compound 2-146 (50-60% yield).

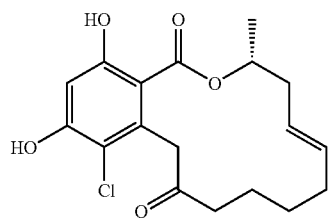

Selected example of compounds 2-146: $^1$H NMR (400 MHz, CDCl$_3$, 25° C.): δ=11.75 (s, 1H), 6.65 (s, 1H), 5.48 (m, 2H), 5.49 (ddt, J=6.1, 3.5, 2.9 Hz, 1H), 4.53 (d, J=17.5 Hz, 1H), 4.04 (d, J=17.7 Hz, 1H), 2.61-2.54 (m, 2H), 2.48-2.28 (m, 3H), 2.19-2.14 (m, 1H), 2.08-1.99 (m, 1H), 1.72-1.61 (m, 3H), 1.41 (d, J=6.4 Hz, 3H), para-phenol not detected; HRMS (ESI-TOF): m/z: calculated for C$_{18}$H$_{21}$ClO$_5$Na: 375.0970, found 375.1050 [M+Na$^+$].

General procedure for the synthesis of compounds 2-147: The corresponding alcohol R$^2$OH (2.0 equiv.), triphenylphosphine (2.0 equiv.) and PS-DEAD (2.0 equiv., 1.3 mmol·g$^{-1}$) were added to a solution of corresponding compound 2-85a-g or 2-103a-g (1.0 equiv.) in THF (0.05 M) in a sequential manner. The reaction mixture was shaken at room temperature for 8 h, and then the resin was filtered and the filtrates were directly purified by preparative TLC (silica gel, 10% EtOAc/cyclohexane) to afford a mixture of compound 2-147 along with the bis-alkylated product (78% yield).

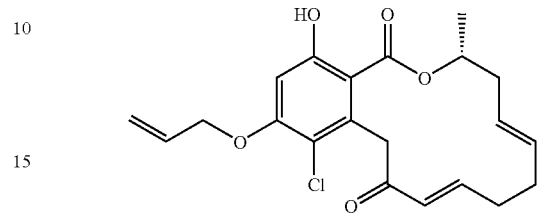

Selected example of compounds 2-147: Mixture with the corresponding bis-allylated compound 1:1; $^1$H NMR (400 MHz, CDCl$_3$, 25° C.): δ=11.83 (s, 1H), 6.82 (ddd, J=15.7, 8.2, 4.6 Hz, 1H), 6.72-6.65 (m, 1H), 6.46 (s, 1H), 6.41 (s, 1H), 6.09-5.98 (m, 3H), 5.82 (d, J=15.7 Hz, 1H), 5.46-5.16 (m, 8H), 4.57-4.54 (m, 3H), 4.51-4.49 (m, 3H), 4.19 (d, J=17.5 Hz, 1H), 4.11 (d, J=14.6 Hz, 1H), 3.78 (d, J=17.0 Hz, 1H), 3.51 (d, J=14.2 Hz, 1H), 2.76-2.69 (m, 1H), 2.38-2.05 (m, 11H), 1.42 (d, J=6.2 Hz, 3H), 1.35 (d, J=6.3 Hz, 3H); mono-allylated compound: HRMS (ESI-TOF): m/z: calculated for C$_{21}$H$_{23}$ClO$_5$Na: 413.1132, found 413.1103 [M+Na$^+$]; bis-allylated compound: HRMS (ESI-TOF): m/z: calculated for C$_{24}$H$_{27}$ClO$_5$Na: 453.1449, found 453.1422 [M+Na$^+$].

General procedure for the synthesis of compounds 2-148: TBD-methyl polystyrene (2.0 equiv., 2.9 mmol·g$^{-1}$) and the corresponding alkyl bromide or chloride (BrCH$_2$COO$^t$Bu, EOMCl, 0.9 equiv.) were added to a solution of the corresponding compound 2-85a-g or 2-103a-g (1.0 equiv.) in CH$_2$Cl$_2$ (0.05 M) at 23° C. and the mixture was shaken for 3 h. The resin was then filtered and the filtrates were concentrated under reduced pressure. Purification by preparative TLC (silica gel, 30% EtOAc/cyclohexane) afforded corresponding compound 2-148 (>90% yield).

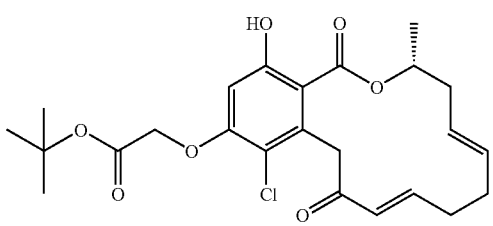

Selected examples of compounds 2-148: $^1$H NMR (400 MHz, CDCl$_3$, 25° C.): δ=11.84 (s, 1H), 6.69 (m, 1H), 6.41 (s, 1H), 5.76 (d, J=15.0 Hz, 1H), 5.43 (m, 1H), 5.26 (ddd, J=15.0, 9.1, 4.8 Hz, 1H), 5.18-5.11 (m, 1H), 4.65 (s, 2H), 4.33 (d, J=17.7 Hz, 1H), 4.16 (d, J=17.5 Hz, 1H), 2.65-2.58 (m, 1H), 2.37-2.34 (m, 2H), 2.25-2.21 (m, 1H), 2.12-2.01 (m, 2H), 1.53 (s, 9H), 1.34 (d, J=6.5 Hz, 3H); HRMS (ESI-TOF): m/z:

calculated for $C_{24}H_{29}ClO_7Na$: 487.1494, found 487.1498 [M+Na$^+$].

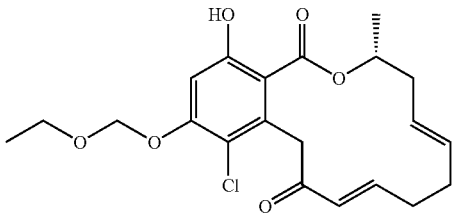

$^1$H NMR (400 MHz, $C_6D_6$, 25° C.): δ=11.76 (s, 1H), 6.86 (s, 1H), 6.70 (dt, J=14.9, 7.3 Hz, 1H), 5.77 (d, J=15.8 Hz, 1H), 5.46-5.42 (m, 1H), 5.37 (s, 2H), 5.30-5.19 (m, 2H), 4.34 (d, J=17.6 Hz, 1H), 4.16 (d, J=18.1 Hz, 1H), 3.80 (q, J=7.0 Hz, 2H), 2.66-2.59 (m, 1H), 2.37-2.34 (m, 2H), 2.26-2.21 (m, 1H), 2.13-2.06 (m, 2H), 1.34 (d, J=6.4 Hz, 3H), 1.27 (t, J=7.0 Hz, 3H); HRMS (ESI-TOF): m/z: calculated for $C_{21}H_{25}O_6ClNa$: 431.1237, found 431.1257 [M+Na$^+$].

General procedure for the synthesis of compounds 2-149: OsO$_4$ (0.1 equiv.) and NMO (1.0 equiv.) were added to a solution of compound 2-85a-g or 2-103a-g (1.0 equiv.) in acetone/H$_2$O 10:1 (0.05 M) at 23° C. and the mixture was stirred for 1 h. The crude mixture was filtered through a pad of silica, concentrated and purified by preparative TLC (silica gel, 30% EtOAc/cyclohexane) to afford 2-149 as a mixture of two diastereoisomers 1:1 (>70% yield).

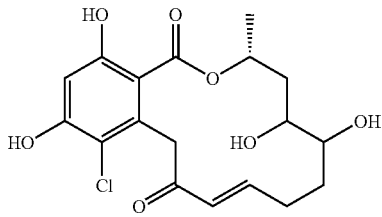

Selected example of compounds 2-149: $^1$H NMR (400 MHz, CD$_3$OD, 25° C.): δ=7.19 (m, 1H), 6.89-6.81 (m, 1H), 6.52 (s, 1H), 6.47 (s, 1H), 6.20 (d, J=16.1 Hz, 1H), 6.04 (d, J=15.6 Hz, 1H), 5.54-5.49 (m, 1H), 5.43-5.36 (m, 1H), 4.50 (d, J=17.7 Hz, 1H), 4.46 (d, J=17.7 Hz, 1H), 4.39 (d, J=17.2 Hz, 1H), 4.07 (d, J=17.2 Hz, 1H), 3.80-3.64 (m, 2H), 3.51-3.46 (m, 2H), 2.62-2.58 (m, 2H), 2.39-2.30 (m, 2H), 2.27-2.18 (m, 2H), 2.08-1.98 (m, 2H), 2.00-1.85 (m, 4H), 1.44 (d, J=6.4 Hz, 6H), phenols and alcohols not detected; HRMS (ESI-TOF): m/z: calculated for $C_{18}H_{21}ClO_7Na$: 407.0868, found 407.1031 [M+Na$^+$].

General procedure for the synthesis of compounds 2-150: Freshly prepared DMDO (1.2 equiv., 0.04 M in acetone) was added to a solution of compound 2-85a-g or 2-103a-g (1.0 equiv.) in CH$_3$CN (0.03 M) at 0° C. and the mixture was stirred for 30 min. After evaporation of the solvents under reduced pressure, purification by preparative TLC (silica gel, 30% EtOAc/cyclohexane) afforded epoxides 2-150 (>90% yield) as a mixture of two diastereoisomers (1:1 to 3:1).

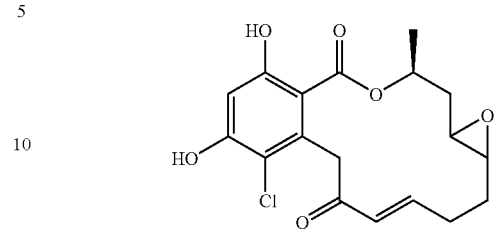

Selected examples of compounds 2-150: $^1$H NMR (400 MHz, $C_6D_6$, 25° C.): δ=11.85 (s, 1H), 6.94-6.87 (m, 2H), 6.69 (s, 1H), 6.65 (s, 1H), 6.24 (bd, J=15.2 Hz, 2H), 6.12 (d, J=15.8 Hz, 1H), 5.41-5.37 (m, 1H), 5.33-5.30 (m, 1H), 4.54 (bd, J=18.1 Hz, 2H), 4.52-4.48 (m, 1H), 4.40-4.34 (m, 1H), 4.27 (d, J=17.5 Hz, 1H), 2.78-2.72 (m, 2H), 2.58-2.55 (m, 4H), 2.47-2.28 (m, 5H), 2.07 (m, 2H), 1.92-1.86 (m, 3H), 1.51 (d, J=6.4 Hz, 3H), 1.35 (d, J=6.4 Hz, 3H), para-phenol not detected; HRMS (ESI-TOF): m/z: calculated for $C_{18}H_{19}O_6ClNa$: 389.0762, found 389.0844 [M+Na$^+$].

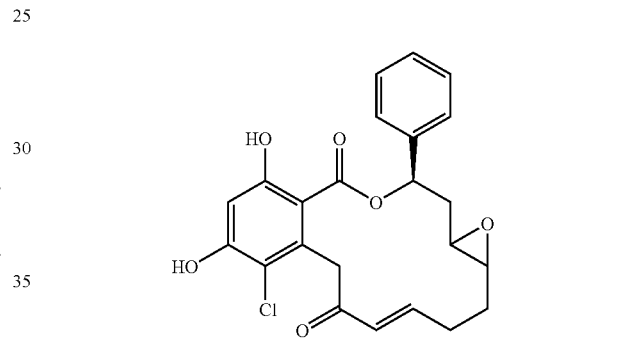

$^1$H NMR (400 MHz, $C_6D_6$, 25° C.): δ=11.80 (2×s, 2H), 7.43-7.18 (m, 10H), 7.03-6.95 (m, 2H), 6.69 (s, 1H), 6.61 (s, 1H), 6.30 (d, J=16.4 Hz, 1H), 6.21 (d, J=15.8 Hz, 1H), 6.15-6.10 (m, 1H), 6.03 (d, J=11.1 Hz, 1H), 4.84 (2×d, J=18.1 Hz, 2H), 4.41 (2×d, J=17.6 Hz, 2H), 2.68-2.60 (m, 4H), 2.41-2.27 (m, 8H), 1.83-1.76 (m, 4H), para-phenol not detected; HRMS (ESI-TOF): m/z: calculated for $C_{23}H_{21}O_6ClNa$: 451.0919, found 451.1028 [M+Na$^+$].

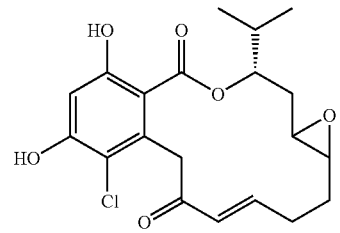

$^1$H NMR (400 MHz, $C_6D_6$, 25° C.): δ=11.56 (2×s, 2H), 6.92-6.82 (m, 2H), 6.71 (s, 1H), 6.67 (s, 1H), 6.20 (m, 3H), 6.06 (d, J=15.8 Hz, 1H), 5.11 (bs, 1H), 5.94 (m, 1H), 4.46 (2×d, J=18.1 Hz, 2H), 4.20 (2×d, J=18.1 Hz, 2H), 2.72-2.70 (m, 2H), 2.53-2.48 (m, 4H), 2.38-2.35 (m, 3H), 2.25-2.13 (m, 5H), 1.84-1.77 (m, 2H), 1.05-1.01 (m, 6H), 0.91-0.88 (m, 3H), 0.86-0.84 (m, 3H), para-phenol not detected; HRMS (ESI-TOF): m/z: calculated for $C_{20}H_{23}O_6ClNa$: 417.1075, found 417.1128 [M+Na$^+$].

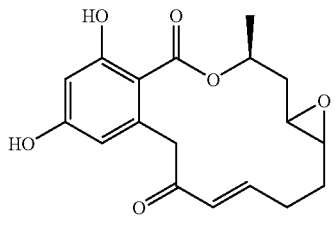

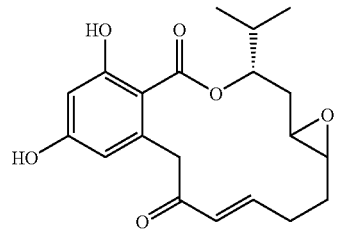

¹H NMR (400 MHz, C₆D₆, 25° C.): δ=11.98 (s, 1H), 6.91-6.83 (m, 1H), 6.43 (d, J=2.3 Hz, 1H), 6.24 (d, J=2.4 Hz, 1H), 6.11 (d, J=15.8 Hz, 1H), 5.35 (bs, 1H), 5.29 (m, 1H), 4.52 (d, J=17.5 Hz, 1H), 3.63 (d, J=17.5 Hz, 1H), 2.77 (m, 2H), 2.57-2.52 (m, 2H), 2.46-2.27 (m, 2H), 2.14-2.10 (m, 1H), 1.93-1.88 (m, 1H), 1.48 (d, J=6.4 Hz, 3H); other isomer: ¹H NMR (400 MHz, C₆D₆, 25° C.): δ=11.67 (s, 1H), 6.89-6.83 (m, 1H), 6.40 (d, J=2.4 Hz, 1H), 6.24 (d, J=2.9 Hz, 1H), 6.21 (d, J=16.4 Hz, 1H), 5.37 (bs, 1H), 5.22 (m, 1H), 4.20 (d, J=17.0 Hz, 1H), 4.06 (d, J=17.0 Hz, 1H), 2.74 (m, 2H), 2.57-2.20 (m, 4H), 1.80-1.76 (m, 1H), 1.68-1.60 (m, 1H), 1.37 (d, J=6.4 Hz, 3H), para-phenol not detected; HRMS (ESI-TOF): m/z: calculated for C₁₈H₂₀O₆Na: 355.1152, found 355.1249 [M+Na⁺].

¹H NMR (400 MHz, C₆D₆, 25° C.): δ=11.77 (s, 1H), 6.92-6.82 (m, 1H), 6.44 (d, J=2.3 Hz, 1H), 6.28 (d, J=2.4 Hz, 1H), 6.09 (d, J=15.8 Hz, 1H), 5.40 (bs, 1H), 4.92 (m, 1H), 4.50 (d, J=17.5 Hz, 1H), 3.61 (d, J=17.5 Hz, 1H), 2.72-2.70 (m, 1H), 2.56-2.45 (m, 2H), 2.38-2.15 (m, 4H), 1.91-1.85 (m, 1H), 1.05-1.01 (m, 6H), para-phenol not detected; other isomer: ¹H NMR (400 MHz, C₆D₆, 25° C.): δ=11.55 (s, 1H), 6.86-6.79 (m, 1H), 6.42 (s, 1H), 6.29 (s, 1H), 6.20 (d, J=15.8 Hz, 1H), 5.40 (m, 1H), 5.16 (m, 1H), 4.14 (s, 1H), 4.12 (s, 1H), 2.72-2.70 (m, 1H), 2.53-2.37 (m, 4H), 2.18-2.10 (m, 2H), 1.92-1.86 (m, 1H), 0.91-0.85 (m, 6H), para-phenol not detected; HRMS (ESI-TOF): m/z: calculated for C₂₀H₂₄O₆Na: 383.1465, found 383.1574 [M+Na⁺].

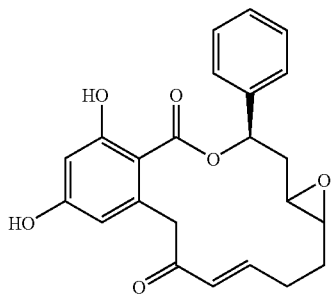

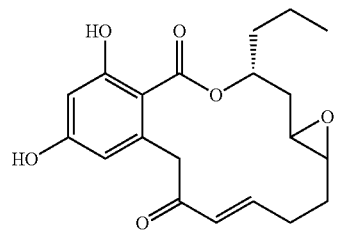

¹H NMR (400 MHz, C₆D₆, 25° C.): δ=11.98 (s, 1H), 6.91-6.83 (m, 1H), 6.43 (d, J=2.3 Hz, 1H), 6.24 (d, J=2.4 Hz, 1H), 6.11 (d, J=15.8 Hz, 1H), 5.35 (bs, 1H), 5.29 (m, 1H), 4.52 (d, J=17.5 Hz, 1H), 3.63 (d, J=17.5 Hz, 1H), 2.77 (bs, 1H), 2.57-2.52 (m, 2H), 2.46-2.27 (m, 2H), 2.14-2.10 (m, 1H), 1.93-1.88 (m, 1H), 1.48 (d, J=6.4 Hz, 3H).

¹H NMR (400 MHz, C₆D₆, 25° C.): δ=11.87 (s, 1H), 6.90-6.82 (m, 1H), 6.43 (s, 1H), 6.26 (s, 1H), 6.10 (d, J=15.2 Hz, 1H), 5.31 (bs, 1H), 5.18 (bs, 1H), 4.46 (d, J=17.5 Hz, 1H), 3.60 (d, J=17.6 Hz, 1H), 2.74 (bs, 1H), 2.57-2.38 (m, 3H), 2.32-2.22 (m, 1H), 2.08-1.82 (m, 2H), 1.73-1.67 (m, 1H), 1.42-1.37 (m, 2H), 1.33-1.28 (m, 2H), 1.01 (t, J=7.3 Hz, 3H); other isomer: ¹H NMR (400 MHz, C₆D₆, 25° C.): δ=11.72 (s, 1H), 6.86-6.80 (m, 1H), 6.41 (s, 1H), 6.27 (s, 1H), 6.21 (d, J=16.4 Hz, 1H), 5.37 (m, 1H), 5.22 (m, 1H), 4.25 (d, J=16.4 Hz, 1H), 3.96 (d, J=16.4 Hz, 1H), 2.74 (bs, 1H), 2.60-2.37 (m, 4H), 1.87-1.78 (m, 2H), 1.70-1.58 (m, 3H), 1.38-1.22 (m, 2H), 0.95 (t, J=7.3 Hz, 3H); HRMS (ESI-TOF): m/z: calculated for C₂₀H₂₄O₆Na: 383.1465, found 383.1492 [M+Na⁺].

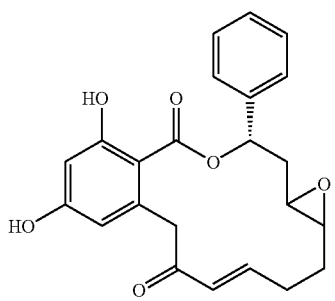

Major isomer: ¹H NMR (400 MHz, C₆D₆, 25° C.): δ=11.90 (s, 1H), 7.41-7.23 (m, 5H), 6.95-6.89 (m, 1H), 6.42 (d, J=2.8 Hz, 1H), 6.27 (d, J=2.9 Hz, 1H), 6.20 (d, J=15.8 Hz, 1H), 6.13 (d, J=4.1 Hz, 1H), 5.51 (m, 1H), 4.79 (d, J=17.5 Hz, 1H), 3.79 (d, J=17.0 Hz, 1H), 2.68-2.55 (m, 3H), 2.44-2.25 (m, 4H), para-phenol not detected; HRMS (ESI-TOF): m/z: calculated for C₂₃H₂₂O₆Na: 417.1309, found 417.1399 [M+Na⁺].

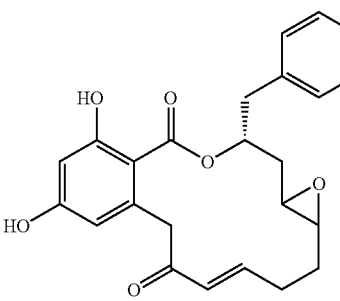

Major isomer: ¹H NMR (400 MHz, C₆D₆, 25° C.): δ=11.94 (s, 1H), 7.36-7.28 (m, 5H), 6.95-6.88 (m, 1H), 6.42 (s, 1H), 6.22 (s, 1H), 6.11 (d, J=15.8 Hz, 1H), 5.47 (m, 1H), 5.41 (bs, 1H), 4.43 (d, J=17.5 Hz, 1H), 3.56 (d, J=17.6 Hz, 1H), 3.19 (dd, J=13.7, 6.0 Hz, 1H), 3.03 (dd, J=13.7, 7.9 Hz, 1H), 2.87 (bs, 1H), 2.70-2.28 (m, 4H), 2.03-1.93 (m, 2H), para-phenol not detected; HRMS (ESI-TOF): m/z: calculated for $C_{24}H_{24}O_6Na$: 431.1465, found 431.1578 [M+Na$^+$].

General procedure for the preparation of macrocycles 2-151: HCl$_{conc.}$ (20.0 equiv.) was added to a solution of compound 2-120 (1.0 equiv.) in dioxane (0.05 M) at 23° C., and the mixture was stirred for 3 h. After this time, the reaction was filtered through a pad of silica, the solvents evaporated under reduced pressure, and purification by preparative TLC (silica gel, 30% EtOAc/cyclohexane) afforded compound 2-151 (>75% yield) as a mixture of two diastereoisomers 1:1.

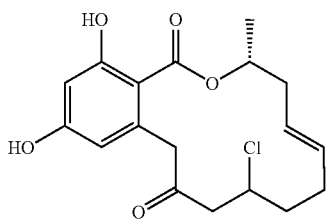

Selected examples of compounds 2-151: $^1$H NMR (400 MHz, CDCl$_3$, 25° C.): δ=12.11 (s, 1H), 11.78 (s, 1H), 6.51 (s, 1H), 6.43 (s, 1H), 6.41 (d, J=2.4 Hz, 1H), 6.37 (d, J=2.7 Hz, 1H), 6.21 (d, J=2.4 Hz, 1H), 6.11 (d, J=2.4 Hz, 1H), 5.59-5.51 (m, 3H), 5.40-5.32 (m, 3H), 4.54 (d, J=17.2 Hz, 1H), 4.42 (d, J=17.2 Hz, 1H), 3.60 (d, J=17.2 Hz, 1H), 3.45 (d, J=17.0 Hz, 1H), 3.28 (dd, J=18.5, 9.4 Hz, 1H), 3.11 (dd, J=13.7, 6.2 Hz, 1H), 3.07 (dd, J=13.4, 4.6 Hz, 1H), 2.76 (dd, J=19.0, 6.2 Hz, 1H), 2.62 (ddd, J=15.5, 8.8, 4.0 Hz, 1H), 2.54 (ddd, J=15.3, 6.2, 3.2 Hz, 1H), 2.40-2.26 (m, 4H), 2.25-2.13 (m, 4H), 2.03-1.91 (m, 2H), 1.42 (d, J=6.4 Hz, 3H), 1.40 (d, J=6.4 Hz, 3H), para-phenol not detected; HRMS (ESI-TOF): m/z: calculated for $C_{18}H_{21}ClO_5Na$: 375.0970, found 375.0928 [M+Na$^+$].

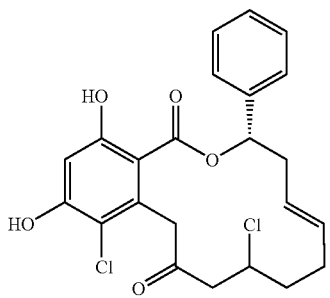

$^1$H NMR (400 MHz, C$_6$D$_6$, 25° C.): δ=11.76 (s, 0.5H), 11.36 (s, 0.5H), 7.40-7.29 (m, 5H), 6.65 (s, 0.5H), 6.62 (s, 0.5H), 6.18 (t, J=5.8 Hz, 1H), 6.14 (s, 0.5H), 6.12 (s, 0.5H), 5.67-5.62 (m, 1H), 5.55-5.49 (m, 1H), 4.93 (d, J=18.1 Hz, 0.5H), 4.80 (d, J=17.1 Hz, 0.5H), 4.58-4.56 (m, 1H), 4.38 (d, J=18.1 Hz, 0.5H), 4.18 (d, J=17.1 Hz, 0.5H), 3.33-3.27 (m, 1H), 3.10 (dd, J=18.4, 3.8 Hz, 0.5H), 2.84-2.68 (m, 2.5H), 2.42-2.32 (m, 2H), 2.23-2.17 (m, 1H), 2.13-2.04 (m, 1H), para-phenol not detected; HRMS (ESI-TOF): m/z: calculated for $C_{23}H_{22}O_5Cl_2Na$: 471.0737, found 471.0754 [M+Na$^+$].

Elimination of β-Cl from compound 2-151: PS-TBD (51 mg, 2.6 mmol·g$^{-1}$) was added to a solution of compound 2-151 (95 mg, 270 μmol) in CH$_2$Cl$_2$ (5 mL) at 23° C., and the mixture was stirred for 8 h. After this time, the reaction was filtered, the solvents were evaporated under reduced pressure, and the remaining residue was purified by flash chromatography (silica gel, 0-30% EtOAc/cyclohexane gradient) to afford 2-103 (84 mg, 98%).

General procedure for the synthesis of compounds 2-152: Compound 2-120a or 2-112a (1.0 equiv.) was dissolved in a 1:5 mixture of TFA/CH$_2$Cl$_2$ and stirred for 2 h at room temperature. Evaporation of the solvents; followed by flash chromatography (silica gel, 0-50% Et$_2$O/hexane), afforded compound 2-152 (~70% yield).

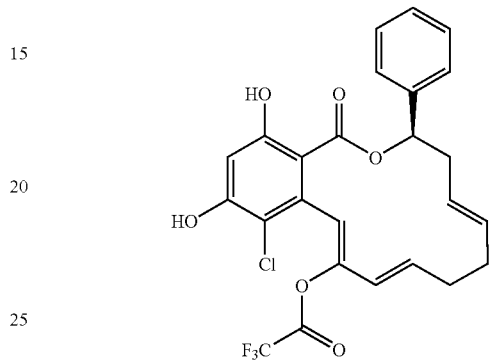

Selected example of compounds 2-152: $^1$H NMR (400 MHz, C$_6$D$_6$, 25° C.): δ=11.74 (s, 1H), 7.22-7.14 (m, 5H), 6.52 (s, 1H), 6.46 (dt, J=15.2, 7.3 Hz, 1H), 6.28 (s, 1H), 5.89 (t, J=7.0 Hz, 1H), 5.76 (s, 1H), 5.59 (d, J=15.2 Hz, 1H), 5.37 (ddd, J=15.2, 6.9, 6.9 Hz, 1H), 5.24 (ddd, J=15.2, 7.3, 7.0 Hz, 1H), 2.56-2.49 (m, 1H), 2.44-2.39 (m, 1H), 2.01-1.92 (m, 4H); $^{13}$C NMR (100 MHz, C$_6$D$_6$, 25° C.): δ=164.8, 162.8, 158.7, 153.1, 137.6, 136.9, 136.1, 133.9, 128.7 (×2), 126.5 (×2), 124.2, 122.0, 102.4, 100.8, 79.9, 39.0, 32.3, 31.4, four quaternary carbons are not detected; HRMS (ESI-TOF): m/z: calculated for $C_{25}H_{20}ClF_3O_6Na$: 531.0793, found 531.0992 [M+Na$^+$].

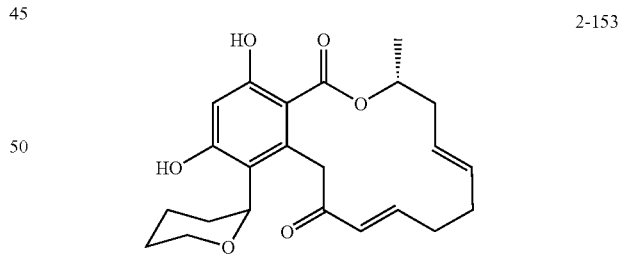

Macrocycle 2-153: DHP (3.7 μL, 40.8 mmol) and PS-TsOH (12.7 mg, 40.8 mmol, 3.2 mmol$^{-1}$) were added to a solution of compound 2-103 (12.9 mg, 40.8 μmol) in CH$_2$Cl$_2$ (1 mL) at 23° C., and the mixture was stirred for 5 h. After this time, the reaction was filtered and the solvents were evaporated under reduced pressure. Purification by preparative TLC (silica gel, 30% EtOAc/cyclohexane) afforded 2-153 (13.8 mg, 85%) as a mixture of two diastereoisomers. $^1$H NMR (400 MHz, CDCl$_3$, 25° C.): δ=12.33 (s, 1H), 12.11 (s, 1H), 9.45 (s, 1H), 9.40 (s, 1H), 6.67, (m, 2H), 6.28 (2×s, 2H), 5.83 (d, J=13.2 Hz, 1H), 5.79 (d, J=12.9 Hz, 1H), 5.35-5.30

(m, 3H), 5.27-5.22 (m, 3H), 5.06 (bd, J=8.2 Hz, 2H), 4.10 (d, J=17.5 Hz, 2H), 3.90-3.85 (m, 1H), 3.80-3.76 (m, 2H), 3.65 (d, J=17.7 Hz, 2H), 3.57-3.52 (m, 2H), 3.46-3.41 (m, 2H), 2.77-2.71 (m, 3H), 2.53-2.49 (m, 3H), 2.36-2.29 (m, 4H), 2.24-1.56 (m, 12H), 1.31 (d, J=6.4 Hz, 3H), 1.28 (d, J=6.4 Hz, 3H); HRMS (ESI-TOF): m/z: calculated for $C_{23}H_{28}O_6Na$: 423.1778, found 423.1778 [M+Na$^+$].

General procedure for the synthesis of compounds 2-154: The hydroxylamine R$^2$ONH$_2$ (5.0 equiv.) was added to a solution of compound 2-120 (1.0 equiv.) in pyridine/AcOH (5:1, 0.03 M) and the mixture was heated up to 40° C. After stirring overnight, the solvents were evaporated under reduced pressure with silica gel. Purification over a short pad of silica gel with a mixture of 30% EtOAc/cyclohexane afforded compound 2-154 (~99%) as a mixture of two diastereoisomers cis/trans.

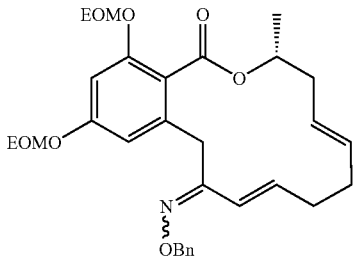

Selected example of compounds 2-154: $^1$H NMR (400 MHz, CDCl$_3$, 25° C.): δ=7.50-7.25 (m, 10H), 6.82 (s, 1H), 6.75 (s, 1H), 6.66 (s, 1H), 6.48 (s, 1H), 6.24-6.11 (m, 2H), 6.11-6.05 (m, 2H), 5.45-5.38 (m, 4H), 5.34-5.31 (m, 14H), 4.50 (d, J=17.2 Hz, 1H), 3.65-3.38 (m, 8H), 3.60 (d, J=17.1 Hz, 1H), 3.54 (d, J=17.1 Hz, 1H), 3.24 (d, J=17.2 Hz, 1H), 2.48-2.36 (m, 4H), 2.21-2.17 (m, 2H), 2.11-2.04 (m, 2H), 1.95-1.83 (m, 2H), 1.62-1.51 (m, 2H), 1.49 (d, J=6.4 Hz, 6H), 1.32-1.20 (m, 12H); $^{13}$C NMR (100 MHz, CDCl$_3$, 25° C.): δ=168.1, 167.9, 159.1, 158.8, 157.2, 155.6, 155.4, 154.2, 140.8, 138.2, 138.2, 137.8, 136.9, 136.7, 132.3, 132.3, 128.3 (×2), 128.3 (×2), 128.2, 128.1 (×2), 128.0 (×2), 127.7, 127.6, 125.5, 118.8, 118.6, 118.3, 108.8, 108.5, 101.7, 101.7, 93.5, 93.4, 93.1 (×2), 77.2, 76.0, 75.9, 71.2, 71.0, 64.5, 64.5, 64.3, 64.3, 40.0, 40.0, 34.9, 32.4, 32.3, 31.6, 31.1, 28.9, 20.3, 20.2, 15.0 (×2), 15.0 (×2); HRMS (ESI-TOF): m/z: calculated for $C_{31}H_{39}NO_7Na$: 560.2619, found 560.2627 [M+Na$^+$].

General procedure for the synthesis of compounds 2-155: PS-TsOH (10.0 equiv., 3.2 mmol·g$^{-1}$) was added to a solution of compound 2-154 (1.0 equiv.) in MeOH (0.02 M) and the suspension was shaken at 40° C. for 4 h. After this time, the reaction mixture was filtered and the methanolic solution concentrated under reduced pressure. The crude product obtained was submitted without further purification to the next step. Thus, DHP (1.0 equiv.) and PS-TsOH (catalytic amount, 3.2 mmol·g$^{-1}$) were added to a solution of this crude in CH$_2$Cl$_2$ (0.02 M) at 23° C., and the mixture was stirred for 5 h. After this time, the mixture was filtered, the solvents were evaporated under reduced pressure, and the remaining residue was purified by preparative TLC (silica gel, 30% EtOAc/cyclohexane) to afford two different diastereoisomers 1:1 of 2-155 (~65% yield).

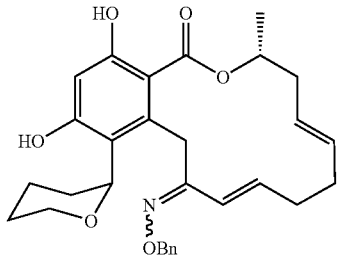

Selected example of compounds 2-155: Less polar diastereoisomer: $^1$H NMR (400 MHz, CDCl$_3$, 25° C.): δ=9.25 (s, 1H), 9.24 (s, 1H), 7.46-7.33 (m, 10H), 6.29 (s, 1H), 6.26 (s, 1H), 6.07-6.02 (m, 2H), 5.75 (d, J=15.8 Hz, 1H), 5.69 (d, J=15.8 Hz, 1H), 5.44-5.38 (m, 6H), 5.23 (s, 4H), 5.03 (d, J=8.8 Hz, 2H), 4.34-4.13 (m, 6H), 3.69-3.63 (m, 2H), 2.70-2.67 (m, 2H), 2.30-2.16 (m, 6H), 2.08-1.94 (m, 8H), 1.73-1.65 (m, 8H), 1.42 (t, J=6.4 Hz, 3H), 1.39 (t, J=7.0 Hz, 3H); HRMS (ESI-TOF): m/z: calculated for $C_{30}H_{35}NO_6Na$: 528.2357, found 528.2562 [M+Na$^+$].

More polar diastereoisomer: $^1$H NMR (400 MHz, CDCl$_3$, 25° C.): δ=11.61 (s, 1H), 9.27 (s, 1H), 7.41-7.33 (m, 5H), 6.62 (d, J=16.4 Hz, 1H), 6.47 (s, 1H), 6.15-6.07 (m, 1H), 5.50-5.38 (m, 3H), 5.16 (s, 2H), 5.04 (d, J=10.5 Hz, 1H), 4.30 (d, J=15.2 Hz, 1H), 4.24 (d, J=10.5 Hz, 1H), 3.84 (d, J=15.2 Hz, 1H), 3.66 (t, J=11.4 Hz, 1H), 2.71-2.65 (m, 1H), 2.28-2.08 (m, 6H), 1.73-1.64 (m, 5H), 1.38 (t, J=7.0 Hz, 3H); HRMS (ESI-TOF): m/z: calculated for $C_{30}H_{35}NO_6Na$: 528.2357, found 528.2494 [M+Na$^+$].

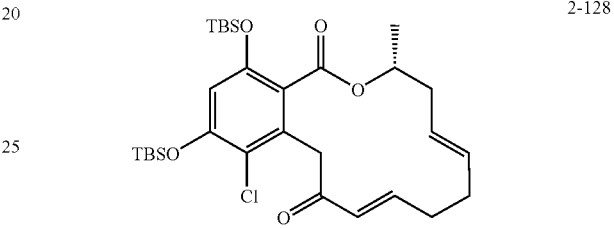

Macrocycle 2-128 from pochonin D (2-85): TBSCl (53.6 mg, 356 μmol) and imidazole (23.6 mg, 356 μmol) were added to a solution of pochonin D (2-85, 25 mg, 71.2 μmol) in DMF (5 mL) and the mixture was stirred for 3 h at room temperature. Purification by column chromatography (silica gel, 0-30% EtOAc/cyclohexane gradient) afforded compound 2-128 (40 mg, 98%).

General procedure for compounds 2-157: The hydroxylamine RONH$_2$ (5.0 equiv.) was added to a solution of compound 2-128 (1.0 equiv.) in pyridine/AcOH (5:1, 250 μL) and the mixture was heated up to 40° C. After stirring overnight, the solvents were evaporated under reduced pressure, and filtration on silica gel with a mixture of 30% EtOAc/cyclohexane afforded two isomers of 2-157 (~90% yield).

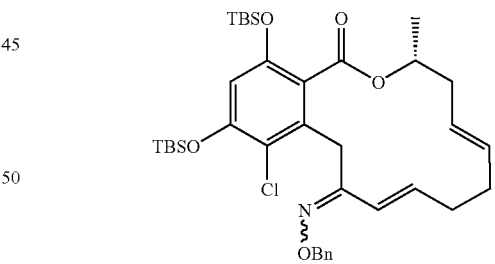

Selected example of compounds 2-157: cis oxime: $^1$H NMR (400 MHz, CDCl$_3$, 25° C.): δ=7.42 (bd, J=6.4 Hz, 2H), 7.36 (bdd, J=7.5, 6.9 Hz, 2H), 7.34-7.32 (m, 1H), 6.52 (d, J=16.1 Hz, 1H), 6.38 (s, 1H), 6.18-6.10 (m, 1H), 5.36-5.32 (m, 2H), 5.16 (bs, 2H), 4.99-4.95 (m, 1H), 3.79-3.76 (m, 2H), 2.40-1.99 (m, 6H), 1.45 (d, J=6.2 Hz, 3H), 1.03 (s, 9H), 0.99 (s, 9H), 0.28 (s, 3H), 0.26 (s, 3H), 0.20 (s, 6H); trans oxime: $^1$H NMR (400 MHz, CDCl$_3$, 25° C.): δ=7.44 (bd, J=6.5 Hz, 2H), 7.37 (bdd, J=7.6, 6.9 Hz, 2H), 7.33-7.31 (m, 1H), 6.41 (s, 1H), 6.04-5.97 (m, 1H), 5.48 (d, J=15.0 Hz, 1H), 5.29-5.27 (m, 1H), 5.22 (bs, 2H), 5.00-4.95 (m, 1H), 3.98-3.89 (m, 2H), 2.39-2.02 (m, 6H), 1.37 (d, J=5.9 Hz, 3H), 1.04 (s, 9H), 0.99 (s, 9H), 0.28 (s, 3H), 0.27 (s, 3H), 0.23 (s, 3H), 0.22 (s, 3H).

General procedure for compounds 2-158: To a solution of corresponding compound 2-157 (1.0 equiv) in THF was added TBAF (2.5 equiv, 1M solution in THF) and the mixture was stirred at room temperature for 2 h. The solvents were then evaporated under reduced pressure, and filtration on silica gel with a mixture of 30% EtOAc/cyclohexane afforded compound 2-158 in >85% yield.

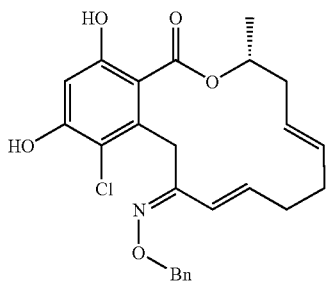

Selected example of compounds 2-158: cis oxime: $^1$H NMR (400 MHz, CDCl$_3$, 25° C.): δ=11.52 (s, 1H), 7.45-7.34 (m, 5H), 6.64 (s, 1H), 6.09-6.02 (m, 2H), 5.34-5.25 (m, 4H), 5.18-5.08 (m, 2H), 4.33 (d, J=17.0 Hz, 1H), 4.15 (d, J=17.6 Hz, 1H), 2.65-2.59 (m, 1H), 2.27-2.14 (m, 3H), 2.04-2.00 (m, 1H), 1.88-1.83 (m, 1H), 1.30 (t, J=6.4 Hz, 3H); HRMS (ESI-TOF): m/z: calculated for C$_{25}$H$_{26}$ClNO$_5$Na: 478.1392, found 478.1372 [M+Na$^+$]. trans oxime: $^1$H NMR (400 MHz, CDCl$_3$, 25° C.): δ=11.73 (s, 1H), 7.32-7.26 (m, 5H), 6.64 (s, 1H), 6.50 (d, J=16.4 Hz, 1H), 6.06-5.98 (m, 2H), 5.43-5.24 (m, 3H), 4.91 (s, 2H), 4.22 (s, 2H), 2.61-2.55 (m, 1H), 2.46-2.33 (m, 2H), 2.20-2.02 (m, 3H), 0.98 (t, J=6.4 Hz, 3H); HRMS (ESI-TOF): m/z: calculated for C$_{25}$H$_{26}$ClNO$_5$Na: 478.1392, found 478.1522 [M+Na$^+$].

(±)-2-159

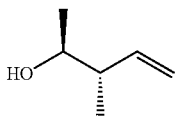

Compound (±)-2-159: A solution of cis-butene oxide (1.75 mL, 20 mmol) in Et$_2$O (10 mL) was cooled to −30° C. Copper iodide (1.14 g, 6 mmol) was added to this solution and then, vinyl magnesium bromide (40 mL, 1M solution in THF, 40 mmol) was added dropwise over a period of 1 h. The reaction mixture was then warmed up to room temperature over 12 h and the reaction turned black. The reaction mixture was quenched slowly with saturated NH$_4$Cl$_{aq}$. (20 mL), stirred for 2 h, extracted with Et$_2$O (20 mL) and dried over MgSO$_4$. Concentration under reduced pressure afforded compound (±)-2-159 (1.3 g, 65%). $^1$H NMR (400 MHz, CDCl$_3$, 25° C.): δ=5.81-5.72 (m, 1H), 5.15 (d, J=13.2 Hz, 2H), 3.59 (m, 1H), 2.23-2.10 (m, 1H), 1.21 (d, J=6.4 Hz, 3H), 1.05 (d, J=7.0 Hz, 3H).

(±)-2-163

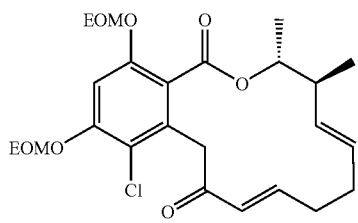

Compound (±)-2-163: In a similar manner as that described for compound 2-112, compound (±)-2-163 was prepared with a 57% yield from (±)-2-162. $^1$H NMR (400 MHz, CDCl$_3$, 25° C.): δ=7.10 (s, 1H), 6.76-6.71 (m, 1H), 5.87 (d, J=15.8 Hz, 1H), 5.32 (s, 2H), 5.25-5.18 (s+m, 4H), 4.87-4.80 (m, 1H), 3.99 (d, J=16.9 Hz, 1H), 3.80-3.71 (m, 5H), 2.32-2.26 (m, 2H), 2.20-2.11 (m, 3H), 1.36 (d, J=6.4 Hz, 3H), 1.25 (t, J=7.0 Hz, 6H), 1.04 (d, J=7.0 Hz, 3H); $^{13}$C NMR (100 MHz, CDCl$_3$, 25° C.): δ=195.7, 166.6, 154.6, 153.8, 147.1, 133.3, 132.8, 120.7, 117.7, 102.9, 93.9, 93.6, 76.2, 64.8, 64.6, 45.1, 41.6, 30.7, 30.7, 18.2, 16.9, 15.0, 15.0.

(±)-2-164

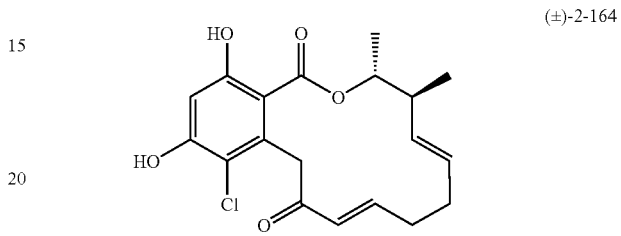

Compound (±)-2-164: In a similar manner as that described for compound 2-85 using PS-TsOH, compound (±)-2-164 was prepared with a 40% yield from (±)-2-163. $^1$H NMR (400 MHz, CDCl$_3$, 25° C.): δ=11.52 (s, 1H), 6.78-6.69 (m, 1H), 6.67 (s, 1H), 6.05 (s, 1H), 5.93 (d, J=16.4 Hz, 1H), 5.47-5.45 (m, 1H), 5.37-5.33 (m, 1H), 5.16 (dd, J=15.8, 7.0 Hz, 1H), 4.48 (bs, 1H), 4.35 (d, J=17.6 Hz, 1H), 2.45-2.26 (m, 5H), 1.27 (d, J=6.4 Hz, 3H), 1.10 (d, J=7.0 Hz, 3H); ESI: m/z: calculated for C$_{18}$H$_{21}$ClO$_5$: 365.12, found 365.22 [M+H$^+$].

Processes for the Preparation of the Compounds of Formulae Ia, Ia', IIa, IIa', IIIa, IVa, and Va:

Modular synthetic processes directed to the synthesis of the resorcylic acid lactones of the invention are presented below. The syntheses developed may utilize resin-assisted or solid phase synthesis to minimize and facilitate the isolation of intermediate and final products.

The following abbreviations are used herein.

Ac Acetyl (CH$_3$C=O)
BBN Borabicyclononane
Bn Benzyl
Bz Benzoyl
Cy$_3$ Cyanine dye labeling reagent
δ Chemical shift (NMR)
DCC Dicyclohexylcarbodiimide
DEAD Diethyl azodicarboxylate
DIAD Diisopropyl azodicarboxylate
d.e. Diastereoisomeric excess
DIBAL or Dibal-H Diisobutylaluminum hydride
DIC N,N'-diisopropylcarbodiimide
DMAP 4-Dimethylaminopyridine
DMF Dimethylformamide
DMSO Dimethylsulfoxide
EC$_{50}$ Plasma concentration required for obtaining 50% of maximum effect in vivo
e.e. Enantiomeric excess
EOM Ethoxymethyl (CH$_3$CH$_2$OCH$_2$—)
FDA Food and Drug Administration Grubbs' II Grubbs' second generation catalyst: (ruthenium [1,3-bis(2,4,6-trimethylphenyl)-2-imidazolinylidene) dichloro(phenylmethylene) (tricyclohexylphosphane)

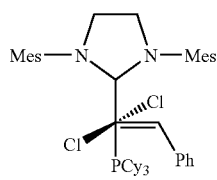

Grubbs' II

HFIP Hexafluoroisopropanol
HPLC High performance chromatography
HRMS High resolution mass spectrometry
HSP90 Heat shock protein 90
Hunig's Base Diisopropylethylamine
$IC_{50}$ Concentration of a drug that is required for 50% inhibition in vitro
$Ipc_2$ Bis-isopinocamphoryl
J Coupling constant
LDA Lithium diisopropylamide
Micromolar concentration ($\mu mol \cdot l^{-1}$)
M.S. Mass spectrum
NMR Nuclear magnetic resonance
PG Protecting Group
PS—Polymer supported
PS-DCC Polymer supported dicyclohexylcarbodiimide
PS-TBD (1,5,7)-Triaza-bicyclo[4.4.0]dodeca-5-ene-7-methyl polystyrene
Pyr or Py Pyridine
rac Racemic
RAL Resorcylic acid lactone
RCM Ring-closing metathesis
$R_f$ Retention factor
RT Room temperature
SEM 2-Trimethylsilylethoxymethoxy
TBAF Tetra-n-butylammonium fluoride
TBAI Tetra-n-butylammonium iodide
TBDPS t-Butyldiphenylsilyl
TBS t-Butyldimethylsilyl
TFA Trifluoroacetic acid
TFAA Trifluoroacetic acetic anhydride
THF Tetrahydrofuran
THP Tetrahydropyran
TLC Thin layer chromatography
TMS Trimethylsilyl
TMSCI Trimethylsilylchloride
TNTU 2-(endo-5-norbornene-2,3-dicarboxylimide)-,1,3,3-tetramethyluronium tetrafluoroborate
Ts Tosyl (p-$CH_3C_6H_4SO_2$)
p-TSOH para-Toluenesulfonic acid A general retrosynthetic disconnection of the synthetic strategy for preparation of the compounds of the invention is shown below (see Barluenga et al., *Angew. Chem. Int. Ed.*, 2008, 47, 4432-4435). A Mitsunobu esterification, an acylation and a ring-closing metathesis are shown as the main disconnections using three building blocks. Using these building blocks and synthetic strategy, a divergent synthesis of the compounds was developed. A similar strategy has been used to prepare a library of pochonin analogues with HSP90 activity (see Moulin et al., *Chem. Eur. J.* 2006, 12, 8819).

Retrosynthetic analysis for compounds of the invention

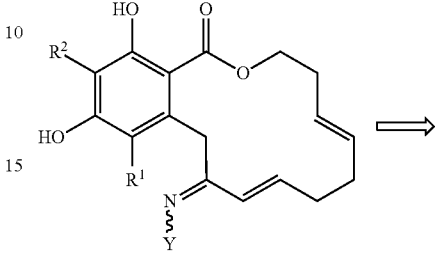

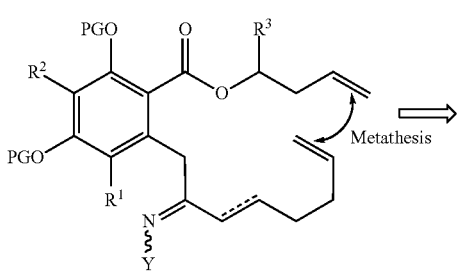

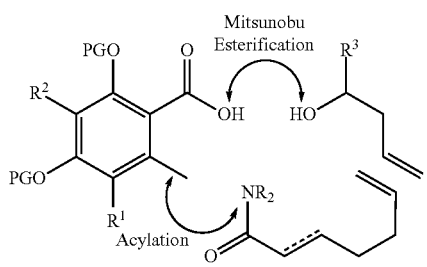

The schemes illustrated below are non-limiting examples of the synthesis of the compounds of the invention and intermediates used to prepare the compounds. It will be apparent to one of skill in the art that the reactions depicted in the schemes may use alternate reagents and conditions to achieve the desired transformation. For example, various protecting groups may be used in the synthesis of the compounds, and the specific groups depicted in the schemes are non-limiting examples. For example, any suitable protecting groups for hydroxy and carboxyl groups taught in Greene et al., *Protective Groups in Organic Synthesis*, John Wiley & Sons, 3rd Ed., 1999 may be used instead of the protecting groups shown. Furthermore, alternate reagents known in the art for the transformations shown, including, for example, the esterification of the aromatic carboxylic acid or the ring closure reaction may be used.

Scheme 1a below shows the general synthetic protocol for one of the compounds of the invention where X=O and n=1, starting from intermediate 1-1, which is formed from readily available protected aromatic precursors by acylation of the benzylic position with a suitably substituted carboxylic acid derivative followed by formation of the substituted oxime by reaction of the acylated aromatic group with a suitable hydroxylamine reagent, such as aminooxyacetic acid. Scheme 2a below provides a non-limiting example of the preparation of an aromatic compound of structure 1-1.

To facilitate the isolation and purification of the intermediates and final compounds, intermediates such as compound 1-1 may be anchored onto a suitably functionalized resin, such as a 2-chlorotrityl resin, by reaction of the carboxylic acid group with the resin. The resin-anchored intermediate 1-2 is deprotected to provide intermediate 1-3 with the free carboxylic acid group.

The carboxylic acid 1-3 is reacted with a suitable alcohol R²OH, which comprises a double bond that may be utilized for a ring-closing metathesis reaction with a suitable catalyst. Various conditions for the formation of an aromatic ester derivative may be used, including, but not limited to a Mitsunobu esterification with, for example, a homoallylic alcohol, to form the corresponding ester (not shown). The resin bound ester is then treated with a catalyst, such as Grubb's second generation catalyst, to effect ring closure to intermediate 1-4. Use of microwave irradiation during the ring closure has been found to improve the efficiency of the metathesis reaction.

It is important to note that the reaction sequence is not possible in the absence of the oxime functionality, since reaction of the corresponding benzylic ketone results in coumarin byproducts (see Barluenga et al., *Chem. Eur. J.* 2005, 11, 4935).

The macrocycles are removed from the resin using, for example, hexafluoropropanol (HFIP) to provide the oxime acid product 1-5. Use of the mild HFIP for the removal of the compounds from the resin left the EOM protecting groups in tact, thus enabling further elaboration of other functionality on the macrocycles. The resulting product may be derivatized by reaction of the free carboxylic acid with a suitable group. Carboxylic acids are very useful for the formation of various derivatives, as known in the art. The free carboxylic acid may be derivatized by reacting with a variety of compounds to form desired products. For example, reaction with R⁴XH (X=O or NH), in the presence of an activating reagent, such as dicyclohexylcarbodiimide (DCC) or an alternate activating reagent, to form the corresponding ester or amide 1-6.

In non-limiting examples, the free carboxylic acid in compound 1-5 may be eracted with an amine or alcohol to form an amide or ester. In some embodiments, the amines shown below are used to form compounds of the invention. It will be apparent that alternate groups may be used to form the corresponding amide or ester.

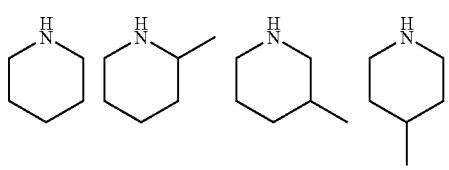

-continued

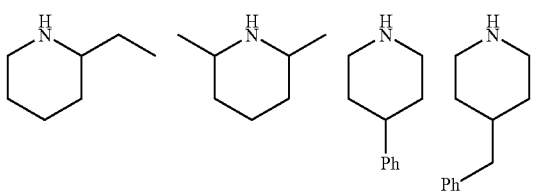

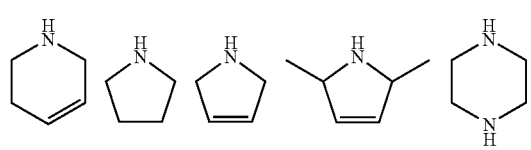

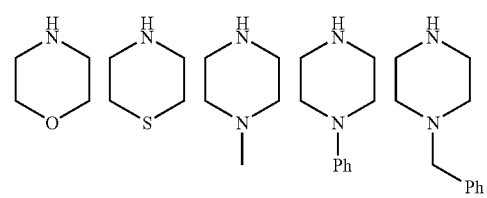

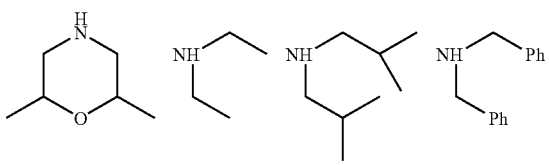

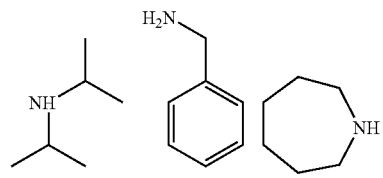

The use of resin-immobilized carbodiimide and sulfonic acid was advantageously used to form various amides and esters from the carboxylic acid moiety liberated upon removal of the macrocycles (compounds 1-5 of Scheme 1aa) from the resin.

Scheme 1a
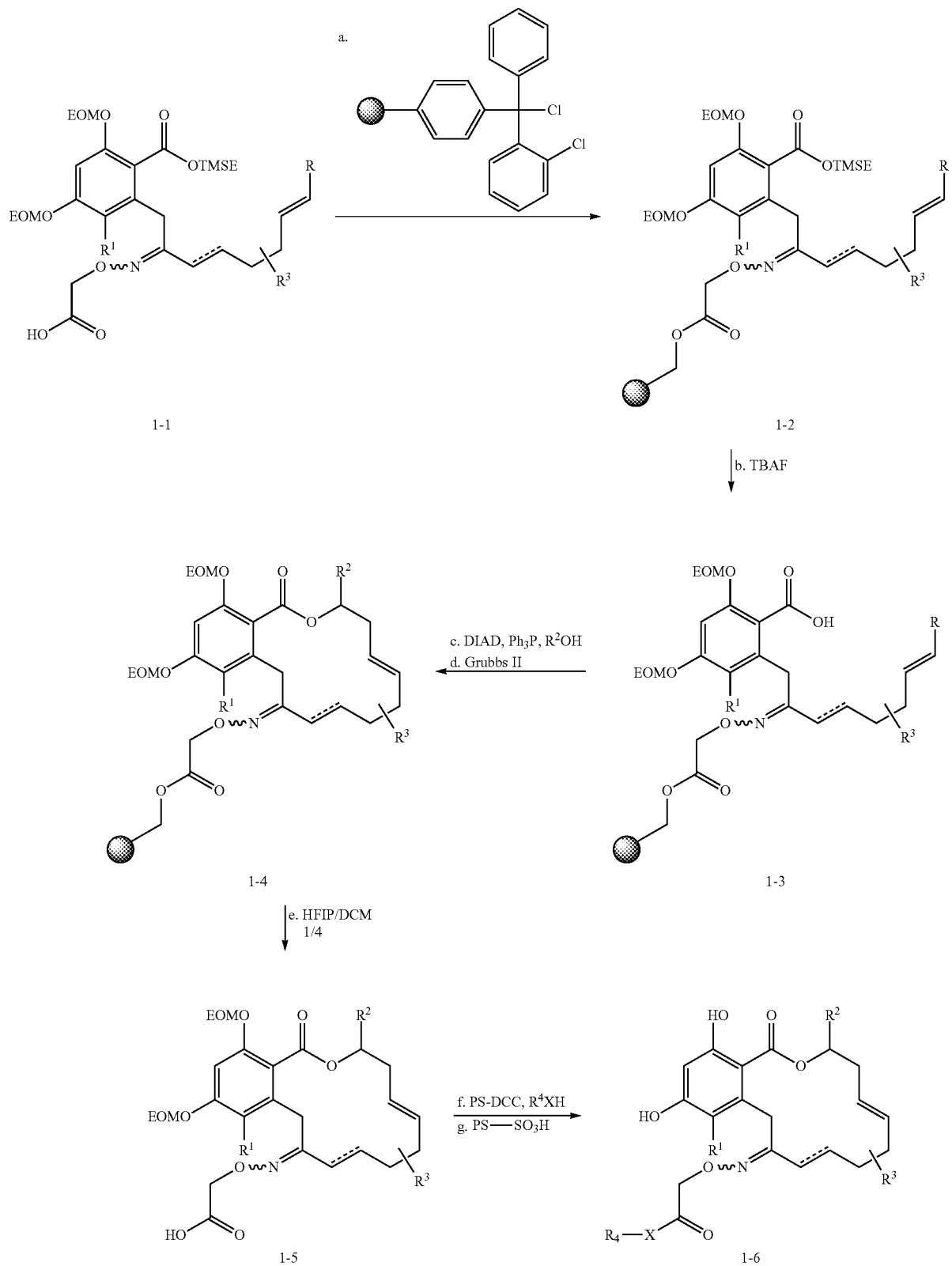
Reagents and conditions: a) PS—ClTr-Cl (3.0 equiv), DIPEA (6.0 equiv), $CH_2Cl_2$, 23° C., 24 h; then AcOH (20 equiv), 23° C., 24 h; b) TBAF (4.0 equiv), 23° C., 4 h; c) $R^2OH$ (5.0 equiv), $Ph_3P$ (2.0 equiv) DIAD (2.0 equiv), toluene, 23° C., 12 h, d) Grubb's II (0.06 equiv), $CH_2Cl_2$, 120° C., MW, 3 x 45 min, e) HFIP/$CH_2Cl_2$ 1/4, 23° C., 3 h, 20-30% over 5 steps; f) PS—DCC (3.0 equiv), DMAP (cat), $R^4XH$ (2.0 equiv), 23° C., 72 h, ~75%; g) PS—$SO_3H$ (10 equiv), MeOH, 23° C., 4 h, ~85%.

Scheme 2a shows an example synthesis of intermediate 1-1 from a suitably protected aromatic carboxylic acid derivative 2-1. Deprotonation of 2-1 with lithium diisopropylamide (LDA) and reaction with Weinreb amide 2-2 followed by quenching with benzoic acid resin affords intermediate 2-3. Reaction of 2-3 with excess hydroxylamine reagent results in formation of the oxime intermediate 2-4, which is utilized further, as described in scheme 1.

enzymatic resolution of the racemic alcohol (H. E. Master et al., *Tet. Lett.*, 37:9253 (1996); S. Singh et al., *Tet. Asymm.*, 13:2679 (2002) or via Brown allylation of the corresponding aldehyde (H. C. Brown and P. K. Jadhav *J. Am. Chem. Soc.*, 105:2092 (1983). The phenyl (3-3a), the pyridinyl (3-3b) and the furyl (3-3c) alcohols were prepared by enzymatic resolution (Scheme 3). Racemic alcohols 3-2a-c were obtained after

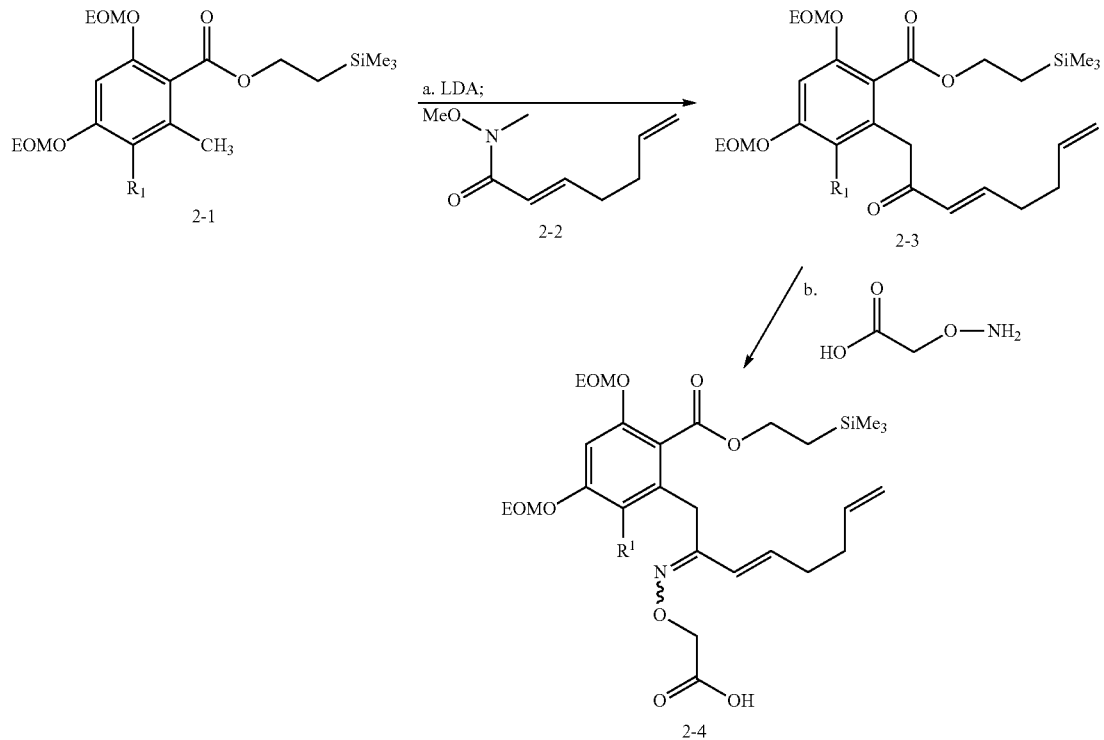

Reagents and conditions: a) LDA (2.0 eq.), THF, -78 C.; 1 eq. of Weinreb amide 2-2 then acidic resin; b) 5.0 eq. of carboxylic acid 2-4, Py/AcOH, 40 C.

In some embodiments non-limiting embodiments, the starting aromatic starting material may be the compound shown below, where $R^1$ is H or halogen, particularly hydrogen and chlolo. As discussed, other protecting groups known in the art may be used for the phenol and carboxyl functional groups.

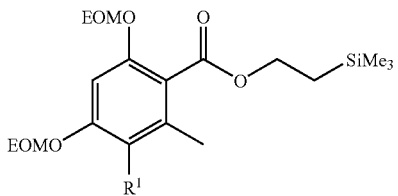

Homoallylic Alcohols

A variety of homoallylic alcohols are commercially available and may be used in the synthesis. Other homoallylic alcohols bearing various substituents may prepared by methods known in the art. Scheme 3a below illustrates a synthesis of various homoallylic alcohols that are not commercially available. In one embodiment, the homoallylic alcohols 3-3 were obtained in their highest enantiomeric form either by Grignard addition of commercially available allylmagnesium bromide on their corresponding aldehyde 3-1a-c.

Scheme 3a: Synthesis of chiral alcohols 3a-c using enzymatic resolution

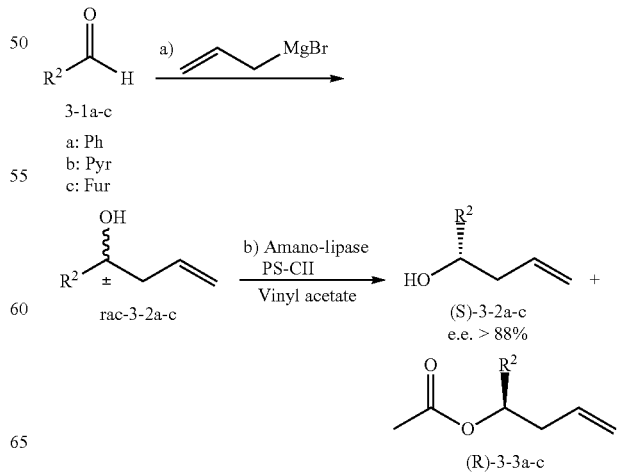

-continued

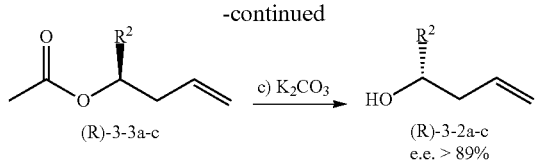

(R)-3-3a-c  →(c) K₂CO₃→  (R)-3-2a-c  e.e. > 89% a) AllylMgBr (1.5 equiv.), THF, 0.5 h, 0° C., 71% (3-2a), 41% (3-2b), 74% (3-2c);
b) R² = Ph: vinyl acetate (32.5 equiv.), Amano Lipase PS-C II (50 mg/mmol of 3-2), 23° C., 30 h (monitored by ¹H NMR), R² = Pyr, Fur: vinyl acetate (10.0 equiv.), Amano Lipase PS-C II (50 mg/mmol of 3-2), THF, 23° C., 5-30 h (monitored by ¹H NMR); c) K₂CO₃ (0.8 equiv.), MeOH, 23° C., 98% ((R)-3-2a, 92% ((R)-3-2b), 84% ((R)-3-2c).

Kinetic enzymatic resolution of racemic alcohols 3-2a-c was realized using the highly efficient Amano lipase (an immobilized version of *Pseudomonas cepacia*). This enzyme catalyzed a selective transesterification of alcohols (R)-3-2a-c with vinyl acetate as an acyl donor, the (S) alcohols 3-2a-c being isolated in excellent yields and good enantiomeric excesses (Table 2).

TABLE 2a

Enantioselective acylation of alcohols rac-3-2a-c by transesterification with lipase

| Entry | Substrate | Time (h) | Conv. Ratio (%) (OH/OAc) | Yield (%) (S)-3-2 | e.e. (%) (S)-3-2 | Yield (%) (R)-3-2 | e.e. (%) (R)-3-2 |
|---|---|---|---|---|---|---|---|
| 1 | rac-3-2a | 30 | 50:50 | 45 | 98 | 49 | 93 |
| 2 | rac-3-2b | 30 | 52:48 | 50 | 89 | 39 | 94 |
| 3 | rac-3-2c | 5 | 49:51 | 44 | 88 | 49 | 89 |

Enantiomeric excess obtained with this methodology are all above 88%. Acetylated alcohols (R)-3-3 were then hydrolysed to the corresponding alcohols (R)-3-2a-c in excellent yields. Scheme 4a below illustrates an alternate process based on Brown allylation for the synthesis of the isopropyl (4-4-d), the propyl (4-4-e) and the benzyl (4-4f) alcohols (Scheme 4).

Scheme 4a: Synthesis of chiral alcohols 4-3d-f using Brown allylation

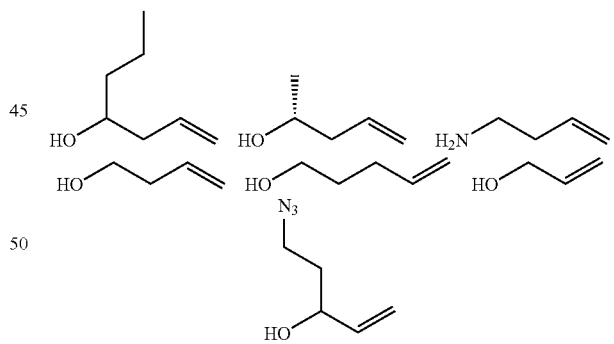

-continued 4-4d: e.e. = 80% (iPr)
4-4e: e.e. = 91% (Pr)
4-4f: e.e. = 95% (Bz)

a) (-)-α-pinene (2.4 equiv.), BH₃•Me₂S (1.0 equiv.), THF, 23° C. for 1 h and then 4° C. for 12 h, 76%; b) MeOH (1.2 equiv.), Et₂O, 0° C., 2 h, 94%; c) AllylMgBr (0.95 equiv.), Et₂O, 0 → 23° C., 1 h, 92%; d) 4-3d-f (1.05 equiv.), Et₂O, -100° C., 0.5 h; 3N NaOH, H₂O₂ 35%, reflux, 3 h, 77-93%. Enantiomeric excesses of alcohols were determined by chiral HPLC analysis after acylation with 3,5-dinitrobenzoyl chloride.

(-)-B-Allyldiisopinocampheylborane (4-2, (-)-Ipc₂BAllyl) was synthesized in a three steps sequence from (-)-α-pinene involving a hydroboration, the formation of the corresponding MeO-borinic ester 4-1 and its treatment with a Grignard reagent. Further condensation on aldehydes 4-3d-f followed by oxidation of the resulting borinates with alkaline hydrogen peroxide allowed the formation of the chiral homoallylic alcohols 4-4-d-f in good enantiomeric excess.

In some embodiments of the invention, homoallylic amines may be used rather than the alcohols. The corresponding amines may be readily prepared from the alcohol by methods known in the art. In some embodiments of the invention, the homoallylic alcohols and amines shown below may be used in the preparation of the compounds of the invention.

Weinreb Amides

A wide variety of Weinreb amides may be used to prepare the compounds of the invention. Weinreb amides are well known in the art, and many Weinreb amides or reagents for the preparation of Weinreb amides are commercially available. Further, methods for the preparation of Weinreb amides are know. For example, a variety of Weinreb amides may be prepared by reacting an aldehyde with the desired functionality with a Weinreb amide ylide (compound 5-4, Scheme 5a) or a Weinreb amide phosphonate (compound 6-6, Scheme 6) to form the desired α,β-unsaturated Weinreb amide. In one embodiment, a Weinreb amide comprising a protected hydroxy group is prepared according to Scheme 5 below.

Scheme 5a: Preparation of Weinreb amides

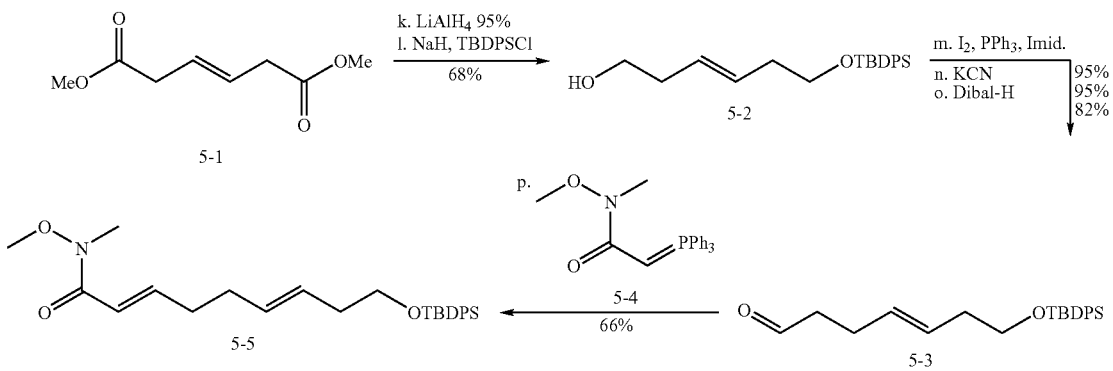

Trans-3-hexenedioic acid dimethyl ester 5-1 was reduced to the corresponding diol with lithium aluminum hydride. The diol was mono-protected as the tert-butyldiphenylsilyl ether 5-2, and the free alcohol was converted to aldehyde 5-3 in three steps via the nitrile. Aldehyde 5-3 was then treated with Weinreb amide ylide 5-4 to produce the diene Weinreb amide 5-5. Various other Weinreb amides may be prepared using compound 5-4 and an aldehyde with the desired functionality.

In another embodiment, Weinreb amides containing a hydroxy substituent may be produced using the synthetic process shown in Scheme 6a.

Scheme 6a: Synthesis of hydroxy-substituted Weinreb amides

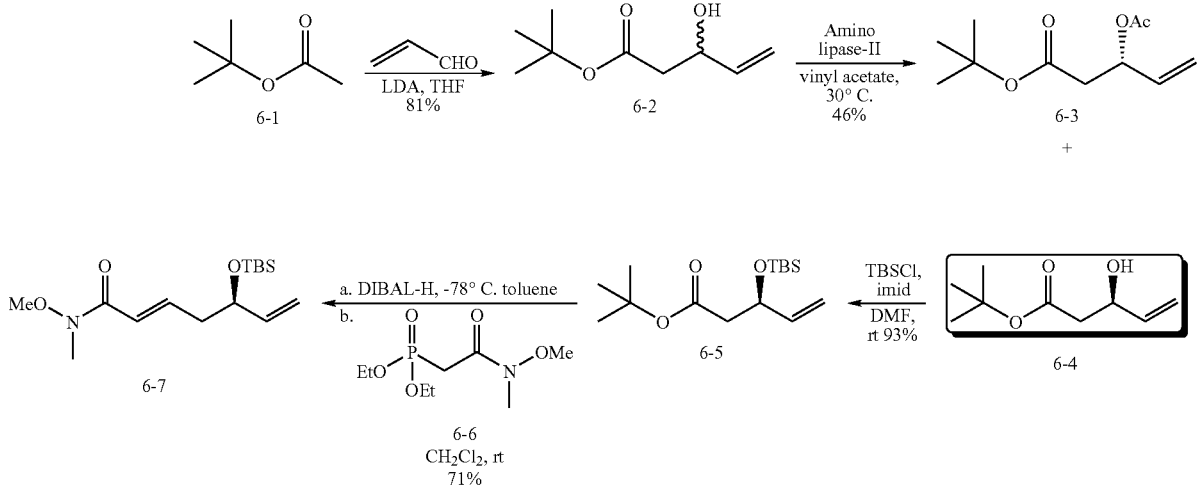

Treatment of t-butylacetate 6-1 with a bulky base, such as LDA, and reaction of the resulting enolate with a vinyl aldehyde provides alcohol 6-2. The racemic alcohol is resolved by treatment with amino lipase PS-C II to produce the chiral acetate 6-3 and the chiral alcohol 6-4. The hydroxy group is suitably protected, for example as the t-butyldimethylsilyl ether 6-5, and the corresponding aldehyde is produced by reaction with DIBAL-H. Reaction with the Weinreb phosphonate 6-6 provides the desired Weinreb amide 6-7.

In non-limiting embodiments, the Weinreb amides shown below may be used to prepare certain compounds of the invention.

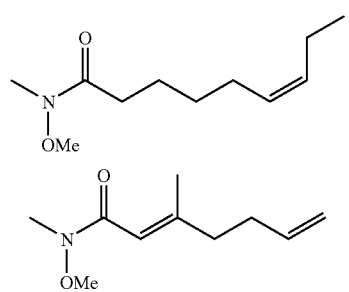

-continued

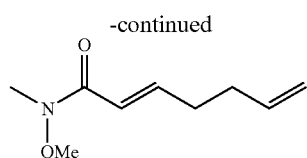

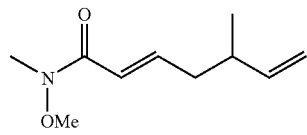

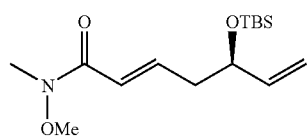

Alkylation of aromatic components such as 2-1 (Scheme 1) with Weinreb amides substituted with a protected hydroxy group or other protected functional group, allow the preparation of compounds comprising a protected hydroxy group on the macrocyclic ring, after deprotection. The hydroxy group may be derivatized to produce a variety of compounds of the invention.

Scheme 7a below illustrates various compounds of the invention prepared from a hydroxy-substituted macrocycle, which is obtained from a corresponding Weinreb amide comprising a protected hydroxy group, such as 6-7. The silyl-protected hydroxy group in compound 7-1 is selectively deprotected to provide compound 7-2 with a free hydroxy group. The nucleophilic hydroxy group in compound 7-2 may be reacted with various reagents to provide derivatized compounds, such as amide 457/458 and azido-substituted compound 459/460. It will be apparent that various other derivatized compounds may be prepared by reacting the free hydroxyl group with a variety of reagents to produce the corresponding derivatized macrocycles of the invention.

Scheme 7a: Derivatives of hydroxy-substituted macrocycles

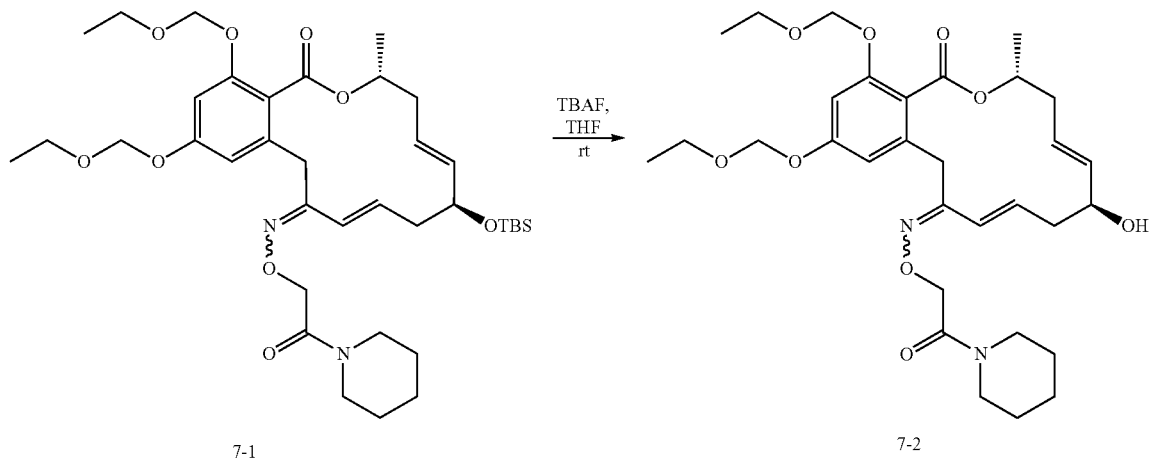

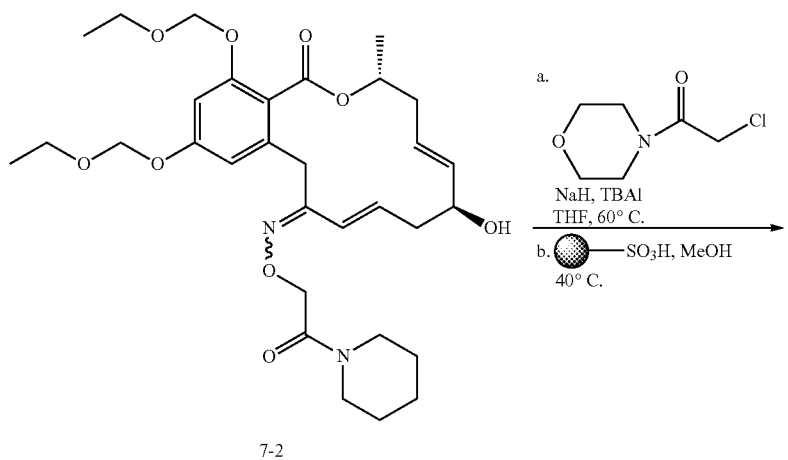

-continued
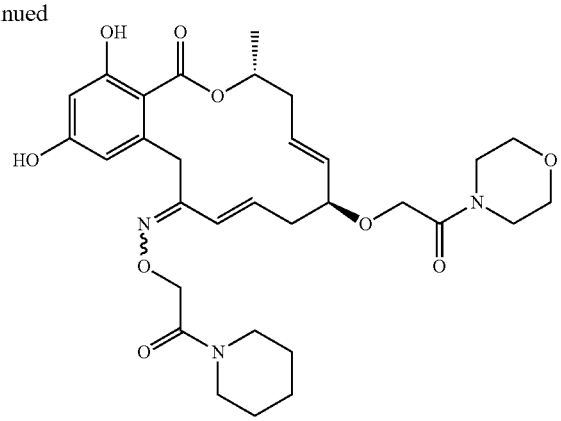
457/458
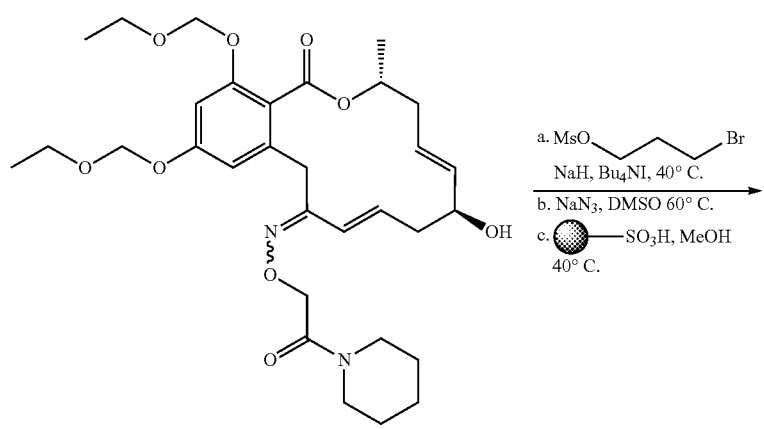
7-2
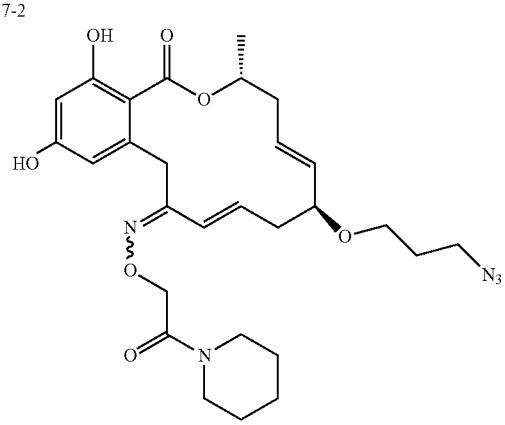
459/460

In another embodiment of the invention, compounds of the invention substituted with an azido group, such as compounds 459/460, may be further elaborated to provide amino-substituted macrocycles by reduction of the azido group. Scheme 8 illustrates the preparation of an amino-substituted compound and the use of the compound for the synthesis of certain amide-containing derivatives. It will be apparent to one of skill in the art that the preparation of amino-substituted macrocycles provides a handle for substitution of the macrocycles with a variety of functional groups by reaction with the nucleophilic amino group.

Reduction of the azido group may be accomplished by various methods, including by treatment with triphenylphosphine, to provide the aminoalkyl-substituted compound 8-1 (Scheme 8a). Use of Weinreb amide intermediates containing an azido group result in compounds with an azido functionality at another position of the macrocycle. The other azide substituted compounds may also be elaborated analogously to produce amino groups. Reaction of the free amino group of 8-1 provides access to a variety of compounds. For example, reaction of the amino group with acetic anhydride yields compound 461, and reaction with an cyanine labeling reagent provides compound 462, containing a fluorophore (see Ernst et al., *Cytometry*, 1989, 10(1), 3-10).

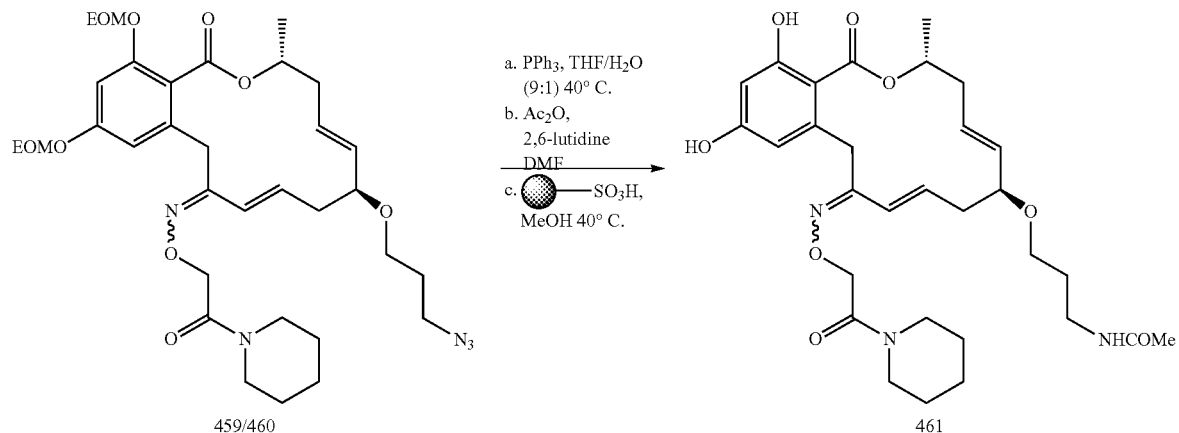

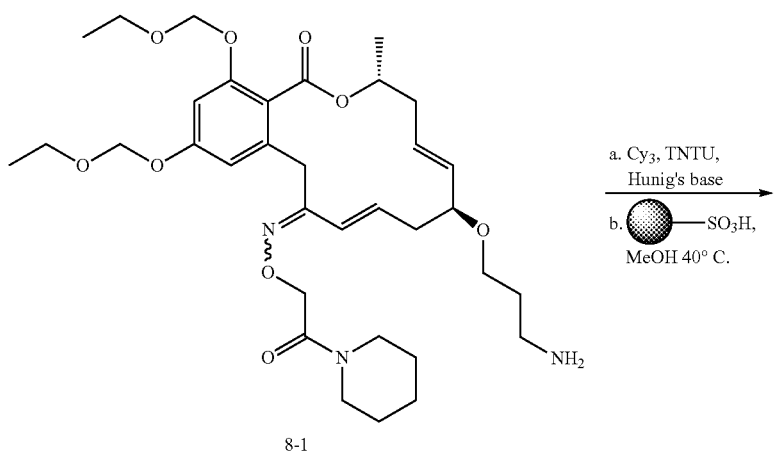

-continued

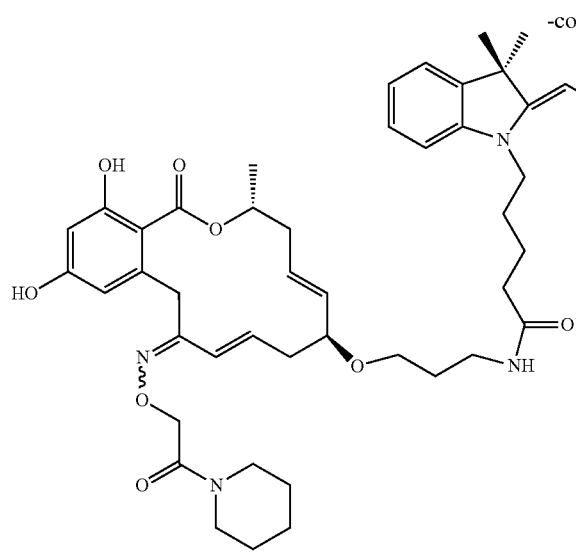
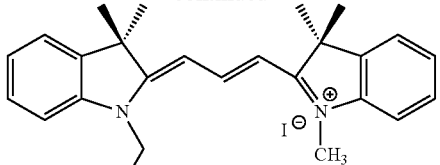

462

Alternatively, hydroxy-substituted macrocycles may be prepared by allylic oxidation of the macrocycle, as illustrated in Scheme 9a. Treatment of a protected macrocycle, such as compound 9-1 with selenium dioxide in ethanol provides the hydroxy-substituted product as a mixture of isomers. The resulting alcohols may be further derivatized, as discussed above, to provide a variety of compounds of the invention. Scheme 9 illustrates the formation of allyl ethers 449 by reaction of the alcohol products with allyl chloride in the presence of a base, such as sodium hydride and subsequent removal of the phenol protecting groups.

Scheme 9a: Allylic oxidation of macrocycles

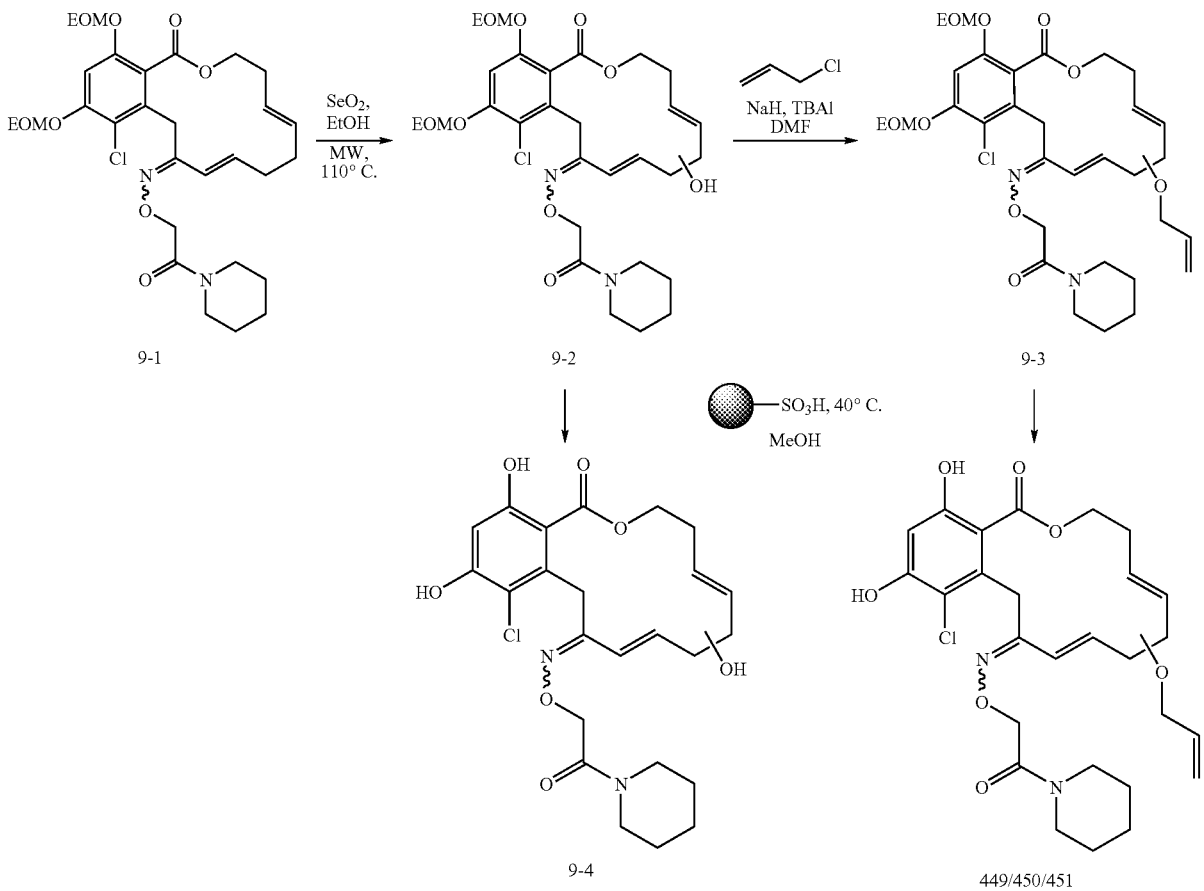

EXAMPLES

General Techniques. All reactions were carried out under a nitrogen atmosphere with dry (anhydrous) solvents under anhydrous conditions, unless otherwise noted. Anhydrous solvents were obtained by passing them through commercially available alumina column (Innovative Technology, Inc.,® VA). All substituted polystyrene resins (100-200 mesh, 1% DVB) were purchased from Novabiochem® or Aldrich®. The Grubbs' II catalyst was purchased from Materia Inc.® Solid phase reactions were carried on a Quest® 210 or round bottom flasks and filtered in fitted funnels. Reactions were monitored by thin layer chromatography (TLC) carried out on 0.25 mm E. Merck® silica gel plates (60E-254) using UV light as visualizing agent and 10% ethanolic phosphomolybdic acid or vanillin solution and heat as developing agents. E. Merck® silica gel (60, particle size 0.040-0.063 mm) was used for flash column chromatography. PTLC (preparative thin layer chromatography) were carried out on 0.25 mm E Merck® silica gel plates. NMR spectra were recorded on a Bruker Advance-400® instrument and calibrated by using residual undeuterated solvent as an internal reference. The following abbreviations were used to explain the multiplicities: s=singlet, d=doublet, t=triplet, q=quartet, m=multiplet, b=broad. IR spectra were recorded on a Perkin-Elmer 1600 series FT-IR spectrometer. LC-MS were recorded using an Agilent 1100® HPLC with a Bruker® micro-TOF instrument (ESI). Unless otherwise stated, a Supelco® C8 (5 cm×4.6 mm, 5 μm particles) column was used with a linear elution gradient from 100% $H_2O$ (0.5% $HCO_2H$) to 100% MeCN in 13 min at a flow rate of 0.5 ml/min. Unless otherwise stated, LDA was prepared at a concentration of 0.566 M by treating a solution of diisopropylamine (1.0 equiv.) in THF at −78° C. with n-butyllithium (1.0 equiv.) and stirred for 30 min at this temperature before use.

Example 1a

Preparation of Weinreb Amides

As discussed above, many Weinreb amides used to prepare the compounds of the invention are prepared by methods known in the art. Characterization data is shown below for selected Weinreb amides used to prepare the compounds of the invention.

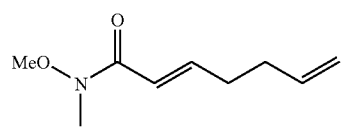

a-1

$^1$H NMR (400 MHz, CDCl$_3$, 25° C.): δ=7.33 (dd, J=15.3, 11.0 Hz, 1H), 6.52 (m, 2H), 5.61 (d, J=16.6 Hz, 1H), 5.48 (d, J=10.2 Hz, 1H), 3.73 (s, 3H), 3.27 (s, 3H); $^{13}$C NMR (100 MHz, CDCl$_3$, 25° C.): δ=166.8, 143.4, 135.1, 124.7, 119.7, 61.7, 32.3; IR (film): $v_{max}$=2936, 1658, 1598, 1427, 1382, 1181, 1095, 1005 cm$^{-1}$.

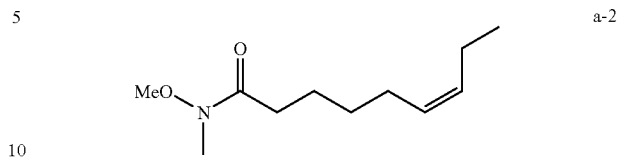

a-2

$^1$H NMR (CDCl$_3$, 400 MHz, 25° C.) δ 5.40-5.26 (m, 2H), 3.67 (s, 3H), 3.17 (s, 3H), 2.41 (t, J=7.4 Hz, 2H), 2.11-1.97 (m, 4H), 1.64 (tt, J=8.7 Hz, J=6.3 Hz, 2H), 1.39 (tt, J=8.6 Hz, J=6.7 Hz, 2H), 0.95 (t, J=7.8 Hz, 3H); $^{13}$C NMR (CDCl$_3$, 100 MHz, 25° C.) δ 131.9, 128.7, 61.2, 31.8 (×2), 29.5, 26.9, 24.3, 20.5, 14.3, one quaternary carbon is missing.

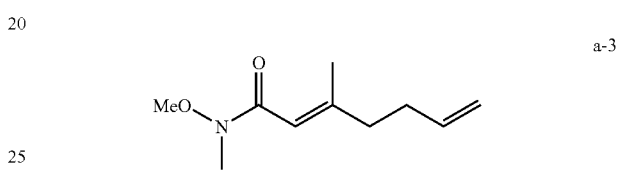

a-3

$^1$H NMR (CDCl$_3$, 400 MHz) δ 5.90 (s, 1H), 5.54-5.60 (m, 1H), 4.82 (d, J=17.0 Hz, 1H), 4.75 (d, J=10.1 Hz, 1H), 3.43 (s, 3H), 2.96 (s, 3H), 2.02 (m, 4H), 1.90 (s, 3H). $^{13}$C NMR (CDCl$_3$, 100 MHz) δ 137.55, 115.09, 114.22, 61.36, 40.26, 31.67, 18.64.

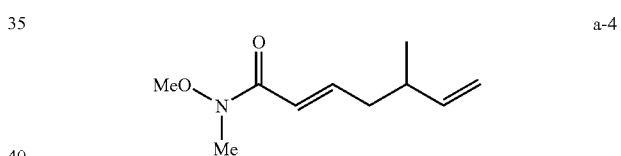

a-4

$^1$H NMR (CDCl$_3$, 400 MHz, 25° C.) δ 6.93 (dt, J=15.5, 7.6 Hz, 1H); 6.39 (d, J=15.5 Hz, 1H); 5.70-5.79 (m, 1H), 4.94-5.02 (m, 2H); 3.69 (s, 3H); 3.23 (s, 3H); 2.18-2.36 (m, 3H); 1.02 (d, J=9.9 Hz, 3H).

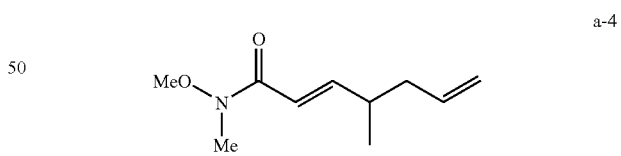

a-4

$^1$H NMR (CDCl$_3$, 400 MHz, 25° C.) δ 6.93 (dt, J=15.5, 7.6 Hz, 1H); 6.39 (d, J=15.5 Hz, 1H); 5.70-5.79 (m, 1H), 4.94-5.02 (m, 2H); 3.69 (s, 3H); 3.23 (s, 3H); 2.18-2.36 (m, 3H); 1.02 (d, J=9.9 Hz, 3H).

Example 2a

Preparation of Hydroxy-Substituted Weinreb Amides

Weinreb amides containing a protected hydroxy group are prepared according to the procedure depicted in Scheme 6 and described below, starting with the preparation of racemic alcohols 6-2.

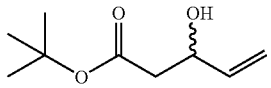
6-2

To the solution of freshly prepared LDA (0.56 M, 60 mmol) at −78° C. under nitrogen was added solution of t-butyl acetate (8.1 mL, 60 mmol, 1.0 equiv.) in THF (10 mL) dropwise. After a further one hour at −78° C., acrolein (4.5 mL, 60 mmol, 1.0 equiv.) in THF (5 mL) was added and the reaction was kept stirring at the same temperature for 5 min. The reaction was quenched with saturated NH$_4$Cl solution and extracted with ethyl acetate (150 mL×3), the combined organic phase was washed by brine (120 mL), dried over anhydrous Na$_2$SO$_4$, and evaporated. The residue underwent flash chromatography column (PE/EA, 8/1) to give the desired compound (8.35 g, 81%). $^1$H (CDCl$_3$, 400 MHz, 25° C.) δ 5.82-5.91 (dt, 1H); 5.30 (dd, J=17.2 Hz, J=0.8 Hz, 1H); 5.14 (dd, J=10.4 Hz, J=0.8 Hz, 1H); 4.48 (m, 1H); 3.13 (d, 1H); 2.46 (m, 2H); 1.46 (s, 9H). $^{13}$H NMR of wh3-27 (CDCl$_3$, 400 MHz, 25° C.) δ 171.5, 138.9, 114.9, 81.2, 68.9, 42.1, 28.0

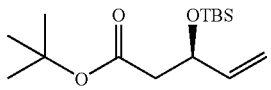
6-5

To the solution of the previously prepared racemic alcohol (8.35 g, 48.5 mmol) in vinyl acetate (120 mL) was added Amino lipase PS-C II (750 mg, 15 mg/mmol) at 30° C. The reaction was stirred for 60 hrs. After filtration, the solution was concentrated and underwent flash chromatography column (PE/EA, 15/1 to 5/1) to give the desired compound (3.86 g) in the yield of 46%. To a solution of this chiral alcohol (3.75 g, 21.7 mmol) in DMF (60 mL) at 0° C. under nitrogen atmosphere, was added imidazole (2.96 g, 43.5 mmol, 2.0 equiv.) and TBSCl (3.93 g, 26.0 mmol, 1.2 equiv.), then the reaction was allowed to warm to 23° C. and stirred for 5 hrs. The reaction was extracted from saturated NH$_4$Cl solution with ethyl acetate (100 mL×3), washed by brine (100 mL), dried over anhydrous Na$_2$SO$_4$. After removal of the solvent, the residue underwent flash column (PE/EA, 50/1) to obtain the TBS protected alcohol (5.85 g, 93%). $^1$H (CDCl$_3$, 400 MHz, 25° C.) δ 5.79-5.88 (dt, 1H); 5.20 (dd, J=16.0 Hz, J=2.8 Hz, 1H); 5.05 (dd, J=10.4 Hz, J=2.8 Hz, 1H); 4.51-4.56 (m, 1H); 2.46 (dd, 1H); 2.34 (dd, 1H); 1.44 (s, 9H); 0.88 (s, 9H); 0.05 (d, 6H). $^{13}$C NMR (CDCl$_3$, 400 MHz, 25° C.) δ 170.3, 140.5, 114.4, 80.4, 70.9, 44.8, 28.1, 25.8, 18.1, −4.4, −5.0.

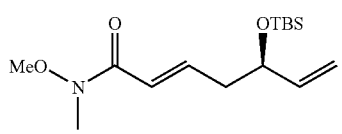
6-7

To the solution of the ester prepared in the precedent procedure (5.85 g, 20.4 mmol) in CH$_2$Cl$_2$ (100 mL) under nitrogen atmosphere, DIBAL (24.5 mL, 1M in toluene, 1.2 equiv.) was added at −78° C. and the reaction was kept stirring at the same temperature for half an hour. Then saturated tartrate salt solution (100 mL) was added to the reaction and stirred for 2 hrs until the system turned clear. The two phases were separated and extracted by CH$_2$Cl$_2$ (100 mL×2), washed by brine, dried over Na$_2$SO$_4$. After removal of the solvent, the residue (4.33 g) obtained was used for the next step without further purification. To the solution of the aldehyde (4.33 g) in CH$_2$Cl$_2$ (100 mL) was added Wittig reagent (7.33 g, 20.2 mmol, 1.0 equiv.) at 23° C. The reaction was stirred overnight. After removal of the solvent under reduced vacuum, the residue underwent flash chromatography (PE/EA=20:1, then 10/1, 3/1) afforded the desired compound (4.25 g) in the yield of 71% for the two steps. $^1$H (CDCl$_3$, 400 MHz, 25° C.) δ 6.89-6.96 (dt, 1H); 6.41 (d, 1H); 5.77-5.85 (m, 1H); 5.18 (dd, 1H); 5.05 (dd, 1H); 4.23 (dd, 1H); 3.67 (s, 3H); 3.22 (s, 3H); 2.42 (dd, 2H); 0.88 (s, 9H); 0.03 (d, 6H), $^{13}$C (CDCl$_3$, 400 MHz, 25° C.) δ 166.6, 143.5, 140.6, 120.9, 114.3, 72.7, 61.6, 41.4, 32.3, 25.8, 18.2, −4.5, −4.9.

Example 3a

Aromatic Components

Various suitably protected aromatic groups are used in the invention. Methods for the preparation of suitable resorcylic acid lactones for the preparation of the macrocycles are known in the art. For example, International Publication No. WO 2008/021213, which is incorporated by reference in its entirety, describes synthetic methods for a variety of derivatives of resorcylic acid, which can be used to prepare the compounds of the invention. Selected characterization data for aromatic compounds used in the invention are provided below.

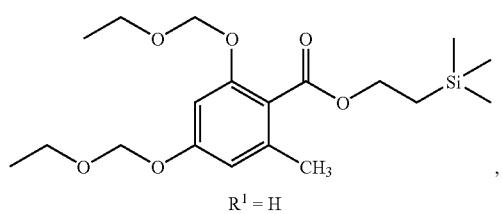

R$^1$ = H $^1$H NMR of ester (CDCl$_3$, 400 MHz, 25° C.) δ 6.69 (s, 1H); 6.52 (s, 1H); 5.19 (s, 2H); 5.17 (s, 2H); 4.37 (t, 2H); 3.66-3.74 (m, 4H); 2.28 (s, 3H); 1.18-1.25 (m, 6H); 1.09 (t, 2H); 0.05 (s, 9H).

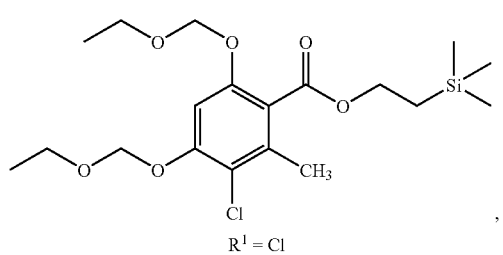

R$^1$ = Cl $^1$H NMR of ester (CDCl$_3$, 400 MHz, 25° C.) δ 6.98 (s, 1H); 5.28 (s, 2H); 5.19 (s, 2H); 4.39 (t, 2H); 3.76 (q, 2H); 3.70 (q, 2H); 2.32 (s, 3H); 1.19-1.23 (m, 6H); 1.10 (t, 2H); 0.05 (s, 9H)

Example 4a

Alkylation Intermediates

The preparation of alkylation intermediates derived from resorcylic acid aromatic derivatives and Weinreb amides is illustrated in Scheme 2. Various different alkylation intermediates, with varying substitution on the aromatic ring and the macrocycle, may be used to prepare the compounds of the invention. These compounds may be prepared from the desired aromatic component and Weinreb amide according to the process depicted in the scheme. Characterization data of selected alkylation intermediates used in the preparation of the compounds of the invention is provided below.

2-5

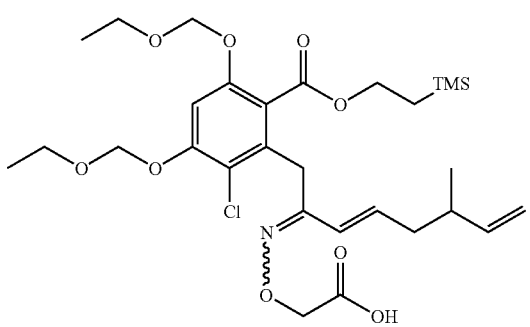

$^1$H NMR two isomers (1:1)(CDCl$_3$, 400 MHz, 25° C.) δ 9.52 (w×2, 2H); 7.04 (s×2, 2H); 6.69 (d, J=16.1 Hz, 1H); 6.26 (dt, J=16.1, 7.0 Hz, 1H); 5.97 (dt, J=16.1, 7.0 Hz, 1H); 5.76 (d, J=16.1 Hz, 1H); 5.53-5.71 (m, 2H); 5.28 (s×2, 4H); 5.18 (s, 2H); 5.17 (s, 2H); 4.91-4.96 (m, 2H); 4.81-4.84 (m, 2H); 4.65 (s, 2H); 4.49 (s, 2H); 4.27-4.33 (m, 4H); 4.02 (s, 2H); 3.87 (s, 2H); 3.67-3.77 (m, 8H); 1.98-2.26 (m, 6H); 1.17-1.22 (m, 12H); 0.99-1.06 (m, 4H); 0.96 (d, J=6.4 Hz, 3H); 0.82 (d, J=6.4 Hz, 3H); 0.05 (s, 9H); 0.03 (s, 9H).

2-6

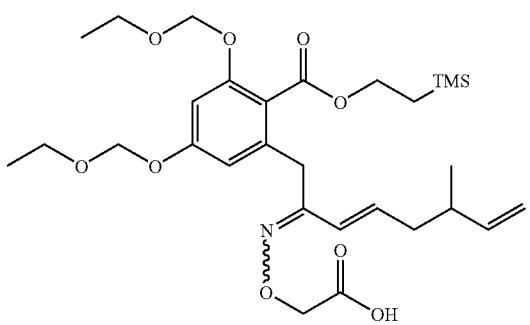

$^1$H NMR of two isomers (2:1) (CDCl$_3$, 400 MHz, 25° C.) δ 9.47 (w×2, 2H); 6.75 (d, J=2.0 Hz, 1H); 6.71 (d, J=2.1 Hz, 1H); 6.67 (d, J=16.1 Hz, 1H); 6.57 (d, J=2.1 Hz, 1H); 6.48 (d, J=2.0 Hz, 1H); 6.21 (dt, J=16.1, 7.0 Hz, 1H); 6.03-6.11 (m, 2H); 5.54-5.68 (m, 2H); 5.19 (s×2, 4H); 5.17 (s, 2H); 5.15 (s, 2H); 4.82-4.88 (m, 4H); 4.67 (s, 2H); 4.66 (s, 2H); 4.36-4.40 (m, 4H); 3.88 (s, 2H); 3.65-3.74 (m, 10H); 2.06-2.21 (m, 6H); 1.17-1.23 (m, 12H); 1.07-1.12 (m, 4H); 0.91 (d, J=6.4 Hz, 3H); 0.86 (d, J=6.4 Hz, 3H); 0.07 (s, 9H); 0.06 (s, 9H)

Example 5a

Preparation of Macrocyclic Compounds of the Invention

General Procedure for the Synthesis of Compounds of the Invention.

The general synthesis of the macrocycles described below is depicted in Scheme 1, starting from carboxylic acid 1-1. To a suspension of 3.0 equiv of polystyrene based chlorotrityl resin (1.1 mmol/g) in CH$_2$Cl$_2$ at room temperature were added 6.0 equiv of Hunig's base and 1.0 equiv of the corresponding acid 1-1 (Scheme 1). After shaking the mixture for 24 hours, the different resins were capped with acetic acid for another 24 hours. After this time the resins were washed with CH$_2$Cl$_2$, DMF, CH$_2$Cl$_2$ and Et$_2$O, then dry and re-suspended in THF. To these suspensions, 4.0 equiv. of TBAF (1M) were added and the mixtures were shaken for 4 hours. The resins were then filtered and washed thoroughly using THF, CH$_2$Cl$_2$, 1% AcOH in CH$_2$Cl$_2$, CH$_2$Cl$_2$, Et$_2$O several times. The completion of the deprotection and total elimination of the tetrabutyl ammonium salts was assessed by LC-MS after cleavage of a very small portion of each resin using a solution of HFIP in CH$_2$Cl$_2$ ¼ for 30 min (LC-MS were recorded using an Agilent 1100 HPLC with a Supelco C8 (5 cm×4.6 mm, 5 µm particles) column using a linear elution gradient from 95% H$_2$O (0.5% HCO$_2$H) to 100% MeCN in 8 min at a flow rate of 0.5 mL/min). The resins were split for further diversification with the different alcohols. The Mitsunobu reactions were carried in dry toluene using 5.0 equiv of the corresponding alcohol R$^2$OH, 2.0 equiv of Ph$_3$P and 2.0 equiv of DIAD and the suspensions were agitated overnight. The productivity of the esterification reactions were assessed by LC-MS after cleavage of a small portion as describe before and the pools which had not proceeded to completion were re-subjected to the same conditions. After washing and drying the resins they were suspended in toluene and submitted to the metathesis reaction. Grubbs' second generation catalyst was added to each suspension (3×0.06 equiv) and the reactions were heated at 120° C. in a CEM microwave reactor for 3×45 min (fresh catalyst was added in each cycle). The resins were then washed with CH$_2$Cl$_2$, DMF, CH$_2$Cl$_2$ and Et$_2$O several times. Then the compounds were cleaved from the resin using a solution of HFIP in CH$_2$Cl$_2$ ¼ for 3 h (re-subjection of the resin to the cleavage conditions afforded minimal quantities of compound suggesting the original cleavage had proceeded to completion) and the corresponding products were purified by PTLC and isolated with yields in between 20 to 30% after 5 steps.

Each compound was dissolved CH$_2$Cl$_2$ and then aliquoted for further amidation. To each vial were added 2.0 equiv of the corresponding amine, 3.0 equiv of PS-DCC (DCC polystyrene resin) and cat DMAP, and the suspensions were stirred for over 72 h. The completion of each reaction was monitored by LC-MS. The corresponding amides were filtered, evaporated and re-dissolved in methanol. To each solution were added 10 equiv of sulfonic acid polystyrene resin and the suspensions were stirred for 4 h at room temperature. The final compounds were filtered and isolated with yields of 75 to 95%.

Characterization data for selected compounds of the invention are provided below.

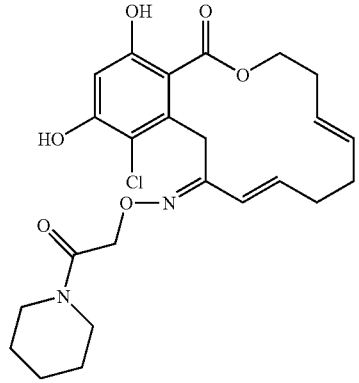

13a

¹H NMR (CDCl₃, 400 MHz, 25° C.) δ 11.64 (s, 1H), 6.64 (s, 1H), 6.01 (dt, J=15.5, 7.5 Hz, 1H), 5.11 (d, J=15.5 Hz, 1H), 5.10-5.03 (m, 2H), 4.85 (s, 2H), 4.37 (t, J=4.8 Hz, 2H), 4.17 (s, 2H), 3.60 (t, J=5.0 Hz, 2H), 3.46 (t, J=5.0 Hz, 2H), 2.34 (q, J=5.4 Hz, 2H), 2.10-2.02 (m, 2H), 1.99-1.92 (m, 2H), 1.70-1.54 (m, 6H), 1 OH signal is not visible; ¹³C NMR (CDCl₃, 100 MHz, 25° C.) δ 170.27, 167.42, 163.21, 157.38, 155.18, 138.21, 135.62, 131.82, 129.13, 124.76, 115.55, 107.60, 103.47, 72.63, 65.03, 46.38, 43.31, 33.21, 32.76, 31.94, 31.84, 26.65, 25.64, 24.57; HRMS (MALDI-TOF) m/z [M+Na]⁺ calcd for C₂₄H₂₉ClN₂O₆Na: 499.1612; found: 499.1638.

The geometry of the oxime was determined by x-ray diffraction. FIG. 3 shows the Wire-frame representation of the crystal structure of 13a.

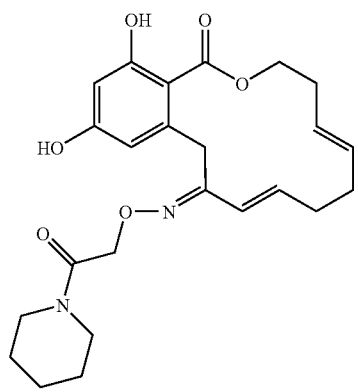

13b

¹H NMR (CDCl₃, 400 MHz) δ 11.60 (s, 1H), 6.88 (d, J=1.9 Hz, 1H), 6.33 (d, J=1.9 Hz, 1H), 6.14 (dt, J=16.1, 7.5 Hz, 1H), 5.83 (d, J=16.1 Hz, 1H), 5.33 (m, 2H), 4.86 (s, 2H), 4.54-4.53 (m, 2H), 4.34 (s, 2H), 3.58-3.55 (m, 2H), 3.40-3.38 (m, 2H), 2.51-2.48 (m, 2H), 2.11-2.07 (m, 4H), 1.61-1.57 (m, 6H), 1OH signal is not visible. ¹³C NMR (CD₃OD, 100 MHz) δ 178.0, 175.8, 168.8, 166.6, 165.7, 147.1, 145.5, 141.0, 139.0, 134.4, 122.6, 115.4, 110.4, 81.4, 73.2, 54.7, 51.6, 41.8, 41.3, 40.0, 37.6, 35.5, 34.8, 33.5; HRMS (MALDI-TOF) m/z [M+Na]⁺ calcd for C₂₄H₃₀N₂O₆Na: 465.2002; found 465.2015.

The geometry of the oxime was determined by x-ray diffraction. FIG. 4 shows the Wire-frame representation of the crystal structure of 13b.

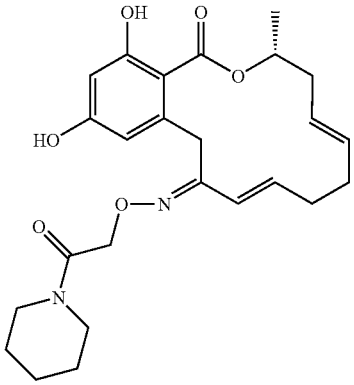

13c

¹H NMR (CDCl₃, 400 MHz) δ 11.27 (brs, 1H), 9.03 (brs, 1H), 6.54 (d, J=2.1 Hz, 1H), (d, J=2.1 Hz, 1H), 6.05 (m, 1H), 5.68 (d, J=15.5 Hz, 1H), 5.43 (m, 2H), 5.28 (m, 1H), 4.87 (d, J=14.5 Hz, 1H), 4.82 (d, J=14.5 Hz, 1H), 4.30 (d, J=15.5 Hz, 1H), 4.17 (d, J=15.5 Hz, 1H), 3.58 (m, 2H), 3.41 (m, 2H), 2.68 (m, 1H), 2.24 (m, 2H), 2.04 (m, 3H), 1.61 (m, 6H), 1.42 (d, J=6.4 Hz, 3H). ¹³C NMR (CDCl₃, 100 MHz) δ 167.42, 164.0, 161.85, 159.06, 141.91, 137.79, 132.77, 126.02, 124.63, 111.20, 104.88, 102.10, 71.42, 71.27, 71.21, 45.92, 43.10, 37.82, 32.31, 30.49, 30.24, 26.22, 25.32, 24.24, 18.92; HRMS (MALDI-TOF) m/z [M+Na]⁺ calcd for C₂₅H₃₂N₂O₆Na: 479.2158; found 479.2351.

The geometry of the oxime was deduced based on the x-ray diffraction of the Z isomer of 13c. FIG. 5 shows the Wireframe representation of the Z isomer of 13c.

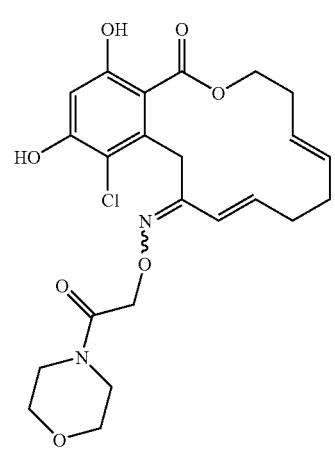

13d

¹H NMR (CD₃OD, 400 MHz) δ 6.84 (d, J=16.1 Hz, 1H), 6.63 (d, J=16.1 Hz, 1H), 6.51 (s, 1H), 6.46 (d, J=2.7 Hz, 1H), 6.21 (dt, J=16.1, 6.9 Hz, 1H), 6.09 (dt, J=16.1, 7.5 Hz, 1H), 5.31-5.23 (m, 4H), 4.91 (d, J=13.3 Hz, 2H), 4.60 (d, J=13.3 Hz, 2H), 4.45-4.39 (m, 4H), 4.18 (s, 4H), 3.76 (m, 4H), 3.69-3.67 (m, 4H), 3.62-3.46 (m, 8H), 2.59-2.55 (m, 1H), 2.45-2.43 (m, 5H), 2.37-2.33 (m, 4H), 2.15-2.14 (m, 2H), 4

OH signals are not visible; HRMS (MALDI-TOF) m/z [M+Na]+ calcd for $C_{23}H_{27}ClN_2O_7Na$: 501.1405; found 501.1424.

The geometry of the oxime was deduced from structure 13a.

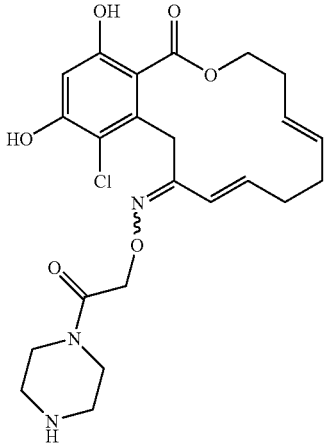

13e

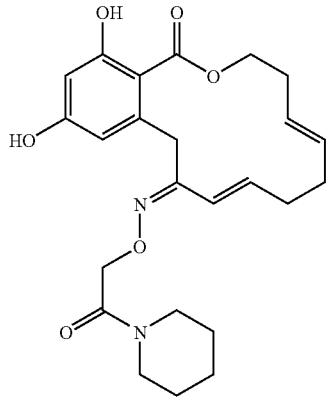

13g $^1$H NMR (CD$_3$OD, 400 MHz) δ 6.64 (d, J=16.1 Hz, 1H), 6.53 (s, 1H), 6.48 (s, 1H), 6.25 (dt, J=16.1, 7.5 Hz, 1H), 6.09 (dt, J=15.6, 7.5 Hz, 1H), 5.52-5.48 (m, 2H), 5.33 (d, J=15.6 Hz, 1H), 5.26-5.24 (m, 2H), 4.94 (s, 2H), 4.68 (s, 2H), 4.44-4.38 (m, 4H), 4.27 (s, 2H), 4.19 (s, 2H), 3.97-3.93 (m, 4H), 3.86-3.76 (m, 4H), 3.34-3.33 (m, 4H), 3.39-3.20 (m, 4H), 2.59-2.55 (m, 1H), 2.48-2.40 (m, 3H), 2.37-2.34 (m, 4H), 2.19-2.15 (m, 2H), 2.10-2.06 (m, 2H), 4 OH and 2 NH are not visible; HRMS (MALDI-TOF) m/z [M+Na]+ calcd for $C_{23}H_{28}ClN_3O_6Na$: 500.1564; found 500.1590.

$^1$H NMR (CDCl$_3$, 400 MHz) δ 11.64 (s, 1H), 6.62 (d, J=16.1 Hz, 1H), 6.62 (d, J=2.7 Hz, 1H), 6.33 (d, J=1.9 Hz, 1H), 6.25 (dt, J=16.1, 7.5 Hz, 1H), 5.35 (m, 2H), 4.79 (s, 2H), 4.54-4.53 (m, 2H), 4.08 (s, 2H), 3.56-3.54 (m, 2H), 3.38-3.37 (m, 2H), 2.50-2.48 (m, 2H), 2.12-2.08 (m, 4H), 1.66-1.57 (m, 6H), 1 OH signal is not visible. $^{13}$C NMR (CDCl$_3$, 100 MHz) δ 170.8, 167.9, 165.7, 162.0, 157.1, 143.1, 141.9, 132.2, 129.2, 118.4, 110.4, 104.4, 102.5, 71.5, 64.5, 46.0, 43.3, 35.1, 32.9, 32.7, 30.9, 26.4, 25.5, 24.5; HRMS (MALDI-TOF) m/z [M+Na]+ calcd for $C_{24}H_{30}N_2O_6Na$: 465.2002; found 465.2027.

The geometry of the oxime was deduced from structure 13b.

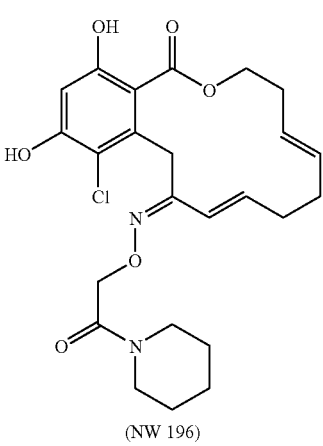

13f
(NW 196)

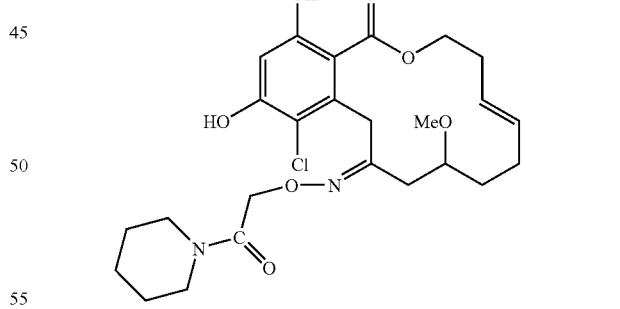

14a $^1$H NMR (DMSO-d6, 400 MHz, 25° C.) δ 10.2 (s, 1H), 6.45 (s, 1H), 6.44 (d, J=16.1 Hz, 1H), 6.12 (dt, J=16.1 6.4 Hz, 1H), 5.31-5.29 (m, 2H), 4.57 (s, 2H), 4.16 (t, J=4.8 Hz, 2H), 3.70 (s, 2H), 3.35-3.30 (m, 4H), 2.31 (m, 2H), 2.08-2.05 (m, 4H), 1.56-1.51 (m, 2H), 1.45-1.35 (m, 4H), 1 OH is not visible; $^{13}$C NMR (DMSO-d6, 100 MHz, 25° C.) δ 167.9, 166.3, 155.4, 155.2, 153.4, 140.6, 134.3, 131.4, 119.4, 113.9, 112.4, 102.1, 71.9, 65.2, 45.4, 42.1, 34.7, 31.8, 31.7, 30.9, 26.0, 25.9, 25.2, 24.0; HRMS (MALDI-TOF) m/z [M+Na]+ calcd for $C_{24}H_{29}ClN_2O_6H$, 499.1612; found 499.1624.

$^1$H NMR (CDCl$_3$, 400 MHz) δ 11.41 (s, 1H), 11.43 (s, 1H), 6.58 (s×2, 2H), 5.56-5.43 (m, 4H), 4.53 (2×bs, 4H), 4.45-4.42 (m, 4H), 4.40 (2×d, J=16.6 Hz, 2H), 3.86 (2×d, J=16.6 Hz, 2H), 3.52-3.50 (m, 4H), 3.46-3.41 (m, 2H), 3.30 (s, 3H), 3.31 (s, 3H), 2.91 (dd, J=14.0, 8.3 Hz, 1H), 2.89-2.85 (m, 1H), 2.52-2.51 (m, 4H), 2.41 (dd, J=14.0, 4.0 Hz, 1H), 2.39-2.35 (m, 1H), 2.16-2.14 (m, 4H), 1.87-1.77 (m, 4H), 1.61-1.59 (m, 4H), 1.49-1.43 (m, 12H), 2 OH signals are not visible; HRMS (MALDI-TOF) m/z [M+Na]+ calcd for $C_{25}H_{33}ClN_2O_7Na$: 531.1874; found 531.1894.

The oxime geometry was assigned by comparison to 14a.

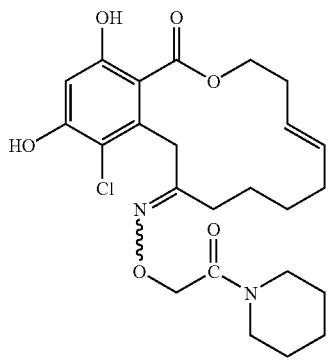
14b

¹H NMR (CDCl₃, 400 MHz, 25° C.) δ 11.44 (s, 1H), 11.32 (s, 1H), 6.61 (s, 1H), 6.57 (s, 1H), 5.55-5.42 (m, 2H), 5.38-5.35 (m, 2H), 4.77 (s, 2H), 4.52 (s, 2H), 4.48-4.44 (m, 4H), 4.22 (s, 2H), 4.17 (s, 2H), 3.58-3.49 (m, 4H), 3.31-3.28 (m, 4H), 2.50-2.46 (m, 2H), 2.42-2.36 (m, 4H), 2.06-1.99 (m, 6H), 1.96-1.92 (m, 4H), 1.66-1.36 (m, 16H), 2 OH signals are not visible; HRMS (MALDI-TOF) m/z [M+Na]⁺ calcd for HRMS (MALDI-TOF) m/z [M+Na]⁺ calcd for $C_{24}H_{31}ClN_2O_6Na$: 501.1768; found: 501.1798.

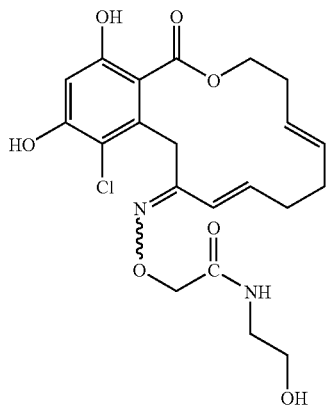
13h

¹H NMR (CDCl₃, 400 MHz, 25° C.) δ 11.35 (s, 1H), 11.14 (s, 1H), 6.63 (s, 1H), 6.56 (s, 1H), 6.48 (d, J=16.4 Hz, 1H), 6.00-5.99 (m, 2H), 5.85 (d, J=16.4 Hz, 1H), 5.37 (s, 2H), 5.15 (s, 2H), 5.14-5.09 (m, 8H), 4.68 (s, 2H), 4.63 (s, 2H), 3.76 (t, J=5.0 Hz, 2H), 3.66 (t, J=4.7 Hz, 2H), 3.52-3.48 (m, 2H), 3.39-3.36 (m, 2H), 2.52-2.48 (m, 2H), 2.41-2.32 (m, 4H), 2.30-2.27 (m, 2H), 2.15-2.10 (m, 4H), 4 OH signals and 2 NH signals are not visible; HRMS (MALDI-TOF) m/z [M+Na]⁺ calcd for HRMS (MALDI-TOF) m/z [M+H]⁺ calcd for $C_{21}H_{25}ClN_2O_7Na$: 475.1248; found: 475.1275.

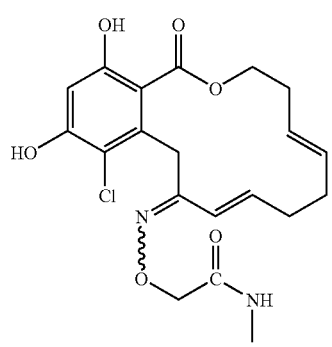
13i

¹H NMR (CDCl₃, 400 MHz, 25° C.) δ 11.46 (s, 1H), 11.02 (s, 1H), 6.65 (s, 1H), 6.65 (d, J=16.6 Hz, 1H), 6.60 (s, 1H), 6.48 (d, J=15.6 Hz, 1H), 6.08-6.00 (m, 2H), 5.34-5.25 (m, 4H), 5.16-5.12 (m, 4H), 5.14 (s, 2H), 5.10 (s, 2H), 4.72 (d, J=16.1 Hz, 1H), 4.65 (d, J=16.1 Hz, 1H), 4.41 (d, J=17.7 Hz, 1H), 4.15 (d, J=17.7 Hz, 1H), 2.91 (d, J=4.8 Hz, 3H), 2.78 (d, J=4.8 Hz, 3H), 2.59-2.52 (m, 1H), 2.51-2.38 (m, 1H), 2.24-2.12 (m, 4H), 2.07-2.00 (m, 4H), 1.95-1.87 (m, 2H), 2 OH signals and 2 NH signals are not visible; HRMS (MALDI-TOF) m/z [M+Na]⁺ calcd for HRMS (MALDI-TOF) m/z [M+Na]⁺ calcd for $C_{20}H_{23}ClN_2O_6Na$: 445.1143; found: 445.1178.

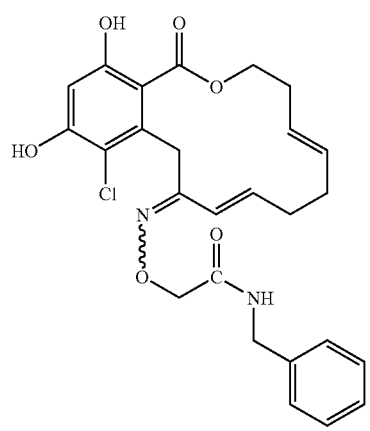
13j

¹H NMR (CDCl₃, 400 MHz, 25° C.) δ 11.32 (s, 1H), 11.04 (s, 1H), 7.32-7.29 (m, 10H), 6.61 (s, 1H), 6.57 (s, 1H), 6.42 (d, J=16.4 Hz, 1H), 6.07 (dt, J=15.8, 6.7 Hz, 1H), 5.99 (dt, J=16.4, 7.3 Hz, 1H), 5.67 (d, J=15.8 Hz, 1H), 5.37-4.95 (m, 8H), 4.73 (s, 2H), 4.69 (s, 2H), 4.64 (s, 2H), 4.56 (s, 2H), 4.54 (s, 2H), 4.52 (s, 2H), 2.34-2.25 (m, 6H), 2.12-2.05 (m, 4H), 2.00-1.99 (m, 2H), 2 OH signals and 2 NH signals are not visible; HRMS (MALDI-TOF) m/z [M+Na]⁺ calcd for HRMS (MALDI-TOF) m/z [M+Na]⁺ calcd for $C_{26}H_{27}ClN_2O_6Na$: 521.1456; found: 521.1498.

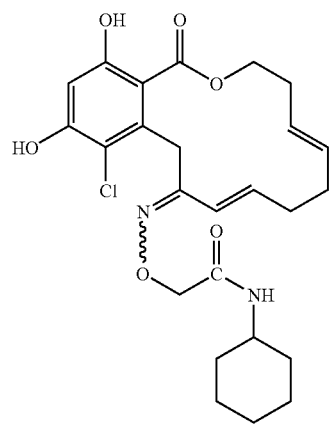
13k

¹H NMR (acetone-d6, 400 MHz, 25° C.) δ 6.62 (d, J=15.8 Hz, 1H), 6.56 (s, 1H), 6.27 (s, 1H), 6.14 (dt, J=15.8, 8.5 Hz, 1H), 6.02 (dt, J=15.5, 7.6 Hz, 1H), 5.37-5.34 (m, 5H), 5.26 (s, 1H), 5.22 (s, 1H), 4.55-4.52 (m, 2H), 4.51 (s, 2H), 4.49 (s, 2H), 4.43-4.41 (m, 2H), 4.26 (s, 2H), 4.19 (s, 2H), 3.76-3.70

(m, 1H), 3.61-3.54 (m, 1H), 2.49-2.47 (m, 2H), 2.40-2.36 (m, 2H), 2.16-1.99 (m, 8H), 1.88-1.84 (m, 4H), 1.73-1.66 (m, 4H), 1.62-1.58 (m, 4H), 1.37-1.16 (m, 8H), 2 OH signals and 2 NH signals are not visible; HRMS (MALDI-TOF) m/z [M+Na]$^+$ calcd for HRMS (MALDI-TOF) m/z [M+Na]$^+$ calcd for $C_{25}H_{31}ClN_2O_6Na$: 513.1769; found: 513.1788.

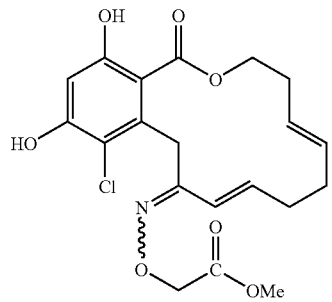

131

$^1$H NMR (CDCl$_3$, 400 MHz, 25° C.) δ 11.20 (s, 1H), 11.00 (s, 1H), 6.62 (s, 1H), 6.56 (s, 1H), 6.55 (d, J=15.7 Hz, 1H), 6.20-6.14 (m, 1H), 6.02 (dt, J=15.7, 7.32 Hz, 1H), 5.84 (d, J=16.4 Hz, 1H), 5.18-5.06 (m, 4H), 4.74 (s, 2H), 4.58-4.55 (m, 4H), 4.44 (s, 2H), 4.26 (s, 2H), 4.22 (s, 2H), 3.78 (s, 3H), 3.66 (s, 3H), 2.51-2.48 (m, 1H), 2.39-2.36 (m, 3H), 2.32-2.29 (m, 1H), 2.26-2.24 (m, 1H), 2.14-2.06 (m, 4H), 2.00-1.99 (m, 2H), 2 OH signals are not visible; HRMS (MALDI-TOF) m/z [M+H]$^+$ calcd for HRMS (MALDI-TOF) m/z [M+Na]$^+$ calcd for $C_{20}H_{22}ClNO_7Na$: 446.0983; found: 446.0975.

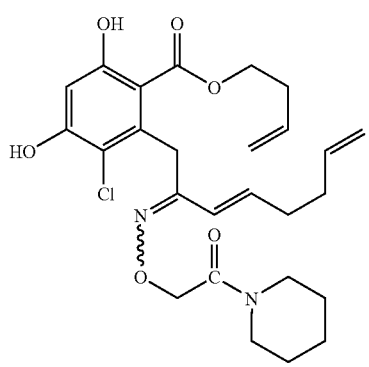

13m $^1$H NMR (CDCl$_3$, 400 MHz, 25° C.) δ 11.57 (s, 1H), 11.44 (s, 1H), 6.91 (d, J=16.1 Hz, 1H), 6.61 (s, 1H), 6.57 (s, 1H), 6.27 (dt, J=16.1, 6.96 Hz, 1H), 6.02 (dt, J=15.6, 6.44 Hz, 1H), 5.71-5.88 (m, 3H), 5.58-5.67 (m, 1H), 5.50 (d, J=15.6 Hz, 1H), 4.99-5.15 (m, 6H), 4.84-4.91 (m, 2H), 4.80 (s, 2H), 4.50 (s, 2H), 4.30-4.36 (dt×2, J=12.3, 6.48 Hz, 4H), 4.23 (s, 2H), 4.19 (s, 2H), 3.23-3.58 (m, 8H), 2.38-2.48 (m, 4H), 2.31-2.37 (m, 2H), 2.21-2.26 (m, 2H), 2.00-2.04 (m, 4H), 1.44-1.66 (m, 12H); HRMS (MALDI-TOF) m/z [M+Na]$^+$ calcd for HRMS (MALDI-TOF) m/z [M+Na]$^+$ calcd for $C_{26}H_{33}ClN_2O_6Na$: 527.1925; found: 527.1906.

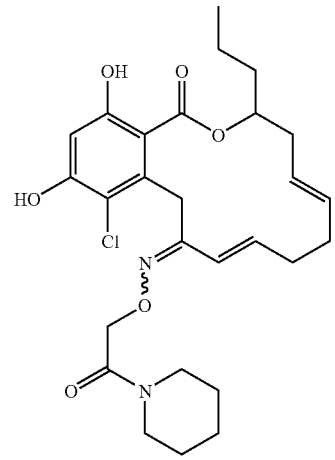

394

Mixture of isomers 3:1 in the oxime. Major isomer E: $^1$H NMR (CDCl$_3$, 400 MHz, 25° C.) δ 11.46 (bs, 1H), 6.63 (s, 1H), 6.03 (m, 1H), 5.30-5.05 (m, 2H), 5.13 (d, J=16.1 Hz, 1H), 4.84 (s, 1H), 4.82 (s, 1H), 4.27 (s, 1H), 4.15 (s, 1H), 3.65-3.40 (m, 4H), 3.34-3.21 (m, 1H), 2.65-1.92 (m, 6H), 1.35-1.20 (m, 6H), 0.97 (t, J=7.3 Hz, 3H), 0.91 (q, J=7.3 Hz, 2H), 0.90 (q, J=7.3 Hz, 2H).

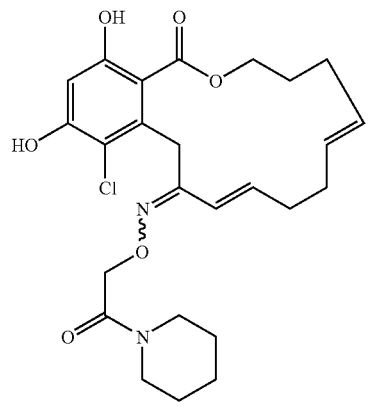

396

Mixture of isomers 4:1 in the oxime. Major isomer E $^1$H NMR (CDCl$_3$, 400 MHz, 25° C.) δ 11.31 (s, 1H), 6.41 (s, 1H), 6.22 (m, 1H), 5.50 (d, J=15.8 Hz, 1H), 5.44-5.26 (m, 2H), 4.79 (s, 2H), 4.49 (t, J=5.6 Hz, 2H), 4.21 (s, 2H), 3.62-3.37 (m, 4H), 2.33-1.93 (m, 8H), 1.34-1.21 (m, 4H), 0.93-0.79 (m, 2H).

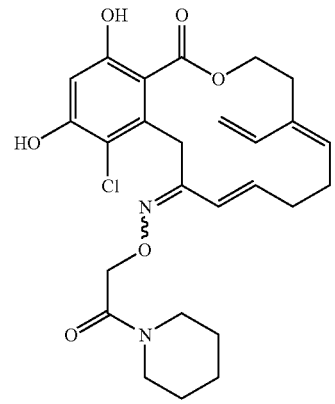

397

Mixture of isomers 3:1 in the oxime. Major isomer E $^1$H NMR (CDCl$_3$, 400 MHz, 25° C.) δ 12.07 (s, 1H), 6.56 (s, 1H), 6.20-5.88 (m, 1H), 6.03 (d, J=16 Hz, 1H), 5.60-5.46 (m, 1H), 4.92 (d, J=23.1 Hz, 2H), 4.53-4.44 (m, 1H), 4.48 (s, 2H), 4.08 (s, 2H), 3.60-3.32 (m, 4H), 3.20 (m, 2H), 2.75 (t, J=6.3 Hz, 2H), 2.50-2.39 (m, 2H), 2.28-2.15 (m, 2H), 1.37-1.23 (m, 4H), 0.93-0.78 (m, 2H).

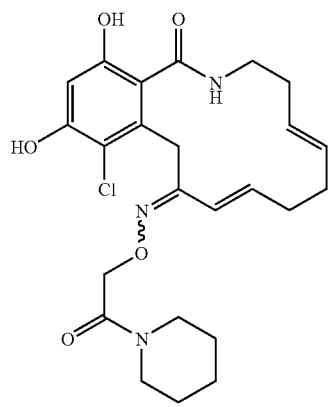

395

Mixture of isomers 3:1 in the oxime. Major isomer E $^1$H NMR (CDCl$_3$, 400 MHz, 25° C.) δ 10.58 (s, 1H), 6.64 (s, 1H), 6.22-6.15 (m, 1H), 5.41 (d, J=13.3 Hz, 1H), 5.31 (s, 2H), 5.27-5.13 (m, 2H), 4.61 (s, 2H), 4.03 (t, J=7 Hz, 2H), 3.63-3.37 (m, 4H), 2.56-2.02 (m, 6H), 1.38-1.22 (m, 4H), 0.93-0.78 (m, 2H).

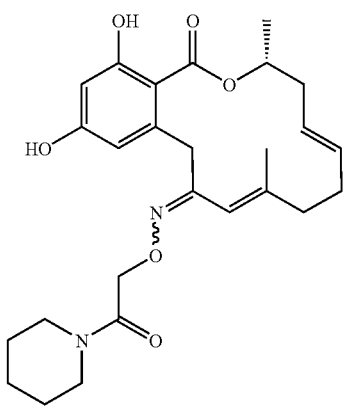

336

Mixture of isomers 1:1 in the oxime. $^1$H NMR (CDCl$_3$, 400 MHz) δ 11.92 (brs, 1H), 11.77 (brs, 1H), 6.56 (d, J=2.4 Hz, 1H), 6.53 (d, J=2.4 Hz, 1H), 6.36 (d, J=2.4 Hz, 1H), 6.35 (d, J=2.8 Hz, 1H), 5.43-5.17 (m, 6H), 5.11 (s, 1H), 5.02 (s, 1H), 4.88 (d, J=14.4 Hz, 1H), 4.81-4.74 (m, 2H), 4.70 (d, J=14.4 Hz, 1H), 4.46 (d, J=13.6 Hz, 1H), 4.16-4.09 (m, 2H), 3.96 (d, J=15.6 Hz, 1H), 3.64-3.37 (m, 8H), 2.78-2.60 (m, 4H), 2.23-2.12 (m, 8H), 1.79 (s, 3H), 1.65-1.56 (m, 12H), 1.53 (s, 3H), 1.35 (d, J=6.4 Hz, 3H), 1.29 (d, J=6.4 Hz, 3H).

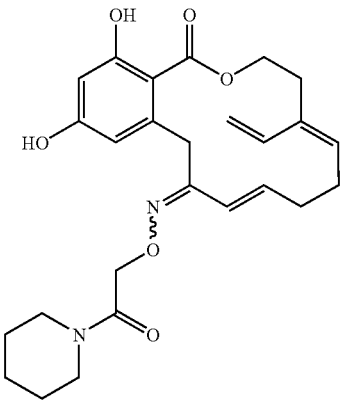

341

Mixture of isomers 1:1 in the oxime. $^1$H NMR (CDCl$_3$, 400 MHz) δ 10.95 (brs, 2H), 7.11 (d, J=2.4 Hz, 2H), 6.32 (d, J=2.4 Hz, 2H), 6.09-6.01 (m, 2H), 5.95 (d, J=16.8 Hz, 2H), 5.91 (d, J=16.4 Hz, 2H), 5.76-5.68 (m, 2H), 5.11 (s, 2H), 4.94 (s, 2H), 4.84 (s, 4H), 4.57 (t, J=5.2 Hz, 4H), 4.26 (s, 4H), 3.59-3.53 (m, 4H), 3.39-3.33 (m, 4H), 2.67 (t, J=5.2 Hz, 4H), 2.23-2.17 (m, 8H), 1.60-1.52 (m, 8H), 1.36-1.28 (m, 4H).

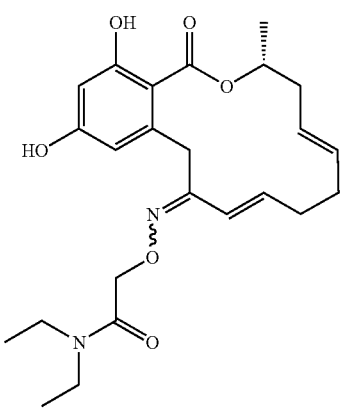

335

Mixture of isomers 1:1 in the oxime. $^1$H NMR (CDCl$_3$, 400 MHz) δ 11.21 (brs, 1H), 6.67 (d, J=2.4 Hz, 1H), 6.62 (d, J=16.4 Hz, 1H), 6.30 (d, J=2.8 Hz, 1H), 6.23-6.15 (m, 1H), 5.52-5.44 (m, 1H), 5.40-5.31 (m, 1H), 4.82 (d, J=14.8 Hz, 1H), 4.75 (d, J=14.8 Hz, 1H), 4.51 (d, J=14.8 Hz, 1H), 4.21 (t, J=6.2 Hz, 1H), 3.66 (d, J=15.2 Hz, 1H), 3.44-3.35 (m, 2H), 3.34-3.28 (m, 2H), 2.33-2.20 (m, 2H), 2.14-1.98 (m, 4H), 1.45 (d, J=6.8 Hz, 3H), 1.14 (t, J=7.2 Hz, 3H), 0.92 (t, J=7.6 Hz, 3H). HRMS (MALDI-TOF) m/z [M+Na]$^+$ calcd for C$_{24}$H$_{32}$NaN$_2$O$_6$: 467.2158; found: 467.2176

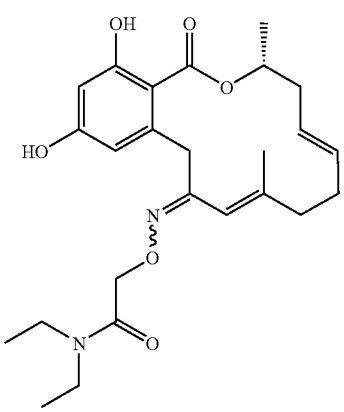

351

387

Mixture of isomers 1:1 in the oxime. $^1$H NMR (CDCl$_3$, 400 MHz) δ 11.92 (brs, 1H), 11.83 (brs, 1H), 6.98 (d, J=2.4 Hz, 2H), 6.34-6.33 (m, 2H), 5.38-5.15 (m, 6H), 4.93 (d, J=14.4 Hz, 2H), 4.79-4.68 (m, 2H), 4.75 (d, J=14.4 Hz, 2H), 4.27 (d, J=14.4 Hz, 2H), 4.04 (d, J=14.4 Hz, 2H), 3.44-3.26 (m, 8H), 2.24-2.19 (m, 4H), 1.74-1.72 (m, 14H), 1.36 (d, J=6.8 Hz, 6H), 1.34 (d, J=6.8 Hz, 6H), 1.27-1.21 (m, 6H), 1.14 (t, J=7.4 Hz, 6H). HRMS (MALDI-TOF) m/z [M+H]$^+$ calcd for C$_{25}$H$_{35}$N$_2$O$_6$: 459.2495; found: 459.2499

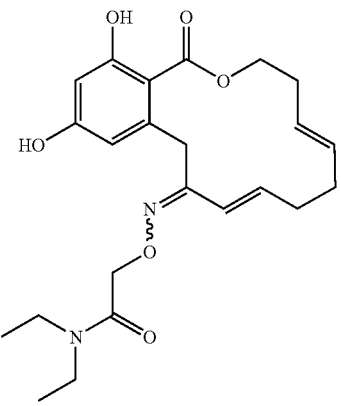

357

Mixture of isomers 1:1 in the oxime. $^1$H NMR (CDCl$_3$, 400 MHz) δ 11.70 (brs, 1H), 11.69 (brs, 1H), 6.99 (brs, 1H), 6.72 (d, J=2.8 Hz, 1H), 6.64 (d, J=16.4 Hz, 1H), 6.32 (d, J=2.4 Hz, 1H), 6.31 (d, J=2.4 Hz, 1H), 6.28-6.17 (m, 2H), 5.91 (d, J=16 Hz, 1H), 5.38-5.33 (m, 4H), 4.87 (s, 2H), 4.79 (s, 2H), 4.57-4.53 (m, 4H), 4.34 (s, 2H), 4.07 (s, 2H), 3.43-3.37 (m, 4H), 3.34-3.28 (q, J=7.2 Hz, 4H), 2.53-2.48 (m, 4H), 2.16-1.97 (m, 8H), 1.29-1.24 (m, 12H). HRMS (MALDI-TOF) m/z [M+H]$^+$ calcd for C$_{23}$H$_{31}$N$_2$O$_6$: 431.2182; found: 431.2186

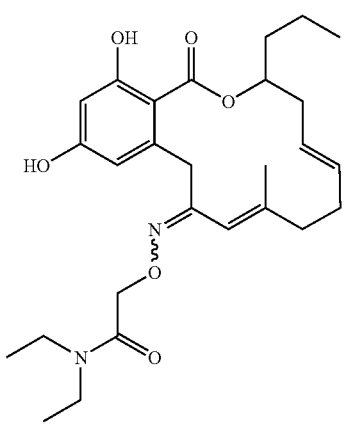

362

Mixture of isomers 7:1 in the oxime. Major isomer E $^1$H NMR (CDCl$_3$, 400 MHz) δ 11.82 (brs, 1H), 7.75 (brs, 1H), 7.02 (d, J=2.4 Hz, 1H), 6.34 (d, J=2.4 Hz, 1H), 5.35-5.28 (m, 1H), 5.20 (s, 1H), 5.14-5.10 (m, 1H), 4.94 (d, J=14.4 Hz, 1H), 4.74 (d, J=14.4 Hz, 1H), 4.31 (d, J=14.4 Hz, 1H), 4.07 (d, J=14.4 Hz, 1H), 3.44-3.28 (m, 4H), 2.70-2.63 (m, 1H), 2.25-2.18 (m, 2H), 2.14-2.07 (m, 2H), 1.73-1.72 (m, 6H), 1.25-1.21 (m, 6H), 1.14 (t, J=7.2 Hz, 3H), 0.95 (t, J=7.2 Hz, 3H). HRMS (MALDI-TOF) m/z [M+Na]$^+$ calcd for C$_{27}$H$_{38}$NaN$_2$O$_6$: 509.2627; found: 509.2652

388

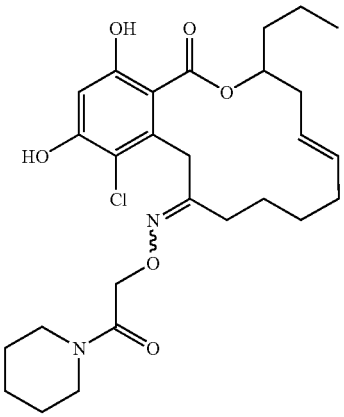

352

Mixture of isomers 1:1 in the oxime. $^1$H NMR (CDCl$_3$, 400 MHz) δ 11.79 (brs, 1H), 11.03 (brs, 1H), 6.61 (s, 1H), 6.08 (s, 1H), 5.42-5.28 (m, 6H), 4.79 (d, J=13.2 Hz, 2H), 4.74 (d, J=13.6 Hz, 2H), 4.39 (m, 2H), 4.27-4.23 (m, 3H), 3.61-3.54 (m, 4H), 3.51-3.45 (m, 4H), 2.53-2.47 (m, 2H), 2.33-2.20 (m, 4H), 2.06-1.91 (m, 8H), 1.70-1.58 (m, 12H), 1.44-129 (m, 13H), 0.95 (t, J=7.2 Hz, 6H). HRMS (MALDI-TOF) m/z [M+Na]$^+$ calcd for C$_{27}$H$_{37}$ClNaN$_2$O$_6$: 543.2237; found: 543.2263

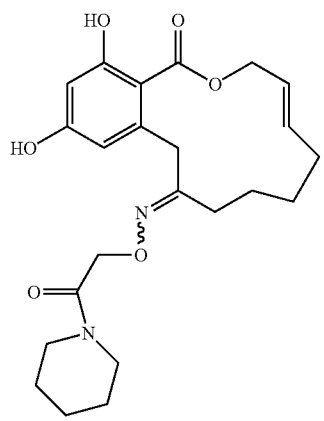

353

HRMS (MALDI-TOF) m/z [M+Na]$^+$ calcd for C$_{23}$H$_{30}$NaN$_2$O$_6$: 453.2001; found: 453.2010

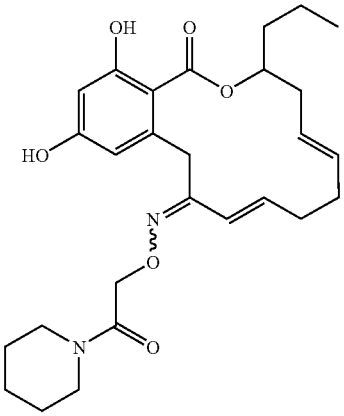

358

Mixture of isomers 1:1 in the oxime. ¹H NMR (CDCl₃, 400 MHz) δ 6.99 (brs, 1H), 6.68 (d, J=2.4 Hz, 1H), 6.61 (d, J=16.8 Hz, 1H), 6.32 (d, J=2.4 Hz, 1H), 6.30 (d, J=2.4 Hz, 1H), 6.25-6.10 (m, 2H), 5.89 (d, J=16.4 Hz, 1H), 5.50-5.31 (m, 4H), 4.94 (d, J=14.4 Hz, 2H), 4.84-4.76 (m, 4H), 4.50 (d, J=15.2 Hz, 1H), 4.44 (d, J=14.4 Hz, 1H), 4.29 (d, J=14.4 Hz, 1H), 4.21 (t, J=6.0 Hz, 1H), 2.72-2.61 (m, 4H), 2.35-2.19 (m, 6H), 2.15-1.96 (m, 8H), 1.93-1.82 (m, 3H), 1.38-1.28 (m, 11H), 0.96 (t, J=7.6 Hz, 3H), 0.92 (t, J=7.6 Hz, 3H). HRMS (MALDI-TOF) m/z [M+H]⁺ calcd for $C_{27}H_{37}N_2O_6$: 485.2651; found: 485.2611

359

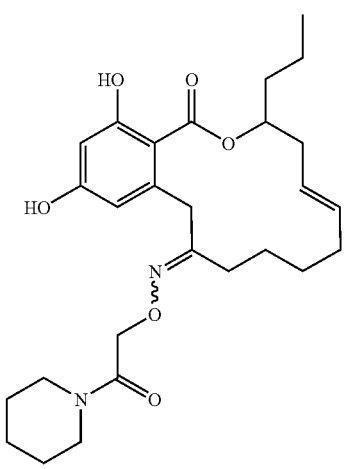

HRMS (MALDI-TOF) m/z [M+Na]⁺ calcd for $C_{27}H_{38}NaN_2O_6$: 509.2628; found: 509.2639

356

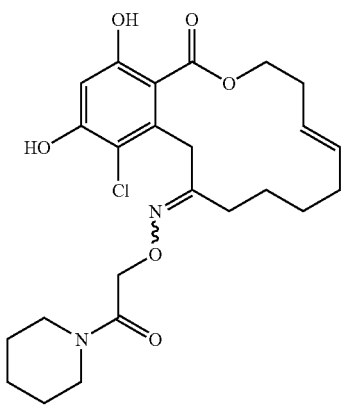

Mixture of isomers 1:1 in the oxime. ¹H NMR (CDCl₃, 400 MHz) δ 6.61 (s, 1H), 6.05 (s, 1H), 5.41-5.26 (m, 6H), 4.80-4.75 (m, 3H), 4.58-4.47 (m, 4H), 4.30-4.17 (m, 3H), 4.21 (t, 2H, J=5.6 Hz), 4.05-4.01 (m, 2H), 3.61-3.54 (m, 4H), 3.49-3.42 (m, 4H), 2.46-2.40 (m, 2H), 2.24-2.20 (m, 3H), 2.07-1.90 (m, 8H), 1.34-1.28 (m, 15H). HRMS (MALDI-TOF) m/z [M+Na]⁺ calcd for $C_{27}H_{31}NaN_2O_6$: 501.1768; found: 501.1718

363

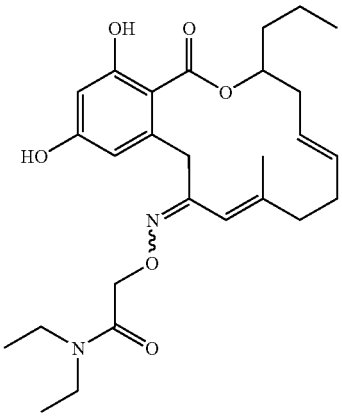

Mixture of isomers 5:1 in the oxime. Major isomer E ¹H NMR (CDCl₃, 400 MHz) δ 11.85 (brs, 1H), 7.12 (d, J=2.4 Hz, 1H), 6.34 (d, J=2.4 Hz, 1H), 5.38-5.31 (m, 2H), 5.25 (s, 1H), 5.23-5.11 (m, 2H), 4.96 (d, J=14.4 Hz, 1H), 4.74 (d, J=14.4 Hz, 1H), 4.34 (d, J=14 Hz, 1H), 4.21 (t, J=6 Hz, 1H), 4.10 (d, J=14 Hz, 1H), 3.43-3.27 (m, 4H), 1.70 (s, 3H), 1.61-1.59 (m, 4H), 1.37-1.29 (m, 7H), 1.13 (t, J=7.2 Hz, 3H), 0.95 (t, J=7.2 Hz, 3H). HRMS (MALDI-TOF) m/z [M+Na]⁺ calcd for $C_{27}H_{38}NaN_2O_6$: 509.2627; found: 509.2680

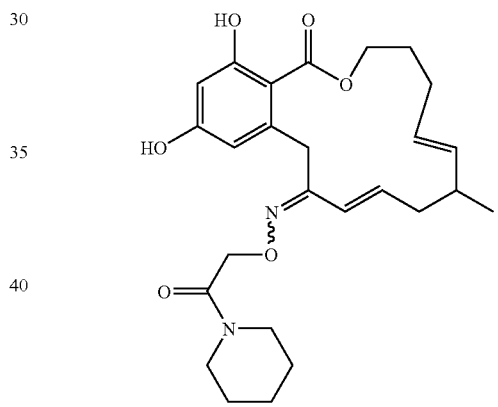

HRMS (MALDI-TOF) m/z [M+Na]⁺ calcd for $C_{26}H_{34}NaN_2O_6$: 493.2314; found: 493.2331

365

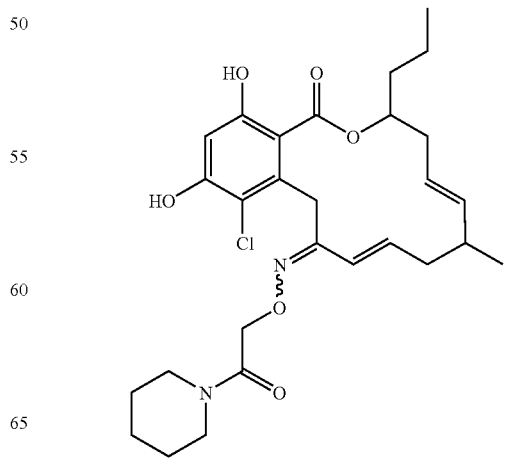

391
HRMS (MALDI-TOF) m/z [M+Na]+ calcd for C28H37ClNaN2O6: 555.2238; found: 555.2242
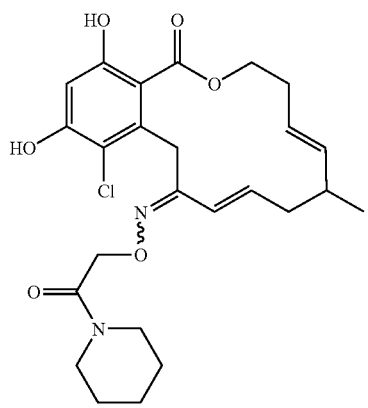
366
HRMS (MALDI-TOF) m/z [M+Na]+ calcd for C25H31ClNaN2O6: 513.1768; found: 513.1780
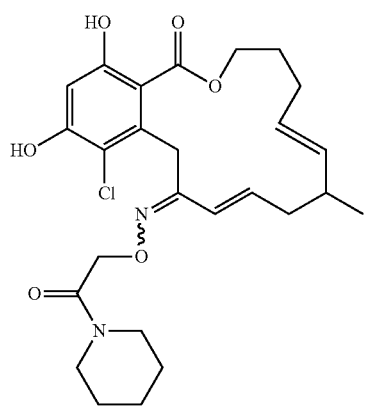
367
HRMS (MALDI-TOF) m/z [M+Na]+ calcd for C26H33ClNaN2O6: 527.1925; found: 527.1939
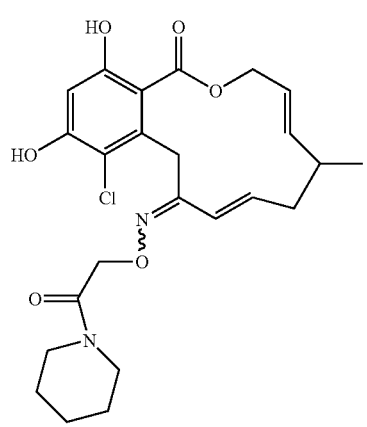
368
392
HRMS (MALDI-TOF) m/z [M+Na]+ calcd for C24H29ClNaN2O6: 499.1612; found: 499.1626
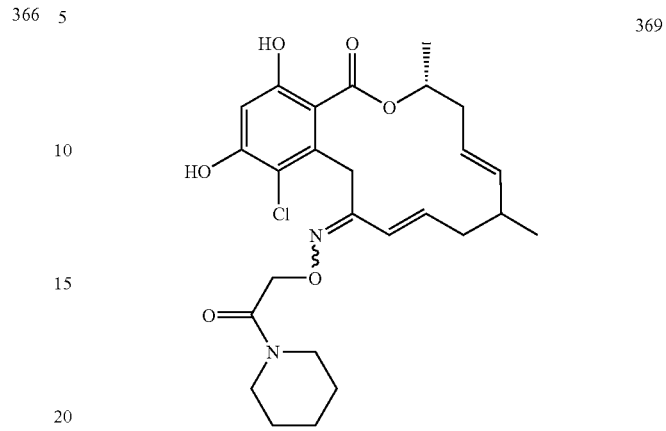
369
HRMS (MALDI-TOF) m/z [M+Na]+ calcd for C26H33ClNaN2O6: 527.1925; found: 527.1932
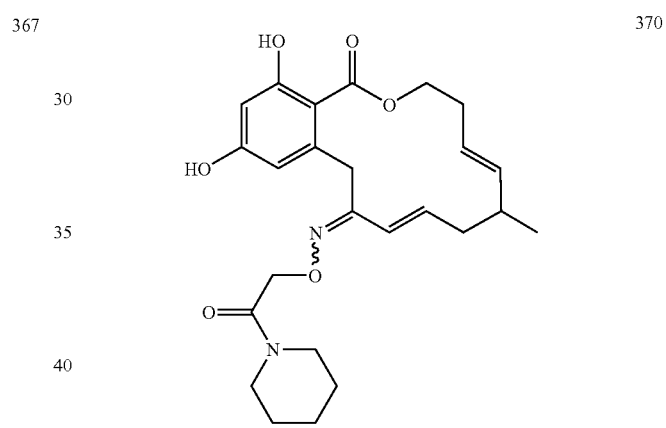
370
HRMS (MALDI-TOF) m/z [M+Na]+ calcd for C25H32NaN2O6: 479.2158; found: 479.2174
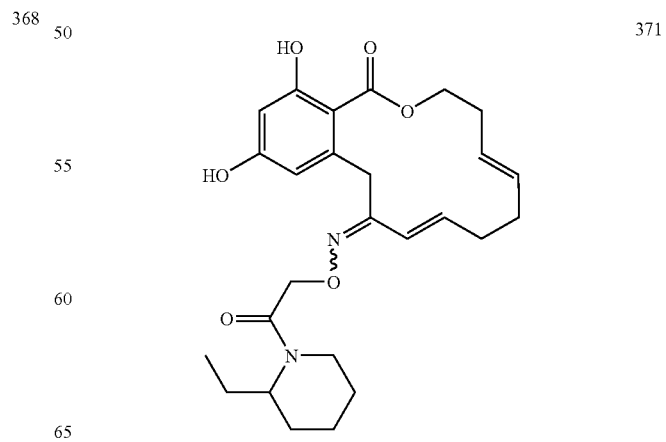
371

393

HRMS (MALDI-TOF) m/z [M+Na]+ calcd for C26H34NaN7O6: 493.2315; found: 493.2319

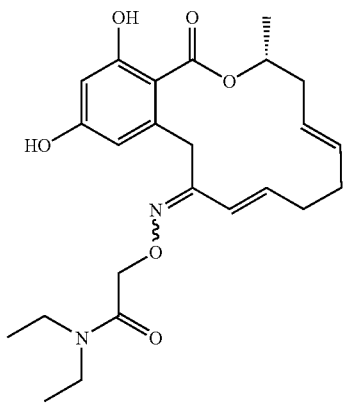

354

Mixture of isomers 4:1 in the oxime. Major isomer E ¹H NMR (CDCl₃, 400 MHz) δ 7.40 (d, J=2.4 Hz, 1H), 6.31 (d, J=2.4 Hz, 1H), 6.19-6.11 (m, 1H), 5.89 (d, J=16 Hz, 1H), 5.53-5.46 (m, 1H), 5.41-5.32 (m, 1H), 4.93 (d, J=14.8 Hz, 1H), 4.81 (d, J=14.8 Hz, 1H), 4.44 (d, J=14.8 Hz, 1H), 4.28 (d, J=14.8 Hz, 1H), 4.21 (t, J=5.6 Hz, 1H), 3.44-3.29 (m, 2H), 2.35-2.20 (m, 2H), 2.13-2.01 (m, 2H), 1.45 (d, J=6.8 Hz, 3H), 1.37-1.28 (m, 4H), 1.14 (t, J=7.2 Hz, 3H), 0.92 (t, J=7.6H, 3Hz). HRMS (MALDI-TOF) m/z [M+Na]+ calcd for C24H32NaN2O6: 467.2158; found: 467.2147

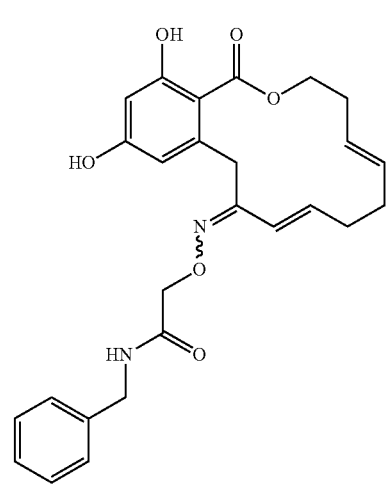

378

Mixture of isomers 1:1 in the oxime. ¹H NMR (CDCl₃, 400 MHz) δ 11.60 (brs, 1H), 11.42 (brs, 1H), 7.35-7.28 (m, 9H), 6.69-6.62 (m, 2H), 6.49 (d, J=16 Hz, 1H), 6.36 (d, J=2.4 Hz, 1H), 6.33 (d, J=2.4 Hz, 1H), 6.32 (d, J=2.4 Hz, 1H), 6.28-6.24 (m, 1H), 6.23 (d, J=2.8H, 1H), 6.10 (dt, J=16, 7.2 Hz, 1H), 5.73 (d, J=16 Hz, 1H), 5.36-5.31 (m, 2H), 5.27-5.18 (m, 2H), 4.70 (s, 2H), 4.65 (s, 2H), 4.55-4.51 (m, 5H), 4.45 (t, J=5.3 Hz, 2H), 4.27 (s, 2H), 4.08 (s, 2H), 2.50-2.42 (m, 4H), 2.17-2.07 (m, 8H). HRMS (MALDI-TOF) m/z [M+H]+ calcd for C26H29N2O6: 465.2025; found: 465.1981

394

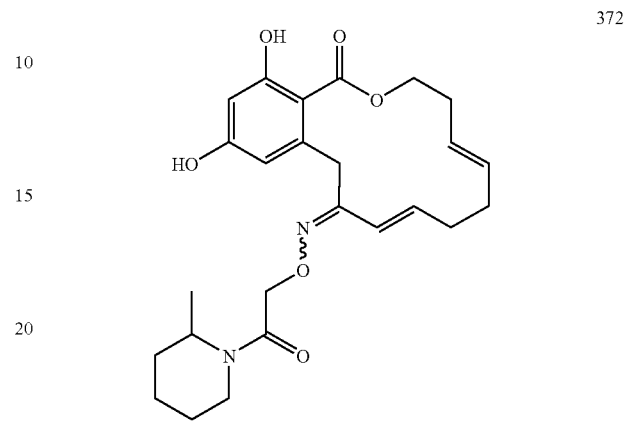

372

Mixture of isomers 1:1 in the oxime. ¹H NMR (CDCl₃, 400 MHz) δ 11.67 (brs, 1H), 11.65 (brs, 1H), 8.00 (brs, 1H), 7.77 (brs, 1H), 7.13 (brs, 1H), 6.63-6.59 (m, 2H), 6.32 (2d, J=2.8 Hz, 2H), 6.27-6.12 (m, 2H), 5.86 (d, J=16.4 Hz, 1H), 5.37-5.33 (m, 4H), 4.95-4.72 (m, 4H), 4.57-4.51 (m, 4H), 4.34 (s, 2H), 4.10 (d, J=15.2 Hz, 1H), 4.03 (d, J=15.2 Hz, 1H), 3.58-3.48 (m, 2H), 3.20-3.09 (m, 2H), 2.77-2.69 (m, 2H), 2.53-2.45 (m, 4H), 2.17-2.05 (m, 8H), 1.71-1.32 (m, 12H), 1.30-1.12 (m, 6H). HRMS (MALDI-TOF) m/z [M+H]+ calcd for C25H33N2O6: 457.2338; found: 457.2332

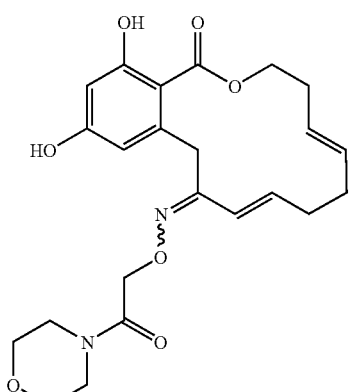

380

Mixture of isomers 1:1 in the oxime. ¹H NMR (CDCl₃, 400 MHz) δ 11.66 (brs, 1H), 11.64 (brs, 1H), 7.56 (brs, 1H), 7.36 (brs, 1H), 6.95 (d, J=2.8 Hz, 1H), 6.59-6.54 (m, 2H), 6.33 (d, J=2.8 Hz, 1H), 6.32 (d, J=2.8 Hz, 1H), 6.28-6.13 (m, 2H), 5.84 (d, J=16.1 Hz, 1H), 5.38-5.32 (m, 4H), 4.85 (s, 2H), 4.78 (s, 2H), 4.54 (t, J=5.2 Hz, 4H), 4.33 (s, 2H), 4.07 (s, 2H), 3.71-3.64 (m, 12H), 3.52-3.48 (m, 4H), 2.50 (brt, J=4.8 Hz, 4H), 2.17-2.07 (m, 8H). HRMS (MALDI-TOF) m/z [M+Na]+ calcd for C23H28NaN2O: 467.1794; found: 467.1765

395

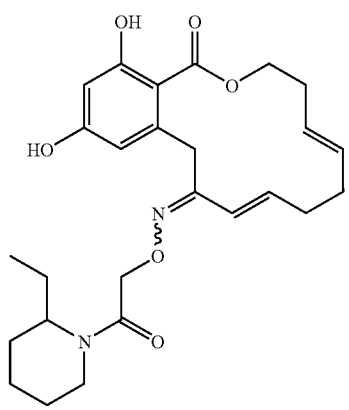

371

Mixture of isomers 1:1 in the oxime. ¹H NMR (CDCl₃, 400 MHz) δ 11.62 (brs, 2H), 6.96 (d, J=2 Hz, 1H), 6.58 (d, J=2.8 Hz, 1H), 6.60 (d, J=2.8 Hz, 1H), 6.32 (brd, J=2.4 Hz, 2H), 6.24-6.10 (m, 2H), 5.81 (d, J=16 Hz, 1H), 5.35-5.32 (m, 3H), 4.92-4.72 (m, 4H), 4.56-4.45 (m, 4H), 4.31 (brs, 2H), 4.04 (brs, 2H), 3.75-3.67 (m, 1H), 3.59-3.51 (m, 1H), 3.12-3.03 (m, 1H), 2.64 (t, J=12.8 Hz, 1H), 2.52-2.46 (m, 4H), 2.14-2.04 (m, 8H), 1.70-1.58 (m, 10H). HRMS (MALDI-TOF) m/z [M+Na]⁺ calcd for $C_{26}H_{34}NaN_2O_6$: 493.2314; found: 493.2332

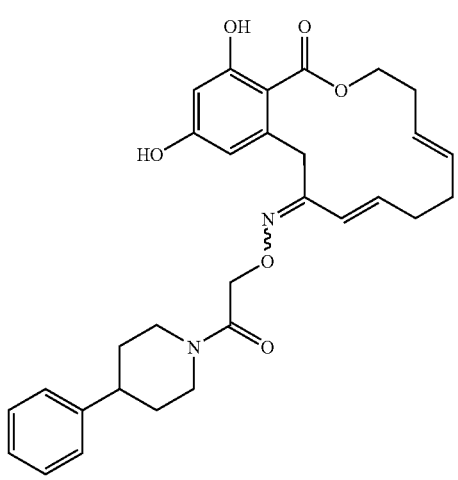

376

Mixture of isomers 1:1 in the oxime. ¹H NMR (CDCl₃, 400 MHz) δ 11.65 (brs, 2H), 7.32-7.27 (m, 4H), 7.24-7.10 (m, 6H), 7.01 (d, J=2.4 Hz, 1H), 6.64-6.59 (m, 2H), 6.34-6.33 (m, 2H), 6.28-6.18 (m, 2H), 5.85 (d, J=16 Hz, 1H), 5.37-5.32 (m, 4H), 4.85 (s, 2H), 4.72-4.69 (m, 2H), 4.56-4.51 (m, 4H), 4.15 (d, J=15.2 Hz, 2H), 4.02 (d, J=15.2 Hz, 2H), 3.96-3.92 (m, 2H), 3.21-3.11 (m, 2H), 2.76-2.67 (m, 4H), 2.54-2.45 (m, 4H), 2.12-2.02 (m, 10H), 1.90-1.87 (m, 4H), 1.67-1.58 (m, 4H). HRMS (MALDI-TOF) m/z [M+Na]⁺ calcd for $C_{30}H_{34}NaN_2O_6$: 541.2314; found: 541.2314

396

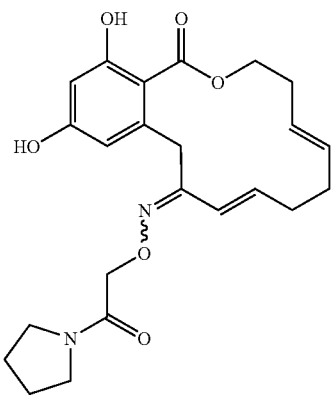

388

Mixture of isomers 1:1 in the oxime. ¹H NMR (CDCl₃, 400 MHz) δ 11.65 (brs, 1H), 11.64 (brs, 1H), 8.70 (brs, 1H), 8.27 (brs, 1H), 7.04 (d, J=2.4 Hz, 1H), 6.64-6.60 (m, 2H), 6.26-6.11 (m, 2H), 6.32 (2d, J=2.6 Hz, 2H), 5.82 (d, J=16 Hz, 1H), 5.36-5.32 (m, 4H), 4.76 (s, 2H), 4.70 (s, 2H), 4.53 (brt, J=5.2 Hz, 4H), 4.33 (s, 2H), 4.05 (s, 2H), 3.51 (brt, J=6.8 Hz, 4H), 3.44 (q, J=7.2 Hz, 4H), 2.52-2.46 (m, 4H), 2.16-2.05 (m, 8H), 2.02-1.93 (m, 4H), 1.90-1.84 (m, 4H). HRMS (MALDI-TOF) m/z [M+H]⁺ calcd for $C_{23}H_{29}N_2O_6$: 429.2025; found: 429.2003

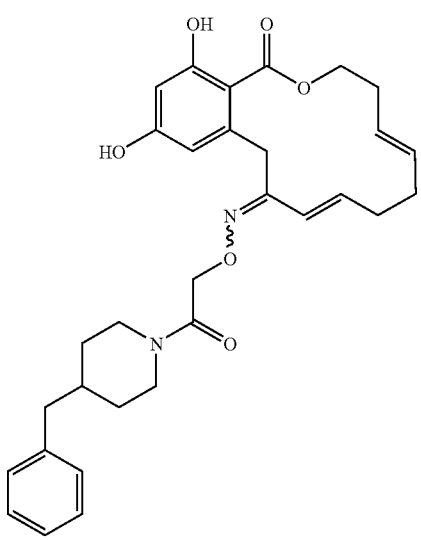

377

Mixture of isomers 1:1 in the oxime. ¹H NMR (CDCl₃, 400 MHz) δ 11.66 (brs, 1H), 11.64 (brs, 1H), 8.15 (brs, 1H), 7.86 (brs, 1H), 7.31-7.27 (m, 4H), 7.21-7.18 (m, 2H), 7.15-7.10

(m, 4H), 7.00 (brs, 1H), 6.60 (d, J=15.6 Hz, 1H), 6.59 (d, J=2.4 Hz, 1H), 6.32 (2d, J=2.4 Hz, 2H), 6.27-6.11 (m, 2H), 5.85 (d, J=16 Hz, 1H), 5.36-5.32 (m, 4H), 4.84 (s, 2H), 4.77 (s, 2H), 4.59-4.48 (m, 4H), 4.33 (s, 2H), 4.11 (d, J=15.2 Hz, 1H), 4.02 (d, J=15.6 Hz, 1H), 3.78-3.71 (m, 2H), 3.01-2.92 (m, 2H), 2.59-2.47 (m, 8H), 2.12-2.07 (m, 8H), 1.82-1.68 (m, 6H), 1.36-1.30 (m, 8H). HRMS (MALDI-TOF) m/z [M+H]$^+$ calcd for C$_{31}$H$_{37}$N$_2$O$_6$: 533.2651; found: 533.2625

1H), 6.61-6.57 (m, 2H), 6.33-6.32 (m, 2H), 6.25-6.10 (m, 2H), 5.82 (d, J=16 Hz, 1H), 5.36-5.31 (m, 4H), 4.85 (s, 2H), 4.78 (s, 2H), 4.58-4.48 (m, 4H), 4.41-4.32 (m, 4H), 4.12-3.98 (m, 2H), 3.72-3.58 (m, 2H), 3.02-2.93 (m, 1H), 2.72-2.62 (m, 2H), 2.53-2.45 (m, 4H), 2.35-2.28 (m, 1H), 2.16-2.04 (m, 8H), 1.86-1.39 (m, 8H), 1.17-1.07 (m, 2H), 0.93-0.88 (m, 6H). HRMS (MALDI-TOF) m/z [M+H]$^+$ calcd for C$_{25}$H$_{33}$N$_2$O$_6$: 457.2338; found: 457.2380

379

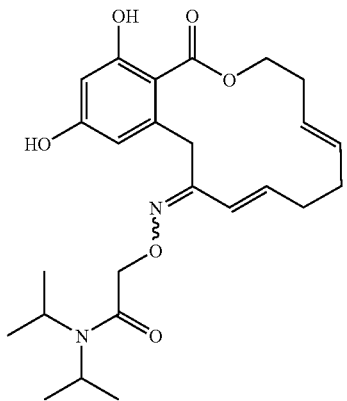

Mixture of isomers 1:1 in the oxime. $^1$H NMR (CDCl$_3$, 400 MHz) δ 11.72 (brs, 1H), 11.71 (brs, 1H), 6.71 (d, 1H, J=2.4 Hz), 6.67 (d, 1H, J=16.4 Hz), 6.35 (2d, 2H, J=3 Hz), 6.31-6.18 (m, 2H), 5.93 (d, 1H, J=16.4 Hz), 5.41-5.36 (m, 4H), 4.86 (s, 2H), 4.77 (s, 2H), 4.60-4.54 (m, 4H), 4.37 (s, 2H), 4.10 (s, 2H), 3.94-3.86 (m, 2H), 3.62-3.49 (m, 2H), 2.55-2.49 (m, 4H), 2.20-2.10 (m, 8H), 1.44-1.25 (m, 24H). HRMS (MALDI-TOF) m/z [M+H]$^+$ calcd for C$_{25}$H$_{35}$N$_2$O$_6$: 459.2495; found: 459.2514

373

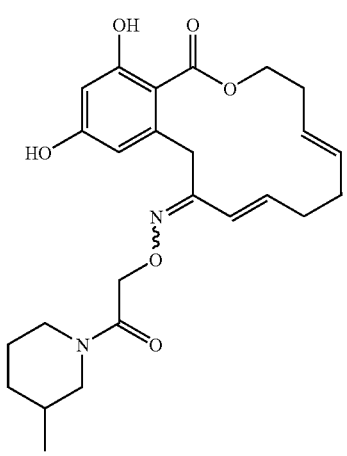

Mixture of isomers 1:1 in the oxime. $^1$H NMR (CDCl$_3$, 400 MHz) δ 11.65 (brs, 1H), 11.64 (brs, 1H), 7.00 (d, J=24 Hz,

374

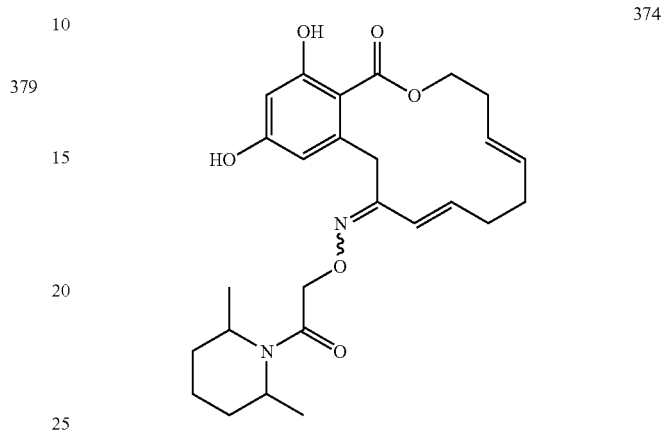

Mixture of isomers 1:1 in the oxime. $^1$H NMR (CDCl$_3$, 400 MHz) δ 11.67 (brs, 2H), 6.99 (s, 1H), 6.68-6.63 (m, 2H), 6.32 (d, J=2.4 Hz, 1H), 6.31 (d, J=2.8 Hz, 1H), 6.27-6.14 (m, 2H), 5.90 (d, J=16 Hz, 1H), 5.37-5.34 (m, 4H), 4.77 (s, 2H), 4.63-4.46 (m, 4H), 4.36 (brs, 2H), 4.21 (t, J=6 Hz, 4H), 4.05-3.92 (m, 4H), 2.55-2.46 (m, 4H), 2.17-2.06 (m, 8H), 1.37-1.28 (m, 12H), 0.93-0.86 (m, 12H). HRMS (MALDI-TOF) m/z [M+Na]$^+$ calcd for C$_{26}$H$_{34}$NaN$_2$O$_6$: 493.2314; found: 493.2314

382

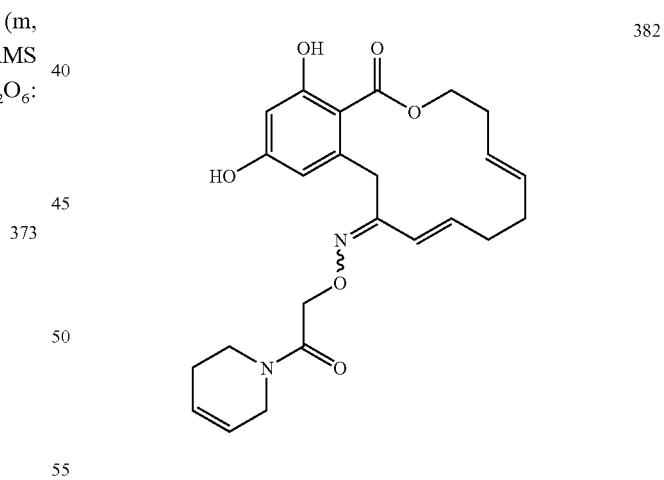

Mixture of isomers 2:1 in the oxime. Major isomer E $^1$H NMR (CDCl$_3$, 400 MHz) 11.62 (brs, 1H), 6.98 (m, 1H), 6.57 (m, 2H), 6.32 (m, 2H), 6.18 (m, 2H), 5.82 (d, J=15.6 Hz, 1H), 5.67 (m, 2H), 5.33 (m, 4H), 4.87 (d, J=13.6 Hz, 2H), 4.80 (d, J=10.8 Hz, 2H), 4.53 (m, 3H), 4.33 (s, 2H), 4.05 (brs, 4H), 3.73 (m, 2H), 3.69 (q, J=6 Hz, 2H), 3.52 (q, J=5.2 Hz, 2H), 2.48 (m, 5H), 2.13 (m, 13H). HRMS (MALDI-TOF) m/z [M+Na]$^+$ calcd for C$_{24}$H$_{28}$NaN$_2$O$_6$: 463.1845; found: 463.1870

399

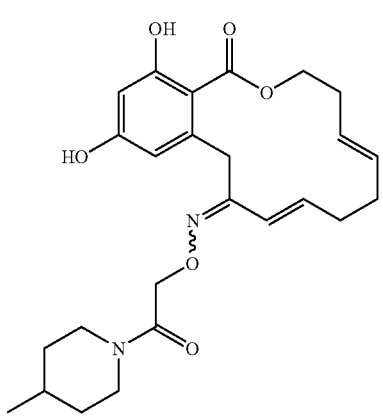

375

Mixture of isomers 1:1 in the oxime. $^1$H NMR (CDCl$_3$, 400 MHz) δ 11.66 (brs, 1H), 11.64 (brs, 1H), 8.29 (brs, 2H), 6.89 (d, J=2.8 Hz, 1H), 6.59 (d, J=16H, 1Hz), 6.57 (d, J=2.4 Hz, 1H), 6.33-6.32 (m, 2H), 6.24-6.09 (m, 2H), 5.79 (d, J=16 Hz, 1H), 5.34-5.30 (m, 4H), 4.85 (s, 2H), 4.78 (s, 2H), 4.56-4.48 (m, 4H), 4.31 (s, 2H), 4.10 (d, J=15.6 Hz, 1H), 4.05 (d, J=15.6 Hz, 1H), 3.80-3.71 (m, 2H), 3.06-2.96 (m, 2H), 2.61 (dt, J=12.8, 2.6 Hz, 2H), 2.52-2.46 (m, 4H), 2.16-2.05 (m, 8H), 1.71-1.58 (m, 6H), 1.17-1.05 (m, 4H), 0.94 (d, J=5.6 Hz, 3H), 0.93 0.94 (d, J=5.6 Hz, 3H). HRMS (MALDI-TOF) m/z [M+Na]$^+$ calcd for C$_{25}$H$_{32}$NaN$_2$O$_6$: 479.2158; found: 479.2182

400

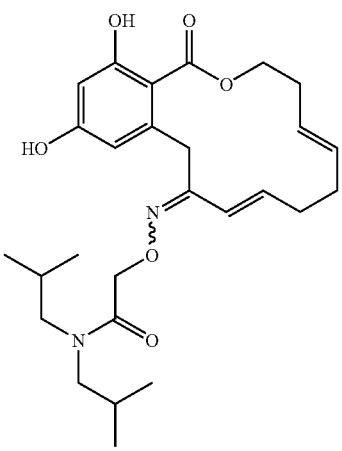

390

Mixture of isomers 1:1 in the oxime. $^1$H NMR (CDCl$_3$, 400 MHz) δ 11.65 (brs, 2H), 7.06 (d, J=2.4 Hz, 1H), 6.62-6.57 (m, 2H), 6.33 (d, J=2.4 Hz, 2H), 6.21-6.11 (m, 2H), 5.81 (d, J=16.4 Hz, 1H), 5.37-5.29 (m, 4H), 4.86 (s, 2H), 4.79 (s, 2H), 4.52 (brt, J=5.2 Hz, 4H), 4.31 (s, 2H), 4.02 (s, 2H), 3.21 (m, 4H), 3.09 (dd, J=10.8, 8.0 Hz, 4H), 2.52-2.44 (m, 4H), 2.11-1.91 (m, 12H), 0.95 (d, J=6.8 Hz, 6H), 0.93 (d, J=6.8 Hz, 6H), 0.88 (d, J=6.8 Hz, 6H), 0.86 (d, J=6.8 Hz, 6H). HRMS (MALDI-TOF) m/z [M+Na]$^+$ calcd for C$_{27}$H$_{38}$NaN$_2$O$_6$: 509.2627; found: 509.2626

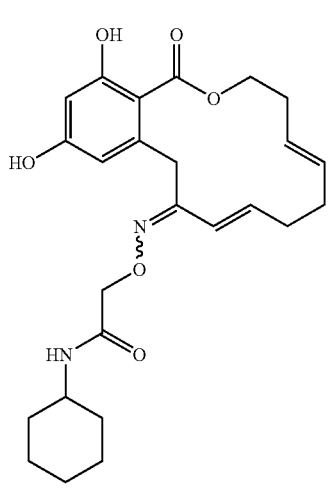

383

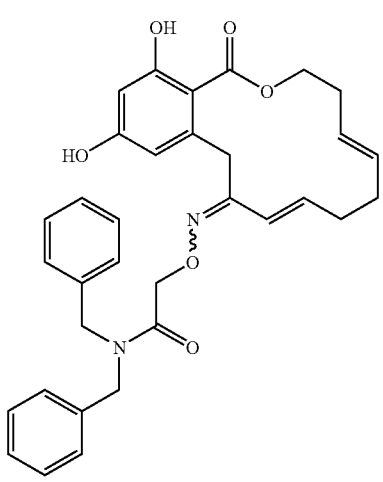

381

Mixture of isomers 1:1 in the oxime. $^1$H NMR (CDCl$_3$, 400 MHz) δ 11.60 (brs, 1H), 11.47 (brs, 1H), 8.58 (brs, 2H), 6.53 (d, J=16.4 Hz, 1H), 6.50 (d, J=2.4 Hz, 1H), 6.35 (d, J=2.4 Hz, 1H), 6.34 (d, J=2.4 Hz, 1H), 6.30 (d, J=2.4 Hz, 1H), 6.31-6.27 (m, 2H), 6.14 (m, 1H), 5.39-5.31 (m, 4H), 4.61 (s, 2H), 4.56-4.53 (m, 6H), 4.33 (s, 2H), 4.09 (s, 2H), 3.86-3.75 (m, 2H), 2.53-2.48 (m, 4I), 2.17-2.09 (m, 8H), 1.93-1.86 (m, 4H), 1.70-1.55 (m, 8H), 1.39-1.11 (m, 8H). HRMS (MALDI-TOF) m/z [M+Na]$^+$ calcd for C$_{25}$H$_{32}$NaN$_2$O$_6$: 479.2158; found: 479.2157

Mixture of isomers 1:1 in the oxime. $^1$H NMR (CDCl$_3$, 400 MHz) δ 11.67 (brs, 1H), 11.66 (brs, 1H), 7.38-7.28 (m, 12H), 7.22-7.14 (m, 8H), 6.94 (d, J=2.4 Hz, 1H), 6.57-6.53 (m, 2H), 6.33 (brd, J=2.4 Hz, 2H), 6.22-6.12 (m, 2H), 5.85 (d, J=16 Hz, 1H), 5.35-5.32 (m, 4H), 4.93 (s, 2H), 4.86 (s, 2H), 4.62 (s, 2H), 4.60 (s, 2H), 4.53 (brt, J=5.2 Hz, 4H), 4.46 (s, 2H), 4.43 (s, 2H), 4.30 (s, 2H), 4.07 (s, 2H), 3.52-3.46 (m, 4H), 2.16-2.07 (m, 8H). HRMS (MALDI-TOF) m/z [M+Na]$^+$ calcd for C$_{33}$H$_{34}$NaN$_2$O$_6$: 577.2314; found: 577.2278

401

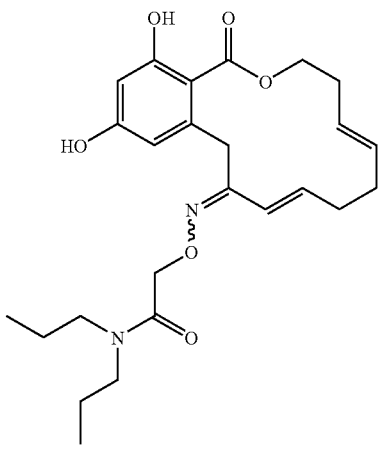

389

Mixture of isomers 1:1 in the oxime. $^1$H NMR (CDCl$_3$, 400 MHz) δ 11.66 (brs, 1H), 11.65 (brs, 1H), 7.05 (d, J=2.4 Hz, 1H), 6.62-6.55 (m, 2H), 6.32-6.29 (m, 2H), 6.23-6.11 (m, 2H), 5.82 (d, J=16 Hz, 1H), 5.34-5.29 (m, 4H), 4.85 (s, 2H), 4.77 (s, 2H), 4.54 (brt, J=5.2 Hz, 4H), 4.32 (s, 2H), 4.04 (s, 2H), 3.32-3.27 (m, 4H), 3.21-3.15 (m, 4H), 2.52-2.42 (m, 4H), 2.10-2.04 (m, 8H), 1.67-1.51 (m, 8H), 0.96-0.86 (m, 12H). HRMS (MALDI-TOF) m/z [M+Na]$^+$ calcd for C$_{25}$H$_{34}$NaN$_2$O$_6$: 481.2314; found: 481.2307

402

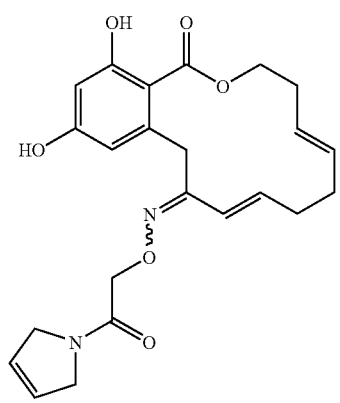

386

Mixture of isomers 1:1 in the oxime. $^1$H NMR (CDCl$_3$, 400 MHz) δ 11.64 (brs, 2H), 6.98 (d, J=2.3 Hz, 1H), 6.61 (d, J=16.3 Hz, 1H), 6.58 (d, J=2.4 Hz, 1H), 6.31 (2d, J=2.2 Hz, 2H), 6.27-6.12 (m, 2H), 5.87-5.78 (m, 5H), 5.45-5.33 (m, 4H), 4.74 (s, 2H), 4.69 (s, 2H), 4.53 (t, J=5.3 Hz, 4H), 4.33 (s, 2H), 4.28-4.25 (m, 8H), 4.05 (s, 2H), 2.52-2.46 (m, 4H), 2.17-2.05 (m, 8H). HRMS (MALDI-TOF) m/z [M+H]$^+$ calcd for C$_{23}$H$_{27}$N$_2$O$_6$: 427.1869; found: 427.1902

384

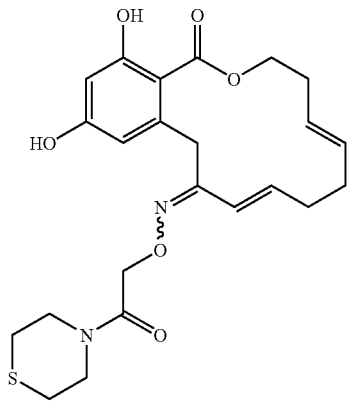

387

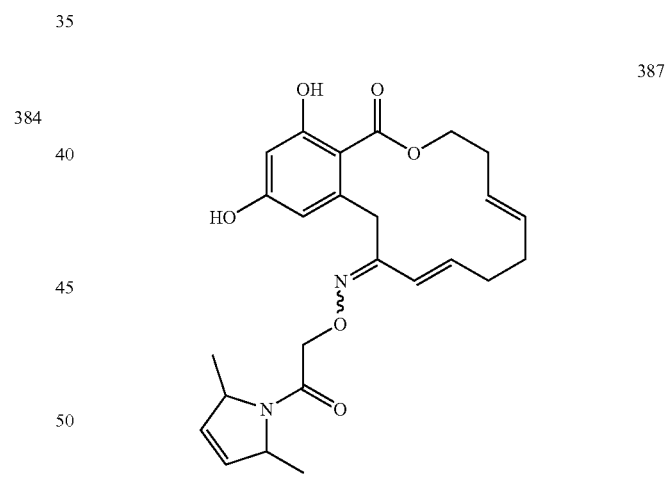

Mixture of isomers 1:1 in the oxime. $^1$H NMR (CDCl$_3$, 400 MHz) δ 11.63 (brs, 2H), 6.88 (d, J=2.0 Hz, 1H), 6.55 (d, J=16.4 Hz, 1H), 6.43 (d, J=2.4 Hz, 1H), 6.32 (d, J=2.4 Hz 1H), 6.30 (d, J=2 Hz, 1H), 6.28-6.13 (m, 2H), 5.84 (d, J=16.1 Hz, 1H), 5.36-5.33 (m, 4H), 4.82 (s, 2H), 4.73 (s, 2H), 4.54 (t, J=5.5 Hz, 4H), 4.32 (s, 2H), 4.09 (s, 2H), 3.91-3.85 (m, 4H), 3.79-3.70 (m, 4H), 2.65-2.60 (m, 8H), 2.49 (brt, J=5.1 Hz, 4H), 2.17-2.04 (m, 8H). HRMS (MALDI-TOF) m/z [M+H]$^+$ calcd for C$_{23}$H$_{28}$N$_2$O$_6$: 461.1746; found: 461.1765

Mixture of isomers 1:1 in the oxime. $^1$H NMR (CDCl$_3$, 400 MHz) δ 11.68 (brs, 2H), 7.16 (d, J=2.8 Hz, 1H), 6.63 (d, J=16.3 Hz, 1H), 6.60 (d, J=2.0 Hz, 1H), 6.31 (brs, 2H), 6.26-6.13 (m, 2H), 5.85 (d, J=16.0 Hz, 1H), 5.77-5.76 (m, 4H), 5.44-5.34 (m, 4H), 4.87-4.59 (m, 10H), 4.48-4.43 (m, 2H), 4.33 (brs, 2H), 4.19 (d, J=15.3 Hz, 1H), 3.91 (d, J=15.3 Hz, 1H), 2.54-2.44 (m, 4H), 2.19-2.05 (m, 8H), 1.36-1.30 (m, 12H). HRMS (MALDI-TOF) m/z [M+H]$^+$ calcd for C$_{25}$H$_{31}$N$_2$O$_6$: 455.2182; found: 455.2195

403

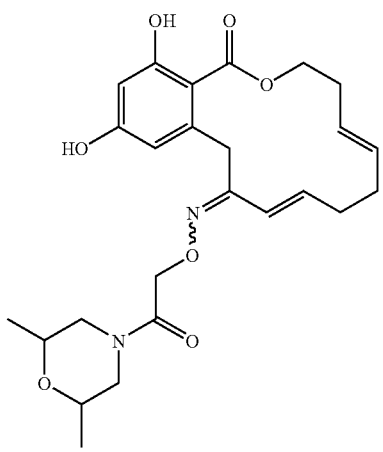

Mixture of isomers 1:1 in the oxime. $^1$H NMR (CDCl$_3$, 400 MHz) δ 11.66 (brs, 1H), 11.63 (brs, 1H), 6.93 (d, J=2.4 Hz, 1H), 6.57 (d, J=16.0 Hz, 1H), 6.52 (d, J=2.4 Hz, 1H), 6.32 (d, J=2.4 Hz, 1H), 6.31 (d, J=2.4 Hz, 1H), 6.29-6.12 (m, 2H), 5.84 (d, J=16.0 Hz, 1H), 5.38-5.32 (m, 4H), 4.91-4.71 (m, 4H), 4.59-4.49 (m, 4H), 4.37-4.26 (m, 4H), 4.13-3.97 (m, 4H), 3.78-3.68 (m, 2H), 3.62-3.52 (m, 2H), 3.35-3.15 (m, 4H), 2.50 (brt, J=5.2 Hz, 4H), 2.18-2.08 (m, 8H), 1.24-1.18 (m, 12H). HRMS (MALDI-TOF) m/z [M+Na]$^+$ calcd for C$_{25}$H$_{32}$NaN$_2$O$_7$: 495.2107; found: 495.2067

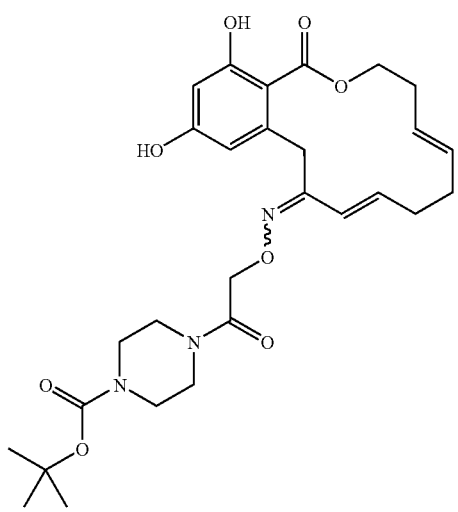

Mixture of isomers 1:1 in the oxime. $^1$H NMR (CDCl$_3$, 400 MHz) δ 11.65 (brs, 1H), 11.64 (brs, 1H), 6.92 (d, J=2.0 Hz, 1H), 6.57 (d, J=16.4 Hz, 1H), 6.52 (d, J=2.4 Hz, 1H), 6.32 (d, J=2.4 Hz, 1H), 6.31 (d, J=2.4 Hz, 1H), 6.28-6.13 (m, 2H), 5.84 (d, J=16 Hz, 1H), 5.38-5.31 (m, 4H), 4.86 (s, 2H), 4.77 (s, 2H), 4.56-4.52 (m, 4H), 4.34 (s, 2H), 4.07 (s, 2H), 3.61-3.45 (m, 16H), 2.54-2.46 (m, 4H), 2.16-2.05 (m, 8H), 1.47 (s, 18H). HRMS (MALDI-TOF) m/z [M+Na]$^+$ calcd for C$_{28}$H$_{37}$NaN$_3$O$_8$: 566.2478; found: 566.2459

404

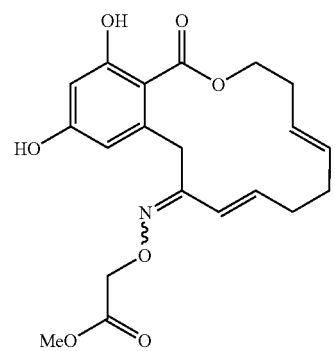

Mixture of isomers 1:1 in the oxime. $^1$H NMR (CDCl$_3$, 400 MHz) δ 11.70 (brs, 1H), 11.68 (brs, 1H), 6.84 (d, J=2.4 Hz, 1H), 6.61 (d, J=16.4 Hz, 1H), 6.53 (d, J=2.4 Hz, 1H), 6.34 (d, J=2.4 Hz, 1H), 6.32 (d, J=2.4 Hz, 1H), 6.28-6.13 (m, 2H), 5.86 (d, J=16.4 Hz, 1H), 5.38-5.33 (m, 4H), 4.75 (s, 2H), 4.68 (s, 2H), 4.57-4.54 (m, 4H), 4.36 (s, 2H), 4.08 (s, 2H), 3.79 (2s, 6H), 2.54-2.48 (m, 4H), 2.17-2.04 (m, 8H).

Mixture of isomers 1:1 in the oxime. $^1$H NMR (CDCl$_3$, 400 MHz) δ 6.94 (d, J=2.4 Hz, 1H), 6.52 (d, J=16.0 Hz, 1H), 6.34 (d, J=2.8 Hz, 1H), 6.32 (d, J=2.0 Hz, 1H), 6.29 (d, J=2.4 Hz, 1H), 6.25-6.12 (m, 2H), 5.86 (d, J=16.0 Hz, 1H), 5.38-5.32 (m, 4H), 4.85 (s, 2H), 4.71 (s, 2H), 4.57-4.52 (m, 4H), 4.35 (s, 2H), 4.14 (s, 2H), 3.73-3.58 (m, 8H), 3.02-2.87 (m, 8H), 2.54-2.48 (m, 4H), 2.14-2.09 (m, 8H). HRMS (MALDI-TOF) m/z [M+Na]$^+$ calcd for C$_{23}$H$_{29}$NaN$_3$O$_6$: 466.1954; found: 466.1938

Mixture of isomers 1:1 in the oxime. ¹H NMR (CDCl₃, 400 MHz) δ 11.94 (brs, 1H), 11.80 (brs, 1H), 6.80 (d, J=2.4 Hz, 2H), 6.35 (d, J=2.4 Hz, 2H), 5.45-5.09 (m, 6H), 4.93 (d, J=14.4 Hz, 2H), 4.82-4.68 (m, 2H), 4.76 (d, J=14.4 Hz, 2H), 4.28 (d, J=14.8 Hz, 2H), 4.06 (d, J=14.4 Hz, 2H), 3.63-3.33 (m, 8H), 2.34-1.96 (m, 10H), 1.70-1.55 (m, 12H), 1.45-1.29 (m, 10H), 1.75 (s, 3H), 1.25 (s, 3H), 0.94 (t, J=7.2 Hz, 6H). HRMS (MALDI-TOF) m/z [M+Na]⁺ calcd for $C_{28}H_{38}NaN_2O_6$: 521.2627; found: 521.2630

349

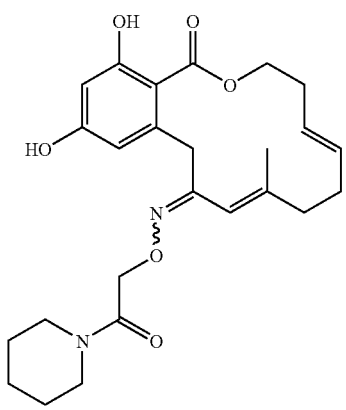

Mixture of isomers 1:1 in the oxime. ¹H NMR (CDCl₃, 400 MHz) δ 11.92 (brs, 1H), 11.84 (brs, 1H), 7.08-7.05 (m, 2H), 6.35-6.33 (m, 2H), 5.50-5.20 (m, 6H), 4.87 (s, 2H), 4.73 (s, 2H), 4.44-4.35 (m, 4H), 3.92 (s, 2H), 3.60-3.49 (m, 4H), 3.44-3.33 (m, 4H), 2.47-2.38 (m, 4H), 2.21-1.99 (m, 8H), 1.81-1.76 (m, 6H), 1.70-1.62 (m, 14H). HRMS (MALDI-TOF) m/z [M+H]⁺ calcd for $C_{25}H_{33}N_2O_6$: 457.2338; found: 457.2339

352

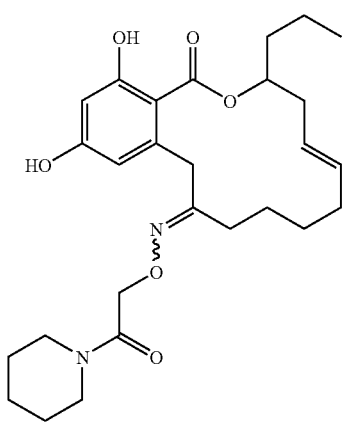

Mixture of isomers 1:1 in the oxime. ¹H NMR (CDCl₃, 400 MHz) δ 11.61 (brs, 1H), 11.57 (brs, 1H), 7.86 (brs, 1H), 7.64 (brs, 1H), 7.00 (d, J=2.4 Hz, 1H), 6.51 (d, J=2.4 Hz, 1H), 6.34 (brd, J=2.0 Hz, 2H), 5.46-5.32 (m, 4H), 5.28-5.22 (m, 2H), 4.90 (d, J=14.8 Hz, 1H), 4.83 (d, J=14.4 Hz, 1H), 4.72 (d, J=14.4 Hz, 1H), 4.71 (d, J=14.8 Hz, 1H), 4.35 (d, J=16.0 Hz, 1H), 4.25-4.17 (m, 3H), 4.09 (d, J=15.2 Hz, 1H), 3.62-3.51 (m, 4H), 3.43-3.38 (m, 4H), 2.67-2.61 (m, 2H), 2.35-2.28 (m, 2H), 2.06-1.95 (m, 4H), 1.90-1.78 (m, 6H), 1.68-1.58 (m, 14H), 1.44-1.31 (m, 11H), 0.94 (m, 6H). HRMS (MALDI-TOF) m/z [M+H]⁺ calcd for $C_{27}H_{39}N_2O_6$: 487.2808; found: 487.2806

457

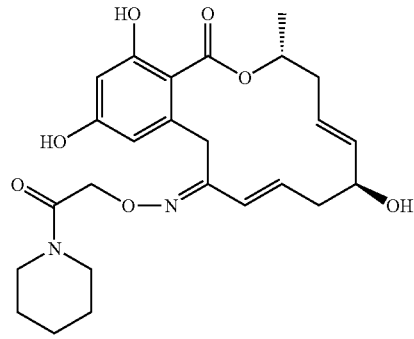

¹H (E-isomer, MeOD, 400 MHz, 25° C.) δ 6.26 (d, J=2.4 Hz, 1H); 6.24 (d, J=2.4 Hz, 1H); 6.05 (d, J=16.4 Hz, 1H); 5.86-5.93 (m, 1H); 5.60-5.67 (m, 1H); 5.44-5.50 (dt, 1H); 5.20-5.31 (m, 1H); 4.88 (dd, 2H); 4.44 (d, 1H); 3.95-4.01 (m, 1H); 3.53-3.67 (m, 4H); 3.45 (d, 1H); 2.58 (dd, 1H); 2.40-2.48 (m, 2H); 2.20 (dd, 1H); 1.64-1.76 (m, 6H); 1.48 (d, 3H). ¹³C (MeOD, 100 MHz, 25° C.) δ 170.4, 169.6, 169.3 (×2), 161.6 (×2), 159.5, 159.4, 156.7, 140.7, 139.8, 139.4, 136.9, 136.8, 135.8, 129.4, 129.3, 127.8, 121.1, 108.3, 108.1, 102.2, 102.1, 93.4, 73.8, 73.7, 72.8, 72.7, 72.6, 72.4, 72.3, 47.3, 47.2, 47.0, 44.6, 44.2, 44.1, 41.5, 41.0, 40.4, 40.1, 35.8, 29.7, 27.4, 27.3, 26.7, 26.6, 25.4, 24.4, 20.4, 20.2

476

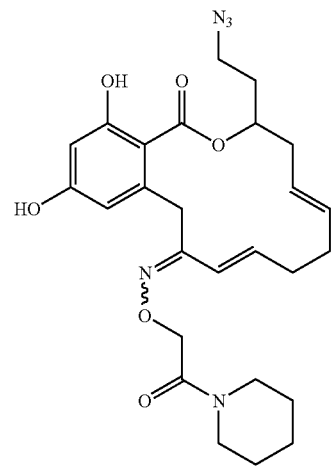

HRMS (MALDI-TOF) m/z [M+H]⁺ calcd for $C_{26}H_{34}N_5O_6$: 512.2431; found: 512.2406

Example 6a

Derivitization of Hydroxy-Substituted Macrocycles

The preparation of compounds of the invention that contain hydroxy substituents on the macrocycle may be prepared from Weinreb amides substituted with a protected hydroxy group or by oxidation of the final macrocycle, as depicted in Scheme 9a above. Macrocycles containing hydroxy substituents may be derivatized by reagents that are reactive to hydroxy groups to produce macrocycles substituted with varying groups on the macrocyclic ring. The use of orthogonal protecting groups on Weinreb amide precursors allows the selective liberation and reaction of macrocycle hydroxy groups.

In one non-limiting embodiment of the invention, macrocycles containing hydroxy substituents may be alkylated with electrophiles to produce macrocycles substituted with varying groups on the macrocyclic ring.

Deprotection of Hydroxy Group

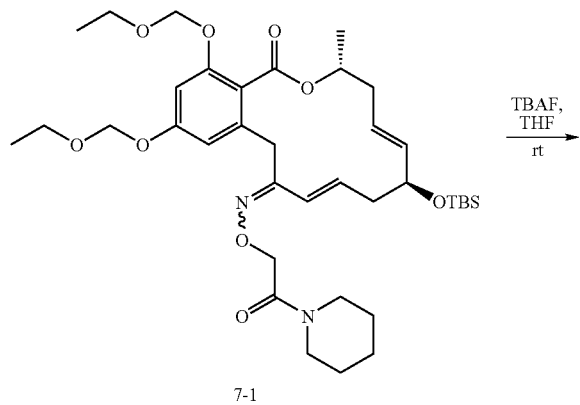

7-1

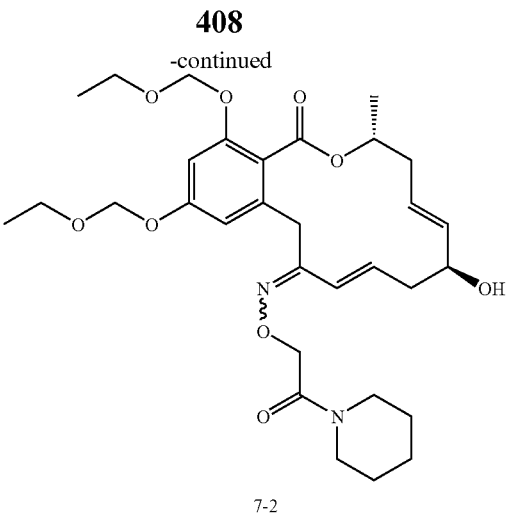

7-2

A solution of the totally protected compound (140 mg, 0.2 mmol) in THF (3 mL) was treated with the solution of TBAF in THF (0.3 mL, 1M in THF, 1.5 equiv.) at 0° C. The reaction was allowed to warm to 23° C. and for another 3 hrs. The reaction was extracted from sat. $NH_4Cl$ solution with ethyl acetate (10 mL×3), washed by brine (15 mL), dried over anhydrous $Na_2SO_4$, and concentrated. Flash chromatography column (EA as eluent) gave desired compound (104 mg) in the yield of 88%.

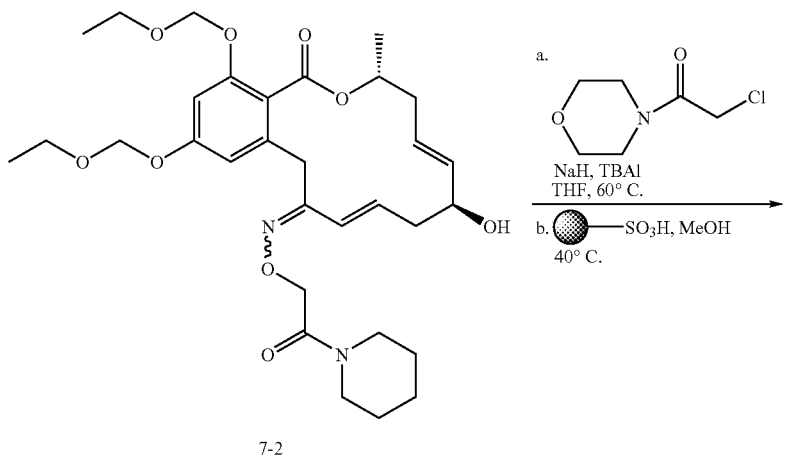

7-2

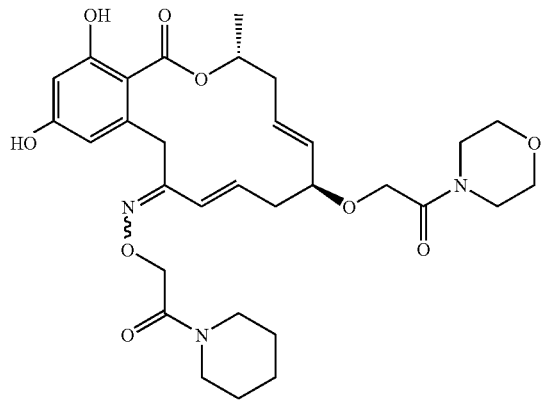

457/458

Reaction with α-Halo Carbonyl Groups

To a solution of the free alcohol (50 mg, 0.085 mmol) in THF (0.6 mL) at 0° C. under nitrogen atmosphere, NaH (20 mg, 0.5 mmol, 5.8 equiv.) was added and the reaction kept stirring for another half hour. Then Bu$_4$NI (10 mg, 0.027 mmol, 0.3 equiv) and chloride (79 mg, 0.51 mmol, 6.0 equiv.) was added sequentially at the same temperature. The reaction was warmed up slowly, heated to 60° C. overnight. The mixture was extracted from sat. NH$_4$Cl and ethyl acetate, and the organic phases were combined, washed by brine, dried over anhydrous Na$_2$SO$_4$, and concentrated. Flash chromatography (PE/EA, 1/2, EA, then EA/MeOH, 20:1) afforded the desired compound (36 mg). The solution of the compound previously obtained (36 mg, 0.05 mmol) in MeOH (5 mL) was treated with sulfonic acid resin (83 mg, 3 mmol/g, 5.0 equiv.) at 40° C. After stirring for 2 hours, the reaction was diluted with CH$_2$Cl$_2$ (5 mL), filtered, rinsed with MeOH and CH$_2$Cl$_2$. The filtrate was concentrated and underwent reverse phase column (CH$_3$CN/H$_2$O, 10%, 20%, 30%) to give the desired compound (19 mg). HRMS (MALDI-TOF) m/z [M+H]$^+$ calcd for C$_{31}$H$_{41}$N$_3$O$_9$: 600.2921; found: 600.2919.

Reaction with Alkyl Halides and Formation of Azido-Substituted Macrocycles

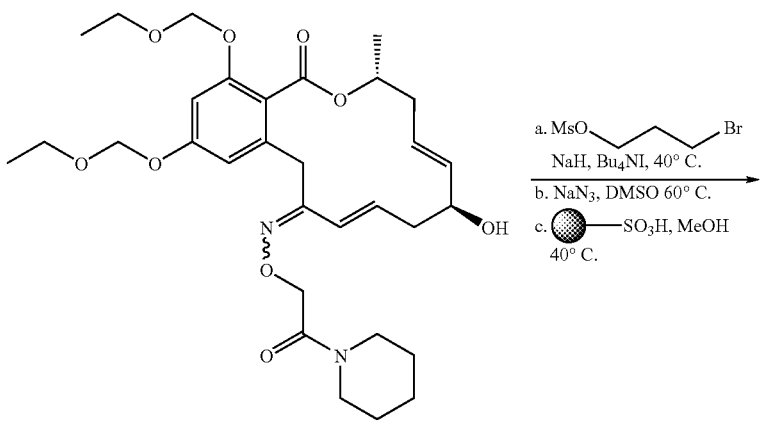

7-2

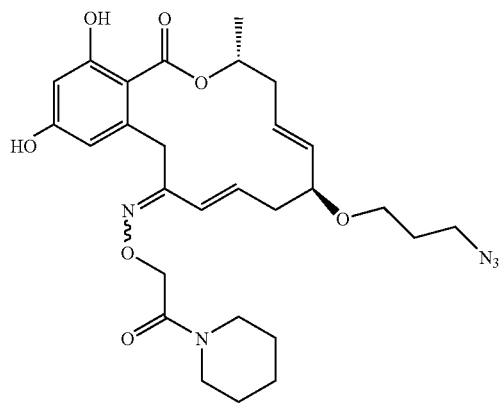

459/460

To the solution of the free alcohol (20 mg, 0.034 mmol) in THF (0.5 mL) at 0° C. under nitrogen atmosphere, NaH (9.8 mg, 0.24 mmol, 7.2 equiv.) was added and the reaction kept stirring for another half hour. Then Bu$_4$NI (13 mg, 0.038 mmol, 1.1 equiv) and bromide (35 mg, 0.16 mmol, 4.7 equiv.) was added sequentially at the same temperature. The reaction was warmed up slowly and then heated to 23° C. for 4 hrs. The mixture was extracted from sat. NH$_4$Cl and ethyl acetate, and the organic phases were combined, washed by brine, dried over anhydrous Na$_2$SO$_4$, and concentrated. The residue obtained was submitted to the next step without further purification. To a solution of the crude mixture obtained previously in DMSO (0.8 mL) was added NaN$_3$ (35 mg) at 60° C. and stirred for 2 hrs. The reaction was extracted from sat. NH$_4$Cl and ethyl acetate and the organic phases were combined, washed by brine, dried over anhydrous Na$_2$SO$_4$, and concentrated. The residue underwent flash chromatography (PE/EA, 1/1) to give the desired compound (4 mg). The solution of this compound (4 mg, 0.006 mmol) in MeOH (1 mL) was treated with sulfonic acid resin (20 mg, 3 mmol/g, 10.0 equiv.) at 40° C. After stirring for 4 hours, the reaction was diluted with CH$_2$Cl$_2$ (2 mL), filtered, rinsed with MeOH and CH$_2$Cl$_2$. The filtrate was concentrated and preparative TLC (Hex/EA, 1/2) gave the desired compound (point 1, 4.5 mg, point 2, 1.3 mg). HRMS (MALDI-TOF) m/z [M+H]$^+$ calcd for C$_{28}$H$_{38}$N$_5$O$_7$: 556.2771; found: 556.2745.

Amino-Substituted Macrocycles and Derivatives

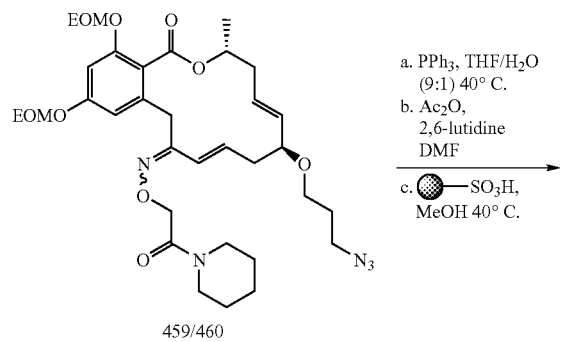

459/460

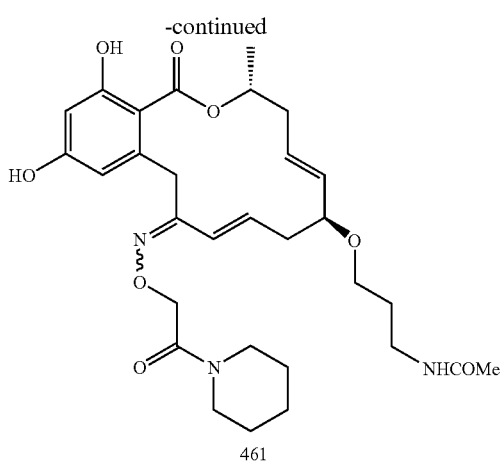

461

To the solution of the azide (30 mg, 0.044) in THF/H$_2$O (0.9/0.1 mL) was added triphenyl phosphine (23 mg, 0.088 mmol, 2 equiv.) at 40° C. and the reaction was stirred for 1d. After evaporation to get rid of the solvent, the residue underwent flash chromatography (PE/EA, 1/1 then MeOH/NEt$_3$, 20/1) to afford the desired amine. To a solution of the amine (8 mg, 0.012 mmol) in DMF (2 mL) was added 2,6-lutidine (5 drops) and Ac$_2$O sequentially at 0° C. under nitrogen atmosphere and the reaction was warmed up to 23° C. and kept stirring for 1 hour. The mixture was extracted from sat. NH$_4$Cl and ethyl acetate, and the organic phases were combined, washed by brine, dried over anhydrous Na$_2$SO$_4$, and concentrated. The residue obtained was submitted to the next step without further purification. The solution of the crude compound obtained in MeOH (1 mL) was treated with sulfonic acid resin (30 mg, 3 mmol/g) at 40° C. After stirring for 1 hour, the reaction was filtered, rinsed with MeOH and CH$_2$Cl$_2$. The filtrate was concentrated and preparative TLC (EA/MeOH, 10/1) gave the desired compound (1.9 mg). HRMS (MALDI-TOF) m/z [M+H]$^+$ calcd for C$_{30}$H$_{42}$N$_3$O$_8$: 572.2972; found: 572.2940.

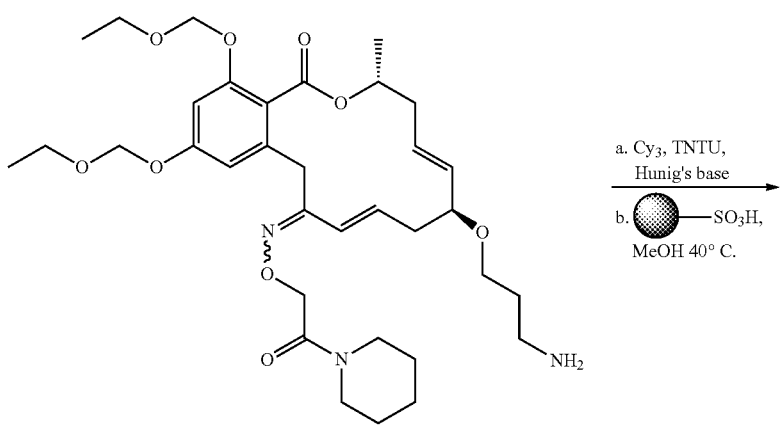

8-1

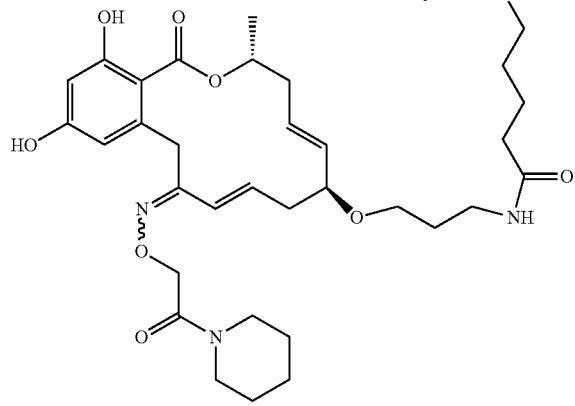

462

To the solution of the amine (11 mg, 0.017 mmol) in DMF (1 mL) was added TNTU (10 mg, 1.35 equiv.), Hunig's base (20 μL, 3.0 equiv.), and fluorophore (15 mg, 1.5 equiv.) sequentially at 0° C. under nitrogen atmosphere and the reaction was warmed up to 23° C. and kept stirring for 1 hour. The reaction was concentrated, and the residue underwent flash chromatography (PE/EA, 1/2, then $CH_2Cl_2$/MeOH, 10/1) to give the protected compound. The solution of the Cy3 labeled protected compound in MeOH (2 mL) was treated with sulfonic acid resin (30 mg, 3 mmol/g) at 40° C. After stirring for 2 hours, the reaction was filtered, rinsed with MeOH and DCM. The filtrate was concentrated and preparative TLC ($CH_2Cl_2$/MeOH, 10/1) gave the desired deprotected Cy3 labeled compound. MS (ES) m/z $[M]^+$ calcd for $C_{57}H_{72}N_5O_8$: 954.54; found: 954.53.

Example 7a

Alternate Synthesis of Hydroxy-Substituted Macrocycles

In addition to use of hydroxy-substituted Weinreb amides for the preparation of hydroxy substituted macrocycles, hydroxy groups may be introduced into the macrocycle by the mild allylic oxidation of the compounds, as depicted in Scheme 9a and described below.

To a solution of bis protected macrocycle (100 mg, 0.17 mmol) in EtOH (1 mL) was added selenium dioxide (56 mg, 0.51 mmol, 3.0 equiv.). The reaction underwent microwave reaction at 110° C. for 2 h. Then the mixture was filtered and the filtrate concentrated, flash chromatography (PE/EA, 1/1, 1/2, 1/4) gave the desired compound as a mixture of isomers (70 mg). To a solution of the previously obtained mixture (15 mg, 0.025 mmol) in DMF (1.5 mL) at 0° C. under nitrogen atmosphere, NaH (6 mg, 0.15 mmol, 9.0 equiv.) was added and the reaction kept stirring for another half hour. Then $Bu_4NI$ (10 mg, 0.027 mmol, 1.1 equiv) and allyl chloride (50 μL, 20 equiv.) was added sequentially at the same temperature. The reaction was warmed up to 23° C. and stirred for 1 hour. The mixture was extracted from sat. $NH_4Cl$ and ethyl acetate, and the organic phases were combined, washed by brine, dried over anhydrous $Na_2SO_4$, and concentrated. Flash chromatography (PE/EA, 3/1) afforded the desired compound (6 mg). A solution of the allylated alcohol (6 mg, 0.009 mmol) in MeOH (1 mL) was treated with sulfonic acid resin (20 mg, 3 mmol/g, 6.7 equiv.) at 40° C. After stirring for 2 hours, the reaction was diluted with $CH_2Cl_2$ (3 mL), filtered, rinsed with MeOH and $CH_2Cl_2$. The filtrate was concentrated and underwent preparative TLC (Hex/EA, 1/2) to give the desired compound.

Example 8a

Additional Azide Derivatives

The azide containing macrocycle may be modified to produce amino-substituted compounds and derivatives thereof, similarly to Example 6 above.

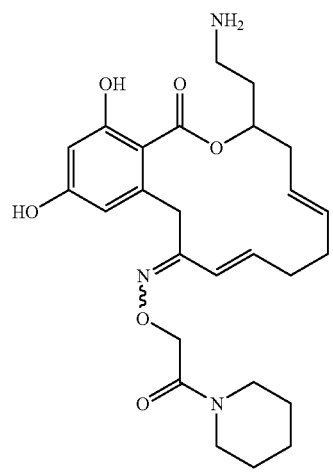

477

To a solution of the azide analog (280 mg, 0.424 mmol, 1 eq.) in THF/$H_2O$ (9/1) mixture (42 mL) was added $PPh_3$ (333.6 mg, 1.272 mmol, 3 eq.). The resulting mixture was stirred overnight at 40° C. Then, the solution was evaporated to dryness without any work-up. The crude was purified on silica chromatography (CH$_2$Cl$_2$/MeOH=20/1) to yield the corresponding amine as a white solid (232.6 mg, 0.366 mmol, 86%). HRMS (MALDI-TOF) m/z [M+H]$^+$ calcd for C$_{32}$H$_{47}$ClN$_3$O$_8$: 636.3052: found: 636.3071.

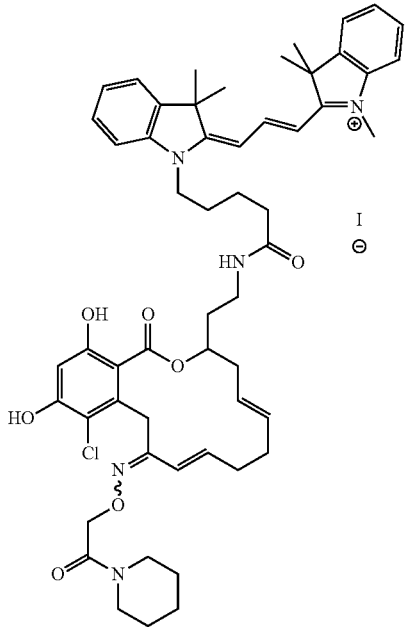

A solution of TNTU (8.52 mg, 23.3 μmol, 1.35 eq.), DIPEA (8.6 μL, 51.9 μmol, 3 eq.) and Cy3 (14.8 mg, 25.9 μmol, 1.5 eq.) in dry NMP (0.3 mL) was shaken 45 min at room temperature. Then, the pre-activated acid was added to a solution of the previous amine (11 mg, 17.3 mmol, 1 eq.) in 0.3 mL of NMP. After 12 hours the reaction mixture was diluted with AcOEt, washed with water (2 mL), KOH 2N (3 mL), dried with Na$_2$SO$_4$, and evaporated to dryness. The crude was purified on silica chromatography (CH$_2$Cl$_2$/MeOH=8/1) to yield the corresponding Cy3 labeled compound as a pink solid (20 mg, quantitative). MS (ES) m/z [M]$^+$ calcd for C$_{61}$H$_{79}$ClN$_5$O$_9$: 1061.56; found: 1061.25.

The description and examples provided herein are merely illustrative, and the invention is not so limited. Numerous variations, permutations and derivatives of these compounds, procedures and uses will occur to those of ordinary skill in the art, and are contemplated within the scope of the invention.

We claim:

1. A method of inhibiting or reducing the growth or number of NF2-deficient tumor cells or NF1-deficient tumor cells comprising contacting said NF2-deficient tumor cells or NF1-deficient tumor cells with at least one compound of formula I or I', or a tautomer thereof, a pharmaceutically acceptable salt, solvate, ester or prodrug thereof:

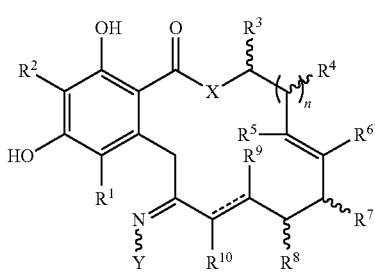

I, I' wherein:

X is O, S or NR;

Y is —OR, —O—(CH$_2$)$_m$COOR, —O—(CH$_2$)$_m$CON(R)$_2$, —N(R)$_2$, —N(R)SOR or —N(R)SO$_2$R, wherein the groups bound to the nitrogen atom may be in Z- or E-configuration;

R$^1$ and R$^2$ are independently hydrogen, halogen, OR, N(R)$_2$, SR, azido, nitro, cyano, aliphatic, aryl, alkylaryl, arylalkyl, heterocyclyl, heteroaryl, —S(O)R, —S(O)$_2$R, —SO$_2$N(R)$_2$, —N(R)SO$_2$R, —N(CO)R, —N(CO)N(R)$_2$, —N(CO)OR, —O(CO)R, —(CO)R, —(CO)OR, —(CO)N(R)$_2$, —O(CO)OR, or —O(CO)N(R)$_2$;

R$^3$, R$^4$, R$^5$, R$^6$, R$^7$, R$^8$, R$^9$ and R$^{10}$ are independently hydrogen, halogen, azido, nitro, cyano, aliphatic, alkylaryl, aralkyl, aryl, heteroalkyl, alkylheteroaryl, heterocyclyl, heteroaryl, OR, N(R)$_2$, SR, —O(CH$_2$)$_m$N(R)C(O)(CH$_2$)$_p$R, —O(CH$_2$)$_m$C(O)(CH$_2$)$_p$R, —O(CH$_2$)$_m$C(O)(CH$_2$)$_p$N(R)$_2$, —O(CH$_2$)$_m$C(O)(CH$_2$)$_p$OR, —O(CH$_2$)$_m$N(R)C(O)(CH$_2$)$_p$OR, —O(CH$_2$)$_m$N(R)C(O)(CH$_2$)$_p$N(R)$_2$, —O(CH$_2$)$_m$OC(O)(CH$_2$)$_p$OR, —O(CH$_2$)$_m$OC(O)(CH$_2$)$_p$N(R)$_2$, —NR(CH$_2$)$_m$N(R)C(O)(CH$_2$)$_p$R, —NR(CH$_2$)$_m$OC(O)(CH$_2$)$_p$R, —NR(CH$_2$)$_m$C(O)(CH$_2$)$_p$N(R)$_2$, —NR(CH$_2$)$_m$C(O)(CH$_2$)$_p$OR, —NR(CH$_2$)$_m$N(R)C(O)(CH$_2$)$_p$OR, —NR(CH$_2$)$_m$N(R)C(O)(CH$_2$)$_p$N(R)$_2$, —NR(CH$_2$)$_m$OC(O)(CH$_2$)$_p$OR, —NR(CH$_2$)$_m$OC(O)(CH$_2$)$_p$N(R)$_2$, —(CH$_2$)$_m$N(R)C(O)(CH$_2$)$_p$R, —(CH$_2$)$_m$OC(O)(CH$_2$)$_p$R, —(CH$_2$)$_m$C(O)(CH$_2$)$_p$N(R)$_2$, —(CH$_2$)$_m$C(O)(CH$_2$)$_p$OR, —(CH$_2$)$_m$N(R)C(O)(CH$_2$)$_p$OR, —(CH$_2$)$_m$N(R)C(O)(CH$_2$)$_p$N(R)$_2$, —(CH$_2$)$_m$OC(O)(CH$_2$)$_p$OR, —(CH$_2$)$_m$OC(O)(CH$_2$)$_p$N(R)$_2$, —(CH$_2$)$_m$N$_3$, —O(CH$_2$)$_m$N$_3$—(CH$_2$)$_m$N(R)$_2$, —(CH$_2$)$_m$OR, —(CH$_2$)$_m$S(O)(CH$_2$)$_p$R, —(CH$_2$)$_m$S(O)$_2$(CH$_2$)$_p$R, —(CH$_2$)$_m$SO$_2$(CH$_2$)$_p$N(R)$_2$, or (CH$_2$)$_m$N(R)SO$_2$(CH$_2$)$_p$R; and each R is independently R$^{11}$, hydrogen, aliphatic, amino, azido, cyano, nitro, alkylamino, dialkylamino, OH, alkoxy, carbonylamino, aminocarbonyl, alkoxycarbonyl, carbonyloxy, carboxy, acyl, aryl, alkaryl, arylalkyl including benzyl, heteroalkyl, heteroaryl, heterocyclyl, or a protecting group; or two R on the same nitrogen are taken together with the nitrogen to form a 5-8 membered heterocyclic or heteroaryl ring; wherein where a group contains more than one R substituent; wherein R is optionally substituted, and each R can be the same or different;

R$^{11}$ is the group:

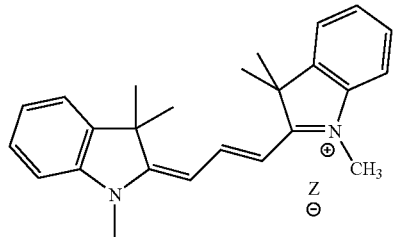

where Z is an inorganic or organic counterion;

n is 0, 1 or 2;

m and p are independently 0, 1, 2, 3, 4 or 5; and the dashed lines indicate either a single or a double bond, where the valence requirements are fulfilled by additional hydrogen atoms; and wherein in formula I', when n is 1, and X is O and a double bond is present between the carbon atoms bearing R$^9$ and R$^{10}$, then at least one of R$^5$, R$^6$, R$^7$, R$^8$, R$^9$ or R$^{10}$ is not hydrogen; and wherein in formula I', when n is 1 and X is O and the bond between the carbon atoms bearing $R^9$ and $R^{10}$ is a single bond, then at least one of $R^5$, $R^6$, $R^7$ or $R^8$ is not hydrogen.

2. The method of claim 1, wherein X is O or NR; and Y is —OR, —O—$(CH_2)_m$COOR or —O—$(CH_2)_m$CON$(R)_2$.

3. The method of claim 1, wherein $R^1$ and $R^2$ are independently hydrogen or halogen.

4. The method of claim 1, wherein the compound has the formula II or II':

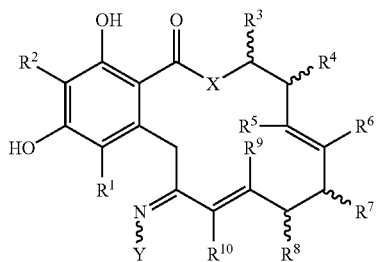

wherein in formula II', when X is O, then at least one of $R^5$, or $R^{10}$ is not hydrogen.

5. The method of claim 1, wherein the compound has the formula III or III':

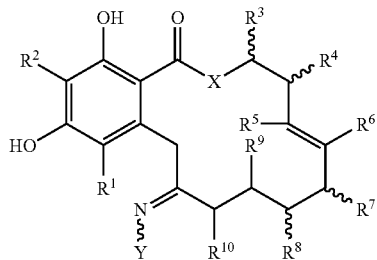

wherein in formula III', at least one of $R^5$, $R^6$, $R^7$ or $R^8$ is not hydrogen.

6. The method of claim 1, wherein the compound has the formula IV:

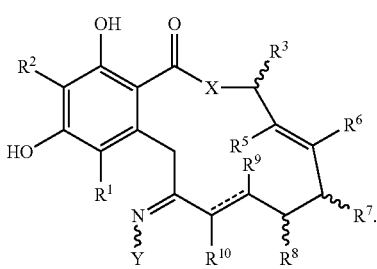

7. The method of claim 1, wherein the compound has the formula V:

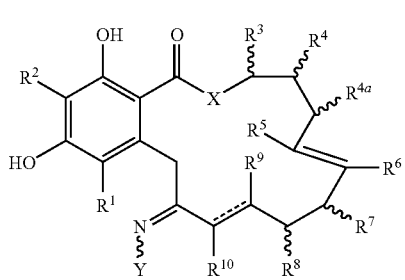

wherein $R^{4a}$ is halogen, azido, nitro, cyano, aliphatic, alkylaryl, aralkyl, aryl, heteroalkyl, alkylheteroaryl, heterocyclyl, heteroaryl, OR, N$(R)_2$, SR, —O$(CH_2)_m$N(R)C(O)$(CH_2)_p$R, —O$(CH_2)_m$OC(O)$(CH_2)_p$R, —O$(CH_2)_m$C(O)$(CH_2)_p$N$(R)_2$, —O$(CH_2)_m$C(O)$(CH_2)_p$OR, —O$(CH_2)_m$N(R)C(O)$(CH_2)_p$OR, —O$(CH_2)_m$N(R)C(O)$(CH_2)_p$N$(R)_2$, —O$(CH_2)_m$OC(O)$(CH_2)_p$OR, —O$(CH_2)_m$OC(O)$(CH_2)_p$N$(R)_2$, —NR$(CH_2)_m$N(R)C(O)$(CH_2)_p$R, —NR$(CH_2)_m$OC(O)$(CH_2)_p$R, —NR$(CH_2)_m$C(O)$(CH_2)_p$N$(R)_2$, —NR$(CH_2)_m$C(O)$(CH_2)_p$OR, —NR$(CH_2)_m$N(R)C(O)$(CH_2)_p$OR, —NR$(CH_2)_m$N(R)C(O)$(CH_2)_p$N$(R)_2$, —NR$(CH_2)_m$OC(O)$(CH_2)_p$OR, —NR$(CH_2)_m$OC(O)$(CH_2)_p$N$(R)_2$, —$(CH_2)_m$N(R)C(O)$(CH_2)_p$R, —$(CH_2)_m$OC(O)$(CH_2)_p$R, —$(CH_2)_m$C(O)$(CH_2)_p$N$(R)_2$, —$(CH_2)_m$C(O)$(CH_2)_p$OR, —$(CH_2)_m$N(R)C(O)$(CH_2)_p$OR, —$(CH_2)_m$N(R)C(O)$(CH_2)_p$N$(R)_2$, —$(CH_2)_m$C(O)$(CH_2)_p$OR, —$(CH_2)_m$OC(O)$(CH_2)_p$N$(R)_2$, —$(CH_2)_m$N$_3$, —O$(CH_2)_m$N$_3$—$(CH_2)_m$N$(R)_2$, —$(CH_2)_m$OR, —$(CH_2)_m$S(O)$(CH_2)_p$R, —$(CH_2)_m$S(O)$_2$$(CH_2)_p$R, —$(CH_2)_m$SO$_2$$(CH_2)_p$N$(R)_2$, or —$(CH_2)_m$N(R)SO$_2$$(CH_2)_p$R.

8. A method of inhibiting or reducing the growth or number of NF2-deficient tumor cells or NF1-deficient tumor cells comprising contacting said NF2-deficient tumor cells or NF1-deficient tumor cells with at least one compound, or a tautomer thereof, a pharmaceutically acceptable salt, solvate, ester or prodrug thereof, selected from

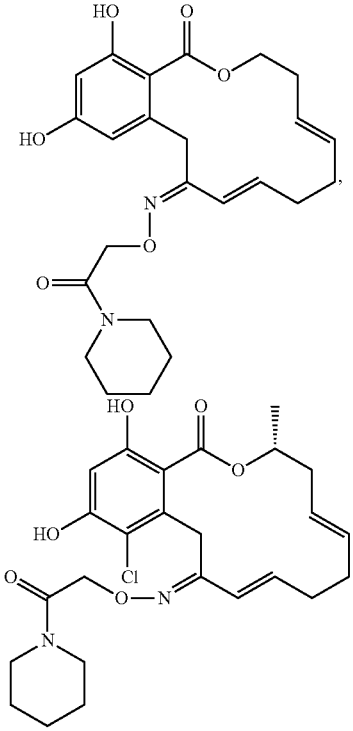

419
-continued
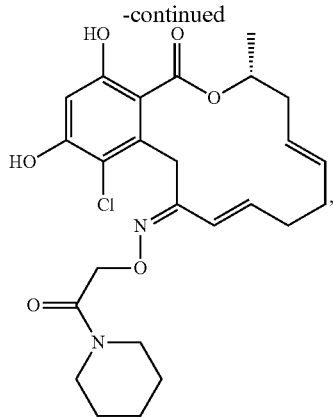,
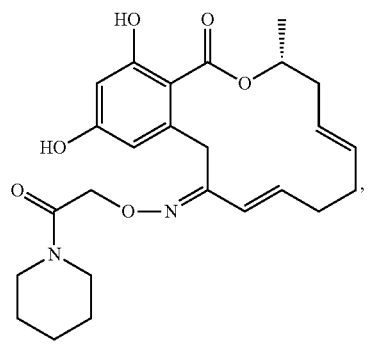,
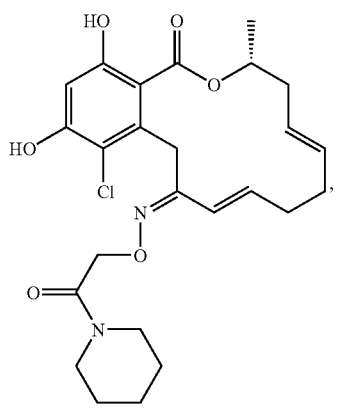,
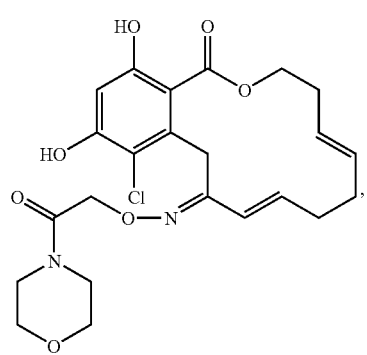,
420
-continued
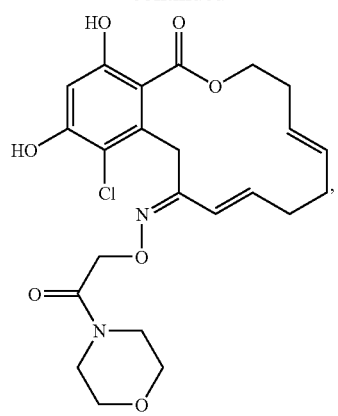,
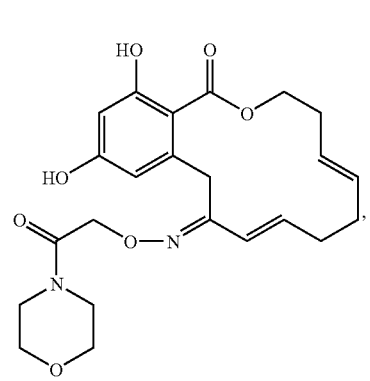,
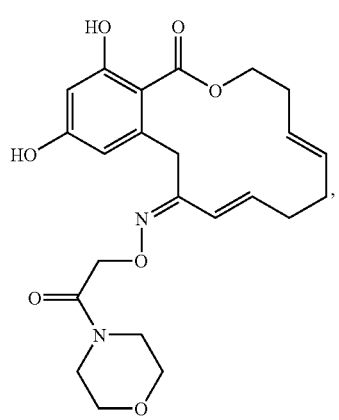,
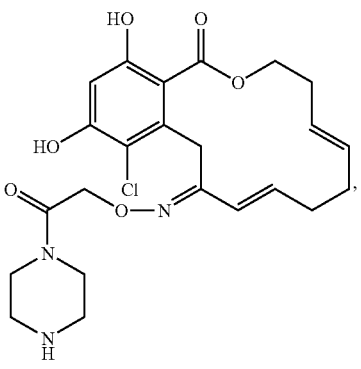, 421
-continued
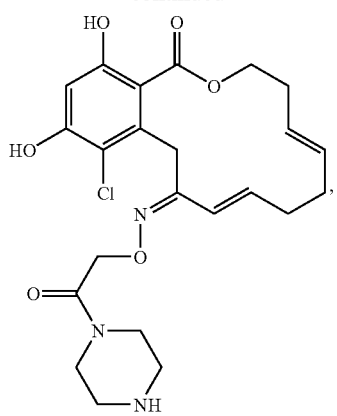
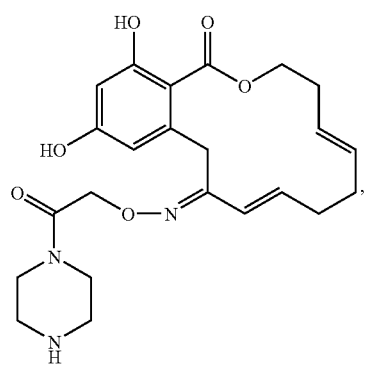
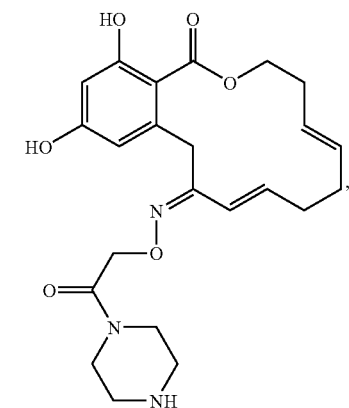
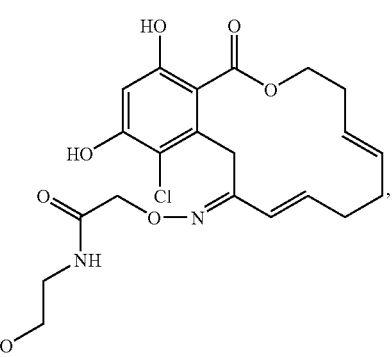
422
-continued
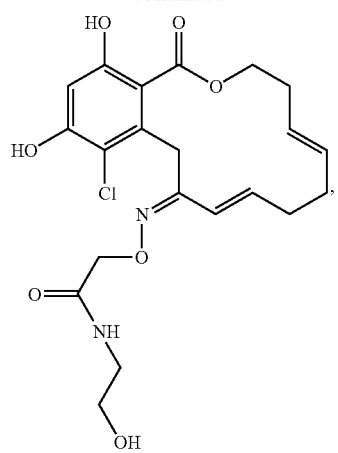
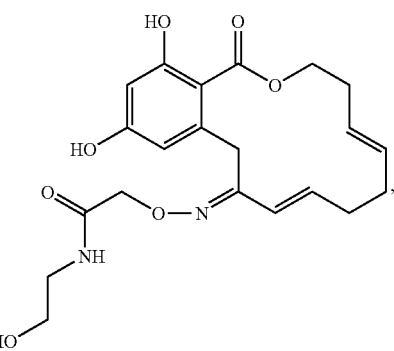
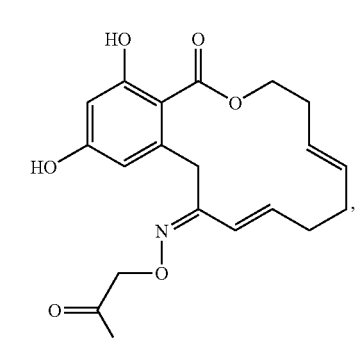
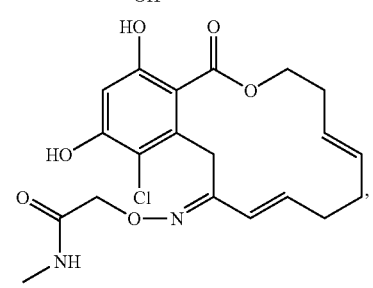

423
-continued
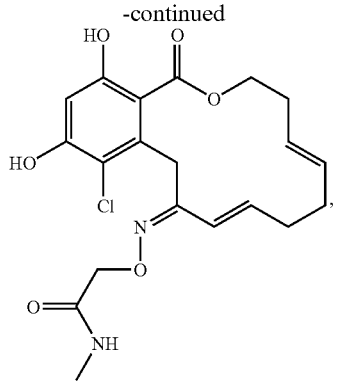
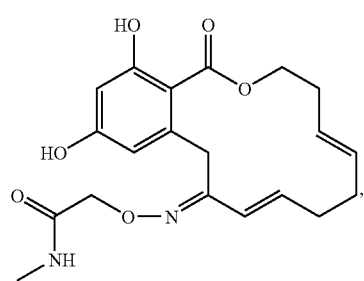
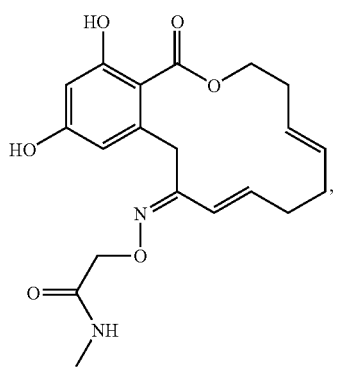
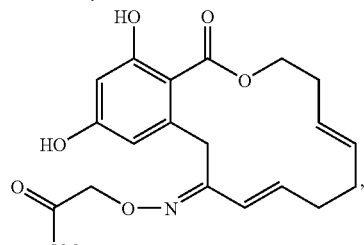
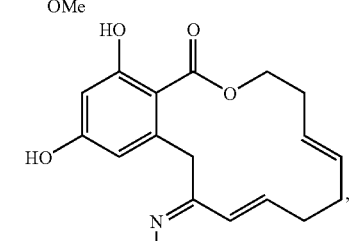
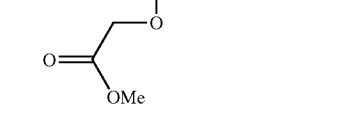
424
-continued
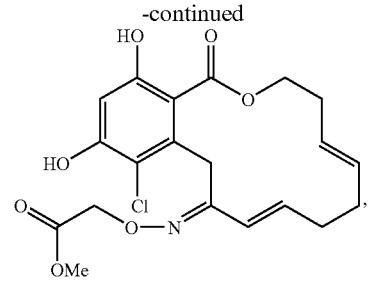
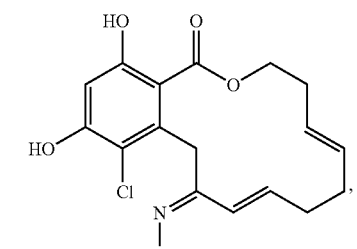
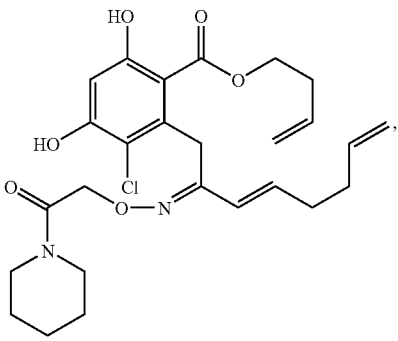
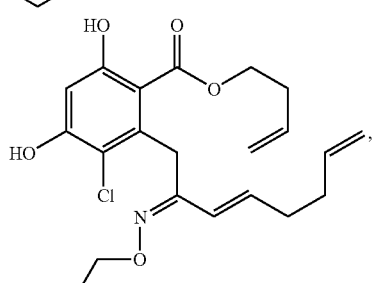
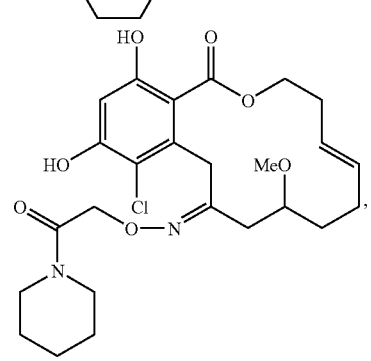

425
-continued
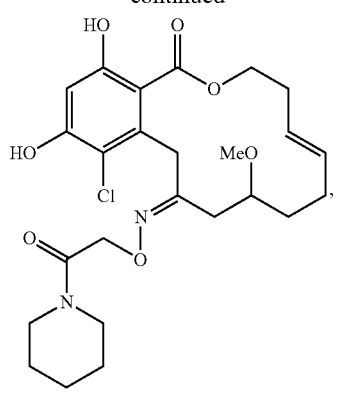
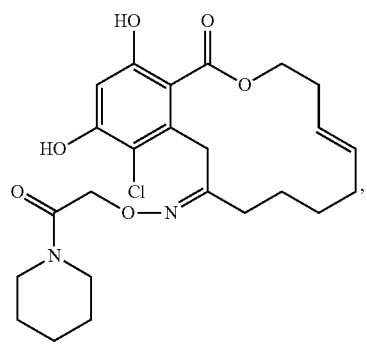
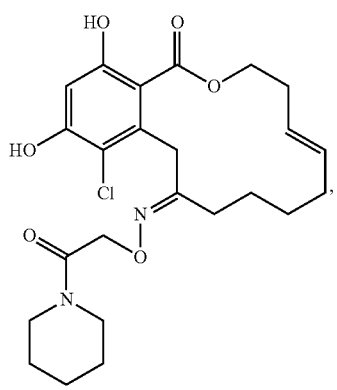
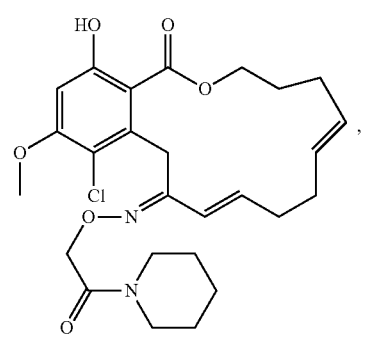
426
-continued
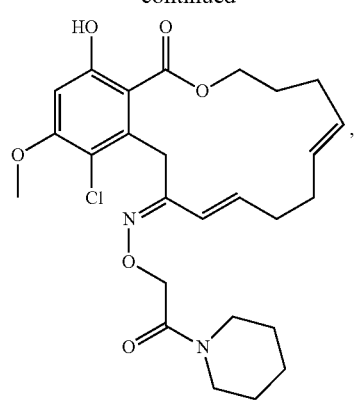
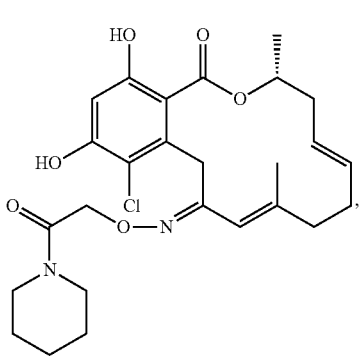
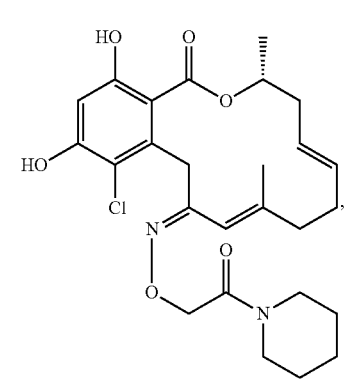
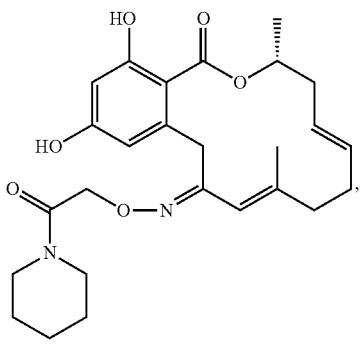

427
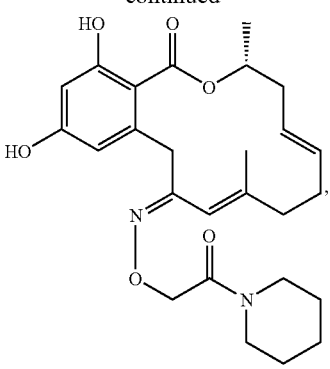
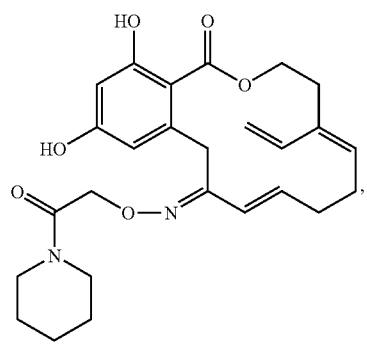
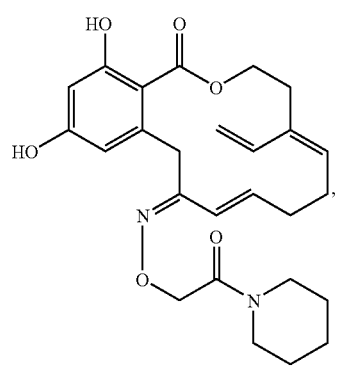
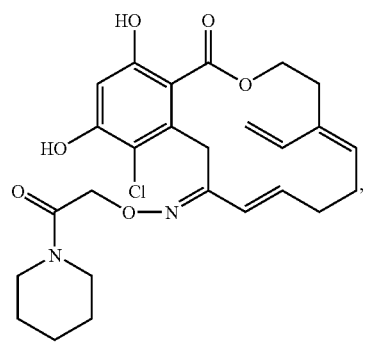
428
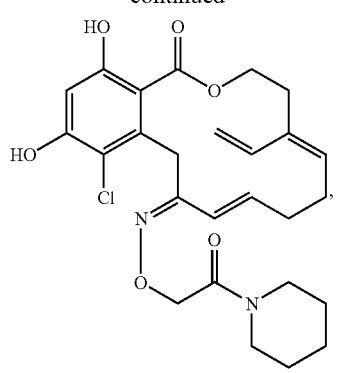
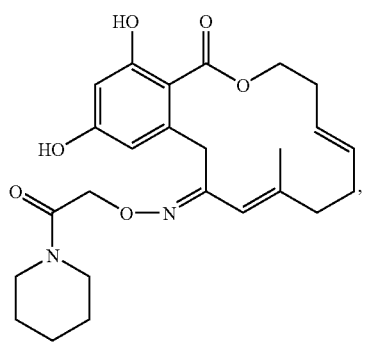
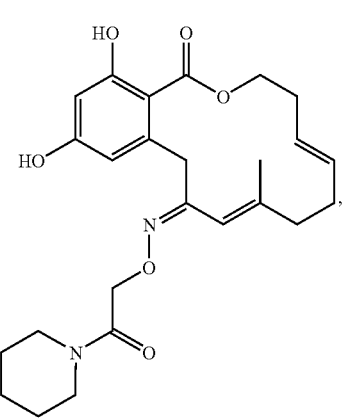
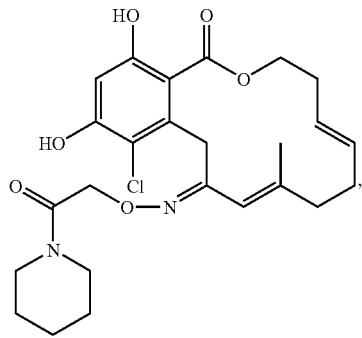

429
-continued
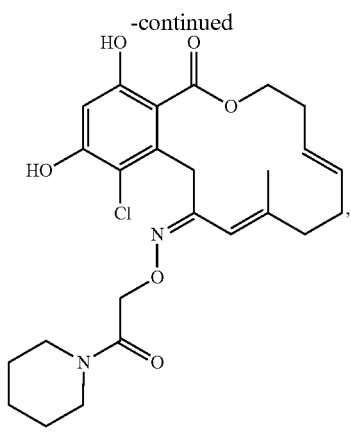
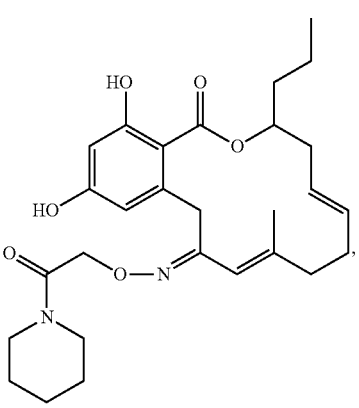
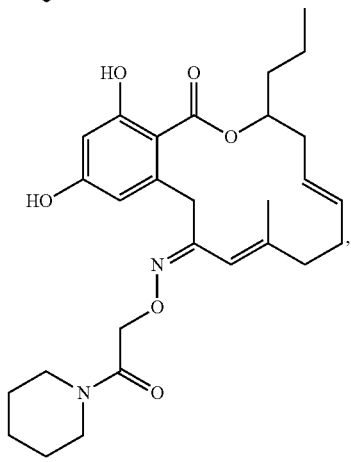
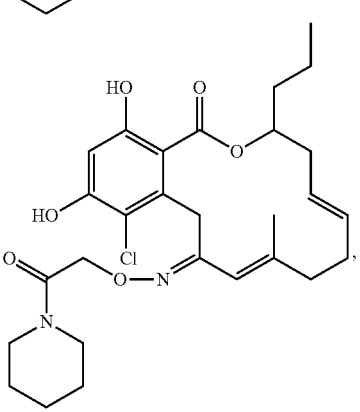
430
-continued
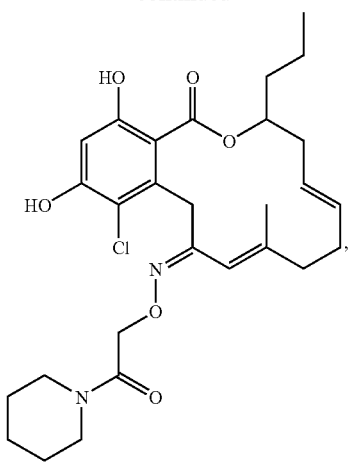
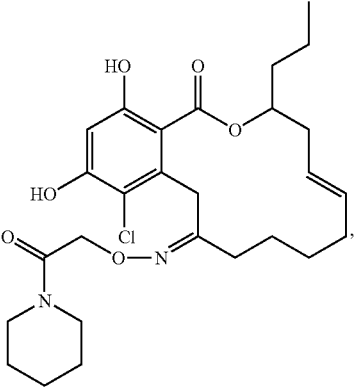
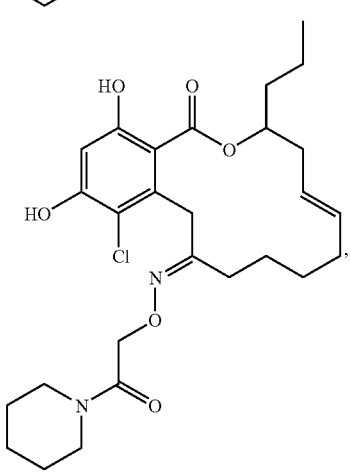
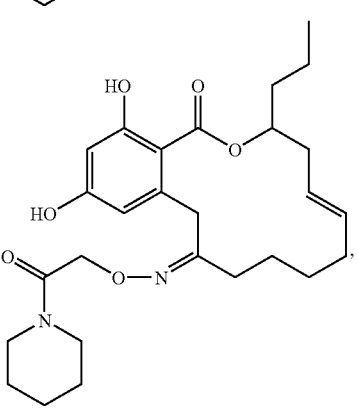

431
-continued
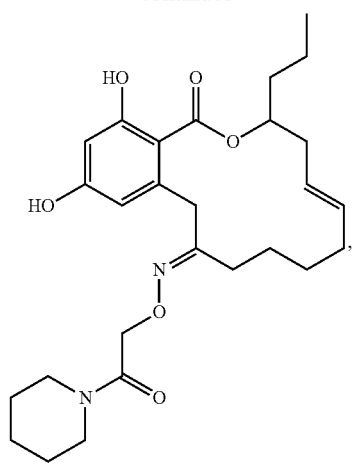
432
-continued
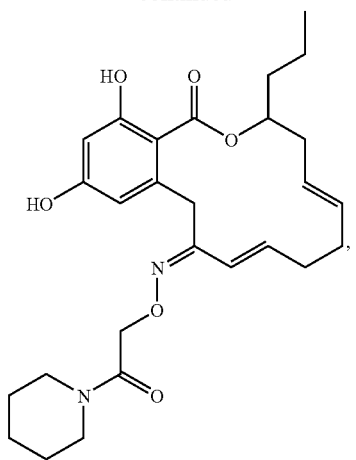

433
-continued
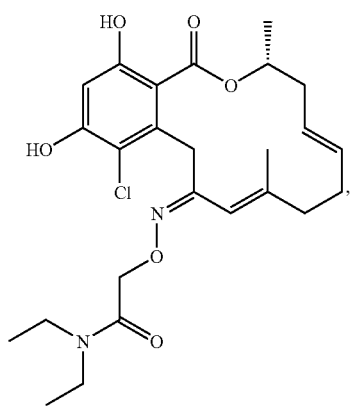
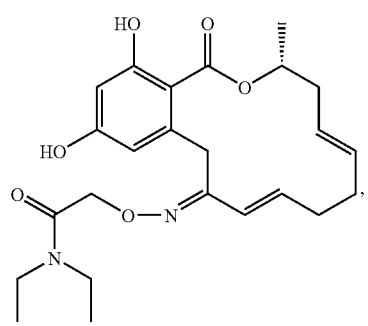
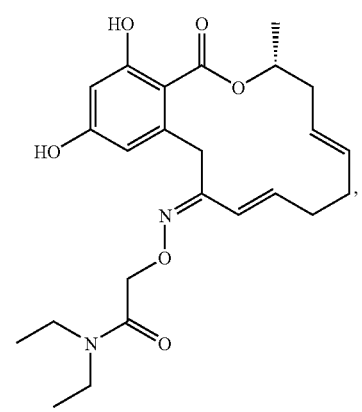
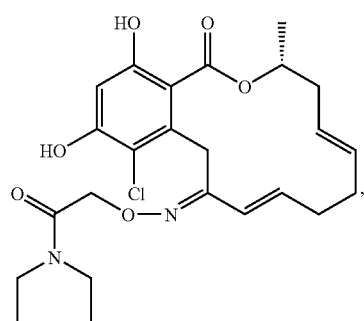
434
-continued
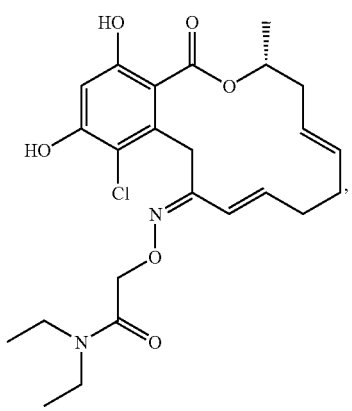
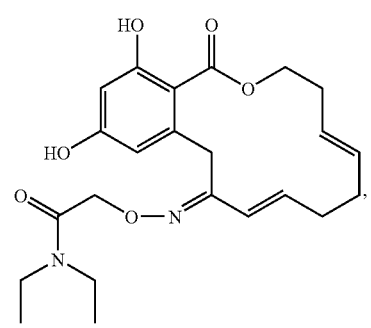
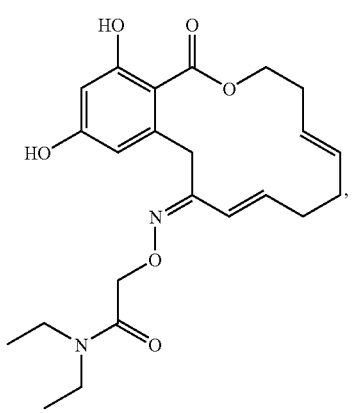
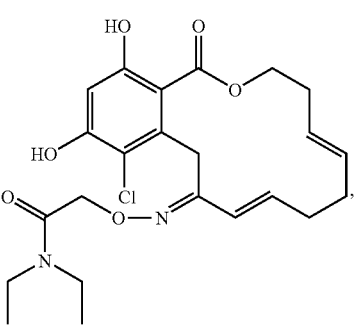

435
-continued
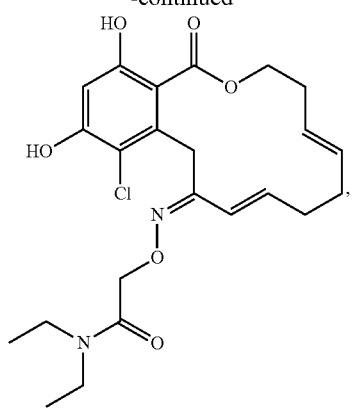
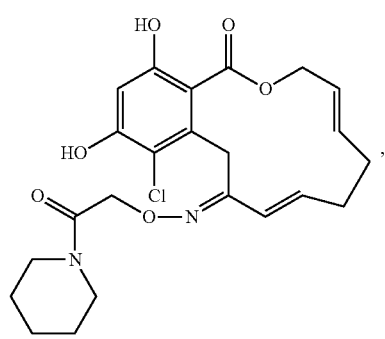
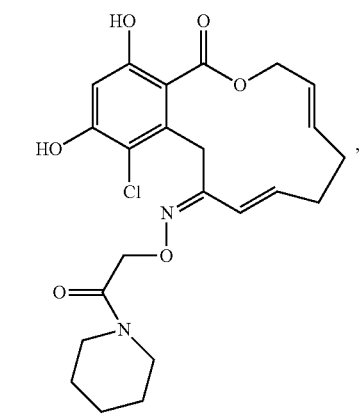
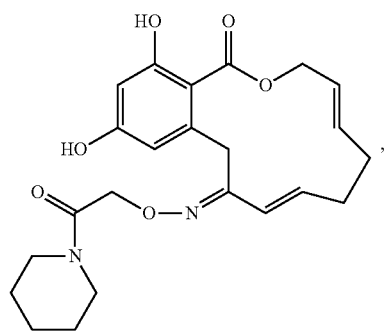
436
-continued
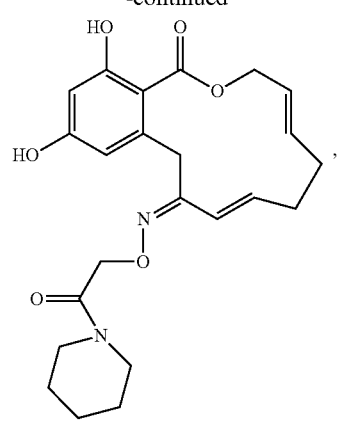
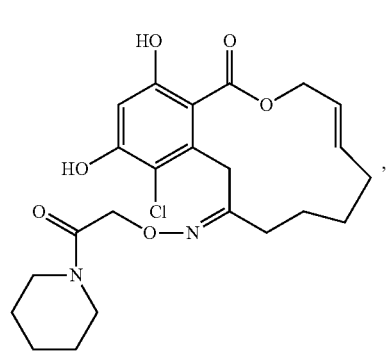
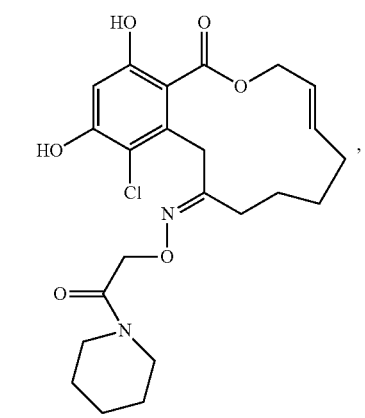
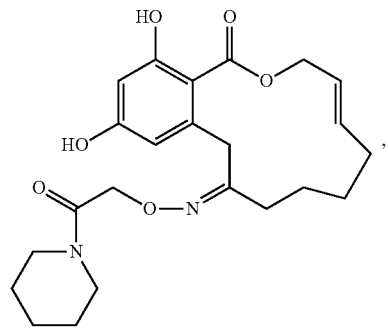

437
-continued
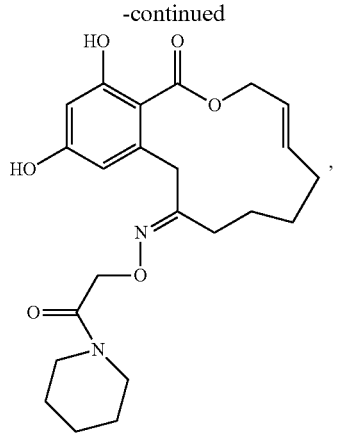
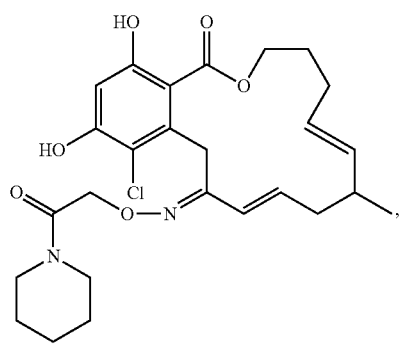
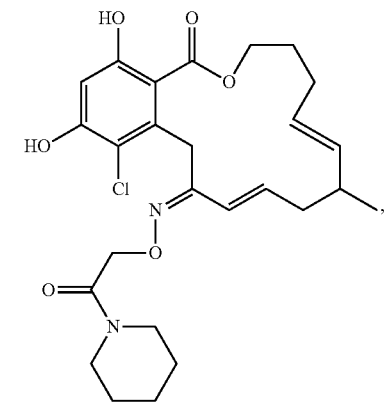
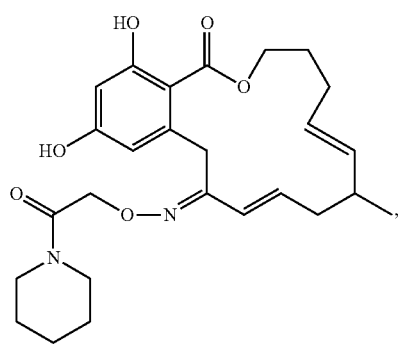
438
-continued
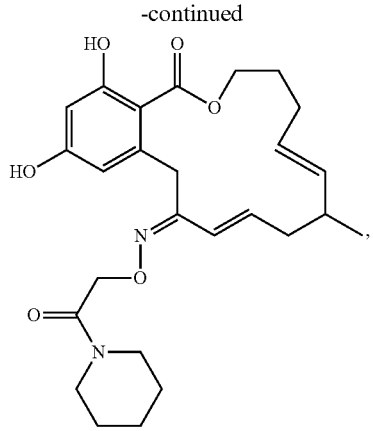
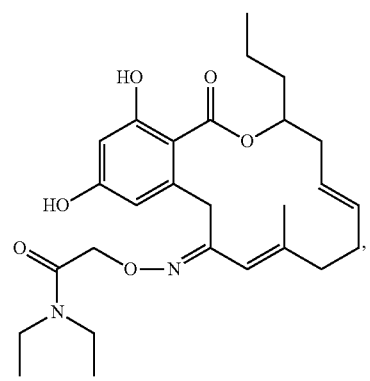
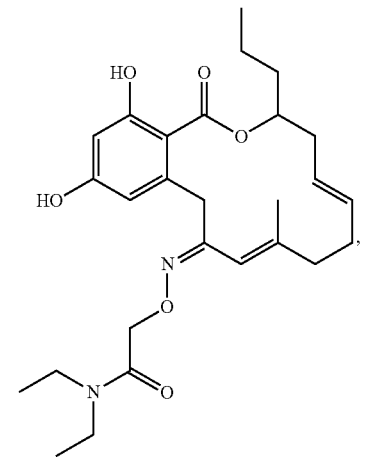
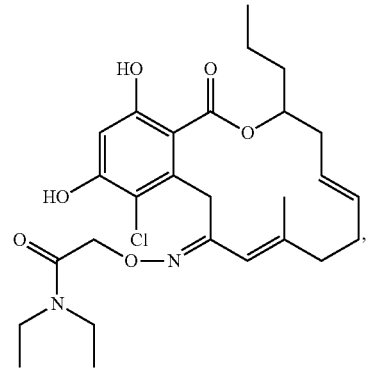

| 439 -continued | 440 -continued |
|---|---|
| 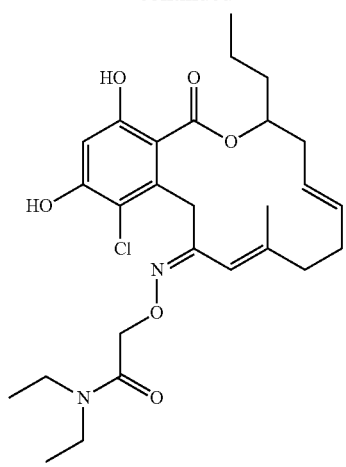 | 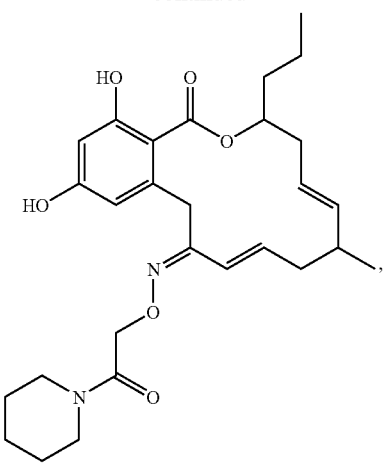 |
| 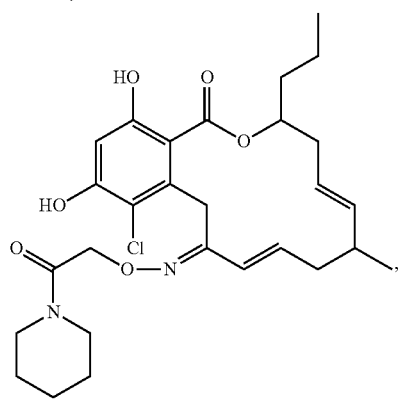 | 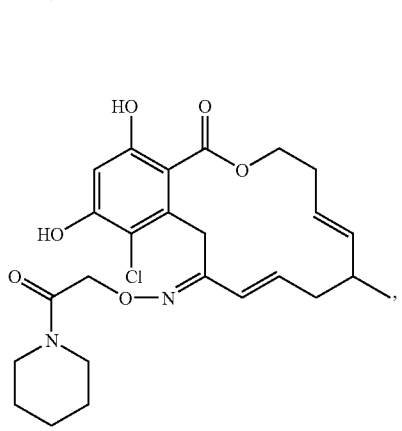 |
| 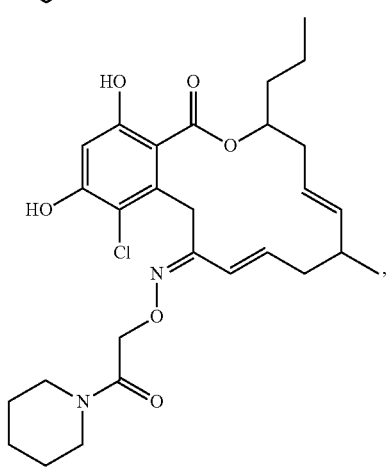 | 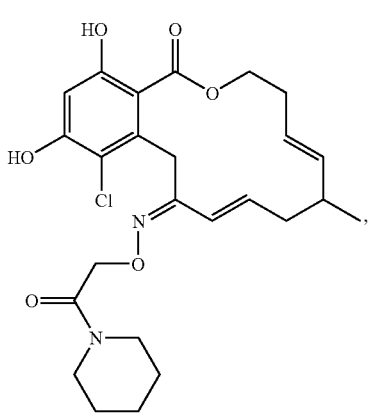 |
| 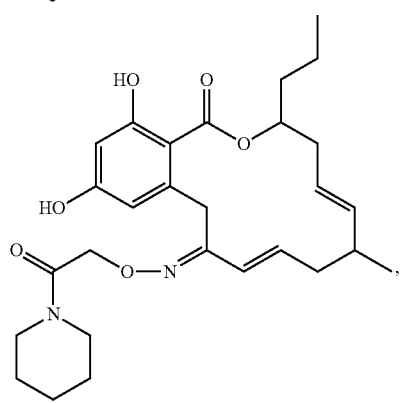 | 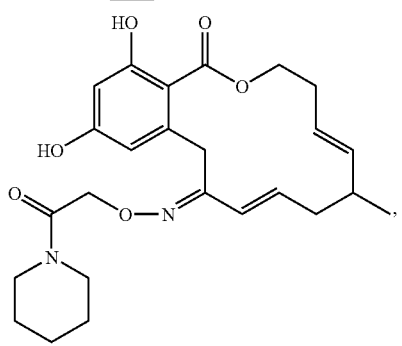 |

441
-continued
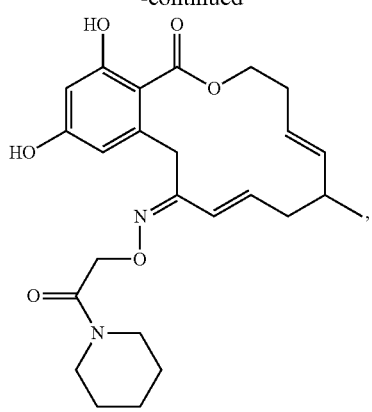
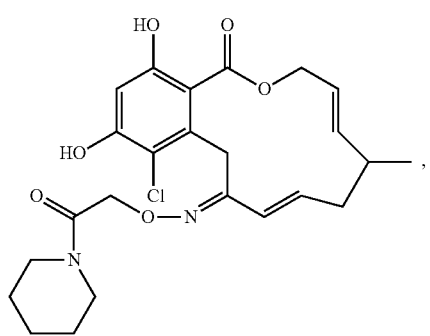
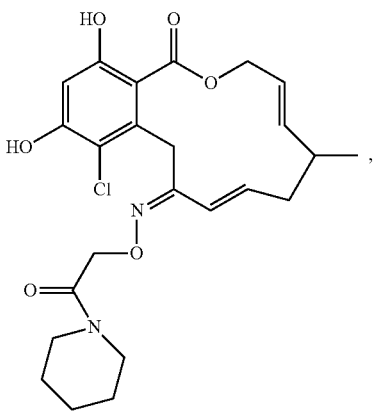
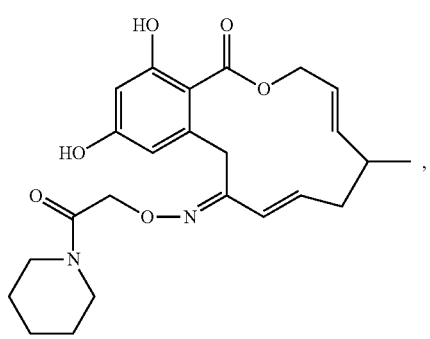
442
-continued
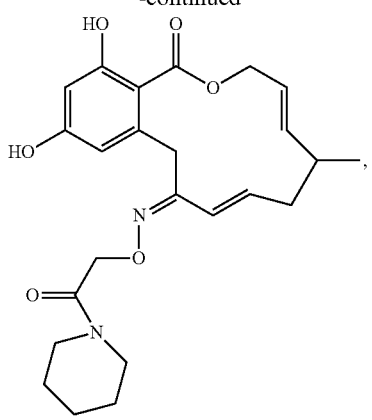
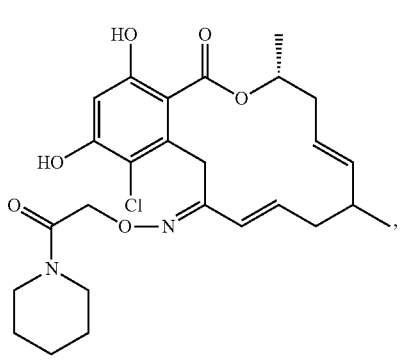
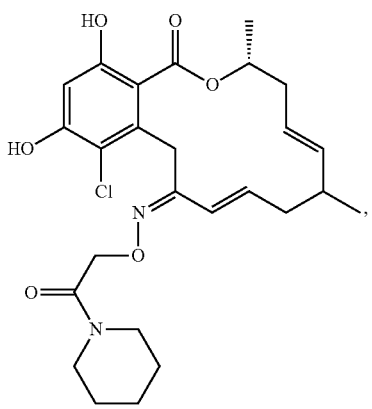
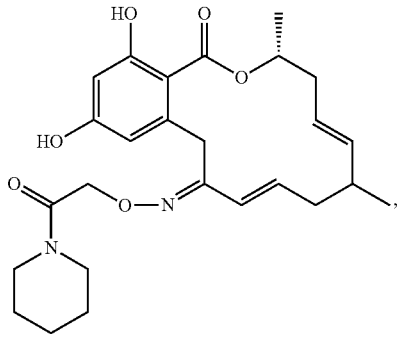

443
-continued
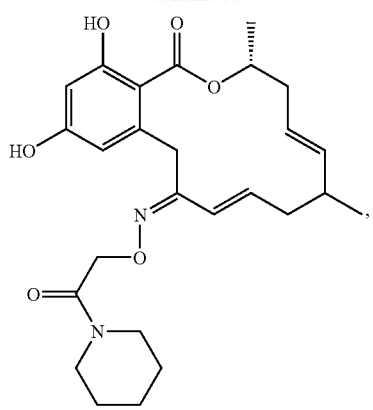
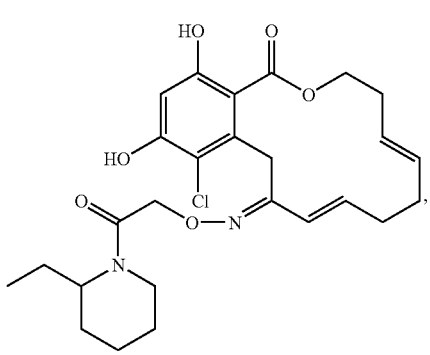
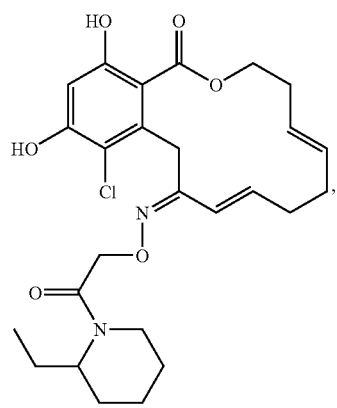
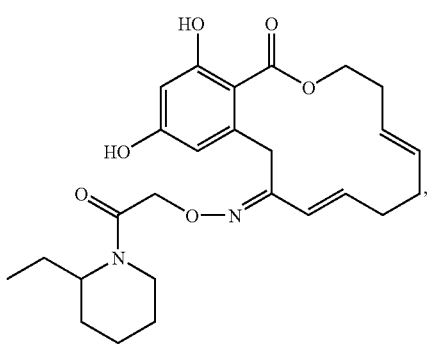
444
-continued
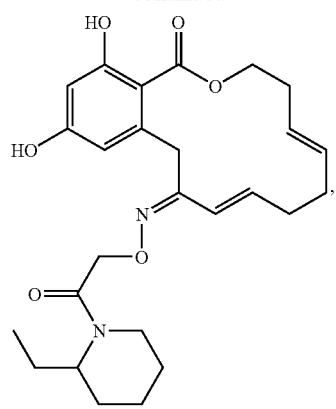
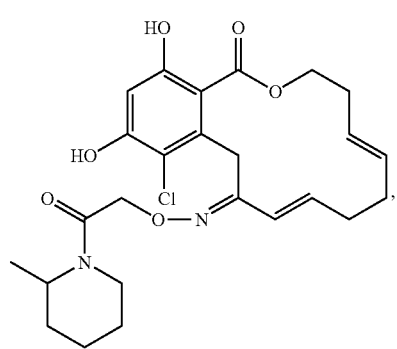
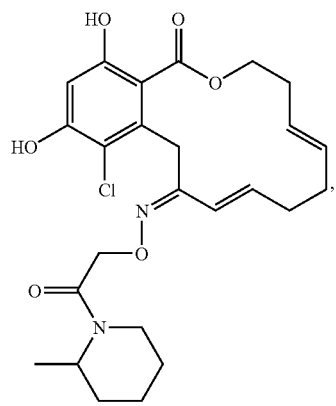
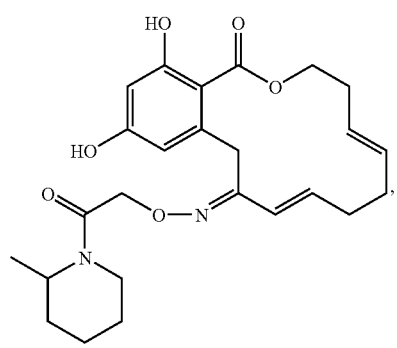

445
-continued
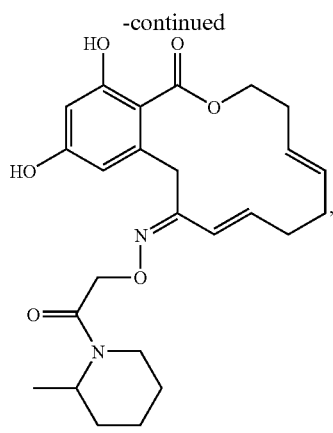
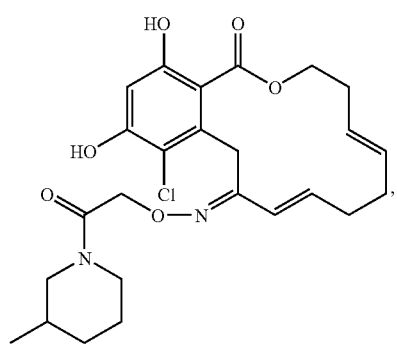
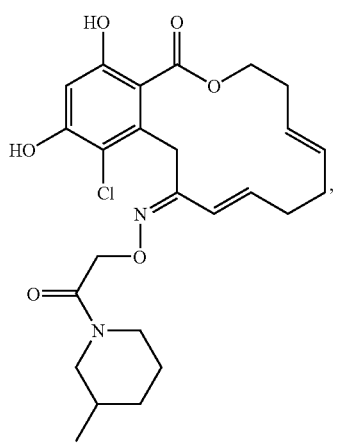
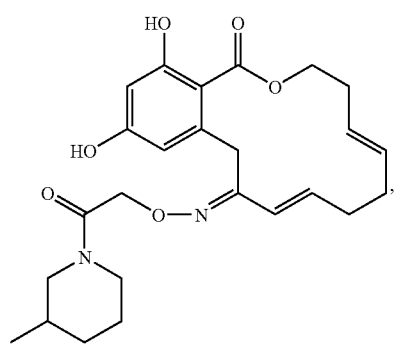
446
-continued
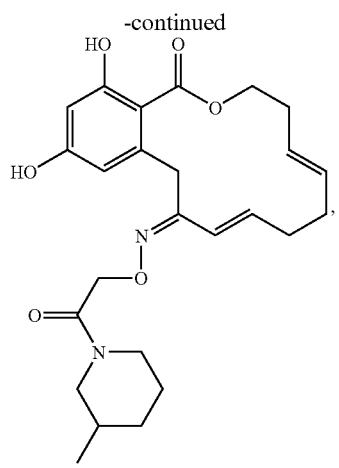
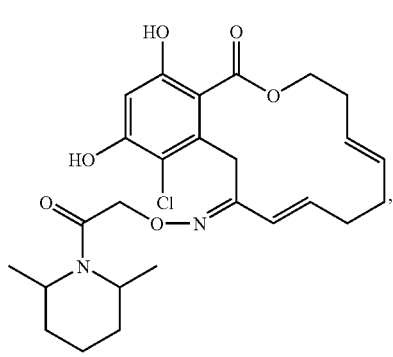
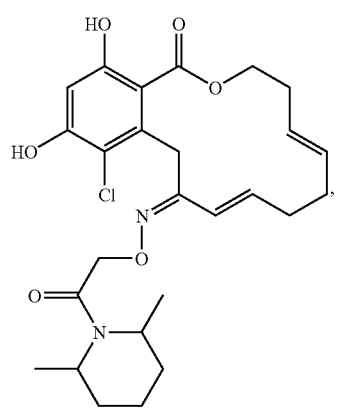
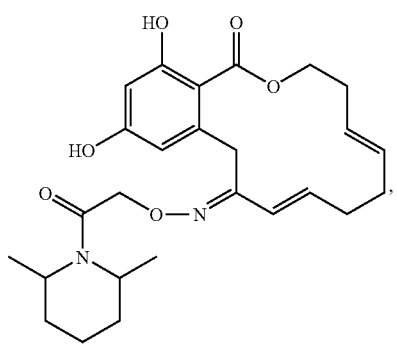

447
-continued
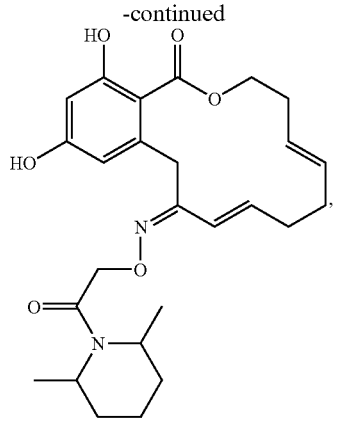
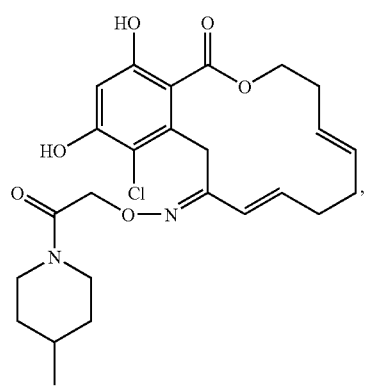
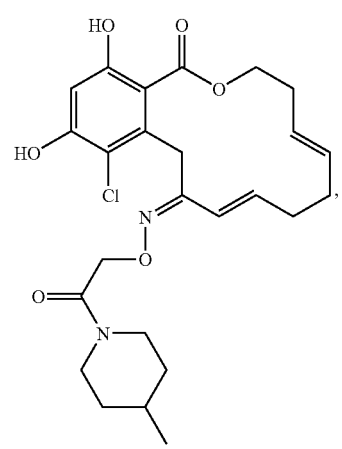
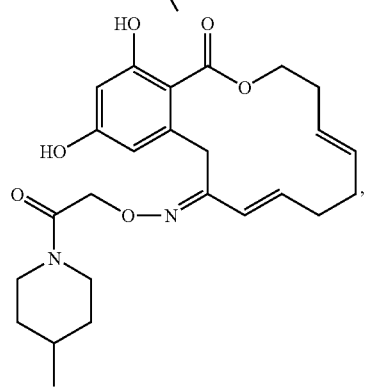
448
-continued
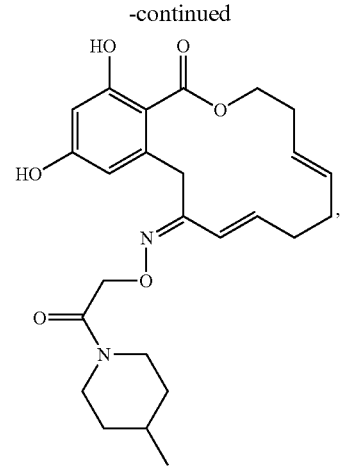
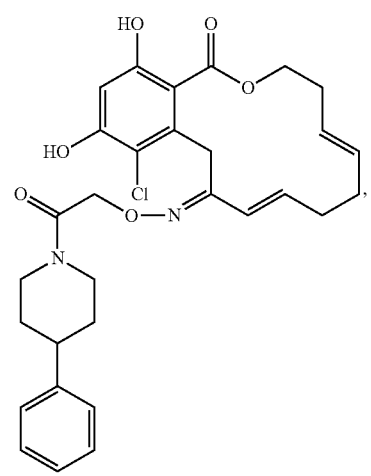
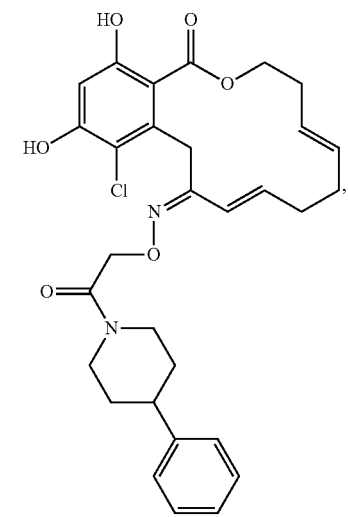

449
-continued
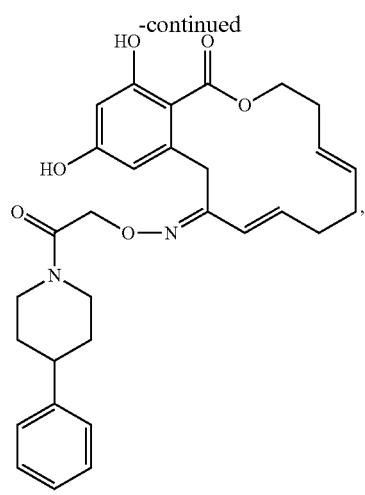
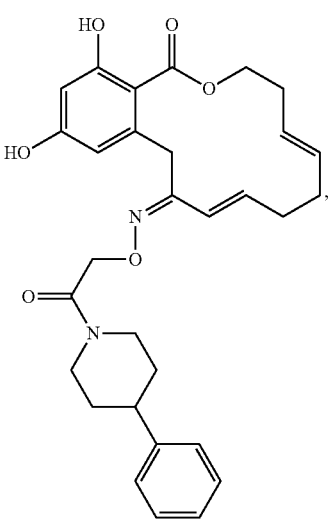
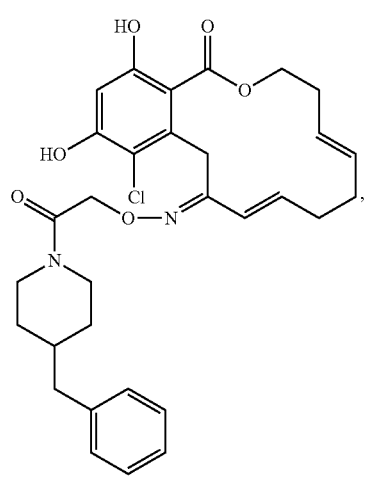
450
-continued
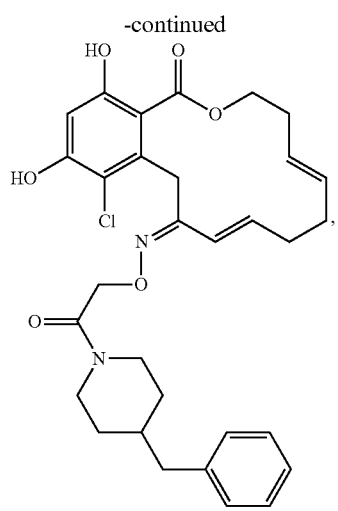
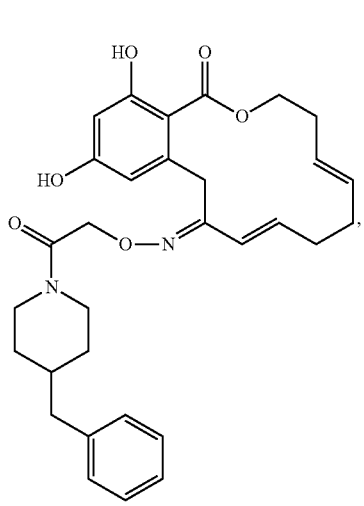
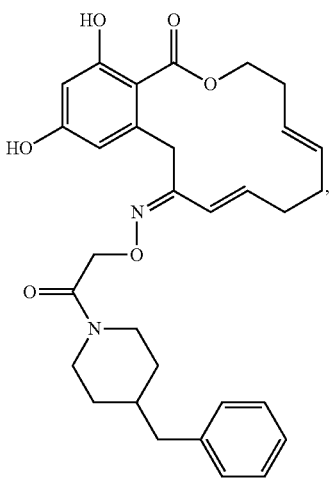

451
-continued
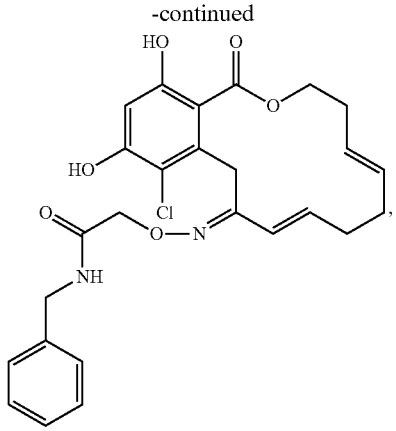
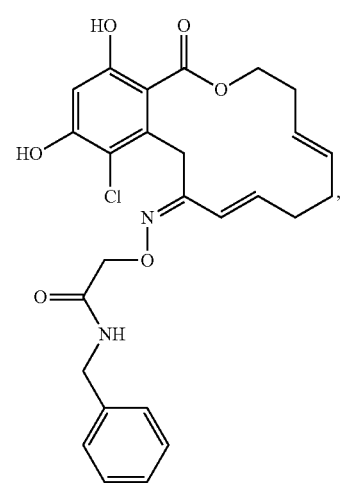
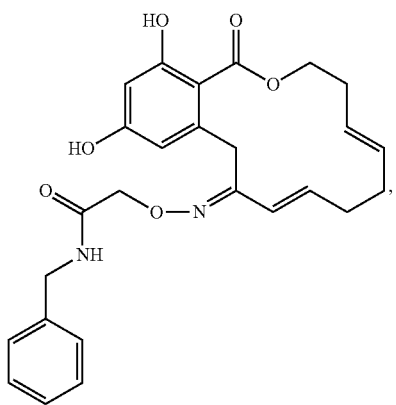
452
-continued
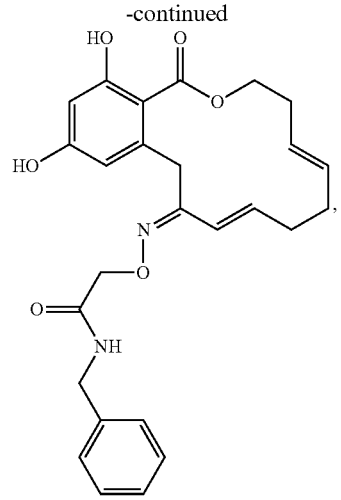
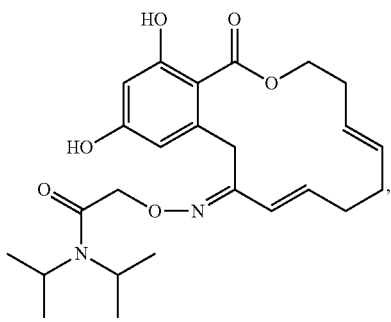
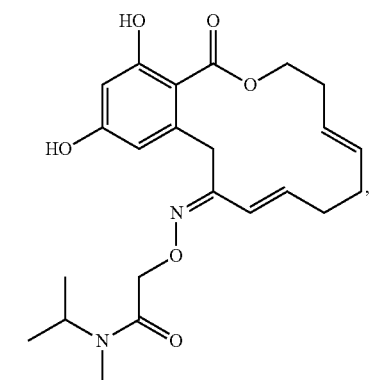
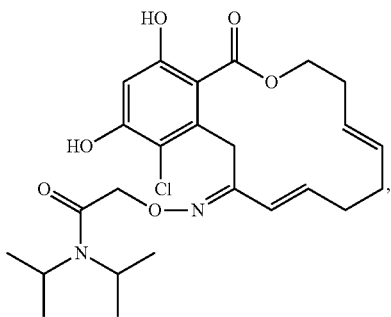

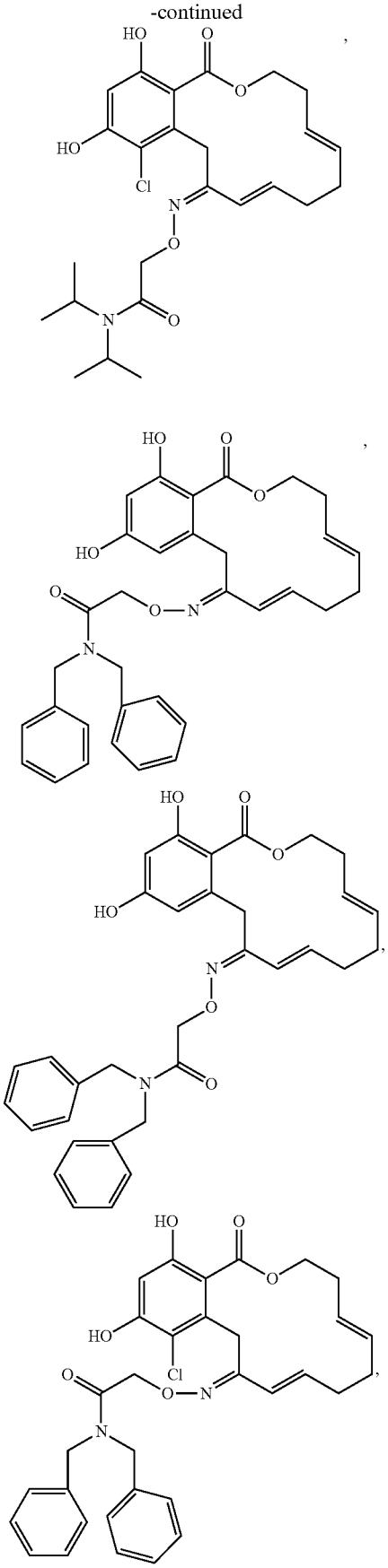

455
-continued
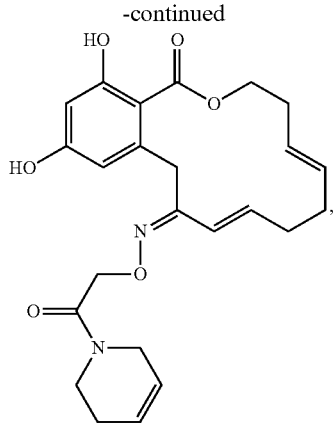
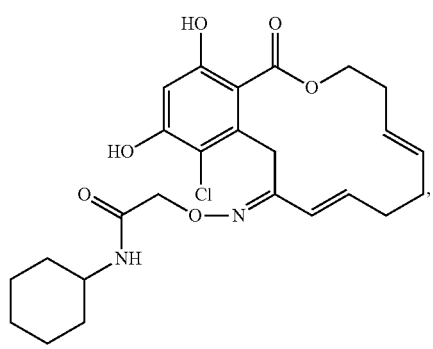
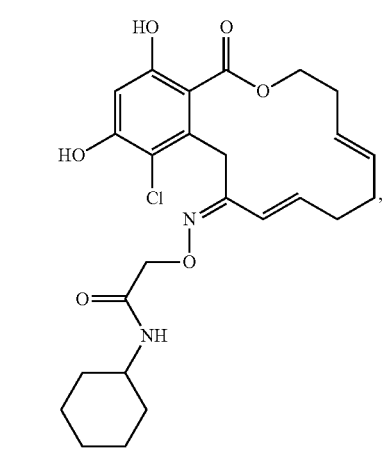
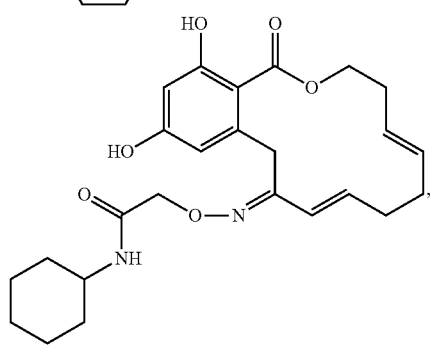
456
-continued
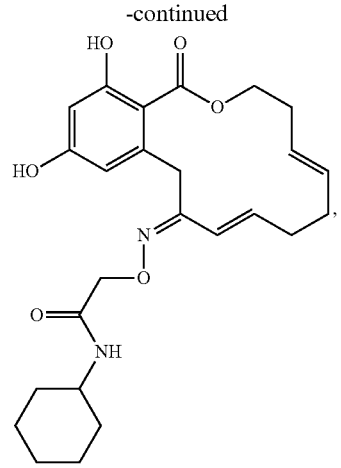
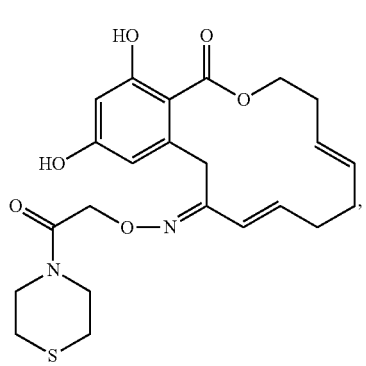
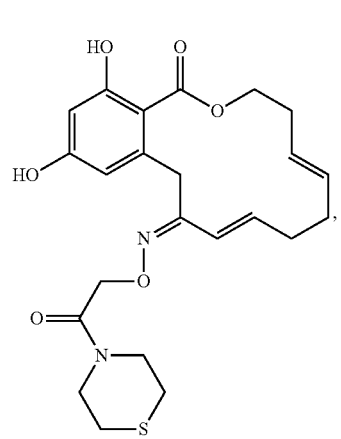
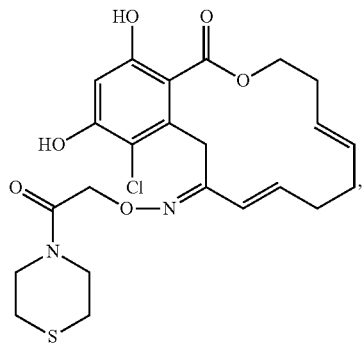

457
-continued
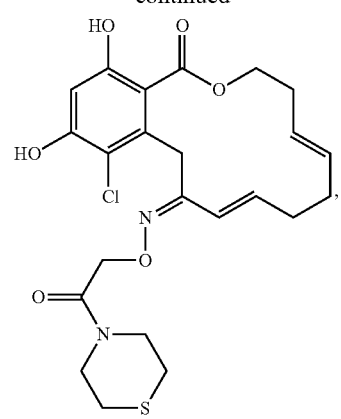
,
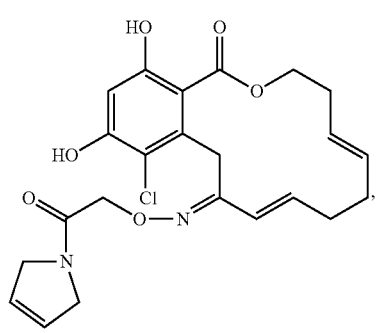
,
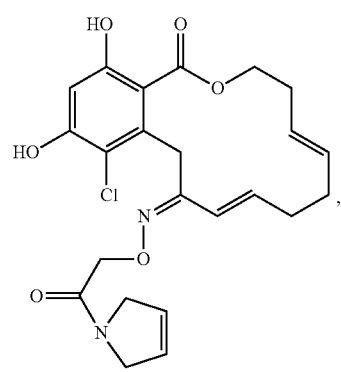
,
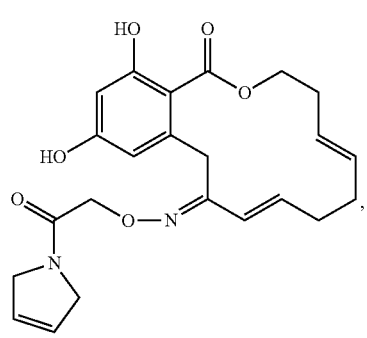
,
458
-continued
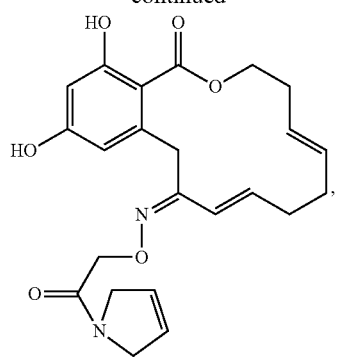
,
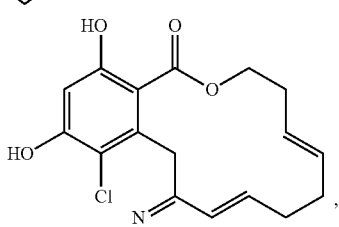
,
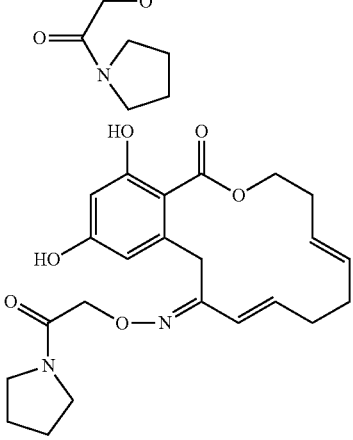
,
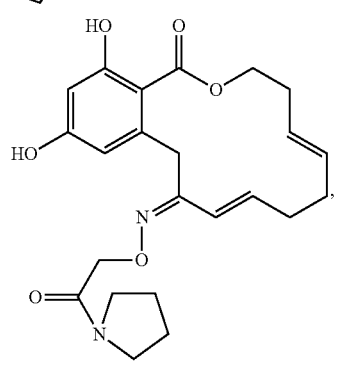
,

459
-continued
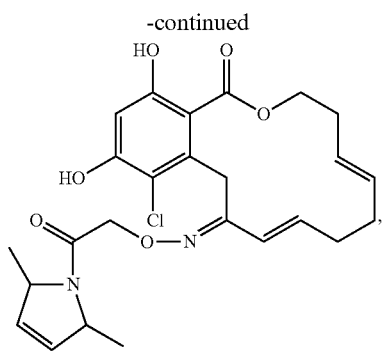
,
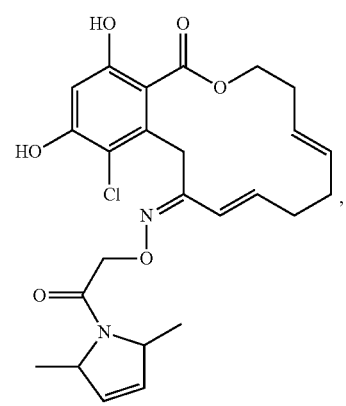
,
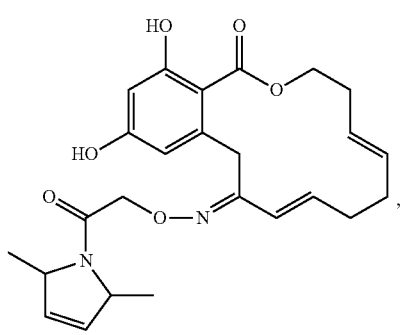
,
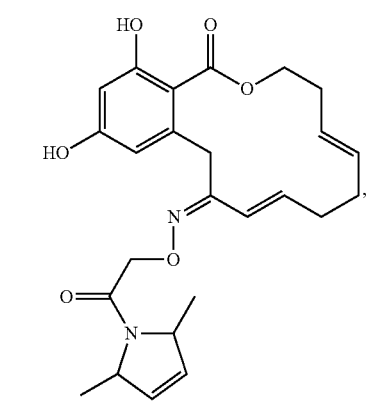
,
460
-continued
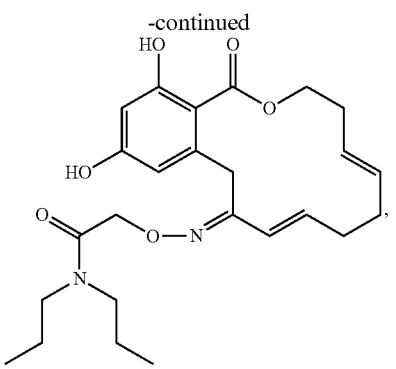
,
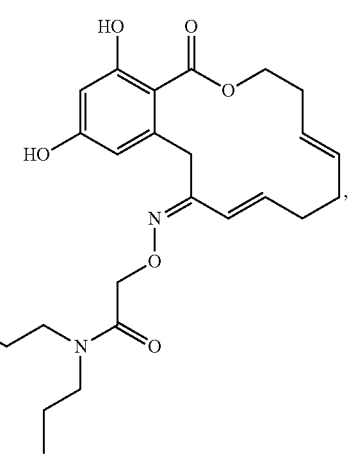
,
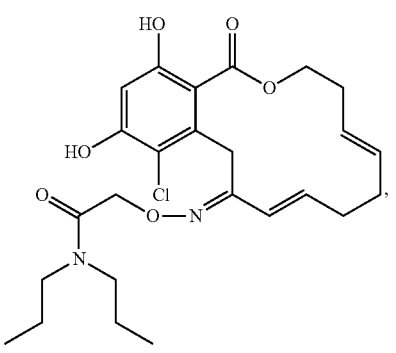
,
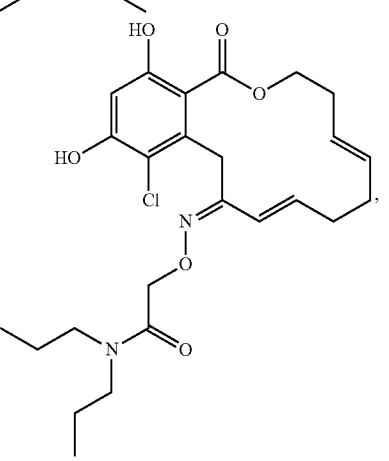
,

461
-continued
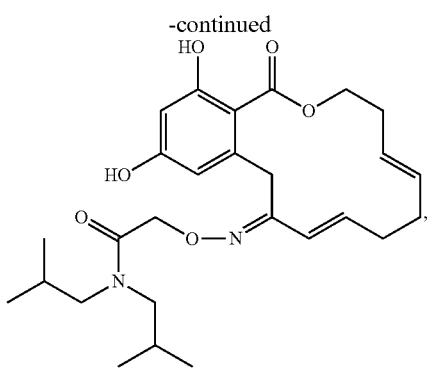
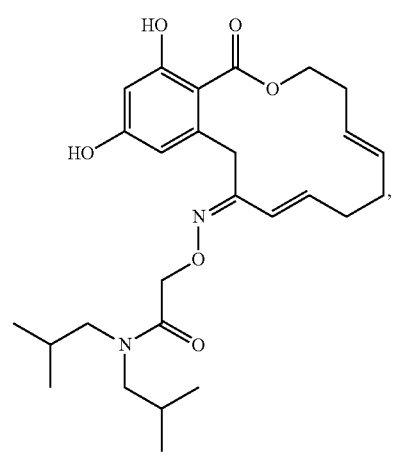
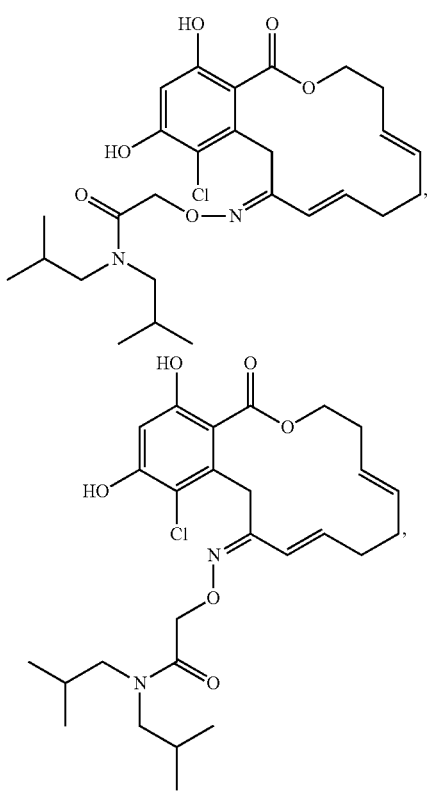
462
-continued
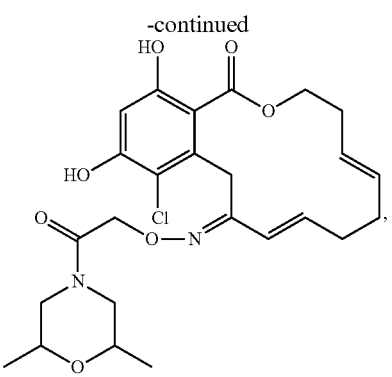
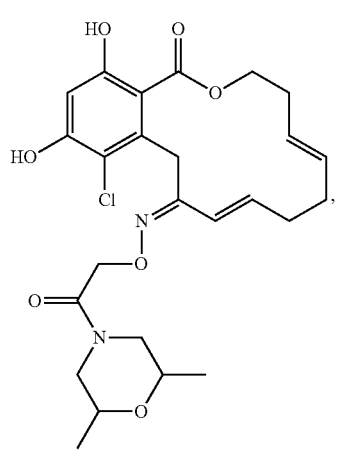
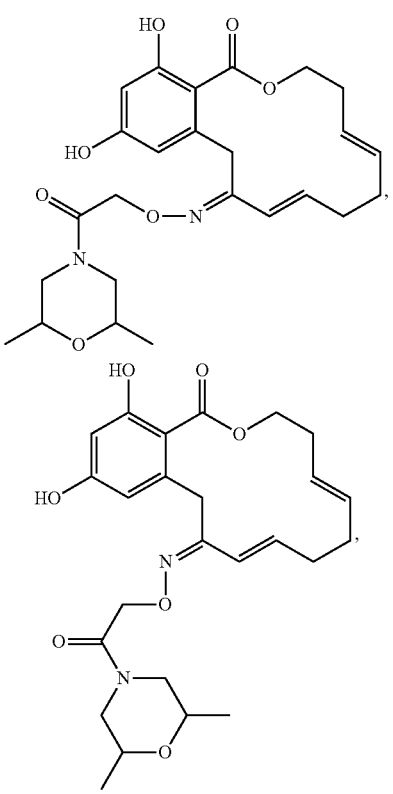

463
-continued
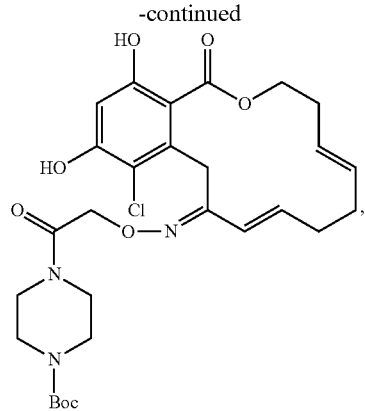
,
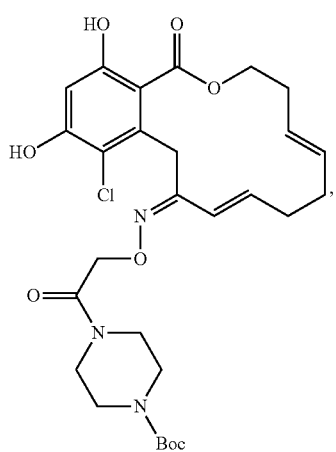
,
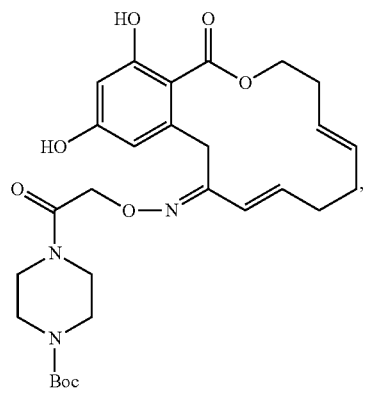
,
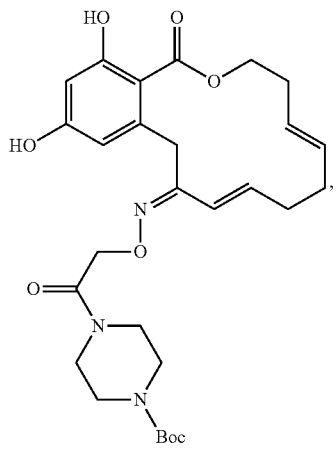
,
464
-continued
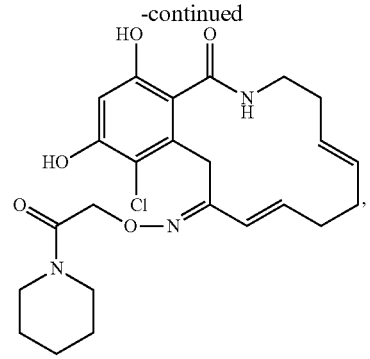
,
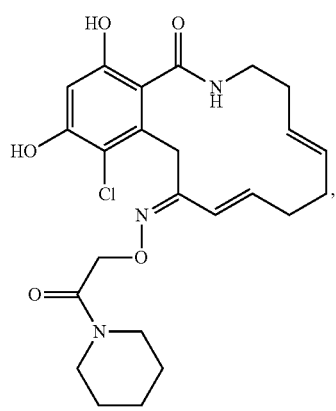
,
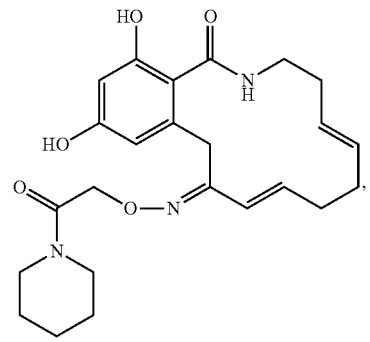
,
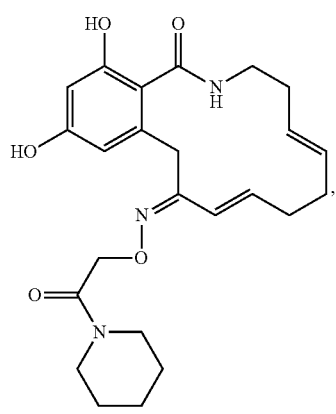
, 465
-continued
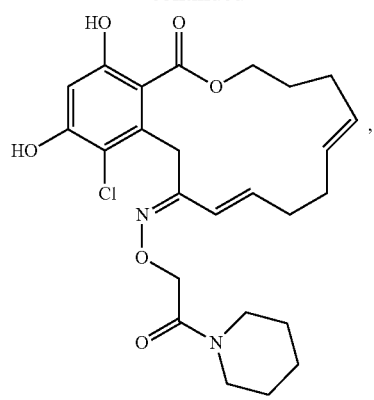,
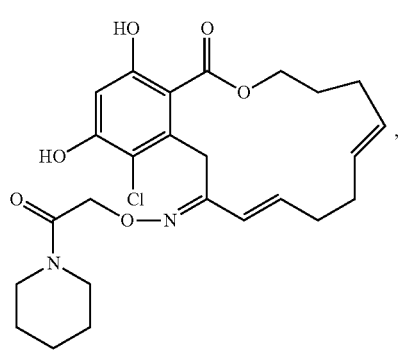,
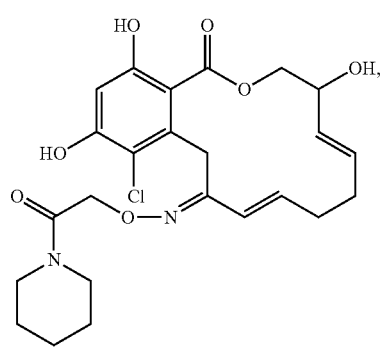,
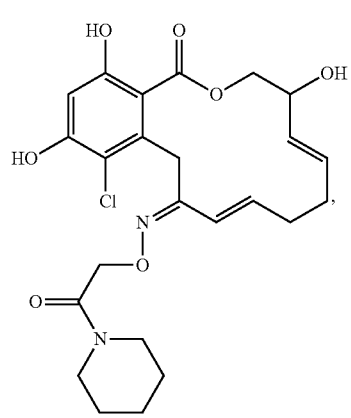,
466
-continued
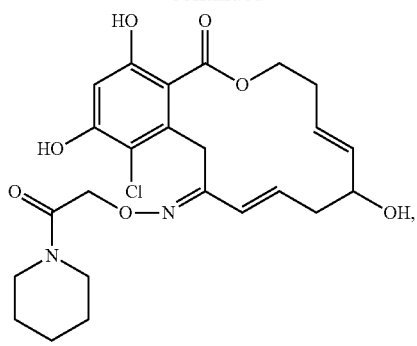,
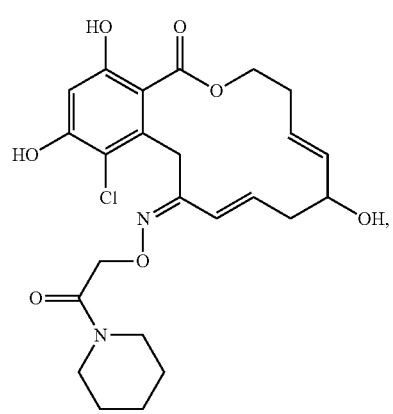,
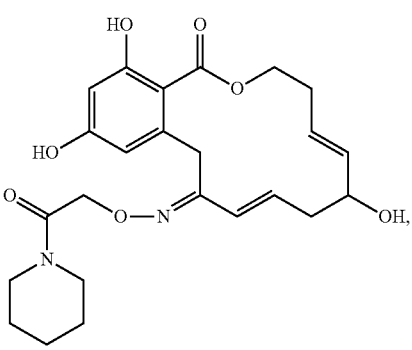,
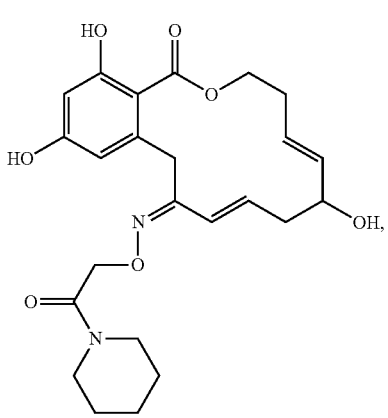, 467
-continued
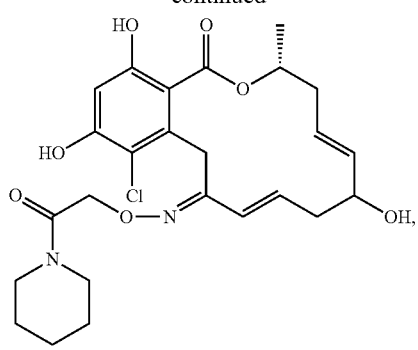
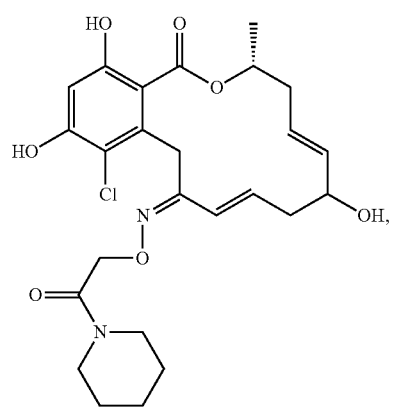
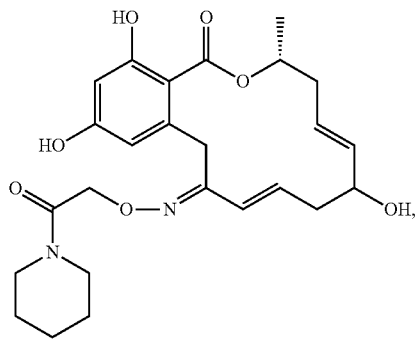
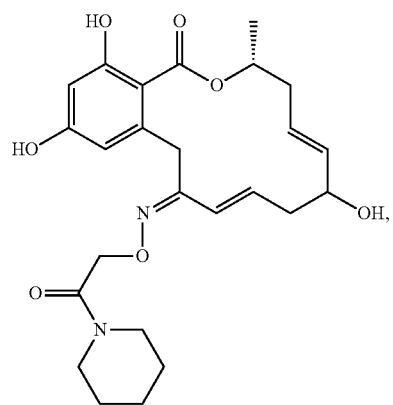
468
-continued
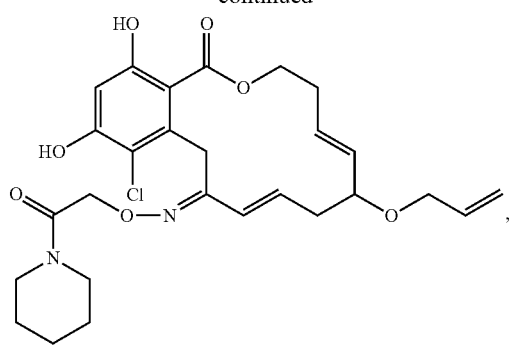
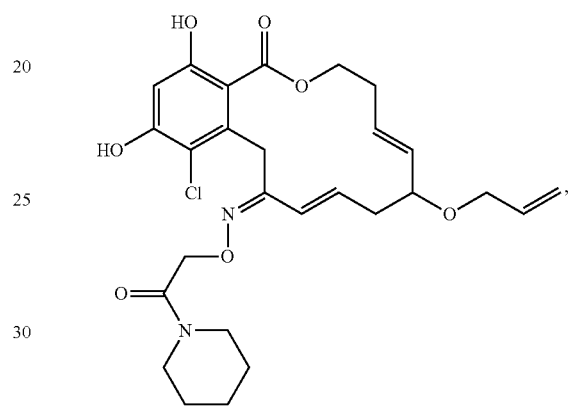
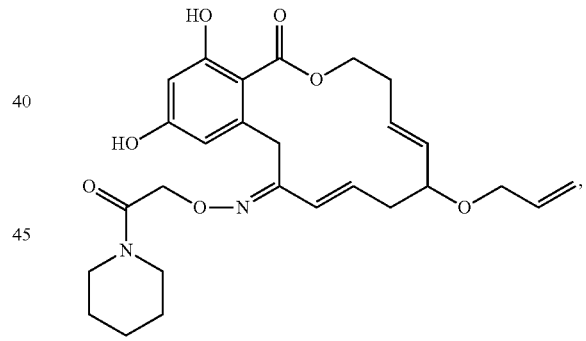
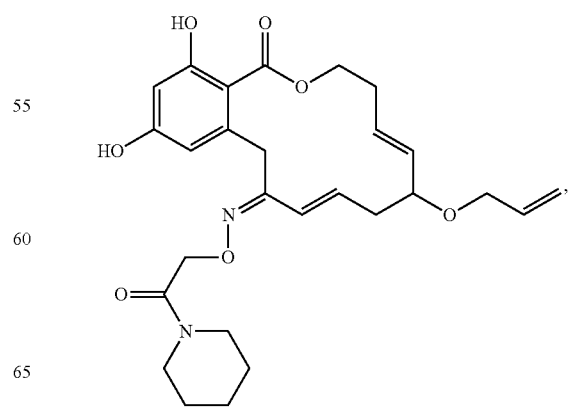

469
-continued
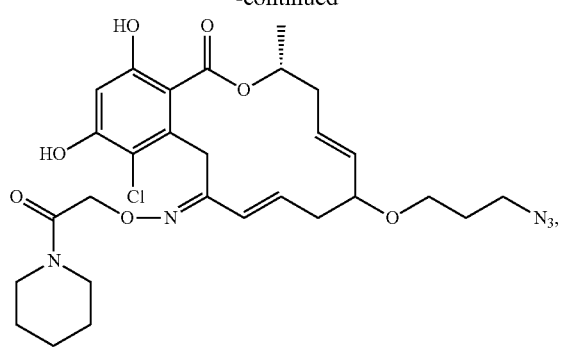
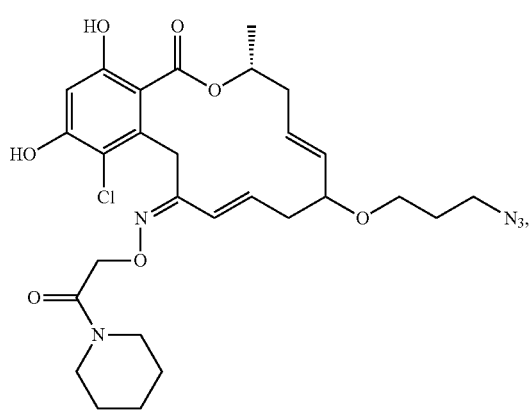
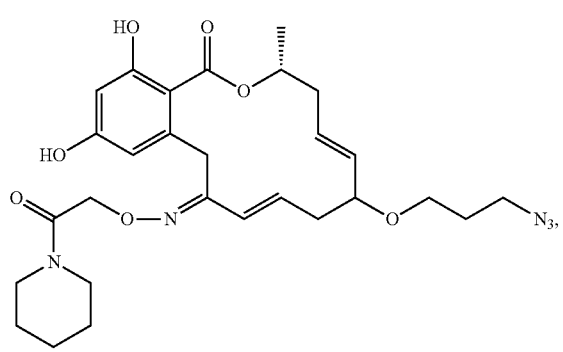
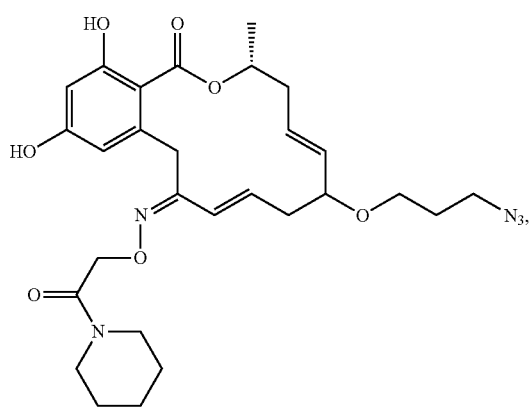
470
-continued
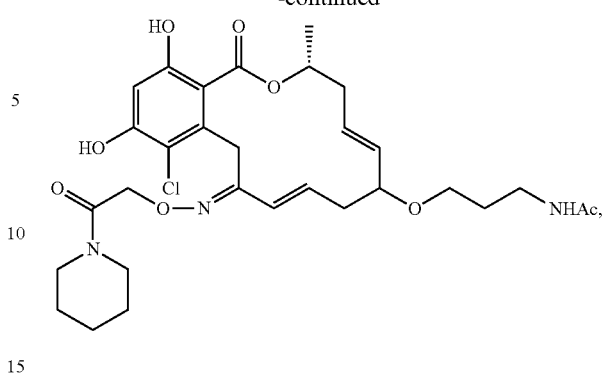
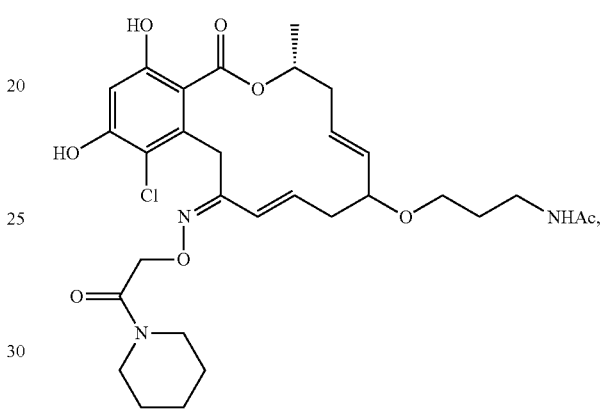
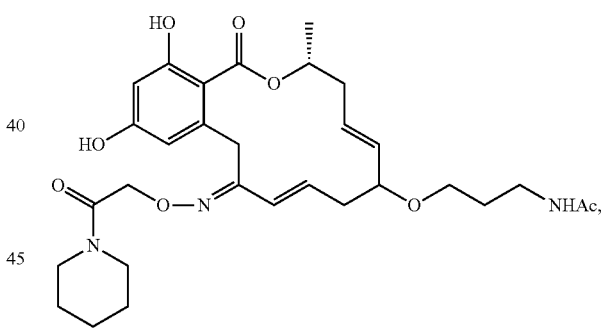
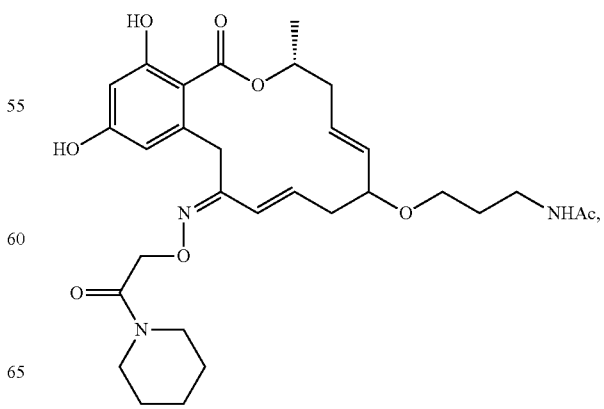

471
-continued
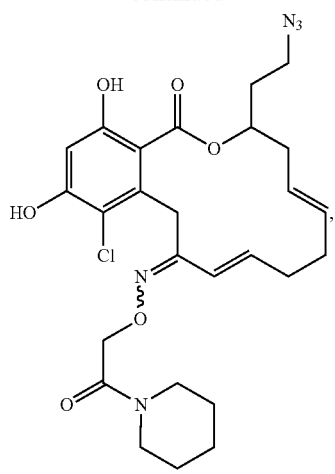
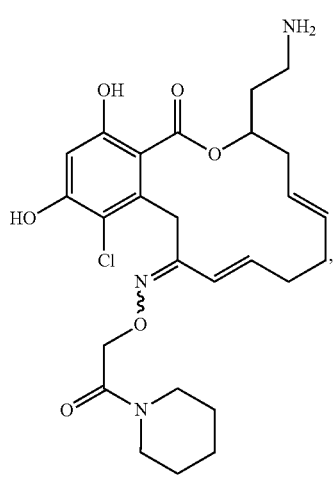
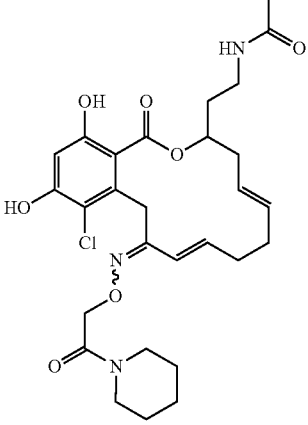
472
-continued
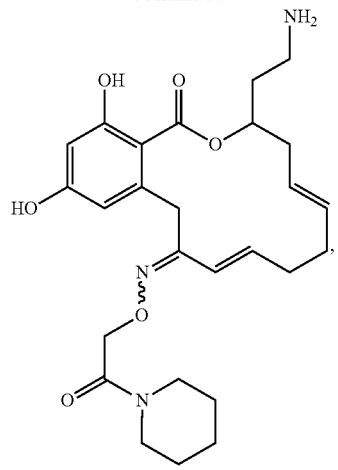
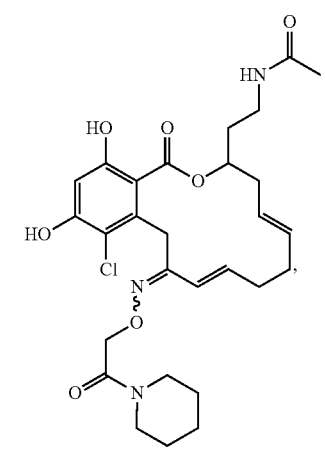
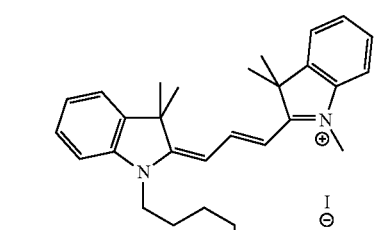

473
-continued
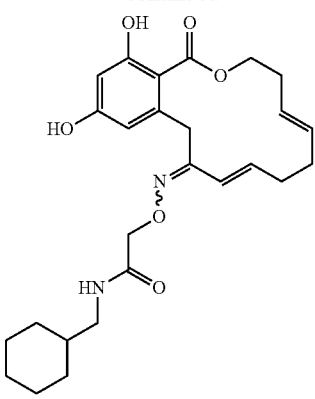
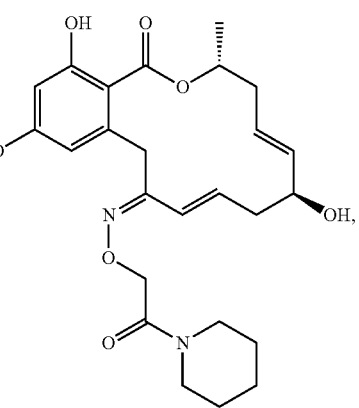
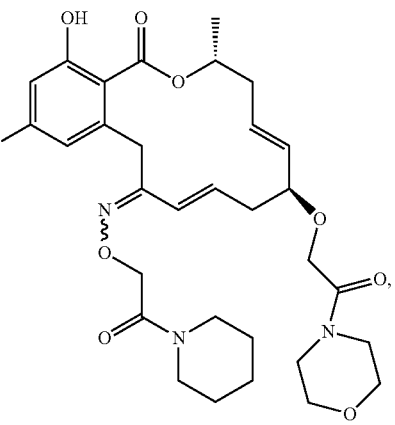
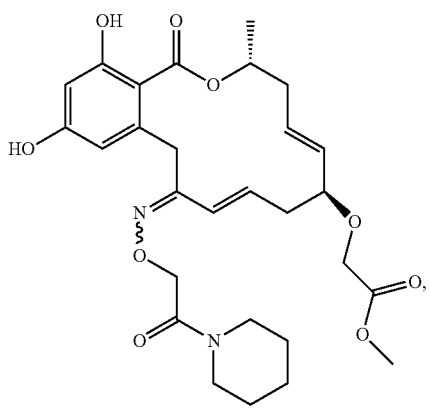
474
-continued
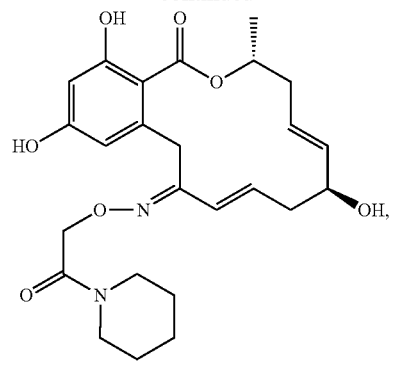
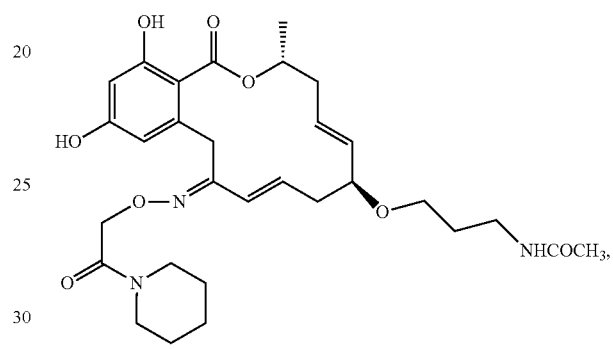
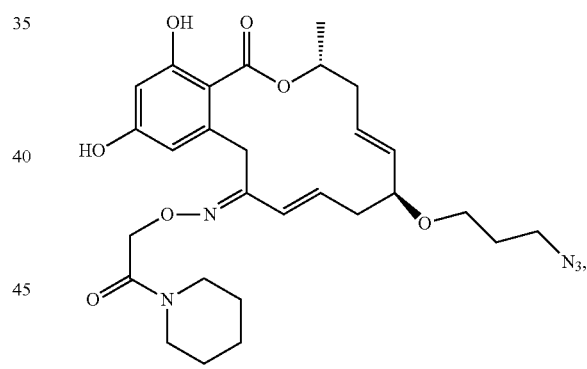
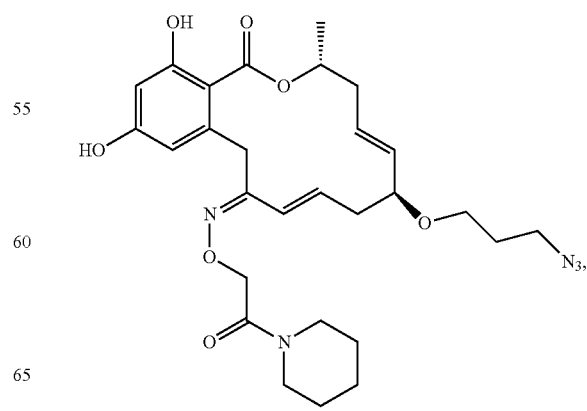

-continued

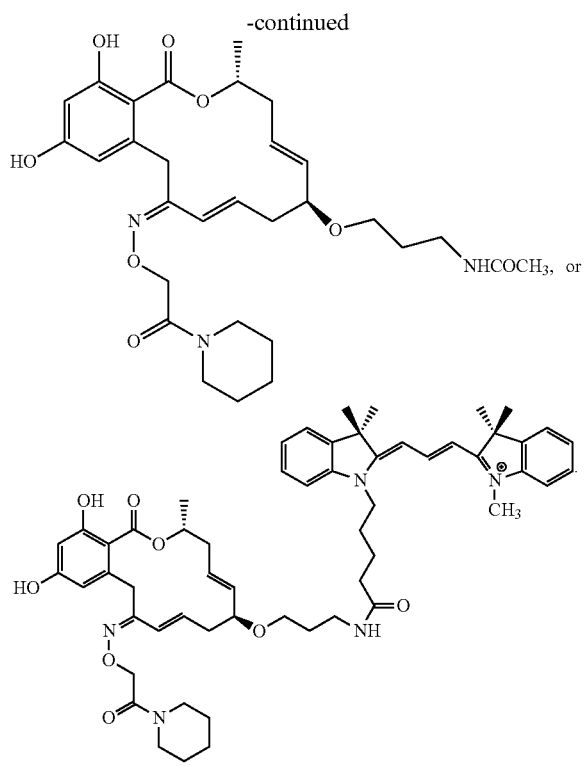

9. The method of claim 1, wherein at least one compound of formula I or I' inhibits or slows growth of one or more NF2-deficient tumor cells or NF1-deficient tumor cells, reduces the number of said tumors or inhibits and/or reduces associated symptoms as compared to no treatment with the at least one compound of formula I or I'.

10. The method of claim 9, wherein the one or more NF2-deficient tumor cells are selected from the group consisting of cells from vestibular schwannomas; spinal cord schwannomas; sporadic schwannomas; peripheral nerve schwannomas; schwannoma; meningioma; mesothelioma; ependymoma; glioma and astrocytoma; and wherein said NF1-deficient tumor cells are selected from the group consisting of cells from dermal and plexiform neurofibromas, optic pathway astrocytomas, optic neuromas, optic gliomas, cerebral astrocytomas, cerebral gliomas, ependymomas, pheochromocytomas and ganglioneuromas, rhabdomyosarcomas, neurofibrosarcomas, malignant peripheral nerve sheath tumors ("MPNST"), malignant schwannomas, and JMML.

11. The method of claim 9, wherein contact of said NF2-deficient tumor cells or said NF1-deficient tumor cells with said at least one compound of formula I results in a reduction in HSP90 function and/or an upregulation of HSP70.

12. The method of claim 9, further comprises contacting said NF2-deficient tumor cells or NF1-deficient tumor cells with at least one additional active agent.

13. The method of claim 12, wherein the at least one additional active agent comprises a heat shock protein 90 (HSP90) inhibitor or a cytotoxic agent; and wherein the HSP90 inhibitor is selected from the group consisting of (1) 17-AAG or a derivative thereof; (2) a purine scaffold-based HSP90 inhibitor or a derivative thereof; (3) a pyrazole scaffold-based HSP90 inhibitor or a derivative thereof; (4) an imidazole scaffold-based HSP90 inhibitor or a derivative thereof; (5) a tetrahydroindolone- or tetrahydroindazolone-based HSP90 inhibitor or a derivative thereof; (6) Novobiocin or a derivative thereof; (7) NZ28 (NCS-134754) or a derivative thereof; (8) a HSP90 modulator; (9) a biological agent or molecule; and (10) a combination thereof.

* * * * *